US010655109B2

(12) United States Patent
Collins et al.

(10) Patent No.: US 10,655,109 B2
(45) Date of Patent: May 19, 2020

(54) RECOMBINANT RESPIRATORY SYNCYTIAL VIRUS STAINS WITH MUTATIONS IN THE M2-2 ORF PROVIDING A RANGE OF ATTENUATION PHENOTYPES

(71) Applicant: The United States of America, as represented by the Secretary, Department of Health and Human Services, Bethesda, MD (US)

(72) Inventors: Peter L. Collins, Silver Spring, MD (US); Ursula J. Buchholz, Silver Spring, MD (US); Cindy Luongo, Bethesda, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 0 days.

(21) Appl. No.: 16/061,314

(22) PCT Filed: Dec. 12, 2016

(86) PCT No.: PCT/US2016/066146

§ 371 (c)(1),
(2) Date: Jun. 11, 2018

(87) PCT Pub. No.: WO2017/100759

PCT Pub. Date: Jun. 15, 2017

(65) Prior Publication Data

US 2019/0040365 A1 Feb. 7, 2019

Related U.S. Application Data

(60) Provisional application No. 62/266,199, filed on Dec. 11, 2015.

(51) Int. Cl.

| | |
|---|---|
| ***C12N 7/00*** | (2006.01) |
| ***A61K 39/12*** | (2006.01) |
| ***C07K 14/005*** | (2006.01) |
| ***A61K 39/155*** | (2006.01) |
| *A61K 39/00* | (2006.01) |

(52) U.S. Cl.

CPC ................ *C12N 7/00* (2013.01); *A61K 39/12* (2013.01); *A61K 39/155* (2013.01); *C07K 14/005* (2013.01); *A61K 2039/522* (2013.01); *A61K 2039/5254* (2013.01); *A61K 2039/543* (2013.01); *C12N 2760/18521* (2013.01); *C12N 2760/18522* (2013.01); *C12N 2760/18534* (2013.01); *C12N 2760/18562* (2013.01)

(58) Field of Classification Search

None

See application file for complete search history.

(56) References Cited

U.S. PATENT DOCUMENTS

| | | | | |
|---|---|---|---|---|
| 6,713,066 | B1 | 3/2004 | Collins et al. | |
| 7,465,574 | B2 | 12/2008 | Jin et al. | |
| 2004/0005542 | A1 | 1/2004 | Krempl et al. | |
| 2015/0118732 | A1 | 4/2015 | Collins et al. | |
| 2016/0228536 | A1* | 8/2016 | Schickli ................. | A61K 39/12 |

FOREIGN PATENT DOCUMENTS

| | | |
|---|---|---|
| WO | WO 2002/044334 | 6/2002 |
| WO | WO 2013/154728 | 10/2013 |

OTHER PUBLICATIONS

Bermingham, et al. "The M2-2 protein of human respiratory syncytial virus is a regulatory factor involved in the balance between RNA replication and transcription." *Proceedings of the National Academy of Sciences* 96, No. 20 (1999): 11259-11264.

Bernstein, et al. "Phase 1 study of the safety and immunogenicity of a live, attenuated respiratory syncytial virus and parainfluenza virus type 3 vaccine in seronegative children." *The Pediatric Infectious Disease Journal* 31, No. 2 (2012): 109-114.

Bukreyev, et al. "Respiratory syncytial virus can tolerate an intergenic sequence of at least 160 nucleotides with little effect on transcription or replication in vitro and in vivo." *Journal of Virology* 74, No. 23 (2000): 11017-11026.

Bukreyev, et al. "Granulocyte-macrophage colony-stimulating factor expressed by recombinant respiratory syncytial virus attenuates viral replication and increases the level of pulmonary antigen-presenting cells." *Journal of Virology* 75, No. 24 (2001): 12128-12140.

Bukreyev, et al. "Recombinant respiratory syncytial virus from which the entire SH gene has been deleted grows efficiently in cell culture and exhibits site-specific attenuation in the respiratory tract of the mouse." *Journal of Virology* 71, No. 12 (1997): 8973-8982.

Chirkova, et al. "Respiratory syncytial virus G protein CX3C motif impairs human airway epithelial and immune cell responses." *Journal of Virology* 87, No. 24 (2013): 13466-13479.

(Continued)

*Primary Examiner* — Nianxiang Zou

(74) *Attorney, Agent, or Firm* — Klarquist Sparkman, LLP

(57) ABSTRACT

Provided herein are novel recombinant respiratory syncytial viruses (RSV) having an attenuated phenotype that contain mutations in the M2-2 open reading frame that interfere with the expression of the M2-2 protein. The M2-2 mutations may be present in combination with mutations at other loci. Using methods described herein, combinations of mutations are provided to achieve desired levels of attenuation. The recombinant RSV strains described here are suitable for use as live-attenuated RSV vaccines. Also provided are polynucleotide sequences of the described viruses, as well as methods for producing and using the viruses.

24 Claims, 20 Drawing Sheets

Specification includes a Sequence Listing.

(56) References Cited

OTHER PUBLICATIONS

Collins, et al. "Production of infectious human respiratory syncytial virus from cloned cDNA confirms an essential role for the transcription elongation factor from the 5'proximal open reading frame of the M2 mRNA in gene expression and provides a capability for vaccine development." *Proceedings of the National Academy of Sciences* 92, No. 25 (1995): 11563-11567.
Collins, et al. "Rational design of live-attenuated recombinant vaccine virus for human respiratory syncytial virus by reverse genetics." In *Advances in Virus Research,* vol. 54, pp. 423-451. Academic Press, 1999.
Collins, et al. "Respiratory syncytial virus: reverse genetics and vaccine strategies." *Virology* 296, No. 2 (2002): 204-211.
Connors, et al. "A cold-passaged, attenuated strain of human respiratory syncytial virus contains mutations in the F and L genes." *Virology* 208, No. 2 (1995): 478-484.
Firestone, et al. "Nucleotide sequence analysis of the respiratory syncytial virus subgroup A cold-passaged (cp) temperature sensitive (ts) cpts-248/404 live attenuated virus vaccine candidate." *Virology* 225, No. 2 (1996): 419-422.
Jin, et al. "Recombinant respiratory syncytial viruses with deletions in the NS1, NS2, SH, and M2-2 genes are attenuated in vitro and in vivo." *Virology* 273, No. 1 (2000): 210-218.
Jin, et al. "Respiratory syncytial virus that lacks open reading frame 2 of the M2 gene (M2-2) has altered growth characteristics and is attenuated in rodents," *Journal of Virology* 74, No. 1 (2000): 74-82.
Juhasz, et al. "The two amino acid substitutions in the L protein of cpts530/1009, a live-attenuated respiratory syncytial virus candidate vaccine, are independent temperature-sensitive and attenuation mutations." *Vaccine* 17, No. 11-12 (1999): 1416-1424.
Karron, et al. "Respiratory syncytial virus (RSV) SH and G proteins are not essential for viral replication in vitro: clinical evaluation and molecular characterization of a cold-passaged, attenuated RSV subgroup B mutant." *Proceedings of the National Academy of Sciences* 94, No. 25 (1997): 13961-13966.
Karron, et al. "A gene deletion that up-regulates viral gene expression yields an attenuated RSV vaccine with improved antibody responses in children." *Science Translational Medicine* 7, No. 312 (2015): 312ra175-312ra175.
Karron, et al. "Identification of a recombinant live attenuated respiratory syncytial virus vaccine candidate that is highly attenuated in infants." *The Journal of Infectious Diseases* 191, No. 7 (2005): 1093-1104.
Karron, et al. "Live-attenuated respiratory syncytial virus vaccines" In *Challenges and Opportunities for Respiratory Syncytial Virus Vaccines,* pp. 259-284. Springer, Berlin, Heidelberg, 2013.
Krempl, et al. "Recombinant respiratory syncytial virus with the G and F genes shifted to the promoter-proximal positions," *Journal of Virology* 76, No. 23 (2002): 11931-11942.
Lawlor, et al. "A single amino acid in the F2 subunit of respiratory syncytial virus fusion protein alters growth and fusogenicity." *Journal of General Virology* 94, No. 12 (2013): 2627-2635.
Liang, et al. "Enhanced neutralizing antibody response induced by respiratory syncytial virus prefusion F protein expressed by a vaccine candidate." *Journal of Virology* 89, No. 18 (2015): 9499-9510.
Liang, et al. "Chimeric bovine/human parainfluenza virus type 3 expressing respiratory syncytial virus (RSV) F glycoprotein: effect of insert position on expression, replication, immunogenicity, stability, and protection against RSV infection." *Journal of Virology* 88, No. 8 (2014): 4237-4250.
Luongo, et al. "Codon stabilization analysis of the "248" temperature sensitive mutation for increased phenotypic stability of respiratory syncytial virus vaccine candidates." *Vaccine* 27, No. 41 (2009): 5667-5676.
Luongo, et al. "Increased genetic and phenotypic stability of a promising live-attenuated respiratory syncytial virus vaccine candidate by reverse genetics." *Journal of Virology* 86, No. 19 (2012): 10792-10804.
Luongo, et al. "Respiratory syncytial virus modified by deletions of the NS2 gene and amino acid S1313 of the L polymerase protein is a temperature-sensitive, live-attenuated vaccine candidate that is phenotypically stable at physiological temperature." *Journal of Virology* 87, No. 4 (2013): 1985-1996.
Malkin, et al. "Safety and immunogenicity of a live attenuated RSV vaccine in healthy RSV-seronegative children 5 to 24 months of age." *PloS One* 8, No. 10 (2013): e77104.
McLellan, et al. "Structure of RSV fusion glycoprotein trimer bound to a prefusion-specific neutralizing antibody." *Science* 340, No. 6136 (2013): 1113-1117.
McLellan, et al. "Structure-based design of a fusion glycoprotein vaccine for respiratory syncytial virus." *Science* 342. No. 6158 (2013): 592-598.
Murphy, et al. "An update on approaches to the development of respiratory syncytial virus (RSV) and parainfluenza virus type 3 (PIV3) vaccines." *Virus Research* 32, No. 1 (1994): 13-36.
Murphy, et al. "Live-attenuated virus vaccines for respiratory syncytial and parainfluenza viruses: applications of reverse genetics." *The Journal of Clinical Investigation* 110, No. 1 (2002): 21-27.
Teng, et al. "Recombinant respiratory syncytial virus that does not express the NS1 or M2-2 protein is highly attenuated and immunogenic in chimpanzees." *Journal of Virology* 74, No. 19 (2000): 9317-9321.
Whitehead, et al. "A Single Nucleotide Substitution in the Transcription Start Signal of the M2 Gene of Respiratory Syncytial Virus Vaccine Candidate cpts248/404 is the Major Determinant of the Temperature-Sensitive and Attenuation Phenotypes." *Virology* 247, No. 2 (1998): 232-239.
Whitehead, et al. "Recombinant respiratory syncytial virus bearing a deletion of either the NS2 or SH gene is attenuated in chimpanzees." *Journal of Virology* 73, No. 4 (1999): 3438-3442.
Whitehead, et al. "Recombinant respiratory syncytial virus (RSV) bearing a set of mutations from cold-passaged RSV is attenuated in chimpanzees." *Journal of Virology* 72, No. 5 (1998): 4467-4471.
Wright, et al. "Evaluation of a live, cold-passaged, temperature-sensitive, respiratory syncytial virus vaccine candidate in infancy." *The Journal of Infiytious Diseases* 182, No. 5 (2000): 1331-1342.

* cited by examiner

ΔM2-2 mutation in RSV D46/ΔM2-2 and LID/ΔM2-2

RSV D46/ΔM2-2 and RSV LID/ΔM2-2

```
                                 4497                 4610
             XhoI                                                  PacI
SH ORF  --- GCT CGA GTC AAC ACA TAG    . . .    TAAAGTAGTTAATTAAAAATAG
        --- A   R   V   N   T   TER                        SH gene-end
                                          112-nt
                                          deletion

                                   4497   4610
             XhoI                                      PacI
SH ORF  --- GCT CGA GTT AAT ACT TGA TAAAGTAGTTAATTAAAAATAG
        --- A   R   V   N   T   TER         SH gene-end
```

6120 mutation in the SH gene of RSV LID/ΔM2-2

SH gene deletion in RSV ΔSH/ΔM2-2 and cp/ΔSH/ΔM2-2

Replication of selected ΔM2-2 mutant viruses in African Green Monkeys

Replication of selected ΔM2-2 mutant viruses in African Green Monkeys

D46 and LID viruses bearing the ΔM2-2-*Acl*I mutation

ΔM2-2 viruses with additional modifications to the F and G genes

ΔM2-2 viruses with additional modifications to the F and G genes

FIG. 15

Comparison of P1 virus titers at 32°C, and P2 virus titers at 32°C and 37°C

| Virus | P1 Titer pfu/ml 32°C | P2 Titer pfu/ml 32°C (MOI ~ 0.01) | P2 Titer pfu/ml 37°C (MOI ~ 0.01) |
|---|---|---|---|
| 6120/G001BB/FBB/ΔM2-2 | $1.7*10^7$ | $1.95*10^7$ | $2.35*10^7$ |
| 6120/FBB/G001BB/ΔM2-2 | $3.25*10^7$ | $3.1*10^7$ | $3.3*10^7$ |
| 6120/G001BB/F/ΔM2-2 | $6.66*10^6$ | $4.8*10^7$ | $3.65*10^7$ |
| 6120/G/FBB/ΔM2-2 | $1.8*10^7$ | $1.05*10^7$ | $1.1*10^7$ |
| 6120/G/FBBHEK/ΔM2-2 | $1.55*10^6$ | $7.5*10^6$ | $6.05*10^6$ |
| 6120/G/FBBcpHEK/ΔM2-2 | $5.2*10^6$ | $1.0*10^7$ | $1.4*10^7$ |
| 6120/FBB/G/ΔM2-2 | $2.5*10^7$ | $6.5*10^6$ | $6*10^6$ |
| 6120/G001BB/F001BB/ΔM2-2 | $5.0*10^3$ | $1.1*10^7$ (P3) | $1*10^7$ (P3) |
| wt LID | $2.1*10^7$ | $5*10^6$ | $1.4*10^7$ |
| LID/ΔM2-2 | $4.6*10^6$ | $2.35*10^7$ | $2*10^7$ |

Virus yields for ΔM2-2 viruses with additional modifications to the F and G genes D46/276/ΔM2-2-*AclI*
(mutations relative to D46 with genomic positioning)

SEQUENCE LISTING

<160> NUMBER OF SEQ ID NOS: 21

<210> SEQ ID NO 1
<211> LENGTH: 15223
<212> TYPE: DNA
<213> ORGANISM: respiratory syncytial virus

<400> SEQUENCE: 1

```
acgggaaaaa atgcgtacaa caaacttgca taaaccaaaa aaatggggca aataagaatt     60
tgataagtac cacttaaatt taactccctt ggttagagat gggcagcaat tcattgagta    120
tgataaaagt tagattacaa aatttgtttg acaatgatga agtagcattg ttaaaaataa    180
catgctatac tgataaatta atacatttaa ctaatgcttt ggctaaggca gtgatacata    240
caatcaaatt gaatggcatt gtgtttgtgc atgttattac aagtagtgat atttgcccta    300
ataataatat tgtagtaaaa tccaatttca caacaatgcc agtactacaa aatggaggtt    360
atatatggga aatgatggaa ttaacacatt gctctcaacc taatggtcta ctagatgaca    420
attgtgaaat taaattctcc aaaaaactaa gtgattcaac aatgaccaat tatatgaatc    480
aattatctga attacttgga tttgatctta atccataaat tataattaat atcaactagc    540
aaatcaatgt cactaacacc attagttaat ataaaactta acagaagaca aaaatggggc    600
aaataaatca attcagccaa cccaaccatg gacacaaccc acaatgataa tacaccacaa    660
agactgatga tcacagacat gagaccgttg tcacttgaga ccataataac atcactaacc    720
agagacatca taacacacaa atttatatac ttgataaatc atgaatgcat agtgagaaaa    780
cttgatgaaa gacaggccac atttacattc ctggtcaact atgaaatgaa actattacac    840
aaagtaggaa gcactaaata taaaaaatat actgaataca acacaaaata tggcactttc    900
cctatgccaa tattcatcaa tcatgatggg ttcttagaat gcattggcat taagcctaca    960
aagcatactc ccataatata caagtatgat ctcaatccat aaatttcaac acaatattca   1020
cacaatctaa aacaacaact ctatgcataa ctatactcca tagtccagat ggagcctgaa   1080
aattatagta atttaaaact taaggagaga tataagatag aagatggggc aaatacaacc   1140
atggctctta gcaaagtcaa gttgaatgat acactcaaca aagatcaact tctgtcatcc   1200
agcaaataca ccatccaacg gagcacagga gatagtattg atactcctaa ttatgatgtg   1260
cagaaacaca tcaataagtt atgtggcatg ttattaatca cagaagatgc taatcataaa   1320
ttcactgggt taataggtat gttatatgcg atgtctaggt taggaagaga agacaccata   1380
aaaatactca gagatgcggg atatcatgta aaagcaaatg gagtagatgt aacaacacat   1440
cgtcaagaca ttaatggaaa agaaatgaaa tttgaagtgt taacattggc aagcttaaca   1500
actgaaattc aaatcaacat tgagatagaa tctagaaaat cctacaaaaa aatgctaaaa   1560
gaaatgggag aggtagctcc agaatacagg catgactctc ctgattgtgg gatgataata   1620
ttatgtatag cagcattagt aataactaaa ttagcagcag gggacagatc tggtcttaca   1680
gccgtgatta ggagagctaa taatgtccta aaaaatgaaa tgaaacgtta caaaggctta   1740
ctacccaagg acatagccaa cagcttctat gaagtgtttg aaaaacatcc ccactttata   1800
gatgtttttg ttcattttgg tatagcacaa tcttctacca gaggtggcag tagagttgaa   1860
gggatttttg caggattgtt tatgaatgcc tatggtgcag ggcaagtgat gttacggtgg   1920
```

-continued

```
ggagtcttag caaaatcggt taaaaatatt atgttaggac atgctagtgt gcaagcagaa   1980
atggaacaag ttgttgaggt ttatgaatat gcccaaaaat tgggtggtga agcaggattc   2040
taccatatat tgaacaaccc aaaagcatca ttattatctt tgactcaatt tcctcacttc   2100
tccagtgtag tattaggcaa tgctgctggc ctaggcataa tgggagagta cagaggtaca   2160
ccgaggaatc aagatctata tgatgcagca aaggcatatg ctgaacaact caaagaaaat   2220
ggtgtgatta actacagtgt actagacttg acagcagaag aactagaggc tatcaaacat   2280
cagcttaatc caaaagataa tgatgtagag ctttgagtta ataaaaaatg ggcaaataa   2340
atcatcatgg aaaagtttgc tcctgaattc catggagaag atgcaaacaa cagggctact   2400
aaattcctag aatcaataaa gggcaaattc acatcaccca aagatcccaa gaaaaaagat   2460
agtatcatat ctgtcaactc aatagatata gaagtaacca aagaaagccc tataacatca   2520
aattcaacta ttatcaaccc aacaaatgag acagatgata ctgcagggaa caagcccaat   2580
tatcaaagaa aacctctagt aagtttcaaa gaagacccta caccaagtga taatcccttt   2640
tctaaactat acaaagaaac catagaaaca tttgataaca atgaagaaga atccagctat   2700
tcatacgaag aaataaatga tcagacaaac gataatataa cagcaagatt agataggatt   2760
gatgaaaaat taagtgaaat actaggaatg cttcacacat tagtagtggc aagtgcagga   2820
cctacatctg ctcgggatgg tataagagat gccatggttg gtttaagaga agaaatgata   2880
gaaaaaatca gaactgaagc attaatgacc aatgacagat tagaagctat ggcaagactc   2940
aggaatgagg aaagtgaaaa gatggcaaaa gacacatcag atgaagtgtc tctcaatcca   3000
acatcagaga aattgaacaa cctattggaa gggaatgata gtgacaatga tctatcactt   3060
gaagatttct gattagttac caatcttcac atcaacacac aataccaaca gaagaccaac   3120
aaactaacca acccaatcat ccaaccaaac atccatccgc caatcagcca aacagccaac   3180
aaaacaacca gccaatccaa aactaaccac ccggaaaaaa tctataatat agttacaaaa   3240
aaaggaaagg gtggggcaaa tatggaaaca tacgtgaaca agcttcacga aggctccaca   3300
tacacagctg ctgttcaata caatgtctta gaaaaagacg atgaccctgc atcacttaca   3360
atatgggtgc ccatgttcca atcatctatg ccagcagatt tacttataaa agaactagct   3420
aatgtcaaca tactagtgaa acaaatatcc acacccaagg gaccttcact aagagtcatg   3480
ataaactcaa gaagtgcagt gctagcacaa atgcccagca aatttaccat atgcgctaat   3540
gtgtccttgg atgaaagaag caaactagca tatgatgtaa ccacaccctg tgaaatcaag   3600
gcatgtagtc taacatgcct aaaatcaaaa aatatgttga ctacagttaa agatctcact   3660
atgaagacac tcaaccctac acatgatatt attgctttat gtgaatttga aaacatagta   3720
acatcaaaaa aagtcataat accaacatac ctaagatcca tcagtgtcag aaataaagat   3780
ctgaacacac ttgaaaatat aacaaccact gaattcaaaa atgctatcac aaatgcaaaa   3840
atcatccctt actcaggatt actattagtc atcacagtga ctgacaacaa aggagcattc   3900
aaatacataa agccacaaag tcaattcata gtagatcttg gagcttacct agaaaaagaa   3960
agtatatatt atgttaccac aaattggaag cacacagcta cacgatttgc aatcaaaccc   4020
atggaagatt aacctttttc ctctacatca gtgtgttaat tcatacaaac tttctaccta   4080
cattcttcac ttcaccatca caatcacaaa cactctgtgg ttcaaccaat caaacaaaac   4140
ttatctgaag tcccagatca tcccaagtca ttgtttatca gatctagtac tcaaataagt   4200
taataaaaaa tatacacatg ggcaaataa tcattggagg aaatccaact aatcacaata   4260
tctgttaaca tagacaagtc cacacaccat acagaatcaa ccaatggaaa atacatccat   4320
```

-continued

```
aacaatagaa ttctcaagca aattctggcc ttactttaca ctaatacaca tgatcacaac   4380
aataatctct ttgctaatca taatctccat catgattgca atactaaaca aactttgtga   4440
atataacgta ttccataaca aaacctttga gttaccaaga gctcgagtca acacatagca   4500
ttcatcaatc caacagccca aaacagtaac cttgcattta aaaatgaaca acccctacct   4560
ctttacaaca cctcattaac atcccaccat gcaaaccact atccatacta taaagtagtt   4620
aattaaaaat agtcataaca atgaactagg atatcaagac taacaataac attggggcaa   4680
atgcaaacat gtccaaaaac aaggaccaac gcaccgctaa gacattagaa aggacctggg   4740
acactctcaa tcatttatta ttcatatcat cgtgcttata taagttaaat cttaaatctg   4800
tagcacaaat cacattatcc attctggcaa tgataatctc aacttcactt ataattgcag   4860
ccatcatatt catagcctcg gcaaaccaca aagtcacacc aacaactgca atcatacaag   4920
atgcaacaag ccagatcaag aacacaaccc caacatacct cacccagaat cctcagcttg   4980
gaatcagtcc ctctaatccg tctgaaatta catcacaaat caccaccata ctagcttcaa   5040
caacaccagg agtcaagtca accctgcaat ccacaacagt caagaccaaa aacacaacaa   5100
caactcaaac acaacccagc aagcccacca caaaacaacg ccaaaacaaa ccaccaagca   5160
aacccaataa tgattttcac tttgaagtgt tcaactttgt accctgcagc atatgcagca   5220
acaatccaac ctgctgggct atctgcaaaa gaataccaaa caaaaaacca ggaaagaaaa   5280
ccactaccaa gcccacaaaa aaaccaaccc tcaagacaac caaaaaagat cccaaacctc   5340
aaaccactaa atcaaaggaa gtacccacca ccaagcccac agaagagcca accatcaaca   5400
ccaccaaaac aaacatcata actacactac tcacctccaa caccacagga aatccagaac   5460
tcacaagtca aatggaaacc ttccactcaa cttcctccga aggcaatcca agcccttctc   5520
aagtctctac aacatccgag tacccatcac aaccttcatc tccacccaac acaccacgcc   5580
agtagttact taaaaacata ttatcacaaa aggccttgac caacttaaac agaatcaaaa   5640
taaactctgg ggcaaataac aatggagttg ctaatcctca aagcaaatgc aattaccaca   5700
atcctcactg cagtcacatt ttgttttgct tctggtcaaa acatcactga agaattttat   5760
caatcaacat gcagtgcagt tagcaaaggc tatcttagtg ctctgagaac tggttggtat   5820
accagtgtta taactataga attaagtaat atcaagaaaa ataagtgtaa tggaacagat   5880
gctaaggtaa aattgataaa acaagaatta gataaatata aaaatgctgt aacagaattg   5940
cagttgctca tgcaaagcac acaagcaaca aacaatcgag ccagaagaga actaccaagg   6000
tttatgaatt atacactcaa caatgccaaa aaaaccaatg taacattaag caagaaaagg   6060
aaaagaagat ttcttggttt tttgttaggt gttggatctg caatcgccag tggcgttgct   6120
gtatctaagg tcctgcacct agaaggggaa gtgaacaaga tcaaaagtgc tctactatcc   6180
acaaacaagg ctgtagtcag cttatcaaat ggagttagtg ttttaaccag caaagtgtta   6240
gacctcaaaa actatataga taaacaattg ttacctattg tgaacaagca aagctgcagc   6300
atatcaaata tagaaactgt gatagagttc caacaaaaga acaacagact actagagatt   6360
accagggaat ttagtgttaa tgcaggcgta actacacctg taagcactta catgttaact   6420
aatagtgaat tattgtcatt aatcaatgat atgcctataa caaatgatca gaaaaagtta   6480
atgtccaaca atgttcaaat agttagacag caaagttact ctatcatgtc cataataaaa   6540
gaggaagtct tagcatatgt agtacaatta ccactatatg gtgttataga tacaccctgt   6600
tggaaactac acacatcccc tctatgtaca accaacacaa aagaagggtc caacatctgt   6660
```

-continued

```
ttaacaagaa ctgacagagg atggtactgt gacaatgcag gatcagtatc tttcttccca   6720
caagctgaaa catgtaaagt tcaatcaaat cgagtatttt gtgacacaat gaacagttta   6780
acattaccaa gtgaagtaaa tctctgcaat gttgacatat tcaaccccaa atatgattgt   6840
aaaattatga cttcaaaaac agatgtaagc agctccgtta tcacatctct aggagccatt   6900
gtgtcatgct atggcaaaac taaatgtaca gcatccaata aaaatcgtgg aatcataaag   6960
acattttcta acgggtgcga ttatgtatca aataaagggg tggacactgt gtctgtaggt   7020
aacacattat attatgtaaa taagcaagaa ggtaaaagtc tctatgtaaa aggtgaacca   7080
ataataaatt tctatgaccc attagtattc ccctctgatg aatttgatgc atcaatatct   7140
caagtcaacg agaagattaa ccagagccta gcatttattc gtaaatccga tgaattatta   7200
cataatgtaa atgctggtaa atccaccaca aatatcatga taactactat aattatagtg   7260
attatagtaa tattgttatc attaattgct gttggactgc tcttatactg taaggccaga   7320
agcacaccag tcacactaag caaagatcaa ctgagtggta taaataatat tgcatttagt   7380
aactaaataa aaatagcacc taatcatgtt cttacaatgg tttactatct gctcatagac   7440
aacccatctg tcattggatt ttcttaaaat ctgaacttca tcgaaactct catctataaa   7500
ccatctcact tacactattt aagtagattc ctagtttata gttatataaa acacaattgc   7560
atgccagatt aacttaccat ctgtaaaaat gaaaactggg gcaaatatgt cacgaaggaa   7620
tccttgcaaa tttgaaattc gaggtcattg cttaaatggt aagaggtgtc attttagtca   7680
taattatttt gaatggccac cccatgcact gcttgtaaga caaaacttta tgttaaacag   7740
aatacttaag tctatggata aaagtataga taccttatca gaaataagtg gagctgcaga   7800
gttggacaga acagaagagt atgctcttgg tgtagttgga gtgctagaga gttatatagg   7860
atcaataaac aatataacta aacaatcagc atgtgttgcc atgagcaaac tcctcactga   7920
actcaatagt gatgatatca aaaagctgag ggacaatgaa gagctaaatt cacccaagat   7980
aagagtgtac aatactgtca tatcatatat tgaaagcaac aggaaaaaca ataaacaaac   8040
tatccatctg ttaaaaagat tgccagcaga cgtattgaag aaaaccatca aaaacacatt   8100
ggatatccat aagagcataa ccatcaacaa cccaaaagaa tcaactgtta gtgatacaaa   8160
tgaccatgcc aaaaataatg atactacctg acaaatatcc ttgtagtata acttccatac   8220
taataacaag tagatgtaga gttactatgt ataatcaaaa gaacacacta tatttcaatc   8280
aaaacaaccc aaataaccat atgtactcac cgaatcaaac attcaatgaa atccattgga   8340
cctctcaaga attgattgac acaattcaaa attttctaca acatctaggt attattgagg   8400
atatatatac aatatatata ttagtgtcat aacactcaat tctaacactc accacatcgt   8460
tacattatta attcaaacaa ttcaagttgt gggacaaaat ggatcccatt attaatggaa   8520
attctgctaa tgtttatcta accgatagtt atttaaaagg tgttatctct ttctcagagt   8580
gtaatgcttt aggaagttac atattcaatg gtccttatct caaaaatgat tataccaact   8640
taattagtag acaaaatcca ttaatagaac acatgaatct aaagaaacta aatataacac   8700
agtccttaat atctaagtat cataaaggtg aaataaaatt agaagaacct acttattttc   8760
agtcattact tatgacatac aagagtatga cctcgtcaga acagattgct accactaatt   8820
tacttaaaaa gataataaga agagctatag aaataagtga tgtcaaagtc tatgctatat   8880
tgaataaact agggcttaaa gaaaaggaca agattaaatc caacaatgga caagatgaag   8940
acaactcagt tattacgacc ataatcaaag atgatatact ttcagctgtt aaagataatc   9000
aatctcatct taaagcagac aaaaatcact ctacaaaaca aaaagacaca atcaaaacaa   9060
```

cactcttgaa gaaattgatg tgttcaatgc aacatcctcc atcatggtta atacattggt 9120
ttaacttata cacaaaatta aacaacatat taacacagta tcgatcaaat gaggtaaaaa 9180
accatgggtt tacattgata gataatcaaa ctcttagtgg atttcaattt attttgaacc 9240
aatatggttg tatagtttat cataaggaac tcaaaagaat tactgtgaca acctataatc 9300
aattcttgac atggaaagat attagcctta gtagattaaa tgtttgttta attacatgga 9360
ttagtaactg cttgaacaca ttaaataaaa gcttaggctt aagatgcgga ttcaataatg 9420
ttatcttgac acaactattc ctttatggag attgtatact aaagctattt cacaatgagg 9480
ggttctacat aataaaagag gtagagggat ttattatgtc tctaatttta aatataacag 9540
aagaagatca attcagaaaa cgattttata atagtatgct caacaacatc acagatgctg 9600
ctaataaagc tcagaaaaat ctgctatcaa gagtatgtca tacattatta gataagacag 9660
tgtccgataa tataataaat ggcagatgga taattctatt aagtaagttc cttaaattaa 9720
ttaagcttgc aggtgacaat aaccttaaca atctgagtga actatatttt ttgttcagaa 9780
tatttggaca cccaatggta gatgaaagac aagccatgga tgctgttaaa attaattgca 9840
atgagaccaa attttacttg ttaagcagtc tgagtatgtt aagaggtgcc tttatatata 9900
gaattataaa agggtttgta aataattaca acagatggcc tactttaaga aatgctattg 9960
ttttaccctt aagatggtta acttactata aactaaacac ttatccttct ttgttggaac 10020
ttacagaaag agatttgatt gtgttatcag gactacgttt ctatcgtgag tttcggttgc 10080
ctaaaaaagt ggatcttgaa atgattataa atgataaagc tatatcacct cctaaaaatt 10140
tgatatggac tagtttccct agaaattaca tgccatcaca catacaaaac tatatagaac 10200
atgaaaaatt aaaatttttcc gagagtgata aatcaagaag agtattagag tattatttaa 10260
gagataacaa attcaatgaa tgtgatttat acaactgtgt agttaatcaa agttatctca 10320
acaaccctaa tcatgtggta tcattgacag gcaaagaaag agaactcagt gtaggtagaa 10380
tgtttgcaat gcaaccggga atgttcagac aggttcaaat attggcagag aaaatgatag 10440
ctgaaaacat tttacaattc tttcctgaaa gtcttacaag atatggtgat ctagaactac 10500
aaaaaatatt agaactgaaa gcaggaataa gtaacaaatc aaatcgctac aatgataatt 10560
acaacaatta cattagtaag tgctctatca tcacagatct cagcaaattc aatcaagcat 10620
ttcgatatga aacgtcatgt atttgtagtg atgtgctgga tgaactgcat ggtgtacaat 10680
ctctattttc ctggttacat ttaactattc ctcatgtcac aataatatgc acatataggc 10740
atgcaccccc ctatatagga gatcatattg tagatcttaa caatgtagat gaacaaagtg 10800
gattatatag atatcacatg ggtggcatcg aagggtggtg tcaaaaacta tggaccatag 10860
aagctatatc actattggat ctaatatctc tcaaagggaa attctcaatt actgctttaa 10920
ttaatggtga caatcaatca atagatataa gcaaaccaat cagactcatg gaaggtcaaa 10980
ctcatgctca agcagattat ttgctagcat taaatagcct taaattactg tataaagagt 11040
atgcaggcat aggccacaaa ttaaaaggaa ctgagactta tatatcacga gatatgcaat 11100
ttatgagtaa aacaattcaa cataacggtg tatattaccc agctagtata aagaaagtcc 11160
taagagtggg accgtggata aacactatac ttgatgattt caaagtgagt ctagaatcta 11220
taggtagttt gacacaagaa ttagaatata gaggtgaaag tctattatgc agtttaatat 11280
ttagaaatgt atggttatat aatcagattg ctctacaatt aaaaaatcat gcattatgta 11340
acaataaact atatttggac atattaaagg ttctgaaaca cttaaaaacc ttttttaatc 11400

-continued

```
ttgataatat tgatacagca ttaacattgt atatgaattt acccatgtta tttggtggtg  11460
gtgatcccaa cttgttatat cgaagtttct atagaagaac tcctgacttc ctcacagagg  11520
ctatagttca ctctgtgttc atacttagtt attatacaaa ccatgactta aaagataaac  11580
ttcaagatct gtcagatgat agattgaata agttcttaac atgcataatc acgtttgaca  11640
aaaaccctaa tgctgaattc gtaacattga tgagagatcc tcaagcttta gggtctgaga  11700
gacaagctaa aattactagc gaaatcaata gactggcagt tacagaggtt ttgagtacag  11760
ctccaaacaa aatattctcc aaaagtgcac aacattatac tactacagag atagatctaa  11820
atgatattat gcaaaatata gaacctacat atcctcatgg gctaagagtt gtttatgaaa  11880
gtttaccctt ttataaagca gagaaaatag taaatcttat atcaggtaca aaatctataa  11940
ctaacatact ggaaaaaact tctgccatag acttaacaga tattgataga gccactgaga  12000
tgatgaggaa aaacataact ttgcttataa ggatacttcc attggattgt aacagagata  12060
aaagagagat attgagtatg gaaaacctaa gtattactga attaagcaaa tatgttaggg  12120
aaagatcttg gtctttatcc aatatagttg gtgttacatc acccagtatc atgtatacaa  12180
tggacatcaa atatactaca agcactatat ctagtggcat aattatagag aaatataatg  12240
ttaacagttt aacacgtggt gagagaggac ccactaaacc atgggttggt tcatctacac  12300
aagagaaaaa aacaatgcca gtttataata gacaagtctt aaccaaaaaa cagagagatc  12360
aaatagatct attagcaaaa ttggattggg tgtatgcatc tatagataac aaggatgaat  12420
tcatggaaga actcagcata ggaacccttg ggttaacata tgaaaaggcc aagaaattat  12480
ttccacaata tttaagtgtc aattatttgc atcgccttac agtcagtagt agaccatgtg  12540
aattccctgc atcaatacca gcttatagaa caacaaatta tcactttgac actagcccta  12600
ttaatcgcat attaacagaa aagtatggtg atgaagatat tgacatagta ttccaaaact  12660
gtataagctt tggccttagt ttaatgtcag tagtagaaca atttactaat gtatgtccta  12720
acagaattat tctcatacct aagcttaatg agatacattt gatgaaacct cccatattca  12780
caggtgatgt tgatattcac aagttaaaac aagtgataca aaaacagcat atgtttttac  12840
cagacaaaat aagtttgact caatatgtgg aattattctt aagtaataaa acactcaaat  12900
ctggatctca tgttaattct aatttaatat tggcacataa aatatctgac tattttcata  12960
atacttacat tttaagtact aatttagctg gacattggat tctgattata caacttatga  13020
aagattctaa aggtattttt gaaaaagatt ggggagaggg atatataact gatcatatgt  13080
ttattaattt gaaagttttc ttcaatgctt ataagaccta tctcttgtgt tttcataaag  13140
gttatggcaa agcaaagctg gagtgtgata tgaacacttc agatcttcta tgtgtattgg  13200
aattaataga cagtagttat tggaagtcta tgtctaaggt atttttagaa caaaaagtta  13260
tcaaatacat tcttagccaa gatgcaagtt tacatagagt aaaaggatgt catagcttca  13320
aattatggtt tcttaaacgt cttaatgtag cagaattcac agtttgccct tgggttgtta  13380
acatagatta tcatccaaca catatgaaag caatattaac ttatatagat cttgttagaa  13440
tgggattgat aaatatagat agaatacaca ttaaaaataa acacaaattc aatgatgaat  13500
tttatacttc taatctcttc tacattaatt ataacttctc agataatact catctattaa  13560
ctaaacatat aaggattgct aattctgaat tagaaaataa ttacaacaaa ttatatcatc  13620
ctacaccaga aaccctagag aatatactag ccaatccgat taaaagtaat gacaaaaaga  13680
cactgaatga ctattgtata ggtaaaaatg ttgactcaat aatgttacca ttgttatcta  13740
ataagaagct tattaaatcg tctgcaatga ttagaaccaa ttacagcaaa caagatttgt  13800
```

```
ataatttatt ccctatggtt gtgattgata gaattataga tcattcaggc aatacagcca  13860

aatccaacca actttacact actacttccc accaaatatc cttagtgcac aatagcacat  13920

cactttactg catgcttcct tggcatcata ttaatagatt caattttgta tttagttcta  13980

caggttgtaa aattagtata gagtatattt taaaagatct taaaattaaa gatcccaatt  14040

gtatagcatt cataggtgaa ggagcaggga atttattatt gcgtacagta gtggaacttc  14100

atcctgacat aagatatatt tacagaagtc tgaaagattg caatgatcat agtttaccta  14160

ttgagttttt aaggctgtac aatggacata tcaacattga ttatggtgaa aatttgacca  14220

ttcctgctac agatgcaacc aacaacattc attggtctta tttacatata aagtttgctg  14280

aacctatcag tctttttgtc tgtgatgccg aattgtctgt aacagtcaac tggagtaaaa  14340

ttataataga atggagcaag catgtaagaa agtgcaagta ctgttcctca gttaataaat  14400

gtatgttaat agtaaaatat catgctcaag atgatattga tttcaaatta gacaatataa  14460

ctatattaaa aacttatgta tgcttaggca gtaagttaaa gggatcggag gtttacttag  14520

tccttacaat aggtcctgcg aatatattcc cagtatttaa tgtagtacaa aatgctaaat  14580

tgatactatc aagaaccaaa aatttcatca tgcctaagaa agctgataaa gagtctattg  14640

atgcaaatat taaaagtttg atacccttc tttgttaccc tataacaaaa aaaggaatta  14700

atactgcatt gtcaaaacta aagagtgttg ttagtggaga tatactatca tattctatag  14760

ctggacgtaa tgaagttttc agcaataaac ttataaatca taagcatatg aacatcttaa  14820

aatggttcaa tcatgtttta aatttcagat caacagaact aaactataac catttatata  14880

tggtagaatc tacatatcct tacctaagtg aattgttaaa cagcttgaca accaatgaac  14940

ttaaaaaact gattaaaatc acaggtagtc tgttatacaa ctttcataat gaataatgaa  15000

taaagatctt ataataaaaa ttcccatagc tatacactaa cactgtattc aattatagtt  15060

attaaaaatt aaaaatcata taattttta aataactttt agtgaactaa tcctaaagtt  15120

atcattttaa tcttggagga ataaatttaa accctaatct aattggttta tatgtgtatt  15180

aactaaatta cgagatatta gtttttgaca cttttttct cgt                      15223
```

<210> SEQ ID NO 2
<211> LENGTH: 14982
<212> TYPE: DNA
<213> ORGANISM: Artificial Sequence
<220> FEATURE:
<223> OTHER INFORMATION: recombinant respiratory syncytial virus sequence

<400> SEQUENCE: 2

```
acgggaaaaa atgcgtacaa caaacttgca taaaccaaaa aaatggggca aataagaatt     60

tgataagtac cacttaaatt taactccctt ggttagagat gggcagcaat tcattgagta    120

tgataaaagt tagattacaa aatttgtttg acaatgatga agtagcattg ttaaaaataa    180

catgctatac tgataaatta atacatttaa ctaatgcttt ggctaaggca gtgatacata    240

caatcaaatt gaatggcatt gtgtttgtgc atgttattac aagtagtgat atttgcccta    300

ataataatat tgtagtaaaa tccaatttca caacaatgcc agtactacaa aatggaggtt    360

atatatggga aatgatggaa ttaacacatt gctctcaacc taatggtcta ctagatgaca    420

attgtgaaat taaattctcc aaaaaactaa gtgattcaac aatgaccaat tatatgaatc    480

aattatctga attacttgga tttgatctta atccataaat tataattaat atcaactagc    540

aaatcaatgt cactaacacc attagttaat ataaaactta acagaagaca aaaatggggc    600
```

-continued

```
aaataaatca attcagccaa cccaaccatg gacacaaccc acaatgataa tacaccacaa    660
agactgatga tcacagacat gagaccgttg tcacttgaga ccataataac atcactaacc    720
agagacatca taacacacaa atttatatac ttgataaatc atgaatgcat agtgagaaaa    780
cttgatgaaa gacaggccac atttacattc ctggtcaact atgaaatgaa actattacac    840
aaagtaggaa gcactaaata taaaaaatat actgaataca acacaaaata tggcactttc    900
cctatgccaa tattcatcaa tcatgatggg ttcttagaat gcattggcat taagcctaca    960
aagcatactc ccataatata caagtatgat ctcaatccat aaatttcaac acaatattca   1020
cacaatctaa aacaacaact ctatgcataa ctatactcca tagtccagat ggagcctgaa   1080
aattatagta atttaaaact taaggagaga tataagatag aagatggggc aaatacaacc   1140
atggctctta gcaaagtcaa gttgaatgat acactcaaca aagatcaact tctgtcatcc   1200
agcaaataca ccatccaacg gagcacagga gatagtattg atactcctaa ttatgatgtg   1260
cagaaacaca tcaataagtt atgtggcatg ttattaatca cagaagatgc taatcataaa   1320
ttcactgggt taataggtat gttatatgcg atgtctaggt taggaagaga agacaccata   1380
aaaatactca gagatgcggg atatcatgta aaagcaaatg gagtagatgt aacaacacat   1440
cgtcaagaca ttaatggaaa agaaatgaaa tttgaagtgt taacattggc aagcttaaca   1500
actgaaattc aaatcaacat tgagatagaa tctagaaaat cctacaaaaa aatgctaaaa   1560
gaaatgggag aggtagctcc agaatacagg catgactctc ctgattgtgg gatgataata   1620
ttatgtatag cagcattagt aataactaaa ttagcagcag gggacagatc tggtcttaca   1680
gccgtgatta ggagagctaa taatgtccta aaaaatgaaa tgaaacgtta caaaggctta   1740
ctacccaagg acatagccaa cagcttctat gaagtgtttg aaaaacatcc ccactttata   1800
gatgtttttg ttcattttgg tatagcacaa tcttctacca gaggtggcag tagagttgaa   1860
gggatttttg caggattgtt tatgaatgcc tatggtgcag ggcaagtgat gttacggtgg   1920
ggagtcttag caaaatcggt taaaaatatt atgttaggac atgctagtgt gcaagcagaa   1980
atggaacaag ttgttgaggt ttatgaatat gcccaaaaat tgggtggtga agcaggattc   2040
taccatatat tgaacaaccc aaaagcatca ttattatctt tgactcaatt tcctcacttc   2100
tccagtgtag tattaggcaa tgctgctggc ctaggcataa tgggagagta cagaggtaca   2160
ccgaggaatc aagatctata tgatgcagca aaggcatatg ctgaacaact caaagaaaat   2220
ggtgtgatta actacagtgt actagacttg acagcagaag aactagaggc tatcaaacat   2280
cagcttaatc caaaagataa tgatgtagag ctttgagtta ataaaaaatg gggcaaataa   2340
atcatcatgg aaaagtttgc tcctgaattc catggagaag atgcaaacaa cagggctact   2400
aaattcctag aatcaataaa gggcaaattc acatcaccca aagatcccaa gaaaaaagat   2460
agtatcatat ctgtcaactc aatagatata gaagtaacca aagaaagccc tataacatca   2520
aattcaacta ttatcaaccc aacaaatgag acagatgata ctgcagggaa caagcccaat   2580
tatcaaagaa aacctctagt aagtttcaaa gaagacccta caccaagtga taatcccttt   2640
tctaaactat acaaagaaac catagaaaca tttgataaca atgaagaaga atccagctat   2700
tcatacgaag aaataaatga tcagacaaac gataatataa cagcaagatt agataggatt   2760
gatgaaaaat taagtgaaat actaggaatg cttcacacat tagtagtggc aagtgcagga   2820
cctacatctg ctcgggatgg tataagagat gccatggttg gtttaagaga agaaatgata   2880
gaaaaaatca gaactgaagc attaatgacc aatgacagat tagaagctat ggcaagactc   2940
```

aggaatgagg aaagtgaaaa gatggcaaaa gacacatcag atgaagtgtc tctcaatcca 3000
acatcagaga aattgaacaa cctattggaa gggaatgata gtgacaatga tctatcactt 3060
gaagatttct gattagttac caatcttcac atcaacacac aataccaaca gaagaccaac 3120
aaactaacca acccaatcat ccaaccaaac atccatccgc caatcagcca aacagccaac 3180
aaaacaacca gccaatccaa aactaaccac ccggaaaaaa tctataatat agttacaaaa 3240
aaaggaaagg gtggggcaaa tatggaaaca tacgtgaaca agcttcacga aggctccaca 3300
tacacagctg ctgttcaata caatgtctta gaaaaagacg atgaccctgc atcacttaca 3360
atatgggtgc ccatgttcca atcatctatg ccagcagatt tacttataaa agaactagct 3420
aatgtcaaca tactagtgaa acaaatatcc acacccaagg gaccttcact aagagtcatg 3480
ataaactcaa gaagtgcagt gctagcacaa atgcccagca aatttaccat atgcgctaat 3540
gtgtccttgg atgaaagaag caaactagca tatgatgtaa ccacaccctg tgaaatcaag 3600
gcatgtagtc taacatgcct aaaatcaaaa aatatgttga ctacagttaa agatctcact 3660
atgaagacac tcaaccctac acatgatatt attgctttat gtgaatttga aaacatagta 3720
acatcaaaaa aagtcataat accaacatac ctaagatcca tcagtgtcag aaataaagat 3780
ctgaacacac ttgaaaatat aacaaccact gaattcaaaa atgctatcac aaatgcaaaa 3840
atcatccctt actcaggatt actattagtc atcacagtga ctgacaacaa aggagcattc 3900
aaatacataa agccacaaag tcaattcata gtagatcttg gagcttacct agaaaaagaa 3960
agtatatatt atgttaccac aaattggaag cacacagcta cacgatttgc aatcaaaccc 4020
atggaagatt aacctttttc ctctacatca gtgtgttaat tcatacaaac tttctaccta 4080
cattcttcac ttcaccatca caatcacaaa cactctgtgg ttcaaccaat caaacaaaac 4140
ttatctgaag tcccagatca tcccaagtca ttgtttatca gatctagtac tcaaataagt 4200
taataaaaaa tatacacatg gggcaaataa tcattggagg aaatccaact aatcacaata 4260
tctgttaaca tagacaagtc cacacaccat acagaatcaa ccaatggaaa atacatccat 4320
aacaatagaa ttctcaagca aattctggcc ttactttaca ctaatacaca tgatcacaac 4380
aataatctct ttgctaatca taatctccat catgattgca atactaaaca aactttgtga 4440
atataacgta ttccataaca aaacctttga gttaccaaga gctcgagtca acacatagca 4500
ttcatcaatc caacagccca aaacagtaac cttgcattta aaaatgaaca accccctacct 4560 ctttacaaca cctcattaac atcccaccat gcaaaccact atccatacta taaagtagtt 4620
aattaaaaat agtcataaca atgaactagg atatcaagac taacaataac attggggcaa 4680
atgcaaacat gtccaaaaac aaggaccaac gcaccgctaa gacattagaa aggacctggg 4740
acactctcaa tcatttatta ttcatatcat cgtgcttata taagttaaat cttaaatctg 4800
tagcacaaat cacattatcc attctggcaa tgataatctc aacttcactt ataattgcag 4860
ccatcatatt catagcctcg gcaaaccaca aagtcacacc aacaactgca atcatacaag 4920
atgcaacaag ccagatcaag aacacaaccc caacatacct cacccagaat cctcagcttg 4980
gaatcagtcc ctctaatccg tctgaaatta catcacaaat caccaccata ctagcttcaa 5040
caacaccagg agtcaagtca accctgcaat ccacaacagt caagaccaaa aacacaacaa 5100
caactcaaac acaacccagc aagcccacca caaaacaacg ccaaaacaaa ccaccaagca 5160
aacccaataa tgattttcac tttgaagtgt tcaactttgt accctgcagc atatgcagca 5220
acaatccaac ctgctgggct atctgcaaaa gaataccaaa caaaaaacca ggaaagaaaa 5280
ccactaccaa gcccacaaaa aaaccaaccc tcaagacaac caaaaaagat cccaaacctc 5340

```
aaaccactaa atcaaaggaa gtacccacca ccaagcccac agaagagcca accatcaaca   5400
ccaccaaaac aaacatcata actacactac tcacctccaa caccacagga aatccagaac   5460
tcacaagtca aatggaaacc ttccactcaa cttcctccga aggcaatcca agcccttctc   5520
aagtctctac aacatccgag tacccatcac aaccttcatc tccacccaac acaccacgcc   5580
agtagttact taaaaacata ttatcacaaa aggccttgac caacttaaac agaatcaaaa   5640
taaactctgg ggcaaataac aatggagttg ctaatcctca aagcaaatgc aattaccaca   5700
atcctcactg cagtcacatt ttgttttgct tctggtcaaa acatcactga agaattttat   5760
caatcaacat gcagtgcagt tagcaaaggc tatcttagtg ctctgagaac tggttggtat   5820
accagtgtta taactataga attaagtaat atcaagaaaa ataagtgtaa tggaacagat   5880
gctaaggtaa aattgataaa acaagaatta gataaatata aaaatgctgt aacagaattg   5940
cagttgctca tgcaaagcac acaagcaaca aacaatcgag ccagaagaga actaccaagg   6000
tttatgaatt atacactcaa caatgccaaa aaaaccaatg taacattaag caagaaaagg   6060
aaaagaagat ttcttggttt tttgttaggt gttggatctg caatcgccag tggcgttgct   6120
gtatctaagg tcctgcacct agaaggggaa gtgaacaaga tcaaaagtgc tctactatcc   6180
acaaacaagg ctgtagtcag cttatcaaat ggagttagtg ttttaaccag caaagtgtta   6240
gacctcaaaa actatataga taaacaattg ttacctattg tgaacaagca aagctgcagc   6300
atatcaaata tagaaactgt gatagagttc caacaaaaga acaacagact actagagatt   6360
accagggaat ttagtgttaa tgcaggcgta actacacctg taagcactta catgttaact   6420
aatagtgaat tattgtcatt aatcaatgat atgcctataa caaatgatca gaaaaagtta   6480
atgtccaaca atgttcaaat agttagacag caaagttact ctatcatgtc cataataaaa   6540
gaggaagtct tagcatatgt agtacaatta ccactatatg gtgttataga tacaccctgt   6600
tggaaactac acacatcccc tctatgtaca accaacacaa aagaagggtc caacatctgt   6660
ttaacaagaa ctgacagagg atggtactgt gacaatgcag gatcagtatc tttcttccca   6720
caagctgaaa catgtaaagt tcaatcaaat cgagtatttt gtgacacaat gaacagttta   6780
acattaccaa gtgaagtaaa tctctgcaat gttgacatat tcaaccccaa atatgattgt   6840
aaaattatga cttcaaaaac agatgtaagc agctccgtta tcacatctct aggagccatt   6900
gtgtcatgct atggcaaaac taaatgtaca gcatccaata aaaatcgtgg aatcataaag   6960
acattttcta acgggtgcga ttatgtatca aataaagggg tggacactgt gtctgtaggt   7020
aacacattat attatgtaaa taagcaagaa ggtaaaagtc tctatgtaaa aggtgaacca   7080
ataataaatt tctatgaccc attagtattc ccctctgatg aatttgatgc atcaatatct   7140
caagtcaacg agaagattaa ccagagccta gcatttattc gtaaatccga tgaattatta   7200
cataatgtaa atgctggtaa atccaccaca aatatcatga taactactat aattatagtg   7260
attatagtaa tattgttatc attaattgct gttggactgc tcttatactg taaggccaga   7320
agcacaccag tcacactaag caaagatcaa ctgagtggta taaataatat tgcatttagt   7380
aactaaataa aaatagcacc taatcatgtt cttacaatgg tttactatct gctcatagac   7440
aacccatctg tcattggatt ttcttaaaat ctgaacttca tcgaaactct catctataaa   7500
ccatctcact tacactattt aagtagattc ctagtttata gttatataaa acacaattgc   7560
atgccagatt aacttaccat ctgtaaaaat gaaaactggg gcaaatatgt cacgaaggaa   7620
tccttgcaaa tttgaaattc gaggtcattg cttaaatggt aagaggtgtc attttagtca   7680
```

```
taattatttt gaatggccac cccatgcact gcttgtaaga caaaacttta tgttaaacag   7740
aatacttaag tctatggata aaagtataga taccttatca gaaataagtg gagctgcaga   7800
gttggacaga acagaagagt atgctcttgg tgtagttgga gtgctagaga gttatatagg   7860
atcaataaac aatataacta aacaatcagc atgtgttgcc atgagcaaac tcctcactga   7920
actcaatagt gatgatatca aaaagctgag ggacaatgaa gagctaaatt cacccaagat   7980
aagagtgtac aatactgtca tatcatatat tgaaagcaac aggaaaaaca ataaacaaac   8040
tatccatctg ttaaaaagat tgccagcaga cgtattgaag aaaaccatca aaaacacatt   8100
ggatatccat aagagcataa ccatcaacaa cccaaaagaa tcaactgtta gtgatacaaa   8160
cgaccacgcc aaaaataacg atactaccta acactcaatt ctaacactca ccacatcgtt   8220
acattattaa ttcaaacaat tcaagttgtg ggacaaaatg gatcccatta ttaatggaaa   8280
ttctgctaat gtttatctaa ccgatagtta tttaaaaggt gttatctctt tctcagagtg   8340
taatgcttta ggaagttaca tattcaatgg tccttatctc aaaaatgatt ataccaactt   8400
aattagtaga caaaatccat taatagaaca catgaatcta aagaaactaa atataacaca   8460
gtccttaata tctaagtatc ataaaggtga aataaaatta gaagaaccta cttattttca   8520
gtcattactt atgacataca agagtatgac ctcgtcagaa cagattgcta ccactaattt   8580
acttaaaaag ataataagaa gagctataga aataagtgat gtcaaagtct atgctatatt   8640
gaataaacta gggcttaaag aaaaggacaa gattaaatcc aacaatggac aagatgaaga   8700
caactcagtt attacgacca taatcaaaga tgatatactt tcagctgtta aagataatca   8760
atctcatctt aaagcagaca aaaatcactc tacaaaacaa aaagacacaa tcaaaacaac   8820
actcttgaag aaattgatgt gttcaatgca acatcctcca tcatggttaa tacattggtt   8880
taacttatac acaaaattaa acaacatatt aacacagtat cgatcaaatg aggtaaaaaa   8940
ccatgggttt acattgatag ataatcaaac tcttagtgga tttcaattta ttttgaacca   9000
atatggttgt atagtttatc ataaggaact caaaagaatt actgtgacaa cctataatca   9060
attcttgaca tggaaagata ttagccttag tagattaaat gtttgtttaa ttacatggat   9120
tagtaactgc ttgaacacat taaataaaag cttaggctta agatgcggat tcaataatgt   9180
tatcttgaca caactattcc tttatggaga ttgtatacta aagctatttc acaatgaggg   9240
gttctacata ataaaagagg tagagggatt tattatgtct ctaattttaa atataacaga   9300
agaagatcaa ttcagaaaac gattttataa tagtatgctc aacaacatca cagatgctgc   9360
taataaagct cagaaaaatc tgctatcaag agtatgtcat acattattag ataagacagt   9420
gtccgataat ataataaatg gcagatggat aattctatta agtaagttcc ttaaattaat   9480
taagcttgca ggtgacaata accttaacaa tctgagtgaa ctatattttt tgttcagaat   9540
atttggacac ccaatggtag atgaaagaca agccatggat gctgttaaaa ttaattgcaa   9600
tgagaccaaa ttttacttgt taagcagtct gagtatgtta agaggtgcct ttatatatag   9660
aattataaaa gggtttgtaa ataattacaa cagatggcct actttaagaa atgctattgt   9720
tttaccctta agatggttaa cttactataa actaaacact tatccttctt tgttggaact   9780
tacagaaaga gatttgattg tgttatcagg actacgtttc tatcgtgagt ttcggttgcc   9840
taaaaaagtg gatcttgaaa tgattataaa tgataaagct atatcacctc ctaaaaattt   9900
gatatggact agtttcccta gaaattacat gccatcacac atacaaaact atatagaaca   9960
tgaaaaatta aaattttccg agagtgataa atcaagaaga gtattagagt attatttaag  10020
agataacaaa ttcaatgaat gtgatttata caactgtgta gttaatcaaa gttatctcaa  10080
```

caaccctaat catgtggtat cattgacagg caaagaaaga gaactcagtg taggtagaat 10140
gtttgcaatg caaccgggaa tgttcagaca ggttcaaata ttggcagaga aaatgatagc 10200
tgaaaacatt ttacaattct ttcctgaaag tcttacaaga tatggtgatc tagaactaca 10260
aaaaatatta gaactgaaag caggaataag taacaaatca aatcgctaca atgataatta 10320
caacaattac attagtaagt gctctatcat cacagatctc agcaaattca atcaagcatt 10380
tcgatatgaa acgtcatgta tttgtagtga tgtgctggat gaactgcatg gtgtacaatc 10440
tctattttcc tggttacatt taactattcc tcatgtcaca ataatatgca catataggca 10500
tgcacccccc tatataggag atcatattgt agatcttaac aatgtagatg aacaaagtgg 10560
attatataga tatcacatgg gtggcatcga agggtggtgt caaaaactat ggaccataga 10620
agctatatca ctattggatc taatatctct caaagggaaa ttctcaatta ctgctttaat 10680
taatggtgac aatcaatcaa tagatataag caaaccaatc agactcatgg aaggtcaaac 10740
tcatgctcaa gcagattatt tgctagcatt aaatagcctt aaattactgt ataaagagta 10800
tgcaggcata ggccacaaat taaaaggaac tgagacttat atatcacgag atatgcaatt 10860
tatgagtaaa acaattcaac ataacggtgt atattaccca gctagtataa agaaagtcct 10920
aagagtggga ccgtggataa acactatact tgatgatttc aaagtgagtc tagaatctat 10980
aggtagtttg acacaagaat tagaatatag aggtgaaagt ctattatgca gtttaatatt 11040
tagaaatgta tggttatata atcagattgc tctacaatta aaaaatcatg cattatgtaa 11100
caataaacta tatttggaca tattaaaggt tctgaaacac ttaaaaacct tttttaatct 11160
tgataatatt gatacagcat taacattgta tatgaattta cccatgttat ttggtggtgg 11220
tgatcccaac ttgttatatc gaagtttcta tagaagaact cctgacttcc tcacagaggc 11280
tatagttcac tctgtgttca tacttagtta ttatacaaac catgacttaa aagataaact 11340
tcaagatctg tcagatgata gattgaataa gttcttaaca tgcataatca cgtttgacaa 11400
aaaccctaat gctgaattcg taacattgat gagagatcct caagctttag ggtctgagag 11460
acaagctaaa attactagcg aaatcaatag actggcagtt acagaggttt tgagtacagc 11520
tccaaacaaa atattctcca aaagtgcaca acattatact actacagaga tagatctaaa 11580
tgatattatg caaaatatag aacctacata tcctcatggg ctaagagttg tttatgaaag 11640
tttacccttt tataaagcag agaaaatagt aaatcttata tcaggtacaa aatctataac 11700
taacatactg gaaaaaactt ctgccataga cttaacagat attgatagag ccactgagat 11760
gatgaggaaa aacataactt tgcttataag gatacttcca ttggattgta acagagataa 11820
aagagagata ttgagtatgg aaaacctaag tattactgaa ttaagcaaat atgttaggga 11880
aagatcttgg tctttatcca atatagttgg tgttacatca cccagtatca tgtatacaat 11940
ggacatcaaa tatactacaa gcactatatc tagtggcata attatagaga aatataatgt 12000
taacagttta acacgtggtg agagaggacc cactaaacca tgggttggtt catctacaca 12060
agagaaaaaa acaatgccag tttataatag acaagtctta accaaaaaac agagagatca 12120
aatagatcta ttagcaaaat tggattgggt gtatgcatct atagataaca aggatgaatt 12180
catggaagaa ctcagcatag gaacccttgg gttaacatat gaaaaggcca agaaattatt 12240
tccacaatat ttaagtgtca attatttgca tcgccttaca gtcagtagta gaccatgtga 12300
attccctgca tcaataccag cttatagaac aacaaattat cactttgaca ctagccctat 12360
taatcgcata ttaacagaaa agtatggtga tgaagatatt gacatagtat tccaaaactg 12420

-continued

```
tataagcttt ggccttagtt taatgtcagt agtagaacaa tttactaatg tatgtcctaa  12480
cagaattatt ctcataccta agcttaatga gatacatttg atgaaacctc ccatattcac  12540
aggtgatgtt gatattcaca agttaaaaca agtgatacaa aaacagcata tgtttttacc  12600
agacaaaata agtttgactc aatatgtgga attattctta agtaataaaa cactcaaatc  12660
tggatctcat gttaattcta atttaatatt ggcacataaa atatctgact attttcataa  12720
tacttacatt ttaagtacta atttagctgg acattggatt ctgattatac aacttatgaa  12780
agattctaaa ggtatttttg aaaaagattg gggagaggga tatataactg atcatatgtt  12840
tattaatttg aaagtttctt tcaatgctta taagacctat ctcttgtgtt ttcataaagg  12900
ttatggcaaa gcaaagctgg agtgtgatat gaacacttca gatcttctat gtgtattgga  12960
attaatagac agtagttatt ggaagtctat gtctaaggta tttttagaac aaaaagttat  13020
caaatacatt cttagccaag atgcaagttt acatagagta aaaggatgtc atagcttcaa  13080
attatggttt cttaaacgtc ttaatgtagc agaattcaca gtttgccctt gggttgttaa  13140
catagattat catccaacac atatgaaagc aatattaact tatatagatc ttgttagaat  13200
gggattgata aatatagata gaatacacat taaaaataaa cacaaattca atgatgaatt  13260
ttatacttct aatctcttct acattaatta taacttctca gataatactc atctattaac  13320
taaacatata aggattgcta attctgaatt agaaaataat tacaacaaat tatatcatcc  13380
tacaccagaa accctagaga atatactagc caatccgatt aaaagtaatg acaaaaagac  13440
actgaatgac tattgtatag gtaaaaatgt tgactcaata atgttaccat tgttatctaa  13500
taagaagctt attaaatcgt ctgcaatgat tagaaccaat tacagcaaac aagatttgta  13560
taatttattc cctatggttg tgattgatag aattatagat cattcaggca atacagccaa  13620
atccaaccaa ctttacacta ctacttccca ccaaatatcc ttagtgcaca atagcacatc  13680
actttactgc atgcttcctt ggcatcatat taatagattc aattttgtat ttagttctac  13740
aggttgtaaa attagtatag agtatatttt aaaagatctt aaaattaaag atcccaattg  13800
tatagcattc ataggtgaag gagcagggaa tttattattg cgtacagtag tggaacttca  13860
tcctgacata agatatattt acagaagtct gaaagattgc aatgatcata gtttacctat  13920
tgagttttta aggctgtaca atggacatat caacattgat tatggtgaaa atttgaccat  13980
tcctgctaca gatgcaacca acaacattca ttggtcttat ttacatataa agtttgctga  14040
acctatcagt ctttttgtct gtgatgccga attgtctgta acagtcaact ggagtaaaat  14100
tataatagaa tggagcaagc atgtaagaaa gtgcaagtac tgttcctcag ttaataaatg  14160
tatgttaata gtaaaatatc atgctcaaga tgatattgat ttcaaattag acaatataac  14220
tatattaaaa acttatgtat gcttaggcag taagttaaag ggatcggagg tttacttagt  14280
ccttacaata ggtcctgcga atatattccc agtatttaat gtagtacaaa atgctaaatt  14340
gatactatca agaaccaaaa atttcatcat gcctaagaaa gctgataaag agtctattga  14400
tgcaaatatt aaaagtttga taccctttct ttgttaccct ataacaaaaa aaggaattaa  14460
tactgcattg tcaaaactaa agagtgttgt tagtggagat atactatcat attctatagc  14520
tggacgtaat gaagttttca gcaataaact tataaatcat aagcatatga acatcttaaa  14580
atggttcaat catgttttaa atttcagatc aacagaacta aactataacc atttatatat  14640
ggtagaatct acatatcctt acctaagtga attgttaaac agcttgacaa ccaatgaact  14700
taaaaaactg attaaaatca caggtagtct gttatacaac tttcataatg aataatgaat  14760
aaagatctta taataaaaat tcccatagct atacactaac actgtattca attatagtta  14820
```

ttaaaaatta aaaatcatat aattttttaa ataactttta gtgaactaat cctaaagtta 14880
tcattttaat cttggaggaa taaatttaaa ccctaatcta attggtttat atgtgtatta 14940
actaaattac gagatattag tttttgacac tttttttctc gt 14982

<210> SEQ ID NO 3
<211> LENGTH: 14989
<212> TYPE: DNA
<213> ORGANISM: Artificial Sequence
<220> FEATURE:
<223> OTHER INFORMATION: recombinant respiratory syncytial virus sequence

<400> SEQUENCE: 3
acgggaaaaa atgcgtacaa caaacttgca taaaccaaaa aaatggggca aataagaatt 60
tgataagtac cacttaaatt taactccctt ggttagagat gggcagcaat tcattgagta 120
tgataaaagt tagattacaa aatttgtttg acaatgatga agtagcattg ttaaaaataa 180
catgctatac tgataaatta atacatttaa ctaatgcttt ggctaaggca gtgatacata 240
caatcaaatt gaatggcatt gtgtttgtgc atgttattac aagtagtgat atttgcccta 300
ataataatat tgtagtaaaa tccaatttca caacaatgcc agtactacaa aatggaggtt 360
atatatggga aatgatggaa ttaacacatt gctctcaacc taatggtcta ctagatgaca 420
attgtgaaat taaattctcc aaaaaactaa gtgattcaac aatgaccaat tatatgaatc 480
aattatctga attacttgga tttgatctta atccataaat tataattaat atcaactagc 540
aaatcaatgt cactaacacc attagttaat ataaaactta acagaagaca aaaatggggc 600
aaataaatca attcagccaa cccaaccatg gacacaaccc acaatgataa tacaccacaa 660
agactgatga tcacagacat gagaccgttg tcacttgaga ccataataac atcactaacc 720
agagacatca taacacacaa atttatatac ttgataaatc atgaatgcat agtgagaaaa 780
cttgatgaaa gacaggccac atttacattc ctggtcaact atgaaatgaa actattacac 840
aaagtaggaa gcactaaata taaaaaatat actgaataca acacaaaata tggcactttc 900
cctatgccaa tattcatcaa tcatgatggg ttcttagaat gcattggcat taagcctaca 960
aagcatactc ccataatata caagtatgat ctcaatccat aaatttcaac acaatattca 1020
cacaatctaa aacaacaact ctatgcataa ctatactcca tagtccagat ggagcctgaa 1080
aattatagta atttaaaact taaggagaga tataagatag aagatggggc aaatacaacc 1140
atggctctta gcaaagtcaa gttgaatgat acactcaaca aagatcaact tctgtcatcc 1200
agcaaataca ccatccaacg gagcacagga gatagtattg atactcctaa ttatgatgtg 1260
cagaaacaca tcaataagtt atgtggcatg ttattaatca cagaagatgc taatcataaa 1320
ttcactgggt taataggtat gttatatgcg atgtctaggt taggaagaga agacaccata 1380
aaaatactca gagatgcggg atatcatgta aaagcaaatg gagtagatgt aacaacacat 1440
cgtcaagaca ttaatggaaa agaaatgaaa tttgaagtgt taacattggc aagcttaaca 1500
actgaaattc aaatcaacat tgagatagaa tctagaaaat cctacaaaaa aatgctaaaa 1560
gaaatgggag aggtagctcc agaatacagg catgactctc ctgattgtgg gatgataata 1620
ttatgtatag cagcattagt aataactaaa ttagcagcag gggacagatc tggtcttaca 1680
gccgtgatta ggagagctaa taatgtccta aaaaatgaaa tgaaacgtta caaaggctta 1740
ctacccaagg acatagccaa cagcttctat gaagtgtttg aaaaacatcc ccactttata 1800
gatgtttttg ttcattttgg tatagcacaa tcttctacca gaggtggcag tagagttgaa 1860

-continued

```
gggatttttg caggattgtt tatgaatgcc tatggtgcag ggcaagtgat gttacggtgg   1920
ggagtcttag caaaatcggt taaaaatatt atgttaggac atgctagtgt gcaagcagaa   1980
atggaacaag ttgttgaggt ttatgaatat gcccaaaaat tgggtggtga agcaggattc   2040
taccatatat tgaacaaccc aaaagcatca ttattatctt tgactcaatt tcctcacttc   2100
tccagtgtag tattaggcaa tgctgctggc ctaggcataa tgggagagta cagaggtaca   2160
ccgaggaatc aagatctata tgatgcagca aaggcatatg ctgaacaact caaagaaaat   2220
ggtgtgatta actacagtgt actagacttg acagcagaag aactagaggc tatcaaacat   2280
cagcttaatc caaaagataa tgatgtagag ctttgagtta ataaaaaatg gggcaaataa   2340
atcatcatgg aaaagtttgc tcctgaattc catggagaag atgcaaacaa cagggctact   2400
aaattcctag aatcaataaa gggcaaattc acatcaccca aagatcccaa gaaaaaagat   2460
agtatcatat ctgtcaactc aatagatata gaagtaacca aagaaagccc tataacatca   2520
aattcaacta ttatcaaccc aacaaatgag acagatgata ctgcagggaa caagcccaat   2580
tatcaaagaa aacctctagt aagtttcaaa gaagacccta caccaagtga taatcccttt   2640
tctaaactat acaaagaaac catagaaaca tttgataaca atgaagaaga atccagctat   2700
tcatacgaag aaataaatga tcagacaaac gataatataa cagcaagatt agataggatt   2760
gatgaaaaat taagtgaaat actaggaatg cttcacacat tagtagtggc aagtgcagga   2820
cctacatctg ctcgggatgg tataagagat gccatggttg gtttaagaga agaaatgata   2880
gaaaaaatca gaactgaagc attaatgacc aatgacagat tagaagctat ggcaagactc   2940
aggaatgagg aaagtgaaaa gatggcaaaa gacacatcag atgaagtgtc tctcaatcca   3000
acatcagaga aattgaacaa cctattggaa gggaatgata gtgacaatga tctatcactt   3060
gaagatttct gattagttac caatcttcac atcaacacac aataccaaca gaagaccaac   3120
aaactaacca acccaatcat ccaaccaaac atccatccgc caatcagcca aacagccaac   3180
aaaacaacca gccaatccaa aactaaccac ccggaaaaaa tctataatat agttacaaaa   3240
aaaggaaagg gtggggcaaa tatggaaaca tacgtgaaca agcttcacga aggctccaca   3300
tacacagctg ctgttcaata caatgtctta gaaaaagacg atgaccctgc atcacttaca   3360
atatgggtgc ccatgttcca atcatctatg ccagcagatt tacttataaa agaactagct   3420
aatgtcaaca tactagtgaa acaaatatcc acacccaagg gaccttcact aagagtcatg   3480
ataaactcaa gaagtgcagt gctagcacaa atgcccagca aatttaccat atgcgctaat   3540
gtgtccttgg atgaaagaag caaactagca tatgatgtaa ccacaccctg tgaaatcaag   3600
gcatgtagtc taacatgcct aaaatcaaaa aatatgttga ctacagttaa agatctcact   3660
atgaagacac tcaaccctac acatgatatt attgctttat gtgaatttga aaacatagta   3720
acatcaaaaa aagtcataat accaacatac ctaagatcca tcagtgtcag aaataaagat   3780
ctgaacacac ttgaaaatat aacaaccact gaattcaaaa atgctatcac aaatgcaaaa   3840
atcatccctt actcaggatt actattagtc atcacagtga ctgacaacaa aggagcattc   3900
aaatacataa agccacaaag tcaattcata gtagatcttg gagcttacct agaaaaagaa   3960
agtatatatt atgttaccac aaattggaag cacacagcta cacgatttgc aatcaaaccc   4020
atggaagatt aaccttttc ctctacatca gtgtgttaat tcatacaaac tttctaccta    4080
cattcttcac ttcaccatca caatcacaaa cactctgtgg ttcaaccaat caaacaaaac   4140
ttatctgaag tcccagatca tcccaagtca ttgtttatca gatctagtac tcaaataagt   4200
```

-continued

```
taataaaaaa tatacacatg gggcaaataa tcattggagg aaatccaact aatcacaata   4260
tctgttaaca tagacaagtc cacacaccat acagaatcaa ccaatggaaa atacatccat   4320
aacaatagaa ttctcaagca aattctggcc ttactttaca ctaatacaca tgatcacaac   4380
aataatctct ttgctaatca taatctccat catgattgca atactaaaca aactttgtga   4440
atataacgta ttccataaca aaacctttga gttaccaaga gctcgagtca acacatagca   4500
ttcatcaatc caacagccca aaacagtaac cttgcattta aaaatgaaca acccctacct   4560
ctttacaaca cctcattaac atcccaccat gcaaaccact atccatacta taaagtagtt   4620
aattaaaaat agtcataaca atgaactagg atatcaagac taacaataac attggggcaa   4680
atgcaaacat gtccaaaaac aaggaccaac gcaccgctaa gacattagaa aggacctggg   4740
acactctcaa tcatttatta ttcatatcat cgtgcttata taagttaaat cttaaatctg   4800
tagcacaaat cacattatcc attctggcaa tgataatctc aacttcactt ataattgcag   4860
ccatcatatt catagcctcg gcaaaccaca aagtcacacc aacaactgca atcatacaag   4920
atgcaacaag ccagatcaag aacacaaccc caacatacct cacccagaat cctcagcttg   4980
gaatcagtcc ctctaatccg tctgaaatta catcacaaat caccaccata ctagcttcaa   5040
caacaccagg agtcaagtca accctgcaat ccacaacagt caagaccaaa aacacaacaa   5100
caactcaaac acaacccagc aagcccacca caaaacaacg ccaaaacaaa ccaccaagca   5160
aacccaataa tgattttcac tttgaagtgt tcaactttgt accctgcagc atatgcagca   5220
acaatccaac ctgctgggct atctgcaaaa gaataccaaa caaaaaacca ggaaagaaaa   5280
ccactaccaa gcccacaaaa aaaccaaccc tcaagacaac caaaaaagat cccaaacctc   5340
aaaccactaa atcaaaggaa gtacccacca ccaagcccac agaagagcca accatcaaca   5400
ccaccaaaac aaacatcata actacactac tcacctccaa caccacagga aatccagaac   5460
tcacaagtca aatggaaacc ttccactcaa cttcctccga aggcaatcca agcccttctc   5520
aagtctctac aacatccgag tacccatcac aaccttcatc tccacccaac acaccacgcc   5580
agtagttact taaaaacata ttatcacaaa aggccttgac caacttaaac agaatcaaaa   5640
taaactctgg ggcaaataac aatggagttg ctaatcctca aagcaaatgc aattaccaca   5700
atcctcactg cagtcacatt ttgttttgct tctggtcaaa acatcactga agaattttat   5760
caatcaacat gcagtgcagt tagcaaaggc tatcttagtg ctctgagaac tggttggtat   5820
accagtgtta taactataga attaagtaat atcaagaaaa ataagtgtaa tggaacagat   5880
gctaaggtaa aattgataaa acaagaatta gataaatata aaaatgctgt aacagaattg   5940
cagttgctca tgcaaagcac acaagcaaca aacaatcgag ccagaagaga actaccaagg   6000
tttatgaatt atacactcaa caatgccaaa aaaaccaatg taacattaag caagaaaagg   6060
aaaagaagat ttcttggttt tttgttaggt gttggatctg caatcgccag tggcgttgct   6120
gtatctaagg tcctgcacct agaaggggaa gtgaacaaga tcaaaagtgc tctactatcc   6180
acaaacaagg ctgtagtcag cttatcaaat ggagttagtg ttttaaccag caaagtgtta   6240
gacctcaaaa actatataga taaacaattg ttacctattg tgaacaagca aagctgcagc   6300
atatcaaata tagaaactgt gatagagttc caacaaaaga acaacagact actagagatt   6360
accagggaat ttagtgttaa tgcaggcgta actacacctg taagcactta catgttaact   6420
aatagtgaat tattgtcatt aatcaatgat atgcctataa caaatgatca gaaaaagtta   6480
atgtccaaca atgttcaaat agttagacag caaagttact ctatcatgtc cataataaaa   6540
gaggaagtct tagcatatgt agtacaatta ccactatatg gtgttataga tacaccctgt   6600
```

-continued

```
tggaaactac acacatcccc tctatgtaca accaacacaa aagaagggtc caacatctgt   6660
ttaacaagaa ctgacagagg atggtactgt gacaatgcag gatcagtatc tttcttccca   6720
caagctgaaa catgtaaagt tcaatcaaat cgagtatttt gtgacacaat gaacagttta   6780
acattaccaa gtgaagtaaa tctctgcaat gttgacatat tcaaccccaa atatgattgt   6840
aaaattatga cttcaaaaac agatgtaagc agctccgtta tcacatctct aggagccatt   6900
gtgtcatgct atggcaaaac taaatgtaca gcatccaata aaaatcgtgg aatcataaag   6960
acattttcta acgggtgcga ttatgtatca aataaagggg tggacactgt gtctgtaggt   7020
aacacattat attatgtaaa taagcaagaa ggtaaaagtc tctatgtaaa aggtgaacca   7080
ataataaatt tctatgaccc attagtattc ccctctgatg aatttgatgc atcaatatct   7140
caagtcaacg agaagattaa ccagagccta gcatttattc gtaaatccga tgaattatta   7200
cataatgtaa atgctggtaa atccaccaca aatatcatga taactactat aattatagtg   7260
attatagtaa tattgttatc attaattgct gttggactgc tcttatactg taaggccaga   7320
agcacaccag tcacactaag caaagatcaa ctgagtggta taaataatat tgcatttagt   7380
aactaaataa aaatagcacc taatcatgtt cttacaatgg tttactatct gctcatagac   7440
aacccatctg tcattggatt ttcttaaaat ctgaacttca tcgaaactct catctataaa   7500
ccatctcact tacactattt aagtagattc ctagtttata gttatataaa acacaattgc   7560
atgccagatt aacttaccat ctgtaaaaat gaaaactggg gcaaatatgt cacgaaggaa   7620
tccttgcaaa tttgaaattc gaggtcattg cttaaatggt aagaggtgtc attttagtca   7680
taattatttt gaatggccac cccatgcact gcttgtaaga caaaacttta tgttaaacag   7740
aatacttaag tctatggata aaagtataga taccttatca gaaataagtg gagctgcaga   7800
gttggacaga acagaagagt atgctcttgg tgtagttgga gtgctagaga gttatatagg   7860
atcaataaac aatataacta aacaatcagc atgtgttgcc atgagcaaac tcctcactga   7920
actcaatagt gatgatatca aaaagctgag ggacaatgaa gagctaaatt cacccaagat   7980
aagagtgtac aatactgtca tatcatatat tgaaagcaac aggaaaaaca ataaacaaac   8040
tatccatctg ttaaaaagat tgccagcaga cgtattgaag aaaaccatca aaaacacatt   8100
ggatatccat aagagcataa ccatcaacaa cccaaaagaa tcaactgtta gtgatacaaa   8160
tgaccatgcc aaaaataatg atactacctg acaaataacg ttcaattcta acactcacca   8220
catcgttaca ttattaattc aaacaattca agttgtggga caaaatggat cccattatta   8280
atggaaattc tgctaatgtt tatctaaccg atagttattt aaaaggtgtt atctctttct   8340
cagagtgtaa tgctttagga agttacatat tcaatggtcc ttatctcaaa aatgattata   8400
ccaacttaat tagtagacaa aatccattaa tagaacacat gaatctaaag aaactaaata   8460
taacacagtc cttaatatct aagtatcata aaggtgaaat aaaattagaa gaacctactt   8520
attttcagtc attacttatg acatacaaga gtatgacctc gtcagaacag attgctacca   8580
ctaatttact taaaaagata ataagaagag ctatagaaat aagtgatgtc aaagtctatg   8640
ctatattgaa taaactaggg cttaaagaaa aggacaagat taaatccaac aatggacaag   8700
atgaagacaa ctcagttatt acgaccataa tcaaagatga tatactttca gctgttaaag   8760
ataatcaatc tcatcttaaa gcagacaaaa atcactctac aaaacaaaaa gacacaatca   8820
aaacaacact cttgaagaaa ttgatgtgtt caatgcaaca tcctccatca tggttaatac   8880
attggtttaa cttatacaca aaattaaaca acatattaac acagtatcga tcaaatgagg   8940
```

taaaaaacca tgggtttaca ttgatagata atcaaactct tagtggattt caatttattt 9000
tgaaccaata tggttgtata gtttatcata aggaactcaa aagaattact gtgacaacct 9060
ataatcaatt cttgacatgg aaagatatta gccttagtag attaaatgtt tgtttaatta 9120
catggattag taactgcttg aacacattaa ataaaagctt aggcttaaga tgcggattca 9180
ataatgttat cttgacacaa ctattccttt atggagattg tatactaaag ctatttcaca 9240
atgaggggtt ctacataata aaagaggtag agggatttat tatgtctcta attttaaata 9300
taacagaaga agatcaattc agaaaacgat tttataatag tatgctcaac aacatcacag 9360
atgctgctaa taaagctcag aaaaatctgc tatcaagagt atgtcataca ttattagata 9420
agacagtgtc cgataatata ataaatggca gatggataat tctattaagt aagttcctta 9480
aattaattaa gcttgcaggt gacaataacc ttaacaatct gagtgaacta tattttttgt 9540
tcagaatatt tggacaccca atggtagatg aaagacaagc catggatgct gttaaaatta 9600
attgcaatga gaccaaattt tacttgttaa gcagtctgag tatgttaaga ggtgccttta 9660
tatatagaat tataaaaggg tttgtaaata attacaacag atggcctact ttaagaaatg 9720
ctattgtttt acccttaaga tggttaactt actataaact aaacacttat ccttctttgt 9780
tggaacttac agaaagagat ttgattgtgt tatcaggact acgtttctat cgtgagtttc 9840
ggttgcctaa aaaagtggat cttgaaatga ttataaatga taaagctata tcacctccta 9900
aaaatttgat atggactagt ttccctagaa attacatgcc atcacacata caaaactata 9960
tagaacatga aaaattaaaa ttttccgaga gtgataaatc aagaagagta ttagagtatt 10020
atttaagaga taacaaattc aatgaatgtg atttatacaa ctgtgtagtt aatcaaagtt 10080
atctcaacaa ccctaatcat gtggtatcat tgacaggcaa agaaagagaa ctcagtgtag 10140
gtagaatgtt tgcaatgcaa ccgggaatgt tcagacaggt tcaaatattg gcagagaaaa 10200
tgatagctga aaacatttta caattctttc ctgaaagtct tacaagatat ggtgatctag 10260
aactacaaaa aatattagaa ctgaaagcag gaataagtaa caaatcaaat cgctacaatg 10320
ataattacaa caattacatt agtaagtgct ctatcatcac agatctcagc aaattcaatc 10380
aagcatttcg atatgaaacg tcatgtattt gtagtgatgt gctggatgaa ctgcatggtg 10440
tacaatctct attttcctgg ttacatttaa ctattcctca tgtcacaata atatgcacat 10500
ataggcatgc acccccctat ataggagatc atattgtaga tcttaacaat gtagatgaac 10560
aaagtggatt atatagatat cacatgggtg gcatcgaagg gtggtgtcaa aaactatgga 10620
ccatagaagc tatatcacta ttggatctaa tatctctcaa agggaaattc tcaattactg 10680
ctttaattaa tggtgacaat caatcaatag atataagcaa accaatcaga ctcatggaag 10740
gtcaaactca tgctcaagca gattatttgc tagcattaaa tagccttaaa ttactgtata 10800
aagagtatgc aggcataggc cacaaattaa aaggaactga gacttatata tcacgagata 10860
tgcaatttat gagtaaaaca attcaacata acggtgtata ttacccagct agtataaaga 10920
aagtcctaag agtgggaccg tggataaaca ctatacttga tgatttcaaa gtgagtctag 10980
aatctatagg tagtttgaca caagaattag aatatagagg tgaaagtcta ttatgcagtt 11040
taatatttag aaatgtatgg ttatataatc agattgctct acaattaaaa aatcatgcat 11100
tatgtaacaa taaactatat ttggacatat taaaggttct gaaacactta aaaacctttt 11160
ttaatcttga taatattgat acagcattaa cattgtatat gaatttaccc atgttatttg 11220
gtggtggtga tcccaacttg ttatatcgaa gtttctatag aagaactcct gacttcctca 11280
cagaggctat agttcactct gtgttcatac ttagttatta tacaaaccat gacttaaaag 11340
ataaacttca agatctgtca gatgatagat tgaataagtt cttaacatgc ataatcacgt 11400
ttgacaaaaa ccctaatgct gaattcgtaa cattgatgag agatcctcaa gctttagggt 11460
ctgagagaca agctaaaatt actagcgaaa tcaatagact ggcagttaca gaggttttga 11520
gtacagctcc aaacaaaata ttctccaaaa gtgcacaaca ttatactact acagagatag 11580
atctaaatga tattatgcaa aatatagaac ctacatatcc tcatgggcta agagttgttt 11640
atgaaagttt accctttat aaagcagaga aaatagtaaa tcttatatca ggtacaaaat 11700
ctataactaa catactggaa aaaacttctg ccatagactt aacagatatt gatagagcca 11760
ctgagatgat gaggaaaaac ataactttgc ttataaggat acttccattg gattgtaaca 11820
gagataaaag agagatattg agtatggaaa acctaagtat tactgaatta agcaaatatg 11880
ttagggaaag atcttggtct ttatccaata tagttggtgt tacatcaccc agtatcatgt 11940
atacaatgga catcaaatat actacaagca ctatatctag tggcataatt atagagaaat 12000
ataatgttaa cagtttaaca cgtggtgaga gaggacccac taaaccatgg gttggttcat 12060
ctacacaaga gaaaaaaaca atgccagttt ataatagaca agtcttaacc aaaaaacaga 12120
gagatcaaat agatctatta gcaaaattgg attgggtgta tgcatctata gataacaagg 12180
atgaattcat ggaagaactc agcataggaa cccttgggtt aacatatgaa aaggccaaga 12240
aattatttcc acaatattta agtgtcaatt atttgcatcg ccttacagtc agtagtagac 12300
catgtgaatt ccctgcatca ataccagctt atagaacaac aaattatcac tttgacacta 12360
gccctattaa tcgcatatta acagaaaagt atggtgatga agatattgac atagtattcc 12420
aaaactgtat aagctttggc cttagtttaa tgtcagtagt agaacaattt actaatgtat 12480
gtcctaacag aattattctc atacctaagc ttaatgagat acatttgatg aaacctccca 12540
tattcacagg tgatgttgat attcacaagt taaaacaagt gatacaaaaa cagcatatgt 12600
ttttaccaga caaaataagt ttgactcaat atgtggaatt attcttaagt aataaaacac 12660
tcaaatctgg atctcatgtt aattctaatt taatattggc acataaaata tctgactatt 12720
ttcataatac ttacatttta agtactaatt tagctggaca ttggattctg attatacaac 12780
ttatgaaaga ttctaaaggt atttttgaaa aagattgggg agagggatat ataactgatc 12840
atatgtttat taatttgaaa gttttcttca atgcttataa gacctatctc ttgtgttttc 12900
ataaaggtta tggcaaagca aagctggagt gtgatatgaa cacttcagat cttctatgtg 12960
tattggaatt aatagacagt agttattgga agtctatgtc taaggtattt ttagaacaaa 13020
aagttatcaa atacattctt agccaagatg caagtttaca tagagtaaaa ggatgtcata 13080
gcttcaaatt atggtttctt aaacgtctta atgtagcaga attcacagtt tgcccttggg 13140
ttgttaacat agattatcat ccaacacata tgaaagcaat attaacttat atagatcttg 13200
ttagaatggg attgataaat atagatagaa tacacattaa aaataaacac aaattcaatg 13260
atgaatttta tacttctaat ctcttctaca ttaattataa cttctcagat aatactcatc 13320
tattaactaa acatataagg attgctaatt ctgaattaga aaataattac aacaaattat 13380
atcatcctac accagaaacc ctagagaata tactagccaa tccgattaaa agtaatgaca 13440
aaaagacact gaatgactat tgtataggta aaaatgttga ctcaataatg ttaccattgt 13500
tatctaataa gaagcttatt aaatcgtctg caatgattag aaccaattac agcaaacaag 13560
atttgtataa tttattccct atggttgtga ttgatagaat tatagatcat tcaggcaata 13620
cagccaaatc caaccaactt tacactacta cttcccacca aatatcctta gtgcacaata 13680
gcacatcact ttactgcatg cttccttggc atcatattaa tagattcaat tttgtattta 13740
gttctacagg ttgtaaaatt agtatagagt atattttaaa agatcttaaa attaaagatc 13800
ccaattgtat agcattcata ggtgaaggag cagggaattt attattgcgt acagtagtgg 13860
aacttcatcc tgacataaga tatatttaca gaagtctgaa agattgcaat gatcatagtt 13920
tacctattga gtttttaagg ctgtacaatg gacatatcaa cattgattat ggtgaaaatt 13980
tgaccattcc tgctacagat gcaaccaaca acattcattg gtcttattta catataaagt 14040
ttgctgaacc tatcagtctt tttgtctgtg atgccgaatt gtctgtaaca gtcaactgga 14100
gtaaaattat aatagaatgg agcaagcatg taagaaagtg caagtactgt tcctcagtta 14160
ataaatgtat gttaatagta aaatatcatg ctcaagatga tattgatttc aaattagaca 14220
atataactat attaaaaact tatgtatgct taggcagtaa gttaaaggga tcggaggttt 14280
acttagtcct tacaataggt cctgcgaata tattcccagt atttaatgta gtacaaaatg 14340
ctaaattgat actatcaaga accaaaaatt tcatcatgcc taagaaagct gataaagagt 14400
ctattgatgc aaatattaaa agtttgatac cctttctttg ttaccctata acaaaaaaag 14460
gaattaatac tgcattgtca aaactaaaga gtgttgttag tggagatata ctatcatatt 14520
ctatagctgg acgtaatgaa gttttcagca ataaacttat aaatcataag catatgaaca 14580
tcttaaaatg gttcaatcat gttttaaatt tcagatcaac agaactaaac tataaccatt 14640
tatatatggt agaatctaca tatccttacc taagtgaatt gttaaacagc ttgacaacca 14700
atgaacttaa aaaactgatt aaaatcacag gtagtctgtt atacaacttt cataatgaat 14760
aatgaataaa gatcttataa taaaaattcc catagctata cactaacact gtattcaatt 14820
atagttatta aaaattaaaa atcatataat tttttaaata acttttagtg aactaatcct 14880
aaagttatca ttttaatctt ggaggaataa atttaaaccc taatctaatt ggtttatatg 14940
tgtattaact aaattacgag atattagttt ttgacacttt ttttctcgt 14989

<210> SEQ ID NO 4
<211> LENGTH: 14989
<212> TYPE: DNA
<213> ORGANISM: Artificial Sequence
<220> FEATURE:
<223> OTHER INFORMATION: recombinant respiratory syncytial virus sequence

<400> SEQUENCE: 4
acgggaaaaa atgcgtacaa caaacttgca taaaccaaaa aaatggggca aataagaatt 60
tgataagtac cacttaaatt taactccctt ggttagagat gggcagcaat tcattgagta 120
tgataaaagt tagattacaa aatttgtttg acaatgatga agtagcattg ttaaaaataa 180
catgctatac tgataaatta atacatttaa ctaatgcttt ggctaaggca gtgatacata 240
caatcaaatt gaatggcatt gtgtttgtgc atgttattac aagtagtgat atttgcccta 300
ataataatat tgtagtaaaa tccaatttca caacaatgcc agtactacaa aatggaggtt 360
atatatggga aatgatggaa ttaacacatt gctctcaacc taatggtcta ctagatgaca 420
attgtgaaat taaattctcc aaaaaactaa gtgattcaac aatgaccaat tatatgaatc 480
aattatctga attacttgga tttgatctta atccataaat tataattaat atcaactagc 540
aaatcaatgt cactaacacc attagttaat ataaaactta acagaagaca aaaatggggc 600
aaataaatca attcagccaa cccaaccatg gacacaaccc acaatgataa tacaccacaa 660
agactgatga tcacagacat gagaccgttg tcacttgaga ccataataac atcactaacc 720

-continued

```
agagacatca taacacacaa atttatatac ttgataaatc atgaatgcat agtgagaaaa    780
cttgatgaaa gacaggccac atttacattc ctggtcaact atgaaatgaa actattacac    840
aaagtaggaa gcactaaata taaaaaatat actgaataca acacaaaata tggcactttc    900
cctatgccaa tattcatcaa tcatgatggg ttcttagaat gcattggcat taagcctaca    960
aagcatactc ccataatata caagtatgat ctcaatccat aaatttcaac acaatattca   1020
cacaatctaa aacaacaact ctatgcataa ctatactcca tagtccagat ggagcctgaa   1080
aattatagta atttaaaact taaggagaga tataagatag aagatggggc aaatacaacc   1140
atggctctta gcaaagtcaa gttgaatgat acactcaaca aagatcaact tctgtcatcc   1200
agcaaataca ccatccaacg gagcacagga gatagtattg atactcctaa ttatgatgtg   1260
cagaaacaca tcaataagtt atgtggcatg ttattaatca cagaagatgc taatcataaa   1320
ttcactgggt taataggtat gttatatgcg atgtctaggt taggaagaga agacaccata   1380
aaaatactca gagatgcggg atatcatgta aaagcaaatg gagtagatgt aacaacacat   1440
cgtcaagaca ttaatggaaa agaaatgaaa tttgaagtgt taacattggc aagcttaaca   1500
actgaaattc aaatcaacat tgagatagaa tctagaaaat cctacaaaaa aatgctaaaa   1560
gaaatgggag aggtagctcc agaatacagg catgactctc ctgattgtgg gatgataata   1620
ttatgtatag cagcattagt aataactaaa ttagcagcag gggacagatc tggtcttaca   1680
gccgtgatta ggagagctaa taatgtccta aaaaatgaaa tgaaacgtta caaaggctta   1740
ctacccaagg acatagccaa cagcttctat gaagtgtttg aaaaacatcc ccactttata   1800
gatgtttttg ttcattttgg tatagcacaa tcttctacca gaggtggcag tagagttgaa   1860
gggatttttg caggattgtt tatgaatgcc tatggtgcag ggcaagtgat gttacggtgg   1920
ggagtcttag caaaatcggt taaaaatatt atgttaggac atgctagtgt gcaagcagaa   1980
atggaacaag ttgttgaggt ttatgaatat gcccaaaaat tgggtggtga agcaggattc   2040
taccatatat tgaacaaccc aaaagcatca ttattatctt tgactcaatt tcctcacttc   2100
tccagtgtag tattaggcaa tgctgctggc ctaggcataa tgggagagta cagaggtaca   2160
ccgaggaatc aagatctata tgatgcagca aaggcatatg ctgaacaact caaagaaaat   2220
ggtgtgatta actacagtgt actagacttg acagcagaag aactagaggc tatcaaacat   2280
cagcttaatc caaaagataa tgatgtagag ctttgagtta ataaaaaatg gggcaaataa   2340
atcatcatgg aaaagtttgc tcctgaattc catggagaag atgcaaacaa cagggctact   2400
aaattcctag aatcaataaa gggcaaattc acatcaccca aagatcccaa gaaaaaagat   2460
agtatcatat ctgtcaactc aatagatata gaagtaacca aagaaagccc tataacatca   2520
aattcaacta ttatcaaccc aacaaatgag acagatgata ctgcagggaa caagcccaat   2580
tatcaaagaa aacctctagt aagtttcaaa gaagacccta caccaagtga taatcccttt   2640
tctaaactat acaaagaaac catagaaaca tttgataaca atgaagaaga atccagctat   2700
tcatacgaag aaataaatga tcagacaaac gataatataa cagcaagatt agataggatt   2760
gatgaaaaat taagtgaaat actaggaatg cttcacacat tagtagtggc aagtgcagga   2820
cctacatctg ctcgggatgg tataagagat gccatggttg gtttaagaga agaaatgata   2880
gaaaaaatca gaactgaagc attaatgacc aatgacagat tagaagctat ggcaagactc   2940
aggaatgagg aaagtgaaaa gatggcaaaa gacacatcag atgaagtgtc tctcaatcca   3000
acatcagaga aattgaacaa cctattggaa gggaatgata gtgacaatga tctatcactt   3060
gaagatttct gattagttac caatcttcac atcaacacac aataccaaca gaagaccaac   3120
```

aaactaacca acccaatcat ccaaccaaac atccatccgc caatcagcca aacagccaac 3180
aaaacaacca gccaatccaa aactaaccac ccggaaaaaa tctataatat agttacaaaa 3240
aaaggaaagg gtggggcaaa tatggaaaca tacgtgaaca agcttcacga aggctccaca 3300
tacacagctg ctgttcaata caatgtctta gaaaaagacg atgaccctgc atcacttaca 3360
atatgggtgc ccatgttcca atcatctatg ccagcagatt tacttataaa agaactagct 3420
aatgtcaaca tactagtgaa acaaatatcc acacccaagg gaccttcact aagagtcatg 3480
ataaactcaa gaagtgcagt gctagcacaa atgcccagca aatttaccat atgcgctaat 3540
gtgtccttgg atgaaagaag caaactagca tatgatgtaa ccacaccctg tgaaatcaag 3600
gcatgtagtc taacatgcct aaaatcaaaa aatatgttga ctacagttaa agatctcact 3660
atgaagacac tcaaccctac acatgatatt attgctttat gtgaatttga aaacatagta 3720
acatcaaaaa aagtcataat accaacatac ctaagatcca tcagtgtcag aaataaagat 3780
ctgaacacac ttgaaaatat aacaaccact gaattcaaaa atgctatcac aaatgcaaaa 3840
atcatccctt actcaggatt actattagtc atcacagtga ctgacaacaa aggagcattc 3900
aaatacataa agccacaaag tcaattcata gtagatcttg gagcttacct agaaaaagaa 3960
agtatatatt atgttaccac aaattggaag cacacagcta cacgatttgc aatcaaaccc 4020
atggaagatt aaccttttc ctctacatca gtgtgttaat tcatacaaac tttctaccta 4080
cattcttcac ttcaccatca caatcacaaa cactctgtgg ttcaaccaat caaacaaaac 4140
ttatctgaag tcccagatca tcccaagtca ttgtttatca gatctagtac tcaaataagt 4200
taataaaaaa tatacacatg gggcaaataa tcattggagg aaatccaact aatcacaata 4260
tctgttaaca tagacaagtc cacacaccat acagaatcaa ccaatggaaa atacatccat 4320
aacaatagaa ttctcaagca aattctggcc ttactttaca ctaatacaca tgatcacaac 4380
aataatctct ttgctaatca taatctccat catgattgca atactaaaca aactttgtga 4440
atataacgta ttccataaca aaacctttga gttaccaaga gctcgagtca acacatagca 4500
ttcatcaatc caacagccca aaacagtaac cttgcattta aaaatgaaca acccctacct 4560
ctttacaaca cctcattaac atcccaccat gcaaaccact atccatacta taaagtagtt 4620
aattaaaaat agtcataaca atgaactagg atatcaagac taacaataac attggggcaa 4680
atgcaaacat gtccaaaaac aaggaccaac gcaccgctaa gacattagaa aggacctggg 4740
acactctcaa tcatttatta ttcatatcat cgtgcttata taagttaaat cttaaatctg 4800
tagcacaaat cacattatcc attctggcaa tgataatctc aacttcactt ataattgcag 4860
ccatcatatt catagcctcg gcaaaccaca aagtcacacc aacaactgca atcatacaag 4920
atgcaacaag ccagatcaag aacacaaccc caacatacct cacccagaat cctcagcttg 4980
gaatcagtcc ctctaatccg tctgaaatta catcacaaat caccaccata ctagcttcaa 5040
caacaccagg agtcaagtca accctgcaat ccacaacagt caagaccaaa aacacaacaa 5100
caactcaaac acaacccagc aagcccacca caaaacaacg ccaaaacaaa ccaccaagca 5160
aacccaataa tgattttcac tttgaagtgt tcaactttgt accctgcagc atatgcagca 5220
acaatccaac ctgctgggct atctgcaaaa gaataccaaa caaaaaacca ggaaagaaaa 5280
ccactaccaa gcccacaaaa aaaccaaccc tcaagacaac caaaaaagat cccaaacctc 5340
aaaccactaa atcaaaggaa gtacccacca ccaagcccac agaagagcca accatcaaca 5400
ccaccaaaac aaacatcata actacactac tcacctccaa caccacagga aatccagaac 5460

-continued

```
tcacaagtca aatggaaacc ttccactcaa cttcctccga aggcaatcca agcccttctc   5520
aagtctctac aacatccgag tacccatcac aaccttcatc tccacccaac acaccacgcc   5580
agtagttact taaaaacata ttatcacaaa aggccttgac caacttaaac agaatcaaaa   5640
taaactctgg ggcaaataac aatggagttg ctaatcctca aagcaaatgc aattaccaca   5700
atcctcactg cagtcacatt ttgttttgct tctggtcaaa acatcactga agaatttttat  5760
caatcaacat gcagtgcagt tagcaaaggc tatcttagtg ctctgagaac tggttggtat   5820
accagtgtta taactataga attaagtaat atcaagaaaa ataagtgtaa tggaacagat   5880
gctaaggtaa aattgataaa acaagaatta gataaatata aaaatgctgt aacagaattg   5940
cagttgctca tgcaaagcac acaagcaaca aacaatcgag ccagaagaga actaccaagg   6000
tttatgaatt atacactcaa caatgccaaa aaaaccaatg taacattaag caagaaaagg   6060
aaaagaagat ttcttggttt tttgttaggt gttggatctg caatcgccag tggcgttgct   6120
gtatctaagg tcctgcacct agaaggggaa gtgaacaaga tcaaaagtgc tctactatcc   6180
acaaacaagg ctgtagtcag cttatcaaat ggagttagtg ttttaaccag caaagtgtta   6240
gacctcaaaa actatataga taaacaattg ttacctattg tgaacaagca aagctgcagc   6300
atatcaaata tagaaactgt gatagagttc caacaaaaga acaacagact actagagatt   6360
accagggaat ttagtgttaa tgcaggcgta actacacctg taagcactta catgttaact   6420
aatagtgaat tattgtcatt aatcaatgat atgcctataa caaatgatca gaaaaagtta   6480
atgtccaaca atgttcaaat agttagacag caaagttact ctatcatgtc cataataaaa   6540
gaggaagtct tagcatatgt agtacaatta ccactatatg gtgttataga tacaccctgt   6600
tggaaactac acacatcccc tctatgtaca accaacacaa aagaagggtc caacatctgt   6660
ttaacaagaa ctgacagagg atggtactgt gacaatgcag gatcagtatc tttcttccca   6720
caagctgaaa catgtaaagt tcaatcaaat cgagtatttt gtgacacaat gaacagttta   6780
acattaccaa gtgaagtaaa tctctgcaat gttgacatat tcaaccccaa atatgattgt   6840
aaaattatga cttcaaaaac agatgtaagc agctccgtta tcacatctct aggagccatt   6900
gtgtcatgct atggcaaaac taaatgtaca gcatccaata aaaatcgtgg aatcataaag   6960
acattttcta acgggtgcga ttatgtatca aataaagggg tggacactgt gtctgtaggt   7020
aacacattat attatgtaaa taagcaagaa ggtaaaagtc tctatgtaaa aggtgaacca   7080
ataataaatt tctatgaccc attagtattc ccctctgatg aatttgatgc atcaatatct   7140
caagtcaacg agaagattaa ccagagccta gcatttattc gtaaatccga tgaattatta   7200
cataatgtaa atgctggtaa atccaccaca aatatcatga taactactat aattatagtg   7260
attatagtaa tattgttatc attaattgct gttggactgc tcttatactg taaggccaga   7320
agcacaccag tcacactaag caaagatcaa ctgagtggta taaataatat tgcatttagt   7380
aactaaataa aaatagcacc taatcatgtt cttacaatgg tttactatct gctcatagac   7440
aacccatctg tcattggatt ttcttaaaat ctgaacttca tcgaaactct catctataaa   7500
ccatctcact tacactattt aagtagattc ctagtttata gttatataaa acacaattgc   7560
atgccagatt aacttaccat ctgtaaaaat gaaaactggg gcaaatatgt cacgaaggaa   7620
tccttgcaaa tttgaaattc gaggtcattg cttaaatggt aagaggtgtc attttagtca   7680
taattatttt gaatggccac cccatgcact gcttgtaaga caaaacttta tgttaaacag   7740
aatacttaag tctatggata aaagtataga taccttatca gaaataagtg gagctgcaga   7800
gttggacaga acagaagagt atgctcttgg tgtagttgga gtgctagaga gttatatagg   7860
```

atcaataaac aatataacta aacaatcagc atgtgttgcc atgagcaaac tcctcactga 7920
actcaatagt gatgatatca aaaagctgag ggacaatgaa gagctaaatt cacccaagat 7980
aagagtgtac aatactgtca tatcatatat tgaaagcaac aggaaaaaca ataaacaaac 8040
tatccatctg ttaaaaagat tgccagcaga cgtattgaag aaaaccatca aaaacacatt 8100
ggatatccat aagagcataa ccatcaacaa cccaaaagaa tcaactgtta gtgatacaaa 8160
tgaccatgcc aaaaataatg atactacctg acaaataagc ttcaattcta acactcacca 8220
catcgttaca ttattaattc aaacaattca agttgtggga caaaatggat cccattatta 8280
atggaaattc tgctaatgtt tatctaaccg atagttattt aaaaggtgtt atctctttct 8340
cagagtgtaa tgctttagga agttacatat tcaatggtcc ttatctcaaa aatgattata 8400
ccaacttaat tagtagacaa aatccattaa tagaacacat gaatctaaag aaactaaata 8460
taacacagtc cttaatatct aagtatcata aaggtgaaat aaaattagaa gaacctactt 8520
attttcagtc attacttatg acatacaaga gtatgacctc gtcagaacag attgctacca 8580
ctaatttact taaaaagata ataagaagag ctatagaaat aagtgatgtc aaagtctatg 8640
ctatattgaa taaactaggg cttaaagaaa aggacaagat taaatccaac aatggacaag 8700
atgaagacaa ctcagttatt acgaccataa tcaaagatga tatactttca gctgttaaag 8760
ataatcaatc tcatcttaaa gcagacaaaa atcactctac aaaacaaaaa gacacaatca 8820
aaacaacact cttgaagaaa ttgatgtgtt caatgcaaca tcctccatca tggttaatac 8880
attggtttaa cttatacaca aaattaaaca acatattaac acagtatcga tcaaatgagg 8940
taaaaaacca tgggtttaca ttgatagata atcaaactct tagtggattt caatttattt 9000
tgaaccaata tggttgtata gtttatcata aggaactcaa aagaattact gtgacaacct 9060
ataatcaatt cttgacatgg aaagatatta gccttagtag attaaatgtt tgtttaatta 9120
catggattag taactgcttg aacacattaa ataaaagctt aggcttaaga tgcggattca 9180
ataatgttat cttgacacaa ctattccttt atggagattg tatactaaag ctatttcaca 9240
atgaggggtt ctacataata aaagaggtag agggatttat tatgtctcta attttaaata 9300
taacagaaga agatcaattc agaaaacgat tttataatag tatgctcaac aacatcacag 9360
atgctgctaa taaagctcag aaaaatctgc tatcaagagt atgtcataca ttattagata 9420
agacagtgtc cgataatata ataaatggca gatggataat tctattaagt aagttcctta 9480
aattaattaa gcttgcaggt gacaataacc ttaacaatct gagtgaacta tattttttgt 9540
tcagaatatt tggacaccca atggtagatg aaagacaagc catggatgct gttaaaatta 9600
attgcaatga gaccaaattt tacttgttaa gcagtctgag tatgttaaga ggtgccttta 9660
tatatagaat tataaaaggg tttgtaaata attacaacag atggcctact ttaagaaatg 9720
ctattgtttt acccttaaga tggttaactt actataaact aaacacttat ccttctttgt 9780
tggaacttac agaaagagat ttgattgtgt tatcaggact acgtttctat cgtgagtttc 9840
ggttgcctaa aaaagtggat cttgaaatga ttataaatga taaagctata tcacctccta 9900
aaaatttgat atggactagt ttccctagaa attacatgcc atcacacata caaaactata 9960
tagaacatga aaaattaaaa ttttccgaga gtgataaatc aagaagagta ttagagtatt 10020
atttaagaga taacaaattc aatgaatgtg atttatacaa ctgtgtagtt aatcaaagtt 10080
atctcaacaa ccctaatcat gtggtatcat tgacaggcaa agaaagagaa ctcagtgtag 10140
gtagaatgtt tgcaatgcaa ccgggaatgt tcagacaggt tcaaatattg gcagagaaaa 10200

-continued

```
tgatagctga aaacatttta caattctttc ctgaaagtct tacaagatat ggtgatctag  10260
aactacaaaa aatattagaa ctgaaagcag gaataagtaa caaatcaaat cgctacaatg  10320
ataattacaa caattacatt agtaagtgct ctatcatcac agatctcagc aaattcaatc  10380
aagcatttcg atatgaaacg tcatgtattt gtagtgatgt gctggatgaa ctgcatggtg  10440
tacaatctct attttcctgg ttacatttaa ctattcctca tgtcacaata atatgcacat  10500
ataggcatgc acccccctat ataggagatc atattgtaga tcttaacaat gtagatgaac  10560
aaagtggatt atatagatat cacatgggtg gcatcgaagg gtggtgtcaa aaactatgga  10620
ccatagaagc tatatcacta ttggatctaa tatctctcaa agggaaattc tcaattactg  10680
ctttaattaa tggtgacaat caatcaatag atataagcaa accaatcaga ctcatggaag  10740
gtcaaactca tgctcaagca gattatttgc tagcattaaa tagccttaaa ttactgtata  10800
aagagtatgc aggcataggc cacaaattaa aaggaactga gacttatata tcacgagata  10860
tgcaatttat gagtaaaaca attcaacata acggtgtata ttacccagct agtataaaga  10920
aagtcctaag agtgggaccg tggataaaca ctatacttga tgatttcaaa gtgagtctag  10980
aatctatagg tagtttgaca caagaattag aatatagagg tgaaagtcta ttatgcagtt  11040
taatatttag aaatgtatgg ttatataatc agattgctct acaattaaaa aatcatgcat  11100
tatgtaacaa taaactatat ttggacatat taaaggttct gaaacactta aaaacctttt  11160
ttaatcttga taatattgat acagcattaa cattgtatat gaatttaccc atgttatttg  11220
gtggtggtga tcccaacttg ttatatcgaa gtttctatag aagaactcct gacttcctca  11280
cagaggctat agttcactct gtgttcatac ttagttatta tacaaaccat gacttaaaag  11340
ataaacttca agatctgtca gatgatagat tgaataagtt cttaacatgc ataatcacgt  11400
ttgacaaaaa ccctaatgct gaattcgtaa cattgatgag agatcctcaa gctttagggt  11460
ctgagagaca agctaaaatt actagcgaaa tcaatagact ggcagttaca gaggttttga  11520
gtacagctcc aaacaaaata ttctccaaaa gtgcacaaca ttatactact acagagatag  11580
atctaaatga tattatgcaa aatatagaac ctacatatcc tcatgggcta agagttgttt  11640
atgaaagttt acccttttat aaagcagaga aaatagtaaa tcttatatca ggtacaaaat  11700
ctataactaa catactggaa aaaacttctg ccatagactt aacagatatt gatagagcca  11760
ctgagatgat gaggaaaaac ataactttgc ttataaggat acttccattg gattgtaaca  11820
gagataaaag agagatattg agtatggaaa acctaagtat tactgaatta agcaaatatg  11880
ttagggaaag atcttggtct ttatccaata tagttggtgt tacatcaccc agtatcatgt  11940
atacaatgga catcaaatat actacaagca ctatatctag tggcataatt atagagaaat  12000
ataatgttaa cagtttaaca cgtggtgaga gaggacccac taaaccatgg gttggttcat  12060
ctacacaaga gaaaaaaaca atgccagttt ataatagaca agtcttaacc aaaaaacaga  12120
gagatcaaat agatctatta gcaaaattgg attgggtgta tgcatctata gataacaagg  12180
atgaattcat ggaagaactc agcataggaa cccttgggtt aacatatgaa aaggccaaga  12240
aattatttcc acaatattta agtgtcaatt atttgcatcg ccttacagtc agtagtagac  12300
catgtgaatt ccctgcatca ataccagctt atagaacaac aaattatcac tttgacacta  12360
gccctattaa tcgcatatta acagaaaagt atggtgatga agatattgac atagtattcc  12420
aaaactgtat aagctttggc cttagtttaa tgtcagtagt agaacaattt actaatgtat  12480
gtcctaacag aattattctc atacctaagc ttaatgagat acatttgatg aaacctccca  12540
tattcacagg tgatgttgat attcacaagt taaaacaagt gatacaaaaa cagcatatgt  12600
```

ttttaccaga caaaataagt ttgactcaat atgtggaatt attcttaagt aataaaacac 12660
tcaaatctgg atctcatgtt aattctaatt taatattggc acataaaata tctgactatt 12720
ttcataatac ttacatttta agtactaatt tagctggaca ttggattctg attatacaac 12780
ttatgaaaga ttctaaaggt atttttgaaa aagattgggg agagggatat ataactgatc 12840
atatgtttat taatttgaaa gtttcttca atgcttataa gacctatctc ttgtgttttc 12900
ataaaggtta tggcaaagca aagctggagt gtgatatgaa cacttcagat cttctatgtg 12960
tattggaatt aatagacagt agttattgga agtctatgtc taaggtattt ttagaacaaa 13020
aagttatcaa atacattctt agccaagatg caagtttaca tagagtaaaa ggatgtcata 13080
gcttcaaatt atggtttctt aaacgtctta atgtagcaga attcacagtt tgcccttggg 13140
ttgttaacat agattatcat ccaacacata tgaaagcaat attaacttat atagatcttg 13200
ttagaatggg attgataaat atagatagaa tacacattaa aaataaacac aaattcaatg 13260
atgaatttta tacttctaat ctcttctaca ttaattataa cttctcagat aatactcatc 13320
tattaactaa acatataagg attgctaatt ctgaattaga aaataattac aacaaattat 13380
atcatcctac accagaaacc ctagagaata tactagccaa tccgattaaa agtaatgaca 13440
aaaagacact gaatgactat tgtataggta aaaatgttga ctcaataatg ttaccattgt 13500
tatctaataa gaagcttatt aaatcgtctg caatgattag aaccaattac agcaaacaag 13560
atttgtataa tttattccct atggttgtga ttgatagaat tatagatcat tcaggcaata 13620
cagccaaatc caaccaactt tacactacta cttcccacca aatatcctta gtgcacaata 13680
gcacatcact ttactgcatg cttccttggc atcatattaa tagattcaat tttgtattta 13740
gttctacagg ttgtaaaatt agtatagagt atattttaaa agatcttaaa attaaagatc 13800
ccaattgtat agcattcata ggtgaaggag cagggaattt attattgcgt acagtagtgg 13860
aacttcatcc tgacataaga tatatttaca gaagtctgaa agattgcaat gatcatagtt 13920
tacctattga gtttttaagg ctgtacaatg gacatatcaa cattgattat ggtgaaaatt 13980
tgaccattcc tgctacagat gcaaccaaca acattcattg gtcttattta catataaagt 14040
ttgctgaacc tatcagtctt tttgtctgtg atgccgaatt gtctgtaaca gtcaactgga 14100
gtaaaattat aatagaatgg agcaagcatg taagaaagtg caagtactgt tcctcagtta 14160
ataaatgtat gttaatagta aaatatcatg ctcaagatga tattgatttc aaattagaca 14220
atataactat attaaaaact tatgtatgct taggcagtaa gttaaaggga tcggaggttt 14280
acttagtcct tacaataggt cctgcgaata tattcccagt atttaatgta gtacaaaatg 14340
ctaaattgat actatcaaga accaaaaatt tcatcatgcc taagaaagct gataaagagt 14400
ctattgatgc aaatattaaa agtttgatac cctttctttg ttaccctata acaaaaaaag 14460
gaattaatac tgcattgtca aaactaaaga gtgttgttag tggagatata ctatcatatt 14520
ctatagctgg acgtaatgaa gttttcagca ataaacttat aaatcataag catatgaaca 14580
tcttaaaatg gttcaatcat gttttaaatt tcagatcaac agaactaaac tataaccatt 14640
tatatatggt agaatctaca tatccttacc taagtgaatt gttaaacagc ttgacaacca 14700
atgaacttaa aaaactgatt aaaatcacag gtagtctgtt atacaacttt cataatgaat 14760
aatgaataaa gatcttataa taaaaattcc catagctata cactaacact gtattcaatt 14820
atagttatta aaaattaaaa atcatataat tttttaaata acttttagtg aactaatcct 14880
aaagttatca ttttaatctt ggaggaataa atttaaaccc taatctaatt ggtttatatg 14940
tgtattaact aaattacgag atattagttt ttgacacttt ttttctcgt 14989

<210> SEQ ID NO 5
<211> LENGTH: 14870
<212> TYPE: DNA
<213> ORGANISM: Artificial Sequence
<220> FEATURE:
<223> OTHER INFORMATION: recombinant respiratory syncytial virus
sequence

<400> SEQUENCE: 5
acgggaaaaa atgcgtacaa caaacttgca taaaccaaaa aaatggggca aataagaatt 60
tgataagtac cacttaaatt taactccctt ggttagagat gggcagcaat tcattgagta 120
tgataaaagt tagattacaa aatttgtttg acaatgatga agtagcattg ttaaaaataa 180
catgctatac tgataaatta atacatttaa ctaatgcttt ggctaaggca gtgatacata 240
caatcaaatt gaatggcatt gtgtttgtgc atgttattac aagtagtgat atttgcccta 300
ataataatat tgtagtaaaa tccaatttca caacaatgcc agtactacaa aatggaggtt 360
atatatggga aatgatggaa ttaacacatt gctctcaacc taatggtcta ctagatgaca 420
attgtgaaat taaattctcc aaaaaactaa gtgattcaac aatgaccaat tatatgaatc 480
aattatctga attacttgga tttgatctta atccataaat tataattaat atcaactagc 540
aaatcaatgt cactaacacc attagttaat ataaaactta acagaagaca aaaatggggc 600
aaataaatca attcagccaa cccaaccatg gacacaaccc acaatgataa tacaccacaa 660
agactgatga tcacagacat gagaccgttg tcacttgaga ccataataac atcactaacc 720
agagacatca taacacacaa atttatatac ttgataaatc atgaatgcat agtgagaaaa 780
cttgatgaaa gacaggccac atttacattc ctggtcaact atgaaatgaa actattacac 840
aaagtaggaa gcactaaata taaaaaatat actgaataca acacaaaata tggcactttc 900
cctatgccaa tattcatcaa tcatgatggg ttcttagaat gcattggcat taagcctaca 960
aagcatactc ccataatata caagtatgat ctcaatccat aaatttcaac acaatattca 1020
cacaatctaa aacaacaact ctatgcataa ctatactcca tagtccagat ggagcctgaa 1080
aattatagta atttaaaact taaggagaga tataagatag aagatggggc aaatacaacc 1140
atggctctta gcaaagtcaa gttgaatgat acactcaaca aagatcaact tctgtcatcc 1200
agcaaataca ccatccaacg gagcacagga gatagtattg atactcctaa ttatgatgtg 1260
cagaaacaca tcaataagtt atgtggcatg ttattaatca cagaagatgc taatcataaa 1320
ttcactgggt taataggtat gttatatgcg atgtctaggt taggaagaga agacaccata 1380
aaaatactca gagatgcggg atatcatgta aaagcaaatg gagtagatgt aacaacacat 1440
cgtcaagaca ttaatggaaa agaaatgaaa tttgaagtgt taacattggc aagcttaaca 1500
actgaaattc aaatcaacat tgagatagaa tctagaaaat cctacaaaaa aatgctaaaa 1560
gaaatgggag aggtagctcc agaatacagg catgactctc ctgattgtgg gatgataata 1620
ttatgtatag cagcattagt aataactaaa ttagcagcag gggacagatc tggtcttaca 1680
gccgtgatta ggagagctaa taatgtccta aaaaatgaaa tgaaacgtta caaaggctta 1740
ctacccaagg acatagccaa cagcttctat gaagtgtttg aaaaacatcc ccactttata 1800
gatgtttttg ttcattttgg tatagcacaa tcttctacca gaggtggcag tagagttgaa 1860
gggatttttg caggattgtt tatgaatgcc tatggtgcag ggcaagtgat gttacggtgg 1920
ggagtcttag caaaatcggt taaaaatatt atgttaggac atgctagtgt gcaagcagaa 1980

-continued

```
atggaacaag ttgttgaggt ttatgaatat gcccaaaaat tgggtggtga agcaggattc   2040
taccatatat tgaacaaccc aaaagcatca ttattatctt tgactcaatt tcctcacttc   2100
tccagtgtag tattaggcaa tgctgctggc ctaggcataa tgggagagta cagaggtaca   2160
ccgaggaatc aagatctata tgatgcagca aaggcatatg ctgaacaact caaagaaaat   2220
ggtgtgatta actacagtgt actagacttg acagcagaag aactagaggc tatcaaacat   2280
cagcttaatc caaaagataa tgatgtagag ctttgagtta ataaaaaatg ggcaaataa    2340
atcatcatgg aaaagtttgc tcctgaattc catggagaag atgcaaacaa cagggctact   2400
aaattcctag aatcaataaa gggcaaattc acatcaccca aagatcccaa gaaaaaagat   2460
agtatcatat ctgtcaactc aatagatata gaagtaacca aagaaagccc tataacatca   2520
aattcaacta ttatcaaccc aacaaatgag acagatgata ctgcagggaa caagcccaat   2580
tatcaaagaa aacctctagt aagtttcaaa gaagacccta caccaagtga taatcccttt   2640
tctaaactat acaaagaaac catagaaaca tttgataaca atgaagaaga atccagctat   2700
tcatacgaag aaataaatga tcagacaaac gataatataa cagcaagatt agataggatt   2760
gatgaaaaat taagtgaaat actaggaatg cttcacacat tagtagtggc aagtgcagga   2820
cctacatctg ctcgggatgg tataagagat gccatggttg gtttaagaga agaaatgata   2880
gaaaaaatca gaactgaagc attaatgacc aatgacagat tagaagctat ggcaagactc   2940
aggaatgagg aaagtgaaaa gatggcaaaa gacacatcag atgaagtgtc tctcaatcca   3000
acatcagaga aattgaacaa cctattggaa gggaatgata gtgacaatga tctatcactt   3060
gaagatttct gattagttac caatcttcac atcaacacac aataccaaca gaagaccaac   3120
aaactaacca acccaatcat ccaaccaaac atccatccgc caatcagcca aacagccaac   3180
aaaacaacca gccaatccaa aactaaccac ccggaaaaaa tctataatat agttacaaaa   3240
aaaggaaagg gtggggcaaa tatggaaaca tacgtgaaca agcttcacga aggctccaca   3300
tacacagctg ctgttcaata caatgtctta gaaaaagacg atgaccctgc atcacttaca   3360
atatgggtgc ccatgttcca atcatctatg ccagcagatt tacttataaa agaactagct   3420
aatgtcaaca tactagtgaa acaaatatcc acacccaagg gaccttcact aagagtcatg   3480
ataaactcaa gaagtgcagt gctagcacaa atgcccagca aatttaccat atgcgctaat   3540
gtgtccttgg atgaaagaag caaactagca tatgatgtaa ccacaccctg tgaaatcaag   3600
gcatgtagtc taacatgcct aaaatcaaaa aatatgttga ctacagttaa agatctcact   3660
atgaagacac tcaaccctac acatgatatt attgctttat gtgaatttga aaacatagta   3720
acatcaaaaa aagtcataat accaacatac ctaagatcca tcagtgtcag aaataaagat   3780
ctgaacacac ttgaaaatat aacaaccact gaattcaaaa atgctatcac aaatgcaaaa   3840
atcatccctt actcaggatt actattagtc atcacagtga ctgacaacaa aggagcattc   3900
aaatacataa agccacaaag tcaattcata gtagatcttg gagcttacct agaaaaagaa   3960
agtatatatt atgttaccac aaattggaag cacacagcta cacgatttgc aatcaaaccc   4020
atggaagatt aacctttttc ctctacatca gtgtgttaat tcatacaaac tttctaccta   4080
cattcttcac ttcaccatca caatcacaaa cactctgtgg ttcaaccaat caaacaaaac   4140
ttatctgaag tcccagatca tcccaagtca ttgtttatca gatctagtac tcaaataagt   4200
taataaaaaa tatacacatg ggcaaataa tcattggagg aaatccaact aatcacaata    4260
tctgttaaca tagacaagtc cacacaccat acagaatcaa ccaatggaaa atacatccat   4320
aacaatagaa ttctcaagca aattctggcc ttactttaca ctaatacaca tgatcacaac   4380
```

```
aataatctct ttgctaatca taatctccat catgattgca atactaaaca aactttgtga   4440
atataacgta ttccataaca aaacctttga gttaccaaga gctcgagtta atacttgata   4500
aagtagttaa ttaaaaatag tcataacaat gaactaggat atcaagacta acaataacat   4560
tggggcaaat gcaaacatgt ccaaaaacaa ggaccaacgc accgctaaga cattagaaag   4620
gacctgggac actctcaatc atttattatt catatcatcg tgcttatata agttaaatct   4680
taaatctgta gcacaaatca cattatccat tctggcaatg ataatctcaa cttcacttat   4740
aattgcagcc atcatattca tagcctcggc aaaccacaaa gtcacaccaa caactgcaat   4800
catacaagat gcaacaagcc agatcaagaa cacaacccca acatacctca cccagaatcc   4860
tcagcttgga atcagtccct ctaatccgtc tgaaattaca tcacaaatca ccaccatact   4920
agcttcaaca acaccaggag tcaagtcaac cctgcaatcc acaacagtca agaccaaaaa   4980
cacaacaaca actcaaacac aacccagcaa gcccaccaca aaacaacgcc aaaacaaacc   5040
accaagcaaa cccaataatg attttcactt tgaagtgttc aactttgtac cctgcagcat   5100
atgcagcaac aatccaacct gctgggctat ctgcaaaaga ataccaaaca aaaaaccagg   5160
aaagaaaacc actaccaagc ccacaaaaaa accaaccctc aagacaacca aaaaagatcc   5220
caaacctcaa accactaaat caaaggaagt acccaccacc aagcccacag aagagccaac   5280
catcaacacc accaaaacaa acatcataac tacactactc acctccaaca ccacaggaaa   5340
tccagaactc acaagtcaaa tggaaacctt ccactcaact tcctccgaag gcaatccaag   5400
cccttctcaa gtctctacaa catccgagta cccatcacaa ccttcatctc cacccaacac   5460
accacgccag tagttactta aaaacatatt atcacaaaag gccttgacca acttaaacag   5520
aatcaaaata aactctgggg caaataacaa tggagttgct aatcctcaaa gcaaatgcaa   5580
ttaccacaat cctcactgca gtcacatttt gttttgcttc tggtcaaaac atcactgaag   5640
aattttatca atcaacatgc agtgcagtta gcaaaggcta tcttagtgct ctgagaactg   5700
gttggtatac cagtgttata actatagaat taagtaatat caagaaaaat aagtgtaatg   5760
gaacagatgc taaggtaaaa ttgataaaac aagaattaga taaatataaa aatgctgtaa   5820
cagaattgca gttgctcatg caaagcacac aagcaacaaa caatcgagcc agaagagaac   5880
taccaaggtt tatgaattat acactcaaca atgccaaaaa aaccaatgta acattaagca   5940
agaaaaggaa aagaagattt cttggttttt tgttaggtgt tggatctgca atcgccagtg   6000
gcgttgctgt atctaaggtc ctgcacctag aaggggaagt gaacaagatc aaaagtgctc   6060
tactatccac aaacaaggct gtagtcagct tatcaaatgg agttagtgtt ttaaccagca   6120
aagtgttaga cctcaaaaac tatatagata aacaattgtt acctattgtg aacaagcaaa   6180
gctgcagcat atcaaatata gaaactgtga tagagttcca acaaaagaac aacagactac   6240
tagagattac cagggaattt agtgttaatg caggcgtaac tacacctgta agcacttaca   6300
tgttaactaa tagtgaatta ttgtcattaa tcaatgatat gcctataaca aatgatcaga   6360
aaaagttaat gtccaacaat gttcaaatag ttagacagca aagttactct atcatgtcca   6420
taataaaaga ggaagtctta gcatatgtag tacaattacc actatatggt gttatagata   6480
caccctgttg gaaactacac acatcccctc tatgtacaac caacacaaaa gaagggtcca   6540
acatctgttt aacaagaact gacagaggat ggtactgtga caatgcagga tcagtatctt   6600
tcttcccaca agctgaaaca tgtaaagttc aatcaaatcg agtattttgt gacacaatga   6660
acagtttaac attaccaagt gaagtaaatc tctgcaatgt tgacatattc aaccccaaat   6720
```

-continued

```
atgattgtaa aattatgact tcaaaaacag atgtaagcag ctccgttatc acatctctag   6780
gagccattgt gtcatgctat ggcaaaacta aatgtacagc atccaataaa aatcgtggaa   6840
tcataaagac attttctaac gggtgcgatt atgtatcaaa taaaggggtg gacactgtgt   6900
ctgtaggtaa cacattatat tatgtaaata agcaagaagg taaaagtctc tatgtaaaag   6960
gtgaaccaat aataaatttc tatgacccat tagtattccc ctctgatgaa tttgatgcat   7020
caatatctca agtcaacgag aagattaacc agagcctagc atttattcgt aaatccgatg   7080
aattattaca taatgtaaat gctggtaaat ccaccacaaa tatcatgata actactataa   7140
ttatagtgat tatagtaata ttgttatcat taattgctgt tggactgctc ttatactgta   7200
aggccagaag cacaccagtc acactaagca aagatcaact gagtggtata aataatattg   7260
catttagtaa ctaaataaaa atagcaccta atcatgttct tacaatggtt tactatctgc   7320
tcatagacaa cccatctgtc attggatttt cttaaaatct gaacttcatc gaaactctca   7380
tctataaacc atctcactta cactatttaa gtagattcct agtttatagt tatataaaac   7440
acaattgcat gccagattaa cttaccatct gtaaaaatga aaactggggc aaatatgtca   7500
cgaaggaatc cttgcaaatt tgaaattcga ggtcattgct taaatggtaa gaggtgtcat   7560
tttagtcata attattttga atggccaccc catgcactgc ttgtaagaca aaactttatg   7620
ttaaacagaa tacttaagtc tatggataaa agtatagata ccttatcaga aataagtgga   7680
gctgcagagt tggacagaac agaagagtat gctcttggtg tagttggagt gctagagagt   7740
tatataggat caataaacaa tataactaaa caatcagcat gtgttgccat gagcaaactc   7800
ctcactgaac tcaatagtga tgatatcaaa aagctgaggg acaatgaaga gctaaattca   7860
cccaagataa gagtgtacaa tactgtcata tcatatattg aaagcaacag gaaaaacaat   7920
aaacaaacta tccatctgtt aaaaagattg ccagcagacg tattgaagaa aaccatcaaa   7980
aacacattgg atatccataa gagcataacc atcaacaacc caaaagaatc aactgttagt   8040
gatacaaacg accacgccaa aaataacgat actacctaac actcaattct aacactcacc   8100
acatcgttac attattaatt caaacaattc aagttgtggg acaaaatgga tcccattatt   8160
aatggaaatt ctgctaatgt ttatctaacc gatagttatt taaaaggtgt tatctctttc   8220
tcagagtgta atgctttagg aagttacata ttcaatggtc cttatctcaa aaatgattat   8280
accaacttaa ttagtagaca aaatccatta atagaacaca tgaatctaaa gaaactaaat   8340
ataacacagt ccttaatatc taagtatcat aaaggtgaaa taaaattaga agaacctact   8400
tattttcagt cattacttat gacatacaag agtatgacct cgtcagaaca gattgctacc   8460
actaatttac ttaaaaagat aataagaaga gctatagaaa taagtgatgt caaagtctat   8520
gctatattga ataaactagg gcttaaagaa aaggacaaga ttaaatccaa caatggacaa   8580
gatgaagaca actcagttat tacgaccata atcaaagatg atatactttc agctgttaaa   8640
gataatcaat ctcatcttaa agcagacaaa aatcactcta caaaacaaaa agacacaatc   8700
aaaacaacac tcttgaagaa attgatgtgt tcaatgcaac atcctccatc atggttaata   8760
cattggttta acttatacac aaaattaaac aacatattaa cacagtatcg atcaaatgag   8820
gtaaaaaacc atgggtttac attgatagat aatcaaactc ttagtggatt tcaatttatt   8880
ttgaaccaat atggttgtat agtttatcat aaggaactca aaagaattac tgtgacaacc   8940
tataatcaat tcttgacatg gaaagatatt agccttagta gattaaatgt ttgtttaatt   9000
acatggatta gtaactgctt gaacacatta aataaaagct taggcttaag atgcggattc   9060
aataatgtta tcttgacaca actattcctt tatggagatt gtatactaaa gctatttcac   9120
```

```
aatgaggggt tctacataat aaaagaggta gagggattta ttatgtctct aattttaaat   9180
ataacagaag aagatcaatt cagaaaacga ttttataata gtatgctcaa caacatcaca   9240
gatgctgcta ataaagctca gaaaaatctg ctatcaagag tatgtcatac attattagat   9300
aagacagtgt ccgataatat aataaatggc agatggataa ttctattaag taagttcctt   9360
aaattaatta agcttgcagg tgacaataac cttaacaatc tgagtgaact atatttttttg   9420
ttcagaatat ttggacaccc aatggtagat gaaagacaag ccatggatgc tgttaaaatt   9480
aattgcaatg agaccaaatt ttacttgtta agcagtctga gtatgttaag aggtgccttt   9540
atatatagaa ttataaaagg gtttgtaaat aattacaaca gatggcctac tttaagaaat   9600
gctattgttt taccccttaag atggttaact tactataaac taaacactta tccttctttg   9660
ttggaactta cagaaagaga tttgattgtg ttatcaggac tacgtttcta tcgtgagttt   9720
cggttgccta aaaaagtgga tcttgaaatg attataaatg ataaagctat atcacctcct   9780
aaaaatttga tatggactag tttccctaga aattacatgc catcacacat acaaaactat   9840
atagaacatg aaaaattaaa attttccgag agtgataaat caagaagagt attagagtat   9900
tatttaagag ataacaaatt caatgaatgt gatttataca actgtgtagt taatcaaagt   9960
tatctcaaca accctaatca tgtggtatca ttgacaggca aagaaagaga actcagtgta  10020
ggtagaatgt ttgcaatgca accgggaatg ttcagacagg ttcaaatatt ggcagagaaa  10080
atgatagctg aaaacatttt acaattcttt cctgaaagtc ttacaagata tggtgatcta  10140
gaactacaaa aaatattaga actgaaagca ggaataagta acaaatcaaa tcgctacaat  10200
gataattaca acaattacat tagtaagtgc tctatcatca cagatctcag caaattcaat  10260
caagcatttc gatatgaaac gtcatgtatt tgtagtgatg tgctggatga actgcatggt  10320
gtacaatctc tattttcctg gttacattta actattcctc atgtcacaat aatatgcaca  10380
tataggcatg cacccccccta tataggagat catattgtag atcttaacaa tgtagatgaa  10440
caaagtggat tatatagata tcacatgggt ggcatcgaag ggtggtgtca aaaactatgg  10500
accatagaag ctatatcact attggatcta atatctctca aagggaaatt ctcaattact  10560
gctttaatta atggtgacaa tcaatcaata gatataagca aaccaatcag actcatggaa  10620
ggtcaaactc atgctcaagc agattatttg ctagcattaa atagccttaa attactgtat  10680
aaagagtatg caggcatagg ccacaaatta aaaggaactg agacttatat atcacgagat  10740
atgcaattta tgagtaaaac aattcaacat aacggtgtat attacccagc tagtataaag  10800
aaagtcctaa gagtgggacc gtggataaac actatacttg atgatttcaa agtgagtcta  10860
gaatctatag gtagtttgac acaagaatta gaatatagag gtgaaagtct attatgcagt  10920
ttaatattta gaaatgtatg gttatataat cagattgctc tacaattaaa aaatcatgca  10980
ttatgtaaca ataaactata tttggacata ttaaaggttc tgaaacactt aaaaaccttt  11040
tttaatcttg ataatattga tacagcatta acattgtata tgaatttacc catgttattt  11100
ggtggtggtg atcccaactt gttatatcga agtttctata gaagaactcc tgacttcctc  11160
acagaggcta tagttcactc tgtgttcata cttagttatt atacaaacca tgacttaaaa  11220
gataaacttc aagatctgtc agatgataga ttgaataagt tcttaacatg cataatcacg  11280
tttgacaaaa accctaatgc tgaattcgta acattgatga gagatcctca agctttaggg  11340
tctgagagac aagctaaaat tactagcgaa atcaatagac tggcagttac agaggttttg  11400
agtacagctc caaacaaaat attctccaaa agtgcacaac attatactac tacagagata  11460
```

-continued

```
gatctaaatg atattatgca aaatatagaa cctacatatc ctcatgggct aagagttgtt  11520
tatgaaagtt taccctttta taaagcagag aaaatagtaa atcttatatc aggtacaaaa  11580
tctataacta acatactgga aaaaacttct gccatagact taacagatat tgatagagcc  11640
actgagatga tgaggaaaaa cataactttg cttataagga tacttccatt ggattgtaac  11700
agagataaaa gagagatatt gagtatggaa aacctaagta ttactgaatt aagcaaatat  11760
gttagggaaa gatcttggtc tttatccaat atagttggtg ttacatcacc cagtatcatg  11820
tatacaatgg acatcaaata tactacaagc actatatcta gtggcataat tatagagaaa  11880
tataatgtta acagtttaac acgtggtgag agaggaccca ctaaaccatg ggttggttca  11940
tctacacaag agaaaaaaac aatgccagtt tataatagac aagtcttaac caaaaaacag  12000
agagatcaaa tagatctatt agcaaaattg gattgggtgt atgcatctat agataacaag  12060
gatgaattca tggaagaact cagcatagga acccttgggt taacatatga aaaggccaag  12120
aaattatttc cacaatattt aagtgtcaat tatttgcatc gccttacagt cagtagtaga  12180
ccatgtgaat tccctgcatc aataccagct tatagaacaa caaattatca ctttgacact  12240
agccctatta atcgcatatt aacagaaaag tatggtgatg aagatattga catagtattc  12300
caaaactgta taagctttgg ccttagttta atgtcagtag tagaacaatt tactaatgta  12360
tgtcctaaca gaattattct catacctaag cttaatgaga tacatttgat gaaacctccc  12420
atattcacag gtgatgttga tattcacaag ttaaaacaag tgatacaaaa acagcatatg  12480
tttttaccag acaaaataag tttgactcaa tatgtggaat tattcttaag taataaaaca  12540
ctcaaatctg gatctcatgt taattctaat ttaatattgg cacataaaat atctgactat  12600
tttcataata cttacatttt aagtactaat ttagctggac attggattct gattatacaa  12660
cttatgaaag attctaaagg tatttttgaa aaagattggg gagagggata tataactgat  12720
catatgttta ttaatttgaa agttttcttc aatgcttata agacctatct cttgtgtttt  12780
cataaaggtt atggcaaagc aaagctggag tgtgatatga acacttcaga tcttctatgt  12840
gtattggaat taatagacag tagttattgg aagtctatgt ctaaggtatt tttagaacaa  12900
aaagttatca aatacattct tagccaagat gcaagtttac atagagtaaa aggatgtcat  12960
agcttcaaat tatggtttct taaacgtctt aatgtagcag aattcacagt ttgcccttgg  13020
gttgttaaca tagattatca tccaacacat atgaaagcaa tattaactta tatagatctt  13080
gttagaatgg gattgataaa tatagataga atacacatta aaaataaaca caaattcaat  13140
gatgaatttt atacttctaa tctcttctac attaattata acttctcaga taatactcat  13200
ctattaacta aacatataag gattgctaat tctgaattag aaaataatta caacaaatta  13260
tatcatccta caccagaaac cctagagaat atactagcca atccgattaa aagtaatgac  13320
aaaaagacac tgaatgacta ttgtataggt aaaaatgttg actcaataat gttaccattg  13380
ttatctaata agaagcttat taaatcgtct gcaatgatta gaaccaatta cagcaaacaa  13440
gatttgtata atttattccc tatggttgtg attgatagaa ttatagatca ttcaggcaat  13500
acagccaaat ccaaccaact ttacactact acttcccacc aaatatcctt agtgcacaat  13560
agcacatcac tttactgcat gcttccttgg catcatatta atagattcaa ttttgtattt  13620
agttctacag gttgtaaaat tagtatagag tatattttaa aagatcttaa aattaaagat  13680
cccaattgta tagcattcat aggtgaagga gcagggaatt tattattgcg tacagtagtg  13740
gaacttcatc ctgacataag atatatttac agaagtctga aagattgcaa tgatcatagt  13800
ttacctattg agtttttaag gctgtacaat ggacatatca acattgatta tggtgaaaat  13860
```

```
ttgaccattc ctgctacaga tgcaaccaac aacattcatt ggtcttattt acatataaag  13920

tttgctgaac ctatcagtct ttttgtctgt gatgccgaat tgtctgtaac agtcaactgg  13980

agtaaaatta taatagaatg gagcaagcat gtaagaaagt gcaagtactg ttcctcagtt  14040

aataaatgta tgttaatagt aaaatatcat gctcaagatg atattgattt caaattagac  14100

aatataacta tattaaaaac ttatgtatgc ttaggcagta agttaaaggg atcggaggtt  14160

tacttagtcc ttacaatagg tcctgcgaat atattcccag tatttaatgt agtacaaaat  14220

gctaaattga tactatcaag aaccaaaaat ttcatcatgc ctaagaaagc tgataaagag  14280

tctattgatg caaatattaa aagtttgata ccctttcttt gttaccctat aacaaaaaaa  14340

ggaattaata ctgcattgtc aaaactaaag agtgttgtta gtggagatat actatcatat  14400

tctatagctg gacgtaatga agttttcagc aataaactta taaatcataa gcatatgaac  14460

atcttaaaat ggttcaatca tgttttaaat ttcagatcaa cagaactaaa ctataaccat  14520

ttatatatgg tagaatctac atatccttac ctaagtgaat tgttaaacag cttgacaacc  14580

aatgaactta aaaaactgat taaaatcaca ggtagtctgt tatacaactt tcataatgaa  14640

taatgaataa agatcttata ataaaaattc ccatagctat acactaacac tgtattcaat  14700

tatagttatt aaaaattaaa aatcatataa ttttttaaat aacttttagt gaactaatcc  14760

taaagttatc attttaatct tggaggaata aatttaaacc ctaatctaat tggtttatat  14820

gtgtattaac taaattacga gatattagtt tttgacactt tttttctcgt             14870
```

<210> SEQ ID NO 6
<211> LENGTH: 14877
<212> TYPE: DNA
<213> ORGANISM: Artificial Sequence
<220> FEATURE:
<223> OTHER INFORMATION: recombinant respiratory syncytial virus sequence

<400> SEQUENCE: 6

```
acgggaaaaa atgcgtacaa caaacttgca taaaccaaaa aaatggggca aataagaatt     60

tgataagtac cacttaaatt taactccctt ggttagagat gggcagcaat tcattgagta    120

tgataaaagt tagattacaa aatttgtttg acaatgatga agtagcattg ttaaaaataa    180

catgctatac tgataaatta atacatttaa ctaatgcttt ggctaaggca gtgatacata    240

caatcaaatt gaatggcatt gtgtttgtgc atgttattac aagtagtgat atttgcccta    300

ataataatat tgtagtaaaa tccaatttca caacaatgcc agtactacaa aatggaggtt    360

atatatggga aatgatggaa ttaacacatt gctctcaacc taatggtcta ctagatgaca    420

attgtgaaat taaattctcc aaaaaactaa gtgattcaac aatgaccaat tatatgaatc    480

aattatctga attacttgga tttgatctta atccataaat tataattaat atcaactagc    540

aaatcaatgt cactaacacc attagttaat ataaaactta acagaagaca aaaatggggc    600

aaataaatca attcagccaa cccaaccatg gacacaaccc acaatgataa tacaccacaa    660

agactgatga tcacagacat gagaccgttg tcacttgaga ccataataac atcactaacc    720

agagacatca taacacacaa atttatatac ttgataaatc atgaatgcat agtgagaaaa    780

cttgatgaaa gacaggccac atttacattc ctggtcaact atgaaatgaa actattacac    840

aaagtaggaa gcactaaata taaaaaatat actgaataca acacaaaata tggcactttc    900

cctatgccaa tattcatcaa tcatgatggg ttcttagaat gcattggcat taagcctaca    960

aagcatactc ccataatata caagtatgat ctcaatccat aaatttcaac acaatattca   1020
```

-continued

```
cacaatctaa aacaacaact ctatgcataa ctatactcca tagtccagat ggagcctgaa   1080
aattatagta atttaaaact taaggagaga tataagatag aagatggggc aaatacaacc   1140
atggctctta gcaaagtcaa gttgaatgat acactcaaca aagatcaact tctgtcatcc   1200
agcaaataca ccatccaacg gagcacagga gatagtattg atactcctaa ttatgatgtg   1260
cagaaacaca tcaataagtt atgtggcatg ttattaatca cagaagatgc taatcataaa   1320
ttcactgggt taataggtat gttatatgcg atgtctaggt taggaagaga agacaccata   1380
aaaatactca gagatgcggg atatcatgta aaagcaaatg gagtagatgt aacaacacat   1440
cgtcaagaca ttaatggaaa agaaatgaaa tttgaagtgt taacattggc aagcttaaca   1500
actgaaattc aaatcaacat tgagatagaa tctagaaaat cctacaaaaa aatgctaaaa   1560
gaaatgggag aggtagctcc agaatacagg catgactctc ctgattgtgg gatgataata   1620
ttatgtatag cagcattagt aataactaaa ttagcagcag gggacagatc tggtcttaca   1680
gccgtgatta ggagagctaa taatgtccta aaaaatgaaa tgaaacgtta caaaggctta   1740
ctacccaagg acatagccaa cagcttctat gaagtgtttg aaaaacatcc ccactttata   1800
gatgtttttg ttcattttgg tatagcacaa tcttctacca gaggtggcag tagagttgaa   1860
gggatttttg caggattgtt tatgaatgcc tatggtgcag ggcaagtgat gttacggtgg   1920
ggagtcttag caaaatcggt taaaaatatt atgttaggac atgctagtgt gcaagcagaa   1980
atggaacaag ttgttgaggt ttatgaatat gcccaaaaat tgggtggtga agcaggattc   2040
taccatatat tgaacaaccc aaaagcatca ttattatctt tgactcaatt tcctcacttc   2100
tccagtgtag tattaggcaa tgctgctggc ctaggcataa tgggagagta cagaggtaca   2160
ccgaggaatc aagatctata tgatgcagca aaggcatatg ctgaacaact caaagaaaat   2220
ggtgtgatta actacagtgt actagacttg acagcagaag aactagaggc tatcaaacat   2280
cagcttaatc caaaagataa tgatgtagag ctttgagtta ataaaaaatg ggcaaataa    2340
atcatcatgg aaaagtttgc tcctgaattc catggagaag atgcaaacaa cagggctact   2400
aaattcctag aatcaataaa gggcaaattc acatcaccca aagatcccaa gaaaaaagat   2460
agtatcatat ctgtcaactc aatagatata gaagtaacca aagaaagccc tataacatca   2520
aattcaacta ttatcaaccc aacaaatgag acagatgata ctgcagggaa caagcccaat   2580
tatcaaagaa aacctctagt aagtttcaaa gaagacccta caccaagtga taatcccttt   2640
tctaaactat acaaagaaac catagaaaca tttgataaca atgaagaaga atccagctat   2700
tcatacgaag aaataaatga tcagacaaac gataatataa cagcaagatt agataggatt   2760
gatgaaaaat taagtgaaat actaggaatg cttcacacat tagtagtggc aagtgcagga   2820
cctacatctg ctcgggatgg tataagagat gccatggttg gtttaagaga agaaatgata   2880
gaaaaaatca gaactgaagc attaatgacc aatgacagat tagaagctat ggcaagactc   2940
aggaatgagg aaagtgaaaa gatggcaaaa gacacatcag atgaagtgtc tctcaatcca   3000
acatcagaga aattgaacaa cctattggaa gggaatgata gtgacaatga tctatcactt   3060
gaagatttct gattagttac caatcttcac atcaacacac aataccaaca gaagaccaac   3120
aaactaacca acccaatcat ccaaccaaac atccatccgc caatcagcca aacagccaac   3180
aaaacaacca gccaatccaa aactaaccac ccggaaaaaa tctataatat agttacaaaa   3240
aaaggaaagg gtggggcaaa tatggaaaca tacgtgaaca agcttcacga aggctccaca   3300
tacacagctg ctgttcaata caatgtctta gaaaaagacg atgaccctgc atcacttaca   3360
```

-continued atatgggtgc ccatgttcca atcatctatg ccagcagatt tacttataaa agaactagct 3420
aatgtcaaca tactagtgaa acaaatatcc acacccaagg gaccttcact aagagtcatg 3480
ataaactcaa gaagtgcagt gctagcacaa atgcccagca aatttaccat atgcgctaat 3540
gtgtccttgg atgaaagaag caaactagca tatgatgtaa ccacaccctg tgaaatcaag 3600
gcatgtagtc taacatgcct aaaatcaaaa aatatgttga ctacagttaa agatctcact 3660
atgaagacac tcaaccctac acatgatatt attgctttat gtgaatttga aaacatagta 3720
acatcaaaaa aagtcataat accaacatac ctaagatcca tcagtgtcag aaataaagat 3780
ctgaacacac ttgaaaatat aacaaccact gaattcaaaa atgctatcac aaatgcaaaa 3840
atcatccctt actcaggatt actattagtc atcacagtga ctgacaacaa aggagcattc 3900
aaatacataa agccacaaag tcaattcata gtagatcttg gagcttacct agaaaaagaa 3960
agtatatatt atgttaccac aaattggaag cacacagcta cacgatttgc aatcaaaccc 4020
atggaagatt aacctttttc ctctacatca gtgtgttaat tcatacaaac tttctaccta 4080
cattcttcac ttcaccatca caatcacaaa cactctgtgg ttcaaccaat caaacaaaac 4140
ttatctgaag tcccagatca tcccaagtca ttgtttatca gatctagtac tcaaataagt 4200
taataaaaaa tatacacatg gggcaaataa tcattggagg aaatccaact aatcacaata 4260
tctgttaaca tagacaagtc cacacaccat acagaatcaa ccaatggaaa atacatccat 4320
aacaatagaa ttctcaagca aattctggcc ttactttaca ctaatacaca tgatcacaac 4380
aataatctct ttgctaatca taatctccat catgattgca atactaaaca aactttgtga 4440
atataacgta ttccataaca aaacctttga gttaccaaga gctcgagtta atacttgata 4500
aagtagttaa ttaaaaatag tcataacaat gaactaggat atcaagacta acaataacat 4560
tggggcaaat gcaaacatgt ccaaaaacaa ggaccaacgc accgctaaga cattagaaag 4620
gacctgggac actctcaatc atttattatt catatcatcg tgcttatata agttaaatct 4680
taaatctgta gcacaaatca cattatccat tctggcaatg ataatctcaa cttcacttat 4740
aattgcagcc atcatattca tagcctcggc aaaccacaaa gtcacaccaa caactgcaat 4800
catacaagat gcaacaagcc agatcaagaa cacaacccca acatacctca cccagaatcc 4860
tcagcttgga atcagtccct ctaatccgtc tgaaattaca tcacaaatca ccaccatact 4920
agcttcaaca acaccaggag tcaagtcaac cctgcaatcc acaacagtca agaccaaaaa 4980
cacaacaaca actcaaacac aacccagcaa gcccaccaca aaacaacgcc aaaacaaacc 5040
accaagcaaa cccaataatg attttcactt tgaagtgttc aactttgtac cctgcagcat 5100
atgcagcaac aatccaacct gctgggctat ctgcaaaaga ataccaaaca aaaaaccagg 5160
aaagaaaacc actaccaagc ccacaaaaaa accaaccctc aagacaacca aaaaagatcc 5220
caaacctcaa accactaaat caaaggaagt acccaccacc aagcccacag aagagccaac 5280
catcaacacc accaaaacaa acatcataac tacactactc acctccaaca ccacaggaaa 5340
tccagaactc acaagtcaaa tggaaacctt ccactcaact tcctccgaag gcaatccaag 5400
cccttctcaa gtctctacaa catccgagta cccatcacaa ccttcatctc cacccaacac 5460
accacgccag tagttactta aaaacatatt atcacaaaag gccttgacca acttaaacag 5520
aatcaaaata aactctgggg caaataacaa tggagttgct aatcctcaaa gcaaatgcaa 5580
ttaccacaat cctcactgca gtcacatttt gttttgcttc tggtcaaaac atcactgaag 5640
aattttatca atcaacatgc agtgcagtta gcaaaggcta tcttagtgct ctgagaactg 5700
gttggtatac cagtgttata actatagaat taagtaatat caagaaaaat aagtgtaatg 5760
gaacagatgc taaggtaaaa ttgataaaac aagaattaga taaatataaa aatgctgtaa 5820
cagaattgca gttgctcatg caaagcacac aagcaacaaa caatcgagcc agaagagaac 5880
taccaaggtt tatgaattat acactcaaca atgccaaaaa aaccaatgta acattaagca 5940
agaaaaggaa aagaagattt cttggttttt tgttaggtgt tggatctgca atcgccagtg 6000
gcgttgctgt atctaaggtc ctgcacctag aaggggaagt gaacaagatc aaaagtgctc 6060
tactatccac aaacaaggct gtagtcagct tatcaaatgg agttagtgtt ttaaccagca 6120
aagtgttaga cctcaaaaac tatatagata aacaattgtt acctattgtg aacaagcaaa 6180
gctgcagcat atcaaatata gaaactgtga tagagttcca acaaaagaac aacagactac 6240
tagagattac cagggaattt agtgttaatg caggcgtaac tacacctgta agcacttaca 6300
tgttaactaa tagtgaatta ttgtcattaa tcaatgatat gcctataaca aatgatcaga 6360
aaaagttaat gtccaacaat gttcaaatag ttagacagca aagttactct atcatgtcca 6420
taataaaaga ggaagtctta gcatatgtag tacaattacc actatatggt gttatagata 6480
caccctgttg gaaactacac acatcccctc tatgtacaac caacacaaaa gaagggtcca 6540
acatctgttt aacaagaact gacagaggat ggtactgtga caatgcagga tcagtatctt 6600
tcttcccaca agctgaaaca tgtaaagttc aatcaaatcg agtattttgt gacacaatga 6660
acagtttaac attaccaagt gaagtaaatc tctgcaatgt tgacatattc aaccccaaat 6720
atgattgtaa aattatgact tcaaaaacag atgtaagcag ctccgttatc acatctctag 6780
gagccattgt gtcatgctat ggcaaaacta aatgtacagc atccaataaa aatcgtggaa 6840
tcataaagac attttctaac gggtgcgatt atgtatcaaa taaaggggtg gacactgtgt 6900
ctgtaggtaa cacattatat tatgtaaata agcaagaagg taaaagtctc tatgtaaaag 6960
gtgaaccaat aataaatttc tatgacccat tagtattccc ctctgatgaa tttgatgcat 7020
caatatctca agtcaacgag aagattaacc agagcctagc atttattcgt aaatccgatg 7080
aattattaca taatgtaaat gctggtaaat ccaccacaaa tatcatgata actactataa 7140
ttatagtgat tatagtaata ttgttatcat taattgctgt tggactgctc ttatactgta 7200
aggccagaag cacaccagtc acactaagca aagatcaact gagtggtata aataatattg 7260
catttagtaa ctaaataaaa atagcaccta atcatgttct tacaatggtt tactatctgc 7320
tcatagacaa cccatctgtc attggatttt cttaaaatct gaacttcatc gaaactctca 7380
tctataaacc atctcactta cactatttaa gtagattcct agtttatagt tatataaaac 7440
acaattgcat gccagattaa cttaccatct gtaaaaatga aaactggggc aaatatgtca 7500
cgaaggaatc cttgcaaatt tgaaattcga ggtcattgct taaatggtaa gaggtgtcat 7560
tttagtcata attattttga atggccaccc catgcactgc ttgtaagaca aaactttatg 7620
ttaaacagaa tacttaagtc tatggataaa agtatagata ccttatcaga aataagtgga 7680
gctgcagagt tggacagaac agaagagtat gctcttggtg tagttggagt gctagagagt 7740
tatataggat caataaacaa tataactaaa caatcagcat gtgttgccat gagcaaactc 7800
ctcactgaac tcaatagtga tgatatcaaa aagctgaggg acaatgaaga gctaaattca 7860
cccaagataa gagtgtacaa tactgtcata tcatatattg aaagcaacag gaaaaacaat 7920
aaacaaacta tccatctgtt aaaaagattg ccagcagacg tattgaagaa aaccatcaaa 7980
aacacattgg atatccataa gagcataacc atcaacaacc caaaagaatc aactgttagt 8040
gatacaaatg accatgccaa aaataatgat actacctgac aaataacgtt caattctaac 8100

-continued

```
actcaccaca tcgttacatt attaattcaa acaattcaag ttgtgggaca aaatggatcc   8160
cattattaat ggaaattctg ctaatgttta tctaaccgat agttatttaa aaggtgttat   8220
ctctttctca gagtgtaatg ctttaggaag ttacatattc aatggtcctt atctcaaaaa   8280
tgattatacc aacttaatta gtagacaaaa tccattaata gaacacatga atctaaagaa   8340
actaaatata acacagtcct taatatctaa gtatcataaa ggtgaaataa aattagaaga   8400
acctacttat tttcagtcat tacttatgac atacaagagt atgacctcgt cagaacagat   8460
tgctaccact aatttactta aaaagataat aagaagagct atagaaataa gtgatgtcaa   8520
agtctatgct atattgaata aactagggct taaagaaaag gacaagatta aatccaacaa   8580
tggacaagat gaagacaact cagttattac gaccataatc aaagatgata tactttcagc   8640
tgttaaagat aatcaatctc atcttaaagc agacaaaaat cactctacaa aacaaaaaga   8700
cacaatcaaa acaacactct tgaagaaatt gatgtgttca atgcaacatc ctccatcatg   8760
gttaatacat tggtttaact tatacacaaa attaaacaac atattaacac agtatcgatc   8820
aaatgaggta aaaaaccatg ggtttacatt gatagataat caaactctta gtggatttca   8880
atttattttg aaccaatatg gttgtatagt ttatcataag gaactcaaaa gaattactgt   8940
gacaacctat aatcaattct tgacatggaa agatattagc cttagtagat taaatgtttg   9000
tttaattaca tggattagta actgcttgaa cacattaaat aaaagcttag gcttaagatg   9060
cggattcaat aatgttatct tgacacaact attcctttat ggagattgta tactaaagct   9120
atttcacaat gaggggttct acataataaa agaggtagag ggatttatta tgtctctaat   9180
tttaaatata acagaagaag atcaattcag aaaacgattt tataatagta tgctcaacaa   9240
catcacagat gctgctaata aagctcagaa aaatctgcta tcaagagtat gtcatacatt   9300
attagataag acagtgtccg ataatataat aaatggcaga tggataattc tattaagtaa   9360
gttccttaaa ttaattaagc ttgcaggtga caataacctt aacaatctga gtgaactata   9420
tttttgttc agaatatttg gacacccaat ggtagatgaa agacaagcca tggatgctgt   9480
taaaattaat tgcaatgaga ccaaattta cttgttaagc agtctgagta tgttaagagg   9540
tgcctttata tatagaatta taaaagggtt tgtaaataat tacaacagat ggcctacttt   9600
aagaaatgct attgttttac ccttaagatg gttaacttac tataaactaa acacttatcc   9660
ttctttgttg gaacttacag aaagagattt gattgtgtta tcaggactac gtttctatcg   9720
tgagtttcgg ttgcctaaaa aagtggatct tgaaatgatt ataaatgata aagctatatc   9780
acctcctaaa aatttgatat ggactagttt ccctagaaat tacatgccat cacacataca   9840
aaactatata gaacatgaaa aattaaaatt ttccgagagt gataaatcaa gaagagtatt   9900
agagtattat ttaagagata acaaattcaa tgaatgtgat ttatacaact gtgtagttaa   9960
tcaaagttat ctcaacaacc ctaatcatgt ggtatcattg acaggcaaag aaagagaact  10020
cagtgtaggt agaatgtttg caatgcaacc gggaatgttc agacaggttc aaatattggc  10080
agagaaaatg atagctgaaa acattttaca attctttcct gaaagtctta caagatatgg  10140
tgatctagaa ctacaaaaaa tattagaact gaaagcagga ataagtaaca aatcaaatcg  10200
ctacaatgat aattacaaca attacattag taagtgctct atcatcacag atctcagcaa  10260
attcaatcaa gcatttcgat atgaaacgtc atgtatttgt agtgatgtgc tggatgaact  10320
gcatggtgta caatctctat tttcctggtt acatttaact attcctcatg tcacaataat  10380
atgcacatat aggcatgcac ccccctatat aggagatcat attgtagatc ttaacaatgt  10440
agatgaacaa agtggattat atagatatca catgggtggc atcgaagggt ggtgtcaaaa  10500
```

actatggacc atagaagcta tatcactatt ggatctaata tctctcaaag ggaaattctc 10560
aattactgct ttaattaatg gtgacaatca atcaatagat ataagcaaac caatcagact 10620
catggaaggt caaactcatg ctcaagcaga ttatttgcta gcattaaata gccttaaatt 10680
actgtataaa gagtatgcag gcataggcca caaattaaaa ggaactgaga cttatatatc 10740
acgagatatg caatttatga gtaaaacaat tcaacataac ggtgtatatt acccagctag 10800
tataaagaaa gtcctaagag tgggaccgtg gataaacact atacttgatg atttcaaagt 10860
gagtctagaa tctataggta gtttgacaca agaattagaa tatagaggtg aaagtctatt 10920
atgcagttta atatttagaa atgtatggtt atataatcag attgctctac aattaaaaaa 10980
tcatgcatta tgtaacaata aactatattt ggacatatta aaggttctga aacacttaaa 11040
aacctttttt aatcttgata atattgatac agcattaaca ttgtatatga atttacccat 11100
gttatttggt ggtggtgatc ccaacttgtt atatcgaagt ttctatagaa gaactcctga 11160
cttcctcaca gaggctatag ttcactctgt gttcatactt agttattata caaaccatga 11220
cttaaaagat aaacttcaag atctgtcaga tgatagattg aataagttct taacatgcat 11280
aatcacgttt gacaaaaacc ctaatgctga attcgtaaca ttgatgagag atcctcaagc 11340
tttagggtct gagagacaag ctaaaattac tagcgaaatc aatagactgg cagttacaga 11400
ggttttgagt acagctccaa acaaaatatt ctccaaaagt gcacaacatt atactactac 11460
agagatagat ctaaatgata ttatgcaaaa tatagaacct acatatcctc atgggctaag 11520
agttgtttat gaaagtttac ccttttataa agcagagaaa atagtaaatc ttatatcagg 11580
tacaaaatct ataactaaca tactggaaaa aacttctgcc atagacttaa cagatattga 11640
tagagccact gagatgatga ggaaaaacat aactttgctt ataaggatac ttccattgga 11700
ttgtaacaga gataaaagag agatattgag tatggaaaac ctaagtatta ctgaattaag 11760
caaatatgtt agggaaagat cttggtcttt atccaatata gttggtgtta catcacccag 11820
tatcatgtat acaatggaca tcaaatatac tacaagcact atatctagtg gcataattat 11880
agagaaatat aatgttaaca gtttaacacg tggtgagaga ggacccacta aaccatgggt 11940
tggttcatct acacaagaga aaaaaacaat gccagtttat aatagacaag tcttaaccaa 12000
aaaacagaga gatcaaatag atctattagc aaaattggat tgggtgtatg catctataga 12060
taacaaggat gaattcatgg aagaactcag cataggaacc cttgggttaa catatgaaaa 12120
ggccaagaaa ttatttccac aatatttaag tgtcaattat ttgcatcgcc ttacagtcag 12180
tagtagacca tgtgaattcc ctgcatcaat accagcttat agaacaacaa attatcactt 12240
tgacactagc cctattaatc gcatattaac agaaaagtat ggtgatgaag atattgacat 12300
agtattccaa aactgtataa gctttggcct tagtttaatg tcagtagtag aacaatttac 12360
taatgtatgt cctaacagaa ttattctcat acctaagctt aatgagatac atttgatgaa 12420
acctcccata ttcacaggtg atgttgatat tcacaagtta aaacaagtga tacaaaaaca 12480
gcatatgttt ttaccagaca aaataagttt gactcaatat gtggaattat tcttaagtaa 12540
taaaacactc aaatctggat ctcatgttaa ttctaattta atattggcac ataaaatatc 12600
tgactatttt cataatactt acattttaag tactaattta gctggacatt ggattctgat 12660
tatacaactt atgaaagatt ctaaaggtat ttttgaaaaa gattggggag agggatatat 12720
aactgatcat atgtttatta atttgaaagt tttcttcaat gcttataaga cctatctctt 12780
gtgttttcat aaaggttatg gcaaagcaaa gctggagtgt gatatgaaca cttcagatct 12840

-continued

```
tctatgtgta ttggaattaa tagacagtag ttattggaag tctatgtcta aggtattttt  12900

agaacaaaaa gttatcaaat acattcttag ccaagatgca agtttacata gagtaaaagg  12960

atgtcatagc ttcaaattat ggtttcttaa acgtcttaat gtagcagaat tcacagtttg  13020

cccttgggtt gttaacatag attatcatcc aacacatatg aaagcaatat taacttatat  13080

agatcttgtt agaatgggat tgataaatat agatagaata cacattaaaa ataaacacaa  13140

attcaatgat gaattttata cttctaatct cttctacatt aattataact tctcagataa  13200

tactcatcta ttaactaaac atataaggat tgctaattct gaattagaaa ataattacaa  13260

caaattatat catcctacac cagaaaccct agagaatata ctagccaatc cgattaaaag  13320

taatgacaaa aagacactga atgactattg tataggtaaa aatgttgact caataatgtt  13380

accattgtta tctaataaga agcttattaa atcgtctgca atgattagaa ccaattacag  13440

caaacaagat ttgtataatt tattccctat ggttgtgatt gatagaatta tagatcattc  13500

aggcaataca gccaaatcca accaacttta cactactact tcccaccaaa tatccttagt  13560

gcacaatagc acatcacttt actgcatgct tccttggcat catattaata gattcaattt  13620

tgtatttagt tctacaggtt gtaaaattag tatagagtat attttaaaag atcttaaaat  13680

taaagatccc aattgtatag cattcatagg tgaaggagca gggaatttat tattgcgtac  13740

agtagtggaa cttcatcctg acataagata tatttacaga agtctgaaag attgcaatga  13800

tcatagttta cctattgagt ttttaaggct gtacaatgga catatcaaca ttgattatgg  13860

tgaaaatttg accattcctg ctacagatgc aaccaacaac attcattggt cttatttaca  13920

tataaagttt gctgaaccta tcagtctttt tgtctgtgat gccgaattgt ctgtaacagt  13980

caactggagt aaaattataa tagaatggag caagcatgta agaaagtgca agtactgttc  14040

ctcagttaat aaatgtatgt taatagtaaa atatcatgct caagatgata ttgatttcaa  14100

attagacaat ataactatat taaaaactta tgtatgctta ggcagtaagt taaagggatc  14160

ggaggtttac ttagtcctta caataggtcc tgcgaatata ttcccagtat ttaatgtagt  14220

acaaaatgct aaattgatac tatcaagaac caaaaatttc atcatgccta agaaagctga  14280

taaagagtct attgatgcaa atattaaaag tttgataccc tttctttgtt accctataac  14340

aaaaaaagga attaatactg cattgtcaaa actaaagagt gttgttagtg gagatatact  14400

atcatattct atagctggac gtaatgaagt tttcagcaat aaacttataa atcataagca  14460

tatgaacatc ttaaaatggt tcaatcatgt tttaaatttc agatcaacag aactaaacta  14520

taaccattta tatatggtag aatctacata tccttaccta agtgaattgt taaacagctt  14580

gacaaccaat gaacttaaaa aactgattaa aatcacaggt agtctgttat acaactttca  14640

taatgaataa tgaataaaga tcttataata aaaattccca tagctataca ctaacactgt  14700

attcaattat agttattaaa aattaaaaat catataattt tttaaataac ttttagtgaa  14760

ctaatcctaa agttatcatt ttaatcttgg aggaataaat ttaaacccta atctaattgg  14820

tttatatgtg tattaactaa attacgagat attagttttt gacacttttt ttctcgt     14877
```

<210> SEQ ID NO 7
<211> LENGTH: 14877
<212> TYPE: DNA
<213> ORGANISM: Artificial Sequence
<220> FEATURE:
<223> OTHER INFORMATION: recombinant respiratory syncytial virus sequence

<400> SEQUENCE: 7

-continued

```
acgggaaaaa atgcgtacaa caaacttgca taaaccaaaa aaatggggca aataagaatt     60
tgataagtac cacttaaatt taactccctt ggttagagat gggcagcaat tcattgagta    120
tgataaaagt tagattacaa aatttgtttg acaatgatga agtagcattg ttaaaaataa    180
catgctatac tgataaatta atacatttaa ctaatgcttt ggctaaggca gtgatacata    240
caatcaaatt gaatggcatt gtgtttgtgc atgttattac aagtagtgat atttgcccta    300
ataataatat tgtagtaaaa tccaatttca caacaatgcc agtactacaa aatggaggtt    360
atatatggga aatgatggaa ttaacacatt gctctcaacc taatggtcta ctagatgaca    420
attgtgaaat taaattctcc aaaaaactaa gtgattcaac aatgaccaat tatatgaatc    480
aattatctga attacttgga tttgatctta atccataaat tataattaat atcaactagc    540
aaatcaatgt cactaacacc attagttaat ataaaactta acagaagaca aaaatggggc    600
aaataaatca attcagccaa cccaaccatg gacacaaccc acaatgataa tacaccacaa    660
agactgatga tcacagacat gagaccgttg tcacttgaga ccataataac atcactaacc    720
agagacatca taacacacaa atttatatac ttgataaatc atgaatgcat agtgagaaaa    780
cttgatgaaa gacaggccac atttacattc ctggtcaact atgaaatgaa actattacac    840
aaagtaggaa gcactaaata taaaaaatat actgaataca acacaaaata tggcactttc    900
cctatgccaa tattcatcaa tcatgatggg ttcttagaat gcattggcat taagcctaca    960
aagcatactc ccataatata caagtatgat ctcaatccat aaatttcaac acaatattca   1020
cacaatctaa aacaacaact ctatgcataa ctatactcca tagtccagat ggagcctgaa   1080
aattatagta atttaaaact taaggagaga tataagatag aagatggggc aaatacaacc   1140
atggctctta gcaaagtcaa gttgaatgat acactcaaca aagatcaact tctgtcatcc   1200
agcaaataca ccatccaacg gagcacagga gatagtattg atactcctaa ttatgatgtg   1260
cagaaacaca tcaataagtt atgtggcatg ttattaatca cagaagatgc taatcataaa   1320
ttcactgggt taataggtat gttatatgcg atgtctaggt taggaagaga agacaccata   1380
aaaatactca gagatgcggg atatcatgta aaagcaaatg gagtagatgt aacaacacat   1440
cgtcaagaca ttaatggaaa agaaatgaaa tttgaagtgt taacattggc aagcttaaca   1500
actgaaattc aaatcaacat tgagatagaa tctagaaaat cctacaaaaa aatgctaaaa   1560
gaaatgggag aggtagctcc agaatacagg catgactctc ctgattgtgg gatgataata   1620
ttatgtatag cagcattagt aataactaaa ttagcagcag gggacagatc tggtcttaca   1680
gccgtgatta ggagagctaa taatgtccta aaaaatgaaa tgaaacgtta caaaggctta   1740
ctacccaagg acatagccaa cagcttctat gaagtgtttg aaaaacatcc ccactttata   1800
gatgtttttg ttcattttgg tatagcacaa tcttctacca gaggtggcag tagagttgaa   1860
gggatttttg caggattgtt tatgaatgcc tatggtgcag ggcaagtgat gttacggtgg   1920
ggagtcttag caaaatcggt taaaaatatt atgttaggac atgctagtgt gcaagcagaa   1980
atggaacaag ttgttgaggt ttatgaatat gcccaaaaat tgggtggtga agcaggattc   2040
taccatatat tgaacaaccc aaaagcatca ttattatctt tgactcaatt tcctcacttc   2100
tccagtgtag tattaggcaa tgctgctggc ctaggcataa tgggagagta cagaggtaca   2160
ccgaggaatc aagatctata tgatgcagca aaggcatatg ctgaacaact caaagaaaat   2220
ggtgtgatta actacagtgt actagacttg acagcagaag aactagaggc tatcaaacat   2280
cagcttaatc caaaagataa tgatgtagag ctttgagtta ataaaaaatg gggcaaataa   2340
atcatcatgg aaaagtttgc tcctgaattc catggagaag atgcaaacaa cagggctact   2400
```

aaattcctag aatcaataaa gggcaaattc acatcaccca aagatcccaa gaaaaaagat 2460
agtatcatat ctgtcaactc aatagatata gaagtaacca aagaaagccc tataacatca 2520
aattcaacta ttatcaaccc aacaaatgag acagatgata ctgcagggaa caagcccaat 2580
tatcaaagaa aacctctagt aagtttcaaa gaagacccta caccaagtga taatcccttt 2640
tctaaactat acaaagaaac catagaaaca tttgataaca atgaagaaga atccagctat 2700
tcatacgaag aaataaatga tcagacaaac gataatataa cagcaagatt agataggatt 2760
gatgaaaaat taagtgaaat actaggaatg cttcacacat tagtagtggc aagtgcagga 2820
cctacatctg ctcgggatgg tataagagat gccatggttg gtttaagaga agaaatgata 2880
gaaaaaatca gaactgaagc attaatgacc aatgacagat tagaagctat ggcaagactc 2940
aggaatgagg aaagtgaaaa gatggcaaaa gacacatcag atgaagtgtc tctcaatcca 3000
acatcagaga aattgaacaa cctattggaa gggaatgata gtgacaatga tctatcactt 3060
gaagatttct gattagttac caatcttcac atcaacacac aataccaaca gaagaccaac 3120
aaactaacca acccaatcat ccaaccaaac atccatccgc caatcagcca aacagccaac 3180
aaaacaacca gccaatccaa aactaaccac ccggaaaaaa tctataatat agttacaaaa 3240
aaaggaaagg gtggggcaaa tatggaaaca tacgtgaaca agcttcacga aggctccaca 3300
tacacagctg ctgttcaata caatgtctta gaaaaagacg atgaccctgc atcacttaca 3360
atatgggtgc ccatgttcca atcatctatg ccagcagatt tacttataaa agaactagct 3420
aatgtcaaca tactagtgaa acaaatatcc acacccaagg gaccttcact aagagtcatg 3480
ataaactcaa gaagtgcagt gctagcacaa atgcccagca aatttaccat atgcgctaat 3540
gtgtccttgg atgaaagaag caaactagca tatgatgtaa ccacaccctg tgaaatcaag 3600
gcatgtagtc taacatgcct aaaatcaaaa aatatgttga ctacagttaa agatctcact 3660
atgaagacac tcaaccctac acatgatatt attgctttat gtgaatttga aaacatagta 3720
acatcaaaaa aagtcataat accaacatac ctaagatcca tcagtgtcag aaataaagat 3780
ctgaacacac ttgaaaatat aacaaccact gaattcaaaa atgctatcac aaatgcaaaa 3840
atcatccctt actcaggatt actattagtc atcacagtga ctgacaacaa aggagcattc 3900
aaatacataa agccacaaag tcaattcata gtagatcttg gagcttacct agaaaaagaa 3960
agtatatatt atgttaccac aaattggaag cacacagcta cacgatttgc aatcaaaccc 4020
atggaagatt aaccttttc ctctacatca gtgtgttaat tcatacaaac tttctaccta 4080
cattcttcac ttcaccatca caatcacaaa cactctgtgg ttcaaccaat caaacaaaac 4140
ttatctgaag tcccagatca tcccaagtca ttgtttatca gatctagtac tcaaataagt 4200
taataaaaaa tatacacatg ggcaaataa tcattggagg aaatccaact aatcacaata 4260
tctgttaaca tagacaagtc cacacaccat acagaatcaa ccaatggaaa atacatccat 4320
aacaatagaa ttctcaagca aattctggcc ttactttaca ctaatacaca tgatcacaac 4380
aataatctct ttgctaatca taatctccat catgattgca atactaaaca aactttgtga 4440
atataacgta ttccataaca aaacctttga gttaccaaga gctcgagtta atacttgata 4500
aagtagttaa ttaaaaatag tcataacaat gaactaggat atcaagacta acaataacat 4560
tggggcaaat gcaaacatgt ccaaaaacaa ggaccaacgc accgctaaga cattagaaag 4620
gacctgggac actctcaatc atttattatt catatcatcg tgcttatata agttaaatct 4680
taaatctgta gcacaaatca cattatccat tctggcaatg ataatctcaa cttcacttat 4740

-continued aattgcagcc atcatattca tagcctcggc aaaccacaaa gtcacaccaa caactgcaat 4800
catacaagat gcaacaagcc agatcaagaa cacaacccca acatacctca cccagaatcc 4860
tcagcttgga atcagtccct ctaatccgtc tgaaattaca tcacaaatca ccaccatact 4920
agcttcaaca acaccaggag tcaagtcaac cctgcaatcc acaacagtca agaccaaaaa 4980
cacaacaaca actcaaacac aacccagcaa gcccaccaca aaacaacgcc aaaacaaacc 5040
accaagcaaa cccaataatg attttcactt tgaagtgttc aactttgtac cctgcagcat 5100
atgcagcaac aatccaacct gctgggctat ctgcaaaaga ataccaaaca aaaaaccagg 5160
aaagaaaacc actaccaagc ccacaaaaaa accaaccctc aagacaacca aaaaagatcc 5220
caaacctcaa accactaaat caaaggaagt acccaccacc aagcccacag aagagccaac 5280
catcaacacc accaaaacaa acatcataac tacactactc acctccaaca ccacaggaaa 5340
tccagaactc acaagtcaaa tggaaacctt ccactcaact tcctccgaag gcaatccaag 5400
cccttctcaa gtctctacaa catccgagta cccatcacaa ccttcatctc cacccaacac 5460
accacgccag tagttactta aaaacatatt atcacaaaag gccttgacca acttaaacag 5520
aatcaaaata aactctgggg caaataacaa tggagttgct aatcctcaaa gcaaatgcaa 5580
ttaccacaat cctcactgca gtcacatttt gttttgcttc tggtcaaaac atcactgaag 5640
aattttatca atcaacatgc agtgcagtta gcaaaggcta tcttagtgct ctgagaactg 5700
gttggtatac cagtgttata actatagaat taagtaatat caagaaaaat aagtgtaatg 5760
gaacagatgc taaggtaaaa ttgataaaac aagaattaga taaatataaa aatgctgtaa 5820
cagaattgca gttgctcatg caaagcacac aagcaacaaa caatcgagcc agaagagaac 5880
taccaaggtt tatgaattat acactcaaca atgccaaaaa aaccaatgta acattaagca 5940
agaaaaggaa aagaagattt cttggttttt tgttaggtgt tggatctgca atcgccagtg 6000
gcgttgctgt atctaaggtc ctgcacctag aaggggaagt gaacaagatc aaaagtgctc 6060
tactatccac aaacaaggct gtagtcagct tatcaaatgg agttagtgtt ttaaccagca 6120
aagtgttaga cctcaaaaac tatatagata aacaattgtt acctattgtg aacaagcaaa 6180
gctgcagcat atcaaatata gaaactgtga tagagttcca acaaaagaac aacagactac 6240
tagagattac cagggaattt agtgttaatg caggcgtaac tacacctgta agcacttaca 6300
tgttaactaa tagtgaatta ttgtcattaa tcaatgatat gcctataaca aatgatcaga 6360
aaaagttaat gtccaacaat gttcaaatag ttagacagca aagttactct atcatgtcca 6420
taataaaaga ggaagtctta gcatatgtag tacaattacc actatatggt gttatagata 6480
caccctgttg gaaactacac acatcccctc tatgtacaac caacacaaaa gaagggtcca 6540
acatctgttt aacaagaact gacagaggat ggtactgtga caatgcagga tcagtatctt 6600
tcttcccaca agctgaaaca tgtaaagttc aatcaaatcg agtattttgt gacacaatga 6660
acagtttaac attaccaagt gaagtaaatc tctgcaatgt tgacatattc aaccccaaat 6720
atgattgtaa aattatgact tcaaaaacag atgtaagcag ctccgttatc acatctctag 6780
gagccattgt gtcatgctat ggcaaaacta aatgtacagc atccaataaa aatcgtggaa 6840
tcataaagac attttctaac gggtgcgatt atgtatcaaa taaaggggtg gacactgtgt 6900
ctgtaggtaa cacattatat tatgtaaata agcaagaagg taaaagtctc tatgtaaaag 6960
gtgaaccaat aataaatttc tatgacccat tagtattccc ctctgatgaa tttgatgcat 7020
caatatctca agtcaacgag aagattaacc agagcctagc atttattcgt aaatccgatg 7080
aattattaca taatgtaaat gctggtaaat ccaccacaaa tatcatgata actactataa 7140

-continued

```
ttatagtgat tatagtaata ttgttatcat taattgctgt tggactgctc ttatactgta   7200
aggccagaag cacaccagtc acactaagca aagatcaact gagtggtata aataatattg   7260
catttagtaa ctaaataaaa atagcaccta atcatgttct tacaatggtt tactatctgc   7320
tcatagacaa cccatctgtc attggatttt cttaaaatct gaacttcatc gaaactctca   7380
tctataaacc atctcactta cactatttaa gtagattcct agtttatagt tatataaaac   7440
acaattgcat gccagattaa cttaccatct gtaaaaatga aaactggggc aaatatgtca   7500
cgaaggaatc cttgcaaatt tgaaattcga ggtcattgct taaatggtaa gaggtgtcat   7560
tttagtcata attattttga atggccaccc catgcactgc ttgtaagaca aaactttatg   7620
ttaaacagaa tacttaagtc tatggataaa agtatagata ccttatcaga aataagtgga   7680
gctgcagagt tggacagaac agaagagtat gctcttggtg tagttggagt gctagagagt   7740
tatataggat caataaacaa tataactaaa caatcagcat gtgttgccat gagcaaactc   7800
ctcactgaac tcaatagtga tgatatcaaa aagctgaggg acaatgaaga gctaaattca   7860
cccaagataa gagtgtacaa tactgtcata tcatatattg aaagcaacag gaaaaacaat   7920
aaacaaacta tccatctgtt aaaaagattg ccagcagacg tattgaagaa aaccatcaaa   7980
aacacattgg atatccataa gagcataacc atcaacaacc caaaagaatc aactgttagt   8040
gatacaaatg accatgccaa aaataatgat actacctgac aaataagctt caattctaac   8100
actcaccaca tcgttacatt attaattcaa acaattcaag ttgtgggaca aaatggatcc   8160
cattattaat ggaaattctg ctaatgttta tctaaccgat agttatttaa aaggtgttat   8220
ctctttctca gagtgtaatg ctttaggaag ttacatattc aatggtcctt atctcaaaaa   8280
tgattatacc aacttaatta gtagacaaaa tccattaata gaacacatga atctaaagaa   8340
actaaatata acacagtcct taatatctaa gtatcataaa ggtgaaataa aattagaaga   8400
acctacttat tttcagtcat tacttatgac atacaagagt atgacctcgt cagaacagat   8460
tgctaccact aatttactta aaaagataat aagaagagct atagaaataa gtgatgtcaa   8520
agtctatgct atattgaata aactagggct taaagaaaag gacaagatta aatccaacaa   8580
tggacaagat gaagacaact cagttattac gaccataatc aaagatgata tactttcagc   8640
tgttaaagat aatcaatctc atcttaaagc agacaaaaat cactctacaa aacaaaaaga   8700
cacaatcaaa acaacactct tgaagaaatt gatgtgttca atgcaacatc ctccatcatg   8760
gttaatacat tggtttaact tatacacaaa attaaacaac atattaacac agtatcgatc   8820
aaatgaggta aaaaaccatg ggtttacatt gatagataat caaactctta gtggatttca   8880
atttattttg aaccaatatg gttgtatagt ttatcataag gaactcaaaa gaattactgt   8940
gacaacctat aatcaattct tgacatggaa agatattagc cttagtagat taaatgtttg   9000
tttaattaca tggattagta actgcttgaa cacattaaat aaaagcttag gcttaagatg   9060
cggattcaat aatgttatct tgacacaact attcctttat ggagattgta tactaaagct   9120
atttcacaat gaggggttct acataataaa agaggtagag ggatttatta tgtctctaat   9180
tttaaatata acagaagaag atcaattcag aaaacgattt tataatagta tgctcaacaa   9240
catcacagat gctgctaata aagctcagaa aaatctgcta tcaagagtat gtcatacatt   9300
attagataag acagtgtccg ataatataat aaatggcaga tggataattc tattaagtaa   9360
gttccttaaa ttaattaagc ttgcaggtga caataacctt aacaatctga gtgaactata   9420
tttttgttc agaatatttg gacacccaat ggtagatgaa agacaagcca tggatgctgt   9480
```

-continued

```
taaaattaat tgcaatgaga ccaaatttta cttgttaagc agtctgagta tgttaagagg   9540
tgcctttata tatagaatta taaaagggtt tgtaaataat tacaacagat ggcctacttt   9600
aagaaatgct attgttttac ccttaagatg gttaacttac tataaactaa acacttatcc   9660
ttctttgttg gaacttacag aaagagattt gattgtgtta tcaggactac gtttctatcg   9720
tgagtttcgg ttgcctaaaa aagtggatct tgaaatgatt ataaatgata aagctatatc   9780
acctcctaaa aatttgatat ggactagttt ccctagaaat tacatgccat cacacataca   9840
aaactatata gaacatgaaa aattaaaatt ttccgagagt gataaatcaa gaagagtatt   9900
agagtattat ttaagagata acaaattcaa tgaatgtgat ttatacaact gtgtagttaa   9960
tcaaagttat ctcaacaacc ctaatcatgt ggtatcattg acaggcaaag aaagagaact  10020
cagtgtaggt agaatgtttg caatgcaacc gggaatgttc agacaggttc aaatattggc  10080
agagaaaatg atagctgaaa acattttaca attctttcct gaaagtctta caagatatgg  10140
tgatctagaa ctacaaaaaa tattagaact gaaagcagga ataagtaaca aatcaaatcg  10200
ctacaatgat aattacaaca attacattag taagtgctct atcatcacag atctcagcaa  10260
attcaatcaa gcatttcgat atgaaacgtc atgtatttgt agtgatgtgc tggatgaact  10320
gcatggtgta caatctctat tttcctggtt acatttaact attcctcatg tcacaataat  10380
atgcacatat aggcatgcac ccccctatat aggagatcat attgtagatc ttaacaatgt  10440
agatgaacaa agtggattat atagatatca catgggtggc atcgaagggt ggtgtcaaaa  10500
actatggacc atagaagcta tatcactatt ggatctaata tctctcaaag ggaaattctc  10560
aattactgct ttaattaatg gtgacaatca atcaatagat ataagcaaac caatcagact  10620
catggaaggt caaactcatg ctcaagcaga ttatttgcta gcattaaata gccttaaatt  10680
actgtataaa gagtatgcag gcataggcca caaattaaaa ggaactgaga cttatatatc  10740
acgagatatg caatttatga gtaaaacaat tcaacataac ggtgtatatt acccagctag  10800
tataaagaaa gtcctaagag tgggaccgtg gataaacact atacttgatg atttcaaagt  10860
gagtctagaa tctataggta gtttgacaca agaattagaa tatagaggtg aaagtctatt  10920
atgcagttta atatttagaa atgtatggtt atataatcag attgctctac aattaaaaaa  10980
tcatgcatta tgtaacaata aactatattt ggacatatta aaggttctga aacacttaaa  11040
aaccttttttt aatcttgata atattgatac agcattaaca ttgtatatga atttacccat  11100
gttatttggt ggtggtgatc ccaacttgtt atatcgaagt ttctatagaa gaactcctga  11160
cttcctcaca gaggctatag ttcactctgt gttcatactt agttattata caaaccatga  11220
cttaaaagat aaacttcaag atctgtcaga tgatagattg aataagttct taacatgcat  11280
aatcacgttt gacaaaaacc ctaatgctga attcgtaaca ttgatgagag atcctcaagc  11340
tttagggtct gagagacaag ctaaaattac tagcgaaatc aatagactgg cagttacaga  11400
ggttttgagt acagctccaa acaaaaatatt ctccaaaagt gcacaacatt atactactac  11460
agagatagat ctaaatgata ttatgcaaaa tatagaacct acatatcctc atgggctaag  11520
agttgtttat gaaagtttac ccttttataa agcagagaaa atagtaaatc ttatatcagg  11580
tacaaaatct ataactaaca tactggaaaa aacttctgcc atagacttaa cagatattga  11640
tagagccact gagatgatga ggaaaaacat aactttgctt ataaggatac ttccattgga  11700
ttgtaacaga gataaaagag agatattgag tatggaaaac ctaagtatta ctgaattaag  11760
caaatatgtt agggaaagat cttggtcttt atccaatata gttggtgtta catcacccag  11820
tatcatgtat acaatggaca tcaaatatac tacaagcact atatctagtg gcataattat  11880
```

-continued

```
agagaaatat aatgttaaca gtttaacacg tggtgagaga ggacccacta aaccatgggt  11940
tggttcatct acacaagaga aaaaaacaat gccagtttat aatagacaag tcttaaccaa  12000
aaaacagaga gatcaaatag atctattagc aaaattggat tgggtgtatg catctataga  12060
taacaaggat gaattcatgg aagaactcag cataggaacc cttgggttaa catatgaaaa  12120
ggccaagaaa ttatttccac aatatttaag tgtcaattat ttgcatcgcc ttacagtcag  12180
tagtagacca tgtgaattcc ctgcatcaat accagcttat agaacaacaa attatcactt  12240
tgacactagc cctattaatc gcatattaac agaaaagtat ggtgatgaag atattgacat  12300
agtattccaa aactgtataa gctttggcct tagtttaatg tcagtagtag aacaatttac  12360
taatgtatgt cctaacagaa ttattctcat acctaagctt aatgagatac atttgatgaa  12420
acctcccata ttcacaggtg atgttgatat tcacaagtta aaacaagtga tacaaaaaca  12480
gcatatgttt ttaccagaca aaataagttt gactcaatat gtggaattat tcttaagtaa  12540
taaaacactc aaatctggat ctcatgttaa ttctaattta atattggcac ataaaatatc  12600
tgactatttt cataatactt acattttaag tactaattta gctggacatt ggattctgat  12660
tatacaactt atgaaagatt ctaaaggtat ttttgaaaaa gattggggag agggatatat  12720
aactgatcat atgtttatta atttgaaagt tttcttcaat gcttataaga cctatctctt  12780
gtgttttcat aaaggttatg gcaaagcaaa gctggagtgt gatatgaaca cttcagatct  12840
tctatgtgta ttggaattaa tagacagtag ttattggaag tctatgtcta aggtattttt  12900
agaacaaaaa gttatcaaat acattcttag ccaagatgca agtttacata gagtaaaagg  12960
atgtcatagc ttcaaattat ggtttcttaa acgtcttaat gtagcagaat tcacagtttg  13020
cccttgggtt gttaacatag attatcatcc aacacatatg aaagcaatat taacttatat  13080
agatcttgtt agaatgggat tgataaatat agatagaata cacattaaaa ataaacacaa  13140
attcaatgat gaattttata cttctaatct cttctacatt aattataact tctcagataa  13200
tactcatcta ttaactaaac atataaggat tgctaattct gaattagaaa ataattacaa  13260
caaattatat catcctacac cagaaaccct agagaatata ctagccaatc cgattaaaag  13320
taatgacaaa aagacactga atgactattg tataggtaaa aatgttgact caataatgtt  13380
accattgtta tctaataaga agcttattaa atcgtctgca atgattagaa ccaattacag  13440
caaacaagat ttgtataatt tattccctat ggttgtgatt gatagaatta tagatcattc  13500
aggcaataca gccaaatcca accaacttta cactactact tcccaccaaa tatccttagt  13560
gcacaatagc acatcacttt actgcatgct tccttggcat catattaata gattcaattt  13620
tgtatttagt tctacaggtt gtaaaattag tatagagtat attttaaaag atcttaaaat  13680
taaagatccc aattgtatag cattcatagg tgaaggagca gggaatttat tattgcgtac  13740
agtagtggaa cttcatcctg acataagata tatttacaga agtctgaaag attgcaatga  13800
tcatagttta cctattgagt ttttaaggct gtacaatgga catatcaaca ttgattatgg  13860
tgaaaatttg accattcctg ctacagatgc aaccaacaac attcattggt cttatttaca  13920
tataaagttt gctgaaccta tcagtctttt tgtctgtgat gccgaattgt ctgtaacagt  13980
caactggagt aaaattataa tagaatggag caagcatgta agaaagtgca agtactgttc  14040
ctcagttaat aaatgtatgt taatagtaaa atatcatgct caagatgata ttgatttcaa  14100
attagacaat ataactatat taaaaactta tgtatgctta ggcagtaagt taaagggatc  14160
ggaggtttac ttagtcctta caataggtcc tgcgaatata ttcccagtat ttaatgtagt  14220
```

acaaaatgct aaattgatac tatcaagaac caaaaatttc atcatgccta agaaagctga 14280
taaagagtct attgatgcaa atattaaaag tttgataccc tttctttgtt accctataac 14340
aaaaaaagga attaatactg cattgtcaaa actaaagagt gttgttagtg gagatatact 14400
atcatattct atagctggac gtaatgaagt tttcagcaat aaacttataa atcataagca 14460
tatgaacatc ttaaaatggt tcaatcatgt tttaaatttc agatcaacag aactaaacta 14520
taaccattta tatatggtag aatctacata tccttaccta agtgaattgt taaacagctt 14580
gacaaccaat gaacttaaaa aactgattaa aatcacaggt agtctgttat acaactttca 14640
taatgaataa tgaataaaga tcttataata aaaattccca tagctataca ctaacactgt 14700
attcaattat agttattaaa aattaaaaat catataattt tttaaataac ttttagtgaa 14760
ctaatcctaa agttatcatt ttaatcttgg aggaataaat ttaaacccta atctaattgg 14820
tttatatgtg tattaactaa attacgagat attagttttt gacacttttt ttctcgt 14877

<210> SEQ ID NO 8
<211> LENGTH: 897
<212> TYPE: DNA
<213> ORGANISM: Artificial Sequence
<220> FEATURE:
<223> OTHER INFORMATION: recombinant respiratory syncytial virus sequence

<400> SEQUENCE: 8
atgtctaaga caaaggatca gcggacagcc aaaacactgg aacggacatg ggataccctg 60
aatcacctcc tcttcatcag cagttgcctg tacaagctca atctgaagtc catcgcccag 120
atcactctct ccatccttgc catgatcatc tctacaagcc tcatcattgc cgcaattatc 180
ttcatcgcca gcgctaacca caaggtcacc cttaccacag ccattattca ggatgccacc 240
aaccagatca agaacacaac ccctacctac ctgacacaga accctcagct tggaatttca 300
ctgagcaacc tgtccgaaac cacatctaaa cctacaacca tcttggctct gaccacacca 360
aacgccgagt ccaccccaca aagtaccaca gtgaagacca aaaacaccac aaccacacag 420
attcagccaa gcaagcctac aactaagcaa aggcagaaca agccacagaa caaacccaac 480
aacgactttc actttgaggt gttcaacttt gtgccctgct ccatttgctc caacaaccct 540
acctgttggg ctatctgcaa gaggatcccc aacaagaagc ccggcaggaa gactactact 600
aagcctacta aacagccagc cattaagacc actaagaagg acccaaagcc acagacaacc 660
aagccaaagg aggtgctcac taccaagccc actgagaagc ccaccattaa caccactaaa 720
accaacatcc gcacaacatt gctgacatca aacattacag agaaccagga gcacacaagc 780
cagaaggaga cactgcatag cactacatcc gaaggcaatc ccagcccaag ccaggtctat 840
actacctcag agtacctgtc ccagagcctg agccctagca acactactag atggtag 897

<210> SEQ ID NO 9
<211> LENGTH: 1725
<212> TYPE: DNA
<213> ORGANISM: Artificial Sequence
<220> FEATURE:
<223> OTHER INFORMATION: recombinant respiratory syncytial virus sequence

<400> SEQUENCE: 9
atggagctcc tcattctcaa agccaacgca atcacaacaa ttctgaccgc cgtcacattc 60
tgctttgcct ccggacagaa catcacagaa gagttttacc aaagtacatg cagcgccgtg 120
agcaaaggct acctgtccgc cctgaggaca gggtggtaca catccgtgat taccattgag 180

```
ctgagtaata tcaagaagaa caagtgcaac ggcactgatg ccaaagtgaa gctcattaaa    240

caggaactcg ataagtacaa gaacgccgtg actgagctcc agctgctgat gcagtcaact    300

caggctacaa acaacagagc ccggagggag ctgcccaggt ttatgaacta caccctgaac    360

aacgccaaga agaccaacgt gacattgagc aagaagagga agcggcggtt cctggggttc    420

ttgctaggtg tgggcagcgc tattgcttct ggcgtcgccg tctccaaggt gctgcacctg    480

gaaggcgaag tgaataagat taagtccgca ctgcttagca ccaataaggc cgtcgtgagc    540

ctgtctaacg gagtgagtgt gctcacaagc aaggtcctcg atctcaagaa ctacattgat    600

aagcagctcc tgcccatcgt caacaagcag tcatgctcca ttagtaacat cgagaccgtg    660

attgaatttc aacagaagaa caaccggctc ctggagatta ctagggagtt cagcgtgaac    720

gccggggtga caacaccagt ctccacctat atgcttacca acagcgagtt gctctccctg    780

attaacgata tgccaattac aaacgaccag aagaagctga tgtcaaacaa cgtccagatt    840

gtccggcagc agtcctactc aatcatgtcc attattaagg aggaggtcct ggcttacgtc    900

gtgcagctgc ctctttatgg ggtgatcgac accccttgct ggaagctcca tacatcccct    960

ctgtgcacta ccaacaccaa ggaggggtcc aacatctgct tgacaagaac cgatcgcggc   1020

tggtactgcg ataacgcagg cagtgtctcc ttctttcccc aggccgagac ttgtaaggtg   1080

cagtctaacc gcgtcttctg cgacaccatg aacagcctga cccttcccag cgaggtgaac   1140

ctttgtaacg tggacatctt caacccaaag tatgattgta agattatgac tagcaaaacc   1200

gatgtcagca gcagcgtgat cactagcctg ggcgctatcg tcagctgcta cggaaagact   1260

aagtgcaccg ccagcaacaa gaacagaggc atcatcaaga ccttcagtaa tggatgtgac   1320

tacgtgtcca acaaaggggt ggatacagtg agcgtgggaa acacattgta ctacgtgaac   1380

aaacaggagg ggaagtcctt gtacgtgaag ggtgagccca ttatcaactt ctacgaccct   1440

ctcgtgttcc catcagacga gtttgacgcc tccatctccc aggtgaacga gaagatcaat   1500

cagtcactgg cctttattag gaaatccgac gagctgctgc acaacgtcaa cgccggaaag   1560

tctaccacta acatcatgat caccacaatc atcattgtga tcatcgtcat cctcctgagc   1620

ttgatcgctg tcgggttgct gttgtactgc aaggcccggt ccacacccgt gactctgagc   1680

aaggaccagc tgtctggcat taacaacatc gcctttagca actaa                   1725
```

<210> SEQ ID NO 10
<211> LENGTH: 1725
<212> TYPE: DNA
<213> ORGANISM: Artificial Sequence
<220> FEATURE:
<223> OTHER INFORMATION: recombinant respiratory syncytial virus sequence

<400> SEQUENCE: 10

```
atggatttgc caatcctcaa gacaaatgct attaccacaa tccttgctgc agtcacactc     60

tgtttcgctt ccagtcaaaa tatcactgaa gaattttatc aatcaacatg cagtgcagtt    120

agcaaaggct atcttagtgc tctaagaact ggttggtata ctagtgttat aactatagaa    180

ttaagtaata tcaaagaaaa taagtgtaat ggaacagacg ctaaggtaaa attgataaaa    240

caagaattag ataaatataa aaatgctgta acagaactgc agttgctcat gcaaagcacg    300

ccagcatcca acaatcgagc cagaagagaa ctaccaagat ttatgaatta tacactcaac    360

aataccaaaa acaccaatgt aacattaagc aagaaaagga aaagaagatt tcttggcttt    420

ttgttagggg ttggatctgc aatcgccagt ggcattgctg tatctaaggt cctgcactta    480
```

```
gaaggggaag tgaacaaaat caaaagtgct ctactatcca caaacaaggc tgtagtcagc    540

ttatctaatg gagtcagtgt cttaaccagc aaagtgttag atctcaaaaa ctatatagat    600

aaacagttgt tacctattgt gaacaagcaa agctgcagca tatcaaacat tgaaactgtg    660

atagagttcc aacaaaagaa caacagacta ctagagatta ccagggaatt tagtgttaat    720

gcaggtgtaa ctacacctgt aagcacttat atgttaacta atagtgaatt attatcatta    780

atcaatgata tgcctataac aaatgatcag aaaaagttaa tgtccaacaa tgttcaaata    840

gttagacagc aaagttactc tatcatgtca ataataaagg aggaagtctt agcatatgta    900

gtacaattac cactatatgg tgtaatagat acaccttgtt ggaaactgca cacatcccct    960

ctatgtacaa cctacacaaa ggaagggtcc aacatctgct taacaagaac cgacagggga   1020

tggtactgtg acaatgcagg atcagtatct tttttcccac aagctgaaac atgtaaagtt   1080

caatcgaatc gggtattttg tgacacaatg aacagtttaa cattaccaag tgaggtaaat   1140

ctctgcaaca ttgacatatt caaccccaaa tatgattgca aaattatgac ttcaaaaaca   1200

gatgtaagta gctctgttat cacatctcta ggagccattg tgtcatgcta tggcaaaacc   1260

aaatgtacag catccaataa aaatcgtggg atcataaaga cattttctaa tgggtgtgat   1320

tatgtatcaa ataagggggt ggatactgtg tctgtaggta atacattata ttatgtaaat   1380

aagcaagaag gcaaaagtct ctatgtaaaa ggtgaaccaa taataaattt ctatgatcca   1440

ttagttttcc cctctgatga atttgatgca tcaatatctc aagtcaatga gaagattaac   1500

cagagtctag catttatccg taaatcagat gaattattac ataatgtaaa tgctggtaaa   1560

tccaccacaa atatcatgat aactactata attatagtaa ttgtagtaat attgttatca   1620

ttaattgcag ttggactgct tctatactgc aaggccagaa gcacaccagt cacactaagt   1680

aaggatcaac tgagtggtat aaacaatatt gcatttagta gctga                   1725
```

```
<210> SEQ ID NO 11
<211> LENGTH: 1725
<212> TYPE: DNA
<213> ORGANISM: Artificial Sequence
<220> FEATURE:
<223> OTHER INFORMATION: recombinant respiratory syncytial virus
      sequence

<400> SEQUENCE: 11
```

```
atggaccttc caatcctgaa gaccaacgct atcaccacca tcctcgcagc tgtgactctt     60

tgtttcgcat cctcccaaaa catcaccgaa gagttctacc agtccacctg ttccgcagtg    120

tctaagggat accttagcgc tctcagaacc ggatggtaca catccgtgat cactatcgaa    180

ctgagcaaca tcaaggagaa caagtgcaac ggcaccgacg ctaaggtgaa gctcatcaag    240

caggaactgg acaagtacaa gaacgccgtg accgaacttc agctccttat gcagtctacc    300

ccagcttcca acaacagagc cagaagggag ctcccaaggt ttatgaacta caccctcaac    360

aacaccaaga acaccaacgt gaccctgtcc aagaagagga agaggcggtt ccttggattc    420

ctcttgggag tcggatctgc tatcgcctca ggcattgccg tcagtaaagt gttgcatttg    480

gagggcgagg tcaacaaaat caagtccgcc ttgttgtcca ctaacaaggc cgtcgtgtct    540

ttgtccaacg ggtgtctgt cttgacaagt aaggtgttgg acttgaagaa ctacatcgac     600

aagcagctgc tgcctatcgt caacaagcag tcctgctcta tcagcaacat cgagaccgtg    660

atcgagttcc agcagaagaa caaccggctg ctggagatca caagggagtt cagtgtcaac    720

gccggcgtca caacacctgt gtcaacttat atgctgacaa actcagagct gctgtcactg    780
```

-continued

```
atcaacgaca tgcctatcac caacgaccag aagaagctga tgagcaacaa cgtgcagatc    840

gtgaggcagc agtcatacag catcatgtcc atcatcaagg aggaagtcct ggcctacgtg    900

gtccaactgc ctctgtacgg cgtgattgat actccatgtt ggaagctgca cacatcacca    960

ctgtgtacca cttacaccaa ggaggggagt aacatctgcc tgactcggac agatagaggg   1020

tggtattgcg ataatgccgg cagtgtctcc tttttccccc aggccgagac ttgcaaagtc   1080

cagagcaatc gcgtgttttg cgatacaatg aatagcctga cactccccag cgaggtgaat   1140

ctctgcaata ttgatatttt caaccccaag tacgactgca agatcatgac cagcaagacc   1200

gacgtcagca gcagcgtgat tactagcctc ggagccattg tgagctgcta tgggaaaaca   1260

aaatgcacag cctccaacaa aaacagaggc attatcaaga ctttctccaa cgggtgcgat   1320

tacgtgtcca acaagggcgt ggatactgtg agcgtgggga acacactcta ctacgtgaac   1380

aaacaggagg ggaaaagcct gtacgtgaaa ggcgagccca ttattaactt ttacgaccct   1440

ctggtgtttc ccagcgatga gtttgatgcc agcatctccc aggtgaacga gaagattaac   1500

cagtccctcg cctttattcg caagagcgat gagctgctgc acaacgtgaa cgccggcaag   1560

tccactacaa acattatgat tacaacaatt attattgtca ttgtcgtcat tctgctcagc   1620

ctgattgccg tcggcctgct gctctactgc aaggccaggt ccacacccgt gacactcagc   1680

aaggatcagc tgtccggcat taacaacatt gcctttagca gctaa                   1725
```

<210> SEQ ID NO 12
<211> LENGTH: 13
<212> TYPE: PRT
<213> ORGANISM: Artificial Sequence
<220> FEATURE:
<223> OTHER INFORMATION: recombinant respiratory syncytial virus sequence

<400> SEQUENCE: 12

```
Ser Asp Thr Asn Asp His Ala Lys Asn Asn Asp Thr Thr
1               5                   10
```

<210> SEQ ID NO 13
<211> LENGTH: 15
<212> TYPE: PRT
<213> ORGANISM: Artificial Sequence
<220> FEATURE:
<223> OTHER INFORMATION: recombinant respiratory syncytial virus sequence

<400> SEQUENCE: 13

```
Met Thr Met Pro Lys Ile Met Ile Leu Pro Asp Lys Tyr Pro Cys
1               5                   10                  15
```

<210> SEQ ID NO 14
<211> LENGTH: 5
<212> TYPE: PRT
<213> ORGANISM: Artificial Sequence
<220> FEATURE:
<223> OTHER INFORMATION: recombinant respiratory syncytial virus sequence

<400> SEQUENCE: 14

```
Ala Arg Val Asn Thr
1               5
```

<210> SEQ ID NO 15
<211> LENGTH: 14982
<212> TYPE: DNA

<213> ORGANISM: Artificial Sequence
<220> FEATURE:
<223> OTHER INFORMATION: recombinant respiratory syncytial virus
sequence

<400> SEQUENCE: 15
acgggaaaaa atgcgtacaa caaacttgca taaaccaaaa aaatggggca aataagaatt 60
tgataagtac cacttaaatt taactccctt ggttagagat gggcagcaat tcattgagta 120
tgataaaagt tagattacaa aatttgtttg acaatgatga agtagcattg ttaaaaataa 180
catgctatac tgataaatta atacatttaa ctaatgcttt ggctaaggca gtgatacata 240
caatcaaatt gaatggcatt gtgtttgtgc atgttattac aagtagtgat atttgcccta 300
ataataatat tgtagtaaaa tccaatttca caacaatgcc agtactacaa aatggaggtt 360
atatatggga aatgatggaa ttaacacatt gctctcaacc taatggtcta ctagatgaca 420
attgtgaaat taaattctcc aaaaaactaa gtgattcaac aatgaccaat tatatgaatc 480
aattatctga attacttgga tttgatctta atccataaat tataattaat atcaactagc 540
aaatcaatgt cactaacacc attagttaat ataaaactta acagaagaca aaaatggggc 600
aaataaatca attcagccaa cccaaccatg gacacaaccc acaatgataa tacaccacaa 660
agactgatga tcacagacat gagaccgttg tcacttgaga ccataataac atcactaacc 720
agagacatca taacacacaa atttatatac ttgataaatc atgaatgcat agtgagaaaa 780
cttgatgaaa gacaggccac atttacattc ctggtcaact atgaaatgaa actattacac 840
aaagtaggaa gcactaaata taaaaaatat actgaataca acacaaaata tggcactttc 900
cctatgccaa tattcatcaa tcatgatggg ttcttagaat gcattggcat taagcctaca 960
aagcatactc ccataatata caagtatgat ctcaatccat aaatttcaac acaatattca 1020
cacaatctaa aacaacaact ctatgcataa ctatactcca tagtccagat ggagcctgaa 1080
aattatagta atttaaaact taaggagaga tataagatag aagatggggc aaatacaacc 1140
atggctctta gcaaagtcaa gttgaatgat acactcaaca aagatcaact tctgtcatcc 1200
agcaaataca ccatccaacg gagcacagga gatagtattg atactcctaa ttatgatgtg 1260
cagaaacaca tcaataagtt atgtggcatg ttattaatca cagaagatgc taatcataaa 1320
ttcactgggt taataggtat gttatatgcg atgtctaggt taggaagaga agacaccata 1380
aaaatactca gagatgcggg atatcatgta aaagcaaatg gagtagatgt aacaacacat 1440
cgtcaagaca ttaatggaaa agaaatgaaa tttgaagtgt taacattggc aagcttaaca 1500
actgaaattc aaatcaacat tgagatagaa tctagaaaat cctacaaaaa aatgctaaaa 1560
gaaatgggag aggtagctcc agaatacagg catgactctc ctgattgtgg gatgataata 1620
ttatgtatag cagcattagt aataactaaa ttagcagcag gggacagatc tggtcttaca 1680
gccgtgatta ggagagctaa taatgtccta aaaaatgaaa tgaaacgtta caaaggctta 1740
ctacccaagg acatagccaa cagcttctat gaagtgtttg aaaaacatcc ccactttata 1800
gatgtttttg ttcattttgg tatagcacaa tcttctacca gaggtggcag tagagttgaa 1860
gggatttttg caggattgtt tatgaatgcc tatggtgcag ggcaagtgat gttacggtgg 1920
ggagtcttag caaaatcgat taaaaatatt atgttaggac atgctagtgt gcaagcagaa 1980
atggaacaag ttgttgaggt ttatgaatat gcccaaaaat tgggtggtga agcaggattc 2040
taccatatat tgaacaaccc aaaagcatca ttattatctt tgactcaatt tcctcacttc 2100
tccagtgtag tattaggcaa tgctgctggc ctaggcataa tgggagagta cagaggtaca 2160

-continued

```
ccgaggaatc aagatctata tgatgcagca aaggcatatg ctgaacaact caaagaaaat   2220
ggtgtgatta actacagtgt actagacttg acagcagaag aactagaggc tatcaaacat   2280
cagcttaatc caaaagataa tgatgtagag ctttgagtta ataaaaaatg ggcaaataa    2340
atcatcatgg aaaagtttgc tcctgaattc catggagaag atgcaaacaa cagggctact   2400
aaattcctag aatcaataaa gggcaaattc acatcaccca aagatcccaa gaaaaaagat   2460
agtatcatat ctgtcaactc aatagatata gaagtaacca aagaaagccc tataacatca   2520
aattcaacta ttatcaaccc aacaaatgag acagatgata ctgcagggaa caagcccaat   2580
tatcaaagaa aacctctagt aagtttcaaa gaagacccta caccaagtga taatcccttt   2640
tctaaactat acaaagaaac catagaaaca tttgataaca atgaagaaga atccagctat   2700
tcatacgaag aaataaatga tcagacaaac gataatataa cagcaagatt agataggatt   2760
gatgaaaaat taagtgaaat actaggaatg cttcacacat tagtagtggc aagtgcagga   2820
cctacatctg ctcgggatgg tataagagat gccatggttg gtttaagaga agaaatgata   2880
gaaaaaatca gaactgaagc attaatgacc aatgacagat tagaagctat ggcaagactc   2940
aggaatgagg aaagtgaaaa gatggcaaaa gacacatcag atgaagtgtc tctcaatcca   3000
acatcagaga aattgaacaa cctattggaa gggaatgata gtgacaatga tctatcactt   3060
gaagatttct gattagttac caatcttcac atcaacacac aataccaaca gaagaccaac   3120
aaactaacca acccaatcat ccaaccaaac atccatccgc caatcagcca aacagccaac   3180
aaaacaacca gccaatccaa aactaaccac ccggaaaaaa tctataatat agttacaaaa   3240
aaaggaaagg gtggggcaaa tatggaaaca tacgtgaaca agcttcacga aggctccaca   3300
tacacagctg ctgttcaata caatgtctta gaaaaagacg atgaccctgc atcacttaca   3360
atatgggtgc ccatgttcca atcatctatg ccagcagatt tacttataaa agaactagct   3420
aatgtcaaca tactagtgaa acaaatatcc acacccaagg gaccttcact aagagtcatg   3480
ataaactcaa gaagtgcagt gctagcacaa atgcccagca aatttaccat atgcgctaat   3540
gtgtccttgg atgaaagaag caaactagca tatgatgtaa ccacaccctg tgaaatcaag   3600
gcatgtagtc taacatgcct aaaatcaaaa aatatgttga ctacagttaa agatctcact   3660
atgaagacac tcaaccctac acatgatatt attgctttat gtgaatttga aaacatagta   3720
acatcaaaaa aagtcataat accaacatac ctaagatcca tcagtgtcag aaataaagat   3780
ctgaacacac ttgaaaatat aacaaccact gaattcaaaa atgctatcac aaatgcaaaa   3840
atcatccctt actcaggatt actattagtc atcacagtaa ctgacaacaa aggagcattc   3900
aaatacataa agccacaaag tcaattcata gtagatcttg gagcttacct agaaaaagaa   3960
agtatatatt atgttaccac aaattggaag cacacagcta cacgatttgc aatcaaaccc   4020
atggaagatt aaccttttc ctctacatca gtgtgttaat tcatacaaac tttctaccta    4080
cattcttcac ttcaccatca caatcacaaa cactctgtgg ttcaaccaat caaacaaaac   4140
ttatctgaag tcccagatca tcccaagtca ttgtttatca gatctagtac tcaaataagt   4200
taataaaaaa tatacacatg ggcaaataa tcattggagg aaatccaact aatcacaata    4260
tctgttaaca tagacaagtc cacacaccat acagaatcaa ccaatggaaa atacatccat   4320
aacaatagaa ttctcaagca aattctggcc ttactttaca ctaatacaca tgatcacaac   4380
aataatctct ttgctaatca taatctccat catgattgca atactaaaca aactttgtga   4440
atataacgta ttccataaca aaacctttga gttaccaaga gctcgagtca acacatagca   4500
ttcatcaatc caacagccca aaacagtaac cttgcattta aaaatgaaca acccctacct   4560
```

-continued

```
ctttacaaca cctcattaac atcccaccat gcaaaccact atccatacta taaagtagtt   4620
aattaaaaat agtcataaca atgaactagg atatcaagac taacaataac attggggcaa   4680
atgcaaacat gtccaaaaac aaggaccaac gcaccgctaa gacattagaa aggacctggg   4740
acactctcaa tcatttatta ttcatatcat cgtgcttata taagttaaat cttaaatctg   4800
tagcacaaat cacattatcc attctggcaa tgataatctc aacttcactt ataattgcag   4860
ccatcatatt catagcctcg gcaaaccaca aagtcacacc aacaactgca atcatacaag   4920
atgcaacaag ccagatcaag aacacaaccc caacatacct cacccagaat cctcagcttg   4980
gaatcagtcc ctctaatccg tctgaaatta catcacaaat caccaccata ctagcttcaa   5040
caacaccagg agtcaagtca accctgcaat ccacaacagt caagaccaaa aacacaacaa   5100
caactcaaac acaacccagc aagcccacca caaaacaacg ccaaaacaaa ccaccaagca   5160
aacccaataa tgattttcac tttgaagtgt tcaactttgt accctgcagc atatgcagca   5220
acaatccaac ctgctgggct atctgcaaaa gaataccaaa caaaaaacca ggaaagaaaa   5280
ccactaccaa gcccacaaaa aaaccaaccc tcaagacaac caaaaaagat cccaaacctc   5340
aaaccactaa atcaaaggaa gtacccacca ccaagcccac agaagagcca accatcaaca   5400
ccaccaaaac aaacatcata actacactac tcacctccaa caccacagga aatccagaac   5460
tcacaagtca aatggaaacc ttccactcaa cttcctccga aggcaatcca agcccttctc   5520
aagtctctac aacatccgag tacccatcac aaccttcatc tccacccaac acaccacgcc   5580
agtagttact taaaaacata ttatcacaaa aggccttgac caacttaaac agaatcaaaa   5640
taaactctgg ggcaaataac aatggagttg ctaatcctca aagcaaatgc aattaccaca   5700
atcctcactg cagtcacatt ttgttttgct tctggtcaaa acatcactga agaattttat   5760
caatcaacat gcagtgcagt tagcaaaggc tatcttagtg ctctgagaac tggttggtat   5820
accagtgtta taactataga attaagtaat atcaagaaaa ataagtgtaa tggaacagat   5880
gctaaggtaa aattgataaa acaagaatta gataaatata aaaatgctgt aacagaattg   5940
cagttgctca tgcaaagcac acaagcaaca aacaatcgag ccagaagaga actaccaagg   6000
tttatgaatt atacactcaa caatgccaaa aaaaccaatg taacattaag caagaaaagg   6060
aaaagaagat ttcttggttt tttgttaggt gttggatctg caatcgccag tggcgttgct   6120
gtatctaagg tcctgcacct agaaggggaa gtgaacaaga tcaaaagtgc tctactatcc   6180
acaaacaagg ctgtagtcag cttatcaaat ggagttagtg ttttaaccag caaagtgtta   6240
gacctcaaaa actatataga taaacaattg ttacctattg tgaacaagca aagctgcagc   6300
atatcaaata tagcaactgt gatagagttc caacaaaaga acaacagact actagagatt   6360
accagggaat ttagtgttaa tgcaggcgta actacacctg taagcactta catgttaact   6420
aatagtgaat tattgtcatt aatcaatgat atgcctataa caaatgatca gaaaaagtta   6480
atgtccaaca atgttcaaat agttagacag caaagttact ctatcatgtc cataataaaa   6540
gaggaagtct tagcatatgt agtacaatta ccactatatg gtgttataga tacaccctgt   6600
tggaaactac acacatcccc tctatgtaca accaacacaa aagaagggtc caacatctgt   6660
ttaacaagaa ctgacagagg atggtactgt gacaatgcag gatcagtatc tttcttccca   6720
caagctgaaa catgtaaagt tcaatcaaat cgagtatttt gtgacacaat gaacagttta   6780
acattaccaa gtgaagtaaa tctctgcaat gttgacatat tcaaccccaa atatgattgt   6840
aaaattatga cttcaaaaac agatgtaagc agctccgtta tcacatctct aggagccatt   6900
```

-continued

```
gtgtcatgct atggcaaaac taaatgtaca gcatccaata aaaatcgtgg aatcataaag   6960
acattttcta acgggtgcga ttatgtatca aataaagggg tggacactgt gtctgtaggt   7020
aacacattat attatgtaaa taagcaagaa ggtaaaagtc tctatgtaaa aggtgaacca   7080
ataataaatt tctatgaccc attagtattc ccctctgatg aatttgatgc atcaatatct   7140
caagtcaacg agaagattaa ccagagccta gcatttattc gtaaatccga tgaattatta   7200
cataatgtaa atgctggtaa atccaccata aatatcatga taactactat aattatagtg   7260
attatagtaa tattgttatc attaattgct gttggactgc tcttatactg taaggccaga   7320
agcacaccag tcacactaag caaagatcaa ctgagtggta taaataatat tgcatttagt   7380
aactaaataa aaatagcacc taatcatgtt cttacaatgg tttactatct gctcatagac   7440
aacccatctg tcattggatt ttcttaaaat ctgaacttca tcgaaactct catctataaa   7500
ccatctcact tacactattt aagtagattc ctagtttata gttatataaa acacaattgc   7560
atgccagatt aacttaccat ctgtaaaaat gaaaactggg gcaaatatgt cacgaaggaa   7620
tccttgcaaa tttgaaattc gaggtcattg cttaaatggt aagaggtgtc attttagtca   7680
taattatttt gaatggccac cccatgcact gcttgtaaga caaaacttta tgttaaacag   7740
aatacttaag tctatggata aaagtataga taccttatca gaaataagtg gagctgcaga   7800
gttggacaga acagaagagt atgctcttgg tgtagttgga gtgctagaga gttatatagg   7860
atcaataaac aatataacta aacaatcagc atgtgttgcc atgagcaaac tcctcactga   7920
actcaatagt gatgatatca aaaagctgag ggacaatgaa gagctaaatt cacccaagat   7980
aagagtgtac aatactgtca tatcatatat tgaaagcaac aggaaaaaca ataaacaaac   8040
tatccatctg ttaaaaagat tgccagcaga cgtattgaag aaaaccatca aaaacacatt   8100
ggatatccat aagagcataa ccatcaacaa cccaaaagaa tcaactgtta gtgatacaaa   8160
cgaccacgcc aaaaataacg atactaccta acactcaatt ctaacactca ccacatcgtt   8220
acattattaa ttcaaacaat tcaagttgtg ggacaaaatg gatcccatta ttaatggaaa   8280
ttctgctaat gtttatctaa ccgatagtta tttaaaaggt gttatctctt tctcagagtg   8340
taatgcttta ggaagttaca tattcaatgg tccttatctc aaaaatgatt ataccaactt   8400
aattagtaga caaaatccat taatagaaca catgaatcta aagaaactaa atataacaca   8460
gtccttaata tctaagtatc ataaaggtga aataaaatta gaagaaccta cttattttca   8520
gtcattactt atgacataca agagtatgac ctcgtcagaa cagattgcta ccactaattt   8580
acttaaaaag ataataagaa gagctataga aataagtgat gtcaaagtct atgctatatt   8640
gaataaacta gggcttaaag aaaaggacaa gattaaatcc aacaatggac aagatgaaga   8700
caactcagtt attacgacca taatcaaaga tgatatactt tcagctgtta aagataatca   8760
atctcatctt aaagcagaca aaaatcactc tacaaaacaa aaagacacaa tcaaaacaac   8820
actcttgaag aaattgatgt gttcaatgca acatcctcca tcatggttaa tacattggtt   8880
taacttatac acaaaattaa acaacatatt aacacagtat cgatcaaatg aggtaaaaaa   8940
ccatgggttt acattgatag ataatcaaac tcttagtgga tttcaattta ttttgaacca   9000
atatggttgt atagtttatc ataaggaact caaaagaatt actgtgacaa cctataatca   9060
attcttgaca tggaaagata ttagccttag tagattaaat gtttgtttaa ttacatggat   9120
tagtaactgc ttgaacacat taaataaaag cttaggctta agatgcggat tcaataatgt   9180
tatcttgaca caactattcc tttatggaga ttacatacta aagctatttc acaatgaggg   9240
gttctacata ataaaagagg tagagggatt tattatgtct ctaattttaa atataacaga   9300
```

```
agaagatcaa ttcagaaaac gattttataa tagtatgctc aacaacatca cagatgctgc   9360
taataaagct cagaaaaatc tgctatcaag agtatgtcat acattattag ataagacagt   9420
gtccgataat ataataaatg gcagatggat aattctatta agtaagttcc ttaaattaat   9480
taagcttgca ggtgacaata accttaacaa tctgagtgaa ctatattttt tgttcagaat   9540
atttggacac ccaatggtag atgaaagaca agccatggat gctgttaaaa ttaattgcaa   9600
tgagaccaaa ttttacttgt taagcagtct gagtatgtta agaggtgcct ttatatatag   9660
aattataaaa gggtttgtaa ataattacaa cagatggcct actttaagaa atgctattgt   9720
tttaccctta agatggttaa cttactataa actaaacact tatccttctt tgttggaact   9780
tacagaaaga gatttgattg tgttatcagg actacgtttc tatcgtgagt ttcggttgcc   9840
taaaaaagtg gatcttgaaa tgattataaa tgataaagct atatcacctc ctaaaaattt   9900
gatatggact agtttcccta gaaattacat gccatcacac atacaaaact atatagaaca   9960
tgaaaaatta aaattttccg agagtgataa atcaagaaga gtattagagt attatttaag  10020
agataacaaa ttcaatgaat gtgatttata caactgtgta gttaatcaaa gttatctcaa  10080
caaccctaat catgtggtat cattgacagg caaagaaaga gaactcagtg taggtagaat  10140
gtttgcaatg caaccgggaa tgttcagaca ggttcaaata ttggcagaga aaatgatagc  10200
tgaaaacatt ttacaattct ttcctgaaag tcttacaaga tatggtgatc tagaactaca  10260
aaaaatatta gaactgaaag caggaataag taacaaatca aatcgctaca atgataatta  10320
caacaattac attagtaagt gctctatcat cacagatctc agcaaattca atcaagcatt  10380
tcgatatgaa acgtcatgta tttgtagtga tgtgctggat gaactgcatg gtgtacaatc  10440
tctattttcc tggttacatt taactattcc tcatgtcaca ataaatatgca catataggca  10500
tgcacccccc tatataggag atcatattgt agatcttaac aatgtagatg aacaaagtgg  10560
attatataga tatcacatgg gtggcatcga agggtggtgt caaaaactat ggaccataga  10620
agctatatca ctattggatc taatatctct caaagggaaa ttctcaatta ctgctttaat  10680
taatggtgac aatcaatcaa tagatataag caaaccaatc agactcatgg aaggtcaaac  10740
tcatgctcaa gcagattatt tgctagcatt aaatagcctt aaattactgt ataaagagta  10800
tgcaggcata ggccacaaat taaaaggaac tgagacttat atatcacgag atatgcaatt  10860
tatgagtaaa acaattcaac ataacggtgt atattaccca gctagtataa agaaagtcct  10920
aagagtggga ccgtggataa acactatact tgatgatttc aaagtgagtc tagaatctat  10980
aggtagtttg acacaagaat tagaatatag aggtgaaagt ctattatgca gtttaatatt  11040
tagaaatgta tggttatata atcagattgc tctacaatta aaaaatcatg cattatgtaa  11100
caataaacta tatttggaca tattaaaggt tctgaaacac ttaaaaacct tttttaatct  11160
tgataatatt gatacagcat taacattgta tatgaattta cccatgttat ttggtggtgg  11220
tgatcccaac ttgttatatc gaagtttcta tagaagaact cctgacttcc tcacagaggc  11280
tatagttcac tctgtgttca tacttagtta ttatacaaac catgacttaa aagataaact  11340
tcaagatctg tcagatgata gattgaataa gttcttaaca tgcataatca cgtttgacaa  11400
aaaccctaat gctgaattcg taacattgat gagagatcct caagctttag ggtctgagag  11460
acaagctaaa attactagcg aaatcaatag actggcagtt acagaggttt tgagtacagc  11520
tccaaacaaa atattctcca aaagtgcaca acattatact actacagaga tagatctaaa  11580
tgatattatg caaaatatag aacctacata tcctcatggg ctaagagttg tttatgaaag  11640
```

-continued

```
tttacccttt tataaagcag agaaaatagt aaatcttata tcaggtacaa aatctataac  11700
taacatactg gaaaaaactt ctgccataga cttaacagat attgatagag ccactgagat  11760
gatgaggaaa aacataactt tgcttataag gatacttcca ttggattgta acagagataa  11820
aagagagata ttgagtatgg aaaacctaag tattactgaa ttaagcaaat atgttaggga  11880
aagatcttgg tctttatcca atatagttgg tgttacatca cccagtatca tgtatacaat  11940
ggacatcaaa tatactacaa gcactatatc tagtggcata attatagaga aatataatgt  12000
taacagttta acacgtggtg agagaggacc cactaaacca tgggttggtt catctacaca  12060
agagaaaaaa acaatgccag tttataatag acaagtctta accaaaaaac agagagatca  12120
aatagatcta ttagcaaaat tggattgggt gtatgcatct atagataaca aggatgaatt  12180
catggaagaa ctcagcatag gaacccttgg gttaacatat gaaaaggcca agaaattatt  12240
tccacaatat ttaagtgtca attatttgca tcgccttaca gtcagtagta gaccatgtga  12300
attccctgca tcaataccag cttatagaac aacaaattat cactttgaca ctagccctat  12360
taatcgcata ttaacagaaa agtatggtga tgaagatatt gacatagtat tccaaaactg  12420
tataagcttt ggccttagtt taatgtcagt agtagaacaa tttactaatg tatgtcctaa  12480
cagaattatt ctcataccta agcttaatga gatacatttg atgaaacctc ccatattcac  12540
aggtgatgtt gatattcaca agttaaaaca agtgatacaa aaacagcata tgtttttacc  12600
agacaaaata agtttgactc aatatgtgga attattctta agtaataaaa cactcaaatc  12660
tggatctcat gttaattcta atttaatatt ggcacataaa atatctgact attttcataa  12720
tacttacatt ttaagtacta atttagctgg acattggatt ctgattatac aacttatgaa  12780
agattctaaa ggtatttttg aaaaagattg gggagaggga tatataactg atcatatgtt  12840
tattaatttg aaagttttct tcaatgctta taagacctat ctcttgtgtt ttcataaagg  12900
ttatggcaaa gcaaagctgg agtgtgatat gaacacttca gatcttctat gtgtattgga  12960
attaatagac agtagttatt ggaagtctat gtctaaggta tttttagaac aaaaagttat  13020
caaatacatt cttagccaag atgcaagttt acatagagta aaaggatgtc atagcttcaa  13080
attatggttt cttaaacgtc ttaatgtagc agaattcaca gtttgccctt gggttgttaa  13140
catagattat catccaacac atatgaaagc aatattaact tatatagatc ttgttagaat  13200
gggattgata aatatagata gaatacacat taaaaataaa cacaaattca atgatgaatt  13260
ttatacttct aatctcttct acattaatta taacttctca gataatactc atctattaac  13320
taaatacata aggattgcta attctgaatt agaaaataat tacaacaaat tatatcatcc  13380
tacaccagaa accctagaga atatactagc caatccgatt aaaagtaatg acaaaaagac  13440
actgaatgac tattgtatag gtaaaaatgt tgactcaata atgttaccat tgttatctaa  13500
taagaagctt attaaatcgt ctgcaatgat tagaaccaat tacagcaaac aagatttgta  13560
taatttattc cctatggttg tgattgatag aattatagat cattcaggca atacagccaa  13620
atccaaccaa ctttacacta ctacttccca ccaaatatcc ttagtgcaca atagcacatc  13680
actttactgc atgcttcctt ggcatcatat taatagattc aattttgtat ttagttctac  13740
aggttgtaaa attagtatag agtatatttt aaaagatctt aaaattaaag atcccaattg  13800
tatagcattc ataggtgaag gagcagggaa tttattattg cgtacagtag tggaacttca  13860
tcctgacata agatatattt acagaagtct gaaagattgc aatgatcata gtttacctat  13920
tgagttttta aggctgtaca atggacatat caacattgat tatggtgaaa atttgaccat  13980
tcctgctaca gatgcaacca acaacattca ttggtcttat ttacatataa agtttgctga  14040
```

acctatcagt ctttttgtct gtgatgccga attgtctgta acagtcaact ggagtaaaat 14100
tataatagaa tggagcaagc atgtaagaaa gtgcaagtac tgttcctcag ttaataaatg 14160
tatgttaata gtaaaatatc atgctcaaga tgatattgat ttcaaattag acaatataac 14220
tatattaaaa acttatgtat gcttaggcag taagttaaag ggatcggagg tttacttagt 14280
ccttacaata ggtcctgcga atatattccc agtatttaat gtagtacaaa atgctaaatt 14340
gatactatca agaaccaaaa atttcatcat gcctaagaaa gctgataaag agtctattga 14400
tgcaaatatt aaaagtttga taccctttct ttgttaccct ataacaaaaa aaggaattaa 14460
tactgcattg tcaaaactaa agagtgttgt tagtggagat atactatcat attctatagc 14520
tggacgtaat gaagttttca gcaataaact tataaatcat aagcatatga acatcttaaa 14580
atggttcaat catgttttaa atttcagatc aacagaacta aactataacc atttatatat 14640
ggtagaatct acatatcctt acctaagtga attgttaaac agcttgacaa ccaatgaact 14700
taaaaaactg attaaaatca caggtagtct gttatacaac tttcataatg aataatgaat 14760
aaagatctta taataaaaat tcccatagct atacactaac actgtattca attatagtta 14820
ttaaaaatta aaaatcatat aatttttaa ataactttta gtgaactaat cctaaagtta 14880
tcattttaat cttggaggaa taaatttaaa ccctaatcta attggtttat atgtgtatta 14940
actaaattac gagatattag tttttgacac tttttttctc gt 14982

<210> SEQ ID NO 16
<211> LENGTH: 14870
<212> TYPE: DNA
<213> ORGANISM: Artificial Sequence
<220> FEATURE:
<223> OTHER INFORMATION: recombinant respiratory syncytial virus sequence

<400> SEQUENCE: 16
acgggaaaaa atgcgtacaa caaacttgca taaaccaaaa aaatggggca aataagaatt 60
tgataagtac cacttaaatt taactccctt ggttagagat gggcagcaat tcattgagta 120
tgataaaagt tagattacaa aatttgtttg acaatgatga agtagcattg ttaaaaataa 180
catgctatac tgataaatta atacatttaa ctaatgcttt ggctaaggca gtgatacata 240
caatcaaatt gaatggcatt gtgtttgtgc atgttattac aagtagtgat atttgcccta 300
ataataatat tgtagtaaaa tccaatttca caacaatgcc agtactacaa aatggaggtt 360
atatatggga aatgatggaa ttaacacatt gctctcaacc taatggtcta ctagatgaca 420
attgtgaaat taaattctcc aaaaaactaa gtgattcaac aatgaccaat tatatgaatc 480
aattatctga attacttgga tttgatctta atccataaat tataattaat atcaactagc 540
aaatcaatgt cactaacacc attagttaat ataaaactta acagaagaca aaaatggggc 600
aaataaatca attcagccaa cccaaccatg gacacaaccc acaatgataa tacaccacaa 660
agactgatga tcacagacat gagaccgttg tcacttgaga ccataataac atcactaacc 720
agagacatca taacacacaa atttatatac ttgataaatc atgaatgcat agtgagaaaa 780
cttgatgaaa gacaggccac atttacattc ctggtcaact atgaaatgaa actattacac 840
aaagtaggaa gcactaaata taaaaaatat actgaataca acacaaaata tggcactttc 900
cctatgccaa tattcatcaa tcatgatggg ttcttagaat gcattggcat taagcctaca 960
aagcatactc ccataatata caagtatgat ctcaatccat aaatttcaac acaatattca 1020
cacaatctaa aacaacaact ctatgcataa ctatactcca tagtccagat ggagcctgaa 1080

-continued

```
aattatagta atttaaaact taaggagaga tataagatag aagatggggc aaatacaacc   1140
atggctctta gcaaagtcaa gttgaatgat acactcaaca aagatcaact tctgtcatcc   1200
agcaaataca ccatccaacg gagcacagga gatagtattg atactcctaa ttatgatgtg   1260
cagaaacaca tcaataagtt atgtggcatg ttattaatca cagaagatgc taatcataaa   1320
ttcactgggt taataggtat gttatatgcg atgtctaggt taggaagaga agacaccata   1380
aaaatactca gagatgcggg atatcatgta aaagcaaatg gagtagatgt aacaacacat   1440
cgtcaagaca ttaatggaaa agaaatgaaa tttgaagtgt taacattggc aagcttaaca   1500
actgaaattc aaatcaacat tgagatagaa tctagaaaat cctacaaaaa aatgctaaaa   1560
gaaatgggag aggtagctcc agaatacagg catgactctc ctgattgtgg gatgataata   1620
ttatgtatag cagcattagt aataactaaa ttagcagcag gggacagatc tggtcttaca   1680
gccgtgatta ggagagctaa taatgtccta aaaaatgaaa tgaaacgtta caaaggctta   1740
ctacccaagg acatagccaa cagcttctat gaagtgtttg aaaaacatcc ccactttata   1800
gatgtttttg ttcattttgg tatagcacaa tcttctacca gaggtggcag tagagttgaa   1860
gggatttttg caggattgtt tatgaatgcc tatggtgcag ggcaagtgat gttacggtgg   1920
ggagtcttag caaaatcggt taaaaatatt atgttaggac atgctagtgt gcaagcagaa   1980
atggaacaag ttgttgaggt ttatgaatat gcccaaaaat tgggtggtga agcaggattc   2040
taccatatat tgaacaaccc aaaagcatca ttattatctt tgactcaatt tcctcacttc   2100
tccagtgtag tattaggcaa tgctgctggc ctaggcataa tgggagagta cagaggtaca   2160
ccgaggaatc aagatctata tgatgcagca aaggcatatg ctgaacaact caaagaaaat   2220
ggtgtgatta actacagtgt actagacttg acagcagaag aactagaggc tatcaaacat   2280
cagcttaatc caaaagataa tgatgtagag ctttgagtta ataaaaaatg gggcaaataa   2340
atcatcatgg aaaagtttgc tcctgaattc catggagaag atgcaaacaa cagggctact   2400
aaattcctag aatcaataaa gggcaaattc acatcaccca aagatcccaa gaaaaaagat   2460
agtatcatat ctgtcaactc aatagatata gaagtaacca aagaaagccc tataacatca   2520
aattcaacta ttatcaaccc aacaaatgag acagatgata ctgcagggaa caagcccaat   2580
tatcaaagaa aacctctagt aagtttcaaa gaagacccta caccaagtga taatcccttt   2640
tctaaactat acaaagaaac catagaaaca tttgataaca atgaagaaga atccagctat   2700
tcatacgaag aaataaatga tcagacaaac gataatataa cagcaagatt agataggatt   2760
gatgaaaaat taagtgaaat actaggaatg cttcacacat tagtagtggc aagtgcagga   2820
cctacatctg ctcgggatgg tataagagat gccatggttg gtttaagaga agaaatgata   2880
gaaaaaatca gaactgaagc attaatgacc aatgacagat tagaagctat ggcaagactc   2940
aggaatgagg aaagtgaaaa gatggcaaaa gacacatcag atgaagtgtc tctcaatcca   3000
acatcagaga aattgaacaa cctattggaa gggaatgata gtgacaatga tctatcactt   3060
gaagatttct gattagttac caatcttcac atcaacacac aataccaaca gaagaccaac   3120
aaactaacca acccaatcat ccaaccaaac atccatccgc caatcagcca aacagccaac   3180
aaaacaacca gccaatccaa aactaaccac ccggaaaaaa tctataatat agttacaaaa   3240
aaaggaaagg gtggggcaaa tatggaaaca tacgtgaaca agcttcacga aggctccaca   3300
tacacagctg ctgttcaata caatgtctta gaaaaagacg atgaccctgc atcacttaca   3360
atatgggtgc ccatgttcca atcatctatg ccagcagatt tacttataaa agaactagct   3420
```

-continued

```
aatgtcaaca tactagtgaa acaaatatcc acacccaagg gaccttcact aagagtcatg   3480
ataaactcaa gaagtgcagt gctagcacaa atgcccagca aatttaccat atgcgctaat   3540
gtgtccttgg atgaaagaag caaactagca tatgatgtaa ccacaccctg tgaaatcaag   3600
gcatgtagtc taacatgcct aaaatcaaaa aatatgttga ctacagttaa agatctcact   3660
atgaagacac tcaaccctac acatgatatt attgctttat gtgaatttga aaacatagta   3720
acatcaaaaa aagtcataat accaacatac ctaagatcca tcagtgtcag aaataaagat   3780
ctgaacacac ttgaaaatat aacaaccact gaattcaaaa atgctatcac aaatgcaaaa   3840
atcatccctt actcaggatt actattagtc atcacagtga ctgacaacaa aggagcattc   3900
aaatacataa agccacaaag tcaattcata gtagatcttg gagcttacct agaaaaagaa   3960
agtatatatt atgttaccac aaattggaag cacacagcta cacgatttgc aatcaaaccc   4020
atggaagatt aaccttttc ctctacatca gtgtgttaat tcatacaaac tttctaccta   4080
cattcttcac ttcaccatca caatcacaaa cactctgtgg ttcaaccaat caaacaaaac   4140
ttatctgaag tcccagatca tcccaagtca ttgtttatca gatctagtac tcaaataagt   4200
taataaaaaa tatacacatg gggcaaataa tcattggagg aaatccaact aatcacaata   4260
tctgttaaca tagacaagtc cacacaccat acagaatcaa ccaatggaaa atacatccat   4320
aacaatagaa ttctcaagca aattctggcc ttactttaca ctaatacaca tgatcacaac   4380
aataatctct ttgctaatca taatctccat catgattgca atactaaaca aactttgtga   4440
atataacgta ttccataaca aaacctttga gttaccaaga gctcgagtta atacttgata   4500
aagtagttaa ttaaaaatag tcataacaat gaactaggat atcaagacta acaataacat   4560
tggggcaaat gcaaacatgt ccaaaaacaa ggaccaacgc accgctaaga cattagaaag   4620
gacctgggac actctcaatc atttattatt catatcatcg tgcttatata agttaaatct   4680
taaatctgta gcacaaatca cattatccat tctggcaatg ataatctcaa cttcacttat   4740
aattgcagcc atcatattca tagcctcggc aaaccacaaa gtcacaccaa caactgcaat   4800
catacaagat gcaacaagcc agatcaagaa cacaacccca acatacctca cccagaatcc   4860
tcagcttgga atcagtccct ctaatccgtc tgaaattaca tcacaaatca ccaccatact   4920
agcttcaaca acaccaggag tcaagtcaac cctgcaatcc acaacagtca agaccaaaaa   4980
cacaacaaca actcaaacac aacccagcaa gcccaccaca aaacaacgcc aaaacaaacc   5040
accaagcaaa cccaataatg attttcactt tgaagtgttc aactttgtac cctgcagcat   5100
atgcagcaac aatccaacct gctgggctat ctgcaaaaga ataccaaaca aaaaaccagg   5160
aaagaaaacc actaccaagc ccacaaaaaa accaaccctc aagacaacca aaaaagatcc   5220
caaacctcaa accactaaat caaaggaagt acccaccacc aagcccacag aagagccaac   5280
catcaacacc accaaaacaa acatcataac tacactactc acctccaaca ccacaggaaa   5340
tccagaactc acaagtcaaa tggaaacctt ccactcaact tcctccgaag gcaatccaag   5400
cccttctcaa gtctctacaa catccgagta cccatcacaa ccttcatctc cacccaacac   5460
accacgccag tagttactta aaaacatatt atcacaaaag gccttgacca acttaaacag   5520
aatcaaaata aactctgggg caaataacaa tggagttgct aatcctcaaa gcaaatgcaa   5580
ttaccacaat cctcactgca gtcacatttt gttttgcttc tggtcaaaac atcactgaag   5640
aattttatca atcaacatgc agtgcagtta gcaaaggcta tcttagtgct ctgagaactg   5700
gttggtatac cagtgttata actatagaat taagtaatat caagaaaaat aagtgtaatg   5760
gaacagatgc taaggtaaaa ttgataaaac aagaattaga taaatataaa aatgctgtaa   5820
```

cagaattgca gttgctcatg caaagcacac aagcaacaaa caatcgagcc agaagagaac 5880
taccaaggtt tatgaattat acactcaaca atgccaaaaa aaccaatgta acattaagca 5940
agaaaaggaa aagaagattt cttggttttt tgttaggtgt tggatctgca atcgccagtg 6000
gcgttgctgt atctaaggtc ctgcacctag aaggggaagt gaacaagatc aaaagtgctc 6060
tactatccac aaacaaggct gtagtcagct tatcaaatgg agttagtgtt ttaaccagca 6120
aagtgttaga cctcaaaaac tatatagata aacaattgtt acctattgtg aacaagcaaa 6180
gctgcagcat atcaaatata gaaactgtga tagagttcca acaaaagaac aacagactac 6240
tagagattac cagggaattt agtgttaatg caggcgtaac tacacctgta agcacttaca 6300
tgttaactaa tagtgaatta ttgtcattaa tcaatgatat gcctataaca aatgatcaga 6360
aaaagttaat gtccaacaat gttcaaatag ttagacagca aagttactct atcatgtcca 6420
taataaaaga ggaagtctta gcatatgtag tacaattacc actatatggt gttatagata 6480
caccctgttg gaaactacac acatcccctc tatgtacaac caacacaaaa gaagggtcca 6540
acatctgttt aacaagaact gacagaggat ggtactgtga caatgcagga tcagtatctt 6600
tcttcccaca agctgaaaca tgtaaagttc aatcaaatcg agtattttgt gacacaatga 6660
acagtttaac attaccaagt gaagtaaatc tctgcaatgt tgacatattc aaccccaaat 6720
atgattgtaa aattatgact tcaaaaacag atgtaagcag ctccgttatc acatctctag 6780
gagccattgt gtcatgctat ggcaaaacta aatgtacagc atccaataaa aatcgtggaa 6840
tcataaagac attttctaac gggtgcgatt atgtatcaaa taaaggggtg gacactgtgt 6900
ctgtaggtaa cacattatat tatgtaaata agcaagaagg taaaagtctc tatgtaaaag 6960
gtgaaccaat aataaatttc tatgacccat tagtattccc ctctgatgaa tttgatgcat 7020
caatatctca agtcaacgag aagattaacc agagcctagc atttattcgt aaatccgatg 7080
aattattaca taatgtaaat gctggtaaat ccaccacaaa tatcatgata actactataa 7140
ttatagtgat tatagtaata ttgttatcat taattgctgt tggactgctc ttatactgta 7200
aggccagaag cacaccagtc acactaagca aagatcaact gagtggtata aataatattg 7260
catttagtaa ctaaataaaa atagcaccta atcatgttct tacaatggtt tactatctgc 7320
tcatagacaa cccatctgtc attggatttt cttaaaatct gaacttcatc gaaactctca 7380
tctataaacc atctcactta cactatttaa gtagattcct agtttatagt tatataaaac 7440
acaattgcat gccagattaa cttaccatct gtaaaaatga aaactggggc aaatatgtca 7500
cgaaggaatc cttgcaaatt tgaaattcga ggtcattgct taaatggtaa gaggtgtcat 7560
tttagtcata attattttga atggccaccc catgcactgc ttgtaagaca aaactttatg 7620
ttaaacagaa tacttaagtc tatggataaa agtatagata ccttatcaga aataagtgga 7680
gctgcagagt tggacagaac agaagagtat gctcttggtg tagttggagt gctagagagt 7740
tatataggat caataaacaa tataactaaa caatcagcat gtgttgccat gagcaaactc 7800
ctcactgaac tcaatagtga tgatatcaaa aagctgaggg acaatgaaga gctaaattca 7860
cccaagataa gagtgtacaa tactgtcata tcatatattg aaagcaacag gaaaaacaat 7920
aaacaaacta tccatctgtt aaaaagattg ccagcagacg tattgaagaa aaccatcaaa 7980
aacacattgg atatccataa gagcataacc atcaacaacc caaaagaatc aactgttagt 8040
gatacaaacg accacgccaa aaataacgat actacctaac actcaattct aacactcacc 8100
acatcgttac attattaatt caaacaattc aagttgtggg acaaaatgga tcccattatt 8160

-continued

```
aatggaaatt ctgctaatgt ttatctaacc gatagttatt taaaaggtgt tatctctttc   8220
tcagagtgta atgctttagg aagttacata ttcaatggtc cttatctcaa aaatgattat   8280
accaacttaa ttagtagaca aaatccatta atagaacaca tgaatctaaa gaaactaaat   8340
ataacacagt ccttaatatc taagtatcat aaaggtgaaa taaaattaga agaacctact   8400
tattttcagt cattacttat gacatacaag agtatgacct cgtcagaaca gattgctacc   8460
actaatttac ttaaaaagat aataagaaga gctatagaaa taagtgatgt caaagtctat   8520
gctatattga ataaactagg gcttaaagaa aaggacaaga ttaaatccaa caatggacaa   8580
gatgaagaca actcagttat tacgaccata atcaaagatg atatactttc agctgttaaa   8640
gataatcaat ctcatcttaa agcagacaaa aatcactcta caaaacaaaa agacacaatc   8700
aaaacaacac tcttgaagaa attgatgtgt tcaatgcaac atcctccatc atggttaata   8760
cattggttta acttatacac aaaattaaac aacatattaa cacagtatcg atcaaatgag   8820
gtaaaaaacc atgggtttac attgatagat aatcaaactc ttagtggatt tcaatttatt   8880
ttgaaccaat atggttgtat agtttatcat aaggaactca aaagaattac tgtgacaacc   8940
tataatcaat tcttgacatg gaaagatatt agccttagta gattaaatgt ttgtttaatt   9000
acatggatta gtaactgctt gaacacatta aataaaagct taggcttaag atgcggattc   9060
aataatgtta tcttgacaca actattcctt tatggagatt gtatactaaa gctatttcac   9120
aatgaggggt tctacataat aaaagaggta gagggattta ttatgtctct aattttaaat   9180
ataacagaag aagatcaatt cagaaaacga ttttataata gtatgctcaa caacatcaca   9240
gatgctgcta ataaagctca gaaaaatctg ctatcaagag tatgtcatac attattagat   9300
aagacagtgt ccgataatat aataaatggc agatggataa ttctattaag taagttcctt   9360
aaattaatta agcttgcagg tgacaataac cttaacaatc tgagtgaact atattttttg   9420
ttcagaatat ttggacaccc aatggtagat gaaagacaag ccatggatgc tgttaaaatt   9480
aattgcaatg agaccaaatt ttacttgtta agcagtctga gtatgttaag aggtgccttt   9540
atatatagaa ttataaaagg gtttgtaaat aattacaaca gatggcctac tttaagaaat   9600
gctattgttt taccettaag atggttaact tactataaac taaacactta tccttctttg   9660
ttggaactta cagaaagaga tttgattgtg ttatcaggac tacgtttcta tcgtgagttt   9720
cggttgccta aaaaagtgga tcttgaaatg attataaatg ataaagctat atcacctcct   9780
aaaaatttga tatggactag tttccctaga aattacatgc catcacacat acaaaactat   9840
atagaacatg aaaaattaaa attttccgag agtgataaat caagaagagt attagagtat   9900
tatttaagag ataacaaatt caatgaatgt gatttataca actgtgtagt taatcaaagt   9960
tatctcaaca accctaatca tgtggtatca ttgacaggca aagaaagaga actcagtgta  10020
ggtagaatgt ttgcaatgca accgggaatg ttcagacagg ttcaaatatt ggcagagaaa  10080
atgatagctg aaaacatttt acaattcttt cctgaaagtc ttacaagata tggtgatcta  10140
gaactacaaa aaatattaga actgaaagca ggaataagta acaaatcaaa tcgctacaat  10200
gataattaca acaattacat tagtaagtgc tctatcatca cagatctcag caaattcaat  10260
caagcatttc gatatgaaac gtcatgtatt tgtagtgatg tgctggatga actgcatggt  10320
gtacaatctc tatttteetg gttacattta actattcctc atgtcacaat aatatgcaca  10380
tataggcatg caccccccta tataggagat catattgtag atcttaacaa tgtagatgaa  10440
caaagtggat tatatagata tcacatgggt ggcatcgaag ggtggtgtca aaaactatgg  10500
accatagaag ctatatcact attggatcta atatctctca aagggaaatt ctcaattact  10560
```

gctttaatta atggtgacaa tcaatcaata gatataagca aaccaatcag actcatggaa 10620
ggtcaaactc atgctcaagc agattatttg ctagcattaa atagccttaa attactgtat 10680
aaagagtatg caggcatagg ccacaaatta aaaggaactg agacttatat atcacgagat 10740
atgcaattta tgagtaaaac aattcaacat aacggtgtat attacccagc tagtataaag 10800
aaagtcctaa gagtgggacc gtggataaac actatacttg atgatttcaa agtgagtcta 10860
gaatctatag gtagtttgac acaagaatta gaatatagag gtgaaagtct attatgcagt 10920
ttaatattta gaaatgtatg gttatataat cagattgctc tacaattaaa aaatcatgca 10980
ttatgtaaca ataaactata tttggacata ttaaaggttc tgaaacactt aaaaaccttt 11040
tttaatcttg ataatattga tacagcatta acattgtata tgaatttacc catgttattt 11100
ggtggtggtg atcccaactt gttatatcga agtttctata gaagaactcc tgacttcctc 11160
acagaggcta tagttcactc tgtgttcata cttagttatt atacaaacca tgacttaaaa 11220
gataaacttc aagatctgtc agatgataga ttgaataagt tcttaacatg cataatcacg 11280
tttgacaaaa accctaatgc tgaattcgta acattgatga gagatcctca agctttaggg 11340
tctgagagac aagctaaaat tactagcgaa atcaatagac tggcagttac agaggttttg 11400
agtacagctc caaacaaaat attctccaaa agtgcacaac attatactac tacagagata 11460
gatctaaatg atattatgca aaatatagaa cctacatatc ctcatgggct aagagttgtt 11520
tatgaaagtt taccctttta taaagcagag aaaatagtaa atcttatatc aggtacaaaa 11580
tctataacta acatactgga aaaaacttct gccatagact taacagatat tgatagagcc 11640
actgagatga tgaggaaaaa cataactttg cttataagga tacttccatt ggattgtaac 11700
agagataaaa gagagatatt gagtatggaa aacctaagta ttactgaatt aagcaaatat 11760
gttagggaaa gatcttggtc tttatccaat atagttggtg ttacatcacc cagtatcatg 11820
tatacaatgg acatcaaata tactacaagc actatatcta gtggcataat tatagagaaa 11880
tataatgtta acagtttaac acgtggtgag agaggaccca ctaaaccatg ggttggttca 11940
tctacacaag agaaaaaaac aatgccagtt tataatagac aagtcttaac caaaaaacag 12000
agagatcaaa tagatctatt agcaaaattg gattgggtgt atgcatctat agataacaag 12060
gatgaattca tggaagaact ctcaatagga acccttgggt taacaaaaga aaaggccaag 12120
aaattatttc cacaatattt aagtgtcaat tatttgcatc gccttacagt cagtagtaga 12180
ccatgtgaat tccctgcatc aataccagct tatagaacaa caaattatca ctttgacact 12240
agccctatta atcgcatatt aacagaaaag tatggtgatg aagatattga catagtattc 12300
caaaactgta taagctttgg ccttagttta atgtcagtag tagaacaatt tactaatgta 12360
tgtcctaaca gaattattct catacctaag cttaatgaga tacatttgat gaaacctccc 12420
atattcacag gtgatgttga tattcacaag ttaaaacaag tgatacaaaa acagcatatg 12480
tttttaccag acaaaataag tttgactcaa tatgtggaat tattcttaag taataaaaca 12540
ctcaaatctg gatctcatgt taattctaat ttaatattgg cacataaaat atctgactat 12600
tttcataata cttacatttt aagtactaat ttagctggac attggattct gattatacaa 12660
cttatgaaag attctaaagg tatttttgaa aaagattggg gagagggata tataactgat 12720
catatgttta ttaatttgaa agttttcttc aatgcttata agacctatct cttgtgtttt 12780
cataaaggtt atggcaaagc aaagctggag tgtgatatga acacttcaga tcttctatgt 12840
gtattggaat taatagacag tagttattgg aagtctatgt ctaaggtatt tttagaacaa 12900

-continued

```
aaagttatca aatacattct tagccaagat gcaagtttac atagagtaaa aggatgtcat  12960
agcttcaaat tatggtttct taaacgtctt aatgtagcag aattcacagt ttgcccttgg  13020
gttgttaaca tagattatca tccaacacat atgaaagcaa tattaactta tatagatctt  13080
gttagaatgg gattgataaa tatagataga atacacatta aaaataaaca caaattcaat  13140
gatgaatttt atacttctaa tctcttctac attaattata acttctcaga taatactcat  13200
ctattaacta aacatataag gattgctaat tctgaattag aaaataatta caacaaatta  13260
tatcatccta caccagaaac cctagagaat atactagcca atccgattaa aagtaatgac  13320
aaaaagacac tgaatgacta ttgtataggt aaaaatgttg actcaataat gttaccattg  13380
ttatctaata agaagcttat taaatcgtct gcaatgatta gaaccaatta cagcaaacaa  13440
gatttgtata atttattccc tatggttgtg attgatagaa ttatagatca ttcaggcaat  13500
acagccaaat ccaaccaact ttacactact acttcccacc aaatatcctt agtgcacaat  13560
agcacatcac tttactgcat gcttccttgg catcatatta atagattcaa ttttgtattt  13620
agttctacag gttgtaaaat tagtatagag tatattttaa aagatcttaa aattaaagat  13680
cccaattgta tagcattcat aggtgaagga gcagggaatt tattattgcg tacagtagtg  13740
gaacttcatc ctgacataag atatatttac agaagtctga aagattgcaa tgatcatagt  13800
ttacctattg agtttttaag gctgtacaat ggacatatca acattgatta tggtgaaaat  13860
ttgaccattc ctgctacaga tgcaaccaac aacattcatt ggtcttattt acatataaag  13920
tttgctgaac ctatcagtct ttttgtctgt gatgccgaat tgtctgtaac agtcaactgg  13980
agtaaaatta taatagaatg gagcaagcat gtaagaaagt gcaagtactg ttcctcagtt  14040
aataaatgta tgttaatagt aaaatatcat gctcaagatg atattgattt caaattagac  14100
aatataacta tattaaaaac ttatgtatgc ttaggcagta agttaaaggg atcggaggtt  14160
tacttagtcc ttacaatagg tcctgcgaat atattcccag tatttaatgt agtacaaaat  14220
gctaaattga tactatcaag aaccaaaaat ttcatcatgc ctaagaaagc tgataaagag  14280
tctattgatg caaatattaa aagtttgata ccctttcttt gttaccctat aacaaaaaaa  14340
ggaattaata ctgcattgtc aaaactaaag agtgttgtta gtggagatat actatcatat  14400
tctatagctg gacgtaatga agttttcagc aataaactta taaatcataa gcatatgaac  14460
atcttaaaat ggttcaatca tgttttaaat ttcagatcaa cagaactaaa ctataaccat  14520
ttatatatgg tagaatctac atatccttac ctaagtgaat tgttaaacag cttgacaacc  14580
aatgaactta aaaaactgat taaaatcaca ggtagtctgt tatacaactt tcataatgaa  14640
taatgaataa agatcttata ataaaaattc ccatagctat acactaacac tgtattcaat  14700
tatagttatt aaaaattaaa aatcatataa tttttaaat aacttttagt gaactaatcc  14760
taaagttatc attttaatct tggaggaata aatttaaacc ctaatctaat tggtttatat  14820
gtgtattaac taaattacga gatattagtt tttgacactt tttttctcgt             14870
```

<210> SEQ ID NO 17
<211> LENGTH: 14870
<212> TYPE: DNA
<213> ORGANISM: Artificial Sequence
<220> FEATURE:
<223> OTHER INFORMATION: recombinant respiratory syncytial virus
      sequence

<400> SEQUENCE: 17

```
acgggaaaaa atgcgtacaa caaacttgca taaaccaaaa aaatggggca aataagaatt     60
```

-continued

```
tgataagtac cacttaaatt taactccctt ggttagagat gggcagcaat tcattgagta    120
tgataaaagt tagattacaa aatttgtttg acaatgatga agtagcattg ttaaaaataa    180
catgctatac tgataaatta atacatttaa ctaatgcttt ggctaaggca gtgatacata    240
caatcaaatt gaatggcatt gtgtttgtgc atgttattac aagtagtgat atttgcccta    300
ataataatat tgtagtaaaa tccaatttca caacaatgcc agtactacaa aatggaggtt    360
atatatggga aatgatggaa ttaacacatt gctctcaacc taatggtcta ctagatgaca    420
attgtgaaat taaattctcc aaaaaactaa gtgattcaac aatgaccaat tatatgaatc    480
aattatctga attacttgga tttgatctta atccataaat tataattaat atcaactagc    540
aaatcaatgt cactaacacc attagttaat ataaaactta acagaagaca aaaatggggc    600
aaataaatca attcagccaa cccaaccatg gacacaaccc acaatgataa tacaccacaa    660
agactgatga tcacagacat gagaccgttg tcacttgaga ccataataac atcactaacc    720
agagacatca taacacacaa atttatatac ttgataaatc atgaatgcat agtgagaaaa    780
cttgatgaaa gacaggccac atttacattc ctggtcaact atgaaatgaa actattacac    840
aaagtaggaa gcactaaata taaaaaatat actgaataca acacaaaata tggcactttc    900
cctatgccaa tattcatcaa tcatgatggg ttcttagaat gcattggcat taagcctaca    960
aagcatactc ccataatata caagtatgat ctcaatccat aaatttcaac acaatattca   1020
cacaatctaa aacaacaact ctatgcataa ctatactcca tagtccagat ggagcctgaa   1080
aattatagta atttaaaact taaggagaga tataagatag aagatggggc aaatacaacc   1140
atggctctta gcaaagtcaa gttgaatgat acactcaaca aagatcaact tctgtcatcc   1200
agcaaataca ccatccaacg gagcacagga gatagtattg atactcctaa ttatgatgtg   1260
cagaaacaca tcaataagtt atgtggcatg ttattaatca cagaagatgc taatcataaa   1320
ttcactgggt taataggtat gttatatgcg atgtctaggt taggaagaga agacaccata   1380
aaaatactca gagatgcggg atatcatgta aaagcaaatg gagtagatgt aacaacacat   1440
cgtcaagaca ttaatggaaa agaaatgaaa tttgaagtgt taacattggc aagcttaaca   1500
actgaaattc aaatcaacat tgagatagaa tctagaaaat cctacaaaaa aatgctaaaa   1560
gaaatgggag aggtagctcc agaatacagg catgactctc ctgattgtgg gatgataata   1620
ttatgtatag cagcattagt aataactaaa ttagcagcag gggacagatc tggtcttaca   1680
gccgtgatta ggagagctaa taatgtccta aaaaatgaaa tgaaacgtta caaaggctta   1740
ctacccaagg acatagccaa cagcttctat gaagtgtttg aaaaacatcc ccactttata   1800
gatgtttttg ttcattttgg tatagcacaa tcttctacca gaggtggcag tagagttgaa   1860
gggatttttg caggattgtt tatgaatgcc tatggtgcag ggcaagtgat gttacggtgg   1920
ggagtcttag caaaatcgat taaaaatatt atgttaggac atgctagtgt gcaagcagaa   1980
atggaacaag ttgttgaggt ttatgaatat gcccaaaaat tgggtggtga agcaggattc   2040
taccatatat tgaacaaccc aaaagcatca ttattatctt tgactcaatt tcctcacttc   2100
tccagtgtag tattaggcaa tgctgctggc ctaggcataa tgggagagta cagaggtaca   2160
ccgaggaatc aagatctata tgatgcagca aaggcatatg ctgaacaact caaagaaaat   2220
ggtgtgatta actacagtgt actagacttg acagcagaag aactagaggc tatcaaacat   2280
cagcttaatc caaaagataa tgatgtagag ctttgagtta ataaaaaatg gggcaaataa   2340
atcatcatgg aaaagtttgc tcctgaattc catggagaag atgcaaacaa cagggctact   2400
aaattcctag aatcaataaa gggcaaattc acatcaccca aagatcccaa gaaaaaagat   2460
```

```
agtatcatat ctgtcaactc aatagatata gaagtaacca aagaaagccc tataacatca   2520
aattcaacta ttatcaaccc aacaaatgag acagatgata ctgcagggaa caagcccaat   2580
tatcaaagaa aacctctagt aagtttcaaa gaagacccta caccaagtga taatcccttt   2640
tctaaactat acaaagaaac catagaaaca tttgataaca atgaagaaga atccagctat   2700
tcatacgaag aaataaatga tcagacaaac gataatataa cagcaagatt agataggatt   2760
gatgaaaaat taagtgaaat actaggaatg cttcacacat tagtagtggc aagtgcagga   2820
cctacatctg ctcgggatgg tataagagat gccatggttg gtttaagaga agaaatgata   2880
gaaaaaatca gaactgaagc attaatgacc aatgacagat tagaagctat ggcaagactc   2940
aggaatgagg aaagtgaaaa gatggcaaaa gacacatcag atgaagtgtc tctcaatcca   3000
acatcagaga aattgaacaa cctattggaa gggaatgata gtgacaatga tctatcactt   3060
gaagatttct gattagttac caatcttcac atcaacacac aataccaaca gaagaccaac   3120
aaactaacca acccaatcat ccaaccaaac atccatccgc caatcagcca aacagccaac   3180
aaaacaacca gccaatccaa aactaaccac ccggaaaaaa tctataatat agttacaaaa   3240
aaaggaaagg gtggggcaaa tatggaaaca tacgtgaaca agcttcacga aggctccaca   3300
tacacagctg ctgttcaata caatgtctta gaaaaagacg atgaccctgc atcacttaca   3360
atatgggtgc ccatgttcca atcatctatg ccagcagatt tacttataaa agaactagct   3420
aatgtcaaca tactagtgaa acaaatatcc acacccaagg gaccttcact aagagtcatg   3480
ataaactcaa gaagtgcagt gctagcacaa atgcccagca aatttaccat atgcgctaat   3540
gtgtccttgg atgaaagaag caaactagca tatgatgtaa ccacaccctg tgaaatcaag   3600
gcatgtagtc taacatgcct aaaatcaaaa aatatgttga ctacagttaa agatctcact   3660
atgaagacac tcaaccctac acatgatatt attgctttat gtgaatttga aaacatagta   3720
acatcaaaaa aagtcataat accaacatac ctaagatcca tcagtgtcag aaataaagat   3780
ctgaacacac ttgaaaatat aacaaccact gaattcaaaa atgctatcac aaatgcaaaa   3840
atcatccctt actcaggatt actattagtc atcacagtga ctgacaacaa aggagcattc   3900
aaatacataa agccacaaag tcaattcata gtagatcttg gagcttacct agaaaaagaa   3960
agtatatatt atgttaccac aaattggaag cacacagcta cacgatttgc aatcaaaccc   4020
atggaagatt aaccttttc ctctacatca gtgtgttaat tcatacaaac tttctaccta   4080
cattcttcac ttcaccatca caatcacaaa cactctgtgg ttcaaccaat caaacaaaac   4140
ttatctgaag tcccagatca tcccaagtca ttgtttatca gatctagtac tcaaataagt   4200
taataaaaaa tatacacatg gggcaaataa tcattggagg aaatccaact aatcacaata   4260
tctgttaaca tagacaagtc cacacaccat acagaatcaa ccaatggaaa atacatccat   4320
aacaatagaa ttctcaagca aattctggcc ttactttaca ctaatacaca tgatcacaac   4380
aataatctct ttgctaatca taatctccat catgattgca atactaaaca aactttgtga   4440
atataacgta ttccataaca aaacctttga gttaccaaga gctcgagtta atacttgata   4500
aagtagttaa ttaaaaatag tcataacaat gaactaggat atcaagacta acaataacat   4560
tggggcaaat gcaaacatgt ccaaaaacaa ggaccaacgc accgctaaga cattagaaag   4620
gacctgggac actctcaatc atttattatt catatcatcg tgcttatata agttaaatct   4680
taaatctgta gcacaaatca cattatccat tctggcaatg ataatctcaa cttcacttat   4740
aattgcagcc atcatattca tagcctcggc aaaccacaaa gtcacaccaa caactgcaat   4800
```

catacaagat gcaacaagcc agatcaagaa cacaacccca acatacctca cccagaatcc 4860
tcagcttgga atcagtccct ctaatccgtc tgaaattaca tcacaaatca ccaccatact 4920
agcttcaaca acaccaggag tcaagtcaac cctgcaatcc acaacagtca agaccaaaaa 4980
cacaacaaca actcaaacac aacccagcaa gcccaccaca aaacaacgcc aaaacaaacc 5040
accaagcaaa cccaataatg attttcactt tgaagtgttc aactttgtac cctgcagcat 5100
atgcagcaac aatccaacct gctgggctat ctgcaaaaga ataccaaaca aaaaaccagg 5160
aaagaaaacc actaccaagc ccacaaaaaa accaaccctc aagacaacca aaaaagatcc 5220
caaacctcaa accactaaat caaaggaagt acccaccacc aagcccacag aagagccaac 5280
catcaacacc accaaaacaa acatcataac tacactactc acctccaaca ccacaggaaa 5340
tccagaactc acaagtcaaa tggaaacctt ccactcaact tcctccgaag gcaatccaag 5400
cccttctcaa gtctctacaa catccgagta cccatcacaa ccttcatctc cacccaacac 5460
accacgccag tagttactta aaaacatatt atcacaaaag gccttgacca acttaaacag 5520
aatcaaaata aactctgggg caaataacaa tggagttgct aatcctcaaa gcaaatgcaa 5580
ttaccacaat cctcactgca gtcacatttt gttttgcttc tggtcaaaac atcactgaag 5640
aattttatca atcaacatgc agtgcagtta gcaaaggcta tcttagtgct ctgagaactg 5700
gttggtatac cagtgttata actatagaat taagtaatat caagaaaaat aagtgtaatg 5760
gaacagatgc taaggtaaaa ttgataaaac aagaattaga taaatataaa aatgctgtaa 5820
cagaattgca gttgctcatg caaagcacac aagcaacaaa caatcgagcc agaagagaac 5880
taccaaggtt tatgaattat acactcaaca atgccaaaaa aaccaatgta acattaagca 5940
agaaaaggaa aagaagattt cttggttttt tgttaggtgt tggatctgca atcgccagtg 6000
gcgttgctgt atctaaggtc ctgcacctag aaggggaagt gaacaagatc aaaagtgctc 6060
tactatccac aaacaaggct gtagtcagct tatcaaatgg agttagtgtt ttaaccagca 6120
aagtgttaga cctcaaaaac tatatagata aacaattgtt acctattgtg aacaagcaaa 6180
gctgcagcat atcaaatata gcaactgtga tagagttcca acaaaagaac aacagactac 6240
tagagattac cagggaattt agtgttaatg caggcgtaac tacacctgta agcacttaca 6300
tgttaactaa tagtgaatta ttgtcattaa tcaatgatat gcctataaca aatgatcaga 6360
aaaagttaat gtccaacaat gttcaaatag ttagacagca aagttactct atcatgtcca 6420
taataaaaga ggaagtctta gcatatgtag tacaattacc actatatggt gttatagata 6480
caccctgttg gaaactacac acatcccctc tatgtacaac caacacaaaa gaagggtcca 6540
acatctgttt aacaagaact gacagaggat ggtactgtga caatgcagga tcagtatctt 6600
tcttcccaca agctgaaaca tgtaaagttc aatcaaatcg agtattttgt gacacaatga 6660
acagtttaac attaccaagt gaagtaaatc tctgcaatgt tgacatattc aaccccaaat 6720
atgattgtaa aattatgact tcaaaaacag atgtaagcag ctccgttatc acatctctag 6780
gagccattgt gtcatgctat ggcaaaacta aatgtacagc atccaataaa aatcgtggaa 6840
tcataaagac attttctaac gggtgcgatt atgtatcaaa taaaggggtg gacactgtgt 6900
ctgtaggtaa cacattatat tatgtaaata agcaagaagg taaaagtctc tatgtaaaag 6960
gtgaaccaat aataaatttc tatgacccat tagtattccc ctctgatgaa tttgatgcat 7020
caatatctca agtcaacgag aagattaacc agagcctagc atttattcgt aaatccgatg 7080
aattattaca taatgtaaat gctggtaaat ccaccataaa tatcatgata actactataa 7140
ttatagtgat tatagtaata ttgttatcat taattgctgt tggactgctc ttatactgta 7200
aggccagaag cacaccagtc acactaagca aagatcaact gagtggtata aataatattg 7260
catttagtaa ctaaataaaa atagcaccta atcatgttct tacaatggtt tactatctgc 7320
tcatagacaa cccatctgtc attggatttt cttaaaatct gaacttcatc gaaactctca 7380
tctataaacc atctcactta cactatttaa gtagattcct agtttatagt tatataaaac 7440
acaattgcat gccagattaa cttaccatct gtaaaaatga aaactggggc aaatatgtca 7500
cgaaggaatc cttgcaaatt tgaaattcga ggtcattgct taaatggtaa gaggtgtcat 7560
tttagtcata attattttga atggccaccc catgcactgc ttgtaagaca aaactttatg 7620
ttaaacagaa tacttaagtc tatggataaa agtatagata ccttatcaga aataagtgga 7680
gctgcagagt tggacagaac agaagagtat gctcttggtg tagttggagt gctagagagt 7740
tatataggat caataaacaa tataactaaa caatcagcat gtgttgccat gagcaaactc 7800
ctcactgaac tcaatagtga tgatatcaaa aagctgaggg acaatgaaga gctaaattca 7860
cccaagataa gagtgtacaa tactgtcata tcatatattg aaagcaacag gaaaaacaat 7920
aaacaaacta tccatctgtt aaaaagattg ccagcagacg tattgaagaa aaccatcaaa 7980
aacacattgg atatccataa gagcataacc atcaacaacc caaaagaatc aactgttagt 8040
gatacaaacg accacgccaa aaataacgat actacctaac actcaattct aacactcacc 8100
acatcgttac attattaatt caaacaattc aagttgtggg acaaaatgga tcccattatt 8160
aatggaaatt ctgctaatgt ttatctaacc gatagttatt taaaaggtgt tatctctttc 8220
tcagagtgta atgctttagg aagttacata ttcaatggtc cttatctcaa aaatgattat 8280
accaacttaa ttagtagaca aaatccatta atagaacaca tgaatctaaa gaaactaaat 8340
ataacacagt ccttaatatc taagtatcat aaaggtgaaa taaaattaga agaacctact 8400
tattttcagt cattacttat gacatacaag agtatgacct cgtcagaaca gattgctacc 8460
actaatttac ttaaaaagat aataagaaga gctatagaaa taagtgatgt caaagtctat 8520
gctatattga ataaactagg gcttaaagaa aaggacaaga ttaaatccaa caatggacaa 8580
gatgaagaca actcagttat tacgaccata atcaaagatg atatactttc agctgttaaa 8640
gataatcaat ctcatcttaa agcagacaaa aatcactcta caaaacaaaa agacacaatc 8700
aaaacaacac tcttgaagaa attgatgtgt tcaatgcaac atcctccatc atggttaata 8760
cattggttta acttatacac aaaattaaac aacatattaa cacagtatcg atcaaatgag 8820
gtaaaaaacc atgggtttac attgatagat aatcaaactc ttagtggatt tcaatttatt 8880
ttgaaccaat atggttgtat agtttatcat aaggaactca aaagaattac tgtgacaacc 8940
tataatcaat tcttgacatg gaaagatatt agccttagta gattaaatgt ttgtttaatt 9000
acatggatta gtaactgctt gaacacatta aataaaagct taggcttaag atgcggattc 9060
aataatgtta tcttgacaca actattcctt tatggagatt acatactaaa gctatttcac 9120
aatgaggggt tctacataat aaaagaggta gagggattta ttatgtctct aattttaaat 9180
ataacagaag aagatcaatt cagaaaacga ttttataata gtatgctcaa caacatcaca 9240
gatgctgcta ataaagctca gaaaaatctg ctatcaagag tatgtcatac attattagat 9300
aagacagtgt ccgataatat aataaatggc agatggataa ttctattaag taagttcctt 9360
aaattaatta agcttgcagg tgacaataac cttaacaatc tgagtgaact atatttttg 9420 ttcagaatat ttggacaccc aatggtagat gaaagacaag ccatggatgc tgttaaaatt 9480
aattgcaatg agaccaaatt ttacttgtta agcagtctga gtatgttaag aggtgccttt 9540

```
atatatagaa ttataaaagg gtttgtaaat aattacaaca gatggcctac tttaagaaat   9600
gctattgttt taccccttaag atggttaact tactataaac taaacactta tccttctttg   9660
ttggaactta cagaaagaga tttgattgtg ttatcaggac tacgtttcta tcgtgagttt   9720
cggttgccta aaaaagtgga tcttgaaatg attataaatg ataaagctat atcacctcct   9780
aaaaatttga tatggactag tttccctaga aattacatgc catcacacat acaaaactat   9840
atagaacatg aaaaattaaa attttccgag agtgataaat caagaagagt attagagtat   9900
tatttaagag ataacaaatt caatgaatgt gatttataca actgtgtagt taatcaaagt   9960
tatctcaaca accctaatca tgtggtatca ttgacaggca aagaaagaga actcagtgta  10020
ggtagaatgt ttgcaatgca accgggaatg ttcagacagg ttcaaatatt ggcagagaaa  10080
atgatagctg aaaacatttt acaattcttt cctgaaagtc ttacaagata tggtgatcta  10140
gaactacaaa aaatattaga actgaaagca ggaataagta acaaatcaaa tcgctacaat  10200
gataattaca acaattacat tagtaagtgc tctatcatca cagatctcag caaattcaat  10260
caagcatttc gatatgaaac gtcatgtatt tgtagtgatg tgctggatga actgcatggt  10320
gtacaatctc tattttcctg gttacattta actattcctc atgtcacaat aatatgcaca  10380
tataggcatg caccccccta tataggagat catattgtag atcttaacaa tgtagatgaa  10440
caaagtggat tatatagata tcacatgggt ggcatcgaag ggtggtgtca aaaactatgg  10500
accatagaag ctatatcact attggatcta atatctctca aagggaaatt ctcaattact  10560
gctttaatta atggtgacaa tcaatcaata gatataagca aaccaatcag actcatggaa  10620
ggtcaaactc atgctcaagc agattatttg ctagcattaa atagccttaa attactgtat  10680
aaagagtatg caggcatagg ccacaaatta aaaggaactg agacttatat atcacgagat  10740
atgcaattta tgagtaaaac aattcaacat aacggtgtat attacccagc tagtataaag  10800
aaagtcctaa gagtgggacc gtggataaac actatacttg atgatttcaa agtgagtcta  10860
gaatctatag gtagtttgac acaagaatta gaatatagag gtgaaagtct attatgcagt  10920
ttaatattta gaaatgtatg gttatataat cagattgctc tacaattaaa aaatcatgca  10980
ttatgtaaca ataaactata tttggacata ttaaaggttc tgaaacactt aaaaaccttt  11040
tttaatcttg ataatattga tacagcatta acattgtata tgaatttacc catgttattt  11100
ggtggtggtg atcccaactt gttatatcga agtttctata gaagaactcc tgacttcctc  11160
acagaggcta tagttcactc tgtgttcata cttagttatt atacaaacca tgacttaaaa  11220
gataaacttc aagatctgtc agatgataga ttgaataagt tcttaacatg cataatcacg  11280
tttgacaaaa accctaatgc tgaattcgta acattgatga gagatcctca agctttaggg  11340
tctgagagac aagctaaaat tactagcgaa atcaatagac tggcagttac agaggttttg  11400
agtacagctc caaacaaaat attctccaaa agtgcacaac attatactac tacagagata  11460
gatctaaatg atattatgca aaatatagaa cctacatatc ctcatgggct aagagttgtt  11520
tatgaaagtt taccctttta taaagcagag aaaatagtaa atcttatatc aggtacaaaa  11580
tctataacta acatactgga aaaaacttct gccatagact taacagatat tgatagagcc  11640
actgagatga tgaggaaaaa cataactttg cttataagga tacttccatt ggattgtaac  11700
agagataaaa gagagatatt gagtatggaa aacctaagta ttactgaatt aagcaaatat  11760
gttagggaaa gatcttggtc tttatccaat atagttggtg ttacatcacc cagtatcatg  11820
tatacaatgg acatcaaata tactacaagc actatatcta gtggcataat tatagagaaa  11880
tataatgtta acagtttaac acgtggtgag agaggaccca ctaaaccatg ggttggttca  11940
```

tctacacaag agaaaaaaac aatgccagtt tataatagac aagtcttaac caaaaaacag 12000
agagatcaaa tagatctatt agcaaaattg gattgggtgt atgcatctat agataacaag 12060
gatgaattca tggaagaact cagcatagga acccttgggt taacatatga aaaggccaag 12120
aaattatttc cacaatattt aagtgtcaat tatttgcatc gccttacagt cagtagtaga 12180
ccatgtgaat tccctgcatc aataccagct tatagaacaa caaattatca ctttgacact 12240
agccctatta atcgcatatt aacagaaaag tatggtgatg aagatattga catagtattc 12300
caaaactgta taagctttgg ccttagttta atgtcagtag tagaacaatt tactaatgta 12360
tgtcctaaca gaattattct catacctaag cttaatgaga tacatttgat gaaacctccc 12420
atattcacag gtgatgttga tattcacaag ttaaaacaag tgatacaaaa acagcatatg 12480
tttttaccag acaaaataag tttgactcaa tatgtggaat tattcttaag taataaaaca 12540
ctcaaatctg gatctcatgt taattctaat ttaatattgg cacataaaat atctgactat 12600
tttcataata cttacatttt aagtactaat ttagctggac attggattct gattatacaa 12660
cttatgaaag attctaaagg tatttttgaa aaagattggg gagagggata tataactgat 12720
catatgttta ttaatttgaa agttttcttc aatgcttata agacctatct cttgtgtttt 12780
cataaaggtt atggcaaagc aaagctggag tgtgatatga acacttcaga tcttctatgt 12840
gtattggaat taatagacag tagttattgg aagtctatgt ctaaggtatt tttagaacaa 12900
aaagttatca aatacattct tagccaagat gcaagtttac atagagtaaa aggatgtcat 12960
agcttcaaat tatggtttct taaacgtctt aatgtagcag aattcacagt ttgcccttgg 13020
gttgttaaca tagattatca tccaacacat atgaaagcaa tattaactta tatagatctt 13080
gttagaatgg gattgataaa tatagataga atacacatta aaaataaaca caaattcaat 13140
gatgaatttt atacttctaa tctcttctac attaattata acttctcaga taatactcat 13200
ctattaacta aatacataag gattgctaat tctgaattag aaaataatta caacaaatta 13260
tatcatccta caccagaaac cctagagaat atactagcca atccgattaa aagtaatgac 13320
aaaaagacac tgaatgacta ttgtataggt aaaaatgttg actcaataat gttaccattg 13380
ttatctaata agaagcttat taaatcgtct gcaatgatta gaaccaatta cagcaaacaa 13440
gatttgtata atttattccc tatggttgtg attgatagaa ttatagatca ttcaggcaat 13500
acagccaaat ccaaccaact ttacactact acttcccacc aaatatcctt agtgcacaat 13560
agcacatcac tttactgcat gcttccttgg catcatatta atagattcaa ttttgtattt 13620
agttctacag gttgtaaaat tagtatagag tatattttaa aagatcttaa aattaaagat 13680
cccaattgta tagcattcat aggtgaagga gcagggaatt tattattgcg tacagtagtg 13740
gaacttcatc ctgacataag atatatttac agaagtctga aagattgcaa tgatcatagt 13800
ttacctattg agtttttaag gctgtacaat ggacatatca acattgatta tggtgaaaat 13860
ttgaccattc ctgctacaga tgcaaccaac aacattcatt ggtcttattt acatataaag 13920
tttgctgaac ctatcagtct ttttgtctgt gatgccgaat tgtctgtaac agtcaactgg 13980
agtaaaatta taatagaatg gagcaagcat gtaagaaagt gcaagtactg ttcctcagtt 14040
aataaatgta tgttaatagt aaaatatcat gctcaagatg atattgattt caaattagac 14100
aatataacta tattaaaaac ttatgtatgc ttaggcagta agttaaaggg atcggaggtt 14160
tacttagtcc ttacaatagg tcctgcgaat atattcccag tatttaatgt agtacaaaat 14220
gctaaattga tactatcaag aaccaaaaat ttcatcatgc ctaagaaagc tgataaagag 14280

```
tctattgatg caaatattaa aagtttgata ccctttcttt gttaccctat aacaaaaaaa  14340

ggaattaata ctgcattgtc aaaactaaag agtgttgtta gtggagatat actatcatat  14400

tctatagctg gacgtaatga agttttcagc aataaactta taaatcataa gcatatgaac  14460

atcttaaaat ggttcaatca tgttttaaat ttcagatcaa cagaactaaa ctataaccat  14520

ttatatatgg tagaatctac atatccttac ctaagtgaat tgttaaacag cttgacaacc  14580

aatgaactta aaaaactgat taaaatcaca ggtagtctgt tatacaactt tcataatgaa  14640

taatgaataa agatcttata ataaaaattc ccatagctat acactaacac tgtattcaat  14700

tatagttatt aaaaattaaa aatcatataa ttttttaaat aacttttagt gaactaatcc  14760

taaagttatc attttaatct tggaggaata aatttaaacc ctaatctaat tggtttatat  14820

gtgtattaac taaattacga gatattagtt tttgacactt tttttctcgt             14870


<210> SEQ ID NO 18
<211> LENGTH: 14989
<212> TYPE: DNA
<213> ORGANISM: Artificial Sequence
<220> FEATURE:
<223> OTHER INFORMATION: recombinant respiratory syncytial virus
      sequence

<400> SEQUENCE: 18

acgggaaaaa atgcgtacaa caaacttgca taaaccaaaa aaatggggca aataagaatt     60

tgataagtac cacttaaatt taactccctt ggttagagat gggcagcaat tcattgagta    120

tgataaaagt tagattacaa aatttgtttg acaatgatga agtagcattg ttaaaaataa    180

catgctatac tgataaatta atacatttaa ctaatgcttt ggctaaggca gtgatacata    240

caatcaaatt gaatggcatt gtgtttgtgc atgttattac aagtagtgat atttgcccta    300

ataataatat tgtagtaaaa tccaatttca caacaatgcc agtactacaa aatggaggtt    360

atatatggga aatgatggaa ttaacacatt gctctcaacc taatggtcta ctagatgaca    420

attgtgaaat taaattctcc aaaaaactaa gtgattcaac aatgaccaat tatatgaatc    480

aattatctga attacttgga tttgatctta atccataaat tataattaat atcaactagc    540

aaatcaatgt cactaacacc attagttaat ataaaactta acagaagaca aaaatggggc    600

aaataaatca attcagccaa cccaaccatg gacacaaccc acaatgataa tacaccacaa    660

agactgatga tcacagacat gagaccgttg tcacttgaga ccataataac atcactaacc    720

agagacatca taacacacaa atttatatac ttgataaatc atgaatgcat agtgagaaga    780

cttgatgaaa gacaggccac atttacattc ctggtcaact atgaaatgaa actattacac    840

aaagtaggaa gcactaaata taaaaaatat actgaataca acacaaaata tggcactttc    900

cctatgccaa tattcatcaa tcatgatggg ttcttagaat gcattggcat taagcctaca    960

aagcatactc ccataatata caagtatgat ctcaatccat aaatttcaac acaatattca   1020

cacaatctaa aacaacaact ctatgcataa ctatactcca tagtccagat ggagcctgaa   1080

aattatagta atttaaaact taaggagaga tataagatag aagatggggc aaatacaacc   1140

atggctctta gcaaagtcaa gttgaatgat acactcaaca aagatcaact tctgtcatcc   1200

agcaaatacg ccatccaacg gagcacagga gatagtattg atactcctaa ttatgatgtg   1260

cagaaacaca tcaataagtt atgtggcatg ttattaatca cagaagatgc taatcataaa   1320

ttcactgggt taataggtat gttatatgcg atgtctaggt taggaagaga agacaccata   1380

aaaatactca gagatgcggg atatcatgta aaagcaaatg gagtagatgt aacaacacat   1440
```

-continued

```
cgtcaagaca ttaatggaaa agaaatgaaa tttgaagtgt taacattggc aagcttaaca   1500
actgaaattc aaatcaacat tgagatagaa tctagaaaat cctacaaaaa aatgctaaaa   1560
gaaatgggag aggtagctcc agaatacagg catgactctc ctgattgtgg gatgataata   1620
ttatgtatag cagcattagt aataactaaa ttagcagcag gggacagatc tggtcttaca   1680
gccgtgatta ggagagctaa taatgtccta aaaaatgaaa tgaaacgtta caaaggctta   1740
ctacccaagg acatagccaa cagcttctat gaagtgtttg aaaaacatcc ccactttata   1800
gatgtttttg ttcattttgg tatagcacaa tcttctacca gaggtggcag tagagttgaa   1860
gggatttttg caggattgtt tatgaatgcc tatggtgcag ggcaagtgat gttacggtgg   1920
ggagtcttag caaaatcggt taaaaatatt atgttaggac atgctagtgt gcaagcagaa   1980
atggaacaag ttgttgaggt ttatgaatat gcccaaaaat tgggtggtga agcaggattc   2040
taccatatat tgaacaaccc aaaagcatca ttattatctt tgactcaatt tcctcacttc   2100
tccagtgtag tattaggcaa tgctgctggc ctaggcataa tgggagagta cagaggtaca   2160
ccgaggaatc aagatctata tgatgcagca aaggcatatg ctgaacaact caaagaaaat   2220
ggtgtgatta actacagtgt actagacttg acagcagaag aactagaggc tatcaaacat   2280
cagcttaatc caaaagataa tgatgtagag ctttgagtta ataaaaaatg gggcaaataa   2340
atcatcatgg aaaagtttgc tcctgaattc catggagaag atgcaaacaa cagggctact   2400
aaattcctag aatcaataaa gggcaaattc acatcaccca aagatcccaa gaaaaaagat   2460
agtatcatat ctgtcaactc aatagatata gaagtaacca aagaaagccc tataacatca   2520
aattcaacta ttatcaaccc aacaaatgag acagatgata ctgcagggaa caagcccaat   2580
tatcaaagaa aacctctagt aagtttcaaa gaagacccta caccaagtga taatcccttt   2640
tctaaactat acaaagaaac catagaaaca tttgataaca atgaagaaga atccagctat   2700
tcatacgaag aaataaatga tcagacaaac gataatataa cagcaagatt agataggatt   2760
gatgaaaaat taagtgaaat actaggaatg cttcacacat tagtagtggc aagtgcagga   2820
cctacatctg ctcgggatgg tataagagat gccatggttg gtttaagaga agaaatgata   2880
gaaaaaatca gaactgaagc attaatgacc aatgacagat tagaagctat ggcaagactc   2940
aggaatgagg aaagtgaaaa gatggcaaaa gacacatcag atgaagtgtc tctcaatcca   3000
acatcagaga aattgaacaa cctattggaa gggaatgata gtgacaatga tctatcactt   3060
gaagatttct gattagttac caatcttcac atcaacacac aataccaaca gaagaccaac   3120
aaactaacca acccaatcat ccaaccaaac atccatccgc caatcagcca aacagccaac   3180
aaaacaacca gccaatccaa aactaaccac ccggaaaaaa tctataatat agttacaaaa   3240
aaaggaaagg gtggggcaaa tatggaaaca tacgtgaaca agcttcacga aggctccaca   3300
tacacagctg ctgttcaata caatgtctta gaaaaagacg atgaccctgc atcacttaca   3360
atatgggtgc ccatgttcca atcatctatg ccagcagatt tacttataaa agaactagct   3420
aatgtcaaca tactagtgaa acaaatatcc acacccaagg gaccttcact aagagtcatg   3480
ataaactcaa gaagtgcagt gctagcacaa atgcccagca aatttaccat atgcgctaat   3540
gtgtccttgg atgaaagaag caaactagca tatgatgtaa ccacaccctg tgaaatcaag   3600
gcatgtagtc taacatgcct aaaatcaaaa aatatgttga ctacagttaa agatctcact   3660
atgaagacac tcaaccctac acatgatatt attgctttat gtgaatttga aaacatagta   3720
acatcaaaaa aagtcataat accaacatac ctaagatcca tcagtgtcag aaataaagat   3780
ctgaacacac ttgaaaatat aacaaccact gaattcaaaa atgctatcac aaatgcaaaa   3840
```

```
atcatccctt actcaggatt actattagtc atcacagtga ctgacaacaa aggagcattc   3900
aaatacataa agccacaaag tcaattcata gtagatcttg gagcttacct agaaaaagaa   3960
agtatatatt atgttaccac aaattggaag cacacagcta cacgatttgc aatcaaaccc   4020
atggaagatt aacctttttc ctctacatca gtgtgttaat tcatacaaac tttctaccta   4080
cattcttcac ttcaccatca caatcacaaa cactctgtgg ttcaaccaat caaacaaaac   4140
ttatctgaag tcccagatca tcccaagtca ttgtttatca gatctagtac tcaaataagt   4200
taataaaaaa tatacacatg gggcaaataa tcattggagg aaatccaact aatcacaata   4260
tctgttaaca tagacaagtc cacacaccat acagaatcaa ccaatggaaa atacatccat   4320
aacaatagaa ttctcaagca aattctggcc ttactttaca ctaatacaca tgatcacaac   4380
aataatctct ttgctaatca taatctccat catgattgca atactaaaca aactttgtga   4440
atataacgta ttccataaca aaacctttga gttaccaaga gctcgagtca acacatagca   4500
ttcatcaatc caacagccca aaacagtaac cttgcattta aaaatgaaca acccctacct   4560
ctttacaaca cctcattaac atcccaccat gcaaaccact atccatacta taaagtagtt   4620
aattaaaaat agtcataaca atgaactagg atatcaagac taacaataac attggggcaa   4680
atgcaaacat gtccaaaaac aaggaccaac gcaccgctaa gacattagaa aggacctggg   4740
acactctcaa tcatttatta ttcatatcat cgtgcttata taagttaaat cttaaatctg   4800
tagcacaaat cacattatcc attctggcaa tgataatctc aacttcactt ataattgcag   4860
ccatcatatt catagcctcg gcaaaccaca aagtcacacc aacaactgca atcatacaag   4920
atgcaacaag ccagatcaag aacacaaccc caacatacct cacccagaat cctcagcttg   4980
gaatcagtcc ctctaatccg tctgaaatta catcacaaat caccaccata ctagcttcaa   5040
caacaccagg agtcaagtca accctgcaat ccacaacagt caagaccaaa aacacaacaa   5100
caactcaaac acaacccagc aagcccacca caaaacaacg ccaaaacaaa ccaccaagca   5160
aacccaataa tgattttcac tttgaagtgt tcaactttgt accctgcagc atatgcagca   5220
acaatccaac ctgctgggct atctgcaaaa gaataccaaa caaaaaacca ggaaagaaaa   5280
ccactaccaa gcccacaaaa aaaccaaccc tcaagacaac caaaaaagat cccaaacctc   5340
aaaccactaa atcaaaggaa gtacccacca ccaagcccac agaagagcca accatcaaca   5400
ccaccaaaac aaacatcata actacactac tcacctccaa caccacagga aatccagaac   5460
tcacaagtca aatggaaacc ttccactcaa cttcctccga aggcaatcca agcccttctc   5520
aagtctctac aacatccgag tacccatcac aaccttcatc tccacccaac acaccacgcc   5580
agtagttact taaaaacata ttatcacaaa aggccttgac caacttaaac agaatcaaaa   5640
taaactctgg ggcaaataac aatggagttg ctaatcctca aagcaaatgc aattaccaca   5700
atcctcactg cagtcacatt ttgttttgct tctggtcaaa acatcactga agaattttat   5760
caatcaacat gcagtgcagt tagcaaaggc tatcttagtg ctctgagaac tggttggtat   5820
accagtgtta taactataga attaagtaat atcaagaaaa ataagtgtaa tggaacagat   5880
gctaaggtaa aattgataaa acaagaatta gataaatata aaaatgctgt aacagaattg   5940
cagttgctca tgcaaagcac acaagcaaca aacaatcgag ccagaagaga actaccaagg   6000
tttatgaatt atacactcaa caatgccaaa aaaaccaatg taacattaag caagaaaagg   6060
aaaagaagat ttcttggttt tttgttaggt gttggatctg caatcgccag tggcgttgct   6120
gtatctaagg tcctgcacct agaaggggaa gtgaacaaga tcaaaagtgc tctactatcc   6180
```

-continued

```
acaaacaagg ctgtagtcag cttatcaaat ggagttagtg ttttaaccag caaagtgtta   6240
gacctcaaaa actatataga taaacaattg ttacctattg tgaacaagca aagctgcagc   6300
atatcaaata tagaaactgt gatagagttc caacaaaaga acaacagact actagagatt   6360
accagggaat ttagtgttaa tgcaggcgta actacacctg taagcactta catgttaact   6420
aatagtgaat tattgtcatt aatcaatgat atgcctataa caaatgatca gaaaaagtta   6480
atgtccaaca atgttcaaat agttagacag caaagttact ctatcatgtc cataataaaa   6540
gaggaagtct tagcatatgt agtacaatta ccactatatg gtgttataga tacaccctgt   6600
tggaaactac acacatcccc tctatgtaca accaacacaa aagaagggtc caacatctgt   6660
ttaacaagaa ctgacagagg atggtactgt gacaatgcag gatcagtatc tttcttccca   6720
caagctgaaa catgtaaagt tcaatcaaat cgagtatttt gtgacacaat gaacagttta   6780
acattaccaa gtgaagtaaa tctctgcaat gttgacatat tcaaccccaa atatgattgt   6840
aaaattatga cttcaaaaac agatgtaagc agctccgtta tcacatctct aggagccatt   6900
gtgtcatgct atggcaaaac taaatgtaca gcatccaata aaaatcgtgg aatcataaag   6960
acattttcta acgggtgcga ttatgtatca aataaagggg tggacactgt gtctgtaggt   7020
aacacattat attatgtaaa taagcaagaa ggtaaaagtc tctatgtaaa aggtgaacca   7080
ataataaatt tctatgaccc attagtattc ccctctgatg aatttgatgc atcaatatct   7140
caagtcaacg agaagattaa ccagagccta gcatttattc gtaaatccga tgaattatta   7200
cataatgtaa atgctggtaa atccaccaca aatatcatga taactactat aattatagtg   7260
attatagtaa tattgttatc attaattgct gttggactgc tcttatactg taaggccaga   7320
agcacaccag tcacactaag caaagatcaa ctgagtggta taaataatat tgcatttagt   7380
aactaaataa aaatagcacc taatcatgtt cttacaatgg tttactatct gctcatagac   7440
aacccatctg tcattggatt ttcttaaaat ctgaacttca tcgaaactct catctataaa   7500
ccatctcact tacactattt aagtagattc ctagtttata gttatataaa acacaattgc   7560
atgccagatt aacttaccat ctgtaaaaat gaaaactggg gcaaatatgt cacgaaggaa   7620
tccttgcaaa tttgaaattc gaggtcattg cttaaatggt aagaggtgtc attttagtca   7680
taattatttt gaatggccac cccatgcact gcttgtaaga caaaacttta tgttaaacag   7740
aatacttaag tctatggata aaagtataga taccttatca gaaataagtg gagctgcaga   7800
gttggacaga acagaagagt atgctcttgg tgtagttgga gtgctagaga gttatatagg   7860
atcaataaac aatataacta aacaatcagc atgtgttgcc atgagcaaac tcctcactga   7920
actcaatagt gatgatatca aaaagctgag ggacaatgaa gagctaaatt cacccaagat   7980
aagagtgtac aatactgtca tatcatatat tgaaagcaac aggaaaaaca ataaacaaac   8040
tatccatctg ttaaaaagat tgccagcaga cgtattgaag aaaaccatca aaaacacatt   8100
ggatatccat aagagcataa ccatcaacaa cccaaaagaa tcaactgtta gtgatacaaa   8160
tgaccatgcc aaaaataatg atactacctg acaaataagc ttcaattcta acactcacca   8220
catcgttaca ttattaattc aaacaattca agttgtggga caaaatggat cccattatta   8280
atggaaattc tgctaatgtt tatctaaccg atagttattt aaaaggtgtt atctctttct   8340
cagagtgtaa tgctttagga agttacatat tcaatggtcc ttatctcaaa aatgattata   8400
ccaacttaat tagtagacaa aatccattaa tagaacacat gaatctaaag aaactaaata   8460
taacacagtc cttaatatct aagtatcata aaggtgaaat aaaattagaa gaacctactt   8520
attttcagtc attacttatg acatacaaga gtatgacctc gtcagaacag attgctacca   8580
```

-continued

```
ctaatttact taaaaagata ataagaagag ctatagaaat aagtgatgtc aaagtctatg   8640
ctatattgaa taaactaggg cttaaagaaa aggacaagat taaatccaac aatggacaag   8700
atgaagacaa ctcagttatt acgaccataa tcaaagatga tatactttca gctgttaaag   8760
ataatcaatc tcatcttaaa gcagacaaaa atcactctac aaaacaaaaa gacacaatca   8820
aaacaacact cttgaagaaa ttgatgtgtt caatgcaaca tcctccatca tggttaatac   8880
attggtttaa cttatacaca aaattaaaca acatattaac acagtatcga tcaaatgagg   8940
taaaaaacca tgggtttaca ttgatagata atcaaactct tagtggattt caatttattt   9000
tgaaccaata tggttgtata gtttatcata aggaactcaa aagaattact gtgacaacct   9060
ataatcaatt cttgacatgg aaagatatta gccttagtag attaaatgtt tgtttaatta   9120
catggattag taactgcttg aacacattaa ataaaagctt aggcttaaga tgcggattca   9180
ataatgttat cttgacacaa ctattccttt atggagattg tatactaaag ctatttcaca   9240
atgaggggtt ctacataata aaagaggtag agggatttat tatgtctcta attttaaata   9300
taacagaaga agatcaattc agaaaacgat tttataatag tatgctcaac aacatcacag   9360
atgctgctaa taaagctcag aaaaatctgc tatcaagagt atgtcataca ttattagata   9420
agacagtgtc cgataatata ataaatggca gatggataat tctattaagt aagttcctta   9480
aattaattaa gcttgcaggt gacaataacc ttaacaatct gagtgaacta tatttttgt    9540
tcagaatatt tggacaccca atggtagatg aaagacaagc catggatgct gttaaaatta   9600
attgcaatga gaccaaattt tacttgttaa gcagtctgag tatgttaaga ggtgccttta   9660
tatatagaat tataaaaggg tttgtaaata attacaacag atggcctact ttaagaaatg   9720
ctattgtttt acccttaaga tggttaactt actataaact aaacacttat ccttctttgt   9780
tggaacttac agaaagagat ttgattgtgt tatcaggact acgtttctat cgtgagtttc   9840
ggttgcctaa aaaagtggat cttgaaatga ttataaatga taaagctata tcacctccta   9900
aaaatttgat atggactagt ttccctagaa attacatgcc atcacacata caaaactata   9960
tagaacatga aaaattaaaa ttttccgaga gtgataaatc aagaagagta ttagagtatt  10020
atttaagaga taacaaattc aatgaatgtg atttatacaa ctgtgtagtt aatcaaagtt  10080
atctcaacaa ccctaatcat gtggtatcat tgacaggcaa agaaagagaa ctcagtgtag  10140
gtagaatgtt tgcaatgcaa ccgggaatgt tcagacaggt tcaaatattg gcagagaaaa  10200
tgatagctga aaacatttta caattctttc ctgaaagtct tacaagatat ggtgatctag  10260
aactacaaaa aatattagaa ctgaaagcag gaataagtaa caaatcaaat cgctacaatg  10320
ataattacaa caattacatt agtaagtgct ctatcatcac agatctcagc aaattcaatc  10380
aagcatttcg atatgaaacg tcatgtattt gtagtgatgt gctggatgaa ctgcatggtg  10440
tacaatctct attttcctgg ttacatttaa ctattcctca tgtcacaata atatgcacat  10500
ataggcatgc acccccctat ataggagatc atattgtaga tcttaacaat gtagatgaac  10560
aaagtggatt atatagatat cacatgggtg gcatcgaagg gtggtgtcaa aaactatgga  10620
ccatagaagc tatatcacta ttggatctaa tatctctcaa agggaaattc tcaattactg  10680
ctttaattaa tggtgacaat caatcaatag atataagcaa accaatcaga ctcatggaag  10740
gtcaaactca tgctcaagca gattatttgc tagcattaaa tagccttaaa ttactgtata  10800
aagagtatgc aggcataggc cacaaattaa aaggaactga gacttatata tcacgagata  10860
tgcaatttat gagtaaaaca attcaacata acggtgtata ttacccagct agtataaaga  10920
```

-continued

```
aagtcctaag agtgggaccg tggataaaca ctatacttga tgatttcaaa gtgagtctag  10980
aatctatagg tagtttgaca caagaattag aatatagagg tgaaagtcta ttatgcagtt  11040
taatatttag aaatgtatgg ttatataatc agattgctct acaattaaaa aatcatgcat  11100
tatgtaacaa taaactatat ttggacatat taaaggttct gaaacactta aaaacctttt  11160
ttaatcttga taatattgat acagcattaa cattgtatat gaatttaccc atgttatttg  11220
gtggtggtga tcccaacttg ttatatcgaa gtttctatag aagaactcct gacttcctca  11280
cagaggctat agttcactct gtgttcatac ttagttatta tacaaaccat gacttaaaag  11340
ataaacttca agatctgtca gatgatagat tgaataagtt cttaacatgc ataatcacgt  11400
ttgacaaaaa ccctaatgct gaattcgtaa cattgatgag agatcctcaa gctttagggt  11460
ctgagagaca agctaaaatt actagcgaaa tcaatagact ggcagttaca gaggttttga  11520
gtacagctcc aaacaaaata ttctccaaaa gtgcacaaca ttatactact acagagatag  11580
atctaaatga tattatgcaa aatatagaac ctacatatcc tcatgggcta agagttgttt  11640
atgaaagttt accctttat aaagcagaga aaatagtaaa tcttatatca ggtacaaaat  11700
ctataactaa catactggaa aaaacttctg ccatagactt aacagatatt gatagagcca  11760
ctgagatgat gaggaaaaac ataactttgc ttataaggat acttccattg gattgtaaca  11820
gagataaaag agagatattg agtatggaaa acctaagtat tactgaatta agcaaatatg  11880
ttagggaaag atcttggtct ttatccaata tagttggtgt tacatcaccc agtatcatgt  11940
atacaatgga catcaaatat actacaagca ctatatctag tggcataatt atagagaaat  12000
ataatgttaa cagtttaaca cgtggtgaga gaggacccac taaaccatgg gttggttcat  12060
ctacacaaga gaaaaaaaca atgccagttt ataatagaca agtcttaacc aaaaaacaga  12120
gagatcaaat agatctatta gcaaaattgg attgggtgta tgcatctata gataacaagg  12180
atgaattcat ggaagaactc agcataggaa cccttgggtt aacatatgaa aaggccaaga  12240
aattatttcc acaatattta agtgtcaatt atttgcatcg ccttacagtc agtagtagac  12300
catgtgaatt ccctgcatca ataccagctt atagaacaac aaattatcac tttgacacta  12360
gccctattaa tcgcatatta acagaaaagt atggtgatga agatattgac atagtattcc  12420
aaaactgtat aagctttggc cttagtttaa tgtcagtagt agaacaattt actaatgtat  12480
gtcctaacag aattattctc atacctaagc ttaatgagat acatttgatg aaacctccca  12540
tattcacagg tgatgttgat attcacaagt taaaacaagt gatacaaaaa cagcatatgt  12600
ttttaccaga caaaataagt ttgactcaat atgtggaatt attcttaagt aataaaacac  12660
tcaaatctgg atctcatgtt aattctaatt taatattggc acataaaata tctgactatt  12720
ttcataatac ttacatttta agtactaatt tagctggaca ttggattctg attatacaac  12780
ttatgaaaga ttctaaaggt atttttgaaa aagattgggg agagggatat ataactgatc  12840
atatgtttat taatttgaaa gttttcttca atgcttataa gacctatctc ttgtgttttc  12900
ataaaggtta tggcaaagca aagctggagt gtgatatgaa cacttcagat cttctatgtg  12960
tattggaatt aatagacagt agttattgga agtctatgtc taaggtattt ttagaacaaa  13020
aagttatcaa atacattctt agccaagatg caagtttaca tagagtaaaa ggatgtcata  13080
gcttcaaatt atggtttctt aaacgtctta atgtagcaga attcacagtt tgcccttggg  13140
ttgttaacat agattatcat ccaacacata tgaaagcaat attaacttat atagatcttg  13200
ttagaatggg attgataaat atagatagaa tacacattaa aaataaacac aaattcaatg  13260
atgaatttta tacttctaat ctcttctaca ttaattataa cttctcagat aatactcatc  13320
```

tattaactaa acatataagg attgctaatt ctgaattaga aaataattac aacaaattat 13380
atcatcctac accagaaacc ctagagaata tactagccaa tccgattaaa agtaatgaca 13440
aaaagacact gaatgactat tgtataggta aaaatgttga ctcaataatg ttaccattgt 13500
tatctaataa gaagcttatt aaatcgtctg caatgattag aaccaattac agcaaacaag 13560
atttgtataa tttattccct atggttgtga ttgatagaat tatagatcat tcaggcaata 13620
cagccaaatc caaccaactt tacactacta cttcccacca aatatcctta gtgcacaata 13680
gcacatcact ttactgcatg cttccttggc atcatattaa tagattcaat tttgtattta 13740
gttctacagg ttgtaaaatt agtatagagt atattttaaa agatcttaaa attaaagatc 13800
ccaattgtat agcattcata ggtgaaggag cagggaattt attattgcgt acagtagtgg 13860
aacttcatcc tgacataaga tatatttaca gaagtctgaa agattgcaat gatcatagtt 13920
tacctattga gtttttaagg ctgtacaatg gacatatcaa cattgattat ggtgaaaatt 13980
tgaccattcc tgctacagat gcaaccaaca acattcattg gtcttattta catataaagt 14040
ttgctgaacc tatcagtctt tttgtctgtg atgccgaatt gtctgtaaca gtcaactgga 14100
gtaaaattat aatagaatgg agcaagcatg taagaaagtg caagtactgt tcctcagtta 14160
ataaatgtat gttaatagta aaatatcatg ctcaagatga tattgatttc aaattagaca 14220
atataactat attaaaaact tatgtatgct taggcagtaa gttaaaggga tcggaggttt 14280
acttagtcct tacaataggt cctgcgaata tattcccagt atttaatgta gtacaaaatg 14340
ctaaattgat actatcaaga accaaaaatt tcatcatgcc taagaaagct gataaagagt 14400
ctattgatgc aaatattaaa agtttgatac cctttctttg ttaccctata acaaaaaaag 14460
gaattaatac tgcattgtca aaactaaaga gtgttgttag tggagatata ctatcatatt 14520
ctatagctgg acgtaatgaa gttttcagca ataaacttat aaatcataag catatgaaca 14580
tcttaaaatg gttcaatcat gttttaaatt tcagatcaac agaactaaac tataaccatt 14640
tatatatggt agaatctaca tatccttacc taagtgaatt gttaaacagc ttgacaacca 14700
atgaacttaa aaaactgatt aaaatcacag gtagtctgtt atacaacttt cataatgaat 14760
aatgaataaa gatcttataa taaaaattcc catagctata cactaacact gtattcaatt 14820
atagttatta aaaattaaaa atcatataat tttttaaata acttttagtg aactaatcct 14880
aaagttatca ttttaatctt ggaggaataa atttaaaccc taatctaatt ggtttatatg 14940
tgtattaact aaattacgag atattagttt ttgacacttt ttttctcgt 14989

<210> SEQ ID NO 19
<211> LENGTH: 14988
<212> TYPE: DNA
<213> ORGANISM: Artificial Sequence
<220> FEATURE:
<223> OTHER INFORMATION: recombinant respiratory syncytial virus sequence

<400> SEQUENCE: 19
acgggaaaaa atgcgtacaa caaacttgca taaaccaaaa aaatggggca aataagaatt 60
tgataagtac cacttaaatt taactccctt ggttagagat gggcagcaat tcattgagta 120
tgataaaagt tagattacaa aatttgtttg acaatgatga agtagcattg ttaaaaataa 180
catgctatac tgataaatta atacatttaa ctaatgcttt ggctaaggca gtgatacata 240
caatcaaatt gaatggcatt gtgtttgtgc atgttattac aagtagtgat atttgcccta 300
ataataatat tgtagtaaaa tccaatttca caacaatgcc agtactacaa aatggaggtt 360

-continued

```
atatatggga aatgatggaa ttaacacatt gctctcaacc taacggtcta ctagatgaca    420
attgtgaaat taaattctcc aaaaaactaa gtgattcaac aatgaccaat tatatgaatc    480
aattatctga attacttgga tttgatctta atccataaat tataattaat atcaactagc    540
aaatcaatgt cactaacacc attagttaat ataaaactta acagaagaca aaaatggggc    600
aaataaatca attcagccaa cccaaccatg gacacaaccc acaatgataa tacaccacaa    660
agactgatga tcacagacat gagaccgttg tcacttgaga ccataataac atcactaacc    720
agagacatca taacacacaa atttatatac ttgataaatc atgaatgcat agtgagaaga    780
cttgatgaaa gacaggccac atttacattc ctggtcaact atgaaatgaa actattacac    840
aaagtaggaa gcactaaata taaaaaatat actgaataca acacaaaata tggcactttc    900
cctatgccaa tattcatcaa tcatgatggg ttcttagaat gcattggcat taagcctaca    960
aagcatactc ccataatata caagtatgat ctcaatccat aaatttcaac acaatattca   1020
cacaatctaa aacaacaact ctatgcataa ctatactcca tagtccagat ggagcctgaa   1080
aattatagta atttaaaatt aaggagagat ataagataga agatggggca aatacaaaga   1140
tggctcttag caaagtcaag ttgaatgata cactcaacaa ggatcaactt ctgtcatcca   1200
gcaaatacgc catccaacgg agcacaggag atagtattga tactcctaat tatgatgtgc   1260
agaaacacat caataagtta tgtggcatgt tattaatcac agaagatgct aatcataaat   1320
tcactgggtt aataggtatg ttatatgcga tgtctaggtt aggaagagaa gacaccataa   1380
aaatactcag agatgcggga tatcatgtaa aagcaaatgg agtagatgta acaacacatc   1440
gtcaagacat taatggaaaa gaaatgaaat ttgaagtgtt aacattggca agcttaacaa   1500
ctgaaattca aatcaacatt gagatagaat ctagaaaatc ctacaaaaaa atgctaaaag   1560
aaatgggaga ggtagctcca gaatacaggc atgactctcc tgattgtggg atgataaatat   1620
tatgtatagc agcattagta ataactaaat tagcagcagg ggacagatct ggtcttacag   1680
ccgtgattag gagagctaat aatgtcctaa aaaatgaaat gaaacgttac aaaggcttac   1740
tacccaagga catagccaac agcttctatg aagtgtttga aaaacatccc cactttatag   1800
atgtttttgt tcattttggt atagcacaat cttctaccag aggtggcagt agagttgaag   1860
ggatttttgc aggattgttt atgaatgcct atggtgcagg gcaagtgatg ttacggtggg   1920
gagtcttagc aaaatcggtt aaaaatatta tgttaggaca tgctagtgtg caagcagaaa   1980
tggaacaagt tgttgaggtt tatgaatatg cccaaaaatt gggtggtgaa gcaggattct   2040
accatatatt gaacaaccca aaagcatcat tattatcttt gactcaattt cctcacttct   2100
ccagtgtagt attaggcaat gctgctggcc taggcataat gggagagtac agaggtacac   2160
cgaggaatca agatctatat gatgcagcaa aggcatatgc tgaacaactc aaagaaaatg   2220
gtgtgattaa ctacagtgta ctagacttga cagcagaaga actagaggct atcaaacatc   2280
agcttaatcc aaaagataat gatgtagagc tttgagttaa taaaaaatgg ggcaaataaa   2340
tcatcatgga aaagtttgct cctgaattcc atggagaaga tgcaaacaac agggctacta   2400
aattcctaga atcaataaag ggcaaattca catcacccaa agatcccaag aaaaaagata   2460
gtatcatatc tgtcaactca atagatatag aagtaaccaa agaaagccct ataacatcaa   2520
attcaactat tatcaaccca acaaatgaga cagatgatac tgcagggaac aagcccaatt   2580
atcaaagaaa acctctagta agtttcaaag aagaccctac accaagtgat aatccctttt   2640
ctaaactata caaagaaacc atagaaacat ttgataacaa tgaagaagaa tccagctatt   2700
```

```
catacgaaga aataaatgat cagacaaacg ataatataac agcaagatta gataggattg   2760
atgaaaaatt aagtgaaata ctaggaatgc ttcacacatt agtagtggca agtgcaggac   2820
ctacatctgc tcgggatggt ataagagatg ccatggttgg tttaagagaa gaaatgatag   2880
aaaaaatcag aactgaagca ttaatgacca atgacagatt agaagctatg gcaagactca   2940
ggaatgagga aagtgaaaag atggcaaaag acacatcaga tgaagtgtct ctcaatccaa   3000
catcagagaa attgaacaac ctattggaag ggaatgatag tgacaatgat ctatcacttg   3060
aagatttctg attagttacc aatcttcaca tcaacacaca ataccaacag aagaccaaca   3120
aactaaccaa cccaatcatc caaccaaaca tccatccgcc aatcagccaa acagccaaca   3180
aaacaaccag ccaatccaaa actaaccacc cggaaaaaat ctataatata gttacaaaaa   3240
aaggaaaggg tggggcaaat atggaaacat acgtgaacaa gcttcacgaa ggctccacat   3300
acacagctgc tgttcaatac aatgtcttag aaaaagacga tgaccctgca tcacttacaa   3360
tatgggtgcc catgttccaa tcatctatgc cagcagattt acttataaaa gaactagcta   3420
atgtcaacat actagtgaaa caaatatcca cacccaaggg accttcacta agagtcatga   3480
taaactcaag aagtgcagtg ctagcacaaa tgcccagcaa atttaccata tgcgctaatg   3540
tgtccttgga tgaaagaagc aaactagcat atgatgtaac cacaccctgt gaaatcaagg   3600
catgtagtct aacatgccta aaatcaaaaa atatgttgac tacagttaaa gatctcacta   3660
tgaagacact caaccctaca catgatatta ttgctttatg tgaatttgaa aacatagtaa   3720
catcaaaaaa agtcataata ccaacatacc taagatccat cagtgtcaga aataaagatc   3780
tgaacacact tgaaaatata acaaccactg aattcaaaaa tgctatcaca aatgcaaaaa   3840
tcatccctta ctcaggatta ctattagtca tcacagtgac tgacaacaaa ggagcattca   3900
aatacataaa gccacaaagt caattcatag tagatcttgg agcttaccta gaaaaagaaa   3960
gtatatatta tgttaccaca aattggaagc acacagctac acgatttgca atcaaaccca   4020
tggaagatta accttttttcc tctacatcag tgtgttaatt catacaaact ttctacctac   4080
attcttcact tcaccatcac aatcacaaac actctgtggt tcaaccaatc aaacaaaact   4140
tatctgaagt cccagatcat cccaagtcat tgtttatcag atctagtact caaataagtt   4200
aataaaaaat atacacatgg ggcaaataat cattggagga aatccaacta atcacaatat   4260
ctgttaacat agacaagtcc acacaccata cagaatcaac caatggaaaa tacatccata   4320
acaatagaat tctcaagcaa attctggcct tactttacac taatacacat gatcacaaca   4380
ataatctctt tgctaatcat aatctccatc atgattgcaa tactaaacaa actttgtgaa   4440
tataacgtat tccataacaa aacctttgag ttaccaagag ctcgagtcaa cacatagcat   4500
tcatcaatcc aacagcccaa aacagtaacc ttgcatttaa aaatgaacaa cccctacctc   4560
tttacaacac ctcattaaca tcccaccatg caaaccacta tccatactat aaagtagtta   4620
attaaaaata gtcataacaa tgaactagga tatcaagact aacaataaca ttggggcaaa   4680
tgcaaacatg tccaaaaaca aggaccaacg caccgctaag acattagaaa ggacctggga   4740
cactctcaat catttattat tcatatcatc gtgcttatat aagttaaatc ttaaatctgt   4800
agcacaaatc acattatcca ttctggcaat gataatctca acttcactta taattgcagc   4860
catcatattc atagcctcgg caaaccacaa agtcacacca acaactgcaa tcatacaaga   4920
tgcaacaagc cagatcaaga acacaacccc aacatacctc acccagaatc ctcagcttgg   4980
aatcagtccc tctaatccgt ctgaaattac atcacaaatc accaccatac tagcttcaac   5040
aacaccagga gtcaagtcaa ccctgcaatc cacaacagtc aagaccaaaa acacaacaac   5100
```

-continued aactcaaaca caacccagca agcccaccac aaaacaacgc caaaacaaac caccaagcaa 5160
acccaataat gattttcact ttgaagtgtt caactttgta ccctgcagca tatgcagcaa 5220
caatccaacc tgctgggcta tctgcaaaag aataccaaac aaaaaaccag gaaagaaaac 5280
cactaccaag cccacaaaaa aaccaaccct caagacaacc aaaaaagatc ccaaacctca 5340
aaccactaaa tcaaaggaag tacccaccac caagcccaca gaagagccaa ccatcaacac 5400
caccaaaaca aacatcataa ctacactact cacctccaac accacaggaa atccagaact 5460
cacaagtcaa atggaaacct tccactcaac ttcctccgaa ggcaatccaa gcccttctca 5520
agtctctaca acatccgagt acccatcaca accttcatct ccacccaaca caccacgcca 5580
gtagttactt aaaaacatat tatcacaaaa agccatgacc aacttaaaca gaatcaaagt 5640
aaactctggg gcaaataaca atggagttgc taatcctcaa agcaaatgca attaccacaa 5700
tcctcactgc agtcacattt tgttttgctt ctggtcaaaa catcactgaa gaattttatc 5760
aatcaacatg cagtgcagtt agcaaaggct atcttagtgc tctgagaact ggttggtata 5820
ccagtgttat aactatagaa ttaagtaata tcaagaaaaa taagtgtaat ggaacagatg 5880
ctaaggtaaa attgataaaa caagaattag ataaatataa aaatgctgta acagaattgc 5940
agttgctcat gcaaagcaca caagcaacaa acaatcgagc cagaagagaa ctaccaaggt 6000
ttatgaatta tacactcaac aatgccaaaa aaaccaatgt aacattaagc aagaaaagga 6060
aaagaagatt tcttggtttt ttgttaggtg ttggatctgc aatcgccagt ggcgttgctg 6120
tatctaaggt cctgcaccta gaaggggaag tgaacaagat caaaagtgct ctactatcca 6180
caaacaaggc tgtagtcagc ttatcaaatg gagtcagtgt cttaaccagc aaagtgttag 6240
acctcaaaaa ctatatagat aaacaattgt tacctattgt gaacaagcaa agctgcagca 6300
tatcaaatat agaaactgtg atagagttcc aacaaaagaa caacagacta ctagagatta 6360
ccagggaatt tagtgttaat gcaggtgtaa ctacacctgt aagcacttac atgttaacta 6420
atagtgaatt attgtcatta atcaatgata tgcctataac aaatgatcag aaaaagttaa 6480
tgtccaacaa tgttcaaata gttagacagc aaagttactc tatcatgtcc ataataaaag 6540
aggaagtctt agcatatgta gtacaattac cactatatgg tgttatagat acaccctgtt 6600
ggaaactaca cacatcccct ctatgtacaa ccaacacaaa agaagggtcc aacatctgtt 6660
taacaagaac tgacagagga tggtactgtg acaatgcagg atcagtatct ttcttcccac 6720
aagctgaaac atgtaaagtt caatcaaatc gagtattttg tgacacaatg aacagtttaa 6780
cattaccaag tgaagtaaat ctctgcaatg ttgacatatt caaccccaaa tatgattgta 6840
aaattatgac ttcaaaaaca gatgtaagca gctccgttat cacatctcta ggagccattg 6900
tgtcatgcta tggcaaaact aaatgtacag catccaataa aaatcgtgga atcataaaga 6960
cattttctaa cgggtgcgat tatgtatcaa ataaaggggt ggacactgtg tctgtaggta 7020
acacattata ttatgtaaat aagcaagaag gtaaaagtct ctatgtaaaa ggtgaaccaa 7080
taataaattt ctatgaccca ttagtattcc cctctgatga atttgatgca tcaatatctc 7140
aagtcaacga gaagattaac cagagcctag catttattcg taaatccgat gaattattac 7200
ataatgtaaa tgccggtaaa tccaccacaa atatcatgat aactactata attatagtga 7260
ttatagtaat attgttatca ttaattgctg ttggactgct cttatactgt aaggccagaa 7320
gcacaccagt cacactaagc aaagatcaac tgagtggtat aaataatatt gcatttagta 7380
actaaataaa aatagcacct aatcatgttc ttacaatggt ttactatctg ctcatagaca 7440

-continued

```
acccatctgt cattggattt tcttaaaatc tgaacttcat tgaaactctc atctataaac   7500
catctcactt acactattta agtagattcc tagtttatag ttatataaaa cacaattgaa   7560
tgccagatta acttaccatc tgtaaaaatg aaaactgggg caaatatgtc acgaaggaat   7620
ccttgcaaat ttgaaattcg aggtcattgc ttaaatggta agaggtgtca ttttagtcat   7680
aattattttg aatggccacc gcatgcactg cttgtaagac aaaactttat gttaaacaga   7740
atacttaagt ctatggataa aagtatagat accttatcag aaataagtgg agctgcagag   7800
ttggacagaa cagaagagta tgctcttggt gtagttggag tgctagagag ttatatagga   7860
tcaataaaca atataactaa acaatcagca tgtgttgcca tgagcaaact cctcactgaa   7920
ctcaatagtg atgatatcaa aaagctgagg gacaatgaag agctaaattc acccaagata   7980
agagtgtaca atactgtcat atcatatatt gaaagcaaca ggaaaaacaa taaacaaact   8040
atccatctgt taaaaagatt gccagcagac gtattgaaga aaaccatcaa aaacacattg   8100
gatatccata agagcataac catcaacaac ccaaaagaat caactgttag tgatacaaat   8160
gaccatgcca aaaataatga tactacctga caaataacgt tcaattctaa cactcaccac   8220
atcgttacat tattaattca aacaattcaa gttgtgggac aaaatggatc ccattattaa   8280
tggaaattct gctaatgttt atctaaccga tagttattta aaaggtgtta tctctttctc   8340
agagtgtaat gctttaggaa gttacatatt caatggtcct tatctcaaaa atgattatac   8400
caacttaatt agtagacaaa atccattaat agaacacatg aatctaaaga aactaaatat   8460
aacacagtcc ttaatatcta agtatcataa aggtgaaata aaattagaag aacctactta   8520
ttttcagtca ttacttatga catacaagag tatgacctcg tcagaacaga ttgctaccac   8580
taatttactt aaaaagataa taagaagagc tatagaaata agtgatgtca aagtctatgc   8640
tatattgaat aaactagggc ttaaagaaaa ggacaagatt aaatccaaca atggacaaga   8700
tgaagacaac tcagttatta cgaccataat caaagatgat atactttcag ctgttaaaga   8760
taatcaatct catcttaaag cagacaaaaa tcactctaca aaacaaaaag acacaatcaa   8820
aacaacactc ttgaagaaat tgatgtgttc aatgcaacat cctccatcat ggttaataca   8880
ttggtttaac ttatacacaa aattaaacaa catattaaca cagtatcgat caaatgaggt   8940
aaaaaaccat gggtttacat tgatagataa tcaaactctt agtggatttc aatttatttt   9000
gaaccaatat ggttgtatag tttatcataa ggaactcaaa agaattactg tgacaaccta   9060
taatcaattc ttgacatgga aagatattag ccttagtaga ttaaatgttt gtttaattac   9120
atggattagt aactgcttga acacattaaa taaaagctta ggcttaagat gcggattcaa   9180
taatgttatc ttgacacaac tattccttta tggagattgt atactaaagc tatttcacaa   9240
tgaggggttc tacataataa aagaggtaga gggatttatt atgtctctaa ttttaaatat   9300
aacagaagaa gatcaattca gaaaacgatt ttataatagt atgctcaaca acatcacaga   9360
tgctgctaat aaagctcaga aaaatctgct atcaagagta tgtcatacat tattagataa   9420
gacagtgtcc gataaatataa taaatggcag atggataatt ctattaagta agttccttaa   9480
attaattaag cttgcaggtg acaataacct taacaatctg agtgaactat attttttgtt   9540
cagaatattt ggacacccaa tggtagatga aagacaagcc atggatgctg ttaaaattaa   9600
ttgcaatgag accaaatttt acttgttaag cagtctgagt atgttaagag gtgcctttat   9660
atatagaatt ataaaagggt ttgtaaataa ttacaacaga tggcctactt taagaaatgc   9720
tattgtttta cccttaagat ggttaactta ctataaacta aacacttatc cttctttgtt   9780
ggaacttaca gaaagagatt tgattgtgtt atcaggacta cgtttctatc gtgagtttcg   9840
```

```
gttgcctaaa aaagtggatc ttgaaatgat tataaatgat aaagctatat cacctcctaa   9900
aaatttgata tggactagtt tccctagaaa ttacatgcca tcacacatac aaaactatat   9960
agaacatgaa aaattaaaat tttccgagag tgataaatca agaagagtat tagagtatta  10020
tttaagagat aacaaattca atgaatgtga tttatacaac tgtgtagtta atcaaagtta  10080
tctcaacaac cctaatcatg tggtatcatt gacaggcaaa gaaagagaac tcagtgtagg  10140
tagaatgttt gcaatgcaac cgggaatgtt cagacaggtt caaatattgg cagagaaaat  10200
gatagctgaa aacattttac aattctttcc tgaaagtctt acaagatatg gtgatctaga  10260
actacaaaaa atattagaat tgaaagcagg aataagtaac aaatcaaatc gctacaatga  10320
taattacaac aattacatta gtaagtgctc tatcatcaca gatctcagca aattcaatca  10380
agcatttcga tatgaaacgt catgtatttg tagtgatgtg ctggatgaac tgcatggtgt  10440
acaatctcta ttttcctggt tacatttaac tattcctcat gtcacaataa tatgcacata  10500
taggcatgca cccccctata taggagatca tattgtagat cttaacaatg tagatgaaca  10560
aagtggatta tatagatatc acatgggtgg catcgaaggg tggtgtcaaa aactatggac  10620
catagaagct atatcactat tggatctaat atctctcaaa gggaaattct caattactgc  10680
tttaattaat ggtgacaatc aatcaataga tataagcaaa ccaatcagac tcatggaagg  10740
tcaaactcat gctcaagcag attatttgct agcattaaat agccttaaat tactgtataa  10800
agagtatgca ggcataggcc acaaattaaa aggaactgag acttatatat cacgagatat  10860
gcaatttatg agtaaaacaa ttcaacataa cggtgtatat tacccagcta gtataaagaa  10920
agtcctaaga gtgggaccgt ggataaacac tatacttgat gatttcaaag tgagtctaga  10980
atctataggt agtttgacac aagaattaga atatagaggt gaaagtctat tatgcagttt  11040
aatatttaga aatgtatggt tatataatca gattgctcta caattaaaaa atcatgcatt  11100
atgtaacaat aaactatatt tggacatatt aaaggttctg aaacacttaa aaaccttttt  11160
taatcttgat aatattgata cagcattaac attgtatatg aatttaccca tgttatttgg  11220
tggtggtgat cccaacttgt tatatcgaag tttctataga agaactcctg acttcctcac  11280
agaggctata gttcactctg tgttcatact tagttattat acaaaccatg acttaaaaga  11340
taaacttcaa gatctgtcag atgatagatt gaataagttc ttaacatgca taatcacgtt  11400
tgacaaaaac cctaatgctg aattcgtaac attgatgaga gatcctcaag ctttagggtc  11460
tgagagacaa gctaaaatta ctagcgaaat caatagactg gcagttacag aggttttgag  11520
tacagctcca aacaaaatat tctccaaaag tgcacaacat tatactacta cagagataga  11580
tctaaatgat attatgcaaa atatagaacc tacatatcct catgggctaa gagttgttta  11640
tgaaagttta cccttttata aagcagagaa aatagtaaat cttatatcag gtacaaaatc  11700
tataactaac atactggaaa aaacttctgc catagactta acagatattg atagagccac  11760
tgagatgatg aggaaaaaca taactttgct tataaggata cttccattgg attgtaacag  11820
agataaaaga gagatattga gtatggaaaa cctaagtatt actgaattaa gcaaatatgt  11880
tagggaaaga tcttggtctt tatccaatat agttggtgtt acatcaccca gtatcatgta  11940
tacaatggac atcaaatata ctacaagcac tatatctagt ggcataatta tagagaaata  12000
taatgttaac agtttaacac gtggtgagag aggacccact aaaccatggg ttggttcatc  12060
tacacaagag aaaaaaacaa tgccagttta taatagacaa gtcttaacca aaaaacagag  12120
agatcaaata gatctattag caaaattgga ttgggtgtat gcatctatag ataacaagga  12180
```

tgaattcatg gaagaactca gcataggaac ccttgggtta acatatgaaa aggccaagaa 12240
attatttcca caatatttaa gtgtcaatta tttgcatcgc cttacagtca gtagtagacc 12300
atgtgaattc cctgcatcaa taccagctta tagaacaaca aattatcact ttgacactag 12360
ccctattaat cgcatattaa cagaaaagta tggtgatgaa gatattgaca tagtattcca 12420
aaactgtata agctttggcc ttagtttaat gtcagtagta gaacaattta ctaatgtatg 12480
tcctaacaga attattctca tacctaagct taatgagata catttgatga aacctcccat 12540
attcacaggt gatgttgata ttcacaagtt aaaacaagtg atacaaaaac agcatatgtt 12600
tttaccagac aaaataagtt tgactcaata tgtggaatta ttcttaagta ataaaacact 12660
caaatctgga tctcatgtta attctaattt aatattggca cataaaatat ctgactattt 12720
tcataatact tacattttaa gtactaattt agctggacat tggattctga ttatacaact 12780
tatgaaagat tctaaaggta tttttgaaaa agattgggga gagggatata taactgatca 12840
tatgtttatt aatttgaaag ttttcttcaa tgcttataag acctatctct tgtgttttca 12900
taaaggttat ggcaaagcaa agctggagtg tgatatgaac acttcagatc ttctatgtgt 12960
attggaatta atagacagta gttattggaa gtctatgtct aaggtatttt tagaacaaaa 13020
agttatcaaa tacattctta gccaagatgc aagtttacat agagtaaaag gatgtcatag 13080
cttcaaatta tggtttctta aacgtcttaa tgtagcagaa ttcacagttt gcccttgggt 13140
tgttaacata gattatcatc caacacatat gaaagcaata ttaacttata tagatcttgt 13200
tagaatggga ttgataaata tagatagaat acacattaaa aataaacaca aattcaatga 13260
tgaattttat acttctaatc tcttctacat taattataac ttctcagata atactcatct 13320
attaactaaa catataagga ttgctaattc tgaattagaa aataattaca acaaattata 13380
tcatcctaca ccagaaacac tagagaatat actagccaat ccgattaaaa gtaatgacaa 13440
aaagacactg aatgactatt gtataggtaa aaatgttgac tcaataatgt taccattgtt 13500
atctaataag aagcttatta aatcgtctgc aatgattaga accaattaca gcaaacaaga 13560
tttgtataat ttattcccta tggttgtgat tgatagaatt atagatcatt caggcaatac 13620
agccaaatcc aaccaacttt acactactac ttcccaccaa atatccttag tgcacaatag 13680
cacatcactt tactgcatgc ttccttggca tcatattaat agattcaatt ttgtatttag 13740
ttctacaggt tgtaaaatta gtatagagta tattttaaaa gatcttaaaa ttaaagatcc 13800
caattgtata gcattcatag gtgaaggagc agggaattta ttattgcgta cagtagtgga 13860
acttcatcct gacataagat atatttacag aagtctgaaa gattgcaatg atcatagttt 13920
acctattgag tttttaaggc tgtacaatgg acatatcaac attgattatg gtgaaaattt 13980
gaccattcct gctacagatg caaccaacaa cattcattgg tcttatttac atataaagtt 14040
tgctgaacct atcagtcttt ttgtctgtga tgccgaattg tctgtaacag tcaactggag 14100
taaaattata atagaatgga gcaagcatgt aagaaagtgc aagtactgtt cctcagttaa 14160
taaatgtatg ttaatagtaa aatatcatgc tcaagatgat attgatttca aattagacaa 14220
tataactata ttaaaaactt atgtatgctt aggcagtaag ttaaagggat cggaggttta 14280
cttagtcctt acaataggtc ctgcgaatat attcccagta tttaatgtag tacaaaatgc 14340
taaattgata ctatcaagaa ccaaaaattt catcatgcct aagaaagctg ataaagagtc 14400
tattgatgca aatattaaaa gtttgatacc ctttctttgt taccctataa caaaaaaagg 14460
aattaatact gcattgtcaa aactaaagag tgttgttagt ggagatatac tatcatattc 14520
tatagctgga cgtaatgaag ttttcagcaa taaacttata aatcataagc atatgaacat 14580

-continued

```
cttaaaatgg ttcaatcatg ttttaaattt cagatcaaca gaactaaact ataaccattt  14640

atatatggta gaatctacat atccttacct aagtgaattg ttaaacagct tgacaaccaa  14700

tgaacttaaa aaactgatta aaatcacagg tagtctgtta tacaactttc ataatgaata  14760

atgaataaag atcttataat aaaaattccc atagctatac actaacactg tattcaatta  14820

tagttattaa aaattaaaaa tcatataatt ttttaaataa cttttagtga actaatccta  14880

aagttatcat tttaatcttg gaggaataaa tttaaaccct aatctaattg gtttatatgt  14940

gtattaacta aattacgaga tattagtttt tgacactttt tttctcgt              14988


<210> SEQ ID NO 20
<211> LENGTH: 10
<212> TYPE: DNA
<213> ORGANISM: respiratory syncytial virus

<400> SEQUENCE: 20

ggggcaaata                                                           10


<210> SEQ ID NO 21
<211> LENGTH: 10
<212> TYPE: DNA
<213> ORGANISM: respiratory syncytial virus

<400> SEQUENCE: 21

ggggcaaaca                                                           10
```

RECOMBINANT RESPIRATORY SYNCYTIAL VIRUS STAINS WITH MUTATIONS IN THE M2-2 ORF PROVIDING A RANGE OF ATTENUATION PHENOTYPES

CROSS REFERENCE TO RELATED APPLICATIONS

This is the U.S. National Stage of International Application No. PCT/US2016/066146, filed Dec. 12, 2016, which was published in English under PCT Article 21(2), which in turn claims the benefit of U.S. Provisional Application No. 62/266,199, filed Dec. 11, 2015. The provisional application is incorporated by reference herein in its entirety.

FIELD

The subject matter disclosed herein relates to respiratory syncytial virus (RSV) and attenuated, mutant strains thereof suitable for use as vaccines.

BACKGROUND

Human respiratory syncytial virus (RSV) infects nearly everyone worldwide early in life and is responsible for considerable mortality and morbidity. In the United States alone, RSV is responsible for 75,000-125,000 hospitalizations yearly, and conservative estimates indicate that RSV is responsible worldwide for 64 million pediatric infections and 160,000 or more pediatric deaths each year. Another notable feature of RSV is that severe infection in infancy frequently is followed by lingering airway dysfunction, including a predisposition to airway reactivity, that in some individuals lasts for years and can extend into adolescence and beyond. RSV infection exacerbates asthma and may be involved in initiating asthma.

RSV is a member of the Paramyxoviridae family and, as such, is an enveloped virus that replicates in the cytoplasm and matures by budding at the host cell plasma membrane. The genome of RSV is a single, negative-sense strand of RNA of 15.2 kilobases that is transcribed by the viral polymerase into 10 mRNAs by a sequential stop-start mechanism that initiates at a single viral promoter at the 3' end of the genome. Each mRNA encodes a single major protein, with the exception of the M2 mRNA that has two overlapping open reading frames (ORFs) encoding two separate proteins M2-1 and M2-2. The 11 RSV proteins are: the RNA-binding nucleoprotein (N), the phosphoprotein (P), the large polymerase protein (L), the attachment glycoprotein (G), the fusion protein (F), the small hydrophobic (SH) surface glycoprotein, the internal matrix protein (M), the two nonstructural proteins NS1 and NS2, and the M2-1 and M2-2 proteins. The RSV gene order is: 3'-NS1-NS2-N-P-M-SH-G-F-M2-L. Each gene is flanked by short conserved transcription signals called the gene-start (GS) signal, present on the upstream end of each gene and involved in initiating transcription of the respective gene, and the gene-end (GE) signal, present at the downstream end of each gene and involved in directing synthesis of a polyA tail followed by release of the mRNA.

The development of RSV vaccines has been in progress since the 1960's but has been complicated by a number of factors. For example, immunization of RSV-naïve infants with inactivated RSV has been shown to prime for enhanced disease upon subsequent natural RSV infection, and studies in experimental animals indicate that disease enhancement also is associated with purified RSV subunit vaccines.

Another obstacle to immune protection is that RSV replicates and causes disease in the superficial cells of the respiratory airway lumen, where immune protection has reduced effectiveness. Thus, immune control of RSV infection is inefficient and often incomplete, and it is important for an RSV vaccine to be as immunogenic as possible. Another obstacle to RSV vaccines is that the magnitude of the protective immune response is roughly proportional to the extent of virus replication (and antigen production). Thus, the attenuation of RSV necessary to make a live vaccine typically is accompanied by a reduction in replication and antigen synthesis, and a concomitant reduction in immunogenicity, and therefore it is beneficial to identify a level of replication that is well tolerated yet satisfactorily immunogenic.

Another obstacle is that RSV grows only to moderate titers in cell culture and is often present in long filaments that are difficult to purify. RSV can readily lose infectivity during handling. Another obstacle is the difficulty in identifying and developing attenuating mutations. Appropriate mutations must be attenuating in vivo, but should be minimally restrictive to replication in vitro, since this is preferred for efficient vaccine manufacture. Another obstacle is genetic instability that is characteristic of RNA viruses, whereby attenuating mutations can revert to the wild-type (wt) assignment or to an alternative assignment that confers a non-attenuated phenotype. Instability and de-attenuation are particularly problematic for point mutations.

Taking these factors together, there is a need for live attenuated RSV strains that replicate efficiently in vitro, are maximally immunogenic, are satisfactorily attenuated, and are refractory to de-attenuation.

SUMMARY

Disclosed herein are mutations that are useful, either individually or in combinations that may include other known mutations, in producing recombinant strains of human RSV exhibiting a range of attenuation phenotypes. The mutations interfere with the expression of the open reading frame (ORF) encoding the viral M2-2 protein. Also disclosed are recombinant strains of RSV which contain such mutations, either alone or in combination with one or more additional mutations at other loci, which can reduce or, alternatively, increase the magnitude of the attenuation phenotype. Thus, disclosed herein are novel live-attenuated RSV strains with a range of attenuation phenotypes suitable for use as RSV vaccines. In some examples, the disclosed embodiments of recombinant RSV are shown to be infectious, attenuated, and self-replicating, and to elicit a surprisingly high titer of neutralizing antibodies in human subjects.

In some embodiments, a recombinant RSV is provided that is attenuated by one or more modifications to the genome of the virus, such as a modification that interferes with the expression of the open reading frame (ORF) encoding the viral M2-2 protein. In some embodiments, the genome of the recombinant RSV comprises one or more modifications comprising a deletion in a M2-2 ORF corresponding to a deletion of 241 nucleotides at positions 8189-8429 of SEQ ID NO: 1, combined with nucleotide mutations, such as T to C substitutions, at positions corresponding to T8161, T8167 and T8179 of SEQ ID NO: 1 ("ΔM2-2"). The nucleotide mutations disrupt translation start codons at these positions. In some embodiments, the genome of the recombinant RSV comprises one or more modifications comprising a deletion in a M2-2 ORF corresponding to a deletion of 234 nucleotides at positions 8203-8436 of SEQ ID NO: 1, combined with nucleotide mutations T8198A and C8200G at positions corresponding to T8198 and C8200 of SEQ ID NO: 1 ("ΔM2-2-AclI"). In some embodiments, the genome of the recombinant RSV comprises one or more modifications comprising a deletion in a M2-2 ORF corresponding to a deletion of 234 nucleotides at positions 8203-8436 of SEQ ID NO: 1, combined with nucleotide mutations T8198A and C8199G at positions corresponding to T8198 and C8199 of SEQ ID NO: 1 ("ΔM2-2-HindIII"), wherein the recombinant RSV genome is a D46 genome attenuated by the one or more modifications.

In addition to the modification that interferes with the expression of the open reading frame (ORF) encoding the viral M2-2 protein, the genome of the recombinant RSV can comprise further modifications to increase or decrease viral attenuation, or other properties of the recombinant virus. In some embodiments the one or more modifications to the genome of the recombinant RSV can further comprise a deletion of 112 nucleotides corresponding to positions 4499-4610 of SEQ ID NO: 1, combined with nucleotide mutations C4489T, C4492T, A4495T, A4497G, and G4498A at positions corresponding to C4489, C4492, A4495, A4497, and G4498 of SEQ ID NO: 1 ("6120"). For example, in some embodiments, the recombinant RSV is attenuated by one or more genomic modifications comprising a deletion in a M2-2 ORF corresponding to a deletion of 234 nucleotides at positions 8203-8436 of SEQ ID NO: 1, combined with nucleotide mutations T8198A and C8199G at positions corresponding to T8198 and C8199 of SEQ ID NO: 1 ("ΔM2-2-HindIII"), and a deletion of 112 nucleotides corresponding to positions 4499-4610 of SEQ ID NO: 1, combined with nucleotide mutations at positions corresponding to C4489T, C4492T, A4495T, A4497G, and G4498A of SEQ ID NO: 1 ("6120").

In some embodiments, the one or more modifications to the genome of the recombinant RSV further comprise nucleotide mutations encoding amino acid substitutions of V267I in the N protein, E218A and T523I in the F protein, and C319Y and H1690Y in the L protein of the RSV ("cp"). In some embodiments, the one or more modifications to the genome of the recombinant RSV further comprise nucleotide mutations to introduce a Y1321K substitution in the L protein of the RSV, and wherein the L protein comprises a S1313 residue, wherein the codons encoding the Y1321K substitution and the S1313 residue are AAA and TCA codons respectively ("1030s"). In some embodiments, the one or more modifications to the genome of the recombinant RSV further comprise nucleotide mutations encoding amino acid substitution K51R in the NS2 protein of the RSV ("NS2"). In some embodiments, the one or more modifications to the genome of the recombinant RSV further comprise nucleotide mutations encoding amino acid substitution T24A in the N protein of the RSV ("N"). In some embodiments, the one or more modifications to the genome of the recombinant RSV further comprise nucleotide mutations encoding amino acid substitution K51R in the NS2 protein and T24A in the N protein of the RSV ("NS2/N"). In some embodiments, the one or more modifications to the genome of the recombinant RSV further comprise a deletion in a SH ORF corresponding to deletion of 419 nucleotides at positions 4198-4616 of SEQ ID NO: 1 ("ΔSH"). In some embodiments, the one or more modifications to the genome of the recombinant RSV further comprise replacing the nucleotide sequence encoding a G protein of the RSV with a corresponding codon optimized nucleotide sequence encoding a G protein from the clinical isolate A/Maryland/001/11 (such as SEQ ID NO: 8, G001BB). In some embodiments, the one or more modifications to the genome of the recombinant RSV further comprise replacing the nucleotide sequence encoding a F protein of the RSV with a corresponding codon-optimized nucleotide sequence set forth as SEQ ID NO: 9 (FBB). In some embodiments, the one or more modifications to the genome of the recombinant RSV further comprise replacing the nucleotide sequence encoding a F protein of the RSV with a corresponding nucleotide sequence set forth as SEQ ID NO: 10 (F001), which encodes the F protein from the clinical isolate A/Maryland/001/11. In some embodiments, the one or more modifications to the genome of the recombinant RSV further comprise replacing the nucleotide sequence encoding a F protein of the RSV with a corresponding codon optimized nucleotide sequence encoding the F protein from the clinical isolate A/Maryland/001/11 (such as SEQ ID NO: 11, F001BB). In some embodiments, the one or more modifications to the genome of the recombinant RSV further comprise nucleotide mutations encoding amino acid substitutions K66E and Q101P in the F protein of the RSV ("HEK"). In some embodiments, the one or more modifications to the genome of the recombinant RSV further comprise nucleotide mutations encoding amino acid substitutions E218A and T523I in the F protein of the RSV (F cp substitutions). In some embodiments, the one or more modifications to the genome of the recombinant RSV further comprise reversing the order of the genes encoding the G and the F proteins in the RSV genome.

In some embodiments, the one or more modifications to the genome of the recombinant RSV further comprise or consist of a combination of mutations selected from any one of: ΔM2-2, cp/ΔM2-2, cp/ΔM2-2/HEK, ΔM2-2/1030s, NS2/N/ΔM2-2, NS2/ΔM2-2, N/ΔM2-2, ΔSH/ΔM2-2, cp/ΔSH/ΔM2-2, 6120/ΔM2-2, 6120/cp/ΔM2-2, 6120/ΔM2-2/1030s, 6120/NS2/N/ΔM2-2, 6120/G001BB/FBB/ΔM2-2, 6120/FBB/G001BB/ΔM2-2, 6120/G001BB/F/ΔM2-2, 6120/G/FBB/ΔM2-2, 6120/G/FBBHEK/ΔM2-2, 6120/G/FBBcpHEK/ΔM2-2, 6120/FBB/G/ΔM2-2, 6120/G001BB/F001BB/ΔM2-2, 6120/NS2/ΔM2-2, or 6120/N/ΔM2-2; or ΔM2-2-AclI, cp/ΔM2-2-AclI, cp/ΔM2-2-AclI/HEK, ΔM2-2-AclI/1030s, NS2/N/ΔM2-2-AclI, NS2/ΔM2-2-AclI, N/ΔM2-2-AclI, ΔSH/ΔM2-2-AclI, cp/ΔSH/ΔM2-2-AclI, 6120/ΔM2-2-AclI, 6120/cp/ΔM2-2-AclI, 6120/ΔM2-2-AclI/1030s, 6120/NS2/N/ΔM2-2-AclI, 6120/G001BB/FBB/ΔM2-2-AclI, 6120/FBB/G001BB/ΔM2-2-AclI, 6120/G001BB/F/ΔM2-2-AclI, 6120/G/FBB/ΔM2-2-AclI, 6120/G/FBBHEK/ΔM2-2-AclI, 6120/G/FBBcpHEK/ΔM2-2-AclI, 6120/FBB/G/ΔM2-2-AclI, 6120/G001BB/F001BB/ΔM2-2-AclI, 6120/NS2/ΔM2-2-AclI, or 6120/N/ΔM2-2-AclI; or ΔM2-2-HindIII; cp/ΔM2-2-HindIII, cp/ΔM2-2-HindIII/HEK, ΔM2-2-HindIII/1030s, NS2/N/ΔM2-2-HindIII, NS2/ΔM2-2-HindIII, N/ΔM2-2-HindIII, ΔSH/ΔM2-2-HindIII, cp/ΔSH/ΔM2-2-HindIII, 6120/ΔM2-2-HindIII, 6120/cp/ΔM2-2-HindIII, 6120/ΔM2-2-HindIII/1030s, 6120/NS2/N/ΔM2-2-HindIII, 6120/G001BB/FBB/ΔM2-2-HindIII, 6120/FBB/G001BB/ΔM2-2-HindIII, 6120/G001BB/F/ΔM2-2-HindIII, 6120/G/FBB/ΔM2-2-HindIII, 6120/G/FBBHEK/ΔM2-2-HindIII, 6120/G/FBBcpHEK/ΔM2-2-HindIII, 6120/FBB/G/ΔM2-2-HindIII, 6120/G001BB/F001BB/ΔM2-2-HindIII, 6120/NS2/ΔM2-2-HindIII, or 6120/N/ΔM2-2-HindIII.

In some embodiments, the genome of the recombinant RSV comprises the one or more mutations as discussed above, and a nucleotide sequence corresponding to a positive-sense sequence at least 90% (such as at least 95% or at least 99%) identical to SEQ ID NO: 1 (D46 sequence). In some embodiments, the genome of the recombinant RSV is a D46 genome modified with the one or more mutations as discussed above. In some embodiments, the genome of the recombinant RSV comprises the 6120 and ΔM2-2 mutations, and a nucleotide sequence corresponding to a positive-sense sequence at least 90% (such as at least 95% or at least 99%) identical to SEQ ID NO: 5 (LID/ΔM2-2 sequence). In some embodiments, the genome of the recombinant RSV comprises the cp and ΔM2-2 mutations, and a nucleotide sequence corresponding to a positive-sense sequence at least 90% (such as at least 95% or at least 99%) identical to SEQ ID NO: 1 (D46 sequence). In some embodiments, the genome of the recombinant RSV comprises the cp and ΔM2-2 mutations, and a nucleotide sequence corresponding to a positive-sense sequence at least 90% (such as at least 95% or at least 99%) identical to SEQ ID NO: 15 (D46/cp/ΔM2-2 sequence). In some embodiments, the genome of the recombinant RSV comprises the 6120, ΔM2-2, and 1030s mutations, and a nucleotide sequence corresponding to a positive-sense sequence at least 90% (such as at least 95% or at least 99%) identical to SEQ ID NO: 16 (LID/ΔM2-2/1030s sequence). In some embodiments, the genome of the recombinant RSV comprises the 6120, cp, and ΔM2-2 mutations, and a nucleotide sequence corresponding to a positive-sense sequence at least 90% (such as at least 95% or at least 99%) identical to SEQ ID NO: 17 (LID/cp/ΔM2-2 sequence). In some embodiments, the genome of the recombinant RSV comprises the NS2, N, ΔM2-2-HindIII mutations, and a nucleotide sequence corresponding to a positive-sense sequence at least 90% (such as at least 95% or at least 99%) identical to SEQ ID NO: 4 (D46/ΔM2-2-HindIII sequence). In some embodiments, the genome of the recombinant RSV comprises the NS2, N, ΔM2-2-HindIII mutations, and a nucleotide sequence corresponding to a positive-sense sequence at least 90% (such as at least 95% or at least 99%) identical to SEQ ID NO: 18 (D46/NS2/N/ΔM2-2-HindIII sequence). In some embodiments, the genome of the recombinant RSV comprises the NS2, N, ΔM2-2-AclI mutations, and a nucleotide sequence corresponding to a positive-sense sequence at least 90% (such as at least 95% or at least 99%) identical to SEQ ID NO: 3 (D46/ΔM2-2-AclII sequence). In some embodiments, the genome of the recombinant RSV comprises the NS2, N, and ΔM2-2-AclI mutations, the following nucleotide mutations with positions relative to SEQ ID NO: 1: 404C, 779G, deletion of C1099, 1139A, 1140G, 1182G, 1210G, 5612A, 5616A, 5640G, 6216C, 6222C, 6387T, 7215C, 7482T, 7560A, 7702G, 10515T, and 13634A; and a nucleotide sequence corresponding to a positive-sense sequence at least 90% (such as at least 95% or at least 99%) identical to SEQ ID NO: 19 (276 sequence).

In some embodiments, the genome of the recombinant RSV is a D46/cp/ΔM2-2 genome, a LID/ΔM2-2/1030s genome, a LID/cp/ΔM2-2 genome, a D46/NS2/N/ΔM2-2-HindIII genome, a LID/ΔM2-2 genome, or a 276 genome. In some embodiments, the genome of the recombinant RSV comprises or consists of a nucleotide sequence corresponding to a positive-sense sequence set forth as any one of SEQ ID NO: 2, SEQ ID NO: 3, SEQ ID NO: 4, SEQ ID NO: 5, SEQ ID NO: 6, SEQ ID NO: 7, SEQ ID NO: 15, SEQ ID NO: 16, SEQ ID NO: 17, SEQ ID NO: 18, or SEQ ID NO: 19.

In some embodiments, the genome of the recombinant RSV comprises a nucleotide sequence corresponding to a positive-sense sequence set forth as SEQ ID NO: 3 further modified by introduction of the following nucleotide mutations relative to SEQ ID NO: 1: 404C, 779G, 1099T, 1139A, 1140G, 1182G, 1210G, 5612A, 5616A, 5640G, 6216C, 6222C, 6387T, 7215C, 7482T, 7560A, 7702G, 10515T, and 13634A. In some embodiments, the genome of the recombinant RSV comprises a nucleotide sequence corresponding to a positive-sense sequence set forth as SEQ ID NO: 3 further modified by introduction of the following nucleotide mutations relative to SEQ ID NO: 1: 404C, 779G, deletion of C1099, 1139A, 1140G, 1182G, 1210G, 5612A, 5616A, 5640G, 6216C, 6222C, 6387T, 7215C, 7482T, 7560A, 7702G, 10515T, and 13634A. In some embodiments, the genome of the recombinant RSV comprises a sequence selected from the group consisting of SEQ ID NO: 2, SEQ ID NO: 3 and SEQ ID NO: 4, further modified by introduction of one or more of the following nucleotide substitutions with positions relative to SEQ ID NO: 1: 404C, 779G, 1099T, 1139A, 1140G, 1182G, 1210G, 1938A, 5612A, 5616A, 5640G, 6216C, 6222C, 6387T, 7215C, 7482T, 7560A, 7702G, 10515T, 13634A, 13901T.

The embodiments of recombinant RSV disclosed herein can be subtype A RSV or a subtype B RSV. The embodiments of recombinant RSV disclosed herein are infectious, attenuated, and self-replicating.

Also provided herein are methods and compositions related to the expression of the disclosed viruses. For example, isolated polynucleotide molecules that include a nucleic acid sequence encoding the genome or antigenome of the described viruses are disclosed.

Pharmaceutical compositions including the recombinant RSV are also provided. The compositions can further include an adjuvant. Methods of eliciting an immune response in a subject by administering an immunogenically effective amount of a disclosed recombinant RSV to the subject are also disclosed. In some embodiments, the subject is a human subject, for example, a human subject between 1 and 6 months of age, or between 1 and 12 months of age, or between 1 and 18 months of age, or older.

The foregoing and other features and advantages of this disclosure will become more apparent from the following detailed description of several embodiments which proceeds with reference to the accompanying drawings.

BRIEF DESCRIPTION OF THE DRAWINGS

(FIG. 1A) Organization of the RSV genome and the overlapping M2-1 and M2-2 ORFs. The three potential ATG translational start codons of the M2-2 ORF are shown. (FIG. 1B) Details of the ΔM2-2 mutation. The upper nucleotide sequence is that of biological wt RSV (M74568) and shows nucleotides corresponding to 8150-8204 and 8247-8440 of SEQ ID NO: 1. The nucleotide numbering between M74568 and SEQ ID NO: 1 is off by one nucleotide because of a single nucleotide insertion at position 1099 of SEQ ID NO: 1 compared to M74568. The amino acid sequence immediately underneath is of the C-terminal end of the M2-1 protein (SEQ ID NO: 12). The next amino acid sequence is the N-terminal residues of the M2-2 protein (SEQ ID NO: 13). The three potential ATG initiation codons for the M2-2 ORF are boxed and in bold. The second nucleotide sequence (for the ΔM2-2 mutation) shows the mutations that silence the M2-2 ORF (nucleotides 8150-8188 and 8430-8440 of SEQ ID NO: 1 are shown, with amino acid sequence SEQ ID NO: 13 shown directly below). For the ΔM2-2 mutation, each of the three potential translational ATG start sites was changed to ACG, and M74568 nucleotides 8188 to 8428 were deleted, removing 241 nucleotides. TER, translation termination codon.

(FIG. 3A) RSV genome map. The arrow indicates the location of the 6120 mutation in the downstream nontranslated region of the SH gene. (FIG. 3B) Details of the 6120 mutation. The upper nucleotide sequence is that of biological wt RSV (M74568) and shows nucleotides 4481-4498 and 4611-4632 of SEQ ID NO: 1, which correspond to the downstream end of the SH gene. The last five codons of the SH ORF are shown, with corresponding amino acid sequence (ARVNT, SEQ ID NO: 14) provided, followed by the translation termination codon (TER). This is followed to the right by the downstream nontranslated region of the SH gene (nucleotides 4611-4632 of SEQ ID NO: 1), with the SH gene-end signal underlined. The three dots represent 112 nucleotides of the downstream nontranslated region (M74568 nucleotides 4498-4609) that are deleted in the 6120 mutation. The lower nucleotide sequence (showing nucleotides 4481-4520 of SEQ ID NO: 5, with corresponding amino acid sequence (ARVNT, SEQ ID NO: 14) provided) depicts the 6120 mutation, which includes the 112-nucleotide deletion as well as five silent point mutations (bold) in the downstream three codons and the termination codon of the SH ORF. Naturally occurring XhoI and Pad restriction sites are italicized.

FIG. 10A shows the organization of the RSV genome and the overlapping M2-1 and M2-2 ORFs. The three potential ATG translational start codons of the M2-2 ORF are shown, but are not modified in ΔM2-2-AclI and ΔM2-2-HindIII mutations. FIG. 10B shows details of the ΔM2-2-AclI and ΔM2-2-HindIII mutations. The upper nucleotide sequence (nucleotides 8150-8204 and 8427-8440 of SEQ ID NO: 1) is that of biological wt RSV (M74568). The amino acid sequences immediately underneath is of the C-terminal end of the M2-1 protein (SEQ ID NO: 12). The next amino acid sequence is that of an N-terminal portion of the M2-2 protein (SEQ ID NO: 13). The three potential ATG initiation codons for the M2-2 ORF are boxed and in bold. The second nucleotide sequence (nucleotides 8150-8202 of SEQ ID NO: 3) shows the sequence of the ΔM2-2-AclI mutation that results from deletion of nucleotides 8202-8435 and introduction of the point mutations T8197A and C8199G to create an AclI site as well as a TAA termination codon at codon 13 in the M2-2 ORF. Amino acid sequences 12 and 13 are shown under the ΔM2-2-AclI sequence. The third nucleotide sequence (nucleotides 8150-8202 of SEQ ID NO: 4) shows the sequence of the ΔM2-2-HindIII mutation that results from deletion of nucleotides 8202-8435 and introduction of the point mutations T8197A and C8198G to create a HindIII site as well as a TAA termination codon at codon 13 in the M2-2 ORF. As shown, the mutated M2-2 ORF in both ΔM2-2-AclI and ΔM2-2-HindIII has the potential to encode a 12-amino acid peptide representing the N-terminal end of the M2-2 protein Amino acid sequences 12 and 13 are shown under the ΔM2-2-HindIII sequence.

FIG. 12A shows the introduction of the K51R and T24A mutations together into the D46/ΔM2-2-AclI backbone and the LID/ΔM2-2-AclI backbone. FIGS. 12B and 12C show the introduction of the K51R and T24A mutations into the D46/ΔM2-2 backbone (FIG. 12B) individually or together, or into the LID/ΔM2-2 backbone (FIG. 12C) individually or together.

FIG. 15. Virus yields in Vero cells for the constructs shown in FIGS. 14A and 14B. The P1 titer is the yield of the first passage (done blindly, i.e., without quantification of the input multiplicity of infection, MOI) following transfection. The P2 titer is the yield of second passage done with an input MOI of 0.01 PFU/cell; note that one virus is represented by P3, the yield of a third passage at MOI 0.001. Wt LID is D46 containing the 6120 mutation.

SEQUENCE LISTING

Figure 1A:
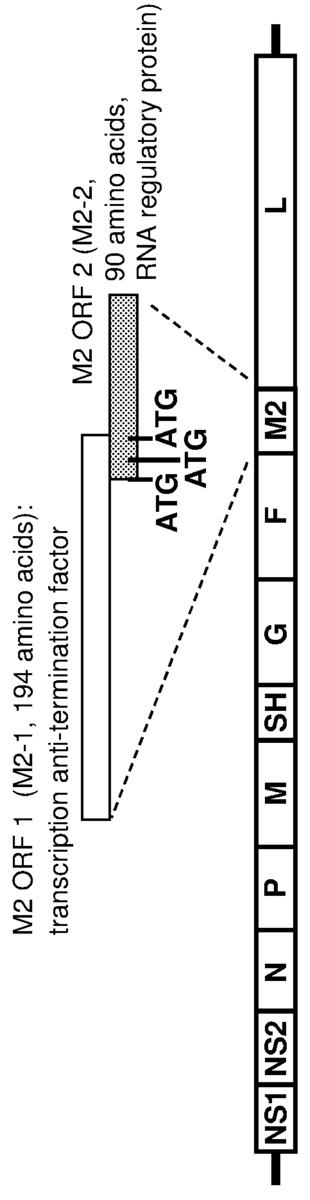
FIGS. 1A and 1B. The "ΔM2-2" mutation in the RSV genome silences the M2-2 ORF in the RSV backbone by introduction of a 241-nt deletion and eliminating three potential translational start codons for the M2-2 protein. Sequence numbering is according to the complete sequence of the wt human RSV strain A2 that is represented by GenBank accession number M74568, which is incorporated by reference herein.

The nucleic and amino acid sequences listed in the accompanying sequence listing are shown using standard letter abbreviations for nucleotide bases, and three letter code for amino acids, as defined in 37 C.F.R. 1.822. The Sequence Listing is submitted as an ASCII text file in the form of the file named "Sequence.txt" (~240 kb), which was created on May 25, 2018, and which is incorporated by reference herein. In the accompanying sequence listing:

SEQ ID NO: 1 is the antigenomic cDNA sequence for recombinant RSV strain D46.

SEQ ID NO: 2 is the antigenomic cDNA sequence for recombinant RSV strain D46/ΔM2-2.

SEQ ID NO: 3 is the antigenomic cDNA sequence for recombinant RSV strain D46/ΔM2-2-AclI.

SEQ ID NO: 4 is the antigenomic cDNA sequence for recombinant RSV strain D46/ΔM2-2-HindIII.

SEQ ID NO: 5 is the antigenomic cDNA sequence for recombinant RSV strain LID/ΔM2-2.

SEQ ID NO: 6 is the antigenomic cDNA sequence for recombinant RSV strain LID/ΔM2-2-AclI.

SEQ ID NO: 7 is the antigenomic cDNA sequence for recombinant RSV strain LID/ΔM2-2-HindIII.

SEQ ID NO: 8 is an exemplary polynucleotide sequence encoding G001BB.

SEQ ID NO: 9 is an exemplary polynucleotide sequence encoding FBB.

SEQ ID NO: 10 is an exemplary polynucleotide sequence encoding F001.

SEQ ID NO: 11 is an exemplary polynucleotide sequence encoding F001BB.

SEQ ID NO: 12 is a C-terminal amino acid sequence of the M2-1 protein (SDTNDHAKNNDTT).

SEQ ID NO: 13 is an N-terminal amino acid sequence of the M2-2 protein (MTMPKIMILPDKYPC).

SEQ ID NO: 14 is a C-terminal amino acid sequence of the SH protein (ARVNT).

SEQ ID NO: 15 is the antigenomic cDNA sequence for recombinant RSV strain D46/cp/ΔM2-2.

SEQ ID NO: 16 is the antigenomic cDNA sequence for recombinant RSV strain LID/ΔM2-2/1030s.

SEQ ID NO: 17 is the antigenomic cDNA sequence for recombinant RSV strain LID/cp/ΔM2-2.

SEQ ID NO: 18 is the antigenomic cDNA sequence for recombinant RSV strain D46/NS2/N/ΔM2-2-HindIII.

SEQ ID NO: 19 is the antigenomic cDNA sequence for recombinant RSV strain "276".

SEQ ID NOs: 20 and 21 are the nucleotide sequences of gene-start transcription signals (GGGGCAAATA and GGGGCAAACA, respectively).

DETAILED DESCRIPTION

Provided herein are recombinant RSV strains suitable for use as attenuated, live vaccines in humans. The RSV strains are produced by introducing mutations that block expression of the M2-2 protein and confer attenuation. Further provided are recombinant RSV strains in which the mutations that block expression of the M2-2 protein are present in combination with one or more additional engineered mutations at one or more other loci that increase or decrease the magnitude of attenuation, providing vaccine candidates with graded degrees of attenuation.

Mutations that reduce or ablate expression of the M2-2 ORF result in up-regulated expression of the viral genes including those encoding protective antigens (Bermingham and Collins. 1999. Proc Natl Acad Sci USA 96:11259-11264), and have the potential to confer increased immunogenicity. However, increased immunogenicity had not previously been demonstrated and was not evident in experimental animals including chimpanzees (Teng, et al. 2000. J Virol 74:9317-9321). Clinical evaluation of the presently disclosed strains which contain the M2-2 mutations described herein demonstrated that these strains exhibit increased immunogenicity. Studies in seronegative infants and children, which represent the primary vaccine target population, showed that the strains disclosed herein were attenuated and generally well-tolerated, and induced a substantial titer of RSV-neutralizing serum antibodies that was significantly greater than that of a previous RSV vaccine candidate (rA2cp248/404/10304SH) that has a different basis of attenuation (i.e., a series of point mutations in several viral genes including the polymerase, which represents a more typical type of live vaccine candidate) and was evaluated in a similar subject population (Karron, et al. 2005. J Infect Dis 191:1093-1104).

Thus, this disclosure provides novel, improved attenuated RSV strains bearing novel M2-2 deletion mutations, which possess increased immunogenicity in humans. The use of a large deletion that ablates most of a viral ORF provides genetic stability. Further, this disclosure provides sets of novel attenuated RSV strains bearing the M2-2 deletion mutations in combination with additional mutations that modify the phenotype. This provides viral strains with graded attenuation phenotypes.

The recombinant RSV strains of the present invention comprise a wild type RSV genome or antigenome containing further modifications or mutations as described in detail below. The wild type RSV virus genome or antigenome encodes the following 11 proteins: the RNA-binding nucleoprotein (N), the phosphoprotein (P), the large polymerase protein (L), the attachment glycoprotein (G), the fusion protein (F), the small hydrophobic (SH) surface glycoprotein, the internal matrix protein (M), the two nonstructural proteins NS1 and NS2, and the M2-1 and M2-2 proteins. The RSV gene order is: 3'-NS1-NS2-N-P-M-SH-G-F-M2-L. The complete amino acid sequences of these proteins are known in the art.

Given that a variety of RSV strains exist (e.g., RSV A2, RSV B1, RSV Long), those skilled in the art will appreciate that certain strains of RSV may have nucleotide or amino acid insertions or deletions that alter the position of a given residue. For example, if a protein of another RSV strain had, in comparison with strain A2, two additional amino acids in the upstream end of the protein, this would cause the amino acid numbering of downstream residues relative to strain A2 to increase by an increment of two. However, because these strains share a large degree of sequence identity, those skilled in the art would be able to determine the location of corresponding sequences by simply aligning the nucleotide or amino acid sequence of the A2 reference strain with that of the strain in question. Therefore, it should be understood that the amino acid and nucleotide positions described herein, though specifically enumerated in the context of this disclosure, can correspond to other positions when a sequence shift has occurred or due to sequence variation between virus strains. In the comparison of a protein, or protein segment, or gene, or genome, or genome segment between two or more related viruses, a "corresponding" amino acid or nucleotide residue is one that is thought to be exactly or approximately equivalent in function in the different species.

Unless context indicates otherwise, the numbering used in this disclosure is based on the sequence of the wild-type RSV A2 strain (GenBank accession number M74568) and viral genomic sequences described are in positive-sense.

In some embodiments of the present invention, the recombinant RSV strains were derived from the recombinant version of strain A2 that is called D46. The complete sequence of D46 is shown in U.S. Pat. No. 6,790,449 and is provided herein as SEQ ID NO: 1. (In some instances and publications, the parent virus and sequence is called D53 rather than D46, a book-keeping difference that refers to the strain of bacteria used to propagate the antigenomic cDNA and has no other known significance or effect. For the purposes of this invention, D46 and D53 are interchangeable.) SEQ ID NO: 1 (the nucleotide sequence of D46) differs from the sequence of RSV A2 strain M74568 in 25 nucleotide positions, which includes a 1-nt insert at position 1099. Therefore, sequence numbering relative to SEQ ID NO: 1 differs from numbering relative to M74568 by increment of 1 nucleotide, when the nucleotide is located at a position beyond nucleotide 1099.

Figure 1B:
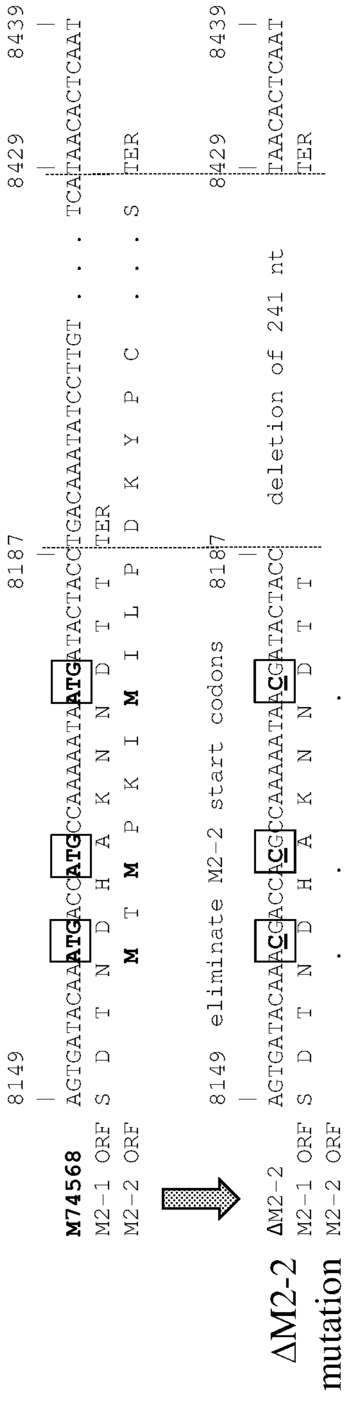

In some embodiments, the RSV genome or antigenome is modified by a deletion in the M2-2 ORF. The RSV M2-2 protein is encoded by the second, downstream ORF in the M2 mRNA, which slightly overlaps the 5'-proximal, upstream M2-1 ORF (FIG. 1A). There are three potential translation start codons that would give rise to products of 90, 88, and 84 amino acids in length for strain A2 (boxed in FIG. 1B). The M2-2 mutations described herein include deletion of large numbers of nucleotides (typically more than 200 nucleotides each) involving most of the M2-2 ORF, and thus largely or completely ablate expression of the M2-2 protein. The M2-2 mutations therefore are refractory to compensation or reversion that might confer loss of attenuation. This genetic stability was confirmed in a clinical study. Most of the previous RSV vaccine candidates have involved attenuating point mutations, which are prone to reversion or compensation resulting in de-attenuation (e.g., Karron, et al. 2005. J Infect Dis 191:1093-1104; Malkin, et al. 2013. PLoS One 8:e77104; Karron, Buchholz, Collins. 2013. Curr Top Microbiol Immunol 372:259-284). De-attenuation has the potential for increased virus replication in a vaccinee, which might result in reactogenicity, and also the potential for spread of under-attenuated derivatives to susceptible contacts. Therefore, the M2-2 mutations described herein obviate a major concern of RSV vaccine development.

In some embodiments, the M2-2 mutation comprises a deletion of 241 nucleotides located at positions 8188-8428 (8189-8429 of SEQ ID NO: 1) and mutations T8160C, T8166C and T8178C (T8161C, T8167C and T8179C of SEQ ID NO: 1) which eliminate the three potential start codons. This mutation is explained in FIGS. 1B and 1*s* referred herein as the "ΔM2-2" mutation.

In some embodiments, the M2-2 mutation comprises a deletion of 234 nucleotides located at positions 8202-8435 (8203-8436 of SEQ ID NO: 1), combined with the presence of 8197A and 8199G (8198A and 8200G of SEQ ID NO: 1) corresponding to the presence of an AclI restriction enzyme site. This mutation is explained in FIG. 10 and is referred herein as the "ΔM2-2-AclI" mutation.

In some embodiments, the M2-2 deletion comprises a mutation of 234 nucleotides located at positions 8202-8435 (8203-8436 of SEQ ID NO: 1), combined with the presence of 8197A and 8198G (8198A and 8199G of SEQ ID NO: 1) corresponding to the presence of a HindIII restriction enzyme site. This mutation is explained in FIG. 10 and referred herein as the "ΔM2-2-HindIII" mutation. In some embodiments the RSV strain used for constructing the strain may be D46 (SEQ ID NO: 1). In that case, the resultant recombinant strain is called D46/ΔM2-2-HindIII.

The presence of the term "ΔM2-2" in a virus name in this disclosure indicates the presence of the ΔM2-2 mutation shown in FIG. 1 in that virus, except in the case of "MEDI/ΔM2-2," which refers to a different mutation that is described in the Examples below. Other mutations are specified by the terms ΔM2-2-AclI or ΔM2-2-HindIII.

Additional mutations may be further introduced in combination with one of the M2-2 mutations defined above to construct additional viral strains with desired characteristics. For example, the added mutations may specify different magnitudes of attenuation, and thus give incremental increases in attenuation. Thus, candidate vaccine strains can be further attenuated by incorporation of at least one, and preferably two or more different attenuating mutations, for example mutations identified from a panel of known, biologically derived mutant RSV strains. A number of such mutations are discussed here as examples. From this exemplary panel a large "menu" of attenuating mutations can be created, in which each mutation can be combined with any other mutation(s) within the panel for calibrating the level of attenuation and other desirable phenotypes. Additional attenuating mutations may be identified in non-RSV negative stranded RNA viruses and incorporated in RSV mutants of the invention by mapping the mutation to a corresponding, homologous site in the recipient RSV genome or antigenome and mutating the existing sequence in the recipient to the mutant genotype (either by an identical or conservative mutation). Additional useful mutations can be determined empirically by mutational analysis using recombinant minigenome systems and infectious virus as described in the references incorporated herein.

In some embodiments, the disclosed recombinant RSV vaccine strains can be produced using a recombinant DNA-based technique called reverse genetics (Collins, et al. 1995. Proc Natl Acad Sci USA 92:11563-11567). This system allows de novo recovery of infectious virus entirely from cDNA in a qualified cell substrate under defined conditions. Reverse genetics provides a means to introduce predetermined mutations into the RSV genome via the cDNA intermediate. Specific attenuating mutations were characterized in preclinical studies and combined to achieve the desired level of attenuation. Derivation of vaccine viruses from cDNA minimizes the risk of contamination with adventitious agents and helps to keep the passage history brief and well documented. Once recovered, the engineered virus strains propagate in the same manner as a biologically derived virus. As a result of passage and amplification, the vaccine viruses do not contain recombinant DNA from the original recovery.

The recombinant virus strains that contain various combinations of mutations discussed herein are for exemplary purposes only and are not meant to limit the scope of the present invention. Other attenuating mutations not described here may also be used in combination with a disclosed M2-2 mutation (such as a ΔM2-2, ΔM2-2-AclI, or ΔM2-2-HindIII mutation).

Figures 3A, 3B:
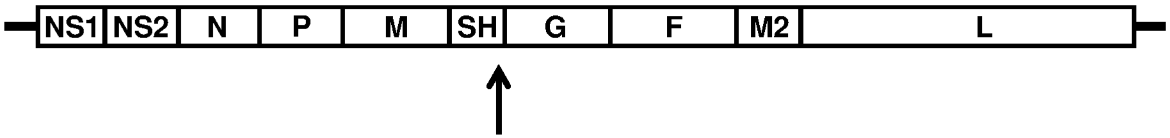
FIGS. 3A and 3B. The "6120" mutation in the RSV genome comprises a 112 nucleotide deletion in the downstream nontranslated region of the SH gene. Sequence numbering is according to the complete sequence of the wt human RSV strain A2 that is represented by GenBank accession number M74568. RSV genome map (FIG. 3A) and downstream end of the SH gene (FIG. 3B) containing the "6120" mutation, which is present in LID/ΔM2-2. In this disclosure, the use of "6120" in a virus name indicates the presence of the 6120 mutation.

For example, in some embodiments, the recombinant RSV strains of the present invention further comprise a deletion of the non-translated sequences. In one embodiment, such deletion occurs in the downstream end of the SH gene, resulting in a mutation called the "6120" mutation herein. The "6120" mutation is shown in FIG. 3. It involves deletion of 112 nucleotides of the downstream non-translated region of the SH gene and the introduction of five translationally-silent point mutations in the last three codons and the termination codon of the SH gene (Bukreyev, et al. 2001. J Virol 75:12128-12140). Presence of the term "LID" or "6120" in a recombinant virus name indicates that the recombinant virus contains the 6120 mutation.

The 6120 mutation stabilizes the antigenomic cDNA in bacteria so that it could be more easily manipulated and prepared. In wt RSV, this mutation was previously found to confer a 5-fold increase in replication efficiency in vitro (Bukreyev, et al. 2001. J Virol 75:12128-12140), whereas it was not thought to increase replication efficiency in vivo. When RSV LID/ΔM2-2 was evaluated for the possibility of increased replication associated with the 6120 mutation, a modest but inconsistent increase in growth efficiency was observed.

The 6120 mutation was associated with increased replication in seronegative infants and children. Thus, the 6120 mutation provided another means to shift the level of attenuation. While the use of this strategy is demonstrated herein in conjunction with a ΔM2-2 mutation, it can be applied to other attenuated strains for the same purpose. Also, the deletion of sequence exemplified by the 6120 mutation in the downstream non-translated region of the SH gene, but in principle could involve any comparable genome sequence that does not contain a critical cis-acting signal (Collins and Karron. 2013. Fields Virology 6th Edition, pp 1086-1123). Genome regions that are candidates for deletion include, but are not limited to, non-translated regions in other genes, in the intergenic regions, and in the trailer region.

In some embodiments the recombinant RSV strains may comprise the "cp" mutation. This mutation refers to a set of five amino acid substitutions in three proteins (N (V267I), F (E218A and T523I), and L (C319Y and H1690Y)) that together (on their own) confer an approximate 10-fold reduction in replication in seronegative chimpanzees, and a reduction in illness (Whitehead, et al. 1998. J Virol 72:4467-4471). It was previously shown that the cp mutation is associated with a moderate attenuation phenotype (Whitehead, et al. 1999. J Virol 72:4467-4471).

In addition, previous analysis of 6 biological viruses that had been derived by chemical mutagenesis of cpRSV and selected for the temperature-sensitive (ts) phenotype yielded a total of 6 independent mutations that each conferred a ts attenuation phenotype and could be used in various combinations. Five of these were amino acid substitutions in the L protein, which were named based on virus number rather than sequence position: "955" (N43I), "530" (F521L), "248" (Q831L), "1009" (M1169V), and "1030" (Y1321N) (Juhasz, et al. 1999. Vaccine 17:1416-1424; Collins, et al. 1999. Adv Virus Res 54:423-451; Firestone, et al. 1996. Virology 225:419-422; Whitehead, et al. 1999. J Virol 73:871-877). The sixth mutation (called "404") was a single nucleotide change in the gene-start transcription signal of the M2 gene (GGGGCAAATA (SEQ ID NO: 20) to GGGGCAAACA (SEQ ID NO: 21), mRNA-sense) (Whitehead, et al. 1998. Virology 247:232-239). Reverse genetics has been used to increase the genetic stability of the 248 and 1030 mutations (Luongo, et al. 2009. Vaccine 27:5667-5676; Luongo, et al. 2012. J Virol 86:10792-10804). In addition, a new attenuating mutation was created by deleting codon 1313 in the L protein and combining it with an I1314L substitution to confer increased genetic stability (Luongo, et al. 2013. J Virol 87:1985-1996).

In some embodiments, the recombinant strains may comprise one or more changes in the F protein, e.g. the "HEK" mutation, which comprises two amino acid substitutions in the F protein namely K66E and Q101P (described in Connors, et al. 1995. Virology 208:478-484; Whitehead, et al. 1998. J Virol 72:4467-4471). The introduction of the HEK amino acid assignments into the strain A2 F sequence of this disclosure results in an F protein amino acid sequence that is identical to that of an early-passage (human embryonic kidney cell passage 7, HEK-7) of the original clinical isolate of strain A2 (Connors, et al. 1995. Virology 208:478-484; Whitehead, et al. 1998. J Virol 72:4467-4471). It results in an F protein that is much less fusogenic and is thought to represent the phenotype of the original A2 strain clinical isolate (Liang et al. J Virol 2015 89:9499-9510). The HEK F protein also forms a more stable trimer (Liang et al. J Virol 2015 89:9499-9510). This may provide a more authentic and immunogenic form of the RSV F protein, possibly enriched for the highly immunogenic pre-fusion conformation (McLellan et al. Science 2013 340(6136):1113-7; Science 2013 342(6158):592-8.). Thus, mutations can be introduced with effects additional to effects on the magnitude of virus replication.

In some embodiments the recombinant strains may comprise one or more changes in the L protein, e.g. the stabilized 1030 or the "1030s" mutation which comprises 1321K (AAA)/13135(TCA) (Luongo, et al. 2012. J Virol 86:10792-10804).

Figure 6:
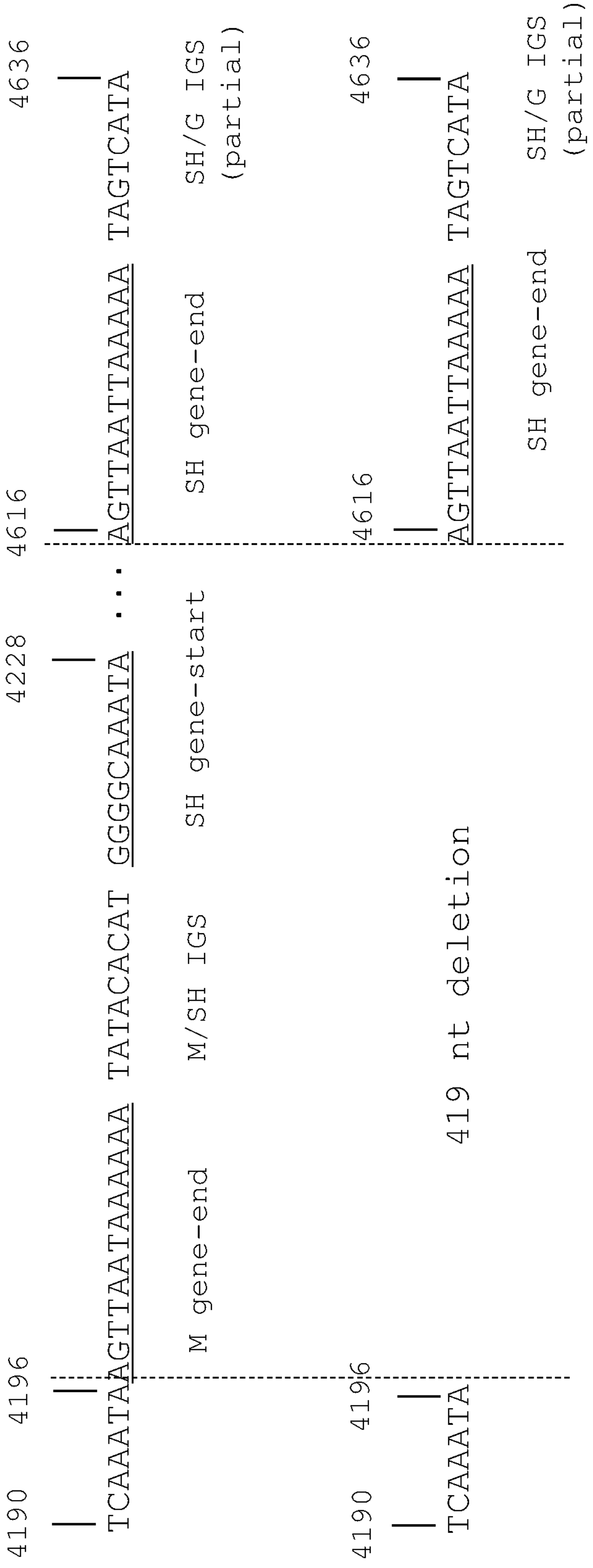
FIG. 6. Details of the "ΔSH" mutation, which is a 419 nucleotide deletion that silences the SH gene. Sequence numbering is according to the complete sequence of the wt human RSV strain A2 that is represented by GenBank accession number M74568. In the upper sequence (showing nucleotides 4191-4229 and 4617-4637 of SEQ ID NO: 1), the features from left to right include: the M gene-end signal (underlined), the M/SH intergenic sequence (IGS), the SH gene-start signal (underlined), three dots that indicate the main body of the SH gene (M74568 nucleotides 4229-4615, which are not shown), the SH gene-end signal (underlined), and part of the SH/G IGS. The bottom sequence (nucleotides 4191-4197 and 4617-4637 of SEQ ID NO: 1) illustrates the 419-nucleotide deletion that yields the ΔSH mutation. Note that, although this is operationally called deletion of the SH gene, the deletion actually spans from immediately upstream of the M gene-end signal to immediately upstream of the SH gene-end signal.

In some embodiments the recombinant strains may comprise deletions of one or more RSV genes. Deletion of the SH, NS1, and NS2 genes individually and in combination has been shown to yield viruses that retain their ability to replicate in cell culture but are attenuated in vivo in the following order of increasing magnitude: SH<NS2<NS1 (Bukreyev, et al. 1997. J Virol 71:8973-8982; Whitehead, et al. 1999. J Virol 73:3438-3442; Teng, et al. 2000. J Virol 74:9317-9321). Therefore, deletion or other mutations of the SH, NS2, or NS1 genes, or parts of their ORFs, may be combined with a disclosed M2-2 mutation (such as a ΔM2-2, ΔM2-2-AclI, or ΔM2-2-HindIII mutation). For example, in some embodiments, the recombinant strains may comprise one or more changes in the SH protein, including an ablation or elimination of the SH protein. In some embodiments, the viral strains comprise a deletion in the SH gene. For example, in some embodiments, the viral strains comprise a 419 nucleotide deletion at position 4197-4615 (4198-4616 of SEQ ID NO: 1), denoted herein as the "ΔSH" mutation. This deletion results in the deletion of M gene-end, M/SH intergenic region, and deletion of the SH ORF as shown in FIG. 6. In some embodiments, the recombinant strains may comprise one or more changes in the NS1 or the NS2 protein, which may include an ablation or elimination of the protein. In some embodiments, the mutation may be an amino acid substitution such as K51R in the NS2 protein. In some embodiments the recombinant strains may comprise one or more changes in the N protein, e.g. an amino acid substitution such as T24A.

Various features can be introduced into RSV strains bearing a disclosed M2-2 mutation (such as a ΔM2-2, ΔM2-2-AclI, or ΔM2-2-HindIII mutation) that change the characteristics of the virus in ways other than attenuation. For instance, codon optimization of the ORFs encoding the proteins may be performed. Major protective antigens F and G can result in increased antigen synthesis. The F and/or G protein gene may be shifted upstream (closer to the promoter) to increase expression. However, the present disclosure also describes unexpected limitations to this strategy in the case of ΔM2-2 recombinant virus strains. The F and/or G protein amino acid sequences can be modified to represent currently-circulating strains, which can be may be relevant in the case of the divergent G protein, or to represent early-passage clinical isolates. Deletions or substitutions may be introduced into the G protein to obtain improved immunogenicity or other desired properties. For example, the CX3C fractalkine motif in the G protein might be ablated to improve immunogenicity (Chirkova et al. J Virol 2013 87:13466-13479).

For example, in some embodiments, the nucleotide sequence encoding the G protein of the RSV may be replaced with a corresponding nucleotide sequence from the clinical isolate A/Maryland/001/11. In some embodiments, the nucleotide sequence encoding the F protein of the RSV may be replaced with a corresponding nucleotide sequence from the clinical isolate A/Maryland/001/11, e.g. F001 (SEQ ID NO: 10).

In some embodiments, a native or naturally occurring nucleotide sequence encoding a protein of the RSV may be replaced with a codon optimized sequence designed for increased expression in a selected host, in particular the human. For example, in some embodiments, the nucleotide sequence encoding the F protein of the RSV may be replaced with the codon optimized sequence FBB ("FBB") (SEQ ID NO: 9). In some embodiments, the nucleotide sequence encoding the F protein of the RSV may be replaced with the codon optimized sequence from the clinical isolate A/Maryland/001/11 ("F001BB") (SEQ ID NO: 11). In some embodiments, the nucleotide sequence encoding the G protein of the RSV may be replaced with the codon optimized nucleotide sequence G001BB (SEQ ID NO: 8) from the clinical isolate A/Maryland/001/11 ("G001BB").

Yet additional aspects of the invention involve changing the position of a gene or altering gene order to create or modify a M2-2 deletion mutant RSV. For example, the NS1, NS2, SH and G genes may be deleted individually, or the NS1 and NS2 gene may be deleted together, thereby shifting the position of each downstream gene relative to the viral promoter. For example, when NS1 and NS2 are deleted together, N is moved from gene position 3 to gene position 1, P from gene position 4 to gene position 2, and so on. Alternatively, deletion of any other gene within the gene order will affect the position (relative to the promoter) only of those genes which are located further downstream. For example, SH occupies position 6 in Wild type virus, and its deletion does not affect M at position 5 (or any other upstream gene) but moves G from position 7 to 6 relative to the promoter. It should be noted that gene deletion also can occur (rarely) in a biologically-derived mutant virus. For example, a subgroup B RSV that had been passaged extensively in cell culture spontaneously deleted the SH and G genes (Karron et al. Proc. Natl. Acad. Sci. USA 94:13961 13966, 1997; incorporated herein by reference).

Gene order shifting modifications (i.e., positional modifications moving one or more genes to a more promoter-proximal or promoter-distal location in the recombinant viral genome) result in viruses with altered biological properties. For example, RSV lacking NS1, NS2, SH, G, NS1 and NS2 together, or SH and G together, have been shown to be attenuated in vitro, in vivo, or both. In particular, the G and F genes may be shifted, singly and in tandem, to a more promoter-proximal position relative to their wild-type gene order. These two proteins normally occupy positions 7 (G) and 8 (F) in the RSV gene order (NS1-NS2-N-P-M-SH-G-FM2-L). In some embodiments, the order of the nucleotide sequences encoding the G and the F proteins may be reversed relative to the naturally occurring order.

The RSV F and G proteins are known to induce RSV neutralizing antibodies, and are the major protective antigens. The F protein generally is considered to be is a more effective neutralization and protective antigen than the G protein. F also is relatively well-conserved among RSV strains, whereas the G protein can be substantially divergent. The divergence in G is a major factor in segregating RSV strains into two antigenic subgroups, A and B (~53% and ~90% amino acid sequence identity between the two subgroups for G and F, respectively). The tools and methods of the present disclosure focus on RSV strain A2 of subgroup A, but can readily be applied to other strains of either subgroup.

In some embodiments, the recombinant RSV strain comprises a recombinant RSV genome comprising the ΔM2-2, ΔM2-2-AclI, or ΔM2-2-HindIII mutation in combination with one or more of the mutations described above. In some embodiments, the recombinant RSV strain comprises a recombinant RSV genome comprising a D46 (SEQ ID NO: 1) genome that has been modified with the ΔM2-2, ΔM2-2-AclI, or ΔM2-2-HindIII mutation, as well as one or more of the above mutations described above.

In some embodiments, the recombinant strain can be a D46-based RSV strain including the "276" mutations, and further including one of the disclosed M2-2 mutations, such as a ΔM2-2, ΔM2-2-AclI, or ΔM2-2-HindIII mutation. As discussed in Example 8, the "276" mutations include the following nucleotide mutations: 404C, 779G, deletion of C1099, 1138A, 1139G, 1181G, 1209G, 5611A, 5615A, 5639G, 6215C, 6221C, 6386T, 7214C, 7481T, 7559A, 7701G, 10514T, and 13633A (relative to SEQ ID NO: 1, these mutations are the following: 404C, 779G, deletion of C1099, 1139A, 1140G, 1182G, 1210G, 5612A, 5616A, 5640G, 6216C, 6222C, 6387T, 7215C, 7482T, 7560A, 7702G, 10515T, and 13634A). An exemplary antigenomic cDNA sequence for a ΔM2-2-HindIII-based RSV strain including the "276" mutations is provided as SEQ ID NO: 19.

In some embodiments, the recombinant RSV strain comprises a genome comprising a nucleotide sequence corresponding to an antigenomic cDNA sequence at least 90% identical (such as at least 95% identical or at least 99% identical) to the antigenomic cDNA sequence set forth as SEQ ID NO: 1, that has been modified to comprise one of the ΔM2-2, ΔM2-2-AclI, or ΔM2-2-HindIII mutations as described above, alone or in combination with one or more of the attenuating mutations provided herein.

In some embodiments, the recombinant RSV strain comprises a genome comprising the cp and ΔM2-2 mutations as described herein, and a nucleotide sequence corresponding to an antigenomic cDNA sequence at least 90% identical, at least 95% identical, and/or at least 99% identical to SEQ ID NO: 1 (D46 sequence).

In some embodiments, the recombinant RSV strain comprises a genome comprising the ΔM2-2 mutation as described herein, and a nucleotide sequence corresponding to an antigenomic cDNA sequence at least 90% identical, at least 95% identical, and/or at least 99% identical to SEQ ID NO: 2 (D46/ΔM2-2 sequence).

In some embodiments, the recombinant RSV strain comprises a genome comprising the ΔM2-2-AclI mutation as described herein, and a nucleotide sequence corresponding to an antigenomic cDNA sequence at least 90% identical, at least 95% identical, and/or at least 99% identical to SEQ ID NO: 3 (D46/ΔM2-2-AclI sequence).

In some embodiments, the recombinant RSV strain comprises a genome comprising the ΔM2-2-HindIII mutation as described herein, and a nucleotide sequence corresponding to an antigenomic cDNA sequence at least 90% identical, at least 95% identical, and/or at least 99% identical to SEQ ID NO: 4 (D46/ΔM2-2-HindIII sequence).

In some embodiments, the recombinant RSV strain comprises a genome comprising the LID and ΔM2-2 mutations as described herein, and a nucleotide sequence corresponding to an antigenomic cDNA sequence at least 90% identical, at least 95% identical, and/or at least 99% identical to SEQ ID NO: 5 (LID/ΔM2-2 sequence).

In some embodiments, the recombinant RSV strain comprises a genome comprising the LID and ΔM2-2-AclI mutations as described herein, and a nucleotide sequence corresponding to an antigenomic cDNA sequence at least 90% identical, at least 95% identical, and/or at least 99% identical to SEQ ID NO: 6 (LID/ΔM2-2-AclI sequence).

In some embodiments, the recombinant RSV strain comprises a genome comprising the LID and ΔM2-2-HindIII mutations as described herein, and a nucleotide sequence corresponding to an antigenomic cDNA sequence at least 90% identical, at least 95% identical, and/or at least 99% identical to SEQ ID NO: 7 (LID/ΔM2-2-HindIII sequence).

In some embodiments, the recombinant RSV strain comprises a genome comprising the cp and ΔM2-2 mutations as described herein, and a nucleotide sequence corresponding to an antigenomic cDNA sequence at least 90% identical, at least 95% identical, and/or at least 99% identical to SEQ ID NO: 15 (D46/cp/ΔM2-2 sequence).

In some embodiments, the recombinant RSV strain comprises a genome comprising the 6120, ΔM2-2, and 1030s mutations as described herein, and a nucleotide sequence corresponding to an antigenomic cDNA sequence at least 90% identical, at least 95% identical, and/or at least 99% identical to SEQ ID NO: 16 (LID/ΔM2-2/1030s sequence).

In some embodiments, the recombinant RSV strain comprises a genome comprising the 6120, cp, and ΔM2-2 mutations as described herein, and a nucleotide sequence corresponding to an antigenomic cDNA sequence at least 90% identical, at least 95% identical, and/or at least 99% identical to SEQ ID NO: 17 (LID/cp/ΔM2-2 sequence).

In some embodiments, the recombinant RSV strain comprises a genome comprising the NS2, N, ΔM2-2-HindIII mutations as described herein, and a nucleotide sequence corresponding to an antigenomic cDNA sequence at least 90% identical, at least 95% identical, and/or at least 99% identical to SEQ ID NO: 4 (D46/ΔM2-2-HindIII sequence).

In some embodiments, the recombinant RSV strain comprises a genome comprising the NS2, N, ΔM2-2-HindIII mutations as described herein, and a nucleotide sequence corresponding to an antigenomic cDNA sequence at least 90% identical, at least 95% identical, and/or at least 99% identical to SEQ ID NO: 18 (D46/NS2/N/ΔM2-2-HindIII sequence).

In some embodiments, the recombinant RSV strain comprises a genome comprising the NS2, N, ΔM2-2-AclI mutations as described herein, and a nucleotide sequence corresponding to an antigenomic cDNA sequence at least 90% identical, at least 95% identical, and/or at least 99% identical to SEQ ID NO: 3 (D46/ΔM2-2-AclII sequence).

In some embodiments, the recombinant RSV strain comprises a genome comprising the NS2, N, and ΔM2-2-AclI mutations as described herein, the following nucleotide mutations with positions relative to SEQ ID NO: 1: 404C, 779G, deletion of C1099, 1139A, 1140G, 1182G, 1210G, 5612A, 5616A, 5640G, 6216C, 6222C, 6387T, 7215C, 7482T, 7560A, 7702G, 10515T, and 13634A; and a nucleotide sequence corresponding to an antigenomic cDNA sequence at least 90% identical, at least 95% identical, and/or at least 99% identical to SEQ ID NO: 19 (276 sequence).

In some embodiments, the recombinant RSV strain comprises a genome comprising a nucleotide sequence corresponding to a positive-sense sequence set forth as any one of SEQ ID NO: 2, SEQ ID NO: 3, SEQ ID NO: 4, SEQ ID NO: 5, SEQ ID NO: 6, SEQ ID NO: 7, SEQ ID NO: 15, SEQ ID NO: 16, SEQ ID NO: 17, SEQ ID NO: 18, or SEQ ID NO: 19.

In several embodiments, the genome of the recombinant RSV comprises the one or more mutations as discussed herein, and any remaining sequence difference of the genome of the recombinant RSV compared to the genomic sequence of D46 RSV (SEQ ID NO: 1) is biologically insignificant (for example, the remaining sequence differences do not include changes to the wild-type genomic sequence that modify a known cis-acting signal or change amino acid coding, or measurably affect in vitro replication or plaque size of the virus).

In addition to the above described mutations, infectious M2-2 deletion mutants (such as a ΔM2-2, ΔM2-2-AclI, or ΔM2-2-HindIII mutant) can incorporate heterologous, coding or non-coding nucleotide sequences from any RSV or RSV-like virus, e.g., human, bovine, ovine, murine (pneumonia virus of mice), or avian (turkey rhinotracheitis virus) pneumovirus, or from another enveloped virus, e. g., parainfluenza virus (PIV). Exemplary heterologous sequences include RSV sequences from one human RSV strain combined with sequences from a different human RSV strain. Alternatively, M2-2 deletion mutants (such as a ΔM2-2, ΔM2-2-AclI, or ΔM2-2-HindIII mutant) may incorporate sequences from two or more, wild-type or mutant human RSV subgroups, for example a combination of human RSV subgroup A and subgroup B sequences. In yet additional aspects, one or more human RSV coding or non-coding polynucleotides are substituted with a counterpart sequence from a heterologous RSV or non-RSV virus to yield novel attenuated vaccine strains.

In addition to the recombinant RSVs having the particular mutations, and the combinations of those mutations, described herein, the disclosed viruses may be modified further as would be appreciated by those skilled in the art. For example, the recombinant RSVs may have one or more of its proteins deleted or otherwise mutated or a heterologous gene from a different organism may be added to the genome or antigenome so that the recombinant RSV expresses or incorporates that protein upon infecting a cell and replicating. Furthermore, those skilled in the art will appreciate that other previously defined mutations known to have an effect on RSV may be combined with one or more of any of the mutations described herein to produce a recombinant RSV with desirable attenuation or stability characteristics.

In some embodiments, the mutations described herein, when used either alone or in combination with another mutation, may provide for different levels of virus attenuation, providing the ability to adjust the balance between attenuation and immunogenicity, and provide a more stable genotype than that of the parental virus.

With regard to sequence numbering of nucleotide and amino acid sequence positions for the described viruses, a convention was used whereby each nucleotide or amino acid residue in a given viral sequence retained the sequence position number that it has in the original 15,222-nucleotide biological wt strain A2 virus (GenBank accession number M74568), irrespective of any modifications. Thus, although a number of genomes contain deletions and/or insertions that cause changes in nucleotide length, and in some cases amino acid length, the numbering of all of the other residues (nucleotide or amino acid) in the genome and encoded proteins remains unchanged. It also is recognized that, even without the expedient of this convention, one skilled in the art can readily identify corresponding sequence positions between viral genomes or proteins that might differ in length, guided by sequence alignments as well as the positions of open reading frames, well-known RNA features such as gene-start and gene-end signals, and amino acid sequence features.

Additional representative viruses from those described in this disclosure may be evaluated in cell culture for infectivity, replication kinetics, yield, efficiency of protein expression, and genetic stability using the methods described herein and illustrated in examples using exemplary recombinant strains. Additional representative strains may be evaluated in rodents and non-human primates for infectivity, replication kinetics, yield, immunogenicity, and genetic stability. While these semi-permissive systems may not reliably detect every difference in replication, substantial differences in particular may be detected (e.g., as between RSV D46/ΔM2-2 and LID/ΔM2-2, Tables 4 and 5). Also recombinant strains may be evaluated directly in seronegative children without the prior steps of evaluation in adults and seropositive children. This may be done, for example, in groups of 10 vaccine recipients and 5 placebo recipients, which is a small number that allows simultaneous evaluation of multiple candidates. Candidates may be evaluated in the period immediately post-immunization for vaccine virus infectivity, replication kinetics, shedding, tolerability, immunogenicity, and genetic stability, and the vaccines may be subjected to surveillance during the following RSV season for safety, RSV disease, and changes in RSV-specific serum antibodies, as described in Karron, et al. 2015, Science Transl Med 2015 7(312):312ra175, which is incorporated herein in its entirety. Thus, analysis of selected representative viruses may provide for relatively rapid triage to narrow down candidates to identify the most optimal.

Reference to a protein or a peptide includes its naturally occurring form, as well as any fragment, domain, or homolog of such protein. As used herein, the term "homolog" is used to refer to a protein or peptide which differs from a naturally occurring protein or peptide (i.e., the "prototype" or "wild-type" protein) by minor modifications to the naturally occurring protein or peptide, but which maintains the basic protein and side chain structure of the naturally occurring form. Such changes include, but are not limited to: changes in one or a few amino acid side chains; changes in one or a few amino acids, including deletions (e.g., a truncated version of the protein or peptide) insertions and/or substitutions; changes in stereochemistry of one or a few atoms; and/or minor derivatizations, including but not limited to: methylation, glycosylation, phosphorylation, acetylation, myristoylation, prenylation, palmitation, amidation. A homolog can have either enhanced, decreased, or substantially similar properties as compared to the naturally occurring protein or peptide. A homolog of a given protein may comprise, consist essentially of, or consist of, an amino acid sequence that is at least about 50%, or at least about 55%, or at least about 60%, or at least about 65%, or at least about 70%, or at least about 75%, or at least about 80%, or at least about 85%, or at least about 90%, or at least about 95%, or at least about 96%, or at least about 97%, or at least about 98%, or at least about 99% identical (or any percent identity between 45% and 99%, in whole integer increments), to the amino acid sequence of the reference protein.

In one aspect of the invention, a selected gene segment, such as one encoding a selected protein or protein region (e.g., a cytoplasmic tail, transmembrane domain or ectodomain, an epitopic site or region, a binding site or region, an active site or region containing an active site, etc.) from one RSV, can be substituted for a counterpart gene segment from the same or different RSV or other source, to yield novel recombinants having desired phenotypic changes compared to wild-type or parent RSV strains. For example, recombinants of this type may express a chimeric protein having a cytoplasmic tail and/or transmembrane domain of one RSV fused to an ectodomain of another RSV. Other exemplary recombinants of this type express duplicate protein regions, such as duplicate immunogenic regions. As used herein, "counterpart" genes, gene segments, proteins or protein regions, are typically from heterologous sources (e.g., from different RSV genes, or representing the same (i.e., homologous or allelic) gene or gene segment in different RSV strains). Typical counterparts selected in this context share gross structural features, e.g., each counterpart may encode a comparable structural "domain," such as a cytoplasmic domain, transmembrane domain, ectodomain, binding site or region, epitopic site or region, etc. Counterpart domains and their encoding gene segments embrace an assemblage of species having a range of size and amino acid (or nucleotide) sequence variations, which range is defined by a common biological activity among the domain or gene segment variants. For example, two selected protein domains encoded by counterpart gene segments within the invention may share substantially the same qualitative activity, such as providing a membrane spanning function, a specific binding activity, an immunological recognition site, etc. More typically, a specific biological activity shared between counterparts, e.g., between selected protein segments or proteins, will be substantially similar in quantitative terms, i.e., they will not vary in respective quantitative activity profiles by more than 30%, preferably by no more than 20%, more preferably by no more than 5-10%.

In alternative aspects of the invention, the infectious RSV produced from a cDNA-expressed genome or antigenome can be any of the RSV or RSV-like strains, e.g., human, bovine, murine, etc., or of any pneumovirus or metapneumovirus, e.g., pneumonia virus of mice or avian metapneumovirus. To engender a protective immune response, the RSV strain may be one which is endogenous to the subject being immunized, such as human RSV being used to immunize humans. The genome or antigenome of endogenous RSV can be modified, however, to express RSV genes or gene segments from a combination of different sources, e.g., a combination of genes or gene segments from different RSV species, subgroups, or strains, or from an RSV and another respiratory pathogen such as human parainfluenza virus (PIV) (see, e.g., Hoffman et al. J. Virol. 71:4272-4277 (1997); Durbin et al. Virology 235(2):323-32 (1997); Murphy et al. U.S. Patent Application Ser. No. 60/047,575, filed May 23, 1997, and the following plasmids for producing infectious PIV clones: p3/7(131) (ATCC 97990); p3/7(131) 2G(ATCC 97889); and p218(131) (ATCC 97991); each deposited Apr. 18, 1997 under the terms of the Budapest Treaty with the American Type Culture Collection (ATCC) of 10801 University Blvd., Manassas, Va. 20110-2209, USA., and granted the above identified accession numbers.

In certain embodiments of the invention, recombinant RSV are provided wherein individual internal genes of a human RSV are replaced with, e.g., a bovine or other RSV counterpart, or with a counterpart or foreign gene from another respiratory pathogen such as PIV. Substitutions, deletions, etc. of RSV genes or gene segments in this context can include part or all of one or more of the NS1, NS2, N, P, M, SH, and L genes, or the M2-1 open reading frames, or non-immunogenic parts of the G and F genes. Also, human RSV cis-acting sequences, such as promoter or transcription signals, can be replaced with, e.g., their bovine RSV counterpart. Reciprocally, means are provided to generate live attenuated bovine RSV by inserting human attenuating genes or cis-acting sequences into a bovine RSV genome or antigenome background.

Thus, infectious recombinant RSV intended for administration to humans can be a human RSV that has been modified to contain genes from, e.g., a bovine RSV or a PIV, such as for the purpose of attenuation. For example, by inserting a gene or gene segment from PIV, a bivalent vaccine to both PIV and RSV is provided. Alternatively, a heterologous RSV species, subgroup or strain, or a distinct respiratory pathogen such as PIV, may be modified, e.g., to contain genes that encode epitopes or proteins which elicit protection against human RSV infection. For example, the human RSV glycoprotein genes can be substituted for the bovine glycoprotein genes such that the resulting bovine RSV, which now bears the human RSV surface glycoproteins and would retain a restricted ability to replicate in a human host due to the remaining bovine genetic background, elicits a protective immune response in humans against human RSV strains.

The ability to analyze and incorporate other types of attenuating mutations into infectious RSV for vaccine development extends to a broad assemblage of targeted changes in RSV clones. For example, any RSV gene which is not essential for growth may be ablated or otherwise modified to yield desired effects on virulence, pathogenesis, immunogenicity and other phenotypic characters. In addition, a variety of other genetic alterations can be produced in a recombinant RSV genome or antigenome for incorporation into infectious recombinant RSV, alone or together with one or more attenuating point mutations adopted from a biologically derived mutant RSV.

As used herein, “heterologous genes” refers to genes taken from different RSV strains or types or non-RSV sources. These heterologous genes can be inserted in whole or in part, the order of genes changed, gene overlap removed, the RSV genome promoter replaced with its antigenome counterpart, portions of genes removed or substituted, and even entire genes deleted. Different or additional modifications in the sequence can be made to facilitate manipulations, such as the insertion of unique restriction sites in various intergenic regions (e.g., a unique StuI site between the G and F genes) or elsewhere. Nontranslated gene sequences can be removed to increase capacity for inserting foreign sequences.

Deletions, insertions, substitutions and other mutations involving changes of whole viral genes or gene segments in recombinant RSV of the invention yield highly stable vaccine candidates, which may be relevant in the case of immunosuppressed individuals. Many of these mutations will result in attenuation of resultant vaccine strains, whereas others will specify different types of desired phenotypic changes. For example, certain viral genes are known which encode proteins that specifically interfere with host immunity (see, e.g., Kato et al., EMBO. J. 16:578-87 (1997). Ablation of such genes in vaccine viruses is expected to reduce virulence and pathogenesis and/or improve immunogenicity.

Other mutations within RSV of the present invention involve replacement of the 3' end of genome with its counterpart from antigenome, which is associated with changes in RNA replication and transcription. In addition, the intergenic regions (Collins et al., Proc. Natl. Acad. Sci. USA 83:4594-4598 (1986)) can be shortened or lengthened or changed in sequence content, and the naturally-occurring gene overlap (Collins et al., Proc. Natl. Acad. Sci. USA 84:5134-5138 (1987)) can be removed or changed to a different intergenic region by the methods described herein.

In another embodiment, a sequence surrounding a translational start site (preferably including a nucleotide in the −3 position) of a selected RSV gene is modified, alone or in combination with introduction of an upstream start codon, to modulate RSV gene expression by specifying up- or down-regulation of translation.

Alternatively, or in combination with other RSV modifications disclosed herein, RSV gene expression can be modulated by altering a transcriptional GS signal of a selected gene(s) of the virus. In one exemplary embodiment, the GS signal of NS2 is modified to include a defined mutation to superimpose a is restriction on viral replication.

Yet additional RSV clones within the invention incorporate modifications to a transcriptional GE signal. For example, RSV clones are provided which substitute or mutate the GE signal of the NS1 and NS2 genes for that of the N gene, resulting in decreased levels of readthrough mRNAs and increased expression of proteins from downstream genes. The resulting recombinant virus exhibits increased growth kinetics and increased plaque size, providing but one example of alteration of RSV growth properties by modification of a cis-acting regulatory element in the RSV genome.

In another aspect, expression of the G protein may be increased by modification of the G mRNA. The G protein is expressed as both a membrane bound and a secreted form, the latter form being expressed by translational initiation at a start site within the G gene translational open reading frame. The secreted form may account for as much as one-half of the expressed G protein. Ablation of the internal start site (e.g., by sequence alteration, deletion, etc.), alone or together with altering the sequence context of the upstream start site yields desired changes in G protein expression. Ablation of the secreted form of the G protein also will improve the quality of the host immune response to exemplary, recombinant RSV, because the soluble form of the G protein is thought to act as a “decoy” to trap neutralizing antibodies. Also, soluble G protein has been implicated in enhanced immunopathology due to its preferential stimulation of a Th2-biased response.

In related aspects, levels of RSV gene expression may be modified at the level of transcription. In one aspect, the position of a selected gene in the RSV gene map may be changed to a more promoter-proximal or promoter-distal position, whereby the gene will be expressed more or less efficiently, respectively. According to this aspect, modulation of expression for specific genes can be achieved yielding reductions or increases of gene expression from two-fold, more typically four-fold, up to ten-fold or more compared to wild-type levels. In one example, the NS2 gene (second in order in the RSV gene map) is substituted in position for the SH gene (sixth in order), yielding a predicted decrease in expression of NS2. Increased expression of selected RSV genes due to positional changes can be achieved up to 10-fold, 30-fold, 50-fold, 100-fold or more, often attended by a commensurate decrease in expression levels for reciprocally, positionally substituted genes.

In some exemplary embodiments, the F and G genes may be transpositioned singly or together to a more promoter-proximal or promoter-distal site within the (recombinant) RSV gene map to achieve higher or lower levels of gene expression, respectively. These and other transpositioning changes yield novel RSV clones having attenuated phenotypes, for example due to decreased expression of selected viral proteins involved in RNA replication. In yet other embodiments, RSV useful in a vaccine formulation may be conveniently modified to accommodate antigenic drift in circulating virus. Typically the modification will be in the G and/or F proteins. The entire G or F gene, or the segments encoding particular immunogenic regions thereof, is incorporated into the RSV genome or antigenome cDNA by replacement of the corresponding region in the infectious clone or by adding one or more copies of the gene such that several antigenic forms are represented.

Progeny virus produced from the modified RSV cDNA are then used in vaccination protocols against the emerging strains. Further, inclusion of the G protein gene of RSV subgroup B as a gene addition will broaden the response to cover a wider spectrum of the relatively diverse subgroup A and B strains present in the human population.

An infectious RSV clone of the invention may also be engineered according to the methods and compositions disclosed herein to enhance its immunogenicity and induce a level of protection greater than that provided by infection with a wild-type RSV or an incompletely attenuated parental virus or clone. For example, an immunogenic epitope from a heterologous RSV strain or type, or from a non-RSV source such as PIV, can be added by appropriate nucleotide changes in the polynucleotide sequence encoding the RSV genome or antigenome. Recombinant RSV can also be engineered to identify and ablate (e.g., by amino acid insertion, substitution or deletion) epitopes associated with undesirable immunopathologic reactions. In other embodiments, an additional gene may inserted into or proximate to the RSV genome or antigenome which is under the control of an independent set of transcription signals. Genes of interest may include, but are not limited to, those encoding cytokines (e.g., IL-2 through IL-15, especially IL-2, IL-6 and IL-12, etc.), gamma-interferon, and include those encoding cytokines (e.g., IL-2 through IL-15, especially IL-2, IL-6 and IL-12, etc.), gamma-interferon, and proteins rich in T helper cell epitopes. The additional protein can be expressed either as a separate protein or as a chimera engineered from a second copy of one of the RSV proteins, such as SH. This provides the ability to modify and improve the immune response against RSV both quantitatively and qualitatively.

In addition to the above described modifications to recombinant RSV, different or additional modifications in RSV clones can be made to facilitate manipulations, such as the insertion of unique restriction sites in various intergenic regions (e.g., a unique StuI site between the G and F genes) or elsewhere. Nontranslated gene sequences can be removed to increase capacity for inserting foreign sequences.

Introduction of the foregoing, defined mutations into an infectious RSV clone can be achieved by a variety of well-known methods. By “infectious clone” is meant cDNA or its product, synthetic or otherwise, which can be transcribed into genomic or antigenomic RNA capable of producing an infectious virus. The term “infectious” refers to a virus or viral structure that is capable of replicating in a cultured cell or animal or human host to produce progeny virus or viral structures capable of the same activity. Thus, defined mutations can be introduced by conventional techniques (e.g., site-directed mutagenesis) into a cDNA copy of the genome or antigenome. The use of antigenome or genome cDNA subfragments to assemble a complete antigenome or genome cDNA is well-known by those of ordinary skill in the art and has the advantage that each region can be manipulated separately (smaller cDNAs are easier to manipulate than large ones) and then readily assembled into a complete cDNA. Thus, the complete antigenome or genome cDNA, or any subfragment thereof, can be used as template for oligonucleotide-directed mutagenesis. A mutated subfragment can then be assembled into the complete antigenome or genome cDNA. Mutations can vary from single nucleotide changes to replacement of large cDNA pieces containing one or more genes or genome regions.

Recombinant RSV may be produced by the intracellular coexpression of a cDNA that encodes the RSV genomic RNA, together with those viral proteins necessary to generate a transcribing, replicating nucleocapsid. Plasmids encoding other RSV proteins may also be included with these essential proteins. Alternatively, RNA may be synthesized in in vitro transcription reactions and transfected into cultured cells.

Accordingly, also described herein are isolated polynucleotides that encode the described mutated viruses, make up the described genomes or antigenomes, express the described genomes or antigenomes, or encode various proteins useful for making recombinant RSV in vitro. Polynucleotides comprising the sequences of any of the SEQ ID NOs described herein are included in the present invention. Further included are polynucleotides comprising sequences that consist or consist essentially of any of the aforementioned sequences, sequences that possess at least about 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 percent identity (or any percent identity in between) to any of the aforementioned SEQ ID NOs, as well as polynucleotides that hybridize to, or are the complements of the aforementioned molecules.

These polynucleotides can be included within or expressed by vectors in order to produce a recombinant RSV. Accordingly, cells transfected with the isolated polynucleotides or vectors are also within the scope of the invention and are exemplified herein.

In related aspects of the invention, compositions (e.g., isolated polynucleotides and vectors incorporating an RSV-encoding cDNA) and methods are provided for producing an isolated infectious recombinant RSV bearing an attenuating, M2-2 deletion mutation (such as a ΔM2-2, ΔM2-2-AclI, or ΔM2-2-HindIII mutant). Included within these aspects of the invention are novel, isolated polynucleotide molecules and vectors incorporating such molecules that comprise a RSV genome or antigenome which is modified as described herein. Also provided is the same or different expression vector comprising one or more isolated polynucleotide molecules encoding the RSV proteins. These proteins also can be expressed directly from the genome or antigenome cDNA. The vector(s) is/are preferably expressed or coexpressed in a cell or cell-free lysate, thereby producing an infectious M2 ORF2 deletion or knock out mutant RSV particle or subviral particle.

In one aspect, a method for producing one or more purified RSV protein(s) is provided which involves infecting a host cell permissive of RSV infection with a recombinant RSV strain under conditions that allow for RSV propagation in the infected cell. After a period of replication in culture, the cells are lysed and recombinant RSV is isolated therefrom. One or more desired RSV protein(s) is purified after isolation of the virus, yielding one or more RSV protein(s) for vaccine, diagnostic and other uses.

The above methods and compositions for producing M2-2 deletion mutants (such as a ΔM2-2, ΔM2-2-AclI, or ΔM2-2-HindIII mutant) yield infectious viral or subviral particles, or derivatives thereof. An infectious virus is comparable to the authentic RSV virus particle and is infectious as is. It can directly infect fresh cells. An infectious subviral particle typically is a subcomponent of the virus particle which can initiate an infection under appropriate conditions. For example, a nucleocapsid containing the genomic or antigenomic RNA and the N, P, L and M2-1 proteins is an example of a subviral particle which can initiate an infection if introduced into the cytoplasm of cells. Subviral particles provided within the invention include viral particles which lack one or more protein(s), protein segment(s), or other viral component(s) not essential for infectivity.

In other embodiments the invention provides a cell or cell free lysate containing an expression vector which comprises an isolated polynucleotide molecule encoding an M2-2 deletion mutant (such as a ΔM2-2, ΔM2-2-AclI, or ΔM2-2-HindIII mutant) RSV genome or antigenome as described above, and an expression vector (the same or different vector) which comprises one or more isolated polynucleotide molecules encoding the N, P, L and RNA polymerase elongation factor proteins of RSV. One or more of these proteins also can be expressed from the genome or antigenome cDNA. Upon expression the genome or antigenome and N, P, L, and RNA polymerase elongation factor proteins combine to produce an infectious RSV viral or sub-viral particle.

The recombinant RSV of the invention are useful in various compositions to generate a desired immune response against RSV in a host susceptible to RSV infection. Attenuated M2-2 deletion mutant (such as a ΔM2-2, ΔM2-2-AclI, or ΔM2-2-HindIII mutant) RSV strains disclosed herein are capable of eliciting a protective immune response in an infected human host, yet are sufficiently attenuated so as to not cause unacceptable symptoms of severe respiratory disease in the immunized host. The attenuated virus or subviral particle may be present in a cell culture supernatant, isolated from the culture, or partially or completely purified. The virus may also be lyophilized, and can be combined with a variety of other components for storage or delivery to a host, as desired.

In another aspect, M2-2 deletion mutants (such as a ΔM2-2, ΔM2-2-AclI, or ΔM2-2-HindIII mutant) may be employed as "vectors" for protective antigens of other pathogens, particularly respiratory tract pathogens such as parainfluenza virus (PIV). For example, recombinant RSV having a M2-2 deletion (such as a ΔM2-2, ΔM2-2-AclI, or ΔM2-2-HindIII mutant) may be engineered which incorporate sequences that encode protective antigens from PIV to produce infectious, attenuated vaccine virus.

In related aspects, the invention provides a method for stimulating the immune system of an individual to elicit an immune response against RSV in a mammalian subject. The method comprises administering an immunogenic formulation of an immunologically sufficient amount of an attenuated, M2-2 deletion mutant RSV as described herein in a physiologically acceptable carrier and/or adjuvant.

The invention further provides novel vaccines comprising a physiologically acceptable carrier and/or adjuvant and an isolated attenuated M2-2 deletion mutant RSV particle or subviral particle. In preferred embodiments, the vaccine is comprised of an M2-2 deletion mutant RSV having at least one; and preferably two or more attenuating mutations or other nucleotide modifications as described above to achieve a suitable balance of attenuation and immunogenicity.

To select candidate vaccine viruses from the host of recombinant RSV strains provided herein, the criteria of viability, efficient replication in vitro, attenuation in vivo, immunogenicity, and phenotypic stability are determined according to well-known methods. Viruses which will be most desired in vaccines of the invention should maintain viability, should replicate sufficiently in vitro well under permissive conditions to make vaccine manufacture possible, should have a stable attenuation phenotype, should be well-tolerated, should exhibit replication in an immunized host (albeit at lower levels), and should effectively elicit production of an immune response in a vaccine sufficient to confer protection against serious disease caused by subsequent infection from wild-type virus.

To propagate a RSV virus for vaccine use and other purposes, a number of cell lines which allow for RSV growth may be used. RSV grows in a variety of human and animal cells. Preferred cell lines for propagating attenuated RS virus for vaccine use include DBSFRhL-2, MRC-5, and Vero cells. Highest virus yields are usually achieved with epithelial cell lines such as Vero cells. Cells are typically inoculated with virus at a multiplicity of infection ranging from about 0.001 to 1.0, or more, and are cultivated under conditions permissive for replication of the virus, e.g., at about 30-37° C. and for about 3-10 days, or as long as necessary for virus to reach an adequate titer. Temperature-sensitive viruses often are grown using 32° C. as the "permissive temperature." Virus is removed from cell culture and separated from cellular components, typically by well-known clarification procedures, e.g., centrifugation, and may be further purified as desired using procedures well known to those skilled in the art.

RSV which has been attenuated as described herein can be tested in various well known and generally accepted in vitro and in vivo models to confirm adequate attenuation, resistance to phenotypic reversion, and immunogenicity for vaccine use. In in vitro assays, the modified virus, which can be a multiply attenuated, biologically derived or recombinant RSV, is tested for temperature sensitivity of virus replication or "ts phenotype," and for the small plaque phenotype. Modified viruses are further tested in animal models of RSV infection. A variety of animal models (e.g., murine, cotton rat, and primate) have been described and are known to those skilled in the art.

In accordance with the foregoing description and based on the Examples below, the invention also provides isolated, infectious RSV compositions for vaccine use. The attenuated virus which is a component of a vaccine is in an isolated and typically purified form. By isolated is meant to refer to RSV which is in other than a native environment of a wild-type virus, such as the nasopharynx of an infected individual. More generally, isolated is meant to include the attenuated virus as a component of a cell culture or other artificial medium. For example, attenuated RSV of the invention may be produced by an infected cell culture, separated from the cell culture and added to a stabilizer.

RSV vaccines of the invention contain as an active ingredient an immunogenically effective amount of RSV produced as described herein. Biologically derived or recombinant RSV can be used directly in vaccine formulations. The biologically derived or recombinantly modified virus may be introduced into a host with a physiologically acceptable carrier and/or adjuvant. Useful carriers are well known in the art, and include, e.g., water, buffered water, 0.4% saline, 0.3% glycine, hyaluronic acid and the like. The resulting aqueous solutions may be packaged for use as is, or in frozen form that is thawed prior to use, or lyophilized, the lyophilized preparation being combined with a sterile solution prior to administration, as mentioned above. The compositions may contain pharmaceutically acceptable auxiliary substances as required to approximate physiological conditions, which include, but are not limited to, pH adjusting and buffering agents, tonicity adjusting agents, wetting agents and the like, for example, sodium acetate, sodium lactate, sodium chloride, potassium chloride, calcium chloride, sucrose, magnesium sulfate, phosphate buffers, HEPES (4-(2-hydroxyethyl)-1-piperazineethanesulfonic acid) buffer, sorbitan monolaurate, and triethanolamine oleate. Acceptable adjuvants include incomplete Freund's adjuvant, aluminum phosphate, aluminum hydroxide, or alum, which are materials well known in the art. Preferred adjuvants also include Stimulon™ QS-21 (Aquila Biopharmaceuticals, Inc., Worchester, Mass.), MPL™ (3-O-deacylated monophosphoryl lipid A; RIBI ImmunoChem Research, Inc., Hamilton, Mont.), and interleukin-12 (Genetics Institute, Cambridge, Mass.).

Upon immunization with a RSV vaccine composition, the host responds to the vaccine by producing antibodies specific for RSV virus proteins, e.g., F and G glycoproteins. In addition, innate and cell-mediated immune responses are induced, which can provide antiviral effectors as well as regulating the immune response. As a result of the vaccination the host becomes at least partially or completely immune to RSV infection, or resistant to developing moderate or severe RSV disease, particularly of the lower respiratory tract.

The vaccine compositions containing the attenuated RSV of the invention are administered to a subject susceptible to or otherwise at risk of RSV infection in an "immunogenically effective dose" which is sufficient to induce or enhance the individual's immune response capabilities against RSV. An RSV vaccine composition may be administered by any suitable method, including but not limited to, via injection, aerosol delivery, nasal spray, nasal droplets, oral inoculation, or topical application. In the case of human subjects, the attenuated virus of the invention is administered according to well established human RSV vaccine protocols (Karron et al. JID 191:1093-104, 2005). Briefly, adults or children are inoculated intranasally via droplet with an immunogenically effective dose of RSV vaccine, typically in a volume of 0.5 ml of a physiologically acceptable diluent or carrier. This has the advantage of simplicity and safety compared to parenteral immunization with a non-replicating vaccine. It also provides direct stimulation of local respiratory tract immunity, which plays a major role in resistance to RSV. Further, this mode of vaccination effectively bypasses the immunosuppressive effects of RSV-specific maternally-derived serum antibodies, which typically are found in the very young. Also, while the parenteral administration of RSV antigens can sometimes be associated with immunopathologic complications, this has not been observed with a live virus.

In some embodiments, the vaccine may be administered intranasally or subcutaneously or intramuscularly. In some embodiments, it may be administered to the upper respiratory tract. This may be performed by any suitable method, including but not limited to, by spray, droplet or aerosol delivery. Often, the composition will be administered to an individual seronegative for antibodies to RSV or possessing transplacentally acquired maternal antibodies to RSV.

In all subjects, the precise amount of RSV vaccine administered and the timing and repetition of administration will be determined by various factors, including the patient's state of health and weight, the mode of administration, the nature of the formulation, etc. Dosages will generally range from about 3.0 $\log_{10}$ to about 6.0 $\log_{10}$ plaque forming units ("PFU") or more of virus per patient, more commonly from about 4.0 $\log_{10}$ to 5.0 $\log_{10}$ PFU virus per patient. In one embodiment, about 5.0 $\log_{10}$ to 6.0 $\log_{10}$ PFU per patient may be administered during infancy, such as between 1 and 6 months of age, and one or more additional booster doses could be given 2-6 months or more later. In another embodiment, young infants could be given a dose of about 5.0 $\log_{10}$ to 6.0 login PFU per patient at approximately 2, 4, and 6 months of age, which is the recommended time of administration of a number of other childhood vaccines. In yet another embodiment, an additional booster dose could be administered at approximately 10-15 months of age. In any event, the vaccine formulations should provide a quantity of attenuated RSV of the invention sufficient to effectively stimulate or induce an anti-RSV immune response (an "effective amount").

In some embodiments, the vaccine may comprise attenuated M2-2 deletion virus that elicits an immune response against a single RSV strain or antigenic subgroup, e.g. A or B, or against multiple RSV strains or subgroups. In this regard, M2-2 deletion mutant RSV can be combined in vaccine formulations with other RSV vaccine strains or subgroups having different immunogenic characteristics for more effective protection against one or multiple RSV strains or subgroups. They may be administered in a vaccine mixture, or administered separately in a coordinated treatment protocol to elicit more effective protection against one RSV strain, or against multiple RSV strains or subgroups.

The resulting immune response can be characterized by a variety of methods. These include taking samples of nasal washes or sera for analysis of RSV-specific antibodies, which can be detected by tests including, but not limited to, complement fixation, plaque neutralization, enzyme-linked immunosorbent assay, luciferase-immunoprecipitation assay, and flow cytometry. In addition, immune responses can be detected by assay of cytokines in nasal washes or sera, ELISPOT of immune cells from either source, quantitative RT-PCR or microarray analysis of nasal wash or serum samples, and restimulation of immune cells from nasal washes or serum by re-exposure to viral antigen in vitro and analysis for the production or display of cytokines, surface markers, or other immune correlates measured by flow cytometry or for cytotoxic activity against indicator target cells displaying RSV antigens. In this regard, individuals are also monitored for signs and symptoms of upper respiratory illness.

The level of attenuation of vaccine virus may be determined by, for example, quantifying the amount of virus present in the respiratory tract of an immunized host and comparing the amount to that produced by wild-type RSV or other attenuated RS viruses which have been evaluated as candidate vaccine strains. For example, the attenuated virus of the invention will have a greater degree of restriction of replication in the upper respiratory tract of a highly susceptible host, such as a chimpanzee, compared to the levels of replication of wild-type virus, e.g., 10- to 1000-fold less. In order to further reduce the development of rhinorrhea, which is associated with the replication of virus in the upper respiratory tract, an ideal vaccine candidate virus should exhibit a restricted level of replication in both the upper and lower respiratory tract. However, the attenuated viruses of the invention should be sufficiently infectious and immunogenic in humans to confer protection in vaccinated individuals. Methods for determining levels of RSV in the nasopharynx of an infected host are well known in the literature. Specimens are obtained by aspiration or washing out of nasopharyngeal secretions and virus quantified in tissue culture or other by laboratory procedure. See, for example, Belshe et al., J. Med. Virology 1:157-162 (1977), Friedewald et al., J. Amer. Med. Assoc. 204:690-694 (1968); Gharpure et al., J. Virol. 3:414-421 (1969); and Wright et al., Arch. Ges. Virusforsch. 41:238-247 (1973). The virus can conveniently be measured in the nasopharynx of host animals, such as chimpanzees.

Additional Embodiments

Clause 1. An isolated polynucleotide molecule encoding a recombinant respiratory syncytial virus (RSV) variant having an attenuated phenotype comprising a RSV genome or antigenome sequence, wherein (a) the RSV genome or antigenome is modified by a deletion in the M2-2 ORF corresponding to a deletion comprising a deletion of 241 nucleotides located at positions 8189-8429 of SEQ ID NO: 1 combined with mutations at positions T8161, T8167 and T8179 of SEQ ID NO: 1; or (b) the RSV genome or antigenome is modified by a deletion in the M2-2 ORF corresponding to a deletion comprising a deletion of 234 nucleotides located at positions 8203-8436 of SEQ ID NO: 1 combined with the presence of 8198A and 8200G of SEQ ID NO: 1; or (c) the RSV genome or antigenome has a positive-sense sequence denoted by SEQ ID NO: 1 modified by a deletion in the M2-2 ORF comprising a deletion of 234 nucleotides located at positions 8203-8436 of SEQ ID NO: 1 combined with the presence of 8198A and 8199G of SEQ ID NO: 1.

Clause 2. The isolated polynucleotide molecule of clause 1, wherein the RSV genome or antigenome recited in a and b has a positive-sense sequence denoted by a sequence that is at least 90% identical to a sequence denoted by SEQ ID NO: 1.

Clause 3. The isolated polynucleotide molecule of clause 1 or 2, wherein the RSV genome or antigenome is further modified by a deletion of 112 nucleotides located at positions 4499-4610 of SEQ ID NO: 1 combined with the mutations C4489T, C4492T, A4495T, A4497G, and G4498A of SEQ ID NO: 1 ("6120").

Clause 4. An isolated polynucleotide molecule encoding a recombinant respiratory syncytial virus (RSV) variant having an attenuated phenotype, comprising a RSV genome or antigenome having a positive-sense sequence denoted by a sequence that is at least 90% identical to SEQ ID NO: 1, wherein the RSV genome or antigenome is modified by a deletion in the M2-2 ORF corresponding to a deletion comprising a deletion of 234 nucleotides located at positions 8203-8436 of SEQ ID NO: 1, wherein the RSV genome or antigenome is further modified by a deletion of 112 nucleotides located at positions 4499-4610 of SEQ ID NO: 1 combined with the mutations C4489T, C4492T, A4495T, A4497G, and G4498A of SEQ ID NO: 1.

Clause 5. The isolated polynucleotide molecule of clause 1, 2, 3 or 4, wherein the RSV genome or antigenome is further modified by introduction of one or more of the following changes to SEQ ID NO: 1:

mutations encoding amino acid substitutions V267I in the N protein, E218A and T523I in the F protein, and C319Y and H1690Y in the L protein of the RSV ("cp");

mutations encoding amino acid substitutions K66E and Q101P in the F protein of the RSV ("HEK");

a deletion of 419 nucleotides located at positions 4198-4616 of SEQ ID NO: 1 which encodes a deletion of the SH protein of the RSV (ΔSH);

a mutation encoding amino acid substitution K51R in the NS2 protein of the RSV ("N52");

a mutation encoding amino acid substitution T24A in the N protein of the RSV ("N");

the nucleotide sequence encoding the G protein of the RSV is replaced with a corresponding codon optimized nucleotide sequence encoding the G protein from the clinical isolate A/Maryland/001/11;

the nucleotide sequence encoding the F protein of the RSV is replaced with a corresponding nucleotide sequence encoding the F protein from the clinical isolate A/Maryland/001/11; or a corresponding codon optimized nucleotide sequence encoding the F protein from the clinical isolate A/Maryland/001/11; or the codon optimized sequence FBB ("FBB"); and the order of the nucleotide sequences encoding the G and the F proteins of the RSV in SEQ ID NO: 1 is reversed.

Clause 6. The isolated polynucleotide molecule of clause 1(a) or 2, comprising a nucleotide sequence of SEQ ID NO: 2.

Clause 7. The isolated polynucleotide molecule of clause 1(b) or 2, comprising a nucleotide sequence of SEQ ID NO: 3.

Clause 8. The isolated polynucleotide molecule of clause 1(c), comprising a nucleotide sequence of SEQ ID NO: 4.

Clause 9. The isolated polynucleotide molecule of clause 3 comprising a nucleotide sequence of SEQ ID NO: 5.

Clause 10. The isolated polynucleotide molecule of clause 3 or 4 comprising a nucleotide sequence of SEQ ID NO: 6.

Clause 11. The isolated polynucleotide molecule of clause 3 or 4 comprising a nucleotide sequence of SEQ ID NO: 7.

Clause 12. The isolated polynucleotide molecule of clause 5, wherein the modified RSV genome or antigenome comprises a combination of mutations selected from the group consisting of:

cp/ΔM2-2, cp/ΔM2-2/HEK, ΔM2-2/1030s, NS2/N/ΔM2-2, NS2/ΔM2-2, N/ΔM2-2, NS2/N/ΔM2-2-AclI, ΔSH/ΔM2-2, cp/ΔSH/ΔM2-2, 6120/cp/ΔM2-2, 6120/ΔM2-2/1030s, 6120/NS2/N/ΔM2-2, 6120/G001BB/FBB/ΔM2-2, 6120/FBB/G001BB/ΔM2-2, 6120/G001BB/F/ΔM2-2, 6120/G/FBB/ΔM2-2, 6120/G/FBB/HEK/ΔM2-2, 6120/G/FBB/cp/HEK/ΔM2-2, 6120/FBB/G/ΔM2-2, 6120/G001BB/F001BB/ΔM2-2, 6120/NS2/ΔM2-2, 6120/N/ΔM2-2, 6120/NS2/N/ΔM2-2-Acl-I, NS2/N/ΔM2-2-HindIII, and 6120/NS2/N/ΔM2-2-HindIII Clause 13. The isolated polynucleotide molecule of clause 1, wherein the RSV genome or antigenome comprises a sequence selected from the group consisting of SEQ ID NO: 2, SEQ ID NO: 3 and SEQ ID NO: 4, further modified by introduction of one or more of the following nucleotide substitutions in SEQ ID NO: 2, SEQ ID NO: 3 and SEQ ID NO: 4: 404C, 779G, 1099T, 1139A, 1140G, 1182G, 1210G, 1939A, 5612A, 5616A, 5640G, 6216C, 6222C, 6387T, 7215C, 7482T, 7560A, 7702G, 10515T, 13634A, 13901T.

Clause 14. The isolated polynucleotide molecule of any one of clauses 1-12, further comprising a previously characterized RSV mutation or deletion.

Clause 15. A vector comprising the isolated polynucleotide molecule of any one of clauses 1-13.

Clause 16. A cell comprising the isolated polynucleotide of any one of clauses 1-13.

Clause 17. A pharmaceutical composition comprising an immunologically effective amount of the recombinant RSV variant encoded by the isolated polynucleotide molecule of any one of clauses 1-13.

Clause 18. A method of vaccinating a subject against RSV comprising administering the pharmaceutical composition of clause 16.

Clause 18. The method of clause 17, wherein the pharmaceutical composition is administered intranasally.

Clause 20. The method of clause 17, wherein the respiratory syncytial virus is administered via injection, aerosol delivery, nasal spray or nasal droplets.

Exemplary Sequences

Antigenomic cDNA sequence of D46

(SEQ ID NO: 1)

ACGGGAAAAAATGCGTACAACAAACTTGCATAAACCAAAAAAATGGGGCAAATAAGAATTTGATAAGTACCACTTAA

ATTTAACTCCCTTGGTTAGAGATGGGCAGCAATTCATTGAGTATGATAAAAGTTAGATTACAAAATTTGTTTGACAA

-continued

| Exemplary Sequences |
|---|
| TGATGAAGTAGCATTGTTAAAAATAACATGCTATACTGATAAATTAATACATTTAACTAATGCTTTGGCTAAGGCAG |
| TGATACATACAATCAAATTGAATGGCATTGTGTTTGTGCATGTTATTACAAGTAGTGATATTTGCCCTAATAATAAT |
| ATTGTAGTAAAATCCAATTTCACAACAATGCCAGTACTACAAAATGGAGGTTATATATGGGAAATGATGGAATTAAC |
| ACATTGCTCTCAACCTAATGGTCTACTAGATGACAATTGTGAAATTAAATTCTCCAAAAAACTAAGTGATTCAACAA |
| TGACCAATTATATGAATCAATTATCTGAATTACTTGGATTTGATCTTAATCCATAAATTATAATTAATATCAACTAG |
| CAAATCAATGTCACTAACACCATTAGTTAATATAAAACTTAACAGAAGACAAAAATGGGGCAAATAAATCAATTCAG |
| CCAACCCAACCATGGACACAACCCACAATGATAATACACCACAAAGACTGATGATCACAGACATGAGACCGTTGTCA |
| CTTGAGACCATAATAACATCACTAACCAGAGACATCATAACACACAAATTTATATACTTGATAAATCATGAATGCAT |
| AGTGAGAAAACTTGATGAAAGACAGGCCACATTTACATTCCTGGTCAACTATGAAATGAAACTATTACACAAAGTAG |
| GAAGCACTAAATATAAAAAATATACTGAATACAACACAAAATATGGCACTTTCCCTATGCCAATATTCATCAATCAT |
| GATGGGTTCTTAGAATGCATTGGCATTAAGCCTACAAAGCATACTCCCATAATATACAAGTATGATCTCAATCCATA |
| AATTTCAACACAATATTCACACAATCTAAAACAACAACTCTATGCATAACTATACTCCATAGTCCAGATGGAGCCTG |
| AAAATTATAGTAATTTAAAACTTAAGGAGAGATATAAGATAGAAGATGGGGCAAATACAACCATGGCTCTTAGCAAA |
| GTCAAGTTGAATGATACACTCAACAAAGATCAACTTCTGTCATCCAGCAAATACACCATCCAACGGAGCACAGGAGA |
| TAGTATTGATACTCCTAATTATGATGTGCAGAAACACATCAATAAGTTATGTGGCATGTTATTAATCACAGAAGATG |
| CTAATCATAAATTCACTGGGTTAATAGGTATGTTATATGCGATGTCTAGGTTAGGAAGAGAAGACACCATAAAAATA |
| CTCAGAGATGCGGGATATCATGTAAAAGCAAATGGAGTAGATGTAACAACACATCGTCAAGACATTAATGGAAAAGA |
| AATGAAATTTGAAGTGTTAACATTGGCAAGCTTAACAACTGAAATTCAAATCAACATTGAGATAGAATCTAGAAAAT |
| CCTACAAAAAAATGCTAAAAGAAATGGGAGAGGTAGCTCCAGAATACAGGCATGACTCTCCTGATTGTGGGATGATA |
| ATATTATGTATAGCAGCATTAGTAATAACTAAATTAGCAGCAGGGGACAGATCTGGTCTTACAGCCGTGATTAGGAG |
| AGCTAATAATGTCCTAAAAAATGAAATGAAACGTTACAAAGGCTTACTACCCAAGGACATAGCCAACAGCTTCTATG |
| AAGTGTTTGAAAAACATCCCCACTTTATAGATGTTTTTGTTCATTTTGGTATAGCACAATCTTCTACCAGAGGTGGC |
| AGTAGAGTTGAAGGGATTTTTGCAGGATTGTTTATGAATGCCTATGGTGCAGGGCAAGTGATGTTACGGTGGGGAGT |
| CTTAGCAAAATCGGTTAAAAATATTATGTTAGGACATGCTAGTGTGCAAGCAGAAATGGAACAAGTTGTTGAGGTTT |
| ATGAATATGCCCAAAAATTGGGTGGTGAAGCAGGATTCTACCATATATTGAACAACCCAAAAGCATCATTATTATCT |
| TTGACTCAATTTCCTCACTTCTCCAGTGTAGTATTAGGCAATGCTGCTGGCCTAGGCATAATGGGAGAGTACAGAGG |
| TACACCGAGGAATCAAGATCTATATGATGCAGCAAAGGCATATGCTGAACAACTCAAAGAAAATGGTGTGATTAACT |
| ACAGTGTACTAGACTTGACAGCAGAAGAACTAGAGGCTATCAAACATCAGCTTAATCCAAAAGATAATGATGTAGAG |
| CTTTGAGTTAATAAAAAATGGGGCAAATAAATCATCATGGAAAAGTTTGCTCCTGAATTCCATGGAGAAGATGCAAA |
| CAACAGGGCTACTAAATTCCTAGAATCAATAAAGGGCAAATTCACATCACCCAAAGATCCCAAGAAAAAAGATAGTA |
| TCATATCTGTCAACTCAATAGATATAGAAGTAACCAAAGAAAGCCCTATAACATCAAATTCAACTATTATCAACCCA |
| ACAAATGAGACAGATGATACTGCAGGGAACAAGCCCAATTATCAAAGAAAACCTCTAGTAAGTTTCAAAGAAGACCC |
| TACACCAAGTGATAATCCCTTTTCTAAACTATACAAAGAAACCATAGAAACATTTGATAACAATGAAGAAGAATCCA |
| GCTATTCATACGAAGAAATAAATGATCAGACAAACGATAATATAACAGCAAGATTAGATAGGATTGATGAAAAATTA |
| AGTGAAATACTAGGAATGCTTCACACATTAGTAGTGGCAAGTGCAGGACCTACATCTGCTCGGGATGGTATAAGAGA |
| TGCCATGGTTGGTTTAAGAGAAGAAATGATAGAAAAAATCAGAACTGAAGCATTAATGACCAATGACAGATTAGAAG |
| CTATGGCAAGACTCAGGAATGAGGAAAGTGAAAAGATGGCAAAAGACACATCAGATGAAGTGTCTCTCAATCCAACA |
| TCAGAGAAATTGAACAACCTATTGGAAGGGAATGATAGTGACAATGATCTATCACTTGAAGATTTCTGATTAGTTAC |
| CAATCTTCACATCAACACACAATACCAACAGAAGACCAACAAACTAACCAACCCAATCATCCAACCAAACATCCATC |

-continued

| Exemplary Sequences |
| --- |
| CGCCAATCAGCCAAACAGCCAACAAAACAACCAGCCAATCCAAAACTAACCACCCGGAAAAAATCTATAATATAGTT |
| ACAAAAAAAGGAAAGGGTGGGGCAAATATGGAAACATACGTGAACAAGCTTCACGAAGGCTCCACATACACAGCTGC |
| TGTTCAATACAATGTCTTAGAAAAAGACGATGACCCTGCATCACTTACAATATGGGTGCCCATGTTCCAATCATCTA |
| TGCCAGCAGATTTACTTATAAAAGAACTAGCTAATGTCAACATACTAGTGAAACAAATATCCACACCCAAGGGACCT |
| TCACTAAGAGTCATGATAAACTCAAGAAGTGCAGTGCTAGCACAAATGCCCAGCAAATTTACCATATGCGCTAATGT |
| GTCCTTGGATGAAAGAAGCAAACTAGCATATGATGTAACCACACCCTGTGAAATCAAGGCATGTAGTCTAACATGCC |
| TAAAATCAAAAAATATGTTGACTACAGTTAAAGATCTCACTATGAAGACACTCAACCCTACACATGATATTATTGCT |
| TTATGTGAATTTGAAAACATAGTAACATCAAAAAAAGTCATAATACCAACATACCTAAGATCCATCAGTGTCAGAAA |
| TAAAGATCTGAACACACTTGAAAATATAACAACCACTGAATTCAAAAATGCTATCACAAATGCAAAAATCATCCCTT |
| ACTCAGGATTACTATTAGTCATCACAGTGACTGACAACAAAGGAGCATTCAAATACATAAAGCCACAAAGTCAATTC |
| ATAGTAGATCTTGGAGCTTACCTAGAAAAAGAAAGTATATATTATGTTACCACAAATTGGAAGCACACAGCTACACG |
| ATTTGCAATCAAACCCATGGAAGATTAACCTTTTTCCTCTACATCAGTGTGTTAATTCATACAAACTTTCTACCTAC |
| ATTCTTCACTTCACCATCACAATCACAAACACTCTGTGGTTCAACCAATCAAACAAAACTTATCTGAAGTCCCAGAT |
| CATCCCAAGTCATTGTTTATCAGATCTAGTACTCAAATAAGTTAATAAAAAATATACACATGGGGCAAATAATCATT |
| GGAGGAAATCCAACTAATCACAATATCTGTTAACATAGACAAGTCCACACACCATACAGAATCAACCAATGGAAAAT |
| ACATCCATAACAATAGAATTCTCAAGCAAATTCTGGCCTTACTTTACACTAATACACATGATCACAACAATAATCTC |
| TTTGCTAATCATAATCTCCATCATGATTGCAATACTAAACAAACTTTGTGAATATAACGTATTCCATAACAAAACCT |
| TTGAGTTACCAAGAGCTCGAGTCAACACATAGCATTCATCAATCCAACAGCCCAAAACAGTAACCTTGCATTTAAAA |
| ATGAACAACCCCTACCTCTTTACAACACCTCATTAACATCCCACCATGCAAACCACTATCCATACTATAAAGTAGTT |
| AATTAAAAATAGTCATAACAATGAACTAGGATATCAAGACTAACAATAACATTGGGGCAAATGCAAACATGTCCAAA |
| AACAAGGACCAACGCACCGCTAAGACATTAGAAAGGACCTGGGACACTCTCAATCATTTATTATTCATATCATCGTG |
| CTTATATAAGTTAAATCTTAAATCTGTAGCACAAATCACATTATCCATTCTGGCAATGATAATCTCAACTTCACTTA |
| TAATTGCAGCCATCATATTCATAGCCTCGGCAAACCACAAAGTCACACCAACAACTGCAATCATACAAGATGCAACA |
| AGCCAGATCAAGAACACAACCCCAACATACCTCACCCAGAATCCTCAGCTTGGAATCAGTCCCTCTAATCCGTCTGA |
| AATTACATCACAAATCACCACCATACTAGCTTCAACAACACCAGGAGTCAAGTCAACCCTGCAATCCACAACAGTCA |
| AGACCAAAAACACAACAACAACTCAAACACAACCCAGCAAGCCCACCACAAAACAACGCCAAAACAAACCACCAAGC |
| AAACCCAATAATGATTTTCACTTTGAAGTGTTCAACTTTGTACCCTGCAGCATATGCAGCAACAATCCAACCTGCTG |
| GGCTATCTGCAAAAGAATACCAAACAAAAAACCAGGAAAGAAAACCACTACCAAGCCCACAAAAAAACCAACCCTCA |
| AGACAACCAAAAAAGATCCCAAACCTCAAACCACTAAATCAAAGGAAGTACCCACCACCAAGCCCACAGAAGAGCCA |
| ACCATCAACACCACCAAAACAAACATCATAACTACACTACTCACCTCCAACACCACAGGAAATCCAGAACTCACAAG |
| TCAAATGGAAACCTTCCACTCAACTTCCTCCGAAGGCAATCCAAGCCCTTCTCAAGTCTCTACAACATCCGAGTACC |
| CATCACAACCTTCATCTCCACCCAACACACCACGCCAGTAGTTACTTAAAAACATATTATCACAAAAGGCCTTGACC |
| AACTTAAACAGAATCAAAATAAACTCTGGGGCAAATAACAATGGAGTTGCTAATCCTCAAAGCAAATGCAATTACCA |
| CAATCCTCACTGCAGTCACATTTTGTTTTGCTTCTGGTCAAAACATCACTGAAGAATTTTATCAATCAACATGCAGT |
| GCAGTTAGCAAAGGCTATCTTAGTGCTCTGAGAACTGGTTGGTATACCAGTGTTATAACTATAGAATTAAGTAATAT |
| CAAGAAAAATAAGTGTAATGGAACAGATGCTAAGGTAAAATTGATAAAACAAGAATTAGATAAATATAAAAATGCTG |
| TAACAGAATTGCAGTTGCTCATGCAAAGCACACAAGCAACAAACAATCGAGCCAGAAGAGAACTACCAAGGTTTATG |
| AATTATACACTCAACAATGCCAAAAAAACCAATGTAACATTAAGCAAGAAAAGGAAAAGAAGATTTCTTGGTTTTTT |

-continued

| Exemplary Sequences |
|---|
| GTTAGGTGTTGGATCTGCAATCGCCAGTGGCGTTGCTGTATCTAAGGTCCTGCACCTAGAAGGGGAAGTGAACAAGA |
| TCAAAAGTGCTCTACTATCCACAAACAAGGCTGTAGTCAGCTTATCAAATGGAGTTAGTGTTTTAACCAGCAAAGTG |
| TTAGACCTCAAAAACTATATAGATAAACAATTGTTACCTATTGTGAACAAGCAAAGCTGCAGCATATCAAATATAGA |
| AACTGTGATAGAGTTCCAACAAAAGAACAACAGACTACTAGAGATTACCAGGGAATTTAGTGTTAATGCAGGCGTAA |
| CTACACCTGTAAGCACTTACATGTTAACTAATAGTGAATTATTGTCATTAATCAATGATATGCCTATAACAAATGAT |
| CAGAAAAAGTTAATGTCCAACAATGTTCAAATAGTTAGACAGCAAAGTTACTCTATCATGTCCATAATAAAAGAGGA |
| AGTCTTAGCATATGTAGTACAATTACCACTATATGGTGTTATAGATACACCCTGTTGGAAACTACACACATCCCCTC |
| TATGTACAACCAACACAAAAGAAGGGTCCAACATCTGTTTAACAAGAACTGACAGAGGATGGTACTGTGACAATGCA |
| GGATCAGTATCTTTCTTCCCACAAGCTGAAACATGTAAAGTTCAATCAAATCGAGTATTTTGTGACACAATGAACAG |
| TTTAACATTACCAAGTGAAGTAAATCTCTGCAATGTTGACATATTCAACCCCAAATATGATTGTAAAATTATGACTT |
| CAAAAACAGATGTAAGCAGCTCCGTTATCACATCTCTAGGAGCCATTGTGTCATGCTATGGCAAAACTAAATGTACA |
| GCATCCAATAAAAATCGTGGAATCATAAAGACATTTTCTAACGGGTGCGATTATGTATCAAATAAAGGGGTGGACAC |
| TGTGTCTGTAGGTAACACATTATATTATGTAAATAAGCAAGAAGGTAAAAGTCTCTATGTAAAAGGTGAACCAATAA |
| TAAATTTCTATGACCCATTAGTATTCCCCTCTGATGAATTTGATGCATCAATATCTCAAGTCAACGAGAAGATTAAC |
| CAGAGCCTAGCATTTATTCGTAAATCCGATGAATTATTACATAATGTAAATGCTGGTAAATCCACCACAAATATCAT |
| GATAACTACTATAATTATAGTGATTATAGTAATATTGTTATCATTAATTGCTGTTGGACTGCTCTTATACTGTAAGG |
| CCAGAAGCACACCAGTCACACTAAGCAAAGATCAACTGAGTGGTATAAATAATATTGCATTTAGTAACTAAATAAAA |
| ATAGCACCTAATCATGTTCTTACAATGGTTTACTATCTGCTCATAGACAACCCATCTGTCATTGGATTTTCTTAAAA |
| TCTGAACTTCATCGAAACTCTCATCTATAAACCATCTCACTTACACTATTTAAGTAGATTCCTAGTTTATAGTTATA |
| TAAAACACAATTGCATGCCAGATTAACTTACCATCTGTAAAAATGAAAACTGGGGCAAATATGTCACGAAGGAATCC |
| TTGCAAATTTGAAATTCGAGGTCATTGCTTAAATGGTAAGAGGTGTCATTTTAGTCATAATTATTTTGAATGGCCAC |
| CCCATGCACTGCTTGTAAGACAAAACTTTATGTTAAACAGAATACTTAAGTCTATGGATAAAAGTATAGATACCTTA |
| TCAGAAATAAGTGGAGCTGCAGAGTTGGACAGAACAGAAGAGTATGCTCTTGGTGTAGTTGGAGTGCTAGAGAGTTA |
| TATAGGATCAATAAACAATATAACTAAACAATCAGCATGTGTTGCCATGAGCAAACTCCTCACTGAACTCAATAGTG |
| ATGATATCAAAAAGCTGAGGGACAATGAAGAGCTAAATTCACCCAAGATAAGAGTGTACAATACTGTCATATCATAT |
| ATTGAAAGCAACAGGAAAAACAATAAACAAACTATCCATCTGTTAAAAAGATTGCCAGCAGACGTATTGAAGAAAAC |
| CATCAAAAACACATTGGATATCCATAAGAGCATAACCATCAACAACCCAAAAGAATCAACTGTTAGTGATACAAATG |
| ACCATGCCAAAAATAATGATACTACCTGACAAATATCCTTGTAGTATAACTTCCATACTAATAACAAGTAGATGTAG |
| AGTTACTATGTATAATCAAAAGAACACACTATATTTCAATCAAAACAACCCAAATAACCATATGTACTCACCGAATC |
| AAACATTCAATGAAATCCATTGGACCTCTCAAGAATTGATTGACACAATTCAAAATTTTCTACAACATCTAGGTATT |
| ATTGAGGATATATATACAATATATATATTAGTGTCATAACACTCAATTCTAACACTCACCACATCGTTACATTATTA |
| ATTCAAACAATTCAAGTTGTGGGACAAAATGGATCCCATTATTAATGGAAATTCTGCTAATGTTTATCTAACCGATA |
| GTTATTTAAAAGGTGTTATCTCTTTCTCAGAGTGTAATGCTTTAGGAAGTTACATATTCAATGGTCCTTATCTCAAA |
| AATGATTATACCAACTTAATTAGTAGACAAAATCCATTAATAGAACACATGAATCTAAAGAAACTAAATATAACACA |
| GTCCTTAATATCTAAGTATCATAAAGGTGAAATAAAATTAGAAGAACCTACTTATTTTCAGTCATTACTTATGACAT |
| ACAAGAGTATGACCTCGTCAGAACAGATTGCTACCACTAATTTACTTAAAAAGATAATAAGAAGAGCTATAGAAATA |
| AGTGATGTCAAAGTCTATGCTATATTGAATAAACTAGGGCTTAAAGAAAAGGACAAGATTAAATCCAACAATGGACA |
| AGATGAAGACAACTCAGTTATTACGACCATAATCAAAGATGATATACTTTCAGCTGTTAAAGATAATCAATCTCATC |
| TTAAAGCAGACAAAAATCACTCTACAAAACAAAAAGACACAATCAAAACAACACTCTTGAAGAAATTGATGTGTTCA |

-continued

| Exemplary Sequences |
|---|
| ATGCAACATCCTCCATCATGGTTAATACATTGGTTTAACTTATACACAAAATTAAACAACATATTAACACAGTATCG |
| ATCAAATGAGGTAAAAAACCATGGGTTTACATTGATAGATAATCAAACTCTTAGTGGATTTCAATTTATTTTGAACC |
| AATATGGTTGTATAGTTTATCATAAGGAACTCAAAAGAATTACTGTGACAACCTATAATCAATTCTTGACATGGAAA |
| GATATTAGCCTTAGTAGATTAAATGTTTGTTTAATTACATGGATTAGTAACTGCTTGAACACATTAAATAAAAGCTT |
| AGGCTTAAGATGCGGATTCAATAATGTTATCTTGACACAACTATTCCTTTATGGAGATTGTATACTAAAGCTATTTC |
| ACAATGAGGGGTTCTACATAATAAAAGAGGTAGAGGGATTTATTATGTCTCTAATTTTAAATATAACAGAAGAAGAT |
| CAATTCAGAAAACGATTTTATAATAGTATGCTCAACAACATCACAGATGCTGCTAATAAAGCTCAGAAAAATCTGCT |
| ATCAAGAGTATGTCATACATTATTAGATAAGACAGTGTCCGATAATATAATAAATGGCAGATGGATAATTCTATTAA |
| GTAAGTTCCTTAAATTAATTAAGCTTGCAGGTGACAATAACCTTAACAATCTGAGTGAACTATATTTTTTGTTCAGA |
| ATATTTGGACACCCAATGGTAGATGAAAGACAAGCCATGGATGCTGTTAAAATTAATTGCAATGAGACCAAATTTTA |
| CTTGTTAAGCAGTCTGAGTATGTTAAGAGGTGCCTTTATATATAGAATTATAAAAGGGTTTGTAAATAATTACAACA |
| GATGGCCTACTTTAAGAAATGCTATTGTTTTACCCTTAAGATGGTTAACTTACTATAAACTAAACACTTATCCTTCT |
| TTGTTGGAACTTACAGAAAGAGATTTGATTGTGTTATCAGGACTACGTTTCTATCGTGAGTTTCGGTTGCCTAAAAA |
| AGTGGATCTTGAAATGATTATAAATGATAAAGCTATATCACCTCCTAAAAATTTGATATGGACTAGTTTCCCTAGAA |
| ATTACATGCCATCACACATACAAAACTATATAGAACATGAAAAATTAAAATTTTCCGAGAGTGATAAATCAAGAAGA |
| GTATTAGAGTATTATTTAAGAGATAACAAATTCAATGAATGTGATTTATACAACTGTGTAGTTAATCAAAGTTATCT |
| CAACAACCCTAATCATGTGGTATCATTGACAGGCAAAGAAAGAGAACTCAGTGTAGGTAGAATGTTTGCAATGCAAC |
| CGGGAATGTTCAGACAGGTTCAAATATTGGCAGAGAAAATGATAGCTGAAAACATTTTACAATTCTTTCCTGAAAGT |
| CTTACAAGATATGGTGATCTAGAACTACAAAAAATATTAGAACTGAAAGCAGGAATAAGTAACAAATCAAATCGCTA |
| CAATGATAATTACAACAATTACATTAGTAAGTGCTCTATCATCACAGATCTCAGCAAATTCAATCAAGCATTTCGAT |
| ATGAAACGTCATGTATTTGTAGTGATGTGCTGGATGAACTGCATGGTGTACAATCTCTATTTTCCTGGTTACATTTA |
| ACTATTCCTCATGTCACAATAATATGCACATATAGGCATGCACCCCCCTATATAGGAGATCATATTGTAGATCTTAA |
| CAATGTAGATGAACAAAGTGGATTATATAGATATCACATGGGTGGCATCGAAGGGTGGTGTCAAAAACTATGGACCA |
| TAGAAGCTATATCACTATTGGATCTAATATCTCTCAAAGGGAAATTCTCAATTACTGCTTTAATTAATGGTGACAAT |
| CAATCAATAGATATAAGCAAACCAATCAGACTCATGGAAGGTCAAACTCATGCTCAAGCAGATTATTTGCTAGCATT |
| AAATAGCCTTAAATTACTGTATAAAGAGTATGCAGGCATAGGCCACAAATTAAAAGGAACTGAGACTTATATATCAC |
| GAGATATGCAATTTATGAGTAAAACAATTCAACATAACGGTGTATATTACCCAGCTAGTATAAAGAAAGTCCTAAGA |
| GTGGGACCGTGGATAAACACTATACTTGATGATTTCAAAGTGAGTCTAGAATCTATAGGTAGTTTGACACAAGAATT |
| AGAATATAGAGGTGAAAGTCTATTATGCAGTTTAATATTTAGAAATGTATGGTTATATAATCAGATTGCTCTACAAT |
| TAAAAAATCATGCATTATGTAACAATAAACTATATTTGGACATATTAAAGGTTCTGAAACACTTAAAAACCTTTTTT |
| AATCTTGATAATATTGATACAGCATTAACATTGTATATGAATTTACCCATGTTATTTGGTGGTGGTGATCCCAACTT |
| GTTATATCGAAGTTTCTATAGAAGAACTCCTGACTTCCTCACAGAGGCTATAGTTCACTCTGTGTTCATACTTAGTT |
| ATTATACAAACCATGACTTAAAAGATAAACTTCAAGATCTGTCAGATGATAGATTGAATAAGTTCTTAACATGCATA |
| ATCACGTTTGACAAAAACCCTAATGCTGAATTCGTAACATTGATGAGAGATCCTCAAGCTTTAGGGTCTGAGAGACA |
| AGCTAAAATTACTAGCGAAATCAATAGACTGGCAGTTACAGAGGTTTTGAGTACAGCTCCAAACAAAATATTCTCCA |
| AAAGTGCACAACATTATACTACTACAGAGATAGATCTAAATGATATTATGCAAAATATAGAACCTACATATCCTCAT |
| GGGCTAAGAGTTGTTTATGAAAGTTTACCCTTTTATAAAGCAGAGAAAATAGTAAATCTTATATCAGGTACAAAATC |
| TATAACTAACATACTGGAAAAAACTTCTGCCATAGACTTAACAGATATTGATAGAGCCACTGAGATGATGAGGAAAA |

-continued

| Exemplary Sequences |
| --- |
| ACATAACTTTGCTTATAAGGATACTTCCATTGGATTGTAACAGAGATAAAAGAGAGATATTGAGTATGGAAAACCTA |
| AGTATTACTGAATTAAGCAAATATGTTAGGGAAAGATCTTGGTCTTTATCCAATATAGTTGGTGTTACATCACCCAG |
| TATCATGTATACAATGGACATCAAATATACTACAAGCACTATATCTAGTGGCATAATTATAGAGAAATATAATGTTA |
| ACAGTTTAACACGTGGTGAGAGAGGACCCACTAAACCATGGGTTGGTTCATCTACACAAGAGAAAAAAACAATGCCA |
| GTTTATAATAGACAAGTCTTAACCAAAAAACAGAGAGATCAAATAGATCTATTAGCAAAATTGGATTGGGTGTATGC |
| ATCTATAGATAACAAGGATGAATTCATGGAAGAACTCAGCATAGGAACCCTTGGGTTAACATATGAAAAGGCCAAGA |
| AATTATTTCCACAATATTTAAGTGTCAATTATTTGCATCGCCTTACAGTCAGTAGTAGACCATGTGAATTCCCTGCA |
| TCAATACCAGCTTATAGAACAACAAATTATCACTTTGACACTAGCCCTATTAATCGCATATTAACAGAAAAGTATGG |
| TGATGAAGATATTGACATAGTATTCCAAAACTGTATAAGCTTTGGCCTTAGTTTAATGTCAGTAGTAGAACAATTTA |
| CTAATGTATGTCCTAACAGAATTATTCTCATACCTAAGCTTAATGAGATACATTTGATGAAACCTCCCATATTCACA |
| GGTGATGTTGATATTCACAAGTTAAAACAAGTGATACAAAAACAGCATATGTTTTTACCAGACAAAATAAGTTTGAC |
| TCAATATGTGGAATTATTCTTAAGTAATAAAACACTCAAATCTGGATCTCATGTTAATTCTAATTTAATATTGGCAC |
| ATAAAATATCTGACTATTTTCATAATACTTACATTTTAAGTACTAATTTAGCTGGACATTGGATTCTGATTATACAA |
| CTTATGAAAGATTCTAAAGGTATTTTTGAAAAAGATTGGGGAGAGGGATATATAACTGATCATATGTTTATTAATTT |
| GAAAGTTTTCTTCAATGCTTATAAGACCTATCTCTTGTGTTTTCATAAAGGTTATGGCAAAGCAAAGCTGGAGTGTG |
| ATATGAACACTTCAGATCTTCTATGTGTATTGGAATTAATAGACAGTAGTTATTGGAAGTCTATGTCTAAGGTATTT |
| TTAGAACAAAAAGTTATCAAATACATTCTTAGCCAAGATGCAAGTTTACATAGAGTAAAAGGATGTCATAGCTTCAA |
| ATTATGGTTTCTTAAACGTCTTAATGTAGCAGAATTCACAGTTTGCCCTTGGGTTGTTAACATAGATTATCATCCAA |
| CACATATGAAAGCAATATTAACTTATATAGATCTTGTTAGAATGGGATTGATAAATATAGATAGAATACACATTAAA |
| AATAAACACAAATTCAATGATGAATTTTATACTTCTAATCTCTTCTACATTAATTATAACTTCTCAGATAATACTCA |
| TCTATTAACTAAACATATAAGGATTGCTAATTCTGAATTAGAAAATAATTACAACAAATTATATCATCCTACACCAG |
| AAACCCTAGAGAATATACTAGCCAATCCGATTAAAAGTAATGACAAAAAGACACTGAATGACTATTGTATAGGTAAA |
| AATGTTGACTCAATAATGTTACCATTGTTATCTAATAAGAAGCTTATTAAATCGTCTGCAATGATTAGAACCAATTA |
| CAGCAAACAAGATTTGTATAATTTATTCCCTATGGTTGTGATTGATAGAATTATAGATCATTCAGGCAATACAGCCA |
| AATCCAACCAACTTTACACTACTACTTCCCACCAAATATCCTTAGTGCACAATAGCACATCACTTTACTGCATGCTT |
| CCTTGGCATCATATTAATAGATTCAATTTTGTATTTAGTTCTACAGGTTGTAAAATTAGTATAGAGTATATTTTAAA |
| AGATCTTAAAATTAAAGATCCCAATTGTATAGCATTCATAGGTGAAGGAGCAGGGAATTTATTATTGCGTACAGTAG |
| TGGAACTTCATCCTGACATAAGATATATTTACAGAAGTCTGAAAGATTGCAATGATCATAGTTTACCTATTGAGTTT |
| TTAAGGCTGTACAATGGACATATCAACATTGATTATGGTGAAAATTTGACCATTCCTGCTACAGATGCAACCAACAA |
| CATTCATTGGTCTTATTTACATATAAAGTTTGCTGAACCTATCAGTCTTTTTGTCTGTGATGCCGAATTGTCTGTAA |
| CAGTCAACTGGAGTAAAATTATAATAGAATGGAGCAAGCATGTAAGAAAGTGCAAGTACTGTTCCTCAGTTAATAAA |
| TGTATGTTAATAGTAAAATATCATGCTCAAGATGATATTGATTTCAAATTAGACAATATAACTATATTAAAAACTTA |
| TGTATGCTTAGGCAGTAAGTTAAAGGGATCGGAGGTTTACTTAGTCCTTACAATAGGTCCTGCGAATATATTCCCAG |
| TATTTAATGTAGTACAAAATGCTAAATTGATACTATCAAGAACCAAAAATTTCATCATGCCTAAGAAAGCTGATAAA |
| GAGTCTATTGATGCAAATATTAAAAGTTTGATACCCTTTCTTTGTTACCCTATAACAAAAAAAGGAATTAATACTGC |
| ATTGTCAAAACTAAAGAGTGTTGTTAGTGGAGATATACTATCATATTCTATAGCTGGACGTAATGAAGTTTTCAGCA |
| ATAAACTTATAAATCATAAGCATATGAACATCTTAAAATGGTTCAATCATGTTTTAAATTTCAGATCAACAGAACTA |
| AACTATAACCATTTATATATGGTAGAATCTACATATCCTTACCTAAGTGAATTGTTAAACAGCTTGACAACCAATGA |
| ACTTAAAAAACTGATTAAAATCACAGGTAGTCTGTTATACAACTTTCATAATGAATAATGAATAAAGATCTTATAAT |

-continued

| Exemplary Sequences |
|---|
| AAAAATTCCCATAGCTATACACTAACACTGTATTCAATTATAGTTATTAAAAATTAAAAATCATATAATTTTTTAAA<br>TAACTTTTAGTGAACTAATCCTAAAGTTATCATTTTAATCTTGGAGGAATAAATTTAAACCCTAATCTAATTGGTTT<br>ATATGTGTATTAACTAAATTACGAGATATTAGTTTTTGACACTTTTTTTCTCGT<br>Antigenomic cDNA sequence of D46/ΔM2-2<br>(SEQ ID NO: 2)<br>ACGGGAAAAAATGCGTACAACAAACTTGCATAAACCAAAAAAATGGGGCAAATAAGAATTTGATAAGTACCACTTAA<br>ATTTAACTCCCTTGGTTAGAGATGGGCAGCAATTCATTGAGTATGATAAAAGTTAGATTACAAAATTTGTTTGACAA<br>TGATGAAGTAGCATTGTTAAAAATAACATGCTATACTGATAAATTAATACATTTAACTAATGCTTTGGCTAAGGCAG<br>TGATACATACAATCAAATTGAATGGCATTGTGTTTGTGCATGTTATTACAAGTAGTGATATTTGCCCTAATAATAAT<br>ATTGTAGTAAAATCCAATTTCACAACAATGCCAGTACTACAAAATGGAGGTTATATATGGGAAATGATGGAATTAAC<br>ACATTGCTCTCAACCTAATGGTCTACTAGATGACAATTGTGAAATTAAATTCTCCAAAAAACTAAGTGATTCAACAA<br>TGACCAATTATATGAATCAATTATCTGAATTACTTGGATTTGATCTTAATCCATAAATTATAATTAATATCAACTAG<br>CAAATCAATGTCACTAACACCATTAGTTAATATAAAACTTAACAGAAGACAAAAATGGGGCAAATAAATCAATTCAG<br>CCAACCCAACCATGGACACAACCCACAATGATAATACACCACAAAGACTGATGATCACAGACATGAGACCGTTGTCA<br>CTTGAGACCATAATAACATCACTAACCAGAGACATCATAACACACAAATTTATATACTTGATAAATCATGAATGCAT<br>AGTGAGAAAACTTGATGAAAGACAGGCCACATTTACATTCCTGGTCAACTATGAAATGAAACTATTACACAAAGTAG<br>GAAGCACTAAATATAAAAAATATACTGAATACAACACAAAATATGGCACTTTCCCTATGCCAATATTCATCAATCAT<br>GATGGGTTCTTAGAATGCATTGGCATTAAGCCTACAAAGCATACTCCCATAATATACAAGTATGATCTCAATCCATA<br>AATTTCAACACAATATTCACACAATCTAAAACAACAACTCTATGCATAACTATACTCCATAGTCCAGATGGAGCCTG<br>AAAATTATAGTAATTTAAAACTTAAGGAGAGATATAAGATAGAAGATGGGGCAAATACAACCATGGCTCTTAGCAAA<br>GTCAAGTTGAATGATACACTCAACAAAGATCAACTTCTGTCATCCAGCAAATACACCATCCAACGGAGCACAGGAGA<br>TAGTATTGATACTCCTAATTATGATGTGCAGAAACACATCAATAAGTTATGTGGCATGTTATTAATCACAGAAGATG<br>CTAATCATAAATTCACTGGGTTAATAGGTATGTTATATGCGATGTCTAGGTTAGGAAGAGAAGACACCATAAAAATA<br>CTCAGAGATGCGGGATATCATGTAAAAGCAAATGGAGTAGATGTAACAACACATCGTCAAGACATTAATGGAAAAGA<br>AATGAAATTTGAAGTGTTAACATTGGCAAGCTTAACAACTGAAATTCAAATCAACATTGAGATAGAATCTAGAAAAT<br>CCTACAAAAAAATGCTAAAAGAAATGGGAGAGGTAGCTCCAGAATACAGGCATGACTCTCCTGATTGTGGGATGATA<br>ATATTATGTATAGCAGCATTAGTAATAACTAAATTAGCAGCAGGGGACAGATCTGGTCTTACAGCCGTGATTAGGAG<br>AGCTAATAATGTCCTAAAAAATGAAATGAAACGTTACAAAGGCTTACTACCCAAGGACATAGCCAACAGCTTCTATG<br>AAGTGTTTGAAAAACATCCCCACTTTATAGATGTTTTTGTTCATTTTGGTATAGCACAATCTTCTACCAGAGGTGGC<br>AGTAGAGTTGAAGGGATTTTTGCAGGATTGTTTATGAATGCCTATGGTGCAGGGCAAGTGATGTTACGGTGGGGAGT<br>CTTAGCAAAATCGGTTAAAAATATTATGTTAGGACATGCTAGTGTGCAAGCAGAAATGGAACAAGTTGTTGAGGTTT<br>ATGAATATGCCCAAAAATTGGGTGGTGAAGCAGGATTCTACCATATATTGAACAACCCAAAAGCATCATTATTATCT<br>TTGACTCAATTTCCTCACTTCTCCAGTGTAGTATTAGGCAATGCTGCTGGCCTAGGCATAATGGGAGAGTACAGAGG<br>TACACCGAGGAATCAAGATCTATATGATGCAGCAAAGGCATATGCTGAACAACTCAAAGAAAATGGTGTGATTAACT<br>ACAGTGTACTAGACTTGACAGCAGAAGAACTAGAGGCTATCAAACATCAGCTTAATCCAAAAGATAATGATGTAGAG<br>CTTTGAGTTAATAAAAAATGGGGCAAATAAATCATCATGGAAAAGTTTGCTCCTGAATTCCATGGAGAAGATGCAAA<br>CAACAGGGCTACTAAATTCCTAGAATCAATAAAGGGCAAATTCACATCACCCAAAGATCCCAAGAAAAAAGATAGTA<br>TCATATCTGTCAACTCAATAGATATAGAAGTAACCAAAGAAAGCCCTATAACATCAAATTCAACTATTATCAACCCA<br>ACAAATGAGACAGATGATACTGCAGGGAACAAGCCCAATTATCAAAGAAAACCTCTAGTAAGTTTCAAAGAAGACCC |

-continued

| Exemplary Sequences |
|---|
| TACACCAAGTGATAATCCCTTTTCTAAACTATACAAAGAAACCATAGAAACATTTGATAACAATGAAGAAGAATCCA |
| GCTATTCATACGAAGAAATAAATGATCAGACAAACGATAATATAACAGCAAGATTAGATAGGATTGATGAAAAATTA |
| AGTGAAATACTAGGAATGCTTCACACATTAGTAGTGGCAAGTGCAGGACCTACATCTGCTCGGGATGGTATAAGAGA |
| TGCCATGGTTGGTTTAAGAGAAGAAATGATAGAAAAAATCAGAACTGAAGCATTAATGACCAATGACAGATTAGAAG |
| CTATGGCAAGACTCAGGAATGAGGAAAGTGAAAAGATGGCAAAAGACACATCAGATGAAGTGTCTCTCAATCCAACA |
| TCAGAGAAATTGAACAACCTATTGGAAGGGAATGATAGTGACAATGATCTATCACTTGAAGATTTCTGATTAGTTAC |
| CAATCTTCACATCAACACACAATACCAACAGAAGACCAACAAACTAACCAACCCAATCATCCAACCAAACATCCATC |
| CGCCAATCAGCCAAACAGCCAACAAAACAACCAGCCAATCCAAAACTAACCACCCGGAAAAAATCTATAATATAGTT |
| ACAAAAAAAGGAAAGGGTGGGGCAAATATGGAAACATACGTGAACAAGCTTCACGAAGGCTCCACATACACAGCTGC |
| TGTTCAATACAATGTCTTAGAAAAAGACGATGACCCTGCATCACTTACAATATGGGTGCCCATGTTCCAATCATCTA |
| TGCCAGCAGATTTACTTATAAAAGAACTAGCTAATGTCAACATACTAGTGAAACAAATATCCACACCCAAGGGACCT |
| TCACTAAGAGTCATGATAAACTCAAGAAGTGCAGTGCTAGCACAAATGCCCAGCAAATTTACCATATGCGCTAATGT |
| GTCCTTGGATGAAAGAAGCAAACTAGCATATGATGTAACCACACCCTGTGAAATCAAGGCATGTAGTCTAACATGCC |
| TAAAATCAAAAAATATGTTGACTACAGTTAAAGATCTCACTATGAAGACACTCAACCCTACACATGATATTATTGCT |
| TTATGTGAATTTGAAAACATAGTAACATCAAAAAAAGTCATAATACCAACATACCTAAGATCCATCAGTGTCAGAAA |
| TAAAGATCTGAACACACTTGAAAATATAACAACCACTGAATTCAAAAATGCTATCACAAATGCAAAAATCATCCCTT |
| ACTCAGGATTACTATTAGTCATCACAGTGACTGACAACAAAGGAGCATTCAAATACATAAAGCCACAAAGTCAATTC |
| ATAGTAGATCTTGGAGCTTACCTAGAAAAAGAAAGTATATATTATGTTACCACAAATTGGAAGCACACAGCTACACG |
| ATTTGCAATCAAACCCATGGAAGATTAACCTTTTTCCTCTACATCAGTGTGTTAATTCATACAAACTTTCTACCTAC |
| ATTCTTCACTTCACCATCACAATCACAAACACTCTGTGGTTCAACCAATCAAACAAAACTTATCTGAAGTCCCAGAT |
| CATCCCAAGTCATTGTTTATCAGATCTAGTACTCAAATAAGTTAATAAAAAATATACACATGGGGCAAATAATCATT |
| GGAGGAAATCCAACTAATCACAATATCTGTTAACATAGACAAGTCCACACACCATACAGAATCAACCAATGGAAAAT |
| ACATCCATAACAATAGAATTCTCAAGCAAATTCTGGCCTTACTTTACACTAATACACATGATCACAACAATAATCTC |
| TTTGCTAATCATAATCTCCATCATGATTGCAATACTAAACAAACTTTGTGAATATAACGTATTCCATAACAAAACCT |
| TTGAGTTACCAAGAGCTCGAGTCAACACATAGCATTCATCAATCCAACAGCCCAAAACAGTAACCTTGCATTTAAAA |
| ATGAACAACCCCTACCTCTTTACAACACCTCATTAACATCCCACCATGCAAACCACTATCCATACTATAAAGTAGTT |
| AATTAAAAATAGTCATAACAATGAACTAGGATATCAAGACTAACAATAACATTGGGGCAAATGCAAACATGTCCAAA |
| AACAAGGACCAACGCACCGCTAAGACATTAGAAAGGACCTGGGACACTCTCAATCATTTATTATTCATATCATCGTG |
| CTTATATAAGTTAAATCTTAAATCTGTAGCACAAATCACATTATCCATTCTGGCAATGATAATCTCAACTTCACTTA |
| TAATTGCAGCCATCATATTCATAGCCTCGGCAAACCACAAAGTCACACCAACAACTGCAATCATACAAGATGCAACA |
| AGCCAGATCAAGAACACAACCCCAACATACCTCACCCAGAATCCTCAGCTTGGAATCAGTCCCTCTAATCCGTCTGA |
| AATTACATCACAAATCACCACCATACTAGCTTCAACAACACCAGGAGTCAAGTCAACCCTGCAATCCACAACAGTCA |
| AGACCAAAAACACAACAACAACTCAAACACAACCCAGCAAGCCCACCACAAAACAACGCCAAAACAAACCACCAAGC |
| AAACCCAATAATGATTTTCACTTTGAAGTGTTCAACTTTGTACCCTGCAGCATATGCAGCAACAATCCAACCTGCTG |
| GGCTATCTGCAAAAGAATACCAAACAAAAAACCAGGAAAGAAAACCACTACCAAGCCCACAAAAAAACCAACCCTCA |
| AGACAACCAAAAAAGATCCCAAACCTCAAACCACTAAATCAAAGGAAGTACCCACCACCAAGCCCACAGAAGAGCCA |
| ACCATCAACACCACCAAAACAAACATCATAACTACACTACTCACCTCCAACACCACAGGAAATCCAGAACTCACAAG |
| TCAAATGGAAACCTTCCACTCAACTTCCTCCGAAGGCAATCCAAGCCCTTCTCAAGTCTCTACAACATCCGAGTACC |
| CATCACAACCTTCATCTCCACCCAACACACCACGCCAGTAGTTACTTAAAAACATATTATCACAAAAGGCCTTGACC |

-continued

| Exemplary Sequences |
|---|
| AACTTAAACAGAATCAAAATAAACTCTGGGGCAAATAACAATGGAGTTGCTAATCCTCAAAGCAAATGCAATTACCA |
| CAATCCTCACTGCAGTCACATTTTGTTTTGCTTCTGGTCAAAACATCACTGAAGAATTTTATCAATCAACATGCAGT |
| GCAGTTAGCAAAGGCTATCTTAGTGCTCTGAGAACTGGTTGGTATACCAGTGTTATAACTATAGAATTAAGTAATAT |
| CAAGAAAAATAAGTGTAATGGAACAGATGCTAAGGTAAAATTGATAAAACAAGAATTAGATAAATATAAAAATGCTG |
| TAACAGAATTGCAGTTGCTCATGCAAAGCACACAAGCAACAAACAATCGAGCCAGAAGAGAACTACCAAGGTTTATG |
| AATTATACACTCAACAATGCCAAAAAAACCAATGTAACATTAAGCAAGAAAAGGAAAAGAAGATTTCTTGGTTTTTT |
| GTTAGGTGTTGGATCTGCAATCGCCAGTGGCGTTGCTGTATCTAAGGTCCTGCACCTAGAAGGGGAAGTGAACAAGA |
| TCAAAAGTGCTCTACTATCCACAAACAAGGCTGTAGTCAGCTTATCAAATGGAGTTAGTGTTTTAACCAGCAAAGTG |
| TTAGACCTCAAAAACTATATAGATAAACAATTGTTACCTATTGTGAACAAGCAAAGCTGCAGCATATCAAATATAGA |
| AACTGTGATAGAGTTCCAACAAAAGAACAACAGACTACTAGAGATTACCAGGGAATTTAGTGTTAATGCAGGCGTAA |
| CTACACCTGTAAGCACTTACATGTTAACTAATAGTGAATTATTGTCATTAATCAATGATATGCCTATAACAAATGAT |
| CAGAAAAAGTTAATGTCCAACAATGTTCAAATAGTTAGACAGCAAAGTTACTCTATCATGTCCATAATAAAAGAGGA |
| AGTCTTAGCATATGTAGTACAATTACCACTATATGGTGTTATAGATACACCCTGTTGGAAACTACACACATCCCCTC |
| TATGTACAACCAACACAAAAGAAGGGTCCAACATCTGTTTAACAAGAACTGACAGAGGATGGTACTGTGACAATGCA |
| GGATCAGTATCTTTCTTCCCACAAGCTGAAACATGTAAAGTTCAATCAAATCGAGTATTTTGTGACACAATGAACAG |
| TTTAACATTACCAAGTGAAGTAAATCTCTGCAATGTTGACATATTCAACCCCAAATATGATTGTAAAATTATGACTT |
| CAAAAACAGATGTAAGCAGCTCCGTTATCACATCTCTAGGAGCCATTGTGTCATGCTATGGCAAAACTAAATGTACA |
| GCATCCAATAAAAATCGTGGAATCATAAAGACATTTTCTAACGGGTGCGATTATGTATCAAATAAAGGGGTGGACAC |
| TGTGTCTGTAGGTAACACATTATATTATGTAAATAAGCAAGAAGGTAAAAGTCTCTATGTAAAAGGTGAACCAATAA |
| TAAATTTCTATGACCCATTAGTATTCCCCTCTGATGAATTTGATGCATCAATATCTCAAGTCAACGAGAAGATTAAC |
| CAGAGCCTAGCATTTATTCGTAAATCCGATGAATTATTACATAATGTAAATGCTGGTAAATCCACCACAAATATCAT |
| GATAACTACTATAATTATAGTGATTATAGTAATATTGTTATCATTAATTGCTGTTGGACTGCTCTTATACTGTAAGG |
| CCAGAAGCACACCAGTCACACTAAGCAAAGATCAACTGAGTGGTATAAATAATATTGCATTTAGTAACTAAATAAAA |
| ATAGCACCTAATCATGTTCTTACAATGGTTTACTATCTGCTCATAGACAACCCATCTGTCATTGGATTTTCTTAAAA |
| TCTGAACTTCATCGAAACTCTCATCTATAAACCATCTCACTTACACTATTTAAGTAGATTCCTAGTTTATAGTTATA |
| TAAAACACAATTGCATGCCAGATTAACTTACCATCTGTAAAAATGAAAACTGGGGCAAATATGTCACGAAGGAATCC |
| TTGCAAATTTGAAATTCGAGGTCATTGCTTAAATGGTAAGAGGTGTCATTTTAGTCATAATTATTTTGAATGGCCAC |
| CCCATGCACTGCTTGTAAGACAAAACTTTATGTTAAACAGAATACTTAAGTCTATGGATAAAAGTATAGATACCTTA |
| TCAGAAATAAGTGGAGCTGCAGAGTTGGACAGAACAGAAGAGTATGCTCTTGGTGTAGTTGGAGTGCTAGAGAGTTA |
| TATAGGATCAATAAACAATATAACTAAACAATCAGCATGTGTTGCCATGAGCAAACTCCTCACTGAACTCAATAGTG |
| ATGATATCAAAAAGCTGAGGGACAATGAAGAGCTAAATTCACCCAAGATAAGAGTGTACAATACTGTCATATCATAT |
| ATTGAAAGCAACAGGAAAAACAATAAACAAACTATCCATCTGTTAAAAAGATTGCCAGCAGACGTATTGAAGAAAAC |
| CATCAAAAACACATTGGATATCCATAAGAGCATAACCATCAACAACCCAAAAGAATCAACTGTTAGTGATACAAACG |
| ACCACGCCAAAAATAACGATACTACCTAACACTCAATTCTAACACTCACCACATCGTTACATTATTAATTCAAACAA |
| TTCAAGTTGTGGGACAAAATGGATCCCATTATTAATGGAAATTCTGCTAATGTTTATCTAACCGATAGTTATTTAAA |
| AGGTGTTATCTCTTTCTCAGAGTGTAATGCTTTAGGAAGTTACATATTCAATGGTCCTTATCTCAAAAATGATTATA |
| CCAACTTAATTAGTAGACAAAATCCATTAATAGAACACATGAATCTAAAGAAACTAAATATAACACAGTCCTTAATA |
| TCTAAGTATCATAAAGGTGAAATAAAATTAGAAGAACCTACTTATTTTCAGTCATTACTTATGACATACAAGAGTAT |

-continued

| Exemplary Sequences |
|---|
| GACCTCGTCAGAACAGATTGCTACCACTAATTTACTTAAAAAGATAATAAGAAGAGCTATAGAAATAAGTGATGTCA |
| AAGTCTATGCTATATTGAATAAACTAGGGCTTAAAGAAAAGGACAAGATTAAATCCAACAATGGACAAGATGAAGAC |
| AACTCAGTTATTACGACCATAATCAAAGATGATATACTTTCAGCTGTTAAAGATAATCAATCTCATCTTAAAGCAGA |
| CAAAAATCACTCTACAAAACAAAAAGACACAATCAAAACAACACTCTTGAAGAAATTGATGTGTTCAATGCAACATC |
| CTCCATCATGGTTAATACATTGGTTTAACTTATACACAAAATTAAACAACATATTAACACAGTATCGATCAAATGAG |
| GTAAAAAACCATGGGTTTACATTGATAGATAATCAAACTCTTAGTGGATTTCAATTTATTTTGAACCAATATGGTTG |
| TATAGTTTATCATAAGGAACTCAAAAGAATTACTGTGACAACCTATAATCAATTCTTGACATGGAAAGATATTAGCC |
| TTAGTAGATTAAATGTTTGTTTAATTACATGGATTAGTAACTGCTTGAACACATTAAATAAAAGCTTAGGCTTAAGA |
| TGCGGATTCAATAATGTTATCTTGACACAACTATTCCTTTATGGAGATTGTATACTAAAGCTATTTCACAATGAGGG |
| GTTCTACATAATAAAAGAGGTAGAGGGATTTATTATGTCTCTAATTTTAAATATAACAGAAGAAGATCAATTCAGAA |
| AACGATTTTATAATAGTATGCTCAACAACATCACAGATGCTGCTAATAAAGCTCAGAAAAATCTGCTATCAAGAGTA |
| TGTCATACATTATTAGATAAGACAGTGTCCGATAATATAATAAATGGCAGATGGATAATTCTATTAAGTAAGTTCCT |
| TAAATTAATTAAGCTTGCAGGTGACAATAACCTTAACAATCTGAGTGAACTATATTTTTTGTTCAGAATATTTGGAC |
| ACCCAATGGTAGATGAAAGACAAGCCATGGATGCTGTTAAAATTAATTGCAATGAGACCAAATTTTACTTGTTAAGC |
| AGTCTGAGTATGTTAAGAGGTGCCTTTATATATAGAATTATAAAAGGGTTTGTAAATAATTACAACAGATGGCCTAC |
| TTTAAGAAATGCTATTGTTTTACCCTTAAGATGGTTAACTTACTATAAACTAAACACTTATCCTTCTTTGTTGGAAC |
| TTACAGAAAGAGATTTGATTGTGTTATCAGGACTACGTTTCTATCGTGAGTTTCGGTTGCCTAAAAAAGTGGATCTT |
| GAAATGATTATAAATGATAAAGCTATATCACCTCCTAAAAATTTGATATGGACTAGTTTCCCTAGAAATTACATGCC |
| ATCACACATACAAAACTATATAGAACATGAAAAATTAAAATTTTCCGAGAGTGATAAATCAAGAAGAGTATTAGAGT |
| ATTATTTAAGAGATAACAAATTCAATGAATGTGATTTATACAACTGTGTAGTTAATCAAAGTTATCTCAACAACCCT |
| AATCATGTGGTATCATTGACAGGCAAAGAAAGAGAACTCAGTGTAGGTAGAATGTTTGCAATGCAACCGGGAATGTT |
| CAGACAGGTTCAAATATTGGCAGAGAAAATGATAGCTGAAAACATTTTACAATTCTTTCCTGAAAGTCTTACAAGAT |
| ATGGTGATCTAGAACTACAAAAAATATTAGAACTGAAAGCAGGAATAAGTAACAAATCAAATCGCTACAATGATAAT |
| TACAACAATTACATTAGTAAGTGCTCTATCATCACAGATCTCAGCAAATTCAATCAAGCATTTCGATATGAAACGTC |
| ATGTATTTGTAGTGATGTGCTGGATGAACTGCATGGTGTACAATCTCTATTTTCCTGGTTACATTTAACTATTCCTC |
| ATGTCACAATAATATGCACATATAGGCATGCACCCCCCTATATAGGAGATCATATTGTAGATCTTAACAATGTAGAT |
| GAACAAAGTGGATTATATAGATATCACATGGGTGGCATCGAAGGGTGGTGTCAAAAACTATGGACCATAGAAGCTAT |
| ATCACTATTGGATCTAATATCTCTCAAAGGGAAATTCTCAATTACTGCTTTAATTAATGGTGACAATCAATCAATAG |
| ATATAAGCAAACCAATCAGACTCATGGAAGGTCAAACTCATGCTCAAGCAGATTATTTGCTAGCATTAAATAGCCTT |
| AAATTACTGTATAAAGAGTATGCAGGCATAGGCCACAAATTAAAAGGAACTGAGACTTATATATCACGAGATATGCA |
| ATTTATGAGTAAAACAATTCAACATAACGGTGTATATTACCCAGCTAGTATAAAGAAAGTCCTAAGAGTGGGACCGT |
| GGATAAACACTATACTTGATGATTTCAAAGTGAGTCTAGAATCTATAGGTAGTTTGACACAAGAATTAGAATATAGA |
| GGTGAAAGTCTATTATGCAGTTTAATATTTAGAAATGTATGGTTATATAATCAGATTGCTCTACAATTAAAAAATCA |
| TGCATTATGTAACAATAAACTATATTTGGACATATTAAAGGTTCTGAAACACTTAAAAACCTTTTTTAATCTTGATA |
| ATATTGATACAGCATTAACATTGTATATGAATTTACCCATGTTATTTGGTGGTGGTGATCCCAACTTGTTATATCGA |
| AGTTTCTATAGAAGAACTCCTGACTTCCTCACAGAGGCTATAGTTCACTCTGTGTTCATACTTAGTTATTATACAAA |
| CCATGACTTAAAAGATAAACTTCAAGATCTGTCAGATGATAGATTGAATAAGTTCTTAACATGCATAATCACGTTTG |
| ACAAAAACCCTAATGCTGAATTCGTAACATTGATGAGAGATCCTCAAGCTTTAGGGTCTGAGAGACAAGCTAAAATT |
| ACTAGCGAAATCAATAGACTGGCAGTTACAGAGGTTTTGAGTACAGCTCCAAACAAAATATTCTCCAAAAGTGCACA |

-continued

| Exemplary Sequences |
| --- |
| ACATTATACTACTACAGAGATAGATCTAAATGATATTATGCAAAATATAGAACCTACATATCCTCATGGGCTAAGAG |
| TTGTTTATGAAAGTTTACCCTTTTATAAAGCAGAGAAAATAGTAAATCTTATATCAGGTACAAAATCTATAACTAAC |
| ATACTGGAAAAAACTTCTGCCATAGACTTAACAGATATTGATAGAGCCACTGAGATGATGAGGAAAAACATAACTTT |
| GCTTATAAGGATACTTCCATTGGATTGTAACAGAGATAAAAGAGAGATATTGAGTATGGAAAACCTAAGTATTACTG |
| AATTAAGCAAATATGTTAGGGAAAGATCTTGGTCTTTATCCAATATAGTTGGTGTTACATCACCCAGTATCATGTAT |
| ACAATGGACATCAAATATACTACAAGCACTATATCTAGTGGCATAATTATAGAGAAATATAATGTTAACAGTTTAAC |
| ACGTGGTGAGAGAGGACCCACTAAACCATGGGTTGGTTCATCTACACAAGAGAAAAAAACAATGCCAGTTTATAATA |
| GACAAGTCTTAACCAAAAAACAGAGAGATCAAATAGATCTATTAGCAAAATTGGATTGGGTGTATGCATCTATAGAT |
| AACAAGGATGAATTCATGGAAGAACTCAGCATAGGAACCCTTGGGTTAACATATGAAAAGGCCAAGAAATTATTTCC |
| ACAATATTTAAGTGTCAATTATTTGCATCGCCTTACAGTCAGTAGTAGACCATGTGAATTCCCTGCATCAATACCAG |
| CTTATAGAACAACAAATTATCACTTTGACACTAGCCCTATTAATCGCATATTAACAGAAAAGTATGGTGATGAAGAT |
| ATTGACATAGTATTCCAAAACTGTATAAGCTTTGGCCTTAGTTTAATGTCAGTAGTAGAACAATTTACTAATGTATG |
| TCCTAACAGAATTATTCTCATACCTAAGCTTAATGAGATACATTTGATGAAACCTCCCATATTCACAGGTGATGTTG |
| ATATTCACAAGTTAAAACAAGTGATACAAAAACAGCATATGTTTTTACCAGACAAAATAAGTTTGACTCAATATGTG |
| GAATTATTCTTAAGTAATAAAACACTCAAATCTGGATCTCATGTTAATTCTAATTTAATATTGGCACATAAAATATC |
| TGACTATTTTCATAATACTTACATTTTAAGTACTAATTTAGCTGGACATTGGATTCTGATTATACAACTTATGAAAG |
| ATTCTAAAGGTATTTTTGAAAAAGATTGGGGAGAGGGATATATAACTGATCATATGTTTATTAATTTGAAAGTTTTC |
| TTCAATGCTTATAAGACCTATCTCTTGTGTTTTCATAAAGGTTATGGCAAAGCAAAGCTGGAGTGTGATATGAACAC |
| TTCAGATCTTCTATGTGTATTGGAATTAATAGACAGTAGTTATTGGAAGTCTATGTCTAAGGTATTTTTAGAACAAA |
| AAGTTATCAAATACATTCTTAGCCAAGATGCAAGTTTACATAGAGTAAAAGGATGTCATAGCTTCAAATTATGGTTT |
| CTTAAACGTCTTAATGTAGCAGAATTCACAGTTTGCCCTTGGGTTGTTAACATAGATTATCATCCAACACATATGAA |
| AGCAATATTAACTTATATAGATCTTGTTAGAATGGGATTGATAAATATAGATAGAATACACATTAAAAATAAACACA |
| AATTCAATGATGAATTTTATACTTCTAATCTCTTCTACATTAATTATAACTTCTCAGATAATACTCATCTATTAACT |
| AAACATATAAGGATTGCTAATTCTGAATTAGAAAATAATTACAACAAATTATATCATCCTACACCAGAAACCCTAGA |
| GAATATACTAGCCAATCCGATTAAAAGTAATGACAAAAAGACACTGAATGACTATTGTATAGGTAAAAATGTTGACT |
| CAATAATGTTACCATTGTTATCTAATAAGAAGCTTATTAAATCGTCTGCAATGATTAGAACCAATTACAGCAAACAA |
| GATTTGTATAATTTATTCCCTATGGTTGTGATTGATAGAATTATAGATCATTCAGGCAATACAGCCAAATCCAACCA |
| ACTTTACACTACTACTTCCCACCAAATATCCTTAGTGCACAATAGCACATCACTTTACTGCATGCTTCCTTGGCATC |
| ATATTAATAGATTCAATTTTGTATTTAGTTCTACAGGTTGTAAAATTAGTATAGAGTATATTTTAAAAGATCTTAAA |
| ATTAAAGATCCCAATTGTATAGCATTCATAGGTGAAGGAGCAGGGAATTTATTATTGCGTACAGTAGTGGAACTTCA |
| TCCTGACATAAGATATATTTACAGAAGTCTGAAAGATTGCAATGATCATAGTTTACCTATTGAGTTTTTAAGGCTGT |
| ACAATGGACATATCAACATTGATTATGGTGAAAATTTGACCATTCCTGCTACAGATGCAACCAACAACATTCATTGG |
| TCTTATTTACATATAAAGTTTGCTGAACCTATCAGTCTTTTTGTCTGTGATGCCGAATTGTCTGTAACAGTCAACTG |
| GAGTAAAATTATAATAGAATGGAGCAAGCATGTAAGAAAGTGCAAGTACTGTTCCTCAGTTAATAAATGTATGTTAA |
| TAGTAAAATATCATGCTCAAGATGATATTGATTTCAAATTAGACAATATAACTATATTAAAAACTTATGTATGCTTA |
| GGCAGTAAGTTAAAGGGATCGGAGGTTTACTTAGTCCTTACAATAGGTCCTGCGAATATATTCCCAGTATTTAATGT |
| AGTACAAAATGCTAAATTGATACTATCAAGAACCAAAAATTTCATCATGCCTAAGAAAGCTGATAAAGAGTCTATTG |
| ATGCAAATATTAAAAGTTTGATACCCTTTCTTTGTTACCCTATAACAAAAAAAGGAATTAATACTGCATTGTCAAAA |

-continued

| Exemplary Sequences |
|---|
| CTAAAGAGTGTTGTTAGTGGAGATATACTATCATATTCTATAGCTGGACGTAATGAAGTTTTCAGCAATAAACTTAT |
| AAATCATAAGCATATGAACATCTTAAAATGGTTCAATCATGTTTTAAATTTCAGATCAACAGAACTAAACTATAACC |
| ATTTATATATGGTAGAATCTACATATCCTTACCTAAGTGAATTGTTAAACAGCTTGACAACCAATGAACTTAAAAAA |
| CTGATTAAAATCACAGGTAGTCTGTTATACAACTTTCATAATGAATAATGAATAAAGATCTTATAATAAAAATTCCC |
| ATAGCTATACACTAACACTGTATTCAATTATAGTTATTAAAAATTAAAAATCATATAATTTTTTAAATAACTTTTAG |
| TGAACTAATCCTAAAGTTATCATTTTAATCTTGGAGGAATAAATTTAAACCCTAATCTAATTGGTTTATATGTGTAT |
| TAACTAAATTACGAGATATTAGTTTTTGACACTTTTTTTCTCGT |
| Antigenomic cDNA sequence of D46/ΔM2-2-AclI (SEQ ID NO: 3) |
| ACGGGAAAAAATGCGTACAACAAACTTGCATAAACCAAAAAAATGGGGCAAATAAGAATTTGATAAGTACCACTTAA |
| ATTTAACTCCCTTGGTTAGAGATGGGCAGCAATTCATTGAGTATGATAAAAGTTAGATTACAAAATTTGTTTGACAA |
| TGATGAAGTAGCATTGTTAAAAATAACATGCTATACTGATAAATTAATACATTTAACTAATGCTTTGGCTAAGGCAG |
| TGATACATACAATCAAATTGAATGGCATTGTGTTTGTGCATGTTATTACAAGTAGTGATATTTGCCCTAATAATAAT |
| ATTGTAGTAAAATCCAATTTCACAACAATGCCAGTACTACAAAATGGAGGTTATATATGGGAAATGATGGAATTAAC |
| ACATTGCTCTCAACCTAATGGTCTACTAGATGACAATTGTGAAATTAAATTCTCCAAAAAACTAAGTGATTCAACAA |
| TGACCAATTATATGAATCAATTATCTGAATTACTTGGATTTGATCTTAATCCATAAATTATAATTAATATCAACTAG |
| CAAATCAATGTCACTAACACCATTAGTTAATATAAAACTTAACAGAAGACAAAAATGGGGCAAATAAATCAATTCAG |
| CCAACCCAACCATGGACACAACCCACAATGATAATACACCACAAAGACTGATGATCACAGACATGAGACCGTTGTCA |
| CTTGAGACCATAATAACATCACTAACCAGAGACATCATAACACACAAATTTATATACTTGATAAATCATGAATGCAT |
| AGTGAGAAAACTTGATGAAAGACAGGCCACATTTACATTCCTGGTCAACTATGAAATGAAACTATTACACAAAGTAG |
| GAAGCACTAAATATAAAAAATATACTGAATACAACACAAAATATGGCACTTTCCCTATGCCAATATTCATCAATCAT |
| GATGGGTTCTTAGAATGCATTGGCATTAAGCCTACAAAGCATACTCCCATAATATACAAGTATGATCTCAATCCATA |
| AATTTCAACACAATATTCACACAATCTAAAACAACAACTCTATGCATAACTATACTCCATAGTCCAGATGGAGCCTG |
| AAAATTATAGTAATTTAAAACTTAAGGAGAGATATAAGATAGAAGATGGGGCAAATACAACCATGGCTCTTAGCAAA |
| GTCAAGTTGAATGATACACTCAACAAAGATCAACTTCTGTCATCCAGCAAATACACCATCCAACGGAGCACAGGAGA |
| TAGTATTGATACTCCTAATTATGATGTGCAGAAACACATCAATAAGTTATGTGGCATGTTATTAATCACAGAAGATG |
| CTAATCATAAATTCACTGGGTTAATAGGTATGTTATATGCGATGTCTAGGTTAGGAAGAGAAGACACCATAAAAATA |
| CTCAGAGATGCGGGATATCATGTAAAAGCAAATGGAGTAGATGTAACAACACATCGTCAAGACATTAATGGAAAAGA |
| AATGAAATTTGAAGTGTTAACATTGGCAAGCTTAACAACTGAAATTCAAATCAACATTGAGATAGAATCTAGAAAAT |
| CCTACAAAAAAATGCTAAAAGAAATGGGAGAGGTAGCTCCAGAATACAGGCATGACTCTCCTGATTGTGGGATGATA |
| ATATTATGTATAGCAGCATTAGTAATAACTAAATTAGCAGCAGGGGACAGATCTGGTCTTACAGCCGTGATTAGGAG |
| AGCTAATAATGTCCTAAAAAATGAAATGAAACGTTACAAAGGCTTACTACCCAAGGACATAGCCAACAGCTTCTATG |
| AAGTGTTTGAAAAACATCCCCACTTTATAGATGTTTTTGTTCATTTTGGTATAGCACAATCTTCTACCAGAGGTGGC |
| AGTAGAGTTGAAGGGATTTTTGCAGGATTGTTTATGAATGCCTATGGTGCAGGGCAAGTGATGTTACGGTGGGGAGT |
| CTTAGCAAAATCGGTTAAAAATATTATGTTAGGACATGCTAGTGTGCAAGCAGAAATGGAACAAGTTGTTGAGGTTT |
| ATGAATATGCCCAAAAATTGGGTGGTGAAGCAGGATTCTACCATATATTGAACAACCCAAAAGCATCATTATTATCT |
| TTGACTCAATTTCCTCACTTCTCCAGTGTAGTATTAGGCAATGCTGCTGGCCTAGGCATAATGGGAGAGTACAGAGG |
| TACACCGAGGAATCAAGATCTATATGATGCAGCAAAGGCATATGCTGAACAACTCAAAGAAAATGGTGTGATTAACT |
| ACAGTGTACTAGACTTGACAGCAGAAGAACTAGAGGCTATCAAACATCAGCTTAATCCAAAAGATAATGATGTAGAG |
| CTTTGAGTTAATAAAAAATGGGGCAAATAAATCATCATGGAAAAGTTTGCTCCTGAATTCCATGGAGAAGATGCAAA |

-continued

| Exemplary Sequences |
|---|
| CAACAGGGCTACTAAATTCCTAGAATCAATAAAGGGCAAATTCACATCACCCAAAGATCCCAAGAAAAAAGATAGTA |
| TCATATCTGTCAACTCAATAGATATAGAAGTAACCAAAGAAAGCCCTATAACATCAAATTCAACTATTATCAACCCA |
| ACAAATGAGACAGATGATACTGCAGGGAACAAGCCCAATTATCAAAGAAAACCTCTAGTAAGTTTCAAAGAAGACCC |
| TACACCAAGTGATAATCCCTTTTCTAAACTATACAAAGAAACCATAGAAACATTTGATAACAATGAAGAAGAATCCA |
| GCTATTCATACGAAGAAATAAATGATCAGACAAACGATAATATAACAGCAAGATTAGATAGGATTGATGAAAAATTA |
| AGTGAAATACTAGGAATGCTTCACACATTAGTAGTGGCAAGTGCAGGACCTACATCTGCTCGGGATGGTATAAGAGA |
| TGCCATGGTTGGTTTAAGAGAAGAAATGATAGAAAAAATCAGAACTGAAGCATTAATGACCAATGACAGATTAGAAG |
| CTATGGCAAGACTCAGGAATGAGGAAAGTGAAAAGATGGCAAAAGACACATCAGATGAAGTGTCTCTCAATCCAACA |
| TCAGAGAAATTGAACAACCTATTGGAAGGGAATGATAGTGACAATGATCTATCACTTGAAGATTTCTGATTAGTTAC |
| CAATCTTCACATCAACACACAATACCAACAGAAGACCAACAAACTAACCAACCCAATCATCCAACCAAACATCCATC |
| CGCCAATCAGCCAAACAGCCAACAAAACAACCAGCCAATCCAAAACTAACCACCCGGAAAAAATCTATAATATAGTT |
| ACAAAAAAAGGAAAGGGTGGGGCAAATATGGAAACATACGTGAACAAGCTTCACGAAGGCTCCACATACACAGCTGC |
| TGTTCAATACAATGTCTTAGAAAAAGACGATGACCCTGCATCACTTACAATATGGGTGCCCATGTTCCAATCATCTA |
| TGCCAGCAGATTTACTTATAAAAGAACTAGCTAATGTCAACATACTAGTGAAACAAATATCCACACCCAAGGGACCT |
| TCACTAAGAGTCATGATAAACTCAAGAAGTGCAGTGCTAGCACAAATGCCCAGCAAATTTACCATATGCGCTAATGT |
| GTCCTTGGATGAAAGAAGCAAACTAGCATATGATGTAACCACACCCTGTGAAATCAAGGCATGTAGTCTAACATGCC |
| TAAAATCAAAAAATATGTTGACTACAGTTAAAGATCTCACTATGAAGACACTCAACCCTACACATGATATTATTGCT |
| TTATGTGAATTTGAAAACATAGTAACATCAAAAAAAGTCATAATACCAACATACCTAAGATCCATCAGTGTCAGAAA |
| TAAAGATCTGAACACACTTGAAAATATAACAACCACTGAATTCAAAAATGCTATCACAAATGCAAAAATCATCCCTT |
| ACTCAGGATTACTATTAGTCATCACAGTGACTGACAACAAAGGAGCATTCAAATACATAAAGCCACAAAGTCAATTC |
| ATAGTAGATCTTGGAGCTTACCTAGAAAAAGAAAGTATATATTATGTTACCACAAATTGGAAGCACACAGCTACACG |
| ATTTGCAATCAAACCCATGGAAGATTAACCTTTTTCCTCTACATCAGTGTGTTAATTCATACAAACTTTCTACCTAC |
| ATTCTTCACTTCACCATCACAATCACAAACACTCTGTGGTTCAACCAATCAAACAAAACTTATCTGAAGTCCCAGAT |
| CATCCCAAGTCATTGTTTATCAGATCTAGTACTCAAATAAGTTAATAAAAAATATACACATGGGGCAAATAATCATT |
| GGAGGAAATCCAACTAATCACAATATCTGTTAACATAGACAAGTCCACACACCATACAGAATCAACCAATGGAAAAT |
| ACATCCATAACAATAGAATTCTCAAGCAAATTCTGGCCTTACTTTACACTAATACACATGATCACAACAATAATCTC |
| TTTGCTAATCATAATCTCCATCATGATTGCAATACTAAACAAACTTTGTGAATATAACGTATTCCATAACAAAACCT |
| TTGAGTTACCAAGAGCTCGAGTCAACACATAGCATTCATCAATCCAACAGCCCAAAACAGTAACCTTGCATTTAAAA |
| ATGAACAACCCCTACCTCTTTACAACACCTCATTAACATCCCACCATGCAAACCACTATCCATACTATAAAGTAGTT |
| AATTAAAAATAGTCATAACAATGAACTAGGATATCAAGACTAACAATAACATTGGGGCAAATGCAAACATGTCCAAA |
| AACAAGGACCAACGCACCGCTAAGACATTAGAAAGGACCTGGGACACTCTCAATCATTTATTATTCATATCATCGTG |
| CTTATATAAGTTAAATCTTAAATCTGTAGCACAAATCACATTATCCATTCTGGCAATGATAATCTCAACTTCACTTA |
| TAATTGCAGCCATCATATTCATAGCCTCGGCAAACCACAAAGTCACACCAACAACTGCAATCATACAAGATGCAACA |
| AGCCAGATCAAGAACACAACCCCAACATACCTCACCCAGAATCCTCAGCTTGGAATCAGTCCCTCTAATCCGTCTGA |
| AATTACATCACAAATCACCACCATACTAGCTTCAACAACACCAGGAGTCAAGTCAACCCTGCAATCCACAACAGTCA |
| AGACCAAAAACACAACAACAACTCAAACACAACCCAGCAAGCCCACCACAAAACAACGCCAAAACAAACCACCAAGC |
| AAACCCAATAATGATTTTCACTTTGAAGTGTTCAACTTTGTACCCTGCAGCATATGCAGCAACAATCCAACCTGCTG |
| GGCTATCTGCAAAAGAATACCAAACAAAAAACCAGGAAAGAAAACCACTACCAAGCCCACAAAAAAACCAACCCTCA |

-continued

| Exemplary Sequences |
|---|
| AGACAACCAAAAAAGATCCCAAACCTCAAACCACTAAATCAAAGGAAGTACCCACCACCAAGCCCACAGAAGAGCCA |
| ACCATCAACACCACCAAAACAAACATCATAACTACACTACTCACCTCCAACACCACAGGAAATCCAGAACTCACAAG |
| TCAAATGGAAACCTTCCACTCAACTTCCTCCGAAGGCAATCCAAGCCCTTCTCAAGTCTCTACAACATCCGAGTACC |
| CATCACAACCTTCATCTCCACCCAACACACCACGCCAGTAGTTACTTAAAAACATATTATCACAAAAGGCCTTGACC |
| AACTTAAACAGAATCAAAATAAACTCTGGGGCAAATAACAATGGAGTTGCTAATCCTCAAAGCAAATGCAATTACCA |
| CAATCCTCACTGCAGTCACATTTTGTTTTGCTTCTGGTCAAAACATCACTGAAGAATTTTATCAATCAACATGCAGT |
| GCAGTTAGCAAAGGCTATCTTAGTGCTCTGAGAACTGGTTGGTATACCAGTGTTATAACTATAGAATTAAGTAATAT |
| CAAGAAAAATAAGTGTAATGGAACAGATGCTAAGGTAAAATTGATAAAACAAGAATTAGATAAATATAAAAATGCTG |
| TAACAGAATTGCAGTTGCTCATGCAAAGCACACAAGCAACAAACAATCGAGCCAGAAGAGAACTACCAAGGTTTATG |
| AATTATACACTCAACAATGCCAAAAAAACCAATGTAACATTAAGCAAGAAAAGGAAAAGAAGATTTCTTGGTTTTTT |
| GTTAGGTGTTGGATCTGCAATCGCCAGTGGCGTTGCTGTATCTAAGGTCCTGCACCTAGAAGGGGAAGTGAACAAGA |
| TCAAAAGTGCTCTACTATCCACAAACAAGGCTGTAGTCAGCTTATCAAATGGAGTTAGTGTTTTAACCAGCAAAGTG |
| TTAGACCTCAAAAACTATATAGATAAACAATTGTTACCTATTGTGAACAAGCAAAGCTGCAGCATATCAAATATAGA |
| AACTGTGATAGAGTTCCAACAAAAGAACAACAGACTACTAGAGATTACCAGGGAATTTAGTGTTAATGCAGGCGTAA |
| CTACACCTGTAAGCACTTACATGTTAACTAATAGTGAATTATTGTCATTAATCAATGATATGCCTATAACAAATGAT |
| CAGAAAAAGTTAATGTCCAACAATGTTCAAATAGTTAGACAGCAAAGTTACTCTATCATGTCCATAATAAAAGAGGA |
| AGTCTTAGCATATGTAGTACAATTACCACTATATGGTGTTATAGATACACCCTGTTGGAAACTACACACATCCCCTC |
| TATGTACAACCAACACAAAAGAAGGGTCCAACATCTGTTTAACAAGAACTGACAGAGGATGGTACTGTGACAATGCA |
| GGATCAGTATCTTTCTTCCCACAAGCTGAAACATGTAAAGTTCAATCAAATCGAGTATTTTGTGACACAATGAACAG |
| TTTAACATTACCAAGTGAAGTAAATCTCTGCAATGTTGACATATTCAACCCCAAATATGATTGTAAAATTATGACTT |
| CAAAAACAGATGTAAGCAGCTCCGTTATCACATCTCTAGGAGCCATTGTGTCATGCTATGGCAAAACTAAATGTACA |
| GCATCCAATAAAAATCGTGGAATCATAAAGACATTTTCTAACGGGTGCGATTATGTATCAAATAAAGGGGTGGACAC |
| TGTGTCTGTAGGTAACACATTATATTATGTAAATAAGCAAGAAGGTAAAAGTCTCTATGTAAAAGGTGAACCAATAA |
| TAAATTTCTATGACCCATTAGTATTCCCCTCTGATGAATTTGATGCATCAATATCTCAAGTCAACGAGAAGATTAAC |
| CAGAGCCTAGCATTTATTCGTAAATCCGATGAATTATTACATAATGTAAATGCTGGTAAATCCACCACAAATATCAT |
| GATAACTACTATAATTATAGTGATTATAGTAATATTGTTATCATTAATTGCTGTTGGACTGCTCTTATACTGTAAGG |
| CCAGAAGCACACCAGTCACACTAAGCAAAGATCAACTGAGTGGTATAAATAATATTGCATTTAGTAACTAAATAAAA |
| ATAGCACCTAATCATGTTCTTACAATGGTTTACTATCTGCTCATAGACAACCCATCTGTCATTGGATTTTCTTAAAA |
| TCTGAACTTCATCGAAACTCTCATCTATAAACCATCTCACTTACACTATTTAAGTAGATTCCTAGTTTATAGTTATA |
| TAAAACACAATTGCATGCCAGATTAACTTACCATCTGTAAAAATGAAAACTGGGGCAAATATGTCACGAAGGAATCC |
| TTGCAAATTTGAAATTCGAGGTCATTGCTTAAATGGTAAGAGGTGTCATTTTAGTCATAATTATTTTGAATGGCCAC |
| CCCATGCACTGCTTGTAAGACAAAACTTTATGTTAAACAGAATACTTAAGTCTATGGATAAAAGTATAGATACCTTA |
| TCAGAAATAAGTGGAGCTGCAGAGTTGGACAGAACAGAAGAGTATGCTCTTGGTGTAGTTGGAGTGCTAGAGAGTTA |
| TATAGGATCAATAAACAATATAACTAAACAATCAGCATGTGTTGCCATGAGCAAACTCCTCACTGAACTCAATAGTG |
| ATGATATCAAAAAGCTGAGGGACAATGAAGAGCTAAATTCACCCAAGATAAGAGTGTACAATACTGTCATATCATAT |
| ATTGAAAGCAACAGGAAAAACAATAAACAAACTATCCATCTGTTAAAAAGATTGCCAGCAGACGTATTGAAGAAAAC |
| CATCAAAAACACATTGGATATCCATAAGAGCATAACCATCAACAACCCAAAAGAATCAACTGTTAGTGATACAAATG |
| ACCATGCCAAAAATAATGATACTACCTGACAAATAACGTTCAATTCTAACACTCACCACATCGTTACATTATTAATT |
| CAAACAATTCAAGTTGTGGGACAAAATGGATCCCATTATTAATGGAAATTCTGCTAATGTTTATCTAACCGATAGTT |

-continued

| Exemplary Sequences |
|---|

ATTTAAAAGGTGTTATCTCTTTCTCAGAGTGTAATGCTTTAGGAAGTTACATATTCAATGGTCCTTATCTCAAAAAT
GATTATACCAACTTAATTAGTAGACAAAATCCATTAATAGAACACATGAATCTAAAGAAACTAAATATAACACAGTC
CTTAATATCTAAGTATCATAAAGGTGAAATAAAATTAGAAGAACCTACTTATTTTCAGTCATTACTTATGACATACA
AGAGTATGACCTCGTCAGAACAGATTGCTACCACTAATTTACTTAAAAAGATAATAAGAAGAGCTATAGAAATAAGT
GATGTCAAAGTCTATGCTATATTGAATAAACTAGGGCTTAAAGAAAAGGACAAGATTAAATCCAACAATGGACAAGA
TGAAGACAACTCAGTTATTACGACCATAATCAAAGATGATATACTTTCAGCTGTTAAAGATAATCAATCTCATCTTA
AAGCAGACAAAAATCACTCTACAAAACAAAAAGACACAATCAAAACAACACTCTTGAAGAAATTGATGTGTTCAATG
CAACATCCTCCATCATGGTTAATACATTGGTTTAACTTATACACAAAATTAAACAACATATTAACACAGTATCGATC
AAATGAGGTAAAAAACCATGGGTTTACATTGATAGATAATCAAACTCTTAGTGGATTTCAATTTATTTTGAACCAAT
ATGGTTGTATAGTTTATCATAAGGAACTCAAAAGAATTACTGTGACAACCTATAATCAATTCTTGACATGGAAAGAT
ATTAGCCTTAGTAGATTAAATGTTTGTTTAATTACATGGATTAGTAACTGCTTGAACACATTAAATAAAAGCTTAGG
CTTAAGATGCGGATTCAATAATGTTATCTTGACACAACTATTCCTTTATGGAGATTGTATACTAAAGCTATTTCACA
ATGAGGGGTTCTACATAATAAAAGAGGTAGAGGGATTTATTATGTCTCTAATTTTAAATATAACAGAAGAAGATCAA
TTCAGAAAACGATTTTATAATAGTATGCTCAACAACATCACAGATGCTGCTAATAAAGCTCAGAAAAATCTGCTATC
AAGAGTATGTCATACATTATTAGATAAGACAGTGTCCGATAATATAATAAATGGCAGATGGATAATTCTATTAAGTA
AGTTCCTTAAATTAATTAAGCTTGCAGGTGACAATAACCTTAACAATCTGAGTGAACTATATTTTTTGTTCAGAATA
TTTGGACACCCAATGGTAGATGAAAGACAAGCCATGGATGCTGTTAAAATTAATTGCAATGAGACCAAATTTTACTT
GTTAAGCAGTCTGAGTATGTTAAGAGGTGCCTTTATATATAGAATTATAAAAGGGTTTGTAAATAATTACAACAGAT
GGCCTACTTTAAGAAATGCTATTGTTTTACCCTTAAGATGGTTAACTTACTATAAACTAAACACTTATCCTTCTTTG
TTGGAACTTACAGAAAGAGATTTGATTGTGTTATCAGGACTACGTTTCTATCGTGAGTTTCGGTTGCCTAAAAAAGT
GGATCTTGAAATGATTATAAATGATAAAGCTATATCACCTCCTAAAAATTTGATATGGACTAGTTTCCCTAGAAATT
ACATGCCATCACACATACAAAACTATATAGAACATGAAAAATTAAAATTTTCCGAGAGTGATAAATCAAGAAGAGTA
TTAGAGTATTATTTAAGAGATAACAAATTCAATGAATGTGATTTATACAACTGTGTAGTTAATCAAAGTTATCTCAA
CAACCCTAATCATGTGGTATCATTGACAGGCAAAGAAAGAGAACTCAGTGTAGGTAGAATGTTTGCAATGCAACCGG
GAATGTTCAGACAGGTTCAAATATTGGCAGAGAAAATGATAGCTGAAAACATTTTACAATTCTTTCCTGAAAGTCTT
ACAAGATATGGTGATCTAGAACTACAAAAAATATTAGAACTGAAAGCAGGAATAAGTAACAAATCAAATCGCTACAA
TGATAATTACAACAATTACATTAGTAAGTGCTCTATCATCACAGATCTCAGCAAATTCAATCAAGCATTTCGATATG
AAACGTCATGTATTTGTAGTGATGTGCTGGATGAACTGCATGGTGTACAATCTCTATTTTCCTGGTTACATTTAACT
ATTCCTCATGTCACAATAATATGCACATATAGGCATGCACCCCCCTATATAGGAGATCATATTGTAGATCTTAACAA
TGTAGATGAACAAAGTGGATTATATAGATATCACATGGGTGGCATCGAAGGGTGGTGTCAAAAACTATGGACCATAG
AAGCTATATCACTATTGGATCTAATATCTCTCAAAGGGAAATTCTCAATTACTGCTTTAATTAATGGTGACAATCAA
TCAATAGATATAAGCAAACCAATCAGACTCATGGAAGGTCAAACTCATGCTCAAGCAGATTATTTGCTAGCATTAAA
TAGCCTTAAATTACTGTATAAAGAGTATGCAGGCATAGGCCACAAATTAAAAGGAACTGAGACTTATATATCACGAG
ATATGCAATTTATGAGTAAAACAATTCAACATAACGGTGTATATTACCCAGCTAGTATAAAGAAAGTCCTAAGAGTG
GGACCGTGGATAAACACTATACTTGATGATTTCAAAGTGAGTCTAGAATCTATAGGTAGTTTGACACAAGAATTAGA
ATATAGAGGTGAAAGTCTATTATGCAGTTTAATATTTAGAAATGTATGGTTATATAATCAGATTGCTCTACAATTAA
AAAATCATGCATTATGTAACAATAAACTATATTTGGACATATTAAAGGTTCTGAAACACTTAAAAACCTTTTTTAAT
CTTGATAATATTGATACAGCATTAACATTGTATATGAATTTACCCATGTTATTTGGTGGTGGTGATCCCAACTTGTT

-continued

| Exemplary Sequences |
|---|
| ATATCGAAGTTTCTATAGAAGAACTCCTGACTTCCTCACAGAGGCTATAGTTCACTCTGTGTTCATACTTAGTTATT |
| ATACAAACCATGACTTAAAAGATAAACTTCAAGATCTGTCAGATGATAGATTGAATAAGTTCTTAACATGCATAATC |
| ACGTTTGACAAAAACCCTAATGCTGAATTCGTAACATTGATGAGAGATCCTCAAGCTTTAGGGTCTGAGAGACAAGC |
| TAAAATTACTAGCGAAATCAATAGACTGGCAGTTACAGAGGTTTTGAGTACAGCTCCAAACAAAATATTCTCCAAAA |
| GTGCACAACATTATACTACTACAGAGATAGATCTAAATGATATTATGCAAAATATAGAACCTACATATCCTCATGGG |
| CTAAGAGTTGTTTATGAAAGTTTACCCTTTTATAAAGCAGAGAAAATAGTAAATCTTATATCAGGTACAAAATCTAT |
| AACTAACATACTGGAAAAAACTTCTGCCATAGACTTAACAGATATTGATAGAGCCACTGAGATGATGAGGAAAAACA |
| TAACTTTGCTTATAAGGATACTTCCATTGGATTGTAACAGAGATAAAAGAGAGATATTGAGTATGGAAAACCTAAGT |
| ATTACTGAATTAAGCAAATATGTTAGGGAAAGATCTTGGTCTTTATCCAATATAGTTGGTGTTACATCACCCAGTAT |
| CATGTATACAATGGACATCAAATATACTACAAGCACTATATCTAGTGGCATAATTATAGAGAAATATAATGTTAACA |
| GTTTAACACGTGGTGAGAGAGGACCCACTAAACCATGGGTTGGTTCATCTACACAAGAGAAAAAAACAATGCCAGTT |
| TATAATAGACAAGTCTTAACCAAAAAACAGAGAGATCAAATAGATCTATTAGCAAAATTGGATTGGGTGTATGCATC |
| TATAGATAACAAGGATGAATTCATGGAAGAACTCAGCATAGGAACCCTTGGGTTAACATATGAAAAGGCCAAGAAAT |
| TATTTCCACAATATTTAAGTGTCAATTATTTGCATCGCCTTACAGTCAGTAGTAGACCATGTGAATTCCCTGCATCA |
| ATACCAGCTTATAGAACAACAAATTATCACTTTGACACTAGCCCTATTAATCGCATATTAACAGAAAAGTATGGTGA |
| TGAAGATATTGACATAGTATTCCAAAACTGTATAAGCTTTGGCCTTAGTTTAATGTCAGTAGTAGAACAATTTACTA |
| ATGTATGTCCTAACAGAATTATTCTCATACCTAAGCTTAATGAGATACATTTGATGAAACCTCCCATATTCACAGGT |
| GATGTTGATATTCACAAGTTAAAACAAGTGATACAAAAACAGCATATGTTTTTACCAGACAAAATAAGTTTGACTCA |
| ATATGTGGAATTATTCTTAAGTAATAAAACACTCAAATCTGGATCTCATGTTAATTCTAATTTAATATTGGCACATA |
| AAATATCTGACTATTTTCATAATACTTACATTTTAAGTACTAATTTAGCTGGACATTGGATTCTGATTATACAACTT |
| ATGAAAGATTCTAAAGGTATTTTTGAAAAAGATTGGGGAGAGGGATATATAACTGATCATATGTTTATTAATTTGAA |
| AGTTTTCTTCAATGCTTATAAGACCTATCTCTTGTGTTTTCATAAAGGTTATGGCAAAGCAAAGCTGGAGTGTGATA |
| TGAACACTTCAGATCTTCTATGTGTATTGGAATTAATAGACAGTAGTTATTGGAAGTCTATGTCTAAGGTATTTTTA |
| GAACAAAAAGTTATCAAATACATTCTTAGCCAAGATGCAAGTTTACATAGAGTAAAAGGATGTCATAGCTTCAAATT |
| ATGGTTTCTTAAACGTCTTAATGTAGCAGAATTCACAGTTTGCCCTTGGGTTGTTAACATAGATTATCATCCAACAC |
| ATATGAAAGCAATATTAACTTATATAGATCTTGTTAGAATGGGATTGATAAATATAGATAGAATACACATTAAAAAT |
| AAACACAAATTCAATGATGAATTTTATACTTCTAATCTCTTCTACATTAATTATAACTTCTCAGATAATACTCATCT |
| ATTAACTAAACATATAAGGATTGCTAATTCTGAATTAGAAAATAATTACAACAAATTATATCATCCTACACCAGAAA |
| CCCTAGAGAATATACTAGCCAATCCGATTAAAAGTAATGACAAAAAGACACTGAATGACTATTGTATAGGTAAAAAT |
| GTTGACTCAATAATGTTACCATTGTTATCTAATAAGAAGCTTATTAAATCGTCTGCAATGATTAGAACCAATTACAG |
| CAAACAAGATTTGTATAATTTATTCCCTATGGTTGTGATTGATAGAATTATAGATCATTCAGGCAATACAGCCAAAT |
| CCAACCAACTTTACACTACTACTTCCCACCAAATATCCTTAGTGCACAATAGCACATCACTTTACTGCATGCTTCCT |
| TGGCATCATATTAATAGATTCAATTTTGTATTTAGTTCTACAGGTTGTAAAATTAGTATAGAGTATATTTTAAAAGA |
| TCTTAAAATTAAAGATCCCAATTGTATAGCATTCATAGGTGAAGGAGCAGGGAATTTATTATTGCGTACAGTAGTGG |
| AACTTCATCCTGACATAAGATATATTTACAGAAGTCTGAAAGATTGCAATGATCATAGTTTACCTATTGAGTTTTTA |
| AGGCTGTACAATGGACATATCAACATTGATTATGGTGAAAATTTGACCATTCCTGCTACAGATGCAACCAACAACAT |
| TCATTGGTCTTATTTACATATAAAGTTTGCTGAACCTATCAGTCTTTTTGTCTGTGATGCCGAATTGTCTGTAACAG |
| TCAACTGGAGTAAAATTATAATAGAATGGAGCAAGCATGTAAGAAAGTGCAAGTACTGTTCCTCAGTTAATAAATGT |
| ATGTTAATAGTAAAATATCATGCTCAAGATGATATTGATTTCAAATTAGACAATATAACTATATTAAAAACTTATGT |

-continued

| Exemplary Sequences |
| --- |

ATGCTTAGGCAGTAAGTTAAAGGGATCGGAGGTTTACTTAGTCCTTACAATAGGTCCTGCGAATATATTCCCAGTAT

TTAATGTAGTACAAAATGCTAAATTGATACTATCAAGAACCAAAAATTTCATCATGCCTAAGAAAGCTGATAAAGAG

TCTATTGATGCAAATATTAAAAGTTTGATACCCTTTCTTTGTTACCCTATAACAAAAAAAGGAATTAATACTGCATT

GTCAAAACTAAAGAGTGTTGTTAGTGGAGATATACTATCATATTCTATAGCTGGACGTAATGAAGTTTTCAGCAATA

AACTTATAAATCATAAGCATATGAACATCTTAAAATGGTTCAATCATGTTTTAAATTTCAGATCAACAGAACTAAAC

TATAACCATTTATATATGGTAGAATCTACATATCCTTACCTAAGTGAATTGTTAAACAGCTTGACAACCAATGAACT

TAAAAAACTGATTAAAATCACAGGTAGTCTGTTATACAACTTTCATAATGAATAATGAATAAAGATCTTATAATAAA

AATTCCCATAGCTATACACTAACACTGTATTCAATTATAGTTATTAAAAATTAAAAATCATATAATTTTTTAAATAA

CTTTTAGTGAACTAATCCTAAAGTTATCATTTTAATCTTGGAGGAATAAATTTAAACCCTAATCTAATTGGTTTATA

TGTGTATTAACTAAATTACGAGATATTAGTTTTTGACACTTTTTTTCTCGT

Antigenomic cDNA sequence of D46/ΔM2-2-HindIII (SEQ ID NO: 4)

ACGGGAAAAAATGCGTACAACAAACTTGCATAAACCAAAAAAATGGGGCAAATAAGAATTTGATAAGTACCACTTAA

ATTTAACTCCCTTGGTTAGAGATGGGCAGCAATTCATTGAGTATGATAAAAGTTAGATTACAAAATTTGTTTGACAA

TGATGAAGTAGCATTGTTAAAAATAACATGCTATACTGATAAATTAATACATTTAACTAATGCTTTGGCTAAGGCAG

TGATACATACAATCAAATTGAATGGCATTGTGTTTGTGCATGTTATTACAAGTAGTGATATTTGCCCTAATAATAAT

ATTGTAGTAAAATCCAATTTCACAACAATGCCAGTACTACAAAATGGAGGTTATATATGGGAAATGATGGAATTAAC

ACATTGCTCTCAACCTAATGGTCTACTAGATGACAATTGTGAAATTAAATTCTCCAAAAAACTAAGTGATTCAACAA

TGACCAATTATATGAATCAATTATCTGAATTACTTGGATTTGATCTTAATCCATAAATTATAATTAATATCAACTAG

CAAATCAATGTCACTAACACCATTAGTTAATATAAAACTTAACAGAAGACAAAAATGGGGCAAATAAATCAATTCAG

CCAACCCAACCATGGACACAACCCACAATGATAATACACCACAAAGACTGATGATCACAGACATGAGACCGTTGTCA

CTTGAGACCATAATAACATCACTAACCAGAGACATCATAACACACAAATTTATATACTTGATAAATCATGAATGCAT

AGTGAGAAAACTTGATGAAAGACAGGCCACATTTACATTCCTGGTCAACTATGAAATGAAACTATTACACAAAGTAG

GAAGCACTAAATATAAAAAATATACTGAATACAACACAAAATATGGCACTTTCCCTATGCCAATATTCATCAATCAT

GATGGGTTCTTAGAATGCATTGGCATTAAGCCTACAAAGCATACTCCCATAATATACAAGTATGATCTCAATCCATA

AATTTCAACACAATATTCACACAATCTAAAACAACAACTCTATGCATAACTATACTCCATAGTCCAGATGGAGCCTG

AAAATTATAGTAATTTAAAACTTAAGGAGAGATATAAGATAGAAGATGGGGCAAATACAACCATGGCTCTTAGCAAA

GTCAAGTTGAATGATACACTCAACAAAGATCAACTTCTGTCATCCAGCAAATACACCATCCAACGGAGCACAGGAGA

TAGTATTGATACTCCTAATTATGATGTGCAGAAACACATCAATAAGTTATGTGGCATGTTATTAATCACAGAAGATG

CTAATCATAAATTCACTGGGTTAATAGGTATGTTATATGCGATGTCTAGGTTAGGAAGAGAAGACACCATAAAAATA

CTCAGAGATGCGGGATATCATGTAAAAGCAAATGGAGTAGATGTAACAACACATCGTCAAGACATTAATGGAAAAGA

AATGAAATTTGAAGTGTTAACATTGGCAAGCTTAACAACTGAAATTCAAATCAACATTGAGATAGAATCTAGAAAAT

CCTACAAAAAAATGCTAAAAGAAATGGGAGAGGTAGCTCCAGAATACAGGCATGACTCTCCTGATTGTGGGATGATA

ATATTATGTATAGCAGCATTAGTAATAACTAAATTAGCAGCAGGGGACAGATCTGGTCTTACAGCCGTGATTAGGAG

AGCTAATAATGTCCTAAAAAATGAAATGAAACGTTACAAAGGCTTACTACCCAAGGACATAGCCAACAGCTTCTATG

AAGTGTTTGAAAAACATCCCCACTTTATAGATGTTTTTGTTCATTTTGGTATAGCACAATCTTCTACCAGAGGTGGC

AGTAGAGTTGAAGGGATTTTTGCAGGATTGTTTATGAATGCCTATGGTGCAGGGCAAGTGATGTTACGGTGGGGAGT

CTTAGCAAAATCGGTTAAAAATATTATGTTAGGACATGCTAGTGTGCAAGCAGAAATGGAACAAGTTGTTGAGGTTT

ATGAATATGCCCAAAAATTGGGTGGTGAAGCAGGATTCTACCATATATTGAACAACCCAAAAGCATCATTATTATCT

-continued

| Exemplary Sequences |
|---|
| TTGACTCAATTTCCTCACTTCTCCAGTGTAGTATTAGGCAATGCTGCTGGCCTAGGCATAATGGGAGAGTACAGAGG |
| TACACCGAGGAATCAAGATCTATATGATGCAGCAAAGGCATATGCTGAACAACTCAAAGAAAATGGTGTGATTAACT |
| ACAGTGTACTAGACTTGACAGCAGAAGAACTAGAGGCTATCAAACATCAGCTTAATCCAAAAGATAATGATGTAGAG |
| CTTTGAGTTAATAAAAAATGGGGCAAATAAATCATCATGGAAAAGTTTGCTCCTGAATTCCATGGAGAAGATGCAAA |
| CAACAGGGCTACTAAATTCCTAGAATCAATAAAGGGCAAATTCACATCACCCAAAGATCCCAAGAAAAAAGATAGTA |
| TCATATCTGTCAACTCAATAGATATAGAAGTAACCAAAGAAAGCCCTATAACATCAAATTCAACTATTATCAACCCA |
| ACAAATGAGACAGATGATACTGCAGGGAACAAGCCCAATTATCAAAGAAAACCTCTAGTAAGTTTCAAAGAAGACCC |
| TACACCAAGTGATAATCCCTTTTCTAAACTATACAAAGAAACCATAGAAACATTTGATAACAATGAAGAAGAATCCA |
| GCTATTCATACGAAGAAATAAATGATCAGACAAACGATAATATAACAGCAAGATTAGATAGGATTGATGAAAAATTA |
| AGTGAAATACTAGGAATGCTTCACACATTAGTAGTGGCAAGTGCAGGACCTACATCTGCTCGGGATGGTATAAGAGA |
| TGCCATGGTTGGTTTAAGAGAAGAAATGATAGAAAAAATCAGAACTGAAGCATTAATGACCAATGACAGATTAGAAG |
| CTATGGCAAGACTCAGGAATGAGGAAAGTGAAAAGATGGCAAAAGACACATCAGATGAAGTGTCTCTCAATCCAACA |
| TCAGAGAAATTGAACAACCTATTGGAAGGGAATGATAGTGACAATGATCTATCACTTGAAGATTTCTGATTAGTTAC |
| CAATCTTCACATCAACACACAATACCAACAGAAGACCAACAAACTAACCAACCCAATCATCCAACCAAACATCCATC |
| CGCCAATCAGCCAAACAGCCAACAAAACAACCAGCCAATCCAAAACTAACCACCCGGAAAAAATCTATAATATAGTT |
| ACAAAAAAAGGAAAGGGTGGGGCAAATATGGAAACATACGTGAACAAGCTTCACGAAGGCTCCACATACACAGCTGC |
| TGTTCAATACAATGTCTTAGAAAAAGACGATGACCCTGCATCACTTACAATATGGGTGCCCATGTTCCAATCATCTA |
| TGCCAGCAGATTTACTTATAAAAGAACTAGCTAATGTCAACATACTAGTGAAACAAATATCCACACCCAAGGGACCT |
| TCACTAAGAGTCATGATAAACTCAAGAAGTGCAGTGCTAGCACAAATGCCCAGCAAATTTACCATATGCGCTAATGT |
| GTCCTTGGATGAAAGAAGCAAACTAGCATATGATGTAACCACACCCTGTGAAATCAAGGCATGTAGTCTAACATGCC |
| TAAAATCAAAAAATATGTTGACTACAGTTAAAGATCTCACTATGAAGACACTCAACCCTACACATGATATTATTGCT |
| TTATGTGAATTTGAAAACATAGTAACATCAAAAAAAGTCATAATACCAACATACCTAAGATCCATCAGTGTCAGAAA |
| TAAAGATCTGAACACACTTGAAAATATAACAACCACTGAATTCAAAAATGCTATCACAAATGCAAAAATCATCCCTT |
| ACTCAGGATTACTATTAGTCATCACAGTGACTGACAACAAAGGAGCATTCAAATACATAAAGCCACAAAGTCAATTC |
| ATAGTAGATCTTGGAGCTTACCTAGAAAAAGAAAGTATATATTATGTTACCACAAATTGGAAGCACACAGCTACACG |
| ATTTGCAATCAAACCCATGGAAGATTAACCTTTTTCCTCTACATCAGTGTGTTAATTCATACAAACTTTCTACCTAC |
| ATTCTTCACTTCACCATCACAATCACAAACACTCTGTGGTTCAACCAATCAAACAAAACTTATCTGAAGTCCCAGAT |
| CATCCCAAGTCATTGTTTATCAGATCTAGTACTCAAATAAGTTAATAAAAAATATACACATGGGGCAAATAATCATT |
| GGAGGAAATCCAACTAATCACAATATCTGTTAACATAGACAAGTCCACACACCATACAGAATCAACCAATGGAAAAT |
| ACATCCATAACAATAGAATTCTCAAGCAAATTCTGGCCTTACTTTACACTAATACACATGATCACAACAATAATCTC |
| TTTGCTAATCATAATCTCCATCATGATTGCAATACTAAACAAACTTTGTGAATATAACGTATTCCATAACAAAACCT |
| TTGAGTTACCAAGAGCTCGAGTCAACACATAGCATTCATCAATCCAACAGCCCAAAACAGTAACCTTGCATTTAAAA |
| ATGAACAACCCCTACCTCTTTACAACACCTCATTAACATCCCACCATGCAAACCACTATCCATACTATAAAGTAGTT |
| AATTAAAAATAGTCATAACAATGAACTAGGATATCAAGACTAACAATAACATTGGGGCAAATGCAAACATGTCCAAA |
| AACAAGGACCAACGCACCGCTAAGACATTAGAAAGGACCTGGGACACTCTCAATCATTTATTATTCATATCATCGTG |
| CTTATATAAGTTAAATCTTAAATCTGTAGCACAAATCACATTATCCATTCTGGCAATGATAATCTCAACTTCACTTA |
| TAATTGCAGCCATCATATTCATAGCCTCGGCAAACCACAAAGTCACACCAACAACTGCAATCATACAAGATGCAACA |
| AGCCAGATCAAGAACACAACCCCAACATACCTCACCCAGAATCCTCAGCTTGGAATCAGTCCCTCTAATCCGTCTGA |
| AATTACATCACAAATCACCACCATACTAGCTTCAACAACACCAGGAGTCAAGTCAACCCTGCAATCCACAACAGTCA |

-continued

Exemplary Sequences

AGACCAAAAACACAACAACAACTCAAACACAACCCAGCAAGCCCACCACAAAACAACGCCAAAACAAACCACCAAGC

AAACCCAATAATGATTTTCACTTTGAAGTGTTCAACTTTGTACCCTGCAGCATATGCAGCAACAATCCAACCTGCTG

GGCTATCTGCAAAAGAATACCAAACAAAAAACCAGGAAAGAAAACCACTACCAAGCCCACAAAAAAACCAACCCTCA

AGACAACCAAAAAAGATCCCAAACCTCAAACCACTAAATCAAAGGAAGTACCCACCACCAAGCCCACAGAAGAGCCA

ACCATCAACACCACCAAAACAAACATCATAACTACACTACTCACCTCCAACACCACAGGAAATCCAGAACTCACAAG

TCAAATGGAAACCTTCCACTCAACTTCCTCCGAAGGCAATCCAAGCCCTTCTCAAGTCTCTACAACATCCGAGTACC

CATCACAACCTTCATCTCCACCCAACACACCACGCCAGTAGTTACTTAAAAACATATTATCACAAAAGGCCTTGACC

AACTTAAACAGAATCAAAATAAACTCTGGGGCAAATAACAATGGAGTTGCTAATCCTCAAAGCAAATGCAATTACCA

CAATCCTCACTGCAGTCACATTTTGTTTTGCTTCTGGTCAAAACATCACTGAAGAATTTTATCAATCAACATGCAGT

GCAGTTAGCAAAGGCTATCTTAGTGCTCTGAGAACTGGTTGGTATACCAGTGTTATAACTATAGAATTAAGTAATAT

CAAGAAAAATAAGTGTAATGGAACAGATGCTAAGGTAAAATTGATAAAACAAGAATTAGATAAATATAAAAATGCTG

TAACAGAATTGCAGTTGCTCATGCAAAGCACACAAGCAACAAACAATCGAGCCAGAAGAGAACTACCAAGGTTTATG

AATTATACACTCAACAATGCCAAAAAAACCAATGTAACATTAAGCAAGAAAAGGAAAAGAAGATTTCTTGGTTTTTT

GTTAGGTGTTGGATCTGCAATCGCCAGTGGCGTTGCTGTATCTAAGGTCCTGCACCTAGAAGGGGAAGTGAACAAGA

TCAAAAGTGCTCTACTATCCACAAACAAGGCTGTAGTCAGCTTATCAAATGGAGTTAGTGTTTTAACCAGCAAAGTG

TTAGACCTCAAAAACTATATAGATAAACAATTGTTACCTATTGTGAACAAGCAAAGCTGCAGCATATCAAATATAGA

AACTGTGATAGAGTTCCAACAAAAGAACAACAGACTACTAGAGATTACCAGGGAATTTAGTGTTAATGCAGGCGTAA

CTACACCTGTAAGCACTTACATGTTAACTAATAGTGAATTATTGTCATTAATCAATGATATGCCTATAACAAATGAT

CAGAAAAAGTTAATGTCCAACAATGTTCAAATAGTTAGACAGCAAAGTTACTCTATCATGTCCATAATAAAAGAGGA

AGTCTTAGCATATGTAGTACAATTACCACTATATGGTGTTATAGATACACCCTGTTGGAAACTACACACATCCCCTC

TATGTACAACCAACACAAAAGAAGGGTCCAACATCTGTTTAACAAGAACTGACAGAGGATGGTACTGTGACAATGCA

GGATCAGTATCTTTCTTCCCACAAGCTGAAACATGTAAAGTTCAATCAAATCGAGTATTTTGTGACACAATGAACAG

TTTAACATTACCAAGTGAAGTAAATCTCTGCAATGTTGACATATTCAACCCCAAATATGATTGTAAAATTATGACTT

CAAAAACAGATGTAAGCAGCTCCGTTATCACATCTCTAGGAGCCATTGTGTCATGCTATGGCAAAACTAAATGTACA

GCATCCAATAAAAATCGTGGAATCATAAAGACATTTTCTAACGGGTGCGATTATGTATCAAATAAAGGGGTGGACAC

TGTGTCTGTAGGTAACACATTATATTATGTAAATAAGCAAGAAGGTAAAAGTCTCTATGTAAAAGGTGAACCAATAA

TAAATTTCTATGACCCATTAGTATTCCCCTCTGATGAATTTGATGCATCAATATCTCAAGTCAACGAGAAGATTAAC

CAGAGCCTAGCATTTATTCGTAAATCCGATGAATTATTACATAATGTAAATGCTGGTAAATCCACCACAAATATCAT

GATAACTACTATAATTATAGTGATTATAGTAATATTGTTATCATTAATTGCTGTTGGACTGCTCTTATACTGTAAGG

CCAGAAGCACACCAGTCACACTAAGCAAAGATCAACTGAGTGGTATAAATAATATTGCATTTAGTAACTAAATAAAA

ATAGCACCTAATCATGTTCTTACAATGGTTTACTATCTGCTCATAGACAACCCATCTGTCATTGGATTTTCTTAAAA

TCTGAACTTCATCGAAACTCTCATCTATAAACCATCTCACTTACACTATTTAAGTAGATTCCTAGTTTATAGTTATA

TAAAACACAATTGCATGCCAGATTAACTTACCATCTGTAAAAATGAAAACTGGGGCAAATATGTCACGAAGGAATCC

TTGCAAATTTGAAATTCGAGGTCATTGCTTAAATGGTAAGAGGTGTCATTTTAGTCATAATTATTTTGAATGGCCAC

CCCATGCACTGCTTGTAAGACAAAACTTTATGTTAAACAGAATACTTAAGTCTATGGATAAAAGTATAGATACCTTA

TCAGAAATAAGTGGAGCTGCAGAGTTGGACAGAACAGAAGAGTATGCTCTTGGTGTAGTTGGAGTGCTAGAGAGTTA

TATAGGATCAATAAACAATATAACTAAACAATCAGCATGTGTTGCCATGAGCAAACTCCTCACTGAACTCAATAGTG

ATGATATCAAAAAGCTGAGGGACAATGAAGAGCTAAATTCACCCAAGATAAGAGTGTACAATACTGTCATATCATAT

-continued

| Exemplary Sequences |
|---|
| ATTGAAAGCAACAGGAAAAACAATAAACAAACTATCCATCTGTTAAAAAGATTGCCAGCAGACGTATTGAAGAAAAC |
| CATCAAAAACACATTGGATATCCATAAGAGCATAACCATCAACAACCCAAAAGAATCAACTGTTAGTGATACAAATG |
| ACCATGCCAAAAATAATGATACTACCTGACAAATAAGCTTCAATTCTAACACTCACCACATCGTTACATTATTAATT |
| CAAACAATTCAAGTTGTGGGACAAAATGGATCCCATTATTAATGGAAATTCTGCTAATGTTTATCTAACCGATAGTT |
| ATTTAAAAGGTGTTATCTCTTTCTCAGAGTGTAATGCTTTAGGAAGTTACATATTCAATGGTCCTTATCTCAAAAAT |
| GATTATACCAACTTAATTAGTAGACAAAATCCATTAATAGAACACATGAATCTAAAGAAACTAAATATAACACAGTC |
| CTTAATATCTAAGTATCATAAAGGTGAAATAAAATTAGAAGAACCTACTTATTTTCAGTCATTACTTATGACATACA |
| AGAGTATGACCTCGTCAGAACAGATTGCTACCACTAATTTACTTAAAAAGATAATAAGAAGAGCTATAGAAATAAGT |
| GATGTCAAAGTCTATGCTATATTGAATAAACTAGGGCTTAAAGAAAAGGACAAGATTAAATCCAACAATGGACAAGA |
| TGAAGACAACTCAGTTATTACGACCATAATCAAAGATGATATACTTTCAGCTGTTAAAGATAATCAATCTCATCTTA |
| AAGCAGACAAAAATCACTCTACAAAACAAAAAGACACAATCAAAACAACACTCTTGAAGAAATTGATGTGTTCAATG |
| CAACATCCTCCATCATGGTTAATACATTGGTTTAACTTATACACAAAATTAAACAACATATTAACACAGTATCGATC |
| AAATGAGGTAAAAAACCATGGGTTTACATTGATAGATAATCAAACTCTTAGTGGATTTCAATTTATTTTGAACCAAT |
| ATGGTTGTATAGTTTATCATAAGGAACTCAAAAGAATTACTGTGACAACCTATAATCAATTCTTGACATGGAAAGAT |
| ATTAGCCTTAGTAGATTAAATGTTTGTTTAATTACATGGATTAGTAACTGCTTGAACACATTAAATAAAAGCTTAGG |
| CTTAAGATGCGGATTCAATAATGTTATCTTGACACAACTATTCCTTTATGGAGATTGTATACTAAAGCTATTTCACA |
| ATGAGGGGTTCTACATAATAAAAGAGGTAGAGGGATTTATTATGTCTCTAATTTTAAATATAACAGAAGAAGATCAA |
| TTCAGAAAACGATTTTATAATAGTATGCTCAACAACATCACAGATGCTGCTAATAAAGCTCAGAAAAATCTGCTATC |
| AAGAGTATGTCATACATTATTAGATAAGACAGTGTCCGATAATATAATAAATGGCAGATGGATAATTCTATTAAGTA |
| AGTTCCTTAAATTAATTAAGCTTGCAGGTGACAATAACCTTAACAATCTGAGTGAACTATATTTTTTGTTCAGAATA |
| TTTGGACACCCAATGGTAGATGAAAGACAAGCCATGGATGCTGTTAAAATTAATTGCAATGAGACCAAATTTTACTT |
| GTTAAGCAGTCTGAGTATGTTAAGAGGTGCCTTTATATATAGAATTATAAAAGGGTTTGTAAATAATTACAACAGAT |
| GGCCTACTTTAAGAAATGCTATTGTTTTACCCTTAAGATGGTTAACTTACTATAAACTAAACACTTATCCTTCTTTG |
| TTGGAACTTACAGAAAGAGATTTGATTGTGTTATCAGGACTACGTTTCTATCGTGAGTTTCGGTTGCCTAAAAAAGT |
| GGATCTTGAAATGATTATAAATGATAAAGCTATATCACCTCCTAAAAATTTGATATGGACTAGTTTCCCTAGAAATT |
| ACATGCCATCACACATACAAAACTATATAGAACATGAAAAATTAAAATTTTCCGAGAGTGATAAATCAAGAAGAGTA |
| TTAGAGTATTATTTAAGAGATAACAAATTCAATGAATGTGATTTATACAACTGTGTAGTTAATCAAAGTTATCTCAA |
| CAACCCTAATCATGTGGTATCATTGACAGGCAAAGAAAGAGAACTCAGTGTAGGTAGAATGTTTGCAATGCAACCGG |
| GAATGTTCAGACAGGTTCAAATATTGGCAGAGAAAATGATAGCTGAAAACATTTTACAATTCTTTCCTGAAAGTCTT |
| ACAAGATATGGTGATCTAGAACTACAAAAAATATTAGAACTGAAAGCAGGAATAAGTAACAAATCAAATCGCTACAA |
| TGATAATTACAACAATTACATTAGTAAGTGCTCTATCATCACAGATCTCAGCAAATTCAATCAAGCATTTCGATATG |
| AAACGTCATGTATTTGTAGTGATGTGCTGGATGAACTGCATGGTGTACAATCTCTATTTTCCTGGTTACATTTAACT |
| ATTCCTCATGTCACAATAATATGCACATATAGGCATGCACCCCCCTATATAGGAGATCATATTGTAGATCTTAACAA |
| TGTAGATGAACAAAGTGGATTATATAGATATCACATGGGTGGCATCGAAGGGTGGTGTCAAAAACTATGGACCATAG |
| AAGCTATATCACTATTGGATCTAATATCTCTCAAAGGGAAATTCTCAATTACTGCTTTAATTAATGGTGACAATCAA |
| TCAATAGATATAAGCAAACCAATCAGACTCATGGAAGGTCAAACTCATGCTCAAGCAGATTATTTGCTAGCATTAAA |
| TAGCCTTAAATTACTGTATAAAGAGTATGCAGGCATAGGCCACAAATTAAAAGGAACTGAGACTTATATATCACGAG |
| ATATGCAATTTATGAGTAAAACAATTCAACATAACGGTGTATATTACCCAGCTAGTATAAAGAAAGTCCTAAGAGTG |
| GGACCGTGGATAAACACTATACTTGATGATTTCAAAGTGAGTCTAGAATCTATAGGTAGTTTGACACAAGAATTAGA |

-continued

| Exemplary Sequences |
| --- |

ATATAGAGGTGAAAGTCTATTATGCAGTTTAATATTTAGAAATGTATGGTTATATAATCAGATTGCTCTACAATTAA
AAAATCATGCATTATGTAACAATAAACTATATTTGGACATATTAAAGGTTCTGAAACACTTAAAAACCTTTTTTAAT
CTTGATAATATTGATACAGCATTAACATTGTATATGAATTTACCCATGTTATTTGGTGGTGGTGATCCCAACTTGTT
ATATCGAAGTTTCTATAGAAGAACTCCTGACTTCCTCACAGAGGCTATAGTTCACTCTGTGTTCATACTTAGTTATT
ATACAAACCATGACTTAAAAGATAAACTTCAAGATCTGTCAGATGATAGATTGAATAAGTTCTTAACATGCATAATC
ACGTTTGACAAAAACCCTAATGCTGAATTCGTAACATTGATGAGAGATCCTCAAGCTTTAGGGTCTGAGAGACAAGC
TAAAATTACTAGCGAAATCAATAGACTGGCAGTTACAGAGGTTTTGAGTACAGCTCCAAACAAAATATTCTCCAAAA
GTGCACAACATTATACTACTACAGAGATAGATCTAAATGATATTATGCAAAATATAGAACCTACATATCCTCATGGG
CTAAGAGTTGTTTATGAAAGTTTACCCTTTTATAAAGCAGAGAAAATAGTAAATCTTATATCAGGTACAAAATCTAT
AACTAACATACTGGAAAAAACTTCTGCCATAGACTTAACAGATATTGATAGAGCCACTGAGATGATGAGGAAAAACA
TAACTTTGCTTATAAGGATACTTCCATTGGATTGTAACAGAGATAAAAGAGAGATATTGAGTATGGAAAACCTAAGT
ATTACTGAATTAAGCAAATATGTTAGGGAAAGATCTTGGTCTTTATCCAATATAGTTGGTGTTACATCACCCAGTAT
CATGTATACAATGGACATCAAATATACTACAAGCACTATATCTAGTGGCATAATTATAGAGAAATATAATGTTAACA
GTTTAACACGTGGTGAGAGAGGACCCACTAAACCATGGGTTGGTTCATCTACACAAGAGAAAAAAACAATGCCAGTT
TATAATAGACAAGTCTTAACCAAAAAACAGAGAGATCAAATAGATCTATTAGCAAAATTGGATTGGGTGTATGCATC
TATAGATAACAAGGATGAATTCATGGAAGAACTCAGCATAGGAACCCTTGGGTTAACATATGAAAAGGCCAAGAAAT
TATTTCCACAATATTTAAGTGTCAATTATTTGCATCGCCTTACAGTCAGTAGTAGACCATGTGAATTCCCTGCATCA
ATACCAGCTTATAGAACAACAAATTATCACTTTGACACTAGCCCTATTAATCGCATATTAACAGAAAAGTATGGTGA
TGAAGATATTGACATAGTATTCCAAAACTGTATAAGCTTTGGCCTTAGTTTAATGTCAGTAGTAGAACAATTTACTA
ATGTATGTCCTAACAGAATTATTCTCATACCTAAGCTTAATGAGATACATTTGATGAAACCTCCCATATTCACAGGT
GATGTTGATATTCACAAGTTAAAACAAGTGATACAAAAACAGCATATGTTTTTACCAGACAAAATAAGTTTGACTCA
ATATGTGGAATTATTCTTAAGTAATAAAACACTCAAATCTGGATCTCATGTTAATTCTAATTTAATATTGGCACATA
AAATATCTGACTATTTTCATAATACTTACATTTTAAGTACTAATTTAGCTGGACATTGGATTCTGATTATACAACTT
ATGAAAGATTCTAAAGGTATTTTTGAAAAAGATTGGGGAGAGGGATATATAACTGATCATATGTTTATTAATTTGAA
AGTTTTCTTCAATGCTTATAAGACCTATCTCTTGTGTTTTCATAAAGGTTATGGCAAAGCAAAGCTGGAGTGTGATA
TGAACACTTCAGATCTTCTATGTGTATTGGAATTAATAGACAGTAGTTATTGGAAGTCTATGTCTAAGGTATTTTTA
GAACAAAAAGTTATCAAATACATTCTTAGCCAAGATGCAAGTTTACATAGAGTAAAAGGATGTCATAGCTTCAAATT
ATGGTTTCTTAAACGTCTTAATGTAGCAGAATTCACAGTTTGCCCTTGGGTTGTTAACATAGATTATCATCCAACAC
ATATGAAAGCAATATTAACTTATATAGATCTTGTTAGAATGGGATTGATAAATATAGATAGAATACACATTAAAAAT
AAACACAAATTCAATGATGAATTTTATACTTCTAATCTCTTCTACATTAATTATAACTTCTCAGATAATACTCATCT
ATTAACTAAACATATAAGGATTGCTAATTCTGAATTAGAAAATAATTACAACAAATTATATCATCCTACACCAGAAA
CCCTAGAGAATATACTAGCCAATCCGATTAAAAGTAATGACAAAAAGACACTGAATGACTATTGTATAGGTAAAAAT
GTTGACTCAATAATGTTACCATTGTTATCTAATAAGAAGCTTATTAAATCGTCTGCAATGATTAGAACCAATTACAG
CAAACAAGATTTGTATAATTTATTCCCTATGGTTGTGATTGATAGAATTATAGATCATTCAGGCAATACAGCCAAAT
CCAACCAACTTTACACTACTACTTCCCACCAAATATCCTTAGTGCACAATAGCACATCACTTTACTGCATGCTTCCT
TGGCATCATATTAATAGATTCAATTTTGTATTTAGTTCTACAGGTTGTAAAATTAGTATAGAGTATATTTTAAAAGA
TCTTAAAATTAAAGATCCCAATTGTATAGCATTCATAGGTGAAGGAGCAGGGAATTTATTATTGCGTACAGTAGTGG
AACTTCATCCTGACATAAGATATATTTACAGAAGTCTGAAAGATTGCAATGATCATAGTTTACCTATTGAGTTTTTA

-continued

| Exemplary Sequences |
|---|
| AGGCTGTACAATGGACATATCAACATTGATTATGGTGAAAATTTGACCATTCCTGCTACAGATGCAACCAACAACAT |
| TCATTGGTCTTATTTACATATAAAGTTTGCTGAACCTATCAGTCTTTTTGTCTGTGATGCCGAATTGTCTGTAACAG |
| TCAACTGGAGTAAAATTATAATAGAATGGAGCAAGCATGTAAGAAAGTGCAAGTACTGTTCCTCAGTTAATAAATGT |
| ATGTTAATAGTAAAATATCATGCTCAAGATGATATTGATTTCAAATTAGACAATATAACTATATTAAAAACTTATGT |
| ATGCTTAGGCAGTAAGTTAAAGGGATCGGAGGTTTACTTAGTCCTTACAATAGGTCCTGCGAATATATTCCCAGTAT |
| TTAATGTAGTACAAAATGCTAAATTGATACTATCAAGAACCAAAAATTTCATCATGCCTAAGAAAGCTGATAAAGAG |
| TCTATTGATGCAAATATTAAAAGTTTGATACCCTTTCTTTGTTACCCTATAACAAAAAAAGGAATTAATACTGCATT |
| GTCAAAACTAAAGAGTGTTGTTAGTGGAGATATACTATCATATTCTATAGCTGGACGTAATGAAGTTTTCAGCAATA |
| AACTTATAAATCATAAGCATATGAACATCTTAAAATGGTTCAATCATGTTTTAAATTTCAGATCAACAGAACTAAAC |
| TATAACCATTTATATATGGTAGAATCTACATATCCTTACCTAAGTGAATTGTTAAACAGCTTGACAACCAATGAACT |
| TAAAAAACTGATTAAAATCACAGGTAGTCTGTTATACAACTTTCATAATGAATAATGAATAAAGATCTTATAATAAA |
| AATTCCCATAGCTATACACTAACACTGTATTCAATTATAGTTATTAAAAATTAAAAATCATATAATTTTTTAAATAA |
| CTTTTAGTGAACTAATCCTAAAGTTATCATTTTAATCTTGGAGGAATAAATTTAAACCCTAATCTAATTGGTTTATA |
| TGTGTATTAACTAAATTACGAGATATTAGTTTTTGACACTTTTTTTCTCGT |
| Antigenomic cDNA sequence of LID/ΔM2-2 |
| (SEQ ID NO: 5) |
| ACGGGAAAAAATGCGTACAACAAACTTGCATAAACCAAAAAAATGGGGCAAATAAGAATTTGATAAGTACCACTTAA |
| ATTTAACTCCCTTGGTTAGAGATGGGCAGCAATTCATTGAGTATGATAAAAGTTAGATTACAAAATTTGTTTGACAA |
| TGATGAAGTAGCATTGTTAAAAATAACATGCTATACTGATAAATTAATACATTTAACTAATGCTTTGGCTAAGGCAG |
| TGATACATACAATCAAATTGAATGGCATTGTGTTTGTGCATGTTATTACAAGTAGTGATATTTGCCCTAATAATAAT |
| ATTGTAGTAAAATCCAATTTCACAACAATGCCAGTACTACAAAATGGAGGTTATATATGGGAAATGATGGAATTAAC |
| ACATTGCTCTCAACCTAATGGTCTACTAGATGACAATTGTGAAATTAAATTCTCCAAAAAACTAAGTGATTCAACAA |
| TGACCAATTATATGAATCAATTATCTGAATTACTTGGATTTGATCTTAATCCATAAATTATAATTAATATCAACTAG |
| CAAATCAATGTCACTAACACCATTAGTTAATATAAAACTTAACAGAAGACAAAAATGGGGCAAATAAATCAATTCAG |
| CCAACCCAACCATGGACACAACCCACAATGATAATACACCACAAAGACTGATGATCACAGACATGAGACCGTTGTCA |
| CTTGAGACCATAATAACATCACTAACCAGAGACATCATAACACACAAATTTATATACTTGATAAATCATGAATGCAT |
| AGTGAGAAAACTTGATGAAAGACAGGCCACATTTACATTCCTGGTCAACTATGAAATGAAACTATTACACAAAGTAG |
| GAAGCACTAAATATAAAAAATATACTGAATACAACACAAAATATGGCACTTTCCCTATGCCAATATTCATCAATCAT |
| GATGGGTTCTTAGAATGCATTGGCATTAAGCCTACAAAGCATACTCCCATAATATACAAGTATGATCTCAATCCATA |
| AATTTCAACACAATATTCACACAATCTAAAACAACAACTCTATGCATAACTATACTCCATAGTCCAGATGGAGCCTG |
| AAAATTATAGTAATTTAAAACTTAAGGAGAGATATAAGATAGAAGATGGGGCAAATACAACCATGGCTCTTAGCAAA |
| GTCAAGTTGAATGATACACTCAACAAAGATCAACTTCTGTCATCCAGCAAATACACCATCCAACGGAGCACAGGAGA |
| TAGTATTGATACTCCTAATTATGATGTGCAGAAACACATCAATAAGTTATGTGGCATGTTATTAATCACAGAAGATG |
| CTAATCATAAATTCACTGGGTTAATAGGTATGTTATATGCGATGTCTAGGTTAGGAAGAGAAGACACCATAAAAATA |
| CTCAGAGATGCGGGATATCATGTAAAAGCAAATGGAGTAGATGTAACAACACATCGTCAAGACATTAATGGAAAAGA |
| AATGAAATTTGAAGTGTTAACATTGGCAAGCTTAACAACTGAAATTCAAATCAACATTGAGATAGAATCTAGAAAAT |
| CCTACAAAAAAATGCTAAAAGAAATGGGAGAGGTAGCTCCAGAATACAGGCATGACTCTCCTGATTGTGGGATGATA |
| ATATTATGTATAGCAGCATTAGTAATAACTAAATTAGCAGCAGGGGACAGATCTGGTCTTACAGCCGTGATTAGGAG |
| AGCTAATAATGTCCTAAAAAATGAAATGAAACGTTACAAAGGCTTACTACCCAAGGACATAGCCAACAGCTTCTATG |
| AAGTGTTTGAAAAACATCCCCACTTTATAGATGTTTTTGTTCATTTTGGTATAGCACAATCTTCTACCAGAGGTGGC |

-continued

| Exemplary Sequences |
| --- |
| AGTAGAGTTGAAGGGATTTTTGCAGGATTGTTTATGAATGCCTATGGTGCAGGGCAAGTGATGTTACGGTGGGGAGT |
| CTTAGCAAAATCGGTTAAAAATATTATGTTAGGACATGCTAGTGTGCAAGCAGAAATGGAACAAGTTGTTGAGGTTT |
| ATGAATATGCCCAAAAATTGGGTGGTGAAGCAGGATTCTACCATATATTGAACAACCCAAAAGCATCATTATTATCT |
| TTGACTCAATTTCCTCACTTCTCCAGTGTAGTATTAGGCAATGCTGCTGGCCTAGGCATAATGGGAGAGTACAGAGG |
| TACACCGAGGAATCAAGATCTATATGATGCAGCAAAGGCATATGCTGAACAACTCAAAGAAAATGGTGTGATTAACT |
| ACAGTGTACTAGACTTGACAGCAGAAGAACTAGAGGCTATCAAACATCAGCTTAATCCAAAAGATAATGATGTAGAG |
| CTTTGAGTTAATAAAAAATGGGGCAAATAAATCATCATGGAAAAGTTTGCTCCTGAATTCCATGGAGAAGATGCAAA |
| CAACAGGGCTACTAAATTCCTAGAATCAATAAAGGGCAAATTCACATCACCCAAAGATCCCAAGAAAAAAGATAGTA |
| TCATATCTGTCAACTCAATAGATATAGAAGTAACCAAAGAAAGCCCTATAACATCAAATTCAACTATTATCAACCCA |
| ACAAATGAGACAGATGATACTGCAGGGAACAAGCCCAATTATCAAAGAAAACCTCTAGTAAGTTTCAAAGAAGACCC |
| TACACCAAGTGATAATCCCTTTTCTAAACTATACAAAGAAACCATAGAAACATTTGATAACAATGAAGAAGAATCCA |
| GCTATTCATACGAAGAAATAAATGATCAGACAAACGATAATATAACAGCAAGATTAGATAGGATTGATGAAAAATTA |
| AGTGAAATACTAGGAATGCTTCACACATTAGTAGTGGCAAGTGCAGGACCTACATCTGCTCGGGATGGTATAAGAGA |
| TGCCATGGTTGGTTTAAGAGAAGAAATGATAGAAAAAATCAGAACTGAAGCATTAATGACCAATGACAGATTAGAAG |
| CTATGGCAAGACTCAGGAATGAGGAAAGTGAAAAGATGGCAAAAGACACATCAGATGAAGTGTCTCTCAATCCAACA |
| TCAGAGAAATTGAACAACCTATTGGAAGGGAATGATAGTGACAATGATCTATCACTTGAAGATTTCTGATTAGTTAC |
| CAATCTTCACATCAACACACAATACCAACAGAAGACCAACAAACTAACCAACCCAATCATCCAACCAAACATCCATC |
| CGCCAATCAGCCAAACAGCCAACAAAACAACCAGCCAATCCAAAACTAACCACCCGGAAAAAATCTATAATATAGTT |
| ACAAAAAAAGGAAAGGGTGGGGCAAATATGGAAACATACGTGAACAAGCTTCACGAAGGCTCCACATACACAGCTGC |
| TGTTCAATACAATGTCTTAGAAAAAGACGATGACCCTGCATCACTTACAATATGGGTGCCCATGTTCCAATCATCTA |
| TGCCAGCAGATTTACTTATAAAAGAACTAGCTAATGTCAACATACTAGTGAAACAAATATCCACACCCAAGGGACCT |
| TCACTAAGAGTCATGATAAACTCAAGAAGTGCAGTGCTAGCACAAATGCCCAGCAAATTTACCATATGCGCTAATGT |
| GTCCTTGGATGAAAGAAGCAAACTAGCATATGATGTAACCACACCCTGTGAAATCAAGGCATGTAGTCTAACATGCC |
| TAAAATCAAAAAATATGTTGACTACAGTTAAAGATCTCACTATGAAGACACTCAACCCTACACATGATATTATTGCT |
| TTATGTGAATTTGAAAACATAGTAACATCAAAAAAAGTCATAATACCAACATACCTAAGATCCATCAGTGTCAGAAA |
| TAAAGATCTGAACACACTTGAAAATATAACAACCACTGAATTCAAAAATGCTATCACAAATGCAAAAATCATCCCTT |
| ACTCAGGATTACTATTAGTCATCACAGTGACTGACAACAAAGGAGCATTCAAATACATAAAGCCACAAAGTCAATTC |
| ATAGTAGATCTTGGAGCTTACCTAGAAAAAGAAAGTATATATTATGTTACCACAAATTGGAAGCACACAGCTACACG |
| ATTTGCAATCAAACCCATGGAAGATTAACCTTTTTCCTCTACATCAGTGTGTTAATTCATACAAACTTTCTACCTAC |
| ATTCTTCACTTCACCATCACAATCACAAACACTCTGTGGTTCAACCAATCAAACAAAACTTATCTGAAGTCCCAGAT |
| CATCCCAAGTCATTGTTTATCAGATCTAGTACTCAAATAAGTTAATAAAAAATATACACATGGGGCAAATAATCATT |
| GGAGGAAATCCAACTAATCACAATATCTGTTAACATAGACAAGTCCACACACCATACAGAATCAACCAATGGAAAAT |
| ACATCCATAACAATAGAATTCTCAAGCAAATTCTGGCCTTACTTTACACTAATACACATGATCACAACAATAATCTC |
| TTTGCTAATCATAATCTCCATCATGATTGCAATACTAAACAAACTTTGTGAATATAACGTATTCCATAACAAAACCT |
| TTGAGTTACCAAGAGCTCGAGTTAATACTTGATAAAGTAGTTAATTAAAAATAGTCATAACAATGAACTAGGATATC |
| AAGACTAACAATAACATTGGGGCAAATGCAAACATGTCCAAAAACAAGGACCAACGCACCGCTAAGACATTAGAAAG |
| GACCTGGGACACTCTCAATCATTTATTATTCATATCATCGTGCTTATATAAGTTAAATCTTAAATCTGTAGCACAAA |
| TCACATTATCCATTCTGGCAATGATAATCTCAACTTCACTTATAATTGCAGCCATCATATTCATAGCCTCGGCAAAC |

-continued

| Exemplary Sequences |
|---|
| CACAAAGTCACACCAACAACTGCAATCATACAAGATGCAACAAGCCAGATCAAGAACACAACCCCAACATACCTCAC |
| CCAGAATCCTCAGCTTGGAATCAGTCCCTCTAATCCGTCTGAAATTACATCACAAATCACCACCATACTAGCTTCAA |
| CAACACCAGGAGTCAAGTCAACCCTGCAATCCACAACAGTCAAGACCAAAAACACAACAACAACTCAAACACAACCC |
| AGCAAGCCCACCACAAAACAACGCCAAAACAAACCACCAAGCAAACCCAATAATGATTTTCACTTTGAAGTGTTCAA |
| CTTTGTACCCTGCAGCATATGCAGCAACAATCCAACCTGCTGGGCTATCTGCAAAAGAATACCAAACAAAAAACCAG |
| GAAAGAAAACCACTACCAAGCCCACAAAAAAACCAACCCTCAAGACAACCAAAAAAGATCCCAAACCTCAAACCACT |
| AAATCAAAGGAAGTACCCACCACCAAGCCCACAGAAGAGCCAACCATCAACACCACCAAAACAAACATCATAACTAC |
| ACTACTCACCTCCAACACCACAGGAAATCCAGAACTCACAAGTCAAATGGAAACCTTCCACTCAACTTCCTCCGAAG |
| GCAATCCAAGCCCTTCTCAAGTCTCTACAACATCCGAGTACCCATCACAACCTTCATCTCCACCCAACACACCACGC |
| CAGTAGTTACTTAAAAACATATTATCACAAAAGGCCTTGACCAACTTAAACAGAATCAAAATAAACTCTGGGGCAAA |
| TAACAATGGAGTTGCTAATCCTCAAAGCAAATGCAATTACCACAATCCTCACTGCAGTCACATTTTGTTTTGCTTCT |
| GGTCAAAACATCACTGAAGAATTTTATCAATCAACATGCAGTGCAGTTAGCAAAGGCTATCTTAGTGCTCTGAGAAC |
| TGGTTGGTATACCAGTGTTATAACTATAGAATTAAGTAATATCAAGAAAAATAAGTGTAATGGAACAGATGCTAAGG |
| TAAAATTGATAAAACAAGAATTAGATAAATATAAAAATGCTGTAACAGAATTGCAGTTGCTCATGCAAAGCACACAA |
| GCAACAAACAATCGAGCCAGAAGAGAACTACCAAGGTTTATGAATTATACACTCAACAATGCCAAAAAAACCAATGT |
| AACATTAAGCAAGAAAAGGAAAAGAAGATTTCTTGGTTTTTTGTTAGGTGTTGGATCTGCAATCGCCAGTGGCGTTG |
| CTGTATCTAAGGTCCTGCACCTAGAAGGGGAAGTGAACAAGATCAAAAGTGCTCTACTATCCACAAACAAGGCTGTA |
| GTCAGCTTATCAAATGGAGTTAGTGTTTTAACCAGCAAAGTGTTAGACCTCAAAAACTATATAGATAAACAATTGTT |
| ACCTATTGTGAACAAGCAAAGCTGCAGCATATCAAATATAGAAACTGTGATAGAGTTCCAACAAAAGAACAACAGAC |
| TACTAGAGATTACCAGGGAATTTAGTGTTAATGCAGGCGTAACTACACCTGTAAGCACTTACATGTTAACTAATAGT |
| GAATTATTGTCATTAATCAATGATATGCCTATAACAAATGATCAGAAAAAGTTAATGTCCAACAATGTTCAAATAGT |
| TAGACAGCAAAGTTACTCTATCATGTCCATAATAAAAGAGGAAGTCTTAGCATATGTAGTACAATTACCACTATATG |
| GTGTTATAGATACACCCTGTTGGAAACTACACACATCCCCTCTATGTACAACCAACACAAAAGAAGGGTCCAACATC |
| TGTTTAACAAGAACTGACAGAGGATGGTACTGTGACAATGCAGGATCAGTATCTTTCTTCCCACAAGCTGAAACATG |
| TAAAGTTCAATCAAATCGAGTATTTTGTGACACAATGAACAGTTTAACATTACCAAGTGAAGTAAATCTCTGCAATG |
| TTGACATATTCAACCCCAAATATGATTGTAAAATTATGACTTCAAAAACAGATGTAAGCAGCTCCGTTATCACATCT |
| CTAGGAGCCATTGTGTCATGCTATGGCAAAACTAAATGTACAGCATCCAATAAAAATCGTGGAATCATAAAGACATT |
| TTCTAACGGGTGCGATTATGTATCAAATAAAGGGGTGGACACTGTGTCTGTAGGTAACACATTATATTATGTAAATA |
| AGCAAGAAGGTAAAAGTCTCTATGTAAAAGGTGAACCAATAATAAATTTCTATGACCCATTAGTATTCCCCTCTGAT |
| GAATTTGATGCATCAATATCTCAAGTCAACGAGAAGATTAACCAGAGCCTAGCATTTATTCGTAAATCCGATGAATT |
| ATTACATAATGTAAATGCTGGTAAATCCACCACAAATATCATGATAACTACTATAATTATAGTGATTATAGTAATAT |
| TGTTATCATTAATTGCTGTTGGACTGCTCTTATACTGTAAGGCCAGAAGCACACCAGTCACACTAAGCAAAGATCAA |
| CTGAGTGGTATAAATAATATTGCATTTAGTAACTAAATAAAAATAGCACCTAATCATGTTCTTACAATGGTTTACTA |
| TCTGCTCATAGACAACCCATCTGTCATTGGATTTTCTTAAAATCTGAACTTCATCGAAACTCTCATCTATAAACCAT |
| CTCACTTACACTATTTAAGTAGATTCCTAGTTTATAGTTATATAAAACACAATTGCATGCCAGATTAACTTACCATC |
| TGTAAAAATGAAAACTGGGGCAAATATGTCACGAAGGAATCCTTGCAAATTTGAAATTCGAGGTCATTGCTTAAATG |
| GTAAGAGGTGTCATTTTAGTCATAATTATTTTGAATGGCCACCCCATGCACTGCTTGTAAGACAAAACTTTATGTTA |
| AACAGAATACTTAAGTCTATGGATAAAAGTATAGATACCTTATCAGAAATAAGTGGAGCTGCAGAGTTGGACAGAAC |
| AGAAGAGTATGCTCTTGGTGTAGTTGGAGTGCTAGAGAGTTATATAGGATCAATAAACAATATAACTAAACAATCAG |

-continued

| Exemplary Sequences |
| --- |
| CATGTGTTGCCATGAGCAAACTCCTCACTGAACTCAATAGTGATGATATCAAAAAGCTGAGGGACAATGAAGAGCTA<br>AATTCACCCAAGATAAGAGTGTACAATACTGTCATATCATATATTGAAAGCAACAGGAAAAACAATAAACAAACTAT<br>CCATCTGTTAAAAAGATTGCCAGCAGACGTATTGAAGAAAACCATCAAAAACACATTGGATATCCATAAGAGCATAA<br>CCATCAACAACCCAAAAGAATCAACTGTTAGTGATACAAACGACCACGCCAAAAATAACGATACTACCTAACACTCA<br>ATTCTAACACTCACCACATCGTTACATTATTAATTCAAACAATTCAAGTTGTGGGACAAAATGGATCCCATTATTAA<br>TGGAAATTCTGCTAATGTTTATCTAACCGATAGTTATTTAAAAGGTGTTATCTCTTTCTCAGAGTGTAATGCTTTAG<br>GAAGTTACATATTCAATGGTCCTTATCTCAAAAATGATTATACCAACTTAATTAGTAGACAAAATCCATTAATAGAA<br>CACATGAATCTAAAGAAACTAAATATAACACAGTCCTTAATATCTAAGTATCATAAAGGTGAAATAAAATTAGAAGA<br>ACCTACTTATTTTCAGTCATTACTTATGACATACAAGAGTATGACCTCGTCAGAACAGATTGCTACCACTAATTTAC<br>TTAAAAAGATAATAAGAAGAGCTATAGAAATAAGTGATGTCAAAGTCTATGCTATATTGAATAAACTAGGGCTTAAA<br>GAAAAGGACAAGATTAAATCCAACAATGGACAAGATGAAGACAACTCAGTTATTACGACCATAATCAAAGATGATAT<br>ACTTTCAGCTGTTAAAGATAATCAATCTCATCTTAAAGCAGACAAAAATCACTCTACAAAACAAAAAGACACAATCA<br>AAACAACACTCTTGAAGAAATTGATGTGTTCAATGCAACATCCTCCATCATGGTTAATACATTGGTTTAACTTATAC<br>ACAAAATTAAACAACATATTAACACAGTATCGATCAAATGAGGTAAAAAACCATGGGTTTACATTGATAGATAATCA<br>AACTCTTAGTGGATTTCAATTTATTTTGAACCAATATGGTTGTATAGTTTATCATAAGGAACTCAAAAGAATTACTG<br>TGACAACCTATAATCAATTCTTGACATGGAAAGATATTAGCCTTAGTAGATTAAATGTTTGTTTAATTACATGGATT<br>AGTAACTGCTTGAACACATTAAATAAAAGCTTAGGCTTAAGATGCGGATTCAATAATGTTATCTTGACACAACTATT<br>CCTTTATGGAGATTGTATACTAAAGCTATTTCACAATGAGGGGTTCTACATAATAAAAGAGGTAGAGGGATTTATTA<br>TGTCTCTAATTTTAAATATAACAGAAGAAGATCAATTCAGAAAACGATTTTATAATAGTATGCTCAACAACATCACA<br>GATGCTGCTAATAAAGCTCAGAAAAATCTGCTATCAAGAGTATGTCATACATTATTAGATAAGACAGTGTCCGATAA<br>TATAATAAATGGCAGATGGATAATTCTATTAAGTAAGTTCCTTAAATTAATTAAGCTTGCAGGTGACAATAACCTTA<br>ACAATCTGAGTGAACTATATTTTTTGTTCAGAATATTTGGACACCCAATGGTAGATGAAAGACAAGCCATGGATGCT<br>GTTAAAATTAATTGCAATGAGACCAAATTTTACTTGTTAAGCAGTCTGAGTATGTTAAGAGGTGCCTTTATATATAG<br>AATTATAAAAGGGTTTGTAAATAATTACAACAGATGGCCTACTTTAAGAAATGCTATTGTTTTACCCTTAAGATGGT<br>TAACTTACTATAAACTAAACACTTATCCTTCTTTGTTGGAACTTACAGAAAGAGATTTGATTGTGTTATCAGGACTA<br>CGTTTCTATCGTGAGTTTCGGTTGCCTAAAAAAGTGGATCTTGAAATGATTATAAATGATAAAGCTATATCACCTCC<br>TAAAAATTTGATATGGACTAGTTTCCCTAGAAATTACATGCCATCACACATACAAAACTATATAGAACATGAAAAAT<br>TAAAATTTTCCGAGAGTGATAAATCAAGAAGAGTATTAGAGTATTATTTAAGAGATAACAAATTCAATGAATGTGAT<br>TTATACAACTGTGTAGTTAATCAAAGTTATCTCAACAACCCTAATCATGTGGTATCATTGACAGGCAAAGAAAGAGA<br>ACTCAGTGTAGGTAGAATGTTTGCAATGCAACCGGGAATGTTCAGACAGGTTCAAATATTGGCAGAGAAAATGATAG<br>CTGAAAACATTTTACAATTCTTTCCTGAAAGTCTTACAAGATATGGTGATCTAGAACTACAAAAAATATTAGAACTG<br>AAAGCAGGAATAAGTAACAAATCAAATCGCTACAATGATAATTACAACAATTACATTAGTAAGTGCTCTATCATCAC<br>AGATCTCAGCAAATTCAATCAAGCATTTCGATATGAAACGTCATGTATTTGTAGTGATGTGCTGGATGAACTGCATG<br>GTGTACAATCTCTATTTTCCTGGTTACATTTAACTATTCCTCATGTCACAATAATATGCACATATAGGCATGCACCC<br>CCCTATATAGGAGATCATATTGTAGATCTTAACAATGTAGATGAACAAAGTGGATTATATAGATATCACATGGGTGG<br>CATCGAAGGGTGGTGTCAAAAACTATGGACCATAGAAGCTATATCACTATTGGATCTAATATCTCTCAAAGGGAAAT<br>TCTCAATTACTGCTTTAATTAATGGTGACAATCAATCAATAGATATAAGCAAACCAATCAGACTCATGGAAGGTCAA<br>ACTCATGCTCAAGCAGATTATTTGCTAGCATTAAATAGCCTTAAATTACTGTATAAAGAGTATGCAGGCATAGGCCA |

-continued

| Exemplary Sequences |
| --- |
| CAAATTAAAAGGAACTGAGACTTATATATCACGAGATATGCAATTTATGAGTAAAACAATTCAACATAACGGTGTAT |
| ATTACCCAGCTAGTATAAAGAAAGTCCTAAGAGTGGGACCGTGGATAAACACTATACTTGATGATTTCAAAGTGAGT |
| CTAGAATCTATAGGTAGTTTGACACAAGAATTAGAATATAGAGGTGAAAGTCTATTATGCAGTTTAATATTTAGAAA |
| TGTATGGTTATATAATCAGATTGCTCTACAATTAAAAAATCATGCATTATGTAACAATAAACTATATTTGGACATAT |
| TAAAGGTTCTGAAACACTTAAAAACCTTTTTTAATCTTGATAATATTGATACAGCATTAACATTGTATATGAATTTA |
| CCCATGTTATTTGGTGGTGGTGATCCCAACTTGTTATATCGAAGTTTCTATAGAAGAACTCCTGACTTCCTCACAGA |
| GGCTATAGTTCACTCTGTGTTCATACTTAGTTATTATACAAACCATGACTTAAAAGATAAACTTCAAGATCTGTCAG |
| ATGATAGATTGAATAAGTTCTTAACATGCATAATCACGTTTGACAAAAACCCTAATGCTGAATTCGTAACATTGATG |
| AGAGATCCTCAAGCTTTAGGGTCTGAGAGACAAGCTAAAATTACTAGCGAAATCAATAGACTGGCAGTTACAGAGGT |
| TTTGAGTACAGCTCCAAACAAAATATTCTCCAAAAGTGCACAACATTATACTACTACAGAGATAGATCTAAATGATA |
| TTATGCAAAATATAGAACCTACATATCCTCATGGGCTAAGAGTTGTTTATGAAAGTTTACCCTTTTATAAAGCAGAG |
| AAAATAGTAAATCTTATATCAGGTACAAAATCTATAACTAACATACTGGAAAAAACTTCTGCCATAGACTTAACAGA |
| TATTGATAGAGCCACTGAGATGATGAGGAAAAACATAACTTTGCTTATAAGGATACTTCCATTGGATTGTAACAGAG |
| ATAAAAGAGAGATATTGAGTATGGAAAACCTAAGTATTACTGAATTAAGCAAATATGTTAGGGAAAGATCTTGGTCT |
| TTATCCAATATAGTTGGTGTTACATCACCCAGTATCATGTATACAATGGACATCAAATATACTACAAGCACTATATC |
| TAGTGGCATAATTATAGAGAAATATAATGTTAACAGTTTAACACGTGGTGAGAGAGGACCCACTAAACCATGGGTTG |
| GTTCATCTACACAAGAGAAAAAAACAATGCCAGTTTATAATAGACAAGTCTTAACCAAAAAACAGAGAGATCAAATA |
| GATCTATTAGCAAAATTGGATTGGGTGTATGCATCTATAGATAACAAGGATGAATTCATGGAAGAACTCAGCATAGG |
| AACCCTTGGGTTAACATATGAAAAGGCCAAGAAATTATTTCCACAATATTTAAGTGTCAATTATTTGCATCGCCTTA |
| CAGTCAGTAGTAGACCATGTGAATTCCCTGCATCAATACCAGCTTATAGAACAACAAATTATCACTTTGACACTAGC |
| CCTATTAATCGCATATTAACAGAAAAGTATGGTGATGAAGATATTGACATAGTATTCCAAAACTGTATAAGCTTTGG |
| CCTTAGTTTAATGTCAGTAGTAGAACAATTTACTAATGTATGTCCTAACAGAATTATTCTCATACCTAAGCTTAATG |
| AGATACATTTGATGAAACCTCCCATATTCACAGGTGATGTTGATATTCACAAGTTAAAACAAGTGATACAAAAACAG |
| CATATGTTTTTACCAGACAAAATAAGTTTGACTCAATATGTGGAATTATTCTTAAGTAATAAAACACTCAAATCTGG |
| ATCTCATGTTAATTCTAATTTAATATTGGCACATAAAATATCTGACTATTTTCATAATACTTACATTTTAAGTACTA |
| ATTTAGCTGGACATTGGATTCTGATTATACAACTTATGAAAGATTCTAAAGGTATTTTTGAAAAAGATTGGGGAGAG |
| GGATATATAACTGATCATATGTTTATTAATTTGAAAGTTTTCTTCAATGCTTATAAGACCTATCTCTTGTGTTTTCA |
| TAAAGGTTATGGCAAAGCAAAGCTGGAGTGTGATATGAACACTTCAGATCTTCTATGTGTATTGGAATTAATAGACA |
| GTAGTTATTGGAAGTCTATGTCTAAGGTATTTTTAGAACAAAAAGTTATCAAATACATTCTTAGCCAAGATGCAAGT |
| TTACATAGAGTAAAAGGATGTCATAGCTTCAAATTATGGTTTCTTAAACGTCTTAATGTAGCAGAATTCACAGTTTG |
| CCCTTGGGTTGTTAACATAGATTATCATCCAACACATATGAAAGCAATATTAACTTATATAGATCTTGTTAGAATGG |
| GATTGATAAATATAGATAGAATACACATTAAAAATAAACACAAATTCAATGATGAATTTTATACTTCTAATCTCTTC |
| TACATTAATTATAACTTCTCAGATAATACTCATCTATTAACTAAACATATAAGGATTGCTAATTCTGAATTAGAAAA |
| TAATTACAACAAATTATATCATCCTACACCAGAAACCCTAGAGAATATACTAGCCAATCCGATTAAAAGTAATGACA |
| AAAAGACACTGAATGACTATTGTATAGGTAAAAATGTTGACTCAATAATGTTACCATTGTTATCTAATAAGAAGCTT |
| ATTAAATCGTCTGCAATGATTAGAACCAATTACAGCAAACAAGATTTGTATAATTTATTCCCTATGGTTGTGATTGA |
| TAGAATTATAGATCATTCAGGCAATACAGCCAAATCCAACCAACTTTACACTACTACTTCCCACCAAATATCCTTAG |
| TGCACAATAGCACATCACTTTACTGCATGCTTCCTTGGCATCATATTAATAGATTCAATTTTGTATTTAGTTCTACA |
| GGTTGTAAAATTAGTATAGAGTATATTTTAAAAGATCTTAAAATTAAAGATCCCAATTGTATAGCATTCATAGGTGA |

-continued

| Exemplary Sequences |
|---|

AGGAGCAGGGAATTTATTATTGCGTACAGTAGTGGAACTTCATCCTGACATAAGATATATTTACAGAAGTCTGAAAG

ATTGCAATGATCATAGTTTACCTATTGAGTTTTTAAGGCTGTACAATGGACATATCAACATTGATTATGGTGAAAAT

TTGACCATTCCTGCTACAGATGCAACCAACAACATTCATTGGTCTTATTTACATATAAAGTTTGCTGAACCTATCAG

TCTTTTTGTCTGTGATGCCGAATTGTCTGTAACAGTCAACTGGAGTAAAATTATAATAGAATGGAGCAAGCATGTAA

GAAAGTGCAAGTACTGTTCCTCAGTTAATAAATGTATGTTAATAGTAAAATATCATGCTCAAGATGATATTGATTTC

AAATTAGACAATATAACTATATTAAAAACTTATGTATGCTTAGGCAGTAAGTTAAAGGGATCGGAGGTTTACTTAGT

CCTTACAATAGGTCCTGCGAATATATTCCCAGTATTTAATGTAGTACAAAATGCTAAATTGATACTATCAAGAACCA

AAAATTTCATCATGCCTAAGAAAGCTGATAAAGAGTCTATTGATGCAAATATTAAAAGTTTGATACCCTTTCTTTGT

TACCCTATAACAAAAAAAGGAATTAATACTGCATTGTCAAAACTAAAGAGTGTTGTTAGTGGAGATATACTATCATA

TTCTATAGCTGGACGTAATGAAGTTTTCAGCAATAAACTTATAAATCATAAGCATATGAACATCTTAAAATGGTTCA

ATCATGTTTTAAATTTCAGATCAACAGAACTAAACTATAACCATTTATATATGGTAGAATCTACATATCCTTACCTA

AGTGAATTGTTAAACAGCTTGACAACCAATGAACTTAAAAAACTGATTAAAATCACAGGTAGTCTGTTATACAACTT

TCATAATGAATAATGAATAAAGATCTTATAATAAAAATTCCCATAGCTATACACTAACACTGTATTCAATTATAGTT

ATTAAAAATTAAAAATCATATAATTTTTTAAATAACTTTTAGTGAACTAATCCTAAAGTTATCATTTTAATCTTGGA

GGAATAAATTTAAACCCTAATCTAATTGGTTTATATGTGTATTAACTAAATTACGAGATATTAGTTTTTGACACTTT

TTTTCTCGT

Antigenomic cDNA sequence of LID/ΔM2-2-AclI (SEQ ID NO: 6)

ACGGGAAAAAATGCGTACAACAAACTTGCATAAACCAAAAAAATGGGGCAAATAAGAATTTGATAAGTACCACTTAA

ATTTAACTCCCTTGGTTAGAGATGGGCAGCAATTCATTGAGTATGATAAAAGTTAGATTACAAAATTTGTTTGACAA

TGATGAAGTAGCATTGTTAAAAATAACATGCTATACTGATAAATTAATACATTTAACTAATGCTTTGGCTAAGGCAG

TGATACATACAATCAAATTGAATGGCATTGTGTTTGTGCATGTTATTACAAGTAGTGATATTTGCCCTAATAATAAT

ATTGTAGTAAAATCCAATTTCACAACAATGCCAGTACTACAAAATGGAGGTTATATATGGGAAATGATGGAATTAAC

ACATTGCTCTCAACCTAATGGTCTACTAGATGACAATTGTGAAATTAAATTCTCCAAAAAACTAAGTGATTCAACAA

TGACCAATTATATGAATCAATTATCTGAATTACTTGGATTTGATCTTAATCCATAAATTATAATTAATATCAACTAG

CAAATCAATGTCACTAACACCATTAGTTAATATAAAACTTAACAGAAGACAAAAATGGGGCAAATAAATCAATTCAG

CCAACCCAACCATGGACACAACCCACAATGATAATACACCACAAAGACTGATGATCACAGACATGAGACCGTTGTCA

CTTGAGACCATAATAACATCACTAACCAGAGACATCATAACACACAAATTTATATACTTGATAAATCATGAATGCAT

AGTGAGAAAACTTGATGAAAGACAGGCCACATTTACATTCCTGGTCAACTATGAAATGAAACTATTACACAAAGTAG

GAAGCACTAAATATAAAAAATATACTGAATACAACACAAAATATGGCACTTTCCCTATGCCAATATTCATCAATCAT

GATGGGTTCTTAGAATGCATTGGCATTAAGCCTACAAAGCATACTCCCATAATATACAAGTATGATCTCAATCCATA

AATTTCAACACAATATTCACACAATCTAAAACAACAACTCTATGCATAACTATACTCCATAGTCCAGATGGAGCCTG

AAAATTATAGTAATTTAAAACTTAAGGAGAGATATAAGATAGAAGATGGGGCAAATACAACCATGGCTCTTAGCAAA

GTCAAGTTGAATGATACACTCAACAAAGATCAACTTCTGTCATCCAGCAAATACACCATCCAACGGAGCACAGGAGA

TAGTATTGATACTCCTAATTATGATGTGCAGAAACACATCAATAAGTTATGTGGCATGTTATTAATCACAGAAGATG

CTAATCATAAATTCACTGGGTTAATAGGTATGTTATATGCGATGTCTAGGTTAGGAAGAGAAGACACCATAAAAATA

CTCAGAGATGCGGGATATCATGTAAAAGCAAATGGAGTAGATGTAACAACACATCGTCAAGACATTAATGGAAAAGA

AATGAAATTTGAAGTGTTAACATTGGCAAGCTTAACAACTGAAATTCAAATCAACATTGAGATAGAATCTAGAAAAT

CCTACAAAAAAATGCTAAAAGAAATGGGAGAGGTAGCTCCAGAATACAGGCATGACTCTCCTGATTGTGGGATGATA

-continued

| Exemplary Sequences |
|---|
| ATATTATGTATAGCAGCATTAGTAATAACTAAATTAGCAGCAGGGGACAGATCTGGTCTTACAGCCGTGATTAGGAG |
| AGCTAATAATGTCCTAAAAAATGAAATGAAACGTTACAAAGGCTTACTACCCAAGGACATAGCCAACAGCTTCTATG |
| AAGTGTTTGAAAAACATCCCCACTTTATAGATGTTTTTGTTCATTTTGGTATAGCACAATCTTCTACCAGAGGTGGC |
| AGTAGAGTTGAAGGGATTTTTGCAGGATTGTTTATGAATGCCTATGGTGCAGGGCAAGTGATGTTACGGTGGGGAGT |
| CTTAGCAAAATCGGTTAAAAATATTATGTTAGGACATGCTAGTGTGCAAGCAGAAATGGAACAAGTTGTTGAGGTTT |
| ATGAATATGCCCAAAAATTGGGTGGTGAAGCAGGATTCTACCATATATTGAACAACCCAAAAGCATCATTATTATCT |
| TTGACTCAATTTCCTCACTTCTCCAGTGTAGTATTAGGCAATGCTGCTGGCCTAGGCATAATGGGAGAGTACAGAGG |
| TACACCGAGGAATCAAGATCTATATGATGCAGCAAAGGCATATGCTGAACAACTCAAAGAAAATGGTGTGATTAACT |
| ACAGTGTACTAGACTTGACAGCAGAAGAACTAGAGGCTATCAAACATCAGCTTAATCCAAAAGATAATGATGTAGAG |
| CTTTGAGTTAATAAAAAATGGGGCAAATAAATCATCATGGAAAAGTTTGCTCCTGAATTCCATGGAGAAGATGCAAA |
| CAACAGGGCTACTAAATTCCTAGAATCAATAAAGGGCAAATTCACATCACCCAAAGATCCCAAGAAAAAAGATAGTA |
| TCATATCTGTCAACTCAATAGATATAGAAGTAACCAAAGAAAGCCCTATAACATCAAATTCAACTATTATCAACCCA |
| ACAAATGAGACAGATGATACTGCAGGGAACAAGCCCAATTATCAAAGAAAACCTCTAGTAAGTTTCAAAGAAGACCC |
| TACACCAAGTGATAATCCCTTTTCTAAACTATACAAAGAAACCATAGAAACATTTGATAACAATGAAGAAGAATCCA |
| GCTATTCATACGAAGAAATAAATGATCAGACAAACGATAATATAACAGCAAGATTAGATAGGATTGATGAAAAATTA |
| AGTGAAATACTAGGAATGCTTCACACATTAGTAGTGGCAAGTGCAGGACCTACATCTGCTCGGGATGGTATAAGAGA |
| TGCCATGGTTGGTTTAAGAGAAGAAATGATAGAAAAAATCAGAACTGAAGCATTAATGACCAATGACAGATTAGAAG |
| CTATGGCAAGACTCAGGAATGAGGAAAGTGAAAAGATGGCAAAAGACACATCAGATGAAGTGTCTCTCAATCCAACA |
| TCAGAGAAATTGAACAACCTATTGGAAGGGAATGATAGTGACAATGATCTATCACTTGAAGATTTCTGATTAGTTAC |
| CAATCTTCACATCAACACACAATACCAACAGAAGACCAACAAACTAACCAACCCAATCATCCAACCAAACATCCATC |
| CGCCAATCAGCCAAACAGCCAACAAAACAACCAGCCAATCCAAAACTAACCACCCGGAAAAAATCTATAATATAGTT |
| ACAAAAAAAGGAAAGGGTGGGGCAAATATGGAAACATACGTGAACAAGCTTCACGAAGGCTCCACATACACAGCTGC |
| TGTTCAATACAATGTCTTAGAAAAAGACGATGACCCTGCATCACTTACAATATGGGTGCCCATGTTCCAATCATCTA |
| TGCCAGCAGATTTACTTATAAAAGAACTAGCTAATGTCAACATACTAGTGAAACAAATATCCACACCCAAGGGACCT |
| TCACTAAGAGTCATGATAAACTCAAGAAGTGCAGTGCTAGCACAAATGCCCAGCAAATTTACCATATGCGCTAATGT |
| GTCCTTGGATGAAAGAAGCAAACTAGCATATGATGTAACCACACCCTGTGAAATCAAGGCATGTAGTCTAACATGCC |
| TAAAATCAAAAAATATGTTGACTACAGTTAAAGATCTCACTATGAAGACACTCAACCCTACACATGATATTATTGCT |
| TTATGTGAATTTGAAAACATAGTAACATCAAAAAAAGTCATAATACCAACATACCTAAGATCCATCAGTGTCAGAAA |
| TAAAGATCTGAACACACTTGAAAATATAACAACCACTGAATTCAAAAATGCTATCACAAATGCAAAAATCATCCCTT |
| ACTCAGGATTACTATTAGTCATCACAGTGACTGACAACAAAGGAGCATTCAAATACATAAAGCCACAAAGTCAATTC |
| ATAGTAGATCTTGGAGCTTACCTAGAAAAAGAAAGTATATATTATGTTACCACAAATTGGAAGCACACAGCTACACG |
| ATTTGCAATCAAACCCATGGAAGATTAACCTTTTTCCTCTACATCAGTGTGTTAATTCATACAAACTTTCTACCTAC |
| ATTCTTCACTTCACCATCACAATCACAAACACTCTGTGGTTCAACCAATCAAACAAAACTTATCTGAAGTCCCAGAT |
| CATCCCAAGTCATTGTTTATCAGATCTAGTACTCAAATAAGTTAATAAAAAATATACACATGGGGCAAATAATCATT |
| GGAGGAAATCCAACTAATCACAATATCTGTTAACATAGACAAGTCCACACACCATACAGAATCAACCAATGGAAAAT |
| ACATCCATAACAATAGAATTCTCAAGCAAATTCTGGCCTTACTTTACACTAATACACATGATCACAACAATAATCTC |
| TTTGCTAATCATAATCTCCATCATGATTGCAATACTAAACAAACTTTGTGAATATAACGTATTCCATAACAAAACCT |
| TTGAGTTACCAAGAGCTCGAGTTAATACTTGATAAAGTAGTTAATTAAAAATAGTCATAACAATGAACTAGGATATC |
| AAGACTAACAATAACATTGGGGCAAATGCAAACATGTCCAAAAACAAGGACCAACGCACCGCTAAGACATTAGAAAG |

-continued

| Exemplary Sequences |
| --- |

GACCTGGGACACTCTCAATCATTTATTATTCATATCATCGTGCTTATATAAGTTAAATCTTAAATCTGTAGCACAAA

TCACATTATCCATTCTGGCAATGATAATCTCAACTTCACTTATAATTGCAGCCATCATATTCATAGCCTCGGCAAAC

CACAAAGTCACACCAACAACTGCAATCATACAAGATGCAACAAGCCAGATCAAGAACACAACCCCAACATACCTCAC

CCAGAATCCTCAGCTTGGAATCAGTCCCTCTAATCCGTCTGAAATTACATCACAAATCACCACCATACTAGCTTCAA

CAACACCAGGAGTCAAGTCAACCCTGCAATCCACAACAGTCAAGACCAAAAACACAACAACAACTCAAACACAACCC

AGCAAGCCCACCACAAAACAACGCCAAAACAAACCACCAAGCAAACCCAATAATGATTTTCACTTTGAAGTGTTCAA

CTTTGTACCCTGCAGCATATGCAGCAACAATCCAACCTGCTGGGCTATCTGCAAAAGAATACCAAACAAAAAACCAG

GAAAGAAAACCACTACCAAGCCCACAAAAAAACCAACCCTCAAGACAACCAAAAAAGATCCCAAACCTCAAACCACT

AAATCAAAGGAAGTACCCACCACCAAGCCCACAGAAGAGCCAACCATCAACACCACCAAAACAAACATCATAACTAC

ACTACTCACCTCCAACACCACAGGAAATCCAGAACTCACAAGTCAAATGGAAACCTTCCACTCAACTTCCTCCGAAG

GCAATCCAAGCCCTTCTCAAGTCTCTACAACATCCGAGTACCCATCACAACCTTCATCTCCACCCAACACACCACGC

CAGTAGTTACTTAAAAACATATTATCACAAAAGGCCTTGACCAACTTAAACAGAATCAAAATAAACTCTGGGGCAAA

TAACAATGGAGTTGCTAATCCTCAAAGCAAATGCAATTACCACAATCCTCACTGCAGTCACATTTTGTTTTGCTTCT

GGTCAAAACATCACTGAAGAATTTTATCAATCAACATGCAGTGCAGTTAGCAAAGGCTATCTTAGTGCTCTGAGAAC

TGGTTGGTATACCAGTGTTATAACTATAGAATTAAGTAATATCAAGAAAAATAAGTGTAATGGAACAGATGCTAAGG

TAAAATTGATAAAACAAGAATTAGATAAATATAAAAATGCTGTAACAGAATTGCAGTTGCTCATGCAAAGCACACAA

GCAACAAACAATCGAGCCAGAAGAGAACTACCAAGGTTTATGAATTATACACTCAACAATGCCAAAAAAACCAATGT

AACATTAAGCAAGAAAAGGAAAAGAAGATTTCTTGGTTTTTTGTTAGGTGTTGGATCTGCAATCGCCAGTGGCGTTG

CTGTATCTAAGGTCCTGCACCTAGAAGGGGAAGTGAACAAGATCAAAAGTGCTCTACTATCCACAAACAAGGCTGTA

GTCAGCTTATCAAATGGAGTTAGTGTTTTAACCAGCAAAGTGTTAGACCTCAAAAACTATATAGATAAACAATTGTT

ACCTATTGTGAACAAGCAAAGCTGCAGCATATCAAATATAGAAACTGTGATAGAGTTCCAACAAAAGAACAACAGAC

TACTAGAGATTACCAGGGAATTTAGTGTTAATGCAGGCGTAACTACACCTGTAAGCACTTACATGTTAACTAATAGT

GAATTATTGTCATTAATCAATGATATGCCTATAACAAATGATCAGAAAAAGTTAATGTCCAACAATGTTCAAATAGT

TAGACAGCAAAGTTACTCTATCATGTCCATAATAAAAGAGGAAGTCTTAGCATATGTAGTACAATTACCACTATATG

GTGTTATAGATACACCCTGTTGGAAACTACACACATCCCCTCTATGTACAACCAACACAAAAGAAGGGTCCAACATC

TGTTTAACAAGAACTGACAGAGGATGGTACTGTGACAATGCAGGATCAGTATCTTTCTTCCCACAAGCTGAAACATG

TAAAGTTCAATCAAATCGAGTATTTTGTGACACAATGAACAGTTTAACATTACCAAGTGAAGTAAATCTCTGCAATG

TTGACATATTCAACCCCAAATATGATTGTAAAATTATGACTTCAAAAACAGATGTAAGCAGCTCCGTTATCACATCT

CTAGGAGCCATTGTGTCATGCTATGGCAAAACTAAATGTACAGCATCCAATAAAAATCGTGGAATCATAAAGACATT

TTCTAACGGGTGCGATTATGTATCAAATAAAGGGGTGGACACTGTGTCTGTAGGTAACACATTATATTATGTAAATA

AGCAAGAAGGTAAAAGTCTCTATGTAAAAGGTGAACCAATAATAAATTTCTATGACCCATTAGTATTCCCCTCTGAT

GAATTTGATGCATCAATATCTCAAGTCAACGAGAAGATTAACCAGAGCCTAGCATTTATTCGTAAATCCGATGAATT

ATTACATAATGTAAATGCTGGTAAATCCACCACAAATATCATGATAACTACTATAATTATAGTGATTATAGTAATAT

TGTTATCATTAATTGCTGTTGGACTGCTCTTATACTGTAAGGCCAGAAGCACACCAGTCACACTAAGCAAAGATCAA

CTGAGTGGTATAAATAATATTGCATTTAGTAACTAAATAAAAATAGCACCTAATCATGTTCTTACAATGGTTTACTA

TCTGCTCATAGACAACCCATCTGTCATTGGATTTTCTTAAAATCTGAACTTCATCGAAACTCTCATCTATAAACCAT

CTCACTTACACTATTTAAGTAGATTCCTAGTTTATAGTTATATAAAACACAATTGCATGCCAGATTAACTTACCATC

TGTAAAAATGAAAACTGGGGCAAATATGTCACGAAGGAATCCTTGCAAATTTGAAATTCGAGGTCATTGCTTAAATG

-continued

| Exemplary Sequences |
|---|
| GTAAGAGGTGTCATTTTAGTCATAATTATTTTGAATGGCCACCCCATGCACTGCTTGTAAGACAAAACTTTATGTTA |
| AACAGAATACTTAAGTCTATGGATAAAAGTATAGATACCTTATCAGAAATAAGTGGAGCTGCAGAGTTGGACAGAAC |
| AGAAGAGTATGCTCTTGGTGTAGTTGGAGTGCTAGAGAGTTATATAGGATCAATAAACAATATAACTAAACAATCAG |
| CATGTGTTGCCATGAGCAAACTCCTCACTGAACTCAATAGTGATGATATCAAAAAGCTGAGGGACAATGAAGAGCTA |
| AATTCACCCAAGATAAGAGTGTACAATACTGTCATATCATATATTGAAAGCAACAGGAAAAACAATAAACAAACTAT |
| CCATCTGTTAAAAAGATTGCCAGCAGACGTATTGAAGAAAACCATCAAAAACACATTGGATATCCATAAGAGCATAA |
| CCATCAACAACCCAAAAGAATCAACTGTTAGTGATACAAATGACCATGCCAAAAATAATGATACTACCTGACAAATA |
| ACGTTCAATTCTAACACTCACCACATCGTTACATTATTAATTCAAACAATTCAAGTTGTGGGACAAAATGGATCCCA |
| TTATTAATGGAAATTCTGCTAATGTTTATCTAACCGATAGTTATTTAAAAGGTGTTATCTCTTTCTCAGAGTGTAAT |
| GCTTTAGGAAGTTACATATTCAATGGTCCTTATCTCAAAAATGATTATACCAACTTAATTAGTAGACAAAATCCATT |
| AATAGAACACATGAATCTAAAGAAACTAAATATAACACAGTCCTTAATATCTAAGTATCATAAAGGTGAAATAAAAT |
| TAGAAGAACCTACTTATTTTCAGTCATTACTTATGACATACAAGAGTATGACCTCGTCAGAACAGATTGCTACCACT |
| AATTTACTTAAAAAGATAATAAGAAGAGCTATAGAAATAAGTGATGTCAAAGTCTATGCTATATTGAATAAACTAGG |
| GCTTAAAGAAAAGGACAAGATTAAATCCAACAATGGACAAGATGAAGACAACTCAGTTATTACGACCATAATCAAAG |
| ATGATATACTTTCAGCTGTTAAAGATAATCAATCTCATCTTAAAGCAGACAAAAATCACTCTACAAAACAAAAAGAC |
| ACAATCAAAACAACACTCTTGAAGAAATTGATGTGTTCAATGCAACATCCTCCATCATGGTTAATACATTGGTTTAA |
| CTTATACACAAAATTAAACAACATATTAACACAGTATCGATCAAATGAGGTAAAAAACCATGGGTTTACATTGATAG |
| ATAATCAAACTCTTAGTGGATTTCAATTTATTTTGAACCAATATGGTTGTATAGTTTATCATAAGGAACTCAAAAGA |
| ATTACTGTGACAACCTATAATCAATTCTTGACATGGAAAGATATTAGCCTTAGTAGATTAAATGTTTGTTTAATTAC |
| ATGGATTAGTAACTGCTTGAACACATTAAATAAAAGCTTAGGCTTAAGATGCGGATTCAATAATGTTATCTTGACAC |
| AACTATTCCTTTATGGAGATTGTATACTAAAGCTATTTCACAATGAGGGGTTCTACATAATAAAAGAGGTAGAGGGA |
| TTTATTATGTCTCTAATTTTAAATATAACAGAAGAAGATCAATTCAGAAAACGATTTTATAATAGTATGCTCAACAA |
| CATCACAGATGCTGCTAATAAAGCTCAGAAAAATCTGCTATCAAGAGTATGTCATACATTATTAGATAAGACAGTGT |
| CCGATAATATAATAAATGGCAGATGGATAATTCTATTAAGTAAGTTCCTTAAATTAATTAAGCTTGCAGGTGACAAT |
| AACCTTAACAATCTGAGTGAACTATATTTTTTGTTCAGAATATTTGGACACCCAATGGTAGATGAAAGACAAGCCAT |
| GGATGCTGTTAAAATTAATTGCAATGAGACCAAATTTTACTTGTTAAGCAGTCTGAGTATGTTAAGAGGTGCCTTTA |
| TATATAGAATTATAAAAGGGTTTGTAAATAATTACAACAGATGGCCTACTTTAAGAAATGCTATTGTTTTACCCTTA |
| AGATGGTTAACTTACTATAAACTAAACACTTATCCTTCTTTGTTGGAACTTACAGAAAGAGATTTGATTGTGTTATC |
| AGGACTACGTTTCTATCGTGAGTTTCGGTTGCCTAAAAAAGTGGATCTTGAAATGATTATAAATGATAAAGCTATAT |
| CACCTCCTAAAAATTTGATATGGACTAGTTTCCCTAGAAATTACATGCCATCACACATACAAAACTATATAGAACAT |
| GAAAAATTAAAATTTTCCGAGAGTGATAAATCAAGAAGAGTATTAGAGTATTATTTAAGAGATAACAAATTCAATGA |
| ATGTGATTTATACAACTGTGTAGTTAATCAAAGTTATCTCAACAACCCTAATCATGTGGTATCATTGACAGGCAAAG |
| AAAGAGAACTCAGTGTAGGTAGAATGTTTGCAATGCAACCGGGAATGTTCAGACAGGTTCAAATATTGGCAGAGAAA |
| ATGATAGCTGAAAACATTTTACAATTCTTTCCTGAAAGTCTTACAAGATATGGTGATCTAGAACTACAAAAAATATT |
| AGAACTGAAAGCAGGAATAAGTAACAAATCAAATCGCTACAATGATAATTACAACAATTACATTAGTAAGTGCTCTA |
| TCATCACAGATCTCAGCAAATTCAATCAAGCATTTCGATATGAAACGTCATGTATTTGTAGTGATGTGCTGGATGAA |
| CTGCATGGTGTACAATCTCTATTTTCCTGGTTACATTTAACTATTCCTCATGTCACAATAATATGCACATATAGGCA |
| TGCACCCCCCTATATAGGAGATCATATTGTAGATCTTAACAATGTAGATGAACAAAGTGGATTATATAGATATCACA |
| TGGGTGGCATCGAAGGGTGGTGTCAAAAACTATGGACCATAGAAGCTATATCACTATTGGATCTAATATCTCTCAAA |

-continued

| Exemplary Sequences |
| --- |
| GGGAAATTCTCAATTACTGCTTTAATTAATGGTGACAATCAATCAATAGATATAAGCAAACCAATCAGACTCATGGA |
| AGGTCAAACTCATGCTCAAGCAGATTATTTGCTAGCATTAAATAGCCTTAAATTACTGTATAAAGAGTATGCAGGCA |
| TAGGCCACAAATTAAAAGGAACTGAGACTTATATATCACGAGATATGCAATTTATGAGTAAAACAATTCAACATAAC |
| GGTGTATATTACCCAGCTAGTATAAAGAAAGTCCTAAGAGTGGGACCGTGGATAAACACTATACTTGATGATTTCAA |
| AGTGAGTCTAGAATCTATAGGTAGTTTGACACAAGAATTAGAATATAGAGGTGAAAGTCTATTATGCAGTTTAATAT |
| TTAGAAATGTATGGTTATATAATCAGATTGCTCTACAATTAAAAAATCATGCATTATGTAACAATAAACTATATTTG |
| GACATATTAAAGGTTCTGAAACACTTAAAAACCTTTTTTAATCTTGATAATATTGATACAGCATTAACATTGTATAT |
| GAATTTACCCATGTTATTTGGTGGTGGTGATCCCAACTTGTTATATCGAAGTTTCTATAGAAGAACTCCTGACTTCC |
| TCACAGAGGCTATAGTTCACTCTGTGTTCATACTTAGTTATTATACAAACCATGACTTAAAAGATAAACTTCAAGAT |
| CTGTCAGATGATAGATTGAATAAGTTCTTAACATGCATAATCACGTTTGACAAAAACCCTAATGCTGAATTCGTAAC |
| ATTGATGAGAGATCCTCAAGCTTTAGGGTCTGAGAGACAAGCTAAAATTACTAGCGAAATCAATAGACTGGCAGTTA |
| CAGAGGTTTTGAGTACAGCTCCAAACAAAATATTCTCCAAAAGTGCACAACATTATACTACTACAGAGATAGATCTA |
| AATGATATTATGCAAAATATAGAACCTACATATCCTCATGGGCTAAGAGTTGTTTATGAAAGTTTACCCTTTTATAA |
| AGCAGAGAAAATAGTAAATCTTATATCAGGTACAAAATCTATAACTAACATACTGGAAAAAACTTCTGCCATAGACT |
| TAACAGATATTGATAGAGCCACTGAGATGATGAGGAAAAACATAACTTTGCTTATAAGGATACTTCCATTGGATTGT |
| AACAGAGATAAAAGAGAGATATTGAGTATGGAAAACCTAAGTATTACTGAATTAAGCAAATATGTTAGGGAAAGATC |
| TTGGTCTTTATCCAATATAGTTGGTGTTACATCACCCAGTATCATGTATACAATGGACATCAAATATACTACAAGCA |
| CTATATCTAGTGGCATAATTATAGAGAAATATAATGTTAACAGTTTAACACGTGGTGAGAGAGGACCCACTAAACCA |
| TGGGTTGGTTCATCTACACAAGAGAAAAAAACAATGCCAGTTTATAATAGACAAGTCTTAACCAAAAAACAGAGAGA |
| TCAAATAGATCTATTAGCAAAATTGGATTGGGTGTATGCATCTATAGATAACAAGGATGAATTCATGGAAGAACTCA |
| GCATAGGAACCCTTGGGTTAACATATGAAAAGGCCAAGAAATTATTTCCACAATATTTAAGTGTCAATTATTTGCAT |
| CGCCTTACAGTCAGTAGTAGACCATGTGAATTCCCTGCATCAATACCAGCTTATAGAACAACAAATTATCACTTTGA |
| CACTAGCCCTATTAATCGCATATTAACAGAAAAGTATGGTGATGAAGATATTGACATAGTATTCCAAAACTGTATAA |
| GCTTTGGCCTTAGTTTAATGTCAGTAGTAGAACAATTTACTAATGTATGTCCTAACAGAATTATTCTCATACCTAAG |
| CTTAATGAGATACATTTGATGAAACCTCCCATATTCACAGGTGATGTTGATATTCACAAGTTAAAACAAGTGATACA |
| AAAACAGCATATGTTTTTACCAGACAAAATAAGTTTGACTCAATATGTGGAATTATTCTTAAGTAATAAAACACTCA |
| AATCTGGATCTCATGTTAATTCTAATTTAATATTGGCACATAAAATATCTGACTATTTTCATAATACTTACATTTTA |
| AGTACTAATTTAGCTGGACATTGGATTCTGATTATACAACTTATGAAAGATTCTAAAGGTATTTTTGAAAAAGATTG |
| GGGAGAGGGATATATAACTGATCATATGTTTATTAATTTGAAAGTTTTCTTCAATGCTTATAAGACCTATCTCTTGT |
| GTTTTCATAAAGGTTATGGCAAAGCAAAGCTGGAGTGTGATATGAACACTTCAGATCTTCTATGTGTATTGGAATTA |
| ATAGACAGTAGTTATTGGAAGTCTATGTCTAAGGTATTTTTAGAACAAAAAGTTATCAAATACATTCTTAGCCAAGA |
| TGCAAGTTTACATAGAGTAAAAGGATGTCATAGCTTCAAATTATGGTTTCTTAAACGTCTTAATGTAGCAGAATTCA |
| CAGTTTGCCCTTGGGTTGTTAACATAGATTATCATCCAACACATATGAAAGCAATATTAACTTATATAGATCTTGTT |
| AGAATGGGATTGATAAATATAGATAGAATACACATTAAAAATAAACACAAATTCAATGATGAATTTTATACTTCTAA |
| TCTCTTCTACATTAATTATAACTTCTCAGATAATACTCATCTATTAACTAAACATATAAGGATTGCTAATTCTGAAT |
| TAGAAAATAATTACAACAAATTATATCATCCTACACCAGAAACCCTAGAGAATATACTAGCCAATCCGATTAAAAGT |
| AATGACAAAAAGACACTGAATGACTATTGTATAGGTAAAAATGTTGACTCAATAATGTTACCATTGTTATCTAATAA |
| GAAGCTTATTAAATCGTCTGCAATGATTAGAACCAATTACAGCAAACAAGATTTGTATAATTTATTCCCTATGGTTG |

-continued

| Exemplary Sequences |
| --- |
| TGATTGATAGAATTATAGATCATTCAGGCAATACAGCCAAATCCAACCAACTTTACACTACTACTTCCCACCAAATA |
| TCCTTAGTGCACAATAGCACATCACTTTACTGCATGCTTCCTTGGCATCATATTAATAGATTCAATTTTGTATTTAG |
| TTCTACAGGTTGTAAAATTAGTATAGAGTATATTTTAAAAGATCTTAAAATTAAAGATCCCAATTGTATAGCATTCA |
| TAGGTGAAGGAGCAGGGAATTTATTATTGCGTACAGTAGTGGAACTTCATCCTGACATAAGATATATTTACAGAAGT |
| CTGAAAGATTGCAATGATCATAGTTTACCTATTGAGTTTTTAAGGCTGTACAATGGACATATCAACATTGATTATGG |
| TGAAAATTTGACCATTCCTGCTACAGATGCAACCAACAACATTCATTGGTCTTATTTACATATAAAGTTTGCTGAAC |
| CTATCAGTCTTTTTGTCTGTGATGCCGAATTGTCTGTAACAGTCAACTGGAGTAAAATTATAATAGAATGGAGCAAG |
| CATGTAAGAAAGTGCAAGTACTGTTCCTCAGTTAATAAATGTATGTTAATAGTAAAATATCATGCTCAAGATGATAT |
| TGATTTCAAATTAGACAATATAACTATATTAAAAACTTATGTATGCTTAGGCAGTAAGTTAAAGGGATCGGAGGTTT |
| ACTTAGTCCTTACAATAGGTCCTGCGAATATATTCCCAGTATTTAATGTAGTACAAAATGCTAAATTGATACTATCA |
| AGAACCAAAAATTTCATCATGCCTAAGAAAGCTGATAAAGAGTCTATTGATGCAAATATTAAAAGTTTGATACCCTT |
| TCTTTGTTACCCTATAACAAAAAAAGGAATTAATACTGCATTGTCAAAACTAAAGAGTGTTGTTAGTGGAGATATAC |
| TATCATATTCTATAGCTGGACGTAATGAAGTTTTCAGCAATAAACTTATAAATCATAAGCATATGAACATCTTAAAA |
| TGGTTCAATCATGTTTTAAATTTCAGATCAACAGAACTAAACTATAACCATTTATATATGGTAGAATCTACATATCC |
| TTACCTAAGTGAATTGTTAAACAGCTTGACAACCAATGAACTTAAAAAACTGATTAAAATCACAGGTAGTCTGTTAT |
| ACAACTTTCATAATGAATAATGAATAAAGATCTTATAATAAAAATTCCCATAGCTATACACTAACACTGTATTCAAT |
| TATAGTTATTAAAAATTAAAAATCATATAATTTTTTAAATAACTTTTAGTGAACTAATCCTAAAGTTATCATTTTAA |
| TCTTGGAGGAATAAATTTAAACCCTAATCTAATTGGTTTATATGTGTATTAACTAAATTACGAGATATTAGTTTTTG |
| ACACTTTTTTTCTCGT |
| Antigenomic cDNA sequence of LID/ΔM2-2-HindIII (SEQ ID NO: 7) |
| ACGGGAAAAAATGCGTACAACAAACTTGCATAAACCAAAAAAATGGGGCAAATAAGAATTTGATAAGTACCACTTAA |
| ATTTAACTCCCTTGGTTAGAGATGGGCAGCAATTCATTGAGTATGATAAAAGTTAGATTACAAAATTTGTTTGACAA |
| TGATGAAGTAGCATTGTTAAAAATAACATGCTATACTGATAAATTAATACATTTAACTAATGCTTTGGCTAAGGCAG |
| TGATACATACAATCAAATTGAATGGCATTGTGTTTGTGCATGTTATTACAAGTAGTGATATTTGCCCTAATAATAAT |
| ATTGTAGTAAAATCCAATTTCACAACAATGCCAGTACTACAAAATGGAGGTTATATATGGGAAATGATGGAATTAAC |
| ACATTGCTCTCAACCTAATGGTCTACTAGATGACAATTGTGAAATTAAATTCTCCAAAAAACTAAGTGATTCAACAA |
| TGACCAATTATATGAATCAATTATCTGAATTACTTGGATTTGATCTTAATCCATAAATTATAATTAATATCAACTAG |
| CAAATCAATGTCACTAACACCATTAGTTAATATAAAACTTAACAGAAGACAAAAATGGGGCAAATAAATCAATTCAG |
| CCAACCCAACCATGGACACAACCCACAATGATAATACACCACAAAGACTGATGATCACAGACATGAGACCGTTGTCA |
| CTTGAGACCATAATAACATCACTAACCAGAGACATCATAACACACAAATTTATATACTTGATAAATCATGAATGCAT |
| AGTGAGAAAACTTGATGAAAGACAGGCCACATTTACATTCCTGGTCAACTATGAAATGAAACTATTACACAAAGTAG |
| GAAGCACTAAATATAAAAAATATACTGAATACAACACAAAATATGGCACTTTCCCTATGCCAATATTCATCAATCAT |
| GATGGGTTCTTAGAATGCATTGGCATTAAGCCTACAAAGCATACTCCCATAATATACAAGTATGATCTCAATCCATA |
| AATTTCAACACAATATTCACACAATCTAAAACAACAACTCTATGCATAACTATACTCCATAGTCCAGATGGAGCCTG |
| AAAATTATAGTAATTTAAAACTTAAGGAGAGATATAAGATAGAAGATGGGGCAAATACAACCATGGCTCTTAGCAAA |
| GTCAAGTTGAATGATACACTCAACAAAGATCAACTTCTGTCATCCAGCAAATACACCATCCAACGGAGCACAGGAGA |
| TAGTATTGATACTCCTAATTATGATGTGCAGAAACACATCAATAAGTTATGTGGCATGTTATTAATCACAGAAGATG |
| CTAATCATAAATTCACTGGGTTAATAGGTATGTTATATGCGATGTCTAGGTTAGGAAGAGAAGACACCATAAAAATA |
| CTCAGAGATGCGGGATATCATGTAAAAGCAAATGGAGTAGATGTAACAACACATCGTCAAGACATTAATGGAAAAGA |

-continued

| Exemplary Sequences |
|---|
| AATGAAATTTGAAGTGTTAACATTGGCAAGCTTAACAACTGAAATTCAAATCAACATTGAGATAGAATCTAGAAAAT |
| CCTACAAAAAAATGCTAAAAGAAATGGGAGAGGTAGCTCCAGAATACAGGCATGACTCTCCTGATTGTGGGATGATA |
| ATATTATGTATAGCAGCATTAGTAATAACTAAATTAGCAGCAGGGGACAGATCTGGTCTTACAGCCGTGATTAGGAG |
| AGCTAATAATGTCCTAAAAAATGAAATGAAACGTTACAAAGGCTTACTACCCAAGGACATAGCCAACAGCTTCTATG |
| AAGTGTTTGAAAAACATCCCCACTTTATAGATGTTTTTGTTCATTTTGGTATAGCACAATCTTCTACCAGAGGTGGC |
| AGTAGAGTTGAAGGGATTTTTGCAGGATTGTTTATGAATGCCTATGGTGCAGGGCAAGTGATGTTACGGTGGGGAGT |
| CTTAGCAAAATCGGTTAAAAATATTATGTTAGGACATGCTAGTGTGCAAGCAGAAATGGAACAAGTTGTTGAGGTTT |
| ATGAATATGCCCAAAAATTGGGTGGTGAAGCAGGATTCTACCATATATTGAACAACCCAAAAGCATCATTATTATCT |
| TTGACTCAATTTCCTCACTTCTCCAGTGTAGTATTAGGCAATGCTGCTGGCCTAGGCATAATGGGAGAGTACAGAGG |
| TACACCGAGGAATCAAGATCTATATGATGCAGCAAAGGCATATGCTGAACAACTCAAAGAAAATGGTGTGATTAACT |
| ACAGTGTACTAGACTTGACAGCAGAAGAACTAGAGGCTATCAAACATCAGCTTAATCCAAAAGATAATGATGTAGAG |
| CTTTGAGTTAATAAAAAATGGGGCAAATAAATCATCATGGAAAAGTTTGCTCCTGAATTCCATGGAGAAGATGCAAA |
| CAACAGGGCTACTAAATTCCTAGAATCAATAAAGGGCAAATTCACATCACCCAAAGATCCCAAGAAAAAAGATAGTA |
| TCATATCTGTCAACTCAATAGATATAGAAGTAACCAAAGAAAGCCCTATAACATCAAATTCAACTATTATCAACCCA |
| ACAAATGAGACAGATGATACTGCAGGGAACAAGCCCAATTATCAAAGAAAACCTCTAGTAAGTTTCAAAGAAGACCC |
| TACACCAAGTGATAATCCCTTTTCTAAACTATACAAAGAAACCATAGAAACATTTGATAACAATGAAGAAGAATCCA |
| GCTATTCATACGAAGAAATAAATGATCAGACAAACGATAATATAACAGCAAGATTAGATAGGATTGATGAAAAATTA |
| AGTGAAATACTAGGAATGCTTCACACATTAGTAGTGGCAAGTGCAGGACCTACATCTGCTCGGGATGGTATAAGAGA |
| TGCCATGGTTGGTTTAAGAGAAGAAATGATAGAAAAAATCAGAACTGAAGCATTAATGACCAATGACAGATTAGAAG |
| CTATGGCAAGACTCAGGAATGAGGAAAGTGAAAAGATGGCAAAAGACACATCAGATGAAGTGTCTCTCAATCCAACA |
| TCAGAGAAATTGAACAACCTATTGGAAGGGAATGATAGTGACAATGATCTATCACTTGAAGATTTCTGATTAGTTAC |
| CAATCTTCACATCAACACACAATACCAACAGAAGACCAACAAACTAACCAACCCAATCATCCAACCAAACATCCATC |
| CGCCAATCAGCCAAACAGCCAACAAAACAACCAGCCAATCCAAAACTAACCACCCGGAAAAAATCTATAATATAGTT |
| ACAAAAAAAGGAAAGGGTGGGGCAAATATGGAAACATACGTGAACAAGCTTCACGAAGGCTCCACATACACAGCTGC |
| TGTTCAATACAATGTCTTAGAAAAAGACGATGACCCTGCATCACTTACAATATGGGTGCCCATGTTCCAATCATCTA |
| TGCCAGCAGATTTACTTATAAAAGAACTAGCTAATGTCAACATACTAGTGAAACAAATATCCACACCCAAGGGACCT |
| TCACTAAGAGTCATGATAAACTCAAGAAGTGCAGTGCTAGCACAAATGCCCAGCAAATTTACCATATGCGCTAATGT |
| GTCCTTGGATGAAAGAAGCAAACTAGCATATGATGTAACCACACCCTGTGAAATCAAGGCATGTAGTCTAACATGCC |
| TAAAATCAAAAAATATGTTGACTACAGTTAAAGATCTCACTATGAAGACACTCAACCCTACACATGATATTATTGCT |
| TTATGTGAATTTGAAAACATAGTAACATCAAAAAAAGTCATAATACCAACATACCTAAGATCCATCAGTGTCAGAAA |
| TAAAGATCTGAACACACTTGAAAATATAACAACCACTGAATTCAAAAATGCTATCACAAATGCAAAAATCATCCCTT |
| ACTCAGGATTACTATTAGTCATCACAGTGACTGACAACAAAGGAGCATTCAAATACATAAAGCCACAAAGTCAATTC |
| ATAGTAGATCTTGGAGCTTACCTAGAAAAAGAAAGTATATATTATGTTACCACAAATTGGAAGCACACAGCTACACG |
| ATTTGCAATCAAACCCATGGAAGATTAACCTTTTTCCTCTACATCAGTGTGTTAATTCATACAAACTTTCTACCTAC |
| ATTCTTCACTTCACCATCACAATCACAAACACTCTGTGGTTCAACCAATCAAACAAAACTTATCTGAAGTCCCAGAT |
| CATCCCAAGTCATTGTTTATCAGATCTAGTACTCAAATAAGTTAATAAAAAATATACACATGGGGCAAATAATCATT |
| GGAGGAAATCCAACTAATCACAATATCTGTTAACATAGACAAGTCCACACACCATACAGAATCAACCAATGGAAAAT |
| ACATCCATAACAATAGAATTCTCAAGCAAATTCTGGCCTTACTTTACACTAATACACATGATCACAACAATAATCTC |

-continued

| Exemplary Sequences |
|---|
| TTTGCTAATCATAATCTCCATCATGATTGCAATACTAAACAAACTTTGTGAATATAACGTATTCCATAACAAAACCT |
| TTGAGTTACCAAGAGCTCGAGTTAATACTTGATAAAGTAGTTAATTAAAAATAGTCATAACAATGAACTAGGATATC |
| AAGACTAACAATAACATTGGGGCAAATGCAAACATGTCCAAAAACAAGGACCAACGCACCGCTAAGACATTAGAAAG |
| GACCTGGGACACTCTCAATCATTTATTATTCATATCATCGTGCTTATATAAGTTAAATCTTAAATCTGTAGCACAAA |
| TCACATTATCCATTCTGGCAATGATAATCTCAACTTCACTTATAATTGCAGCCATCATATTCATAGCCTCGGCAAAC |
| CACAAAGTCACACCAACAACTGCAATCATACAAGATGCAACAAGCCAGATCAAGAACACAACCCCAACATACCTCAC |
| CCAGAATCCTCAGCTTGGAATCAGTCCCTCTAATCCGTCTGAAATTACATCACAAATCACCACCATACTAGCTTCAA |
| CAACACCAGGAGTCAAGTCAACCCTGCAATCCACAACAGTCAAGACCAAAAACACAACAACAACTCAAACACAACCC |
| AGCAAGCCCACCACAAAACAACGCCAAAACAAACCACCAAGCAAACCCAATAATGATTTTCACTTTGAAGTGTTCAA |
| CTTTGTACCCTGCAGCATATGCAGCAACAATCCAACCTGCTGGGCTATCTGCAAAAGAATACCAAACAAAAAACCAG |
| GAAAGAAAACCACTACCAAGCCCACAAAAAAACCAACCCTCAAGACAACCAAAAAAGATCCCAAACCTCAAACCACT |
| AAATCAAAGGAAGTACCCACCACCAAGCCCACAGAAGAGCCAACCATCAACACCACCAAAACAAACATCATAACTAC |
| ACTACTCACCTCCAACACCACAGGAAATCCAGAACTCACAAGTCAAATGGAAACCTTCCACTCAACTTCCTCCGAAG |
| GCAATCCAAGCCCTTCTCAAGTCTCTACAACATCCGAGTACCCATCACAACCTTCATCTCCACCCAACACACCACGC |
| CAGTAGTTACTTAAAAACATATTATCACAAAAGGCCTTGACCAACTTAAACAGAATCAAAATAAACTCTGGGGCAAA |
| TAACAATGGAGTTGCTAATCCTCAAAGCAAATGCAATTACCACAATCCTCACTGCAGTCACATTTTGTTTTGCTTCT |
| GGTCAAAACATCACTGAAGAATTTTATCAATCAACATGCAGTGCAGTTAGCAAAGGCTATCTTAGTGCTCTGAGAAC |
| TGGTTGGTATACCAGTGTTATAACTATAGAATTAAGTAATATCAAGAAAAATAAGTGTAATGGAACAGATGCTAAGG |
| TAAAATTGATAAAACAAGAATTAGATAAATATAAAAATGCTGTAACAGAATTGCAGTTGCTCATGCAAAGCACACAA |
| GCAACAAACAATCGAGCCAGAAGAGAACTACCAAGGTTTATGAATTATACACTCAACAATGCCAAAAAAACCAATGT |
| AACATTAAGCAAGAAAAGGAAAAGAAGATTTCTTGGTTTTTTGTTAGGTGTTGGATCTGCAATCGCCAGTGGCGTTG |
| CTGTATCTAAGGTCCTGCACCTAGAAGGGGAAGTGAACAAGATCAAAAGTGCTCTACTATCCACAAACAAGGCTGTA |
| GTCAGCTTATCAAATGGAGTTAGTGTTTTAACCAGCAAAGTGTTAGACCTCAAAAACTATATAGATAAACAATTGTT |
| ACCTATTGTGAACAAGCAAAGCTGCAGCATATCAAATATAGAAACTGTGATAGAGTTCCAACAAAAGAACAACAGAC |
| TACTAGAGATTACCAGGGAATTTAGTGTTAATGCAGGCGTAACTACACCTGTAAGCACTTACATGTTAACTAATAGT |
| GAATTATTGTCATTAATCAATGATATGCCTATAACAAATGATCAGAAAAAGTTAATGTCCAACAATGTTCAAATAGT |
| TAGACAGCAAAGTTACTCTATCATGTCCATAATAAAAGAGGAAGTCTTAGCATATGTAGTACAATTACCACTATATG |
| GTGTTATAGATACACCCTGTTGGAAACTACACACATCCCCTCTATGTACAACCAACACAAAAGAAGGGTCCAACATC |
| TGTTTAACAAGAACTGACAGAGGATGGTACTGTGACAATGCAGGATCAGTATCTTTCTTCCCACAAGCTGAAACATG |
| TAAAGTTCAATCAAATCGAGTATTTTGTGACACAATGAACAGTTTAACATTACCAAGTGAAGTAAATCTCTGCAATG |
| TTGACATATTCAACCCCAAATATGATTGTAAAATTATGACTTCAAAAACAGATGTAAGCAGCTCCGTTATCACATCT |
| CTAGGAGCCATTGTGTCATGCTATGGCAAAACTAAATGTACAGCATCCAATAAAAATCGTGGAATCATAAAGACATT |
| TTCTAACGGGTGCGATTATGTATCAAATAAAGGGGTGGACACTGTGTCTGTAGGTAACACATTATATTATGTAAATA |
| AGCAAGAAGGTAAAAGTCTCTATGTAAAAGGTGAACCAATAATAAATTTCTATGACCCATTAGTATTCCCCTCTGAT |
| GAATTTGATGCATCAATATCTCAAGTCAACGAGAAGATTAACCAGAGCCTAGCATTTATTCGTAAATCCGATGAATT |
| ATTACATAATGTAAATGCTGGTAAATCCACCACAAATATCATGATAACTACTATAATTATAGTGATTATAGTAATAT |
| TGTTATCATTAATTGCTGTTGGACTGCTCTTATACTGTAAGGCCAGAAGCACACCAGTCACACTAAGCAAAGATCAA |
| CTGAGTGGTATAAATAATATTGCATTTAGTAACTAAATAAAAATAGCACCTAATCATGTTCTTACAATGGTTTACTA |
| TCTGCTCATAGACAACCCATCTGTCATTGGATTTTCTTAAAATCTGAACTTCATCGAAACTCTCATCTATAAACCAT |

-continued

| Exemplary Sequences |
|---|
| CTCACTTACACTATTTAAGTAGATTCCTAGTTTATAGTTATATAAAACACAATTGCATGCCAGATTAACTTACCATC |
| TGTAAAAATGAAAACTGGGGCAAATATGTCACGAAGGAATCCTTGCAAATTTGAAATTCGAGGTCATTGCTTAAATG |
| GTAAGAGGTGTCATTTTAGTCATAATTATTTTGAATGGCCACCCCATGCACTGCTTGTAAGACAAAACTTTATGTTA |
| AACAGAATACTTAAGTCTATGGATAAAAGTATAGATACCTTATCAGAAATAAGTGGAGCTGCAGAGTTGGACAGAAC |
| AGAAGAGTATGCTCTTGGTGTAGTTGGAGTGCTAGAGAGTTATATAGGATCAATAAACAATATAACTAAACAATCAG |
| CATGTGTTGCCATGAGCAAACTCCTCACTGAACTCAATAGTGATGATATCAAAAAGCTGAGGGACAATGAAGAGCTA |
| AATTCACCCAAGATAAGAGTGTACAATACTGTCATATCATATATTGAAAGCAACAGGAAAAACAATAAACAAACTAT |
| CCATCTGTTAAAAAGATTGCCAGCAGACGTATTGAAGAAAACCATCAAAAACACATTGGATATCCATAAGAGCATAA |
| CCATCAACAACCCAAAAGAATCAACTGTTAGTGATACAAATGACCATGCCAAAAATAATGATACTACCTGACAAATA |
| AGCTTCAATTCTAACACTCACCACATCGTTACATTATTAATTCAAACAATTCAAGTTGTGGGACAAAATGGATCCCA |
| TTATTAATGGAAATTCTGCTAATGTTTATCTAACCGATAGTTATTTAAAAGGTGTTATCTCTTTCTCAGAGTGTAAT |
| GCTTTAGGAAGTTACATATTCAATGGTCCTTATCTCAAAAATGATTATACCAACTTAATTAGTAGACAAAATCCATT |
| AATAGAACACATGAATCTAAAGAAACTAAATATAACACAGTCCTTAATATCTAAGTATCATAAAGGTGAAATAAAAT |
| TAGAAGAACCTACTTATTTTCAGTCATTACTTATGACATACAAGAGTATGACCTCGTCAGAACAGATTGCTACCACT |
| AATTTACTTAAAAAGATAATAAGAAGAGCTATAGAAATAAGTGATGTCAAAGTCTATGCTATATTGAATAAACTAGG |
| GCTTAAAGAAAAGGACAAGATTAAATCCAACAATGGACAAGATGAAGACAACTCAGTTATTACGACCATAATCAAAG |
| ATGATATACTTTCAGCTGTTAAAGATAATCAATCTCATCTTAAAGCAGACAAAAATCACTCTACAAAACAAAAAGAC |
| ACAATCAAAACAACACTCTTGAAGAAATTGATGTGTTCAATGCAACATCCTCCATCATGGTTAATACATTGGTTTAA |
| CTTATACACAAAATTAAACAACATATTAACACAGTATCGATCAAATGAGGTAAAAAACCATGGGTTTACATTGATAG |
| ATAATCAAACTCTTAGTGGATTTCAATTTATTTTGAACCAATATGGTTGTATAGTTTATCATAAGGAACTCAAAAGA |
| ATTACTGTGACAACCTATAATCAATTCTTGACATGGAAAGATATTAGCCTTAGTAGATTAAATGTTTGTTTAATTAC |
| ATGGATTAGTAACTGCTTGAACACATTAAATAAAAGCTTAGGCTTAAGATGCGGATTCAATAATGTTATCTTGACAC |
| AACTATTCCTTTATGGAGATTGTATACTAAAGCTATTTCACAATGAGGGGTTCTACATAATAAAAGAGGTAGAGGGA |
| TTTATTATGTCTCTAATTTTAAATATAACAGAAGAAGATCAATTCAGAAAACGATTTTATAATAGTATGCTCAACAA |
| CATCACAGATGCTGCTAATAAAGCTCAGAAAAATCTGCTATCAAGAGTATGTCATACATTATTAGATAAGACAGTGT |
| CCGATAATATAATAAATGGCAGATGGATAATTCTATTAAGTAAGTTCCTTAAATTAATTAAGCTTGCAGGTGACAAT |
| AACCTTAACAATCTGAGTGAACTATATTTTTTGTTCAGAATATTTGGACACCCAATGGTAGATGAAAGACAAGCCAT |
| GGATGCTGTTAAAATTAATTGCAATGAGACCAAATTTTACTTGTTAAGCAGTCTGAGTATGTTAAGAGGTGCCTTTA |
| TATATAGAATTATAAAAGGGTTTGTAAATAATTACAACAGATGGCCTACTTTAAGAAATGCTATTGTTTTACCCTTA |
| AGATGGTTAACTTACTATAAACTAAACACTTATCCTTCTTTGTTGGAACTTACAGAAAGAGATTTGATTGTGTTATC |
| AGGACTACGTTTCTATCGTGAGTTTCGGTTGCCTAAAAAAGTGGATCTTGAAATGATTATAAATGATAAAGCTATAT |
| CACCTCCTAAAAATTTGATATGGACTAGTTTCCCTAGAAATTACATGCCATCACACATACAAAACTATATAGAACAT |
| GAAAAATTAAAATTTTCCGAGAGTGATAAATCAAGAAGAGTATTAGAGTATTATTTAAGAGATAACAAATTCAATGA |
| ATGTGATTTATACAACTGTGTAGTTAATCAAAGTTATCTCAACAACCCTAATCATGTGGTATCATTGACAGGCAAAG |
| AAAGAGAACTCAGTGTAGGTAGAATGTTTGCAATGCAACCGGGAATGTTCAGACAGGTTCAAATATTGGCAGAGAAA |
| ATGATAGCTGAAAACATTTTACAATTCTTTCCTGAAAGTCTTACAAGATATGGTGATCTAGAACTACAAAAAATATT |
| AGAACTGAAAGCAGGAATAAGTAACAAATCAAATCGCTACAATGATAATTACAACAATTACATTAGTAAGTGCTCTA |
| TCATCACAGATCTCAGCAAATTCAATCAAGCATTTCGATATGAAACGTCATGTATTTGTAGTGATGTGCTGGATGAA |

-continued

| Exemplary Sequences |
| --- |
| CTGCATGGTGTACAATCTCTATTTTCCTGGTTACATTTAACTATTCCTCATGTCACAATAATATGCACATATAGGCA |
| TGCACCCCCCTATATAGGAGATCATATTGTAGATCTTAACAATGTAGATGAACAAAGTGGATTATATAGATATCACA |
| TGGGTGGCATCGAAGGGTGGTGTCAAAAACTATGGACCATAGAAGCTATATCACTATTGGATCTAATATCTCTCAAA |
| GGGAAATTCTCAATTACTGCTTTAATTAATGGTGACAATCAATCAATAGATATAAGCAAACCAATCAGACTCATGGA |
| AGGTCAAACTCATGCTCAAGCAGATTATTTGCTAGCATTAAATAGCCTTAAATTACTGTATAAAGAGTATGCAGGCA |
| TAGGCCACAAATTAAAAGGAACTGAGACTTATATATCACGAGATATGCAATTTATGAGTAAAACAATTCAACATAAC |
| GGTGTATATTACCCAGCTAGTATAAAGAAAGTCCTAAGAGTGGGACCGTGGATAAACACTATACTTGATGATTTCAA |
| AGTGAGTCTAGAATCTATAGGTAGTTTGACACAAGAATTAGAATATAGAGGTGAAAGTCTATTATGCAGTTTAATAT |
| TTAGAAATGTATGGTTATATAATCAGATTGCTCTACAATTAAAAAATCATGCATTATGTAACAATAAACTATATTTG |
| GACATATTAAAGGTTCTGAAACACTTAAAAACCTTTTTTAATCTTGATAATATTGATACAGCATTAACATTGTATAT |
| GAATTTACCCATGTTATTTGGTGGTGGTGATCCCAACTTGTTATATCGAAGTTTCTATAGAAGAACTCCTGACTTCC |
| TCACAGAGGCTATAGTTCACTCTGTGTTCATACTTAGTTATTATACAAACCATGACTTAAAAGATAAACTTCAAGAT |
| CTGTCAGATGATAGATTGAATAAGTTCTTAACATGCATAATCACGTTTGACAAAAACCCTAATGCTGAATTCGTAAC |
| ATTGATGAGAGATCCTCAAGCTTTAGGGTCTGAGAGACAAGCTAAAATTACTAGCGAAATCAATAGACTGGCAGTTA |
| CAGAGGTTTTGAGTACAGCTCCAAACAAAATATTCTCCAAAAGTGCACAACATTATACTACTACAGAGATAGATCTA |
| AATGATATTATGCAAAATATAGAACCTACATATCCTCATGGGCTAAGAGTTGTTTATGAAAGTTTACCCTTTTATAA |
| AGCAGAGAAAATAGTAAATCTTATATCAGGTACAAAATCTATAACTAACATACTGGAAAAAACTTCTGCCATAGACT |
| TAACAGATATTGATAGAGCCACTGAGATGATGAGGAAAAACATAACTTTGCTTATAAGGATACTTCCATTGGATTGT |
| AACAGAGATAAAAGAGAGATATTGAGTATGGAAAACCTAAGTATTACTGAATTAAGCAAATATGTTAGGGAAAGATC |
| TTGGTCTTTATCCAATATAGTTGGTGTTACATCACCCAGTATCATGTATACAATGGACATCAAATATACTACAAGCA |
| CTATATCTAGTGGCATAATTATAGAGAAATATAATGTTAACAGTTTAACACGTGGTGAGAGAGGACCCACTAAACCA |
| TGGGTTGGTTCATCTACACAAGAGAAAAAAACAATGCCAGTTTATAATAGACAAGTCTTAACCAAAAAACAGAGAGA |
| TCAAATAGATCTATTAGCAAAATTGGATTGGGTGTATGCATCTATAGATAACAAGGATGAATTCATGGAAGAACTCA |
| GCATAGGAACCCTTGGGTTAACATATGAAAAGGCCAAGAAATTATTTCCACAATATTTAAGTGTCAATTATTTGCAT |
| CGCCTTACAGTCAGTAGTAGACCATGTGAATTCCCTGCATCAATACCAGCTTATAGAACAACAAATTATCACTTTGA |
| CACTAGCCCTATTAATCGCATATTAACAGAAAAGTATGGTGATGAAGATATTGACATAGTATTCCAAAACTGTATAA |
| GCTTTGGCCTTAGTTTAATGTCAGTAGTAGAACAATTTACTAATGTATGTCCTAACAGAATTATTCTCATACCTAAG |
| CTTAATGAGATACATTTGATGAAACCTCCCATATTCACAGGTGATGTTGATATTCACAAGTTAAAACAAGTGATACA |
| AAAACAGCATATGTTTTTACCAGACAAAATAAGTTTGACTCAATATGTGGAATTATTCTTAAGTAATAAAACACTCA |
| AATCTGGATCTCATGTTAATTCTAATTTAATATTGGCACATAAAATATCTGACTATTTTCATAATACTTACATTTTA |
| AGTACTAATTTAGCTGGACATTGGATTCTGATTATACAACTTATGAAAGATTCTAAAGGTATTTTTGAAAAAGATTG |
| GGGAGAGGGATATATAACTGATCATATGTTTATTAATTTGAAAGTTTTCTTCAATGCTTATAAGACCTATCTCTTGT |
| GTTTTCATAAAGGTTATGGCAAAGCAAAGCTGGAGTGTGATATGAACACTTCAGATCTTCTATGTGTATTGGAATTA |
| ATAGACAGTAGTTATTGGAAGTCTATGTCTAAGGTATTTTTAGAACAAAAAGTTATCAAATACATTCTTAGCCAAGA |
| TGCAAGTTTACATAGAGTAAAAGGATGTCATAGCTTCAAATTATGGTTTCTTAAACGTCTTAATGTAGCAGAATTCA |
| CAGTTTGCCCTTGGGTTGTTAACATAGATTATCATCCAACACATATGAAAGCAATATTAACTTATATAGATCTTGTT |
| AGAATGGGATTGATAAATATAGATAGAATACACATTAAAAATAAACACAAATTCAATGATGAATTTTATACTTCTAA |
| TCTCTTCTACATTAATTATAACTTCTCAGATAATACTCATCTATTAACTAAACATATAAGGATTGCTAATTCTGAAT |
| TAGAAAATAATTACAACAAATTATATCATCCTACACCAGAAACCCTAGAGAATATACTAGCCAATCCGATTAAAAGT |

-continued

| Exemplary Sequences |
|---|

AATGACAAAAAGACACTGAATGACTATTGTATAGGTAAAAATGTTGACTCAATAATGTTACCATTGTTATCTAATAA

GAAGCTTATTAAATCGTCTGCAATGATTAGAACCAATTACAGCAAACAAGATTTGTATAATTTATTCCCTATGGTTG

TGATTGATAGAATTATAGATCATTCAGGCAATACAGCCAAATCCAACCAACTTTACACTACTACTTCCCACCAAATA

TCCTTAGTGCACAATAGCACATCACTTTACTGCATGCTTCCTTGGCATCATATTAATAGATTCAATTTTGTATTTAG

TTCTACAGGTTGTAAAATTAGTATAGAGTATATTTTAAAAGATCTTAAAATTAAAGATCCCAATTGTATAGCATTCA

TAGGTGAAGGAGCAGGGAATTTATTATTGCGTACAGTAGTGGAACTTCATCCTGACATAAGATATATTTACAGAAGT

CTGAAAGATTGCAATGATCATAGTTTACCTATTGAGTTTTTAAGGCTGTACAATGGACATATCAACATTGATTATGG

TGAAAATTTGACCATTCCTGCTACAGATGCAACCAACAACATTCATTGGTCTTATTTACATATAAAGTTTGCTGAAC

CTATCAGTCTTTTTGTCTGTGATGCCGAATTGTCTGTAACAGTCAACTGGAGTAAAATTATAATAGAATGGAGCAAG

CATGTAAGAAAGTGCAAGTACTGTTCCTCAGTTAATAAATGTATGTTAATAGTAAAATATCATGCTCAAGATGATAT

TGATTTCAAATTAGACAATATAACTATATTAAAAACTTATGTATGCTTAGGCAGTAAGTTAAAGGGATCGGAGGTTT

ACTTAGTCCTTACAATAGGTCCTGCGAATATATTCCCAGTATTTAATGTAGTACAAAATGCTAAATTGATACTATCA

AGAACCAAAAATTTCATCATGCCTAAGAAAGCTGATAAAGAGTCTATTGATGCAAATATTAAAAGTTTGATACCCTT

TCTTTGTTACCCTATAACAAAAAAAGGAATTAATACTGCATTGTCAAAACTAAAGAGTGTTGTTAGTGGAGATATAC

TATCATATTCTATAGCTGGACGTAATGAAGTTTTCAGCAATAAACTTATAAATCATAAGCATATGAACATCTTAAAA

TGGTTCAATCATGTTTTAAATTTCAGATCAACAGAACTAAACTATAACCATTTATATATGGTAGAATCTACATATCC

TTACCTAAGTGAATTGTTAAACAGCTTGACAACCAATGAACTTAAAAAACTGATTAAAATCACAGGTAGTCTGTTAT

ACAACTTTCATAATGAATAATGAATAAAGATCTTATAATAAAAATTCCCATAGCTATACACTAACACTGTATTCAAT

TATAGTTATTAAAAATTAAAAATCATATAATTTTTTAAATAACTTTTAGTGAACTAATCCTAAAGTTATCATTTTAA

TCTTGGAGGAATAAATTTAAACCCTAATCTAATTGGTTTATATGTGTATTAACTAAATTACGAGATATTAGTTTTTG

ACACTTTTTTTCTCGT

Polynucleotide sequence encoding G001BB (SEQ ID NO: 8)

ATGTCTAAGACAAAGGATCAGCGGACAGCCAAAACACTGGAACGGACATGGGATACCCTGAATCACCTCCTCTTCAT

CAGCAGTTGCCTGTACAAGCTCAATCTGAAGTCCATCGCCCAGATCACTCTCTCCATCCTTGCCATGATCATCTCTA

CAAGCCTCATCATTGCCGCAATTATCTTCATCGCCAGCGCTAACCACAAGGTCACCCTTACCACAGCCATTATTCAG

GATGCCACCAACCAGATCAAGAACACAACCCCTACCTACCTGACACAGAACCCTCAGCTTGGAATTTCACTGAGCAA

CCTGTCCGAAACCACATCTAAACCTACAACCATCTTGGCTCTGACCACACCAAACGCCGAGTCCACCCCACAAAGTA

CCACAGTGAAGACCAAAAACACCACAACCACACAGATTCAGCCAAGCAAGCCTACAACTAAGCAAAGGCAGAACAAG

CCACAGAACAAACCCAACAACGACTTTCACTTTGAGGTGTTCAACTTTGTGCCCTGCTCCATTTGCTCCAACAACCC

TACCTGTTGGGCTATCTGCAAGAGGATCCCCAACAAGAAGCCCGGCAGGAAGACTACTACTAAGCCTACTAAACAGC

CAGCCATTAAGACCACTAAGAAGGACCCAAAGCCACAGACAACCAAGCCAAAGGAGGTGCTCACTACCAAGCCCACT

GAGAAGCCCACCATTAACACCACTAAAACCAACATCCGCACAACATTGCTGACATCAAACATTACAGAGAACCAGGA

GCACACAAGCCAGAAGGAGACACTGCATAGCACTACATCCGAAGGCAATCCCAGCCCAAGCCAGGTCTATACTACCT

CAGAGTACCTGTCCCAGAGCCTGAGCCCTAGCAACACTACTAGATGGTAG

Polynucleotide sequence encoding FBB (SEQ ID NO: 9)

ATGGAGCTCCTCATTCTCAAAGCCAACGCAATCACAACAATTCTGACCGCCGTCACATTCTGCTTTGCCTCCGGACA

GAACATCACAGAAGAGTTTTACCAAAGTACATGCAGCGCCGTGAGCAAAGGCTACCTGTCCGCCCTGAGGACAGGGT

GGTACACATCCGTGATTACCATTGAGCTGAGTAATATCAAGAAGAACAAGTGCAACGGCACTGATGCCAAAGTGAAG

-continued

| Exemplary Sequences |
| --- |
| CTCATTAAACAGGAACTCGATAAGTACAAGAACGCCGTGACTGAGCTCCAGCTGCTGATGCAGTCAACTCAGGCTAC |
| AAACAACAGAGCCCGGAGGGAGCTGCCCAGGTTTATGAACTACACCCTGAACAACGCCAAGAAGACCAACGTGACAT |
| TGAGCAAGAAGAGGAAGCGGCGGTTCCTGGGGTTCTTGCTAGGTGTGGGCAGCGCTATTGCTTCTGGCGTCGCCGTC |
| TCCAAGGTGCTGCACCTGGAAGGCGAAGTGAATAAGATTAAGTCCGCACTGCTTAGCACCAATAAGGCCGTCGTGAG |
| CCTGTCTAACGGAGTGAGTGTGCTCACAAGCAAGGTCCTCGATCTCAAGAACTACATTGATAAGCAGCTCCTGCCCA |
| TCGTCAACAAGCAGTCATGCTCCATTAGTAACATCGAGACCGTGATTGAATTTCAACAGAAGAACAACCGGCTCCTG |
| GAGATTACTAGGGAGTTCAGCGTGAACGCCGGGGTGACAACACCAGTCTCCACCTATATGCTTACCAACAGCGAGTT |
| GCTCTCCCTGATTAACGATATGCCAATTACAAACGACCAGAAGAAGCTGATGTCAAACAACGTCCAGATTGTCCGGC |
| AGCAGTCCTACTCAATCATGTCCATTATTAAGGAGGAGGTCCTGGCTTACGTCGTGCAGCTGCCTCTTTATGGGGTG |
| ATCGACACCCCTTGCTGGAAGCTCCATACATCCCCTCTGTGCACTACCAACACCAAGGAGGGGTCCAACATCTGCTT |
| GACAAGAACCGATCGCGGCTGGTACTGCGATAACGCAGGCAGTGTCTCCTTCTTTCCCCAGGCCGAGACTTGTAAGG |
| TGCAGTCTAACCGCGTCTTCTGCGACACCATGAACAGCCTGACCCTTCCCAGCGAGGTGAACCTTTGTAACGTGGAC |
| ATCTTCAACCCAAAGTATGATTGTAAGATTATGACTAGCAAAACCGATGTCAGCAGCAGCGTGATCACTAGCCTGGG |
| CGCTATCGTCAGCTGCTACGGAAAGACTAAGTGCACCGCCAGCAACAAGAACAGAGGCATCATCAAGACCTTCAGTA |
| ATGGATGTGACTACGTGTCCAACAAAGGGGTGGATACAGTGAGCGTGGGAAACACATTGTACTACGTGAACAAACAG |
| GAGGGGAAGTCCTTGTACGTGAAGGGTGAGCCCATTATCAACTTCTACGACCCTCTCGTGTTCCCATCAGACGAGTT |
| TGACGCCTCCATCTCCCAGGTGAACGAGAAGATCAATCAGTCACTGGCCTTTATTAGGAAATCCGACGAGCTGCTGC |
| ACAACGTCAACGCCGGAAAGTCTACCACTAACATCATGATCACCACAATCATCATTGTGATCATCGTCATCCTCCTG |
| AGCTTGATCGCTGTCGGGTTGCTGTTGTACTGCAAGGCCCGGTCCACACCCGTGACTCTGAGCAAGGACCAGCTGTC |
| TGGCATTAACAACATCGCCTTTAGCAACTAA |
| Polynucleotide sequence encoding F001 (SEQ ID NO: 10) |
| ATGGATTTGCCAATCCTCAAGACAAATGCTATTACCACAATCCTTGCTGCAGTCACACTCTGTTTCGCTTCCAGTCA |
| AAATATCACTGAAGAATTTTATCAATCAACATGCAGTGCAGTTAGCAAAGGCTATCTTAGTGCTCTAAGAACTGGTT |
| GGTATACTAGTGTTATAACTATAGAATTAAGTAATATCAAAGAAAATAAGTGTAATGGAACAGACGCTAAGGTAAAA |
| TTGATAAAACAAGAATTAGATAAATATAAAAATGCTGTAACAGAACTGCAGTTGCTCATGCAAAGCACGCCAGCATC |
| CAACAATCGAGCCAGAAGAGAACTACCAAGATTTATGAATTATACACTCAACAATACCAAAAACACCAATGTAACAT |
| TAAGCAAGAAAAGGAAAAGAAGATTTCTTGGCTTTTTGTTAGGGGTTGGATCTGCAATCGCCAGTGGCATTGCTGTA |
| TCTAAGGTCCTGCACTTAGAAGGGGAAGTGAACAAAATCAAAAGTGCTCTACTATCCACAAACAAGGCTGTAGTCAG |
| CTTATCTAATGGAGTCAGTGTCTTAACCAGCAAAGTGTTAGATCTCAAAAACTATATAGATAAACAGTTGTTACCTA |
| TTGTGAACAAGCAAAGCTGCAGCATATCAAACATTGAAACTGTGATAGAGTTCCAACAAAAGAACAACAGACTACTA |
| GAGATTACCAGGGAATTTAGTGTTAATGCAGGTGTAACTACACCTGTAAGCACTTATATGTTAACTAATAGTGAATT |
| ATTATCATTAATCAATGATATGCCTATAACAAATGATCAGAAAAAGTTAATGTCCAACAATGTTCAAATAGTTAGAC |
| AGCAAAGTTACTCTATCATGTCAATAATAAAGGAGGAAGTCTTAGCATATGTAGTACAATTACCACTATATGGTGTA |
| ATAGATACACCTTGTTGGAAACTGCACACATCCCCTCTATGTACAACCTACACAAAGGAAGGGTCCAACATCTGCTT |
| AACAAGAACCGACAGGGGATGGTACTGTGACAATGCAGGATCAGTATCTTTTTTCCCACAAGCTGAAACATGTAAAG |
| TTCAATCGAATCGGGTATTTTGTGACACAATGAACAGTTTAACATTACCAAGTGAGGTAAATCTCTGCAACATTGAC |
| ATATTCAACCCCAAATATGATTGCAAAATTATGACTTCAAAAACAGATGTAAGTAGCTCTGTTATCACATCTCTAGG |
| AGCCATTGTGTCATGCTATGGCAAAACCAAATGTACAGCATCCAATAAAAATCGTGGGATCATAAAGACATTTTCTA |
| ATGGGTGTGATTATGTATCAAATAAGGGGGTGGATACTGTGTCTGTAGGTAATACATTATATTATGTAAATAAGCAA |

| Exemplary Sequences |
|---|
| GAAGGCAAAAGTCTCTATGTAAAAGGTGAACCAATAATAAATTTCTATGATCCATTAGTTTTCCCCTCTGATGAATT |
| TGATGCATCAATATCTCAAGTCAATGAGAAGATTAACCAGAGTCTAGCATTTATCCGTAAATCAGATGAATTATTAC |
| ATAATGTAAATGCTGGTAAATCCACCACAAATATCATGATAACTACTATAATTATAGTAATTGTAGTAATATTGTTA |
| TCATTAATTGCAGTTGGACTGCTTCTATACTGCAAGGCCAGAAGCACACCAGTCACACTAAGTAAGGATCAACTGAG |
| TGGTATAAACAATATTGCATTTAGTAGCTGA |

Polynucleotide sequence encoding F001BB
(SEQ ID NO: 11)

ATGGACCTTCCAATCCTGAAGACCAACGCTATCACCACCATCCTCGCAGCTGTGACTCTTTGTTTCGCATCCTCCCA

AAACATCACCGAAGAGTTCTACCAGTCCACCTGTTCCGCAGTGTCTAAGGGATACCTTAGCGCTCTCAGAACCGGAT

GGTACACATCCGTGATCACTATCGAACTGAGCAACATCAAGGAGAACAAGTGCAACGGCACCGACGCTAAGGTGAAG

CTCATCAAGCAGGAACTGGACAAGTACAAGAACGCCGTGACCGAACTTCAGCTCCTTATGCAGTCTACCCCAGCTTC

CAACAACAGAGCCAGAAGGGAGCTCCCAAGGTTTATGAACTACACCCTCAACAACACCAAGAACACCAACGTGACCC

TGTCCAAGAAGAGGAAGAGGCGGTTCCTTGGATTCCTCTTGGGAGTCGGATCTGCTATCGCCTCAGGCATTGCCGTC

AGTAAAGTGTTGCATTTGGAGGGCGAGGTCAACAAAATCAAGTCCGCCTTGTTGTCCACTAACAAGGCCGTCGTGTC

TTTGTCCAACGGGGTGTCTGTCTTGACAAGTAAGGTGTTGGACTTGAAGAACTACATCGACAAGCAGCTGCTGCCTA

TCGTCAACAAGCAGTCCTGCTCTATCAGCAACATCGAGACCGTGATCGAGTTCCAGCAGAAGAACAACCGGCTGCTG

GAGATCACAAGGGAGTTCAGTGTCAACGCCGGCGTCACAACACCTGTGTCAACTTATATGCTGACAAACTCAGAGCT

GCTGTCACTGATCAACGACATGCCTATCACCAACGACCAGAAGAAGCTGATGAGCAACAACGTGCAGATCGTGAGGC

AGCAGTCATACAGCATCATGTCCATCATCAAGGAGGAAGTCCTGGCCTACGTGGTCCAACTGCCTCTGTACGGCGTG

ATTGATACTCCATGTTGGAAGCTGCACACATCACCACTGTGTACCACTTACACCAAGGAGGGGAGTAACATCTGCCT

GACTCGGACAGATAGAGGGTGGTATTGCGATAATGCCGGCAGTGTCTCCTTTTTCCCCCAGGCCGAGACTTGCAAAG

TCCAGAGCAATCGCGTGTTTTGCGATACAATGAATAGCCTGACACTCCCCAGCGAGGTGAATCTCTGCAATATTGAT

ATTTTCAACCCCAAGTACGACTGCAAGATCATGACCAGCAAGACCGACGTCAGCAGCAGCGTGATTACTAGCCTCGG

AGCCATTGTGAGCTGCTATGGGAAAACAAAATGCACAGCCTCCAACAAAAACAGAGGCATTATCAAGACTTTCTCCA

ACGGGTGCGATTACGTGTCCAACAAGGGCGTGGATACTGTGAGCGTGGGGAACACACTCTACTACGTGAACAAACAG

GAGGGGAAAAGCCTGTACGTGAAAGGCGAGCCCATTATTAACTTTTACGACCCTCTGGTGTTTCCCAGCGATGAGTT

TGATGCCAGCATCTCCCAGGTGAACGAGAAGATTAACCAGTCCCTCGCCTTTATTCGCAAGAGCGATGAGCTGCTGC

ACAACGTGAACGCCGGCAAGTCCACTACAAACATTATGATTACAACAATTATTATTGTCATTGTCGTCATTCTGCTC

AGCCTGATTGCCGTCGGCCTGCTGCTCTACTGCAAGGCCAGGTCCACACCCGTGACACTCAGCAAGGATCAGCTGTC

CGGCATTAACAACATTGCCTTTAGCAGCTAA

Antigenomic cDNA sequence of D46/cp/ΔM2-2
(SEQ ID NO: 15)

ACGGGAAAAAATGCGTACAACAAACTTGCATAAACCAAAAAAATGGGGCAAATAAGAATTTGATAAGTACCACTTAA
ATTTAACTCCCTTGGTTAGAGATGGGCAGCAATTCATTGAGTATGATAAAAGTTAGATTACAAAATTTGTTTGACAA
TGATGAAGTAGCATTGTTAAAAATAACATGCTATACTGATAAATTAATACATTTAACTAATGCTTTGGCTAAGGCAG
TGATACATACAATCAAATTGAATGGCATTGTGTTTGTGCATGTTATTACAAGTAGTGATATTTGCCCTAATAATAAT
ATTGTAGTAAAATCCAATTTCACAACAATGCCAGTACTACAAAATGGAGGTTATATATGGGAAATGATGGAATTAAC
ACATTGCTCTCAACCTAATGGTCTACTAGATGACAATTGTGAAATTAAATTCTCCAAAAAACTAAGTGATTCAACAA
TGACCAATTATATGAATCAATTATCTGAATTACTTGGATTTGATCTTAATCCATAAATTATAATTAATATCAACTAG
CAAATCAATGTCACTAACACCATTAGTTAATATAAAACTTAACAGAAGACAAAAATGGGGCAAATAAATCAATTCAG

-continued

| Exemplary Sequences |
| --- |
| CCAACCCAACCATGGACACAACCCACAATGATAATACACCACAAAGACTGATGATCACAGACATGAGACCGTTGTCA |
| CTTGAGACCATAATAACATCACTAACCAGAGACATCATAACACACAAATTTATATACTTGATAAATCATGAATGCAT |
| AGTGAGAAAACTTGATGAAAGACAGGCCACATTTACATTCCTGGTCAACTATGAAATGAAACTATTACACAAAGTAG |
| GAAGCACTAAATATAAAAAATATACTGAATACAACACAAAATATGGCACTTTCCCTATGCCAATATTCATCAATCAT |
| GATGGGTTCTTAGAATGCATTGGCATTAAGCCTACAAAGCATACTCCCATAATATACAAGTATGATCTCAATCCATA |
| AATTTCAACACAATATTCACACAATCTAAAACAACAACTCTATGCATAACTATACTCCATAGTCCAGATGGAGCCTG |
| AAAATTATAGTAATTTAAAACTTAAGGAGAGATATAAGATAGAAGATGGGGCAAATACAACCATGGCTCTTAGCAAA |
| GTCAAGTTGAATGATACACTCAACAAAGATCAACTTCTGTCATCCAGCAAATACACCATCCAACGGAGCACAGGAGA |
| TAGTATTGATACTCCTAATTATGATGTGCAGAAACACATCAATAAGTTATGTGGCATGTTATTAATCACAGAAGATG |
| CTAATCATAAATTCACTGGGTTAATAGGTATGTTATATGCGATGTCTAGGTTAGGAAGAGAAGACACCATAAAAATA |
| CTCAGAGATGCGGGATATCATGTAAAAGCAAATGGAGTAGATGTAACAACACATCGTCAAGACATTAATGGAAAAGA |
| AATGAAATTTGAAGTGTTAACATTGGCAAGCTTAACAACTGAAATTCAAATCAACATTGAGATAGAATCTAGAAAAT |
| CCTACAAAAAAATGCTAAAAGAAATGGGAGAGGTAGCTCCAGAATACAGGCATGACTCTCCTGATTGTGGGATGATA |
| ATATTATGTATAGCAGCATTAGTAATAACTAAATTAGCAGCAGGGGACAGATCTGGTCTTACAGCCGTGATTAGGAG |
| AGCTAATAATGTCCTAAAAAATGAAATGAAACGTTACAAAGGCTTACTACCCAAGGACATAGCCAACAGCTTCTATG |
| AAGTGTTTGAAAAACATCCCCACTTTATAGATGTTTTTGTTCATTTTGGTATAGCACAATCTTCTACCAGAGGTGGC |
| AGTAGAGTTGAAGGGATTTTTGCAGGATTGTTTATGAATGCCTATGGTGCAGGGCAAGTGATGTTACGGTGGGGAGT |
| CTTAGCAAAATCGATTAAAAATATTATGTTAGGACATGCTAGTGTGCAAGCAGAAATGGAACAAGTTGTTGAGGTTT |
| ATGAATATGCCCAAAAATTGGGTGGTGAAGCAGGATTCTACCATATATTGAACAACCCAAAAGCATCATTATTATCT |
| TTGACTCAATTTCCTCACTTCTCCAGTGTAGTATTAGGCAATGCTGCTGGCCTAGGCATAATGGGAGAGTACAGAGG |
| TACACCGAGGAATCAAGATCTATATGATGCAGCAAAGGCATATGCTGAACAACTCAAAGAAAATGGTGTGATTAACT |
| ACAGTGTACTAGACTTGACAGCAGAAGAACTAGAGGCTATCAAACATCAGCTTAATCCAAAAGATAATGATGTAGAG |
| CTTTGAGTTAATAAAAAATGGGGCAAATAAATCATCATGGAAAAGTTTGCTCCTGAATTCCATGGAGAAGATGCAAA |
| CAACAGGGCTACTAAATTCCTAGAATCAATAAAGGGCAAATTCACATCACCCAAAGATCCCAAGAAAAAAGATAGTA |
| TCATATCTGTCAACTCAATAGATATAGAAGTAACCAAAGAAAGCCCTATAACATCAAATTCAACTATTATCAACCCA |
| ACAAATGAGACAGATGATACTGCAGGGAACAAGCCCAATTATCAAAGAAAACCTCTAGTAAGTTTCAAAGAAGACCC |
| TACACCAAGTGATAATCCCTTTTCTAAACTATACAAAGAAACCATAGAAACATTTGATAACAATGAAGAAGAATCCA |
| GCTATTCATACGAAGAAATAAATGATCAGACAAACGATAATATAACAGCAAGATTAGATAGGATTGATGAAAAATTA |
| AGTGAAATACTAGGAATGCTTCACACATTAGTAGTGGCAAGTGCAGGACCTACATCTGCTCGGGATGGTATAAGAGA |
| TGCCATGGTTGGTTTAAGAGAAGAAATGATAGAAAAAATCAGAACTGAAGCATTAATGACCAATGACAGATTAGAAG |
| CTATGGCAAGACTCAGGAATGAGGAAAGTGAAAAGATGGCAAAAGACACATCAGATGAAGTGTCTCTCAATCCAACA |
| TCAGAGAAATTGAACAACCTATTGGAAGGGAATGATAGTGACAATGATCTATCACTTGAAGATTTCTGATTAGTTAC |
| CAATCTTCACATCAACACACAATACCAACAGAAGACCAACAAACTAACCAACCCAATCATCCAACCAAACATCCATC |
| CGCCAATCAGCCAAACAGCCAACAAAACAACCAGCCAATCCAAAACTAACCACCCGGAAAAAATCTATAATATAGTT |
| ACAAAAAAAGGAAAGGGTGGGGCAAATATGGAAACATACGTGAACAAGCTTCACGAAGGCTCCACATACACAGCTGC |
| TGTTCAATACAATGTCTTAGAAAAAGACGATGACCCTGCATCACTTACAATATGGGTGCCCATGTTCCAATCATCTA |
| TGCCAGCAGATTTACTTATAAAAGAACTAGCTAATGTCAACATACTAGTGAAACAAATATCCACACCCAAGGGACCT |
| TCACTAAGAGTCATGATAAACTCAAGAAGTGCAGTGCTAGCACAAATGCCCAGCAAATTTACCATATGCGCTAATGT |
| GTCCTTGGATGAAAGAAGCAAACTAGCATATGATGTAACCACACCCTGTGAAATCAAGGCATGTAGTCTAACATGCC |

-continued

| Exemplary Sequences |
| --- |
| TAAAATCAAAAAATATGTTGACTACAGTTAAAGATCTCACTATGAAGACACTCAACCCTACACATGATATTATTGCT |
| TTATGTGAATTTGAAAACATAGTAACATCAAAAAAAGTCATAATACCAACATACCTAAGATCCATCAGTGTCAGAAA |
| TAAAGATCTGAACACACTTGAAAATATAACAACCACTGAATTCAAAAATGCTATCACAAATGCAAAAATCATCCCTT |
| ACTCAGGATTACTATTAGTCATCACAGTaACTGACAACAAAGGAGCATTCAAATACATAAAGCCACAAAGTCAATTC |
| ATAGTAGATCTTGGAGCTTACCTAGAAAAAGAAAGTATATATTATGTTACCACAAATTGGAAGCACACAGCTACACG |
| ATTTGCAATCAAACCCATGGAAGATTAACCTTTTTCCTCTACATCAGTGTGTTAATTCATACAAACTTTCTACCTAC |
| ATTCTTCACTTCACCATCACAATCACAAACACTCTGTGGTTCAACCAATCAAACAAAACTTATCTGAAGTCCCAGAT |
| CATCCCAAGTCATTGTTTATCAGATCTAGTACTCAAATAAGTTAATAAAAAATATACACATGGGGCAAATAATCATT |
| GGAGGAAATCCAACTAATCACAATATCTGTTAACATAGACAAGTCCACACACCATACAGAATCAACCAATGGAAAAT |
| ACATCCATAACAATAGAATTCTCAAGCAAATTCTGGCCTTACTTTACACTAATACACATGATCACAACAATAATCTC |
| TTTGCTAATCATAATCTCCATCATGATTGCAATACTAAACAAACTTTGTGAATATAACGTATTCCATAACAAAACCT |
| TTGAGTTACCAAGAGCTCGAGTCAACACATAGCATTCATCAATCCAACAGCCCAAAACAGTAACCTTGCATTTAAAA |
| ATGAACAACCCCTACCTCTTTACAACACCTCATTAACATCCCACCATGCAAACCACTATCCATACTATAAAGTAGTT |
| AATTAAAAATAGTCATAACAATGAACTAGGATATCAAGACTAACAATAACATTGGGGCAAATGCAAACATGTCCAAA |
| AACAAGGACCAACGCACCGCTAAGACATTAGAAAGGACCTGGGACACTCTCAATCATTTATTATTCATATCATCGTG |
| CTTATATAAGTTAAATCTTAAATCTGTAGCACAAATCACATTATCCATTCTGGCAATGATAATCTCAACTTCACTTA |
| TAATTGCAGCCATCATATTCATAGCCTCGGCAAACCACAAAGTCACACCAACAACTGCAATCATACAAGATGCAACA |
| AGCCAGATCAAGAACACAACCCCAACATACCTCACCCAGAATCCTCAGCTTGGAATCAGTCCCTCTAATCCGTCTGA |
| AATTACATCACAAATCACCACCATACTAGCTTCAACAACACCAGGAGTCAAGTCAACCCTGCAATCCACAACAGTCA |
| AGACCAAAAACACAACAACAACTCAAACACAACCCAGCAAGCCCACCACAAAACAACGCCAAAACAAACCACCAAGC |
| AAACCCAATAATGATTTTCACTTTGAAGTGTTCAACTTTGTACCCTGCAGCATATGCAGCAACAATCCAACCTGCTG |
| GGCTATCTGCAAAAGAATACCAAACAAAAAACCAGGAAAGAAAACCACTACCAAGCCCACAAAAAAACCAACCCTCA |
| AGACAACCAAAAAAGATCCCAAACCTCAAACCACTAAATCAAAGGAAGTACCCACCACCAAGCCCACAGAAGAGCCA |
| ACCATCAACACCACCAAAACAAACATCATAACTACACTACTCACCTCCAACACCACAGGAAATCCAGAACTCACAAG |
| TCAAATGGAAACCTTCCACTCAACTTCCTCCGAAGGCAATCCAAGCCCTTCTCAAGTCTCTACAACATCCGAGTACC |
| CATCACAACCTTCATCTCCACCCAACACACCACGCCAGTAGTTACTTAAAAACATATTATCACAAAAGGCCTTGACC |
| AACTTAAACAGAATCAAAATAAACTCTGGGGCAAATAACAATGGAGTTGCTAATCCTCAAAGCAAATGCAATTACCA |
| CAATCCTCACTGCAGTCACATTTTGTTTTGCTTCTGGTCAAAACATCACTGAAGAATTTTATCAATCAACATGCAGT |
| GCAGTTAGCAAAGGCTATCTTAGTGCTCTGAGAACTGGTTGGTATACCAGTGTTATAACTATAGAATTAAGTAATAT |
| CAAGAAAAATAAGTGTAATGGAACAGATGCTAAGGTAAAATTGATAAAACAAGAATTAGATAAATATAAAAATGCTG |
| TAACAGAATTGCAGTTGCTCATGCAAAGCACACAAGCAACAAACAATCGAGCCAGAAGAGAACTACCAAGGTTTATG |
| AATTATACACTCAACAATGCCAAAAAAACCAATGTAACATTAAGCAAGAAAAGGAAAAGAAGATTTCTTGGTTTTTT |
| GTTAGGTGTTGGATCTGCAATCGCCAGTGGCGTTGCTGTATCTAAGGTCCTGCACCTAGAAGGGGAAGTGAACAAGA |
| TCAAAAGTGCTCTACTATCCACAAACAAGGCTGTAGTCAGCTTATCAAATGGAGTTAGTGTTTTAACCAGCAAAGTG |
| TTAGACCTCAAAAACTATATAGATAAACAATTGTTACCTATTGTGAACAAGCAAAGCTGCAGCATATCAAATATAGc |
| AACTGTGATAGAGTTCCAACAAAAGAACAACAGACTACTAGAGATTACCAGGGAATTTAGTGTTAATGCAGGCGTAA |
| CTACACCTGTAAGCACTTACATGTTAACTAATAGTGAATTATTGTCATTAATCAATGATATGCCTATAACAAATGAT |
| CAGAAAAAGTTAATGTCCAACAATGTTCAAATAGTTAGACAGCAAAGTTACTCTATCATGTCCATAATAAAAGAGGA |

-continued

| Exemplary Sequences |
|---|
| AGTCTTAGCATATGTAGTACAATTACCACTATATGGTGTTATAGATACACCCTGTTGGAAACTACACACATCCCCTC |
| TATGTACAACCAACACAAAAGAAGGGTCCAACATCTGTTTAACAAGAACTGACAGAGGATGGTACTGTGACAATGCA |
| GGATCAGTATCTTTCTTCCCACAAGCTGAAACATGTAAAGTTCAATCAAATCGAGTATTTTGTGACACAATGAACAG |
| TTTAACATTACCAAGTGAAGTAAATCTCTGCAATGTTGACATATTCAACCCCAAATATGATTGTAAAATTATGACTT |
| CAAAAACAGATGTAAGCAGCTCCGTTATCACATCTCTAGGAGCCATTGTGTCATGCTATGGCAAAACTAAATGTACA |
| GCATCCAATAAAAATCGTGGAATCATAAAGACATTTTCTAACGGGTGCGATTATGTATCAAATAAAGGGGTGGACAC |
| TGTGTCTGTAGGTAACACATTATATTATGTAAATAAGCAAGAAGGTAAAAGTCTCTATGTAAAAGGTGAACCAATAA |
| TAAATTTCTATGACCCATTAGTATTCCCCTCTGATGAATTTGATGCATCAATATCTCAAGTCAACGAGAAGATTAAC |
| CAGAGCCTAGCATTTATTCGTAAATCCGATGAATTATTACATAATGTAAATGCTGGTAAATCCACCAtAAATATCAT |
| GATAACTACTATAATTATAGTGATTATAGTAATATTGTTATCATTAATTGCTGTTGGACTGCTCTTATACTGTAAGG |
| CCAGAAGCACACCAGTCACACTAAGCAAAGATCAACTGAGTGGTATAAATAATATTGCATTTAGTAACTAAATAAAA |
| ATAGCACCTAATCATGTTCTTACAATGGTTTACTATCTGCTCATAGACAACCCATCTGTCATTGGATTTTCTTAAAA |
| TCTGAACTTCATCGAAACTCTCATCTATAAACCATCTCACTTACACTATTTAAGTAGATTCCTAGTTTATAGTTATA |
| TAAAACACAATTGCATGCCAGATTAACTTACCATCTGTAAAAATGAAAACTGGGGCAAATATGTCACGAAGGAATCC |
| TTGCAAATTTGAAATTCGAGGTCATTGCTTAAATGGTAAGAGGTGTCATTTTAGTCATAATTATTTTGAATGGCCAC |
| CCCATGCACTGCTTGTAAGACAAAACTTTATGTTAAACAGAATACTTAAGTCTATGGATAAAAGTATAGATACCTTA |
| TCAGAAATAAGTGGAGCTGCAGAGTTGGACAGAACAGAAGAGTATGCTCTTGGTGTAGTTGGAGTGCTAGAGAGTTA |
| TATAGGATCAATAAACAATATAACTAAACAATCAGCATGTGTTGCCATGAGCAAACTCCTCACTGAACTCAATAGTG |
| ATGATATCAAAAAGCTGAGGGACAATGAAGAGCTAAATTCACCCAAGATAAGAGTGTACAATACTGTCATATCATAT |
| ATTGAAAGCAACAGGAAAAACAATAAACAAACTATCCATCTGTTAAAAAGATTGCCAGCAGACGTATTGAAGAAAAC |
| CATCAAAAACACATTGGATATCCATAAGAGCATAACCATCAACAACCCAAAAGAATCAACTGTTAGTGATACAAAcG |
| ACCAcGCCAAAAATAAcGATACTACCTAACACTCAATTCTAACACTCACCACATCGTTACATTATTAATTCAAACAA |
| TTCAAGTTGTGGGACAAAATGGATCCCATTATTAATGGAAATTCTGCTAATGTTTATCTAACCGATAGTTATTTAAA |
| AGGTGTTATCTCTTTCTCAGAGTGTAATGCTTTAGGAAGTTACATATTCAATGGTCCTTATCTCAAAAATGATTATA |
| CCAACTTAATTAGTAGACAAAATCCATTAATAGAACACATGAATCTAAAGAAACTAAATATAACACAGTCCTTAATA |
| TCTAAGTATCATAAAGGTGAAATAAAATTAGAAGAACCTACTTATTTTCAGTCATTACTTATGACATACAAGAGTAT |
| GACCTCGTCAGAACAGATTGCTACCACTAATTTACTTAAAAAGATAATAAGAAGAGCTATAGAAATAAGTGATGTCA |
| AAGTCTATGCTATATTGAATAAACTAGGGCTTAAAGAAAAGGACAAGATTAAATCCAACAATGGACAAGATGAAGAC |
| AACTCAGTTATTACGACCATAATCAAAGATGATATACTTTCAGCTGTTAAAGATAATCAATCTCATCTTAAAGCAGA |
| CAAAAATCACTCTACAAAACAAAAAGACACAATCAAAACAACACTCTTGAAGAAATTGATGTGTTCAATGCAACATC |
| CTCCATCATGGTTAATACATTGGTTTAACTTATACACAAAATTAAACAACATATTAACACAGTATCGATCAAATGAG |
| GTAAAAAACCATGGGTTTACATTGATAGATAATCAAACTCTTAGTGGATTTCAATTTATTTTGAACCAATATGGTTG |
| TATAGTTTATCATAAGGAACTCAAAAGAATTACTGTGACAACCTATAATCAATTCTTGACATGGAAAGATATTAGCC |
| TTAGTAGATTAAATGTTTGTTTAATTACATGGATTAGTAACTGCTTGAACACATTAAATAAAAGCTTAGGCTTAAGA |
| TGCGGATTCAATAATGTTATCTTGACACAACTATTCCTTTATGGAGATTacATACTAAAGCTATTTCACAATGAGGG |
| GTTCTACATAATAAAAGAGGTAGAGGGATTTATTATGTCTCTAATTTTAAATATAACAGAAGAAGATCAATTCAGAA |
| AACGATTTTATAATAGTATGCTCAACAACATCACAGATGCTGCTAATAAAGCTCAGAAAAATCTGCTATCAAGAGTA |
| TGTCATACATTATTAGATAAGACAGTGTCCGATAATATAATAAATGGCAGATGGATAATTCTATTAAGTAAGTTCCT |
| TAAATTAATTAAGCTTGCAGGTGACAATAACCTTAACAATCTGAGTGAACTATATTTTTTGTTCAGAATATTTGGAC |

-continued

| Exemplary Sequences |
|---|
| ACCCAATGGTAGATGAAAGACAAGCCATGGATGCTGTTAAAATTAATTGCAATGAGACCAAATTTTACTTGTTAAGC |
| AGTCTGAGTATGTTAAGAGGTGCCTTTATATATAGAATTATAAAAGGGTTTGTAAATAATTACAACAGATGGCCTAC |
| TTTAAGAAATGCTATTGTTTTACCCTTAAGATGGTTAACTTACTATAAACTAAACACTTATCCTTCTTTGTTGGAAC |
| TTACAGAAAGAGATTTGATTGTGTTATCAGGACTACGTTTCTATCGTGAGTTTCGGTTGCCTAAAAAAGTGGATCTT |
| GAAATGATTATAAATGATAAAGCTATATCACCTCCTAAAAATTTGATATGGACTAGTTTCCCTAGAAATTACATGCC |
| ATCACACATACAAAACTATATAGAACATGAAAAATTAAAATTTTCCGAGAGTGATAAATCAAGAAGAGTATTAGAGT |
| ATTATTTAAGAGATAACAAATTCAATGAATGTGATTTATACAACTGTGTAGTTAATCAAAGTTATCTCAACAACCCT |
| AATCATGTGGTATCATTGACAGGCAAAGAAAGAGAACTCAGTGTAGGTAGAATGTTTGCAATGCAACCGGGAATGTT |
| CAGACAGGTTCAAATATTGGCAGAGAAAATGATAGCTGAAAACATTTTACAATTCTTTCCTGAAAGTCTTACAAGAT |
| ATGGTGATCTAGAACTACAAAAAATATTAGAACTGAAAGCAGGAATAAGTAACAAATCAAATCGCTACAATGATAAT |
| TACAACAATTACATTAGTAAGTGCTCTATCATCACAGATCTCAGCAAATTCAATCAAGCATTTCGATATGAAACGTC |
| ATGTATTTGTAGTGATGTGCTGGATGAACTGCATGGTGTACAATCTCTATTTTCCTGGTTACATTTAACTATTCCTC |
| ATGTCACAATAATATGCACATATAGGCATGCACCCCCCTATATAGGAGATCATATTGTAGATCTTAACAATGTAGAT |
| GAACAAAGTGGATTATATAGATATCACATGGGTGGCATCGAAGGGTGGTGTCAAAAACTATGGACCATAGAAGCTAT |
| ATCACTATTGGATCTAATATCTCTCAAAGGGAAATTCTCAATTACTGCTTTAATTAATGGTGACAATCAATCAATAG |
| ATATAAGCAAACCAATCAGACTCATGGAAGGTCAAACTCATGCTCAAGCAGATTATTTGCTAGCATTAAATAGCCTT |
| AAATTACTGTATAAAGAGTATGCAGGCATAGGCCACAAATTAAAAGGAACTGAGACTTATATATCACGAGATATGCA |
| ATTTATGAGTAAAACAATTCAACATAACGGTGTATATTACCCAGCTAGTATAAAGAAAGTCCTAAGAGTGGGACCGT |
| GGATAAACACTATACTTGATGATTTCAAAGTGAGTCTAGAATCTATAGGTAGTTTGACACAAGAATTAGAATATAGA |
| GGTGAAAGTCTATTATGCAGTTTAATATTTAGAAATGTATGGTTATATAATCAGATTGCTCTACAATTAAAAAATCA |
| TGCATTATGTAACAATAAACTATATTTGGACATATTAAAGGTTCTGAAACACTTAAAAACCTTTTTTAATCTTGATA |
| ATATTGATACAGCATTAACATTGTATATGAATTTACCCATGTTATTTGGTGGTGGTGATCCCAACTTGTTATATCGA |
| AGTTTCTATAGAAGAACTCCTGACTTCCTCACAGAGGCTATAGTTCACTCTGTGTTCATACTTAGTTATTATACAAA |
| CCATGACTTAAAAGATAAACTTCAAGATCTGTCAGATGATAGATTGAATAAGTTCTTAACATGCATAATCACGTTTG |
| ACAAAAACCCTAATGCTGAATTCGTAACATTGATGAGAGATCCTCAAGCTTTAGGGTCTGAGAGACAAGCTAAAATT |
| ACTAGCGAAATCAATAGACTGGCAGTTACAGAGGTTTTGAGTACAGCTCCAAACAAAATATTCTCCAAAAGTGCACA |
| ACATTATACTACTACAGAGATAGATCTAAATGATATTATGCAAAATATAGAACCTACATATCCTCATGGGCTAAGAG |
| TTGTTTATGAAAGTTTACCCTTTTATAAAGCAGAGAAAATAGTAAATCTTATATCAGGTACAAAATCTATAACTAAC |
| ATACTGGAAAAAACTTCTGCCATAGACTTAACAGATATTGATAGAGCCACTGAGATGATGAGGAAAAACATAACTTT |
| GCTTATAAGGATACTTCCATTGGATTGTAACAGAGATAAAAGAGAGATATTGAGTATGGAAAACCTAAGTATTACTG |
| AATTAAGCAAATATGTTAGGGAAAGATCTTGGTCTTTATCCAATATAGTTGGTGTTACATCACCCAGTATCATGTAT |
| ACAATGGACATCAAATATACTACAAGCACTATATCTAGTGGCATAATTATAGAGAAATATAATGTTAACAGTTTAAC |
| ACGTGGTGAGAGAGGACCCACTAAACCATGGGTTGGTTCATCTACACAAGAGAAAAAAACAATGCCAGTTTATAATA |
| GACAAGTCTTAACCAAAAAACAGAGAGATCAAATAGATCTATTAGCAAAATTGGATTGGGTGTATGCATCTATAGAT |
| AACAAGGATGAATTCATGGAAGAACTCAGCATAGGAACCCTTGGGTTAACATATGAAAAGGCCAAGAAATTATTTCC |
| ACAATATTTAAGTGTCAATTATTTGCATCGCCTTACAGTCAGTAGTAGACCATGTGAATTCCCTGCATCAATACCAG |
| CTTATAGAACAACAAATTATCACTTTGACACTAGCCCTATTAATCGCATATTAACAGAAAAGTATGGTGATGAAGAT |
| ATTGACATAGTATTCCAAAACTGTATAAGCTTTGGCCTTAGTTTAATGTCAGTAGTAGAACAATTTACTAATGTATG |

-continued

| Exemplary Sequences |
|---|
| TCCTAACAGAATTATTCTCATACCTAAGCTTAATGAGATACATTTGATGAAACCTCCCATATTCACAGGTGATGTTG |
| ATATTCACAAGTTAAAACAAGTGATACAAAAACAGCATATGTTTTTACCAGACAAAATAAGTTTGACTCAATATGTG |
| GAATTATTCTTAAGTAATAAAACACTCAAATCTGGATCTCATGTTAATTCTAATTTAATATTGGCACATAAAATATC |
| TGACTATTTTCATAATACTTACATTTTAAGTACTAATTTAGCTGGACATTGGATTCTGATTATACAACTTATGAAAG |
| ATTCTAAAGGTATTTTTGAAAAAGATTGGGGAGAGGGATATATAACTGATCATATGTTTATTAATTTGAAAGTTTTC |
| TTCAATGCTTATAAGACCTATCTCTTGTGTTTTCATAAAGGTTATGGCAAAGCAAAGCTGGAGTGTGATATGAACAC |
| TTCAGATCTTCTATGTGTATTGGAATTAATAGACAGTAGTTATTGGAAGTCTATGTCTAAGGTATTTTTAGAACAAA |
| AAGTTATCAAATACATTCTTAGCCAAGATGCAAGTTTACATAGAGTAAAAGGATGTCATAGCTTCAAATTATGGTTT |
| CTTAAACGTCTTAATGTAGCAGAATTCACAGTTTGCCCTTGGGTTGTTAACATAGATTATCATCCAACACATATGAA |
| AGCAATATTAACTTATATAGATCTTGTTAGAATGGGATTGATAAATATAGATAGAATACACATTAAAAATAAACACA |
| AATTCAATGATGAATTTTATACTTCTAATCTCTTCTACATTAATTATAACTTCTCAGATAATACTCATCTATTAACT |
| AAATACATAAGGATTGCTAATTCTGAATTAGAAAATAATTACAACAAATTATATCATCCTACACCAGAAACCCTAGA |
| GAATATACTAGCCAATCCGATTAAAAGTAATGACAAAAAGACACTGAATGACTATTGTATAGGTAAAAATGTTGACT |
| CAATAATGTTACCATTGTTATCTAATAAGAAGCTTATTAAATCGTCTGCAATGATTAGAACCAATTACAGCAAACAA |
| GATTTGTATAATTTATTCCCTATGGTTGTGATTGATAGAATTATAGATCATTCAGGCAATACAGCCAAATCCAACCA |
| ACTTTACACTACTACTTCCCACCAAATATCCTTAGTGCACAATAGCACATCACTTTACTGCATGCTTCCTTGGCATC |
| ATATTAATAGATTCAATTTTGTATTTAGTTCTACAGGTTGTAAAATTAGTATAGAGTATATTTTAAAAGATCTTAAA |
| ATTAAAGATCCCAATTGTATAGCATTCATAGGTGAAGGAGCAGGGAATTTATTATTGCGTACAGTAGTGGAACTTCA |
| TCCTGACATAAGATATATTTACAGAAGTCTGAAAGATTGCAATGATCATAGTTTACCTATTGAGTTTTTAAGGCTGT |
| ACAATGGACATATCAACATTGATTATGGTGAAAATTTGACCATTCCTGCTACAGATGCAACCAACAACATTCATTGG |
| TCTTATTTACATATAAAGTTTGCTGAACCTATCAGTCTTTTTGTCTGTGATGCCGAATTGTCTGTAACAGTCAACTG |
| GAGTAAAATTATAATAGAATGGAGCAAGCATGTAAGAAAGTGCAAGTACTGTTCCTCAGTTAATAAATGTATGTTAA |
| TAGTAAAATATCATGCTCAAGATGATATTGATTTCAAATTAGACAATATAACTATATTAAAAACTTATGTATGCTTA |
| GGCAGTAAGTTAAAGGGATCGGAGGTTTACTTAGTCCTTACAATAGGTCCTGCGAATATATTCCCAGTATTTAATGT |
| AGTACAAAATGCTAAATTGATACTATCAAGAACCAAAAATTTCATCATGCCTAAGAAAGCTGATAAAGAGTCTATTG |
| ATGCAAATATTAAAAGTTTGATACCCTTTCTTTGTTACCCTATAACAAAAAAAGGAATTAATACTGCATTGTCAAAA |
| CTAAAGAGTGTTGTTAGTGGAGATATACTATCATATTCTATAGCTGGACGTAATGAAGTTTTCAGCAATAAACTTAT |
| AAATCATAAGCATATGAACATCTTAAAATGGTTCAATCATGTTTTAAATTTCAGATCAACAGAACTAAACTATAACC |
| ATTTATATATGGTAGAATCTACATATCCTTACCTAAGTGAATTGTTAAACAGCTTGACAACCAATGAACTTAAAAAA |
| CTGATTAAAATCACAGGTAGTCTGTTATACAACTTTCATAATGAATAATGAATAAAGATCTTATAATAAAAATTCCC |
| ATAGCTATACACTAACACTGTATTCAATTATAGTTATTAAAAATTAAAAATCATATAATTTTTTAAATAACTTTTAG |
| TGAACTAATCCTAAAGTTATCATTTTAATCTTGGAGGAATAAATTTAAACCCTAATCTAATTGGTTTATATGTGTAT |
| TAACTAAATTACGAGATATTAGTTTTTGACACTTTTTTTCTCGT |
| Antigenomic cDNA sequence of LID/ΔM2-2/1030s (SEQ ID NO: 16) |
| ACGGGAAAAAATGCGTACAACAAACTTGCATAAACCAAAAAAATGGGGCAAATAAGAATTTGATAAGTACCACTTAA |
| ATTTAACTCCCTTGGTTAGAGATGGGCAGCAATTCATTGAGTATGATAAAAGTTAGATTACAAAATTTGTTTGACAA |
| TGATGAAGTAGCATTGTTAAAAATAACATGCTATACTGATAAATTAATACATTTAACTAATGCTTTGGCTAAGGCAG |
| TGATACATACAATCAAATTGAATGGCATTGTGTTTGTGCATGTTATTACAAGTAGTGATATTTGCCCTAATAATAAT |
| ATTGTAGTAAAATCCAATTTCACAACAATGCCAGTACTACAAAATGGAGGTTATATATGGGAAATGATGGAATTAAC |

-continued

| Exemplary Sequences |
| --- |

ACATTGCTCTCAACCTAATGGTCTACTAGATGACAATTGTGAAATTAAATTCTCCAAAAAACTAAGTGATTCAACAA

TGACCAATTATATGAATCAATTATCTGAATTACTTGGATTTGATCTTAATCCATAAATTATAATTAATATCAACTAG

CAAATCAATGTCACTAACACCATTAGTTAATATAAAACTTAACAGAAGACAAAAATGGGGCAAATAAATCAATTCAG

CCAACCCAACCATGGACACAACCCACAATGATAATACACCACAAAGACTGATGATCACAGACATGAGACCGTTGTCA

CTTGAGACCATAATAACATCACTAACCAGAGACATCATAACACACAAATTTATATACTTGATAAATCATGAATGCAT

AGTGAGAAAACTTGATGAAAGACAGGCCACATTTACATTCCTGGTCAACTATGAAATGAAACTATTACACAAAGTAG

GAAGCACTAAATATAAAAAATATACTGAATACAACACAAAATATGGCACTTTCCCTATGCCAATATTCATCAATCAT

GATGGGTTCTTAGAATGCATTGGCATTAAGCCTACAAAGCATACTCCCATAATATACAAGTATGATCTCAATCCATA

AATTTCAACACAATATTCACACAATCTAAAACAACAACTCTATGCATAACTATACTCCATAGTCCAGATGGAGCCTG

AAAATTATAGTAATTTAAAACTTAAGGAGAGATATAAGATAGAAGATGGGGCAAATACAACCATGGCTCTTAGCAAA

GTCAAGTTGAATGATACACTCAACAAAGATCAACTTCTGTCATCCAGCAAATACACCATCCAACGGAGCACAGGAGA

TAGTATTGATACTCCTAATTATGATGTGCAGAAACACATCAATAAGTTATGTGGCATGTTATTAATCACAGAAGATG

CTAATCATAAATTCACTGGGTTAATAGGTATGTTATATGCGATGTCTAGGTTAGGAAGAGAAGACACCATAAAAATA

CTCAGAGATGCGGGATATCATGTAAAAGCAAATGGAGTAGATGTAACAACACATCGTCAAGACATTAATGGAAAAGA

AATGAAATTTGAAGTGTTAACATTGGCAAGCTTAACAACTGAAATTCAAATCAACATTGAGATAGAATCTAGAAAAT

CCTACAAAAAAATGCTAAAAGAAATGGGAGAGGTAGCTCCAGAATACAGGCATGACTCTCCTGATTGTGGGATGATA

ATATTATGTATAGCAGCATTAGTAATAACTAAATTAGCAGCAGGGGACAGATCTGGTCTTACAGCCGTGATTAGGAG

AGCTAATAATGTCCTAAAAAATGAAATGAAACGTTACAAAGGCTTACTACCCAAGGACATAGCCAACAGCTTCTATG

AAGTGTTTGAAAAACATCCCCACTTTATAGATGTTTTTGTTCATTTTGGTATAGCACAATCTTCTACCAGAGGTGGC

AGTAGAGTTGAAGGGATTTTTGCAGGATTGTTTATGAATGCCTATGGTGCAGGGCAAGTGATGTTACGGTGGGGAGT

CTTAGCAAAATCGGTTAAAAATATTATGTTAGGACATGCTAGTGTGCAAGCAGAAATGGAACAAGTTGTTGAGGTTT

ATGAATATGCCCAAAAATTGGGTGGTGAAGCAGGATTCTACCATATATTGAACAACCCAAAAGCATCATTATTATCT

TTGACTCAATTTCCTCACTTCTCCAGTGTAGTATTAGGCAATGCTGCTGGCCTAGGCATAATGGGAGAGTACAGAGG

TACACCGAGGAATCAAGATCTATATGATGCAGCAAAGGCATATGCTGAACAACTCAAAGAAAATGGTGTGATTAACT

ACAGTGTACTAGACTTGACAGCAGAAGAACTAGAGGCTATCAAACATCAGCTTAATCCAAAAGATAATGATGTAGAG

CTTTGAGTTAATAAAAAATGGGGCAAATAAATCATCATGGAAAAGTTTGCTCCTGAATTCCATGGAGAAGATGCAAA

CAACAGGGCTACTAAATTCCTAGAATCAATAAAGGGCAAATTCACATCACCCAAAGATCCCAAGAAAAAAGATAGTA

TCATATCTGTCAACTCAATAGATATAGAAGTAACCAAAGAAAGCCCTATAACATCAAATTCAACTATTATCAACCCA

ACAAATGAGACAGATGATACTGCAGGGAACAAGCCCAATTATCAAAGAAAACCTCTAGTAAGTTTCAAAGAAGACCC

TACACCAAGTGATAATCCCTTTTCTAAACTATACAAAGAAACCATAGAAACATTTGATAACAATGAAGAAGAATCCA

GCTATTCATACGAAGAAATAAATGATCAGACAAACGATAATATAACAGCAAGATTAGATAGGATTGATGAAAAATTA

AGTGAAATACTAGGAATGCTTCACACATTAGTAGTGGCAAGTGCAGGACCTACATCTGCTCGGGATGGTATAAGAGA

TGCCATGGTTGGTTTAAGAGAAGAAATGATAGAAAAAATCAGAACTGAAGCATTAATGACCAATGACAGATTAGAAG

CTATGGCAAGACTCAGGAATGAGGAAAGTGAAAAGATGGCAAAAGACACATCAGATGAAGTGTCTCTCAATCCAACA

TCAGAGAAATTGAACAACCTATTGGAAGGGAATGATAGTGACAATGATCTATCACTTGAAGATTTCTGATTAGTTAC

CAATCTTCACATCAACACACAATACCAACAGAAGACCAACAAACTAACCAACCCAATCATCCAACCAAACATCCATC

CGCCAATCAGCCAAACAGCCAACAAAACAACCAGCCAATCCAAAACTAACCACCCGGAAAAAATCTATAATATAGTT

ACAAAAAAAGGAAAGGGTGGGGCAAATATGGAAACATACGTGAACAAGCTTCACGAAGGCTCCACATACACAGCTGC

-continued

| Exemplary Sequences |
| --- |
| TGTTCAATACAATGTCTTAGAAAAAGACGATGACCCTGCATCACTTACAATATGGGTGCCCATGTTCCAATCATCTA |
| TGCCAGCAGATTTACTTATAAAAGAACTAGCTAATGTCAACATACTAGTGAAACAAATATCCACACCCAAGGGACCT |
| TCACTAAGAGTCATGATAAACTCAAGAAGTGCAGTGCTAGCACAAATGCCCAGCAAATTTACCATATGCGCTAATGT |
| GTCCTTGGATGAAAGAAGCAAACTAGCATATGATGTAACCACACCCTGTGAAATCAAGGCATGTAGTCTAACATGCC |
| TAAAATCAAAAAATATGTTGACTACAGTTAAAGATCTCACTATGAAGACACTCAACCCTACACATGATATTATTGCT |
| TTATGTGAATTTGAAAACATAGTAACATCAAAAAAAGTCATAATACCAACATACCTAAGATCCATCAGTGTCAGAAA |
| TAAAGATCTGAACACACTTGAAAATATAACAACCACTGAATTCAAAAATGCTATCACAAATGCAAAAATCATCCCTT |
| ACTCAGGATTACTATTAGTCATCACAGTGACTGACAACAAAGGAGCATTCAAATACATAAAGCCACAAAGTCAATTC |
| ATAGTAGATCTTGGAGCTTACCTAGAAAAAGAAAGTATATATTATGTTACCACAAATTGGAAGCACACAGCTACACG |
| ATTTGCAATCAAACCCATGGAAGATTAACCTTTTTCCTCTACATCAGTGTGTTAATTCATACAAACTTTCTACCTAC |
| ATTCTTCACTTCACCATCACAATCACAAACACTCTGTGGTTCAACCAATCAAACAAAACTTATCTGAAGTCCCAGAT |
| CATCCCAAGTCATTGTTTATCAGATCTAGTACTCAAATAAGTTAATAAAAAATATACACATGGGGCAAATAATCATT |
| GGAGGAAATCCAACTAATCACAATATCTGTTAACATAGACAAGTCCACACACCATACAGAATCAACCAATGGAAAAT |
| ACATCCATAACAATAGAATTCTCAAGCAAATTCTGGCCTTACTTTACACTAATACACATGATCACAACAATAATCTC |
| TTTGCTAATCATAATCTCCATCATGATTGCAATACTAAACAAACTTTGTGAATATAACGTATTCCATAACAAAACCT |
| TTGAGTTACCAAGAGCTCGAGTTAATACTTGATAAAGTAGTTAATTAAAAATAGTCATAACAATGAACTAGGATATC |
| AAGACTAACAATAACATTGGGGCAAATGCAAACATGTCCAAAAACAAGGACCAACGCACCGCTAAGACATTAGAAAG |
| GACCTGGGACACTCTCAATCATTTATTATTCATATCATCGTGCTTATATAAGTTAAATCTTAAATCTGTAGCACAAA |
| TCACATTATCCATTCTGGCAATGATAATCTCAACTTCACTTATAATTGCAGCCATCATATTCATAGCCTCGGCAAAC |
| CACAAAGTCACACCAACAACTGCAATCATACAAGATGCAACAAGCCAGATCAAGAACACAACCCCAACATACCTCAC |
| CCAGAATCCTCAGCTTGGAATCAGTCCCTCTAATCCGTCTGAAATTACATCACAAATCACCACCATACTAGCTTCAA |
| CAACACCAGGAGTCAAGTCAACCCTGCAATCCACAACAGTCAAGACCAAAAACACAACAACAACTCAAACACAACCC |
| AGCAAGCCCACCACAAAACAACGCCAAAACAAACCACCAAGCAAACCCAATAATGATTTTCACTTTGAAGTGTTCAA |
| CTTTGTACCCTGCAGCATATGCAGCAACAATCCAACCTGCTGGGCTATCTGCAAAAGAATACCAAACAAAAAACCAG |
| GAAAGAAAACCACTACCAAGCCCACAAAAAAACCAACCCTCAAGACAACCAAAAAAGATCCCAAACCTCAAACCACT |
| AAATCAAAGGAAGTACCCACCACCAAGCCCACAGAAGAGCCAACCATCAACACCACCAAAACAAACATCATAACTAC |
| ACTACTCACCTCCAACACCACAGGAAATCCAGAACTCACAAGTCAAATGGAAACCTTCCACTCAACTTCCTCCGAAG |
| GCAATCCAAGCCCTTCTCAAGTCTCTACAACATCCGAGTACCCATCACAACCTTCATCTCCACCCAACACACCACGC |
| CAGTAGTTACTTAAAAACATATTATCACAAAAGGCCTTGACCAACTTAAACAGAATCAAAATAAACTCTGGGGCAAA |
| TAACAATGGAGTTGCTAATCCTCAAAGCAAATGCAATTACCACAATCCTCACTGCAGTCACATTTTGTTTTGCTTCT |
| GGTCAAAACATCACTGAAGAATTTTATCAATCAACATGCAGTGCAGTTAGCAAAGGCTATCTTAGTGCTCTGAGAAC |
| TGGTTGGTATACCAGTGTTATAACTATAGAATTAAGTAATATCAAGAAAAATAAGTGTAATGGAACAGATGCTAAGG |
| TAAAATTGATAAAACAAGAATTAGATAAATATAAAAATGCTGTAACAGAATTGCAGTTGCTCATGCAAAGCACACAA |
| GCAACAAACAATCGAGCCAGAAGAGAACTACCAAGGTTTATGAATTATACACTCAACAATGCCAAAAAAACCAATGT |
| AACATTAAGCAAGAAAAGGAAAAGAAGATTTCTTGGTTTTTTGTTAGGTGTTGGATCTGCAATCGCCAGTGGCGTTG |
| CTGTATCTAAGGTCCTGCACCTAGAAGGGGAAGTGAACAAGATCAAAAGTGCTCTACTATCCACAAACAAGGCTGTA |
| GTCAGCTTATCAAATGGAGTTAGTGTTTTAACCAGCAAAGTGTTAGACCTCAAAAACTATATAGATAAACAATTGTT |
| ACCTATTGTGAACAAGCAAAGCTGCAGCATATCAAATATAGAAACTGTGATAGAGTTCCAACAAAAGAACAACAGAC |
| TACTAGAGATTACCAGGGAATTTAGTGTTAATGCAGGCGTAACTACACCTGTAAGCACTTACATGTTAACTAATAGT |

-continued

| Exemplary Sequences |
|---|
| GAATTATTGTCATTAATCAATGATATGCCTATAACAAATGATCAGAAAAAGTTAATGTCCAACAATGTTCAAATAGT |
| TAGACAGCAAAGTTACTCTATCATGTCCATAATAAAAGAGGAAGTCTTAGCATATGTAGTACAATTACCACTATATG |
| GTGTTATAGATACACCCTGTTGGAAACTACACACATCCCCTCTATGTACAACCAACACAAAAGAAGGGTCCAACATC |
| TGTTTAACAAGAACTGACAGAGGATGGTACTGTGACAATGCAGGATCAGTATCTTTCTTCCCACAAGCTGAAACATG |
| TAAAGTTCAATCAAATCGAGTATTTTGTGACACAATGAACAGTTTAACATTACCAAGTGAAGTAAATCTCTGCAATG |
| TTGACATATTCAACCCCAAATATGATTGTAAAATTATGACTTCAAAAACAGATGTAAGCAGCTCCGTTATCACATCT |
| CTAGGAGCCATTGTGTCATGCTATGGCAAAACTAAATGTACAGCATCCAATAAAAATCGTGGAATCATAAAGACATT |
| TTCTAACGGGTGCGATTATGTATCAAATAAAGGGGTGGACACTGTGTCTGTAGGTAACACATTATATTATGTAAATA |
| AGCAAGAAGGTAAAAGTCTCTATGTAAAAGGTGAACCAATAATAAATTTCTATGACCCATTAGTATTCCCCTCTGAT |
| GAATTTGATGCATCAATATCTCAAGTCAACGAGAAGATTAACCAGAGCCTAGCATTTATTCGTAAATCCGATGAATT |
| ATTACATAATGTAAATGCTGGTAAATCCACCACAAATATCATGATAACTACTATAATTATAGTGATTATAGTAATAT |
| TGTTATCATTAATTGCTGTTGGACTGCTCTTATACTGTAAGGCCAGAAGCACACCAGTCACACTAAGCAAAGATCAA |
| CTGAGTGGTATAAATAATATTGCATTTAGTAACTAAATAAAAATAGCACCTAATCATGTTCTTACAATGGTTTACTA |
| TCTGCTCATAGACAACCCATCTGTCATTGGATTTTCTTAAAATCTGAACTTCATCGAAACTCTCATCTATAAACCAT |
| CTCACTTACACTATTTAAGTAGATTCCTAGTTTATAGTTATATAAAACACAATTGCATGCCAGATTAACTTACCATC |
| TGTAAAAATGAAAACTGGGGCAAATATGTCACGAAGGAATCCTTGCAAATTTGAAATTCGAGGTCATTGCTTAAATG |
| GTAAGAGGTGTCATTTTAGTCATAATTATTTTGAATGGCCACCCCATGCACTGCTTGTAAGACAAAACTTTATGTTA |
| AACAGAATACTTAAGTCTATGGATAAAAGTATAGATACCTTATCAGAAATAAGTGGAGCTGCAGAGTTGGACAGAAC |
| AGAAGAGTATGCTCTTGGTGTAGTTGGAGTGCTAGAGAGTTATATAGGATCAATAAACAATATAACTAAACAATCAG |
| CATGTGTTGCCATGAGCAAACTCCTCACTGAACTCAATAGTGATGATATCAAAAAGCTGAGGGACAATGAAGAGCTA |
| AATTCACCCAAGATAAGAGTGTACAATACTGTCATATCATATATTGAAAGCAACAGGAAAAACAATAAACAAACTAT |
| CCATCTGTTAAAAAGATTGCCAGCAGACGTATTGAAGAAAACCATCAAAAACACATTGGATATCCATAAGAGCATAA |
| CCATCAACAACCCAAAAGAATCAACTGTTAGTGATACAAACGACCACGCCAAAAATAACGATACTACCTAACACTCA |
| ATTCTAACACTCACCACATCGTTACATTATTAATTCAAACAATTCAAGTTGTGGGACAAAATGGATCCCATTATTAA |
| TGGAAATTCTGCTAATGTTTATCTAACCGATAGTTATTTAAAAGGTGTTATCTCTTTCTCAGAGTGTAATGCTTTAG |
| GAAGTTACATATTCAATGGTCCTTATCTCAAAAATGATTATACCAACTTAATTAGTAGACAAAATCCATTAATAGAA |
| CACATGAATCTAAAGAAACTAAATATAACACAGTCCTTAATATCTAAGTATCATAAAGGTGAAATAAAATTAGAAGA |
| ACCTACTTATTTTCAGTCATTACTTATGACATACAAGAGTATGACCTCGTCAGAACAGATTGCTACCACTAATTTAC |
| TTAAAAAGATAATAAGAAGAGCTATAGAAATAAGTGATGTCAAAGTCTATGCTATATTGAATAAACTAGGGCTTAAA |
| GAAAAGGACAAGATTAAATCCAACAATGGACAAGATGAAGACAACTCAGTTATTACGACCATAATCAAAGATGATAT |
| ACTTTCAGCTGTTAAAGATAATCAATCTCATCTTAAAGCAGACAAAAATCACTCTACAAAACAAAAAGACACAATCA |
| AAACAACACTCTTGAAGAAATTGATGTGTTCAATGCAACATCCTCCATCATGGTTAATACATTGGTTTAACTTATAC |
| ACAAAATTAAACAACATATTAACACAGTATCGATCAAATGAGGTAAAAAACCATGGGTTTACATTGATAGATAATCA |
| AACTCTTAGTGGATTTCAATTTATTTTGAACCAATATGGTTGTATAGTTTATCATAAGGAACTCAAAAGAATTACTG |
| TGACAACCTATAATCAATTCTTGACATGGAAAGATATTAGCCTTAGTAGATTAAATGTTTGTTTAATTACATGGATT |
| AGTAACTGCTTGAACACATTAAATAAAAGCTTAGGCTTAAGATGCGGATTCAATAATGTTATCTTGACACAACTATT |
| CCTTTATGGAGATTGTATACTAAAGCTATTTCACAATGAGGGGTTCTACATAATAAAAGAGGTAGAGGGATTTATTA |
| TGTCTCTAATTTTAAATATAACAGAAGAAGATCAATTCAGAAAACGATTTTATAATAGTATGCTCAACAACATCACA |

| Exemplary Sequences |
|---|
| GATGCTGCTAATAAAGCTCAGAAAAATCTGCTATCAAGAGTATGTCATACATTATTAGATAAGACAGTGTCCGATAA |
| TATAATAAATGGCAGATGGATAATTCTATTAAGTAAGTTCCTTAAATTAATTAAGCTTGCAGGTGACAATAACCTTA |
| ACAATCTGAGTGAACTATATTTTTTGTTCAGAATATTTGGACACCCAATGGTAGATGAAAGACAAGCCATGGATGCT |
| GTTAAAATTAATTGCAATGAGACCAAATTTTACTTGTTAAGCAGTCTGAGTATGTTAAGAGGTGCCTTTATATATAG |
| AATTATAAAAGGGTTTGTAAATAATTACAACAGATGGCCTACTTTAAGAAATGCTATTGTTTTACCCTTAAGATGGT |
| TAACTTACTATAAACTAAACACTTATCCTTCTTTGTTGGAACTTACAGAAAGAGATTTGATTGTGTTATCAGGACTA |
| CGTTTCTATCGTGAGTTTCGGTTGCCTAAAAAAGTGGATCTTGAAATGATTATAAATGATAAAGCTATATCACCTCC |
| TAAAAATTTGATATGGACTAGTTTCCCTAGAAATTACATGCCATCACACATACAAAACTATATAGAACATGAAAAAT |
| TAAAATTTTCCGAGAGTGATAAATCAAGAAGAGTATTAGAGTATTATTTAAGAGATAACAAATTCAATGAATGTGAT |
| TTATACAACTGTGTAGTTAATCAAAGTTATCTCAACAACCCTAATCATGTGGTATCATTGACAGGCAAAGAAAGAGA |
| ACTCAGTGTAGGTAGAATGTTTGCAATGCAACCGGGAATGTTCAGACAGGTTCAAATATTGGCAGAGAAAATGATAG |
| CTGAAAACATTTTACAATTCTTTCCTGAAAGTCTTACAAGATATGGTGATCTAGAACTACAAAAAATATTAGAACTG |
| AAAGCAGGAATAAGTAACAAATCAAATCGCTACAATGATAATTACAACAATTACATTAGTAAGTGCTCTATCATCAC |
| AGATCTCAGCAAATTCAATCAAGCATTTCGATATGAAACGTCATGTATTTGTAGTGATGTGCTGGATGAACTGCATG |
| GTGTACAATCTCTATTTTCCTGGTTACATTTAACTATTCCTCATGTCACAATAATATGCACATATAGGCATGCACCC |
| CCCTATATAGGAGATCATATTGTAGATCTTAACAATGTAGATGAACAAAGTGGATTATATAGATATCACATGGGTGG |
| CATCGAAGGGTGGTGTCAAAAACTATGGACCATAGAAGCTATATCACTATTGGATCTAATATCTCTCAAAGGGAAAT |
| TCTCAATTACTGCTTTAATTAATGGTGACAATCAATCAATAGATATAAGCAAACCAATCAGACTCATGGAAGGTCAA |
| ACTCATGCTCAAGCAGATTATTTGCTAGCATTAAATAGCCTTAAATTACTGTATAAAGAGTATGCAGGCATAGGCCA |
| CAAATTAAAAGGAACTGAGACTTATATATCACGAGATATGCAATTTATGAGTAAAACAATTCAACATAACGGTGTAT |
| ATTACCCAGCTAGTATAAAGAAAGTCCTAAGAGTGGGACCGTGGATAAACACTATACTTGATGATTTCAAAGTGAGT |
| CTAGAATCTATAGGTAGTTTGACACAAGAATTAGAATATAGAGGTGAAAGTCTATTATGCAGTTTAATATTTAGAAA |
| TGTATGGTTATATAATCAGATTGCTCTACAATTAAAAAATCATGCATTATGTAACAATAAACTATATTTGGACATAT |
| TAAAGGTTCTGAAACACTTAAAAACCTTTTTTAATCTTGATAATATTGATACAGCATTAACATTGTATATGAATTTA |
| CCCATGTTATTTGGTGGTGGTGATCCCAACTTGTTATATCGAAGTTTCTATAGAAGAACTCCTGACTTCCTCACAGA |
| GGCTATAGTTCACTCTGTGTTCATACTTAGTTATTATACAAACCATGACTTAAAAGATAAACTTCAAGATCTGTCAG |
| ATGATAGATTGAATAAGTTCTTAACATGCATAATCACGTTTGACAAAAACCCTAATGCTGAATTCGTAACATTGATG |
| AGAGATCCTCAAGCTTTAGGGTCTGAGAGACAAGCTAAAATTACTAGCGAAATCAATAGACTGGCAGTTACAGAGGT |
| TTTGAGTACAGCTCCAAACAAAATATTCTCCAAAAGTGCACAACATTATACTACTACAGAGATAGATCTAAATGATA |
| TTATGCAAAATATAGAACCTACATATCCTCATGGGCTAAGAGTTGTTTATGAAAGTTTACCCTTTTATAAAGCAGAG |
| AAAATAGTAAATCTTATATCAGGTACAAAATCTATAACTAACATACTGGAAAAAACTTCTGCCATAGACTTAACAGA |
| TATTGATAGAGCCACTGAGATGATGAGGAAAAACATAACTTTGCTTATAAGGATACTTCCATTGGATTGTAACAGAG |
| ATAAAAGAGAGATATTGAGTATGGAAAACCTAAGTATTACTGAATTAAGCAAATATGTTAGGGAAAGATCTTGGTCT |
| TTATCCAATATAGTTGGTGTTACATCACCCAGTATCATGTATACAATGGACATCAAATATACTACAAGCACTATATC |
| TAGTGGCATAATTATAGAGAAATATAATGTTAACAGTTTAACACGTGGTGAGAGAGGACCCACTAAACCATGGGTTG |
| GTTCATCTACACAAGAGAAAAAAACAATGCCAGTTTATAATAGACAAGTCTTAACCAAAAAACAGAGAGATCAAATA |
| GATCTATTAGCAAAATTGGATTGGGTGTATGCATCTATAGATAACAAGGATGAATTCATGGAAGAACTCTCAATAGG |
| AACCCTTGGGTTAACAAAAGAAAAGGCCAAGAAATTATTTCCACAATATTTAAGTGTCAATTATTTGCATCGCCTTA |
| CAGTCAGTAGTAGACCATGTGAATTCCCTGCATCAATACCAGCTTATAGAACAACAAATTATCACTTTGACACTAGC |

-continued

| Exemplary Sequences |
|---|

CCTATTAATCGCATATTAACAGAAAAGTATGGTGATGAAGATATTGACATAGTATTCCAAAACTGTATAAGCTTTGG

CCTTAGTTTAATGTCAGTAGTAGAACAATTTACTAATGTATGTCCTAACAGAATTATTCTCATACCTAAGCTTAATG

AGATACATTTGATGAAACCTCCCATATTCACAGGTGATGTTGATATTCACAAGTTAAAACAAGTGATACAAAAACAG

CATATGTTTTTACCAGACAAAATAAGTTTGACTCAATATGTGGAATTATTCTTAAGTAATAAAACACTCAAATCTGG

ATCTCATGTTAATTCTAATTTAATATTGGCACATAAAATATCTGACTATTTTCATAATACTTACATTTTAAGTACTA

ATTTAGCTGGACATTGGATTCTGATTATACAACTTATGAAAGATTCTAAAGGTATTTTTGAAAAAGATTGGGGAGAG

GGATATATAACTGATCATATGTTTATTAATTTGAAAGTTTTCTTCAATGCTTATAAGACCTATCTCTTGTGTTTTCA

TAAAGGTTATGGCAAAGCAAAGCTGGAGTGTGATATGAACACTTCAGATCTTCTATGTGTATTGGAATTAATAGACA

GTAGTTATTGGAAGTCTATGTCTAAGGTATTTTTAGAACAAAAAGTTATCAAATACATTCTTAGCCAAGATGCAAGT

TTACATAGAGTAAAAGGATGTCATAGCTTCAAATTATGGTTTCTTAAACGTCTTAATGTAGCAGAATTCACAGTTTG

CCCTTGGGTTGTTAACATAGATTATCATCCAACACATATGAAAGCAATATTAACTTATATAGATCTTGTTAGAATGG

GATTGATAAATATAGATAGAATACACATTAAAAATAAACACAAATTCAATGATGAATTTTATACTTCTAATCTCTTC

TACATTAATTATAACTTCTCAGATAATACTCATCTATTAACTAAACATATAAGGATTGCTAATTCTGAATTAGAAAA

TAATTACAACAAATTATATCATCCTACACCAGAAACCCTAGAGAATATACTAGCCAATCCGATTAAAAGTAATGACA

AAAAGACACTGAATGACTATTGTATAGGTAAAAATGTTGACTCAATAATGTTACCATTGTTATCTAATAAGAAGCTT

ATTAAATCGTCTGCAATGATTAGAACCAATTACAGCAAACAAGATTTGTATAATTTATTCCCTATGGTTGTGATTGA

TAGAATTATAGATCATTCAGGCAATACAGCCAAATCCAACCAACTTTACACTACTACTTCCCACCAAATATCCTTAG

TGCACAATAGCACATCACTTTACTGCATGCTTCCTTGGCATCATATTAATAGATTCAATTTTGTATTTAGTTCTACA

GGTTGTAAAATTAGTATAGAGTATATTTTAAAAGATCTTAAAATTAAAGATCCCAATTGTATAGCATTCATAGGTGA

AGGAGCAGGGAATTTATTATTGCGTACAGTAGTGGAACTTCATCCTGACATAAGATATATTTACAGAAGTCTGAAAG

ATTGCAATGATCATAGTTTACCTATTGAGTTTTTAAGGCTGTACAATGGACATATCAACATTGATTATGGTGAAAAT

TTGACCATTCCTGCTACAGATGCAACCAACAACATTCATTGGTCTTATTTACATATAAAGTTTGCTGAACCTATCAG

TCTTTTTGTCTGTGATGCCGAATTGTCTGTAACAGTCAACTGGAGTAAAATTATAATAGAATGGAGCAAGCATGTAA

GAAAGTGCAAGTACTGTTCCTCAGTTAATAAATGTATGTTAATAGTAAAATATCATGCTCAAGATGATATTGATTTC

AAATTAGACAATATAACTATATTAAAAACTTATGTATGCTTAGGCAGTAAGTTAAAGGGATCGGAGGTTTACTTAGT

CCTTACAATAGGTCCTGCGAATATATTCCCAGTATTTAATGTAGTACAAAATGCTAAATTGATACTATCAAGAACCA

AAAATTTCATCATGCCTAAGAAAGCTGATAAAGAGTCTATTGATGCAAATATTAAAAGTTTGATACCCTTTCTTTGT

TACCCTATAACAAAAAAAGGAATTAATACTGCATTGTCAAAACTAAAGAGTGTTGTTAGTGGAGATATACTATCATA

TTCTATAGCTGGACGTAATGAAGTTTTCAGCAATAAACTTATAAATCATAAGCATATGAACATCTTAAAATGGTTCA

ATCATGTTTTAAATTTCAGATCAACAGAACTAAACTATAACCATTTATATATGGTAGAATCTACATATCCTTACCTA

AGTGAATTGTTAAACAGCTTGACAACCAATGAACTTAAAAAACTGATTAAAATCACAGGTAGTCTGTTATACAACTT

TCATAATGAATAATGAATAAAGATCTTATAATAAAAATTCCCATAGCTATACACTAACACTGTATTCAATTATAGTT

ATTAAAAATTAAAAATCATATAATTTTTTAAATAACTTTTAGTGAACTAATCCTAAAGTTATCATTTTAATCTTGGA

GGAATAAATTTAAACCCTAATCTAATTGGTTTATATGTGTATTAACTAAATTACGAGATATTAGTTTTTGACACTTT

TTTTCTCGT

Antigenomic cDNA sequence of LID/cp/ΔM2-2

(SEQ ID NO: 17)

ACGGGAAAAAATGCGTACAACAAACTTGCATAAACCAAAAAAATGGGGCAAATAAGAATTTGATAAGTACCACTTAA

ATTTAACTCCCTTGGTTAGAGATGGGCAGCAATTCATTGAGTATGATAAAAGTTAGATTACAAAATTTGTTTGACAA

-continued

| Exemplary Sequences |
|---|
| TGATGAAGTAGCATTGTTAAAAATAACATGCTATACTGATAAATTAATACATTTAACTAATGCTTTGGCTAAGGCAG |
| TGATACATACAATCAAATTGAATGGCATTGTGTTTGTGCATGTTATTACAAGTAGTGATATTTGCCCTAATAATAAT |
| ATTGTAGTAAAATCCAATTTCACAACAATGCCAGTACTACAAAATGGAGGTTATATATGGGAAATGATGGAATTAAC |
| ACATTGCTCTCAACCTAATGGTCTACTAGATGACAATTGTGAAATTAAATTCTCCAAAAAACTAAGTGATTCAACAA |
| TGACCAATTATATGAATCAATTATCTGAATTACTTGGATTTGATCTTAATCCATAAATTATAATTAATATCAACTAG |
| CAAATCAATGTCACTAACACCATTAGTTAATATAAAACTTAACAGAAGACAAAAATGGGGCAAATAAATCAATTCAG |
| CCAACCCAACCATGGACACAACCCACAATGATAATACACCACAAAGACTGATGATCACAGACATGAGACCGTTGTCA |
| CTTGAGACCATAATAACATCACTAACCAGAGACATCATAACACACAAATTTATATACTTGATAAATCATGAATGCAT |
| AGTGAGAAAACTTGATGAAAGACAGGCCACATTTACATTCCTGGTCAACTATGAAATGAAACTATTACACAAAGTAG |
| GAAGCACTAAATATAAAAAATATACTGAATACAACACAAAATATGGCACTTTCCCTATGCCAATATTCATCAATCAT |
| GATGGGTTCTTAGAATGCATTGGCATTAAGCCTACAAAGCATACTCCCATAATATACAAGTATGATCTCAATCCATA |
| AATTTCAACACAATATTCACACAATCTAAAACAACAACTCTATGCATAACTATACTCCATAGTCCAGATGGAGCCTG |
| AAAATTATAGTAATTTAAAACTTAAGGAGAGATATAAGATAGAAGATGGGGCAAATACAACCATGGCTCTTAGCAAA |
| GTCAAGTTGAATGATACACTCAACAAAGATCAACTTCTGTCATCCAGCAAATACACCATCCAACGGAGCACAGGAGA |
| TAGTATTGATACTCCTAATTATGATGTGCAGAAACACATCAATAAGTTATGTGGCATGTTATTAATCACAGAAGATG |
| CTAATCATAAATTCACTGGGTTAATAGGTATGTTATATGCGATGTCTAGGTTAGGAAGAGAAGACACCATAAAAATA |
| CTCAGAGATGCGGGATATCATGTAAAAGCAAATGGAGTAGATGTAACAACACATCGTCAAGACATTAATGGAAAAGA |
| AATGAAATTTGAAGTGTTAACATTGGCAAGCTTAACAACTGAAATTCAAATCAACATTGAGATAGAATCTAGAAAAT |
| CCTACAAAAAAATGCTAAAAGAAATGGGAGAGGTAGCTCCAGAATACAGGCATGACTCTCCTGATTGTGGGATGATA |
| ATATTATGTATAGCAGCATTAGTAATAACTAAATTAGCAGCAGGGGACAGATCTGGTCTTACAGCCGTGATTAGGAG |
| AGCTAATAATGTCCTAAAAAATGAAATGAAACGTTACAAAGGCTTACTACCCAAGGACATAGCCAACAGCTTCTATG |
| AAGTGTTTGAAAAACATCCCCACTTTATAGATGTTTTTGTTCATTTTGGTATAGCACAATCTTCTACCAGAGGTGGC |
| AGTAGAGTTGAAGGGATTTTTGCAGGATTGTTTATGAATGCCTATGGTGCAGGGCAAGTGATGTTACGGTGGGGAGT |
| CTTAGCAAAATCGATTAAAAATATTATGTTAGGACATGCTAGTGTGCAAGCAGAAATGGAACAAGTTGTTGAGGTTT |
| ATGAATATGCCCAAAAATTGGGTGGTGAAGCAGGATTCTACCATATATTGAACAACCCAAAAGCATCATTATTATCT |
| TTGACTCAATTTCCTCACTTCTCCAGTGTAGTATTAGGCAATGCTGCTGGCCTAGGCATAATGGGAGAGTACAGAGG |
| TACACCGAGGAATCAAGATCTATATGATGCAGCAAAGGCATATGCTGAACAACTCAAAGAAAATGGTGTGATTAACT |
| ACAGTGTACTAGACTTGACAGCAGAAGAACTAGAGGCTATCAAACATCAGCTTAATCCAAAAGATAATGATGTAGAG |
| CTTTGAGTTAATAAAAAATGGGGCAAATAAATCATCATGGAAAAGTTTGCTCCTGAATTCCATGGAGAAGATGCAAA |
| CAACAGGGCTACTAAATTCCTAGAATCAATAAAGGGCAAATTCACATCACCCAAAGATCCCAAGAAAAAAGATAGTA |
| TCATATCTGTCAACTCAATAGATATAGAAGTAACCAAAGAAAGCCCTATAACATCAAATTCAACTATTATCAACCCA |
| ACAAATGAGACAGATGATACTGCAGGGAACAAGCCCAATTATCAAAGAAAACCTCTAGTAAGTTTCAAAGAAGACCC |
| TACACCAAGTGATAATCCCTTTTCTAAACTATACAAAGAAACCATAGAAACATTTGATAACAATGAAGAAGAATCCA |
| GCTATTCATACGAAGAAATAAATGATCAGACAAACGATAATATAACAGCAAGATTAGATAGGATTGATGAAAAATTA |
| AGTGAAATACTAGGAATGCTTCACACATTAGTAGTGGCAAGTGCAGGACCTACATCTGCTCGGGATGGTATAAGAGA |
| TGCCATGGTTGGTTTAAGAGAAGAAATGATAGAAAAAATCAGAACTGAAGCATTAATGACCAATGACAGATTAGAAG |
| CTATGGCAAGACTCAGGAATGAGGAAAGTGAAAAGATGGCAAAAGACACATCAGATGAAGTGTCTCTCAATCCAACA |
| TCAGAGAAATTGAACAACCTATTGGAAGGGAATGATAGTGACAATGATCTATCACTTGAAGATTTCTGATTAGTTAC |
| CAATCTTCACATCAACACACAATACCAACAGAAGACCAACAAACTAACCAACCCAATCATCCAACCAAACATCCATC |

-continued

| Exemplary Sequences |
| --- |

CGCCAATCAGCCAAACAGCCAACAAAACAACCAGCCAATCCAAAACTAACCACCCGGAAAAAATCTATAATATAGTT

ACAAAAAAAGGAAAGGGTGGGGCAAATATGGAAACATACGTGAACAAGCTTCACGAAGGCTCCACATACACAGCTGC

TGTTCAATACAATGTCTTAGAAAAAGACGATGACCCTGCATCACTTACAATATGGGTGCCCATGTTCCAATCATCTA

TGCCAGCAGATTTACTTATAAAAGAACTAGCTAATGTCAACATACTAGTGAAACAAATATCCACACCCAAGGGACCT

TCACTAAGAGTCATGATAAACTCAAGAAGTGCAGTGCTAGCACAAATGCCCAGCAAATTTACCATATGCGCTAATGT

GTCCTTGGATGAAAGAAGCAAACTAGCATATGATGTAACCACACCCTGTGAAATCAAGGCATGTAGTCTAACATGCC

TAAAATCAAAAAATATGTTGACTACAGTTAAAGATCTCACTATGAAGACACTCAACCCTACACATGATATTATTGCT

TTATGTGAATTTGAAAACATAGTAACATCAAAAAAAGTCATAATACCAACATACCTAAGATCCATCAGTGTCAGAAA

TAAAGATCTGAACACACTTGAAAATATAACAACCACTGAATTCAAAAATGCTATCACAAATGCAAAAATCATCCCTT

ACTCAGGATTACTATTAGTCATCACAGTGACTGACAACAAAGGAGCATTCAAATACATAAAGCCACAAAGTCAATTC

ATAGTAGATCTTGGAGCTTACCTAGAAAAAGAAAGTATATATTATGTTACCACAAATTGGAAGCACACAGCTACACG

ATTTGCAATCAAACCCATGGAAGATTAACCTTTTTCCTCTACATCAGTGTGTTAATTCATACAAACTTTCTACCTAC

ATTCTTCACTTCACCATCACAATCACAAACACTCTGTGGTTCAACCAATCAAACAAAACTTATCTGAAGTCCCAGAT

CATCCCAAGTCATTGTTTATCAGATCTAGTACTCAAATAAGTTAATAAAAAATATACACATGGGGCAAATAATCATT

GGAGGAAATCCAACTAATCACAATATCTGTTAACATAGACAAGTCCACACACCATACAGAATCAACCAATGGAAAAT

ACATCCATAACAATAGAATTCTCAAGCAAATTCTGGCCTTACTTTACACTAATACACATGATCACAACAATAATCTC

TTTGCTAATCATAATCTCCATCATGATTGCAATACTAAACAAACTTTGTGAATATAACGTATTCCATAACAAAACCT

TTGAGTTACCAAGAGCTCGAGTTAATACTTGATAAAGTAGTTAATTAAAAATAGTCATAACAATGAACTAGGATATC

AAGACTAACAATAACATTGGGGCAAATGCAAACATGTCCAAAAACAAGGACCAACGCACCGCTAAGACATTAGAAAG

GACCTGGGACACTCTCAATCATTTATTATTCATATCATCGTGCTTATATAAGTTAAATCTTAAATCTGTAGCACAAA

TCACATTATCCATTCTGGCAATGATAATCTCAACTTCACTTATAATTGCAGCCATCATATTCATAGCCTCGGCAAAC

CACAAAGTCACACCAACAACTGCAATCATACAAGATGCAACAAGCCAGATCAAGAACACAACCCCAACATACCTCAC

CCAGAATCCTCAGCTTGGAATCAGTCCCTCTAATCCGTCTGAAATTACATCACAAATCACCACCATACTAGCTTCAA

CAACACCAGGAGTCAAGTCAACCCTGCAATCCACAACAGTCAAGACCAAAAACACAACAACAACTCAAACACAACCC

AGCAAGCCCACCACAAAACAACGCCAAAACAAACCACCAAGCAAACCCAATAATGATTTTCACTTTGAAGTGTTCAA

CTTTGTACCCTGCAGCATATGCAGCAACAATCCAACCTGCTGGGCTATCTGCAAAAGAATACCAAACAAAAAACCAG

GAAAGAAAACCACTACCAAGCCCACAAAAAAACCAACCCTCAAGACAACCAAAAAAGATCCCAAACCTCAAACCACT

AAATCAAAGGAAGTACCCACCACCAAGCCCACAGAAGAGCCAACCATCAACACCACCAAAACAAACATCATAACTAC

ACTACTCACCTCCAACACCACAGGAAATCCAGAACTCACAAGTCAAATGGAAACCTTCCACTCAACTTCCTCCGAAG

GCAATCCAAGCCCTTCTCAAGTCTCTACAACATCCGAGTACCCATCACAACCTTCATCTCCACCCAACACACCACGC

CAGTAGTTACTTAAAAACATATTATCACAAAAGGCCTTGACCAACTTAAACAGAATCAAAATAAACTCTGGGGCAAA

TAACAATGGAGTTGCTAATCCTCAAAGCAAATGCAATTACCACAATCCTCACTGCAGTCACATTTTGTTTTGCTTCT

GGTCAAAACATCACTGAAGAATTTTATCAATCAACATGCAGTGCAGTTAGCAAAGGCTATCTTAGTGCTCTGAGAAC

TGGTTGGTATACCAGTGTTATAACTATAGAATTAAGTAATATCAAGAAAAATAAGTGTAATGGAACAGATGCTAAGG

TAAAATTGATAAAACAAGAATTAGATAAATATAAAAATGCTGTAACAGAATTGCAGTTGCTCATGCAAAGCACACAA

GCAACAAACAATCGAGCCAGAAGAGAACTACCAAGGTTTATGAATTATACACTCAACAATGCCAAAAAAACCAATGT

AACATTAAGCAAGAAAAGGAAAAGAAGATTTCTTGGTTTTTTGTTAGGTGTTGGATCTGCAATCGCCAGTGGCGTTG

CTGTATCTAAGGTCCTGCACCTAGAAGGGGAAGTGAACAAGATCAAAAGTGCTCTACTATCCACAAACAAGGCTGTA

-continued

| Exemplary Sequences |
|---|
| GTCAGCTTATCAAATGGAGTTAGTGTTTTAACCAGCAAAGTGTTAGACCTCAAAAACTATATAGATAAACAATTGTT |
| ACCTATTGTGAACAAGCAAAGCTGCAGCATATCAAATATAGCAACTGTGATAGAGTTCCAACAAAAGAACAACAGAC |
| TACTAGAGATTACCAGGGAATTTAGTGTTAATGCAGGCGTAACTACACCTGTAAGCACTTACATGTTAACTAATAGT |
| GAATTATTGTCATTAATCAATGATATGCCTATAACAAATGATCAGAAAAAGTTAATGTCCAACAATGTTCAAATAGT |
| TAGACAGCAAAGTTACTCTATCATGTCCATAATAAAAGAGGAAGTCTTAGCATATGTAGTACAATTACCACTATATG |
| GTGTTATAGATACACCCTGTTGGAAACTACACACATCCCCTCTATGTACAACCAACACAAAAGAAGGGTCCAACATC |
| TGTTTAACAAGAACTGACAGAGGATGGTACTGTGACAATGCAGGATCAGTATCTTTCTTCCCACAAGCTGAAACATG |
| TAAAGTTCAATCAAATCGAGTATTTTGTGACACAATGAACAGTTTAACATTACCAAGTGAAGTAAATCTCTGCAATG |
| TTGACATATTCAACCCCAAATATGATTGTAAAATTATGACTTCAAAAACAGATGTAAGCAGCTCCGTTATCACATCT |
| CTAGGAGCCATTGTGTCATGCTATGGCAAAACTAAATGTACAGCATCCAATAAAAATCGTGGAATCATAAAGACATT |
| TTCTAACGGGTGCGATTATGTATCAAATAAAGGGGTGGACACTGTGTCTGTAGGTAACACATTATATTATGTAAATA |
| AGCAAGAAGGTAAAAGTCTCTATGTAAAAGGTGAACCAATAATAAATTTCTATGACCCATTAGTATTCCCCTCTGAT |
| GAATTTGATGCATCAATATCTCAAGTCAACGAGAAGATTAACCAGAGCCTAGCATTTATTCGTAAATCCGATGAATT |
| ATTACATAATGTAAATGCTGGTAAATCCACCATAAATATCATGATAACTACTATAATTATAGTGATTATAGTAATAT |
| TGTTATCATTAATTGCTGTTGGACTGCTCTTATACTGTAAGGCCAGAAGCACACCAGTCACACTAAGCAAAGATCAA |
| CTGAGTGGTATAAATAATATTGCATTTAGTAACTAAATAAAAATAGCACCTAATCATGTTCTTACAATGGTTTACTA |
| TCTGCTCATAGACAACCCATCTGTCATTGGATTTTCTTAAAATCTGAACTTCATCGAAACTCTCATCTATAAACCAT |
| CTCACTTACACTATTTAAGTAGATTCCTAGTTTATAGTTATATAAAACACAATTGCATGCCAGATTAACTTACCATC |
| TGTAAAAATGAAAACTGGGGCAAATATGTCACGAAGGAATCCTTGCAAATTTGAAATTCGAGGTCATTGCTTAAATG |
| GTAAGAGGTGTCATTTTAGTCATAATTATTTTGAATGGCCACCCCATGCACTGCTTGTAAGACAAAACTTTATGTTA |
| AACAGAATACTTAAGTCTATGGATAAAAGTATAGATACCTTATCAGAAATAAGTGGAGCTGCAGAGTTGGACAGAAC |
| AGAAGAGTATGCTCTTGGTGTAGTTGGAGTGCTAGAGAGTTATATAGGATCAATAAACAATATAACTAAACAATCAG |
| CATGTGTTGCCATGAGCAAACTCCTCACTGAACTCAATAGTGATGATATCAAAAAGCTGAGGGACAATGAAGAGCTA |
| AATTCACCCAAGATAAGAGTGTACAATACTGTCATATCATATATTGAAAGCAACAGGAAAAACAATAAACAAACTAT |
| CCATCTGTTAAAAAGATTGCCAGCAGACGTATTGAAGAAAACCATCAAAAACACATTGGATATCCATAAGAGCATAA |
| CCATCAACAACCCAAAAGAATCAACTGTTAGTGATACAAACGACCACGCCAAAAATAACGATACTACCTAACACTCA |
| ATTCTAACACTCACCACATCGTTACATTATTAATTCAAACAATTCAAGTTGTGGGACAAAATGGATCCCATTATTAA |
| TGGAAATTCTGCTAATGTTTATCTAACCGATAGTTATTTAAAAGGTGTTATCTCTTTCTCAGAGTGTAATGCTTTAG |
| GAAGTTACATATTCAATGGTCCTTATCTCAAAAATGATTATACCAACTTAATTAGTAGACAAAATCCATTAATAGAA |
| CACATGAATCTAAAGAAACTAAATATAACACAGTCCTTAATATCTAAGTATCATAAAGGTGAAATAAAATTAGAAGA |
| ACCTACTTATTTTCAGTCATTACTTATGACATACAAGAGTATGACCTCGTCAGAACAGATTGCTACCACTAATTTAC |
| TTAAAAAGATAATAAGAAGAGCTATAGAAATAAGTGATGTCAAAGTCTATGCTATATTGAATAAACTAGGGCTTAAA |
| GAAAAGGACAAGATTAAATCCAACAATGGACAAGATGAAGACAACTCAGTTATTACGACCATAATCAAAGATGATAT |
| ACTTTCAGCTGTTAAAGATAATCAATCTCATCTTAAAGCAGACAAAAATCACTCTACAAAACAAAAAGACACAATCA |
| AAACAACACTCTTGAAGAAATTGATGTGTTCAATGCAACATCCTCCATCATGGTTAATACATTGGTTTAACTTATAC |
| ACAAAATTAAACAACATATTAACACAGTATCGATCAAATGAGGTAAAAAACCATGGGTTTACATTGATAGATAATCA |
| AACTCTTAGTGGATTTCAATTTATTTTGAACCAATATGGTTGTATAGTTTATCATAAGGAACTCAAAAGAATTACTG |
| TGACAACCTATAATCAATTCTTGACATGGAAAGATATTAGCCTTAGTAGATTAAATGTTTGTTTAATTACATGGATT |
| AGTAACTGCTTGAACACATTAAATAAAAGCTTAGGCTTAAGATGCGGATTCAATAATGTTATCTTGACACAACTATT |

-continued

| Exemplary Sequences |
| --- |

CCTTTATGGAGATTACATACTAAAGCTATTTCACAATGAGGGGTTCTACATAATAAAAGAGGTAGAGGGATTTATTA

TGTCTCTAATTTTAAATATAACAGAAGAAGATCAATTCAGAAAACGATTTTATAATAGTATGCTCAACAACATCACA

GATGCTGCTAATAAAGCTCAGAAAAATCTGCTATCAAGAGTATGTCATACATTATTAGATAAGACAGTGTCCGATAA

TATAATAAATGGCAGATGGATAATTCTATTAAGTAAGTTCCTTAAATTAATTAAGCTTGCAGGTGACAATAACCTTA

ACAATCTGAGTGAACTATATTTTTTGTTCAGAATATTTGGACACCCAATGGTAGATGAAAGACAAGCCATGGATGCT

GTTAAAATTAATTGCAATGAGACCAAATTTTACTTGTTAAGCAGTCTGAGTATGTTAAGAGGTGCCTTTATATATAG

AATTATAAAAGGGTTTGTAAATAATTACAACAGATGGCCTACTTTAAGAAATGCTATTGTTTTACCCTTAAGATGGT

TAACTTACTATAAACTAAACACTTATCCTTCTTTGTTGGAACTTACAGAAAGAGATTTGATTGTGTTATCAGGACTA

CGTTTCTATCGTGAGTTTCGGTTGCCTAAAAAAGTGGATCTTGAAATGATTATAAATGATAAAGCTATATCACCTCC

TAAAAATTTGATATGGACTAGTTTCCCTAGAAATTACATGCCATCACACATACAAAACTATATAGAACATGAAAAAT

TAAAATTTTCCGAGAGTGATAAATCAAGAAGAGTATTAGAGTATTATTTAAGAGATAACAAATTCAATGAATGTGAT

TTATACAACTGTGTAGTTAATCAAAGTTATCTCAACAACCCTAATCATGTGGTATCATTGACAGGCAAAGAAAGAGA

ACTCAGTGTAGGTAGAATGTTTGCAATGCAACCGGGAATGTTCAGACAGGTTCAAATATTGGCAGAGAAAATGATAG

CTGAAAACATTTTACAATTCTTTCCTGAAAGTCTTACAAGATATGGTGATCTAGAACTACAAAAAATATTAGAACTG

AAAGCAGGAATAAGTAACAAATCAAATCGCTACAATGATAATTACAACAATTACATTAGTAAGTGCTCTATCATCAC

AGATCTCAGCAAATTCAATCAAGCATTTCGATATGAAACGTCATGTATTTGTAGTGATGTGCTGGATGAACTGCATG

GTGTACAATCTCTATTTTCCTGGTTACATTTAACTATTCCTCATGTCACAATAATATGCACATATAGGCATGCACCC

CCCTATATAGGAGATCATATTGTAGATCTTAACAATGTAGATGAACAAAGTGGATTATATAGATATCACATGGGTGG

CATCGAAGGGTGGTGTCAAAAACTATGGACCATAGAAGCTATATCACTATTGGATCTAATATCTCTCAAAGGGAAAT

TCTCAATTACTGCTTTAATTAATGGTGACAATCAATCAATAGATATAAGCAAACCAATCAGACTCATGGAAGGTCAA

ACTCATGCTCAAGCAGATTATTTGCTAGCATTAAATAGCCTTAAATTACTGTATAAAGAGTATGCAGGCATAGGCCA

CAAATTAAAAGGAACTGAGACTTATATATCACGAGATATGCAATTTATGAGTAAAACAATTCAACATAACGGTGTAT

ATTACCCAGCTAGTATAAAGAAAGTCCTAAGAGTGGGACCGTGGATAAACACTATACTTGATGATTTCAAAGTGAGT

CTAGAATCTATAGGTAGTTTGACACAAGAATTAGAATATAGAGGTGAAAGTCTATTATGCAGTTTAATATTTAGAAA

TGTATGGTTATATAATCAGATTGCTCTACAATTAAAAAATCATGCATTATGTAACAATAAACTATATTTGGACATAT

TAAAGGTTCTGAAACACTTAAAAACCTTTTTAATCTTGATAATATTGATACAGCATTAACATTGTATATGAATTTA

CCCATGTTATTTGGTGGTGGTGATCCCAACTTGTTATATCGAAGTTTCTATAGAAGAACTCCTGACTTCCTCACAGA

GGCTATAGTTCACTCTGTGTTCATACTTAGTTATTATACAAACCATGACTTAAAAGATAAACTTCAAGATCTGTCAG

ATGATAGATTGAATAAGTTCTTAACATGCATAATCACGTTTGACAAAAACCCTAATGCTGAATTCGTAACATTGATG

AGAGATCCTCAAGCTTTAGGGTCTGAGAGACAAGCTAAAATTACTAGCGAAATCAATAGACTGGCAGTTACAGAGGT

TTTGAGTACAGCTCCAAACAAAATATTCTCCAAAAGTGCACAACATTATACTACTACAGAGATAGATCTAAATGATA

TTATGCAAAATATAGAACCTACATATCCTCATGGGCTAAGAGTTGTTTATGAAAGTTTACCCTTTTATAAAGCAGAG

AAAATAGTAAATCTTATATCAGGTACAAAATCTATAACTAACATACTGGAAAAAACTTCTGCCATAGACTTAACAGA

TATTGATAGAGCCACTGAGATGATGAGGAAAAACATAACTTTGCTTATAAGGATACTTCCATTGGATTGTAACAGAG

ATAAAAGAGAGATATTGAGTATGGAAAACCTAAGTATTACTGAATTAAGCAAATATGTTAGGGAAAGATCTTGGTCT

TTATCCAATATAGTTGGTGTTACATCACCCAGTATCATGTATACAATGGACATCAAATATACTACAAGCACTATATC

TAGTGGCATAATTATAGAGAAATATAATGTTAACAGTTTAACACGTGGTGAGAGAGGACCCACTAAACCATGGGTTG

GTTCATCTACACAAGAGAAAAAAACAATGCCAGTTTATAATAGACAAGTCTTAACCAAAAAACAGAGAGATCAAATA

-continued

| Exemplary Sequences |
| --- |
| GATCTATTAGCAAAATTGGATTGGGTGTATGCATCTATAGATAACAAGGATGAATTCATGGAAGAACTCAGCATAGG |
| AACCCTTGGGTTAACATATGAAAAGGCCAAGAAATTATTTCCACAATATTTAAGTGTCAATTATTTGCATCGCCTTA |
| CAGTCAGTAGTAGACCATGTGAATTCCCTGCATCAATACCAGCTTATAGAACAACAAATTATCACTTTGACACTAGC |
| CCTATTAATCGCATATTAACAGAAAAGTATGGTGATGAAGATATTGACATAGTATTCCAAAACTGTATAAGCTTTGG |
| CCTTAGTTTAATGTCAGTAGTAGAACAATTTACTAATGTATGTCCTAACAGAATTATTCTCATACCTAAGCTTAATG |
| AGATACATTTGATGAAACCTCCCATATTCACAGGTGATGTTGATATTCACAAGTTAAAACAAGTGATACAAAAACAG |
| CATATGTTTTTACCAGACAAAATAAGTTTGACTCAATATGTGGAATTATTCTTAAGTAATAAAACACTCAAATCTGG |
| ATCTCATGTTAATTCTAATTTAATATTGGCACATAAAATATCTGACTATTTTCATAATACTTACATTTTAAGTACTA |
| ATTTAGCTGGACATTGGATTCTGATTATACAACTTATGAAAGATTCTAAAGGTATTTTTGAAAAAGATTGGGGAGAG |
| GGATATATAACTGATCATATGTTTATTAATTTGAAAGTTTTCTTCAATGCTTATAAGACCTATCTCTTGTGTTTTCA |
| TAAAGGTTATGGCAAAGCAAAGCTGGAGTGTGATATGAACACTTCAGATCTTCTATGTGTATTGGAATTAATAGACA |
| GTAGTTATTGGAAGTCTATGTCTAAGGTATTTTTAGAACAAAAAGTTATCAAATACATTCTTAGCCAAGATGCAAGT |
| TTACATAGAGTAAAAGGATGTCATAGCTTCAAATTATGGTTTCTTAAACGTCTTAATGTAGCAGAATTCACAGTTTG |
| CCCTTGGGTTGTTAACATAGATTATCATCCAACACATATGAAAGCAATATTAACTTATATAGATCTTGTTAGAATGG |
| GATTGATAAATATAGATAGAATACACATTAAAAATAAACACAAATTCAATGATGAATTTTATACTTCTAATCTCTTC |
| TACATTAATTATAACTTCTCAGATAATACTCATCTATTAACTAAATACATAAGGATTGCTAATTCTGAATTAGAAAA |
| TAATTACAACAAATTATATCATCCTACACCAGAAACCCTAGAGAATATACTAGCCAATCCGATTAAAAGTAATGACA |
| AAAAGACACTGAATGACTATTGTATAGGTAAAAATGTTGACTCAATAATGTTACCATTGTTATCTAATAAGAAGCTT |
| ATTAAATCGTCTGCAATGATTAGAACCAATTACAGCAAACAAGATTTGTATAATTTATTCCCTATGGTTGTGATTGA |
| TAGAATTATAGATCATTCAGGCAATACAGCCAAATCCAACCAACTTTACACTACTACTTCCCACCAAATATCCTTAG |
| TGCACAATAGCACATCACTTTACTGCATGCTTCCTTGGCATCATATTAATAGATTCAATTTTGTATTTAGTTCTACA |
| GGTTGTAAAATTAGTATAGAGTATATTTTAAAAGATCTTAAAATTAAAGATCCCAATTGTATAGCATTCATAGGTGA |
| AGGAGCAGGGAATTTATTATTGCGTACAGTAGTGGAACTTCATCCTGACATAAGATATATTTACAGAAGTCTGAAAG |
| ATTGCAATGATCATAGTTTACCTATTGAGTTTTTAAGGCTGTACAATGGACATATCAACATTGATTATGGTGAAAAT |
| TTGACCATTCCTGCTACAGATGCAACCAACAACATTCATTGGTCTTATTTACATATAAAGTTTGCTGAACCTATCAG |
| TCTTTTTGTCTGTGATGCCGAATTGTCTGTAACAGTCAACTGGAGTAAAATTATAATAGAATGGAGCAAGCATGTAA |
| GAAAGTGCAAGTACTGTTCCTCAGTTAATAAATGTATGTTAATAGTAAAATATCATGCTCAAGATGATATTGATTTC |
| AAATTAGACAATATAACTATATTAAAAACTTATGTATGCTTAGGCAGTAAGTTAAAGGGATCGGAGGTTTACTTAGT |
| CCTTACAATAGGTCCTGCGAATATATTCCCAGTATTTAATGTAGTACAAAATGCTAAATTGATACTATCAAGAACCA |
| AAAATTTCATCATGCCTAAGAAAGCTGATAAAGAGTCTATTGATGCAAATATTAAAAGTTTGATACCCTTTCTTTGT |
| TACCCTATAACAAAAAAAGGAATTAATACTGCATTGTCAAAACTAAAGAGTGTTGTTAGTGGAGATATACTATCATA |
| TTCTATAGCTGGACGTAATGAAGTTTTCAGCAATAAACTTATAAATCATAAGCATATGAACATCTTAAAATGGTTCA |
| ATCATGTTTTAAATTTCAGATCAACAGAACTAAACTATAACCATTTATATATGGTAGAATCTACATATCCTTACCTA |
| AGTGAATTGTTAAACAGCTTGACAACCAATGAACTTAAAAAACTGATTAAAATCACAGGTAGTCTGTTATACAACTT |
| TCATAATGAATAATGAATAAAGATCTTATAATAAAAATTCCCATAGCTATACACTAACACTGTATTCAATTATAGTT |
| ATTAAAAATTAAAAATCATATAATTTTTTAAATAACTTTTAGTGAACTAATCCTAAAGTTATCATTTTAATCTTGGA |
| GGAATAAATTTAAACCCTAATCTAATTGGTTTATATGTGTATTAACTAAATTACGAGATATTAGTTTTTGACACTTT |
| TTTTCTCGT |

-continued

| Exemplary Sequences |
| --- |

Antigenomic cDNA sequence of D46/NS2/N/ΔM2-2-HindIII (SEQ ID NO: 18)

ACGGGAAAAAATGCGTACAACAAACTTGCATAAACCAAAAAAATGGGGCAAATAAGAATTTGATAAGTACCACTTAA

ATTTAACTCCCTTGGTTAGAGATGGGCAGCAATTCATTGAGTATGATAAAAGTTAGATTACAAAATTTGTTTGACAA

TGATGAAGTAGCATTGTTAAAAATAACATGCTATACTGATAAATTAATACATTTAACTAATGCTTTGGCTAAGGCAG

TGATACATACAATCAAATTGAATGGCATTGTGTTTGTGCATGTTATTACAAGTAGTGATATTTGCCCTAATAATAAT

ATTGTAGTAAAATCCAATTTCACAACAATGCCAGTACTACAAAATGGAGGTTATATATGGGAAATGATGGAATTAAC

ACATTGCTCTCAACCTAATGGTCTACTAGATGACAATTGTGAAATTAAATTCTCCAAAAAACTAAGTGATTCAACAA

TGACCAATTATATGAATCAATTATCTGAATTACTTGGATTTGATCTTAATCCATAAATTATAATTAATATCAACTAG

CAAATCAATGTCACTAACACCATTAGTTAATATAAAACTTAACAGAAGACAAAAATGGGGCAAATAAATCAATTCAG

CCAACCCAACCATGGACACAACCCACAATGATAATACACCACAAAGACTGATGATCACAGACATGAGACCGTTGTCA

CTTGAGACCATAATAACATCACTAACCAGAGACATCATAACACACAAATTTATATACTTGATAAATCATGAATGCAT

AGTGAGAAGACTTGATGAAAGACAGGCCACATTTACATTCCTGGTCAACTATGAAATGAAACTATTACACAAAGTAG

GAAGCACTAAATATAAAAAATATACTGAATACAACACAAAATATGGCACTTTCCCTATGCCAATATTCATCAATCAT

GATGGGTTCTTAGAATGCATTGGCATTAAGCCTACAAAGCATACTCCCATAATATACAAGTATGATCTCAATCCATA

AATTTCAACACAATATTCACACAATCTAAAACAACAACTCTATGCATAACTATACTCCATAGTCCAGATGGAGCCTG

AAAATTATAGTAATTTAAAACTTAAGGAGAGATATAAGATAGAAGATGGGGCAAATACAACCATGGCTCTTAGCAAA

GTCAAGTTGAATGATACACTCAACAAAGATCAACTTCTGTCATCCAGCAAATACGCCATCCAACGGAGCACAGGAGA

TAGTATTGATACTCCTAATTATGATGTGCAGAAACACATCAATAAGTTATGTGGCATGTTATTAATCACAGAAGATG

CTAATCATAAATTCACTGGGTTAATAGGTATGTTATATGCGATGTCTAGGTTAGGAAGAGAAGACACCATAAAAATA

CTCAGAGATGCGGGATATCATGTAAAAGCAAATGGAGTAGATGTAACAACACATCGTCAAGACATTAATGGAAAAGA

AATGAAATTTGAAGTGTTAACATTGGCAAGCTTAACAACTGAAATTCAAATCAACATTGAGATAGAATCTAGAAAAT

CCTACAAAAAAATGCTAAAAGAAATGGGAGAGGTAGCTCCAGAATACAGGCATGACTCTCCTGATTGTGGGATGATA

ATATTATGTATAGCAGCATTAGTAATAACTAAATTAGCAGCAGGGGACAGATCTGGTCTTACAGCCGTGATTAGGAG

AGCTAATAATGTCCTAAAAAATGAAATGAAACGTTACAAAGGCTTACTACCCAAGGACATAGCCAACAGCTTCTATG

AAGTGTTTGAAAAACATCCCCACTTTATAGATGTTTTTGTTCATTTTGGTATAGCACAATCTTCTACCAGAGGTGGC

AGTAGAGTTGAAGGGATTTTTGCAGGATTGTTTATGAATGCCTATGGTGCAGGGCAAGTGATGTTACGGTGGGGAGT

CTTAGCAAAATCGGTTAAAAATATTATGTTAGGACATGCTAGTGTGCAAGCAGAAATGGAACAAGTTGTTGAGGTTT

ATGAATATGCCCAAAAATTGGGTGGTGAAGCAGGATTCTACCATATATTGAACAACCCAAAAGCATCATTATTATCT

TTGACTCAATTTCCTCACTTCTCCAGTGTAGTATTAGGCAATGCTGCTGGCCTAGGCATAATGGGAGAGTACAGAGG

TACACCGAGGAATCAAGATCTATATGATGCAGCAAAGGCATATGCTGAACAACTCAAAGAAAATGGTGTGATTAACT

ACAGTGTACTAGACTTGACAGCAGAAGAACTAGAGGCTATCAAACATCAGCTTAATCCAAAAGATAATGATGTAGAG

CTTTGAGTTAATAAAAAATGGGGCAAATAAATCATCATGGAAAAGTTTGCTCCTGAATTCCATGGAGAAGATGCAAA

CAACAGGGCTACTAAATTCCTAGAATCAATAAAGGGCAAATTCACATCACCCAAAGATCCCAAGAAAAAAGATAGTA

TCATATCTGTCAACTCAATAGATATAGAAGTAACCAAAGAAAGCCCTATAACATCAAATTCAACTATTATCAACCCA

ACAAATGAGACAGATGATACTGCAGGGAACAAGCCCAATTATCAAAGAAAACCTCTAGTAAGTTTCAAAGAAGACCC

TACACCAAGTGATAATCCCTTTTCTAAACTATACAAAGAAACCATAGAAACATTTGATAACAATGAAGAAGAATCCA

GCTATTCATACGAAGAAATAAATGATCAGACAAACGATAATATAACAGCAAGATTAGATAGGATTGATGAAAAATTA

AGTGAAATACTAGGAATGCTTCACACATTAGTAGTGGCAAGTGCAGGACCTACATCTGCTCGGGATGGTATAAGAGA

-continued

| Exemplary Sequences |
| --- |
| TGCCATGGTTGGTTTAAGAGAAGAAATGATAGAAAAAATCAGAACTGAAGCATTAATGACCAATGACAGATTAGAAG |
| CTATGGCAAGACTCAGGAATGAGGAAAGTGAAAAGATGGCAAAAGACACATCAGATGAAGTGTCTCTCAATCCAACA |
| TCAGAGAAATTGAACAACCTATTGGAAGGGAATGATAGTGACAATGATCTATCACTTGAAGATTTCTGATTAGTTAC |
| CAATCTTCACATCAACACACAATACCAACAGAAGACCAACAAACTAACCAACCCAATCATCCAACCAAACATCCATC |
| CGCCAATCAGCCAAACAGCCAACAAAACAACCAGCCAATCCAAAACTAACCACCCGGAAAAAATCTATAATATAGTT |
| ACAAAAAAAGGAAAGGGTGGGGCAAATATGGAAACATACGTGAACAAGCTTCACGAAGGCTCCACATACACAGCTGC |
| TGTTCAATACAATGTCTTAGAAAAAGACGATGACCCTGCATCACTTACAATATGGGTGCCCATGTTCCAATCATCTA |
| TGCCAGCAGATTTACTTATAAAAGAACTAGCTAATGTCAACATACTAGTGAAACAAATATCCACACCCAAGGGACCT |
| TCACTAAGAGTCATGATAAACTCAAGAAGTGCAGTGCTAGCACAAATGCCCAGCAAATTTACCATATGCGCTAATGT |
| GTCCTTGGATGAAAGAAGCAAACTAGCATATGATGTAACCCACACCCTGTGAAATCAAGGCATGTAGTCTAACATGCC |
| TAAAATCAAAAAATATGTTGACTACAGTTAAAGATCTCACTATGAAGACACTCAACCCTACACATGATATTATTGCT |
| TTATGTGAATTTGAAAACATAGTAACATCAAAAAAAGTCATAATACCAACATACCTAAGATCCATCAGTGTCAGAAA |
| TAAAGATCTGAACACACTTGAAAATATAACAACCACTGAATTCAAAAATGCTATCACAAATGCAAAAATCATCCCTT |
| ACTCAGGATTACTATTAGTCATCACAGTGACTGACAACAAAGGAGCATTCAAATACATAAAGCCACAAAGTCAATTC |
| ATAGTAGATCTTGGAGCTTACCTAGAAAAAGAAAGTATATATTATGTTACCACAAATTGGAAGCACACAGCTACACG |
| ATTTGCAATCAAACCCATGGAAGATTAACCTTTTTCCTCTACATCAGTGTGTTAATTCATACAAACTTTCTACCTAC |
| ATTCTTCACTTCACCATCACAATCACAAACACTCTGTGGTTCAACCAATCAAACAAAACTTATCTGAAGTCCCAGAT |
| CATCCCAAGTCATTGTTTATCAGATCTAGTACTCAAATAAGTTAATAAAAAATATACACATGGGGCAAATAATCATT |
| GGAGGAAATCCAACTAATCACAATATCTGTTAACATAGACAAGTCCACACACCATACAGAATCAACCAATGGAAAAT |
| ACATCCATAACAATAGAATTCTCAAGCAAATTCTGGCCTTACTTTACACTAATACACATGATCACAACAATAATCTC |
| TTTGCTAATCATAATCTCCATCATGATTGCAATACTAAACAAACTTTGTGAATATAACGTATTCCATAACAAAACCT |
| TTGAGTTACCAAGAGCTCGAGTCAACACATAGCATTCATCAATCCAACAGCCCAAAACAGTAACCTTGCATTTAAAA |
| ATGAACAACCCCTACCTCTTTACAACACCTCATTAACATCCCACCATGCAAACCACTATCCATACTATAAAGTAGTT |
| AATTAAAAATAGTCATAACAATGAACTAGGATATCAAGACTAACAATAACATTGGGGCAAATGCAAACATGTCCAAA |
| AACAAGGACCAACGCACCGCTAAGACATTAGAAAGGACCTGGGACACTCTCAATCATTTATTATTCATATCATCGTG |
| CTTATATAAGTTAAATCTTAAATCTGTAGCACAAATCACATTATCCATTCTGGCAATGATAATCTCAACTTCACTTA |
| TAATTGCAGCCATCATATTCATAGCCTCGGCAAACCACAAAGTCACACCAACAACTGCAATCATACAAGATGCAACA |
| AGCCAGATCAAGAACACAACCCCAACATACCTCACCCAGAATCCTCAGCTTGGAATCAGTCCCTCTAATCCGTCTGA |
| AATTACATCACAAATCACCACCATACTAGCTTCAACAACACCAGGAGTCAAGTCAACCCTGCAATCCACAACAGTCA |
| AGACCAAAAACACAACAACAACTCAAACACAACCCAGCAAGCCCACCACAAAACAACGCCAAAACAAACCACCAAGC |
| AAACCCAATAATGATTTTCACTTTGAAGTGTTCAACTTTGTACCCTGCAGCATATGCAGCAACAATCCAACCTGCTG |
| GGCTATCTGCAAAAGAATACCAAACAAAAAACCAGGAAAGAAAACCACTACCAAGCCCACAAAAAAACCAACCCTCA |
| AGACAACCAAAAAAGATCCCAAACCTCAAACCACTAAATCAAAGGAAGTACCCACCACCAAGCCCACAGAAGAGCCA |
| ACCATCAACACCACCAAAACAAACATCATAACTACACTACTCACCTCCAACACCACAGGAAATCCAGAACTCACAAG |
| TCAAATGGAAACCTTCCACTCAACTTCCTCCGAAGGCAATCCAAGCCCTTCTCAAGTCTCTACAACATCCGAGTACC |
| CATCACAACCTTCATCTCCACCCAACACACCACGCCAGTAGTTACTTAAAAACATATTATCACAAAAGGCCTTGACC |
| AACTTAAACAGAATCAAAATAAACTCTGGGGCAAATAACAATGGAGTTGCTAATCCTCAAAGCAAATGCAATTACCA |
| CAATCCTCACTGCAGTCACATTTTGTTTTGCTTCTGGTCAAAACATCACTGAAGAATTTTATCAATCAACATGCAGT |
| GCAGTTAGCAAAGGCTATCTTAGTGCTCTGAGAACTGGTTGGTATACCAGTGTTATAACTATAGAATTAAGTAATAT |

-continued

| Exemplary Sequences |
| --- |
| CAAGAAAAATAAGTGTAATGGAACAGATGCTAAGGTAAAATTGATAAAACAAGAATTAGATAAATATAAAAATGCTG |
| TAACAGAATTGCAGTTGCTCATGCAAAGCACACAAGCAACAAACAATCGAGCCAGAAGAGAACTACCAAGGTTTATG |
| AATTATACACTCAACAATGCCAAAAAAACCAATGTAACATTAAGCAAGAAAAGGAAAAGAAGATTTCTTGGTTTTTT |
| GTTAGGTGTTGGATCTGCAATCGCCAGTGGCGTTGCTGTATCTAAGGTCCTGCACCTAGAAGGGGAAGTGAACAAGA |
| TCAAAAGTGCTCTACTATCCACAAACAAGGCTGTAGTCAGCTTATCAAATGGAGTTAGTGTTTTAACCAGCAAAGTG |
| TTAGACCTCAAAAACTATATAGATAAACAATTGTTACCTATTGTGAACAAGCAAAGCTGCAGCATATCAAATATAGA |
| AACTGTGATAGAGTTCCAACAAAAGAACAACAGACTACTAGAGATTACCAGGGAATTTAGTGTTAATGCAGGCGTAA |
| CTACACCTGTAAGCACTTACATGTTAACTAATAGTGAATTATTGTCATTAATCAATGATATGCCTATAACAAATGAT |
| CAGAAAAAGTTAATGTCCAACAATGTTCAAATAGTTAGACAGCAAAGTTACTCTATCATGTCCATAATAAAAGAGGA |
| AGTCTTAGCATATGTAGTACAATTACCACTATATGGTGTTATAGATACACCCTGTTGGAAACTACACACATCCCCTC |
| TATGTACAACCAACACAAAAGAAGGGTCCAACATCTGTTTAACAAGAACTGACAGAGGATGGTACTGTGACAATGCA |
| GGATCAGTATCTTTCTTCCCACAAGCTGAAACATGTAAAGTTCAATCAAATCGAGTATTTTGTGACACAATGAACAG |
| TTTAACATTACCAAGTGAAGTAAATCTCTGCAATGTTGACATATTCAACCCCAAATATGATTGTAAAATTATGACTT |
| CAAAAACAGATGTAAGCAGCTCCGTTATCACATCTCTAGGAGCCATTGTGTCATGCTATGGCAAAACTAAATGTACA |
| GCATCCAATAAAAATCGTGGAATCATAAAGACATTTTCTAACGGGTGCGATTATGTATCAAATAAAGGGGTGGACAC |
| TGTGTCTGTAGGTAACACATTATATTATGTAAATAAGCAAGAAGGTAAAAGTCTCTATGTAAAAGGTGAACCAATAA |
| TAAATTTCTATGACCCATTAGTATTCCCCTCTGATGAATTTGATGCATCAATATCTCAAGTCAACGAGAAGATTAAC |
| CAGAGCCTAGCATTTATTCGTAAATCCGATGAATTATTACATAATGTAAATGCTGGTAAATCCACCACAAATATCAT |
| GATAACTACTATAATTATAGTGATTATAGTAATATTGTTATCATTAATTGCTGTTGGACTGCTCTTATACTGTAAGG |
| CCAGAAGCACACCAGTCACACTAAGCAAAGATCAACTGAGTGGTATAAATAATATTGCATTTAGTAACTAAATAAAA |
| ATAGCACCTAATCATGTTCTTACAATGGTTTACTATCTGCTCATAGACAACCCATCTGTCATTGGATTTTCTTAAAA |
| TCTGAACTTCATCGAAACTCTCATCTATAAACCATCTCACTTACACTATTTAAGTAGATTCCTAGTTTATAGTTATA |
| TAAAACACAATTGCATGCCAGATTAACTTACCATCTGTAAAAATGAAAACTGGGGCAAATATGTCACGAAGGAATCC |
| TTGCAAATTTGAAATTCGAGGTCATTGCTTAAATGGTAAGAGGTGTCATTTTAGTCATAATTATTTTGAATGGCCAC |
| CCCATGCACTGCTTGTAAGACAAAACTTTATGTTAAACAGAATACTTAAGTCTATGGATAAAAGTATAGATACCTTA |
| TCAGAAATAAGTGGAGCTGCAGAGTTGGACAGAACAGAAGAGTATGCTCTTGGTGTAGTTGGAGTGCTAGAGAGTTA |
| TATAGGATCAATAAACAATATAACTAAACAATCAGCATGTGTTGCCATGAGCAAACTCCTCACTGAACTCAATAGTG |
| ATGATATCAAAAAGCTGAGGGACAATGAAGAGCTAAATTCACCCAAGATAAGAGTGTACAATACTGTCATATCATAT |
| ATTGAAAGCAACAGGAAAAACAATAAACAAACTATCCATCTGTTAAAAAGATTGCCAGCAGACGTATTGAAGAAAAC |
| CATCAAAAACACATTGGATATCCATAAGAGCATAACCATCAACAACCCCAAAGAATCAACTGTTAGTGATACAAATG |
| ACCATGCCAAAAATAATGATACTACCTGACAAATAAGCTTCAATTCTAACACTCACCACATCGTTACATTATTAATT |
| CAAACAATTCAAGTTGTGGGACAAAATGGATCCCATTATTAATGGAAATTCTGCTAATGTTTATCTAACCGATAGTT |
| ATTTAAAAGGTGTTATCTCTTTCTCAGAGTGTAATGCTTTAGGAAGTTACATATTCAATGGTCCTTATCTCAAAAAT |
| GATTATACCAACTTAATTAGTAGACAAAATCCATTAATAGAACACATGAATCTAAAGAAACTAAATATAACACAGTC |
| CTTAATATCTAAGTATCATAAAGGTGAAATAAAATTAGAAGAACCTACTTATTTTCAGTCATTACTTATGACATACA |
| AGAGTATGACCTCGTCAGAACAGATTGCTACCACTAATTTACTTAAAAAGATAATAAGAAGAGCTATAGAAATAAGT |
| GATGTCAAAGTCTATGCTATATTGAATAAACTAGGGCTTAAAGAAAAGGACAAGATTAAATCCAACAATGGACAAGA |
| TGAAGACAACTCAGTTATTACGACCATAATCAAAGATGATATACTTTCAGCTGTTAAAGATAATCAATCTCATCTTA |

-continued

| Exemplary Sequences |
|---|
| AAGCAGACAAAAATCACTCTACAAAACAAAAAGACACAATCAAAACAACACTCTTGAAGAAATTGATGTGTTCAATG |
| CAACATCCTCCATCATGGTTAATACATTGGTTTAACTTATACACAAAATTAAACAACATATTAACACAGTATCGATC |
| AAATGAGGTAAAAAACCATGGGTTTACATTGATAGATAATCAAACTCTTAGTGGATTTCAATTTATTTTGAACCAAT |
| ATGGTTGTATAGTTTATCATAAGGAACTCAAAAGAATTACTGTGACAACCTATAATCAATTCTTGACATGGAAAGAT |
| ATTAGCCTTAGTAGATTAAATGTTTGTTTAATTACATGGATTAGTAACTGCTTGAACACATTAAATAAAAGCTTAGG |
| CTTAAGATGCGGATTCAATAATGTTATCTTGACACAACTATTCCTTTATGGAGATTGTATACTAAAGCTATTTCACA |
| ATGAGGGGTTCTACATAATAAAAGAGGTAGAGGGATTTATTATGTCTCTAATTTTAAATATAACAGAAGAAGATCAA |
| TTCAGAAAACGATTTTATAATAGTATGCTCAACAACATCACAGATGCTGCTAATAAAGCTCAGAAAAATCTGCTATC |
| AAGAGTATGTCATACATTATTAGATAAGACAGTGTCCGATAATATAATAAATGGCAGATGGATAATTCTATTAAGTA |
| AGTTCCTTAAATTAATTAAGCTTGCAGGTGACAATAACCTTAACAATCTGAGTGAACTATATTTTTTGTTCAGAATA |
| TTTGGACACCCAATGGTAGATGAAAGACAAGCCATGGATGCTGTTAAAATTAATTGCAATGAGACCAAATTTTACTT |
| GTTAAGCAGTCTGAGTATGTTAAGAGGTGCCTTTATATATAGAATTATAAAAGGGTTTGTAAATAATTACAACAGAT |
| GGCCTACTTTAAGAAATGCTATTGTTTTACCCTTAAGATGGTTAACTTACTATAAACTAAACACTTATCCTTCTTTG |
| TTGGAACTTACAGAAAGAGATTTGATTGTGTTATCAGGACTACGTTTCTATCGTGAGTTTCGGTTGCCTAAAAAAGT |
| GGATCTTGAAATGATTATAAATGATAAAGCTATATCACCTCCTAAAAATTTGATATGGACTAGTTTCCCTAGAAATT |
| ACATGCCATCACACATACAAAACTATATAGAACATGAAAAATTAAAATTTTCCGAGAGTGATAAATCAAGAAGAGTA |
| TTAGAGTATTATTTAAGAGATAACAAATTCAATGAATGTGATTTATACAACTGTGTAGTTAATCAAAGTTATCTCAA |
| CAACCCTAATCATGTGGTATCATTGACAGGCAAAGAAAGAGAACTCAGTGTAGGTAGAATGTTTGCAATGCAACCGG |
| GAATGTTCAGACAGGTTCAAATATTGGCAGAGAAAATGATAGCTGAAAACATTTTACAATTCTTTCCTGAAAGTCTT |
| ACAAGATATGGTGATCTAGAACTACAAAAAATATTAGAACTGAAAGCAGGAATAAGTAACAAATCAAATCGCTACAA |
| TGATAATTACAACAATTACATTAGTAAGTGCTCTATCATCACAGATCTCAGCAAATTCAATCAAGCATTTCGATATG |
| AAACGTCATGTATTTGTAGTGATGTGCTGGATGAACTGCATGGTGTACAATCTCTATTTTCCTGGTTACATTTAACT |
| ATTCCTCATGTCACAATAATATGCACATATAGGCATGCACCCCCCTATATAGGAGATCATATTGTAGATCTTAACAA |
| TGTAGATGAACAAAGTGGATTATATAGATATCACATGGGTGGCATCGAAGGGTGGTGTCAAAAACTATGGACCATAG |
| AAGCTATATCACTATTGGATCTAATATCTCTCAAAGGGAAATTCTCAATTACTGCTTTAATTAATGGTGACAATCAA |
| TCAATAGATATAAGCAAACCAATCAGACTCATGGAAGGTCAAACTCATGCTCAAGCAGATTATTTGCTAGCATTAAA |
| TAGCCTTAAATTACTGTATAAAGAGTATGCAGGCATAGGCCACAAATTAAAAGGAACTGAGACTTATATATCACGAG |
| ATATGCAATTTATGAGTAAAACAATTCAACATAACGGTGTATATTACCCAGCTAGTATAAAGAAAGTCCTAAGAGTG |
| GGACCGTGGATAAACACTATACTTGATGATTTCAAAGTGAGTCTAGAATCTATAGGTAGTTTGACACAAGAATTAGA |
| ATATAGAGGTGAAAGTCTATTATGCAGTTTAATATTTAGAAATGTATGGTTATATAATCAGATTGCTCTACAATTAA |
| AAAATCATGCATTATGTAACAATAAACTATATTTGGACATATTAAAGGTTCTGAAACACTTAAAAACCTTTTTTAAT |
| CTTGATAATATTGATACAGCATTAACATTGTATATGAATTTACCCATGTTATTTGGTGGTGGTGATCCCAACTTGTT |
| ATATCGAAGTTTCTATAGAAGAACTCCTGACTTCCTCACAGAGGCTATAGTTCACTCTGTGTTCATACTTAGTTATT |
| ATACAAACCATGACTTAAAAGATAAACTTCAAGATCTGTCAGATGATAGATTGAATAAGTTCTTAACATGCATAATC |
| ACGTTTGACAAAAACCCTAATGCTGAATTCGTAACATTGATGAGAGATCCTCAAGCTTTAGGGTCTGAGAGACAAGC |
| TAAAATTACTAGCGAAATCAATAGACTGGCAGTTACAGAGGTTTTGAGTACAGCTCCAAACAAAATATTCTCCAAAA |
| GTGCACAACATTATACTACTACAGAGATAGATCTAAATGATATTATGCAAAATATAGAACCTACATATCCTCATGGG |
| CTAAGAGTTGTTTATGAAAGTTTACCCTTTTATAAAGCAGAGAAAATAGTAAATCTTATATCAGGTACAAAATCTAT |
| AACTAACATACTGGAAAAAACTTCTGCCATAGACTTAACAGATATTGATAGAGCCACTGAGATGATGAGGAAAAACA |

-continued

| Exemplary Sequences |
| --- |
| TAACTTTGCTTATAAGGATACTTCCATTGGATTGTAACAGAGATAAAAGAGAGATATTGAGTATGGAAAACCTAAGT |
| ATTACTGAATTAAGCAAATATGTTAGGGAAAGATCTTGGTCTTTATCCAATATAGTTGGTGTTACATCACCCAGTAT |
| CATGTATACAATGGACATCAAATATACTACAAGCACTATATCTAGTGGCATAATTATAGAGAAATATAATGTTAACA |
| GTTTAACACGTGGTGAGAGAGGACCCACTAAACCATGGGTTGGTTCATCTACACAAGAGAAAAAAACAATGCCAGTT |
| TATAATAGACAAGTCTTAACCAAAAAACAGAGAGATCAAATAGATCTATTAGCAAAATTGGATTGGGTGTATGCATC |
| TATAGATAACAAGGATGAATTCATGGAAGAACTCAGCATAGGAACCCTTGGGTTAACATATGAAAAGGCCAAGAAAT |
| TATTTCCACAATATTTAAGTGTCAATTATTTGCATCGCCTTACAGTCAGTAGTAGACCATGTGAATTCCCTGCATCA |
| ATACCAGCTTATAGAACAACAAATTATCACTTTGACACTAGCCCTATTAATCGCATATTAACAGAAAAGTATGGTGA |
| TGAAGATATTGACATAGTATTCCAAAACTGTATAAGCTTTGGCCTTAGTTTAATGTCAGTAGTAGAACAATTTACTA |
| ATGTATGTCCTAACAGAATTATTCTCATACCTAAGCTTAATGAGATACATTTGATGAAACCTCCCATATTCACAGGT |
| GATGTTGATATTCACAAGTTAAAACAAGTGATACAAAAACAGCATATGTTTTTACCAGACAAAATAAGTTTGACTCA |
| ATATGTGGAATTATTCTTAAGTAATAAAACACTCAAATCTGGATCTCATGTTAATTCTAATTTAATATTGGCACATA |
| AAATATCTGACTATTTTCATAATACTTACATTTTAAGTACTAATTTAGCTGGACATTGGATTCTGATTATACAACTT |
| ATGAAAGATTCTAAAGGTATTTTTGAAAAAGATTGGGGAGAGGGATATATAACTGATCATATGTTTATTAATTTGAA |
| AGTTTTCTTCAATGCTTATAAGACCTATCTCTTGTGTTTTCATAAAGGTTATGGCAAAGCAAAGCTGGAGTGTGATA |
| TGAACACTTCAGATCTTCTATGTGTATTGGAATTAATAGACAGTAGTTATTGGAAGTCTATGTCTAAGGTATTTTTA |
| GAACAAAAAGTTATCAAATACATTCTTAGCCAAGATGCAAGTTTACATAGAGTAAAAGGATGTCATAGCTTCAAATT |
| ATGGTTTCTTAAACGTCTTAATGTAGCAGAATTCACAGTTTGCCCTTGGGTTGTTAACATAGATTATCATCCAACAC |
| ATATGAAAGCAATATTAACTTATATAGATCTTGTTAGAATGGGATTGATAAATATAGATAGAATACACATTAAAAAT |
| AAACACAAATTCAATGATGAATTTTATACTTCTAATCTCTTCTACATTAATTATAACTTCTCAGATAATACTCATCT |
| ATTAACTAAACATATAAGGATTGCTAATTCTGAATTAGAAAATAATTACAACAAATTATATCATCCTACACCAGAAA |
| CCCTAGAGAATATACTAGCCAATCCGATTAAAAGTAATGACAAAAAGACACTGAATGACTATTGTATAGGTAAAAAT |
| GTTGACTCAATAATGTTACCATTGTTATCTAATAAGAAGCTTATTAAATCGTCTGCAATGATTAGAACCAATTACAG |
| CAAACAAGATTTGTATAATTTATTCCCTATGGTTGTGATTGATAGAATTATAGATCATTCAGGCAATACAGCCAAAT |
| CCAACCAACTTTACACTACTACTTCCCACCAAATATCCTTAGTGCACAATAGCACATCACTTTACTGCATGCTTCCT |
| TGGCATCATATTAATAGATTCAATTTTGTATTTAGTTCTACAGGTTGTAAAATTAGTATAGAGTATATTTTAAAAGA |
| TCTTAAAATTAAAGATCCCAATTGTATAGCATTCATAGGTGAAGGAGCAGGGAATTTATTATTGCGTACAGTAGTGG |
| AACTTCATCCTGACATAAGATATATTTACAGAAGTCTGAAAGATTGCAATGATCATAGTTTACCTATTGAGTTTTTA |
| AGGCTGTACAATGGACATATCAACATTGATTATGGTGAAAATTTGACCATTCCTGCTACAGATGCAACCAACAACAT |
| TCATTGGTCTTATTTACATATAAAGTTTGCTGAACCTATCAGTCTTTTTGTCTGTGATGCCGAATTGTCTGTAACAG |
| TCAACTGGAGTAAAATTATAATAGAATGGAGCAAGCATGTAAGAAAGTGCAAGTACTGTTCCTCAGTTAATAAATGT |
| ATGTTAATAGTAAAATATCATGCTCAAGATGATATTGATTTCAAATTAGACAATATAACTATATTAAAAACTTATGT |
| ATGCTTAGGCAGTAAGTTAAAGGGATCGGAGGTTTACTTAGTCCTTACAATAGGTCCTGCGAATATATTCCCAGTAT |
| TTAATGTAGTACAAAATGCTAAATTGATACTATCAAGAACCAAAAATTTCATCATGCCTAAGAAAGCTGATAAAGAG |
| TCTATTGATGCAAATATTAAAAGTTTGATACCCTTTCTTTGTTACCCTATAACAAAAAAAGGAATTAATACTGCATT |
| GTCAAAACTAAAGAGTGTTGTTAGTGGAGATATACTATCATATTCTATAGCTGGACGTAATGAAGTTTTCAGCAATA |
| AACTTATAAATCATAAGCATATGAACATCTTAAAATGGTTCAATCATGTTTTAAATTTCAGATCAACAGAACTAAAC |
| TATAACCATTTATATATGGTAGAATCTACATATCCTTACCTAAGTGAATTGTTAAACAGCTTGACAACCAATGAACT |

-continued

| Exemplary Sequences |
|---|
| TAAAAAACTGATTAAAATCACAGGTAGTCTGTTATACAACTTTCATAATGAATAATGAATAAAGATCTTATAATAAA |
| AATTCCCATAGCTATACACTAACACTGTATTCAATTATAGTTATTAAAAATTAAAAATCATATAATTTTTTAAATAA |
| CTTTTAGTGAACTAATCCTAAAGTTATCATTTTAATCTTGGAGGAATAAATTTAAACCCTAATCTAATTGGTTTATA |
| TGTGTATTAACTAAATTACGAGATATTAGTTTTTGACACTTTTTTTCTCGT |
| Antigenomic cDNA sequence of RSV 276 genome (SEQ ID NO: 19) |
| ACGGGAAAAAATGCGTACAACAAACTTGCATAAACCAAAAAAATGGGGCAAATAAGAATTTGATAAGTACCACTTAA |
| ATTTAACTCCCTTGGTTAGAGATGGGCAGCAATTCATTGAGTATGATAAAAGTTAGATTACAAAATTTGTTTGACAA |
| TGATGAAGTAGCATTGTTAAAAATAACATGCTATACTGATAAATTAATACATTTAACTAATGCTTTGGCTAAGGCAG |
| TGATACATACAATCAAATTGAATGGCATTGTGTTTGTGCATGTTATTACAAGTAGTGATATTTGCCCTAATAATAAT |
| ATTGTAGTAAAATCCAATTTCACAACAATGCCAGTACTACAAAATGGAGGTTATATATGGGAAATGATGGAATTAAC |
| ACATTGCTCTCAACCTAACGGTCTACTAGATGACAATTGTGAAATTAAATTCTCCAAAAAACTAAGTGATTCAACAA |
| TGACCAATTATATGAATCAATTATCTGAATTACTTGGATTTGATCTTAATCCATAAATTATAATTAATATCAACTAG |
| CAAATCAATGTCACTAACACCATTAGTTAATATAAAACTTAACAGAAGACAAAAATGGGGCAAATAAATCAATTCAG |
| CCAACCCAACCATGGACACAACCCACAATGATAATACACCACAAAGACTGATGATCACAGACATGAGACCGTTGTCA |
| CTTGAGACCATAATAACATCACTAACCAGAGACATCATAACACACAAATTTATATACTTGATAAATCATGAATGCAT |
| AGTGAGAAGACTTGATGAAAGACAGGCCACATTTACATTCCTGGTCAACTATGAAATGAAACTATTACACAAAGTAG |
| GAAGCACTAAATATAAAAAATATACTGAATACAACACAAAATATGGCACTTTCCCTATGCCAATATTCATCAATCAT |
| GATGGGTTCTTAGAATGCATTGGCATTAAGCCTACAAAGCATACTCCCATAATATACAAGTATGATCTCAATCCATA |
| AATTTCAACACAATATTCACACAATCTAAAACAACAACTCTATGCATAACTATACTCCATAGTCCAGATGGAGCCTG |
| AAAATTATAGTAATTTAAAATTAAGGAGAGATATAAGATAGAAGATGGGGCAAATACAAAGATGGCTCTTAGCAAAG |
| TCAAGTTGAATGATACACTCAACAAGGATCAACTTCTGTCATCCAGCAAATACGCCATCCAACGGAGCACAGGAGAT |
| AGTATTGATACTCCTAATTATGATGTGCAGAAACACATCAATAAGTTATGTGGCATGTTATTAATCACAGAAGATGC |
| TAATCATAAATTCACTGGGTTAATAGGTATGTTATATGCGATGTCTAGGTTAGGAAGAGAAGACACCATAAAAATAC |
| TCAGAGATGCGGGATATCATGTAAAAGCAAATGGAGTAGATGTAACAACACATCGTCAAGACATTAATGGAAAAGAA |
| ATGAAATTTGAAGTGTTAACATTGGCAAGCTTAACAACTGAAATTCAAATCAACATTGAGATAGAATCTAGAAAATC |
| CTACAAAAAAATGCTAAAAGAAATGGGAGAGGTAGCTCCAGAATACAGGCATGACTCTCCTGATTGTGGGATGATAA |
| TATTATGTATAGCAGCATTAGTAATAACTAAATTAGCAGCAGGGGACAGATCTGGTCTTACAGCCGTGATTAGGAGA |
| GCTAATAATGTCCTAAAAAATGAAATGAAACGTTACAAAGGCTTACTACCCAAGGACATAGCCAACAGCTTCTATGA |
| AGTGTTTGAAAAACATCCCCACTTTATAGATGTTTTTGTTCATTTTGGTATAGCACAATCTTCTACCAGAGGTGGCA |
| GTAGAGTTGAAGGGATTTTTGCAGGATTGTTTATGAATGCCTATGGTGCAGGGCAAGTGATGTTACGGTGGGGAGTC |
| TTAGCAAAATCGGTTAAAAATATTATGTTAGGACATGCTAGTGTGCAAGCAGAAATGGAACAAGTTGTTGAGGTTTA |
| TGAATATGCCCAAAAATTGGGTGGTGAAGCAGGATTCTACCATATATTGAACAACCCAAAAGCATCATTATTATCTT |
| TGACTCAATTTCCTCACTTCTCCAGTGTAGTATTAGGCAATGCTGCTGGCCTAGGCATAATGGGAGAGTACAGAGGT |
| ACACCGAGGAATCAAGATCTATATGATGCAGCAAAGGCATATGCTGAACAACTCAAAGAAAATGGTGTGATTAACTA |
| CAGTGTACTAGACTTGACAGCAGAAGAACTAGAGGCTATCAAACATCAGCTTAATCCAAAAGATAATGATGTAGAGC |
| TTTGAGTTAATAAAAAAATGGGGCAAATAAATCATCATGGAAAAGTTTGCTCCTGAATTCCATGGAGAAGATGCAAAC |
| AACAGGGCTACTAAATTCCTAGAATCAATAAAGGGCAAATTCACATCACCCAAAGATCCCAAGAAAAAAGATAGTAT |
| CATATCTGTCAACTCAATAGATATAGAAGTAACCAAAGAAAGCCCTATAACATCAAATTCAACTATTATCAACCCAA |
| CAAATGAGACAGATGATACTGCAGGGAACAAGCCCAATTATCAAAGAAAACCTCTAGTAAGTTTCAAAGAAGACCCT |

-continued

| Exemplary Sequences |
| --- |
| ACACCAAGTGATAATCCCTTTTCTAAACTATACAAAGAAACCATAGAAACATTTGATAACAATGAAGAAGAATCCAG |
| CTATTCATACGAAGAAATAAATGATCAGACAAACGATAATATAACAGCAAGATTAGATAGGATTGATGAAAAATTAA |
| GTGAAATACTAGGAATGCTTCACACATTAGTAGTGGCAAGTGCAGGACCTACATCTGCTCGGGATGGTATAAGAGAT |
| GCCATGGTTGGTTTAAGAGAAGAAATGATAGAAAAAATCAGAACTGAAGCATTAATGACCAATGACAGATTAGAAGC |
| TATGGCAAGACTCAGGAATGAGGAAAGTGAAAAGATGGCAAAAGACACATCAGATGAAGTGTCTCTCAATCCAACAT |
| CAGAGAAATTGAACAACCTATTGGAAGGGAATGATAGTGACAATGATCTATCACTTGAAGATTTCTGATTAGTTACC |
| AATCTTCACATCAACACACAATACCAACAGAAGACCAACAAACTAACCAACCCAATCATCCAACCAAACATCCATCC |
| GCCAATCAGCCAAACAGCCAACAAAACAACCAGCCAATCCAAAACTAACCACCCGGAAAAAATCTATAATATAGTTA |
| CAAAAAAAGGAAAGGGTGGGGCAAATATGGAAACATACGTGAACAAGCTTCACGAAGGCTCCACATACACAGCTGCT |
| GTTCAATACAATGTCTTAGAAAAAGACGATGACCCTGCATCACTTACAATATGGGTGCCCATGTTCCAATCATCTAT |
| GCCAGCAGATTTACTTATAAAAGAACTAGCTAATGTCAACATACTAGTGAAACAAATATCCACACCCAAGGGACCTT |
| CACTAAGAGTCATGATAAACTCAAGAAGTGCAGTGCTAGCACAAATGCCCAGCAAATTTACCATATGCGCTAATGTG |
| TCCTTGGATGAAAGAAGCAAACTAGCATATGATGTAACCACACCCTGTGAAATCAAGGCATGTAGTCTAACATGCCT |
| AAAATCAAAAAATATGTTGACTACAGTTAAAGATCTCACTATGAAGACACTCAACCCTACACATGATATTATTGCTT |
| TATGTGAATTTGAAAACATAGTAACATCAAAAAAAGTCATAATACCAACATACCTAAGATCCATCAGTGTCAGAAAT |
| AAAGATCTGAACACACTTGAAAATATAACAACCACTGAATTCAAAAATGCTATCACAAATGCAAAAATCATCCCTTA |
| CTCAGGATTACTATTAGTCATCACAGTGACTGACAACAAAGGAGCATTCAAATACATAAAGCCACAAAGTCAATTCA |
| TAGTAGATCTTGGAGCTTACCTAGAAAAAGAAAGTATATATTATGTTACCACAAATTGGAAGCACACAGCTACACGA |
| TTTGCAATCAAACCCATGGAAGATTAACCTTTTTCCTCTACATCAGTGTGTTAATTCATACAAACTTTCTACCTACA |
| TTCTTCACTTCACCATCACAATCACAAACACTCTGTGGTTCAACCAATCAAACAAAACTTATCTGAAGTCCCAGATC |
| ATCCCAAGTCATTGTTTATCAGATCTAGTACTCAAATAAGTTAATAAAAAATATACACATGGGGCAAATAATCATTG |
| GAGGAAATCCAACTAATCACAATATCTGTTAACATAGACAAGTCCACACACCATACAGAATCAACCAATGGAAAATA |
| CATCCATAACAATAGAATTCTCAAGCAAATTCTGGCCTTACTTTACACTAATACACATGATCACAACAATAATCTCT |
| TTGCTAATCATAATCTCCATCATGATTGCAATACTAAACAAACTTTGTGAATATAACGTATTCCATAACAAAACCTT |
| TGAGTTACCAAGAGCTCGAGTCAACACATAGCATTCATCAATCCAACAGCCCAAAACAGTAACCTTGCATTTAAAAA |
| TGAACAACCCCTACCTCTTTACAACACCTCATTAACATCCCACCATGCAAACCACTATCCATACTATAAAGTAGTTA |
| ATTAAAAATAGTCATAACAATGAACTAGGATATCAAGACTAACAATAACATTGGGGCAAATGCAAACATGTCCAAAA |
| ACAAGGACCAACGCACCGCTAAGACATTAGAAAGGACCTGGGACACTCTCAATCATTTATTATTCATATCATCGTGC |
| TTATATAAGTTAAATCTTAAATCTGTAGCACAAATCACATTATCCATTCTGGCAATGATAATCTCAACTTCACTTAT |
| AATTGCAGCCATCATATTCATAGCCTCGGCAAACCACAAAGTCACACCAACAACTGCAATCATACAAGATGCAACAA |
| GCCAGATCAAGAACACAACCCCAACATACCTCACCCAGAATCCTCAGCTTGGAATCAGTCCCTCTAATCCGTCTGAA |
| ATTACATCACAAATCACCACCATACTAGCTTCAACAACACCAGGAGTCAAGTCAACCCTGCAATCCACAACAGTCAA |
| GACCAAAAACACAACAACAACTCAAACACAACCCAGCAAGCCCACCACAAAACAACGCCAAAACAAACCACCAAGCA |
| AACCCAATAATGATTTTCACTTTGAAGTGTTCAACTTTGTACCCTGCAGCATATGCAGCAACAATCCAACCTGCTGG |
| GCTATCTGCAAAAGAATACCAAACAAAAAACCAGGAAAGAAAACCACTACCAAGCCCACAAAAAAACCAACCCTCAA |
| GACAACCAAAAAAGATCCCAAACCTCAAACCACTAAATCAAAGGAAGTACCCACCACCAAGCCCACAGAAGAGCCAA |
| CCATCAACACCACCAAAACAAACATCATAACTACACTACTCACCTCCAACACCACAGGAAATCCAGAACTCACAAGT |
| CAAATGGAAACCTTCCACTCAACTTCCTCCGAAGGCAATCCAAGCCCTTCTCAAGTCTCTACAACATCCGAGTACCC |

-continued

| Exemplary Sequences |
| --- |
| ATCACAACCTTCATCTCCACCCAACACACCACGCCAGTAGTTACTTAAAAACATATTATCACAAAAAGCCATGACCA |
| ACTTAAACAGAATCAAAGTAAACTCTGGGGCAAATAACAATGGAGTTGCTAATCCTCAAAGCAAATGCAATTACCAC |
| AATCCTCACTGCAGTCACATTTTGTTTTGCTTCTGGTCAAAACATCACTGAAGAATTTTATCAATCAACATGCAGTG |
| CAGTTAGCAAAGGCTATCTTAGTGCTCTGAGAACTGGTTGGTATACCAGTGTTATAACTATAGAATTAAGTAATATC |
| AAGAAAAATAAGTGTAATGGAACAGATGCTAAGGTAAAATTGATAAAACAAGAATTAGATAAATATAAAAATGCTGT |
| AACAGAATTGCAGTTGCTCATGCAAAGCACACAAGCAACAAACAATCGAGCCAGAAGAGAACTACCAAGGTTTATGA |
| ATTATACACTCAACAATGCCAAAAAAACCAATGTAACATTAAGCAAGAAAAGGAAAAGAAGATTTCTTGGTTTTTTG |
| TTAGGTGTTGGATCTGCAATCGCCAGTGGCGTTGCTGTATCTAAGGTCCTGCACCTAGAAGGGGAAGTGAACAAGAT |
| CAAAAGTGCTCTACTATCCACAAACAAGGCTGTAGTCAGCTTATCAAATGGAGTCAGTGTCTTAACCAGCAAAGTGT |
| TAGACCTCAAAAACTATATAGATAAACAATTGTTACCTATTGTGAACAAGCAAAGCTGCAGCATATCAAATATAGAA |
| ACTGTGATAGAGTTCCAACAAAAGAACAACAGACTACTAGAGATTACCAGGGAATTTAGTGTTAATGCAGGTGTAAC |
| TACACCTGTAAGCACTTACATGTTAACTAATAGTGAATTATTGTCATTAATCAATGATATGCCTATAACAAATGATC |
| AGAAAAAGTTAATGTCCAACAATGTTCAAATAGTTAGACAGCAAAGTTACTCTATCATGTCCATAATAAAAGAGGAA |
| GTCTTAGCATATGTAGTACAATTACCACTATATGGTGTTATAGATACACCCTGTTGGAAACTACACACATCCCCTCT |
| ATGTACAACCAACACAAAAGAAGGGTCCAACATCTGTTTAACAAGAACTGACAGAGGATGGTACTGTGACAATGCAG |
| GATCAGTATCTTTCTTCCCACAAGCTGAAACATGTAAAGTTCAATCAAATCGAGTATTTTGTGACACAATGAACAGT |
| TTAACATTACCAAGTGAAGTAAATCTCTGCAATGTTGACATATTCAACCCCAAATATGATTGTAAAATTATGACTTC |
| AAAAACAGATGTAAGCAGCTCCGTTATCACATCTCTAGGAGCCATTGTGTCATGCTATGGCAAAACTAAATGTACAG |
| CATCCAATAAAAATCGTGGAATCATAAAGACATTTTCTAACGGGTGCGATTATGTATCAAATAAAGGGGTGGACACT |
| GTGTCTGTAGGTAACACATTATATTATGTAAATAAGCAAGAAGGTAAAAGTCTCTATGTAAAAGGTGAACCAATAAT |
| AAATTTCTATGACCCATTAGTATTCCCCTCTGATGAATTTGATGCATCAATATCTCAAGTCAACGAGAAGATTAACC |
| AGAGCCTAGCATTTATTCGTAAATCCGATGAATTATTACATAATGTAAATGCCGGTAAATCCACCACAAATATCATG |
| ATAACTACTATAATTATAGTGATTATAGTAATATTGTTATCATTAATTGCTGTTGGACTGCTCTTATACTGTAAGGC |
| CAGAAGCACACCAGTCACACTAAGCAAAGATCAACTGAGTGGTATAAATAATATTGCATTTAGTAACTAAATAAAAA |
| TAGCACCTAATCATGTTCTTACAATGGTTTACTATCTGCTCATAGACAACCCATCTGTCATTGGATTTTCTTAAAAT |
| CTGAACTTCATTGAAACTCTCATCTATAAACCATCTCACTTACACTATTTAAGTAGATTCCTAGTTTATAGTTATAT |
| AAAACACAATTGAATGCCAGATTAACTTACCATCTGTAAAAATGAAAACTGGGGCAAATATGTCACGAAGGAATCCT |
| TGCAAATTTGAAATTCGAGGTCATTGCTTAAATGGTAAGAGGTGTCATTTTAGTCATAATTATTTTGAATGGCCACC |
| GCATGCACTGCTTGTAAGACAAAACTTTATGTTAAACAGAATACTTAAGTCTATGGATAAAAGTATAGATACCTTAT |
| CAGAAATAAGTGGAGCTGCAGAGTTGGACAGAACAGAAGAGTATGCTCTTGGTGTAGTTGGAGTGCTAGAGAGTTAT |
| ATAGGATCAATAAACAATATAACTAAACAATCAGCATGTGTTGCCATGAGCAAACTCCTCACTGAACTCAATAGTGA |
| TGATATCAAAAAGCTGAGGGACAATGAAGAGCTAAATTCACCCAAGATAAGAGTGTACAATACTGTCATATCATATA |
| TTGAAAGCAACAGGAAAAACAATAAACAAACTATCCATCTGTTAAAAAGATTGCCAGCAGACGTATTGAAGAAAACC |
| ATCAAAAACACATTGGATATCCATAAGAGCATAACCATCAACAACCCAAAAGAATCAACTGTTAGTGATACAAATGA |
| CCATGCCAAAAATAATGATACTACCTGACAAATAACGTTCAATTCTAACACTCACCACATCGTTACATTATTAATTC |
| AAACAATTCAAGTTGTGGGACAAAATGGATCCCATTATTAATGGAAATTCTGCTAATGTTTATCTAACCGATAGTTA |
| TTTAAAAGGTGTTATCTCTTTCTCAGAGTGTAATGCTTTAGGAAGTTACATATTCAATGGTCCTTATCTCAAAAATG |
| ATTATACCAACTTAATTAGTAGACAAAATCCATTAATAGAACACATGAATCTAAAGAAACTAAATATAACACAGTCC |
| TTAATATCTAAGTATCATAAAGGTGAAATAAAATTAGAAGAACCTACTTATTTTCAGTCATTACTTATGACATACAA |

-continued

| Exemplary Sequences |
|---|
| GAGTATGACCTCGTCAGAACAGATTGCTACCACTAATTTACTTAAAAAGATAATAAGAAGAGCTATAGAAATAAGTG |
| ATGTCAAAGTCTATGCTATATTGAATAAACTAGGGCTTAAAGAAAAGGACAAGATTAAATCCAACAATGGACAAGAT |
| GAAGACAACTCAGTTATTACGACCATAATCAAAGATGATATACTTTCAGCTGTTAAAGATAATCAATCTCATCTTAA |
| AGCAGACAAAAATCACTCTACAAAACAAAAAGACACAATCAAAACAACACTCTTGAAGAAATTGATGTGTTCAATGC |
| AACATCCTCCATCATGGTTAATACATTGGTTTAACTTATACACAAAATTAAACAACATATTAACACAGTATCGATCA |
| AATGAGGTAAAAAACCATGGGTTTACATTGATAGATAATCAAACTCTTAGTGGATTTCAATTTATTTTGAACCAATA |
| TGGTTGTATAGTTTATCATAAGGAACTCAAAAGAATTACTGTGACAACCTATAATCAATTCTTGACATGGAAAGATA |
| TTAGCCTTAGTAGATTAAATGTTTGTTTAATTACATGGATTAGTAACTGCTTGAACACATTAAATAAAAGCTTAGGC |
| TTAAGATGCGGATTCAATAATGTTATCTTGACACAACTATTCCTTTATGGAGATTGTATACTAAAGCTATTTCACAA |
| TGAGGGGTTCTACATAATAAAAGAGGTAGAGGGATTTATTATGTCTCTAATTTTAAATATAACAGAAGAAGATCAAT |
| TCAGAAAACGATTTTATAATAGTATGCTCAACAACATCACAGATGCTGCTAATAAAGCTCAGAAAAATCTGCTATCA |
| AGAGTATGTCATACATTATTAGATAAGACAGTGTCCGATAATATAATAAATGGCAGATGGATAATTCTATTAAGTAA |
| GTTCCTTAAATTAATTAAGCTTGCAGGTGACAATAACCTTAACAATCTGAGTGAACTATATTTTTTGTTCAGAATAT |
| TTGGACACCCAATGGTAGATGAAAGACAAGCCATGGATGCTGTTAAAATTAATTGCAATGAGACCAAATTTTACTTG |
| TTAAGCAGTCTGAGTATGTTAAGAGGTGCCTTTATATATAGAATTATAAAAGGGTTTGTAAATAATTACAACAGATG |
| GCCTACTTTAAGAAATGCTATTGTTTTACCCTTAAGATGGTTAACTTACTATAAACTAAACACTTATCCTTCTTTGT |
| TGGAACTTACAGAAAGAGATTTGATTGTGTTATCAGGACTACGTTTCTATCGTGAGTTTCGGTTGCCTAAAAAAGTG |
| GATCTTGAAATGATTATAAATGATAAAGCTATATCACCTCCTAAAAATTTGATATGGACTAGTTTCCCTAGAAATTA |
| CATGCCATCACACATACAAAACTATATAGAACATGAAAAATTAAAATTTTCCGAGAGTGATAAATCAAGAAGAGTAT |
| TAGAGTATTATTTAAGAGATAACAAATTCAATGAATGTGATTTATACAACTGTGTAGTTAATCAAAGTTATCTCAAC |
| AACCCTAATCATGTGGTATCATTGACAGGCAAAGAAAGAGAACTCAGTGTAGGTAGAATGTTTGCAATGCAACCGGG |
| AATGTTCAGACAGGTTCAAATATTGGCAGAGAAAATGATAGCTGAAAACATTTTACAATTCTTTCCTGAAAGTCTTA |
| CAAGATATGGTGATCTAGAACTACAAAAAATATTAGAATTGAAAGCAGGAATAAGTAACAAATCAAATCGCTACAAT |
| GATAATTACAACAATTACATTAGTAAGTGCTCTATCATCACAGATCTCAGCAAATTCAATCAAGCATTTCGATATGA |
| AACGTCATGTATTTGTAGTGATGTGCTGGATGAACTGCATGGTGTACAATCTCTATTTTCCTGGTTACATTTAACTA |
| TTCCTCATGTCACAATAATATGCACATATAGGCATGCACCCCCCTATATAGGAGATCATATTGTAGATCTTAACAAT |
| GTAGATGAACAAAGTGGATTATATAGATATCACATGGGTGGCATCGAAGGGTGGTGTCAAAAACTATGGACCATAGA |
| AGCTATATCACTATTGGATCTAATATCTCTCAAAGGGAAATTCTCAATTACTGCTTTAATTAATGGTGACAATCAAT |
| CAATAGATATAAGCAAACCAATCAGACTCATGGAAGGTCAAACTCATGCTCAAGCAGATTATTTGCTAGCATTAAAT |
| AGCCTTAAATTACTGTATAAAGAGTATGCAGGCATAGGCCACAAATTAAAAGGAACTGAGACTTATATATCACGAGA |
| TATGCAATTTATGAGTAAAACAATTCAACATAACGGTGTATATTACCCAGCTAGTATAAAGAAAGTCCTAAGAGTGG |
| GACCGTGGATAAACACTATACTTGATGATTTCAAAGTGAGTCTAGAATCTATAGGTAGTTTGACACAAGAATTAGAA |
| TATAGAGGTGAAAGTCTATTATGCAGTTTAATATTTAGAAATGTATGGTTATATAATCAGATTGCTCTACAATTAAA |
| AAATCATGCATTATGTAACAATAAACTATATTTGGACATATTAAAGGTTCTGAAACACTTAAAAACCTTTTTTAATC |
| TTGATAATATTGATACAGCATTAACATTGTATATGAATTTACCCATGTTATTTGGTGGTGGTGATCCCAACTTGTTA |
| TATCGAAGTTTCTATAGAAGAACTCCTGACTTCCTCACAGAGGCTATAGTTCACTCTGTGTTCATACTTAGTTATTA |
| TACAAACCATGACTTAAAAGATAAACTTCAAGATCTGTCAGATGATAGATTGAATAAGTTCTTAACATGCATAATCA |
| CGTTTGACAAAAACCCTAATGCTGAATTCGTAACATTGATGAGAGATCCTCAAGCTTTAGGGTCTGAGAGACAAGCT |

-continued

| Exemplary Sequences |
|---|
| AAAATTACTAGCGAAATCAATAGACTGGCAGTTACAGAGGTTTTGAGTACAGCTCCAAACAAAATATTCTCCAAAAG |
| TGCACAACATTATACTACTACAGAGATAGATCTAAATGATATTATGCAAAATATAGAACCTACATATCCTCATGGGC |
| TAAGAGTTGTTTATGAAAGTTTACCCTTTTATAAAGCAGAGAAAATAGTAAATCTTATATCAGGTACAAAATCTATA |
| ACTAACATACTGGAAAAAACTTCTGCCATAGACTTAACAGATATTGATAGAGCCACTGAGATGATGAGGAAAAACAT |
| AACTTTGCTTATAAGGATACTTCCATTGGATTGTAACAGAGATAAAAGAGAGATATTGAGTATGGAAAACCTAAGTA |
| TTACTGAATTAAGCAAATATGTTAGGGAAAGATCTTGGTCTTTATCCAATATAGTTGGTGTTACATCACCCAGTATC |
| ATGTATACAATGGACATCAAATATACTACAAGCACTATATCTAGTGGCATAATTATAGAGAAATATAATGTTAACAG |
| TTTAACACGTGGTGAGAGAGGACCCACTAAACCATGGGTTGGTTCATCTACACAAGAGAAAAAAACAATGCCAGTTT |
| ATAATAGACAAGTCTTAACCAAAAAACAGAGAGATCAAATAGATCTATTAGCAAAATTGGATTGGGTGTATGCATCT |
| ATAGATAACAAGGATGAATTCATGGAAGAACTCAGCATAGGAACCCCTTGGGTTAACATATGAAAAGGCCAAGAAATT |
| ATTTCCACAATATTTAAGTGTCAATTATTTGCATCGCCTTACAGTCAGTAGTAGACCATGTGAATTCCCTGCATCAA |
| TACCAGCTTATAGAACAACAAATTATCACTTTGACACTAGCCCTATTAATCGCATATTAACAGAAAAGTATGGTGAT |
| GAAGATATTGACATAGTATTCCAAAACTGTATAAGCTTTGGCCTTAGTTTAATGTCAGTAGTAGAACAATTTACTAA |
| TGTATGTCCTAACAGAATTATTCTCATACCTAAGCTTAATGAGATACATTTGATGAAACCTCCCATATTCACAGGTG |
| ATGTTGATATTCACAAGTTAAAACAAGTGATACAAAAACAGCATATGTTTTTACCAGACAAAATAAGTTTGACTCAA |
| TATGTGGAATTATTCTTAAGTAATAAAACACTCAAATCTGGATCTCATGTTAATTCTAATTTAATATTGGCACATAA |
| AATATCTGACTATTTTCATAATACTTACATTTTAAGTACTAATTTAGCTGGACATTGGATTCTGATTATACAACTTA |
| TGAAAGATTCTAAAGGTATTTTTGAAAAAGATTGGGGAGAGGGATATATAACTGATCATATGTTTATTAATTTGAAA |
| GTTTTCTTCAATGCTTATAAGACCTATCTCTTGTGTTTTCATAAAGGTTATGGCAAAGCAAAGCTGGAGTGTGATAT |
| GAACACTTCAGATCTTCTATGTGTATTGGAATTAATAGACAGTAGTTATTGGAAGTCTATGTCTAAGGTATTTTTAG |
| AACAAAAAGTTATCAAATACATTCTTAGCCAAGATGCAAGTTTACATAGAGTAAAAGGATGTCATAGCTTCAAATTA |
| TGGTTTCTTAAACGTCTTAATGTAGCAGAATTCACAGTTTGCCCTTGGGTTGTTAACATAGATTATCATCCAACACA |
| TATGAAAGCAATATTAACTTATATAGATCTTGTTAGAATGGGATTGATAAATATAGATAGAATACACATTAAAAATA |
| AACACAAATTCAATGATGAATTTTATACTTCTAATCTCTTCTACATTAATTATAACTTCTCAGATAATACTCATCTA |
| TTAACTAAACATATAAGGATTGCTAATTCTGAATTAGAAAATAATTACAACAAATTATATCATCCTACACCAGAAAC |
| ACTAGAGAATATACTAGCCAATCCGATTAAAAGTAATGACAAAAAGACACTGAATGACTATTGTATAGGTAAAAATG |
| TTGACTCAATAATGTTACCATTGTTATCTAATAAGAAGCTTATTAAATCGTCTGCAATGATTAGAACCAATTACAGC |
| AAACAAGATTTGTATAATTTATTCCCTATGGTTGTGATTGATAGAATTATAGATCATTCAGGCAATACAGCCAAATC |
| CAACCAACTTTACACTACTACTTCCCACCAAATATCCTTAGTGCACAATAGCACATCACTTTACTGCATGCTTCCTT |
| GGCATCATATTAATAGATTCAATTTTGTATTTAGTTCTACAGGTTGTAAAATTAGTATAGAGTATATTTTAAAAGAT |
| CTTAAAATTAAAGATCCCAATTGTATAGCATTCATAGGTGAAGGAGCAGGGAATTTATTATTGCGTACAGTAGTGGA |
| ACTTCATCCTGACATAAGATATATTTACAGAAGTCTGAAAGATTGCAATGATCATAGTTTACCTATTGAGTTTTTAA |
| GGCTGTACAATGGACATATCAACATTGATTATGGTGAAAATTTGACCATTCCTGCTACAGATGCAACCAACAACATT |
| CATTGGTCTTATTTACATATAAAGTTTGCTGAACCTATCAGTCTTTTTGTCTGTGATGCCGAATTGTCTGTAACAGT |
| CAACTGGAGTAAAATTATAATAGAATGGAGCAAGCATGTAAGAAAGTGCAAGTACTGTTCCTCAGTTAATAAATGTA |
| TGTTAATAGTAAAATATCATGCTCAAGATGATATTGATTTCAAATTAGACAATATAACTATATTAAAAACTTATGTA |
| TGCTTAGGCAGTAAGTTAAAGGGATCGGAGGTTTACTTAGTCCTTACAATAGGTCCTGCGAATATATTCCCAGTATT |
| TAATGTAGTACAAAATGCTAAATTGATACTATCAAGAACCAAAAATTTCATCATGCCTAAGAAAGCTGATAAAGAGT |
| CTATTGATGCAAATATTAAAAGTTTGATACCCTTTCTTTGTTACCCTATAACAAAAAAAGGAATTAATACTGCATTG |

-continued

| Exemplary Sequences |
|---|
| TCAAAACTAAAGAGTGTTGTTAGTGGAGATATACTATCATATTCTATAGCTGGACGTAATGAAGTTTTCAGCAATAA |
| ACTTATAAATCATAAGCATATGAACATCTTAAAATGGTTCAATCATGTTTTAAATTTCAGATCAACAGAACTAAACT |
| ATAACCATTTATATATGGTAGAATCTACATATCCTTACCTAAGTGAATTGTTAAACAGCTTGACAACCAATGAACTT |
| AAAAAACTGATTAAAATCACAGGTAGTCTGTTATACAACTTTCATAATGAATAATGAATAAAGATCTTATAATAAAA |
| ATTCCCATAGCTATACACTAACACTGTATTCAATTATAGTTATTAAAAATTAAAAATCATATAATTTTTTAAATAAC |
| TTTTAGTGAACTAATCCTAAAGTTATCATTTTAATCTTGGAGGAATAAATTTAAACCCTAATCTAATTGGTTTATAT |
| GTGTATTAACTAAATTACGAGATATTAGTTTTTGACACTTTTTTTCTCGT |

In summary, the materials, information, and methods described in this disclosure provide an array of attenuated strains with graded attenuation phenotypes, and provide guidance in selecting suitable vaccine candidate strains based on clinical benchmarks. The following examples are provided by way of illustration, not limitation.

EXAMPLES

1. The recombinant RSV strains exemplified in this disclosure were derived from the recombinant version of wt strain A2 that is called D46 (Collins, et al. 1995. Proc Natl Acad Sci USA 92:11563-11567). The complete nucleotide sequence of D46 is shown as SEQ ID NO: 1. The RSV MEDI/ΔM2-2 virus is not derived from D46.

2. In the examples below, when a virus name includes the term "LID" or "6120", this indicates that its backbone contains the "6120" mutation shown in FIG. 3.

3. Viruses are named herein by listing the combination of mutations present in them. The use of the symbol "/" in a virus name (as in RSV D46/cp/ΔM2-2 which denotes RSV D46 comprising the mutations cp and ΔM2-2) has no significance apart from being present to make the name easier to read, particularly when present in text. Hence, RSV D46/cp/ΔM2-2 is the same as RSV D46cpΔM2-2. Also, RSV D46/cp/ΔM2-2 also is the same as RSV D46cpΔM2-2 or RSV D46 cpΔM2-2, etc. Also, a virus name typically begins with RSV, as in RSV D46/cp/ΔM2-2.

4. As noted previously, the "ΔM2-2" mutation refers to the 241-nucleotide deletion together with the three point mutations as shown in FIG. 1. Other mutations that silence the M2-2 ORF are specified by different names, e.g. ΔM2-2-AclI and ΔM2-2-HindIII shown in FIG. 10. The presence of "ΔM2-2" in virus names in this disclosure indicates the presence of the "ΔM2-2" mutation.

5. The magnitude of virus replication in vivo is used as an indication of virus attenuation: specifically, decreased replication in vivo is used as an indicator of increased attenuation, and vice versa. This reflects the general observation that increased RSV replication is associated with increased illness both for wt RSV infection (e.g., El Saleeby, et al. 2011. J Infect Dis 204:996-1002; DeVincenzo, et al. 2010. Am J Respir Crit Care Med 182:1305-1314) and for attenuated RSV candidates in clinical studies (e.g., Karron, et al. 1997. J Infect Dis 176:1428-1436; Karron, et al. 2005. J Infect Dis 191:1093-1104). These terms are used for descriptive purposes, rather than as a limiting definition.

Example 1

This example illustrates design and construction of novel RSV variants bearing a deletion in the M2-2 ORF (ΔM2-2), alone and in combination with additional mutations.

Representative viruses were constructed and evaluated pre-clinically. One representative virus of this panel, and a second M2-2 ORF mutant virus from another source, were evaluated in a phase 1 clinical study in seronegative infants and young children, which constitute the primary pediatric RSV vaccine target group. This example provides new vaccine strains together with clinical benchmarks for representative examples in the most relevant human population.

RSV rA2-K5 Virus.

A RSV strain called RSV rA2-K5 was previously constructed (from the parental wt D46 cDNA-derived virus), in which expression of the M2-2 ORF was silenced by a combination of three types of mutations: (i) introduction of a frame shift midway through the M2-2 ORF, (ii) changing the three potential ATG translational start codons of the M2-2 ORF (see FIG. 1A for a diagram of the RSV genome and overlapping M2-1 and M2-2-ORFs) into ACG codons, and (iii) introducing stop codons into all three registers of the M2-2 sequence shortly after the end of the M2-1 ORF (Bermingham and Collins. 1999. Proc Natl Acad Sci USA 96:11259-11264). This rA2-K5 virus (which is not illustrated in this disclosure) was evaluated for replication in the respiratory tract of seronegative chimpanzees, showing that it was restricted at least 2800-fold in the upper respiratory tract and was not detected in the lower respiratory tract (representing a reduction of at least 55,000-fold) (Teng, et al. 2000. J Virol 74:9317-9321).

Creation of RSV D46/ΔM2-2 and RSV LID/ΔM2-2.

Figure 2:
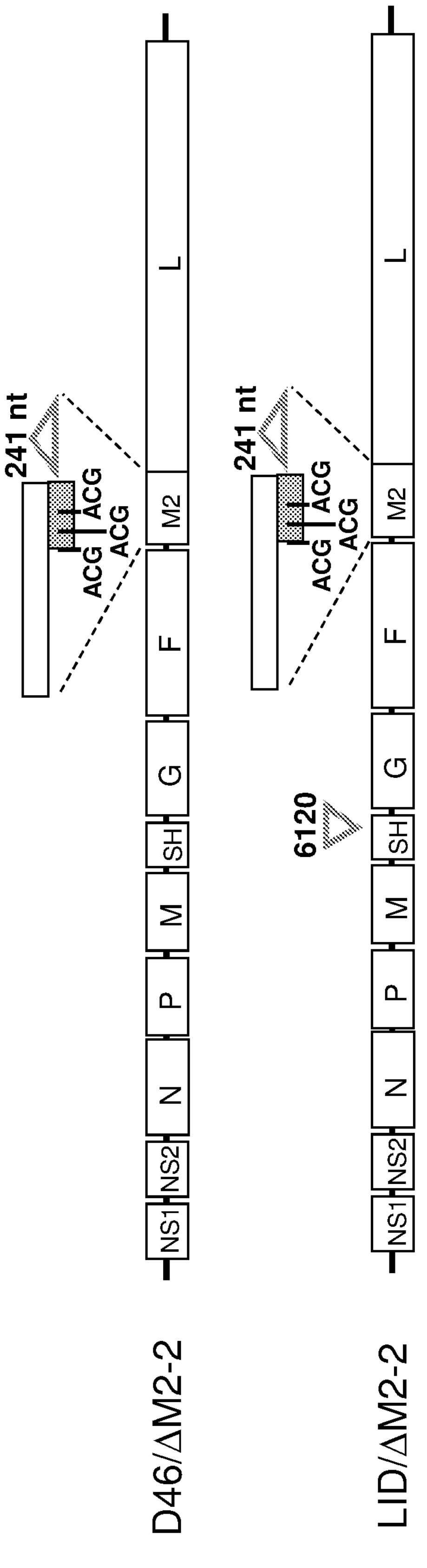
FIG. 2. A depiction of the gene maps of two examples of attenuated recombinant RSVs using the D46 backbone and comprising the ΔM2-2 mutation. These are D46/ΔM2-2 (comprising the ΔM2-2 mutation) and LID/ΔM2-2 (comprising the ΔM2-2 mutation and the "6120" mutation, see FIG. 3) viruses. Antigenomic cDNA sequences of these two constructs are denoted by SEQ ID NO: 2 and SEQ ID NO: 5, respectively.

Additional recombinant virus was constructed in which most of the M2-2 ORF was deleted. The wt D46 cDNA was modified so that each of the three potential translational ATG start codons for the M2-2 ORF was changed to ACG, and nucleotides 8188-8428 were deleted (total deletion of 241 nt), removing most of the M2-2 ORF (FIG. 1). Thus, with all of the known potential ATG translational start sites mutated and most of the ORF deleted, expression of complete M2-2 protein should not be possible, and there should be little or no expression of any truncated M2-2 fragments. A gene map of the resulting RSV D46/ΔM2-2 virus is shown in FIG. 2.

Additional ΔM2-2 mutants were constructed that would have a range of attenuation phenotypes. Because the prototype RSV rA2-K5 virus was highly attenuated in chimpanzees, as noted above (Teng, et al. 2000. J Virol 74:9317-9321), it was possible that a virus in which M2-2 was not expressed might be over-attenuated. On the other hand, it also was possible that it might be under-attenuated, particularly in seronegative infants and young children. Therefore, additional viral variants were constructed to identify derivatives with increased as well as decreased replication.

There was no established method for increasing the replication of an RSV strain, and in particular a ΔM2-2 mutant. It was previously reported that moving the G and F genes from being the $6^{th}$ and $7^{th}$ genes in the gene order (this was done in a virus in which the SH gene had been deleted, and thus G and F were the 6th and 7th genes rather than their native positions as $7^{th}$ and $8^{th}$) to being the 1st and 2nd genes, respectively, resulted in a 10-fold increase in replication in vitro, although there was not a statistically significant increase in replication in mice (Krempl, et al. 2002. J Virol 76:11931-11942) or AGMs. One limitation is that the established pre-clinical assays for evaluating RSV replication and attenuation (e.g., replication in cell lines, rodents, and non-human primates other than chimpanzees) may be relatively semi-permissive and insensitive, making it difficult to demonstrate statistically significant changes in replication efficiency, and therefore any change in replication seems noteworthy even if it is not detected in every assay. Therefore, it was attempted to modify a ΔM2-2/ΔSH virus to move the G and F genes to the promoter-proximal positions. (The ΔSH deletion had been included in an initial study in the wild type backbone [Krempl, et al. 2002. J Virol 76:11931-11942] to avoid instability in this sequence during plasmid amplification in bacteria and was considered incidental, and the ΔSH deletion also was used with the ΔM2-2-backbone.) Several permutations were evaluated, such as in which the G and F genes were placed as the first and second genes, respectively, or as the second and first genes, respectively. However, these modifications reduced virus replication by 100- to 1000-fold, indicating that these particular changes were not well tolerated in infectious virus. It may be that the increase in expression of G and F known to be associated with movement of their genes to the promoter-proximal locations (Krempl, et al. 2002. J Virol 76:11931-11942), combined with an increase in protein expression associated with the ΔM2-2 mutation, was not tolerated by RSV, at least in this ΔM2-2/ΔSH backbone.

Additionally, it is known that changes in genome length can affect the efficiency of replication. Specifically, it has been shown that increasing the length of a paramyxovirus genome can decrease its replication efficiency. For example, increasing the length of the RSV genome by 140 or 160 nucleotides in a fashion that did not perturb gene expression resulted in a 5- to 25-fold restriction for replication in mice (Bukreyev, Murphy, Collins. 2000. J Virol 74:11017-11026). In another study with a related virus, namely human parainfluenza virus type 3 (PIV3), increasing the genome length either by adding additional genes or by increasing the genome length by inserts in non-translated regions (which thus did not change the gene number) retained efficient replication in vitro but was attenuating in hamsters (Skiadopoulos, et al. 2000. Virology 272:225-234). It is presumed that attenuation associated with increased genome length occurs because of the greater burden of replicating a longer genome. The observation that increasing the length of the genome reduced replication efficiency suggested the converse idea, namely that reducing the genome length might increase replication efficiency. To this end, the RSV D46/ΔM2-2 virus was modified to contain a mutation called "6120", resulting in a virus called RSV LID/ΔM2-2 (genome diagram shown in FIG. 2, bottom diagram). In this document, "LID" in a virus name indicates the presence of the 6120 mutation.

The "6120" mutation (FIG. 3) involves deletion of 112 nucleotides of the downstream non-translated region of the SH gene and the introduction of five translationally-silent point mutations in the last three codons and the termination codon of the SH gene (Bukreyev, et al. 2001. J Virol 75:12128-12140). The main purpose in the original design of this mutation was to stabilize the antigenomic cDNA in bacteria so that it could be more easily manipulated and prepared, which indeed was the case. In wt RSV, this mutation was previously found to confer a 5-fold increase in replication efficiency in vitro (Bukreyev, et al. 2001. J Virol 75:12128-12140), whereas it did not appear to increase replication efficiency in mice. When RSV LID/ΔM2-2 was evaluated for the possibility of increased replication in vitro associated with the 6120 mutation, a modest increase in growth efficiency was observed in some experiments but not others.

Inclusion of Additional Mutations in RSV D46/ΔM2-2 and RSV LID/ΔM2-2.

A series of further derivatives of the RSV D46/ΔM2-2 and RSV LID/ΔM2-2 viruses was constructed in which one or more additional mutations were variously inserted into one or both of the viruses, with the goal of achieving a spectrum of further-attenuated viruses.

Figure 4:
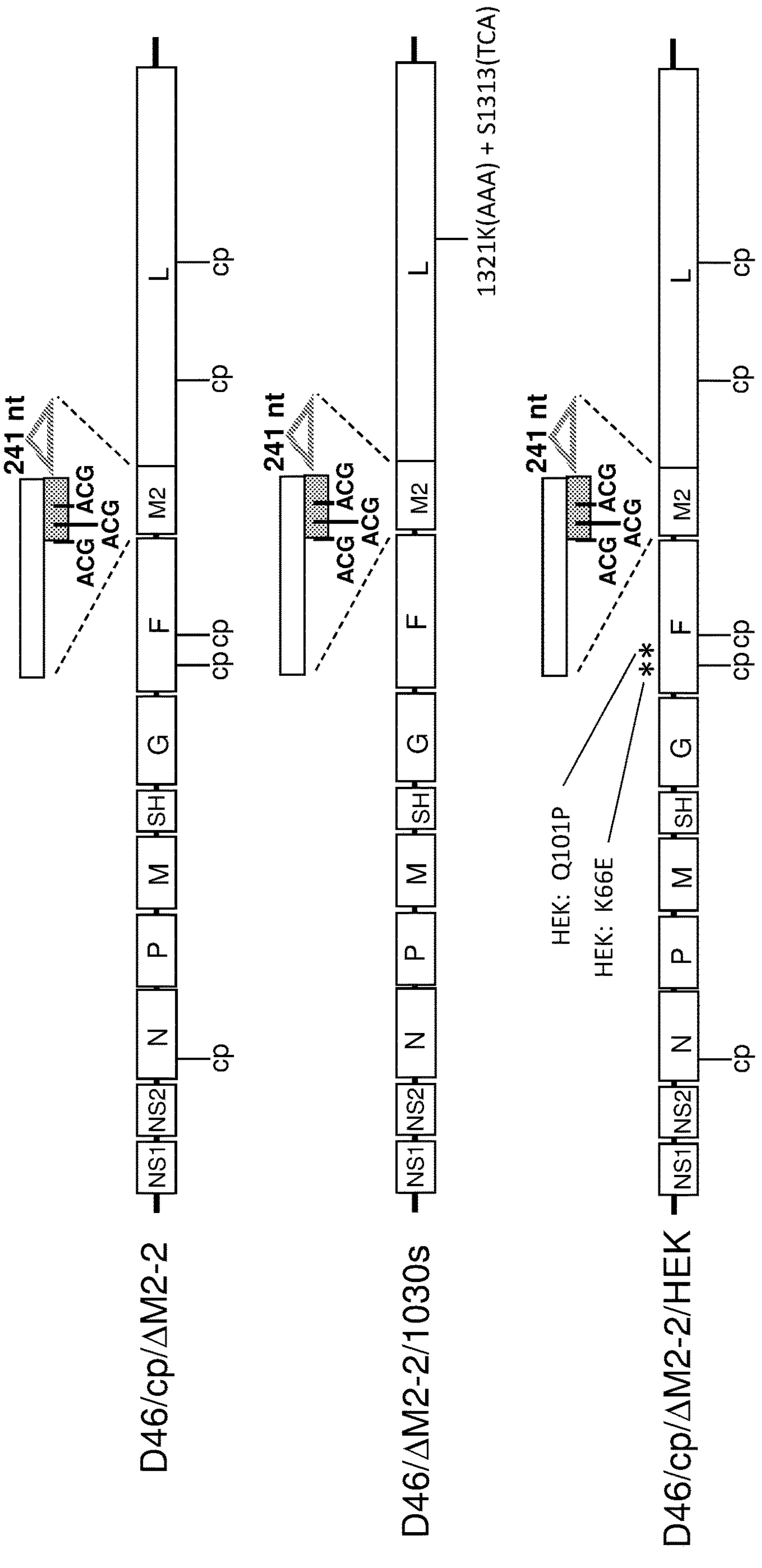
FIG. 4. Schematic diagrams of the genomes of three examples of derivatives of RSV D46/ΔM2-2 that each contains one or more additional attenuating mutations. The ΔM2-2 mutation is depicted. The other attenuating mutations include the set of "cp" mutations (five amino acid substitutions in the N, F, and L proteins: N (V267I), F (E218A and T523I), and L (C319Y and H1690Y)), and the stabilized 1030 mutation ("1030s") mutation in the L protein, which includes a Y1321K substitution generated by introducing an AAA codon for L amino acid 1321, and a stabilizing version of the serine codon at L position 1313 (nt 12435-12437 of SEQ ID NO:1; AGC changed to TCA) (1321K(AAA)+S1313(TCA); Luongo, et al. 2012. J Virol 86:10792-10804). Further mutations are the HEK changes in the F protein (K66E and Q101P)(Connors, et al. 1995. Virology 208:478-484; Whitehead, et al. 1998. J Virol 72:4467-4471).

Examples of derivatives of RSV D46/ΔM2-2 are shown in FIG. 4. For example, the derivative RSV D46/cp/ΔM2-2 virus (FIG. 4, top diagram) combines the ΔM2-2 mutation (FIG. 1) with the "cp" mutations, which is a set of five amino acid substitutions in three proteins (N (V267I), F (E218A and T523I), and L (C319Y and H1690Y)) that together (on their own) confer an approximate 10-fold reduction in replication in seronegative chimpanzees, and a reduction in illness (Whitehead, et al. 1998. J Virol 72:4467-4471). The availability of phenotypic data from chimpanzees is noteworthy because this experimental animal approaches humans in its permissiveness to RSV replication and disease. Note that the D46/cp/ΔM2-2 construct had a single adventitious nucleotide change in the D46 backbone, at the DNA level: specifically there was a silent nucleotide change G3878A, present in the M ORF.

Another derivative, the RSV D46/ΔM2-2/1030s virus (FIG. 4, second diagram from the top), contains the ΔM2-2 mutation in combination with the genetically stabilized 1030 mutation ("1030s"), which consists of 1321K(AAA)/S1313 (TCA) (Luongo, et al. 2012. J Virol 86:10792-10804). The 1030s mutation conferred a 0.6 and 1.5 mean $\log_{10}$ reduction in RSV replication in the upper and lower respiratory tract, respectively, of mice. It also has been evaluated in seronegative chimpanzees, but only in combination with a number of additional attenuating mutations (Luongo, et al. 2012. J Virol 86:10792-10804).

Another derivative, the RSV D46/cp/ΔM2-2/HEK virus (FIG. 4, bottom diagram), combines the cp and ΔM2-2 mutations with the "HEK" mutations. The HEK mutations consist of two amino acid substitutions in the RSV F protein, K66E and Q101P, that match the sequence at the amino acid level to an early-passage of the same strain (A2) called HEK-7, which was derived by passaging the original strain A2 clinical isolate seven times on human embryonic kidney (HEK) cells (Connors, et al. 1995. Virology 208:478-484; Whitehead, et al. 1998. J Virol 72:4467-4471), and which is thought to most closely resemble (and likely be identical to) the original strain A2 clinical isolate (Liang, et al. 2014. J Virol 88:4237-4250; Liang, et al. 2015. J Virol 89:9499-9510). It was previously shown that the HEK mutations stabilized the F protein trimer and conferred a hypofusogenic phenotype that is thought to resemble that of the original clinical isolate (Liang, et al. 2014. J Virol 88:4237-4250; Liang, et al. 2015. J Virol 89:9499-9510). In addition to likely being found in the original strain A2 clinical isolate, the HEK assignments are found in nearly all clinical isolates of RSV subgroup A present in GenBank (Liang, et al. 2015. J Virol 89:9499-9510). Thus, the HEK mutations may provide a more authentic and immunogenic form of the RSV F protein, possibly enriched for the highly immunogenic prefusion conformation (McLellan et al., Science 2013 340 (6136):1113-7; Science 2013 342(6158):592-8.). Thus, rather than necessarily being associated per se with attenuation, the HEK mutations provide a version of the F protein that more accurately reflects the original strain A2 clinical isolate as well as clinical isolates of other RSV strains.

Figure 5:
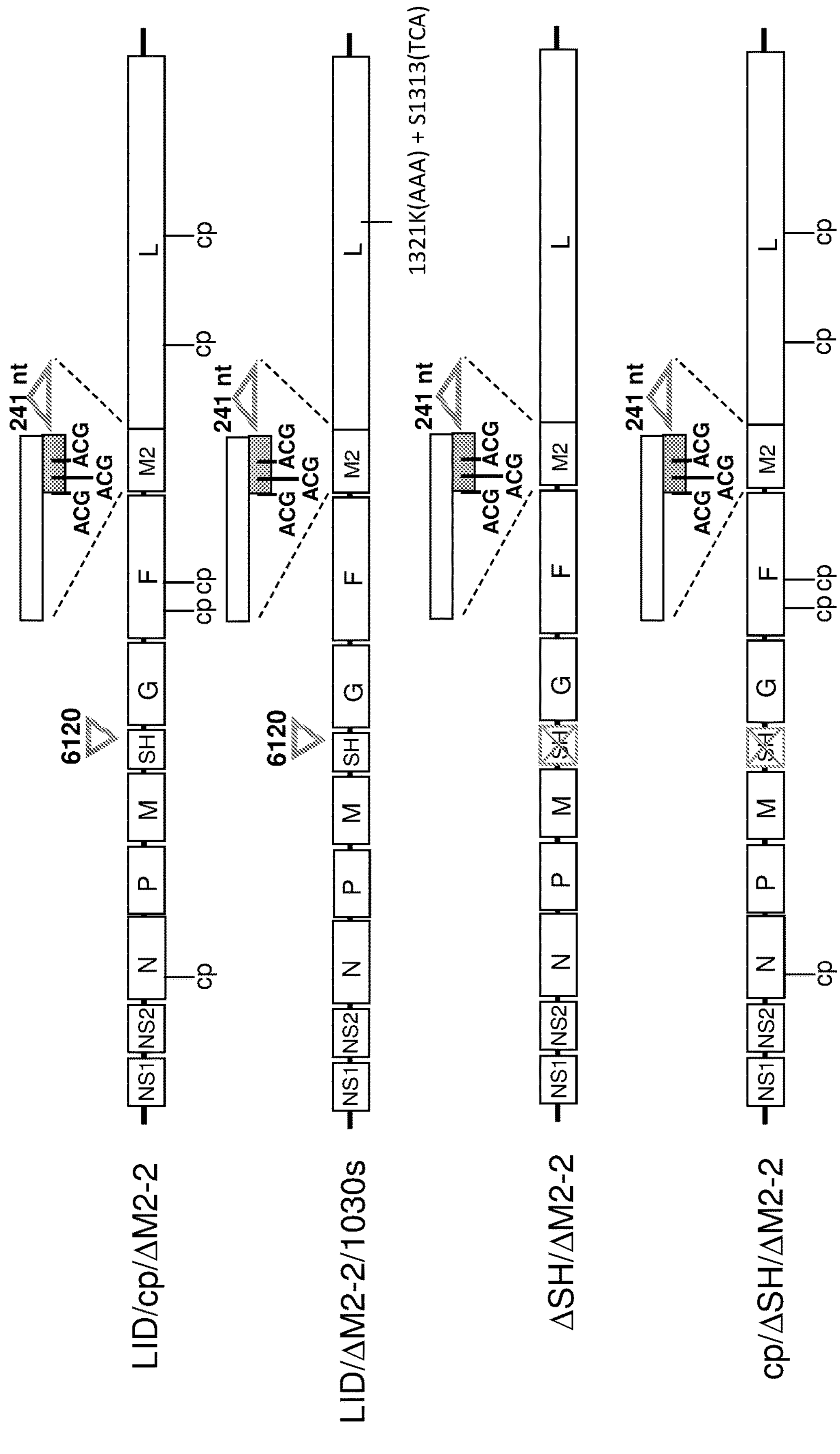
FIG. 5. Schematic diagrams of the genomes of four examples of derivatives of RSV LID/ΔM2-2 that each contains one or more additional attenuating mutations. The "LID" backbone is a D46-based genome containing the "6120" mutation. The ΔM2-2 mutation and the 6120 mutation are indicated. The other attenuating mutations include the set of "cp" mutations (five amino acid substitutions in the N, F, and L proteins: N (V267I), F (E218A and T523I), and L (C319Y and H1690Y)), deletion of the SH gene (see FIG. 6), and the "1030s" mutation in the L protein. Note that viruses from which the entire SH gene has been deleted (RSV ΔSH/ΔM2-2 and RSV cp/4SH/ΔM2-2) are not referred to as "LID" because the SH deletion removes the 6120 mutation.

Examples of derivatives of RSV LID/ΔM2-2 are shown in FIG. 5. One derivative, the RSV LID/cp/ΔM2-2 virus (FIG. 5, top diagram), combines the ΔM2-2 and cp mutations. Another, the RSV LID/ΔM2-2/1030s virus (FIG. 5, second diagram from the top), combines the ΔM2-2 and 1030s mutations. Another, the RSV ΔSH/ΔM2-2 virus (FIG. 5, third diagram from the top), combines the ΔM2-2 mutation with deletion of the SH gene (see FIG. 6 for the details of the construction of the SH deletion). Deletion of the SH gene was previously shown to result in a 40-fold reduction in RSV replication in seronegative chimpanzees, and a reduction in illness (Whitehead, et al. 1999. J Virol 73:3438-3442). Another derivative, the RSV cp/4SH/ΔM2-2 virus (FIG. 5, bottom diagram), combines the ΔM2-2 and cp mutations with deletion of the SH gene. Note that viruses in which the entire SH gene was deleted are not referred to as "LID" because deletion of the SH gene removes the 6120 mutation.

All of the mutants in FIGS. 2, 4, and 5 were readily recovered by reverse genetics using standard methods. However, contrary to expectations based on previous work (e.g., Bukreyev et al., J Virol 1997 71:8973-8982; Whitehead et al. J Virol 73:3438-3442 1999), viruses that contained a ΔSH mutation in the context of a ΔM2-2 mutation replicated approximately 10-fold less efficiently than other ΔM2-2 mutants. This finding illustrates how unanticipated but important effects can emerge when viruses are actually made and evaluated.

Regarding the attenuating mutations noted in FIGS. 4 and 5, previous studies in chimpanzees of the cp, ΔSH, 1030 (the parent of 1030s), and ΔM2-2 mutations indicated that their order of increasing attenuation is: cp≈ΔSH<1030s<ΔM2-2 (Whitehead, et al. 1999. J Virol 73:3438-3442; Whitehead, et al. 1999. J Virol 73:871-877; Teng, et al. 2000. J Virol 74:9317-9321). Thus the cp, ΔSH, and 1030s mutations, when combined singly or in combination with a ΔM2-2 mutation, provide a range of increasing levels of added attenuation. These may be evaluated in a clinical study in the relevant vaccine target population (seronegative infants and young children).

Example 2

This example describes preclinical evaluation of LID and D46 ΔM2-2 viruses.

Figure 7:
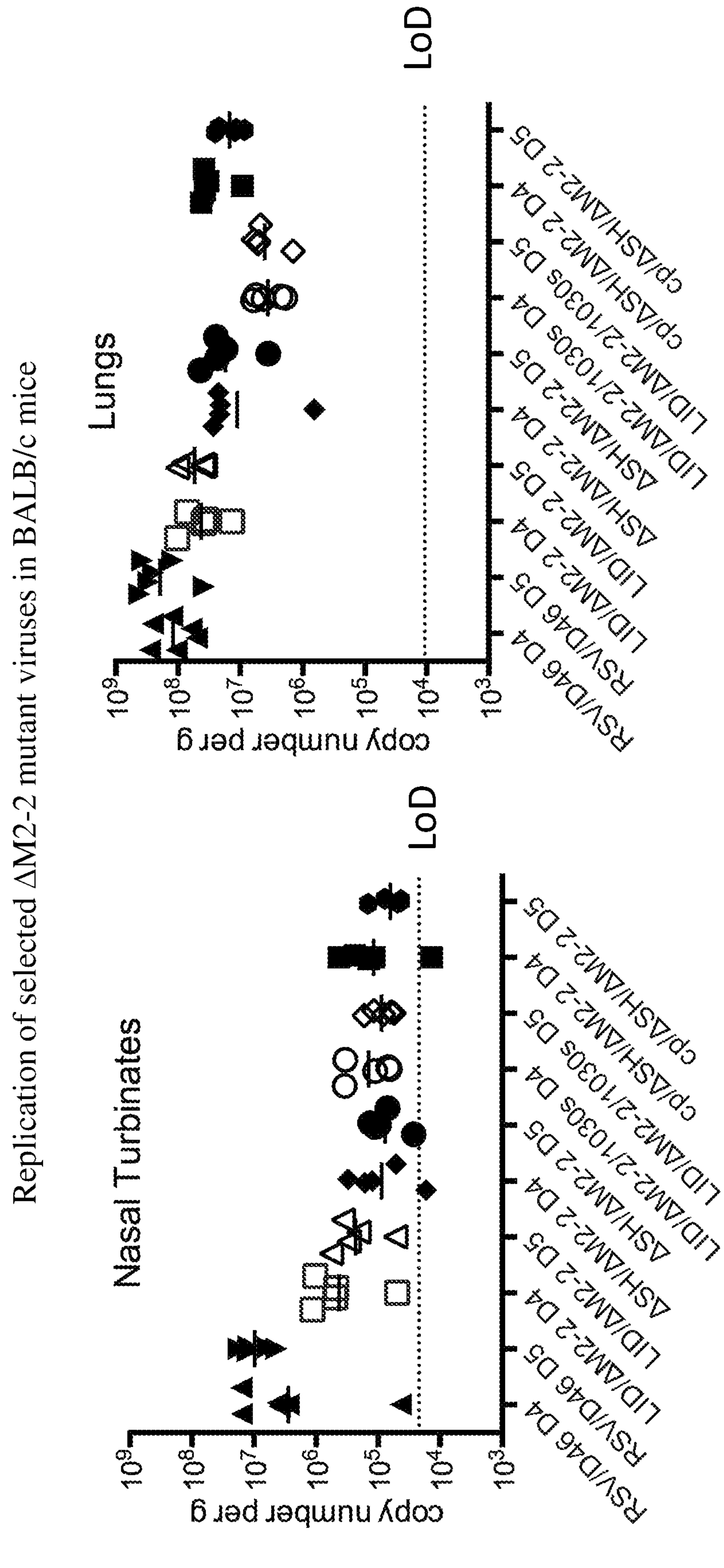
FIG. 7. Replication of exemplary recombinant RSV in BALB/c mice. Results for replication of RSV D46 (the recombinant wt parent), RSV LID/ΔM2-2, RSV ΔSH/ΔM2-2, RSV LID/ΔM2-2/1030s, and RSV cp/ΔSH/ΔM2-2 in the respiratory tract of BALB/c mice, with replication in the nasal turbinates and lungs evaluated by RT-qPCR, is shown. Mice in groups of 10 (or 12 for RSV D46) were inoculated by the intranasal (IN) route with 5.8 $\log_{10}$ PFU of the indicated virus in 0.1 ml. Five mice per virus (or six for RSV D46) were sacrificed on days 4 and 5 (D4, D5), and nasal turbinates and lungs were removed, homogenized, and evaluated by RT-qPCR specific to the RSV M gene, with copy number determined relative to a cloned M cDNA evaluated in parallel. LoD: limit of detection.

Representative viruses of the disclosure were evaluated for replication in the respiratory tract of BALB/c mice, namely: RSV D46 wt, RSV LID/ΔM2-2, RSV ΔSH/ΔM2-2, RSV LID/ΔM2-2/1030s, and RSV cp/ΔSH/ΔM2-2 (FIG. 7). Animals were inoculated intranasally with 5.8 login of the indicated virus and sacrificed on days 4 and 5 post-inoculation, and nasal turbinates and lungs were harvested, homogenized, and evaluated by RT-qPCR, which provides for more sensitive detection than assaying for infectious particles and thus is useful for this semi-permissive experimental animal. This showed that all of the viruses containing attenuating mutations were more restricted than the wt D46 virus. Thus, the further addition of the various attenuating mutations was further attenuating, although the level of replication in this semi-permissive rodent model was so restricted that detailed comparisons were not feasible (FIG. 7).

Figure 8A:
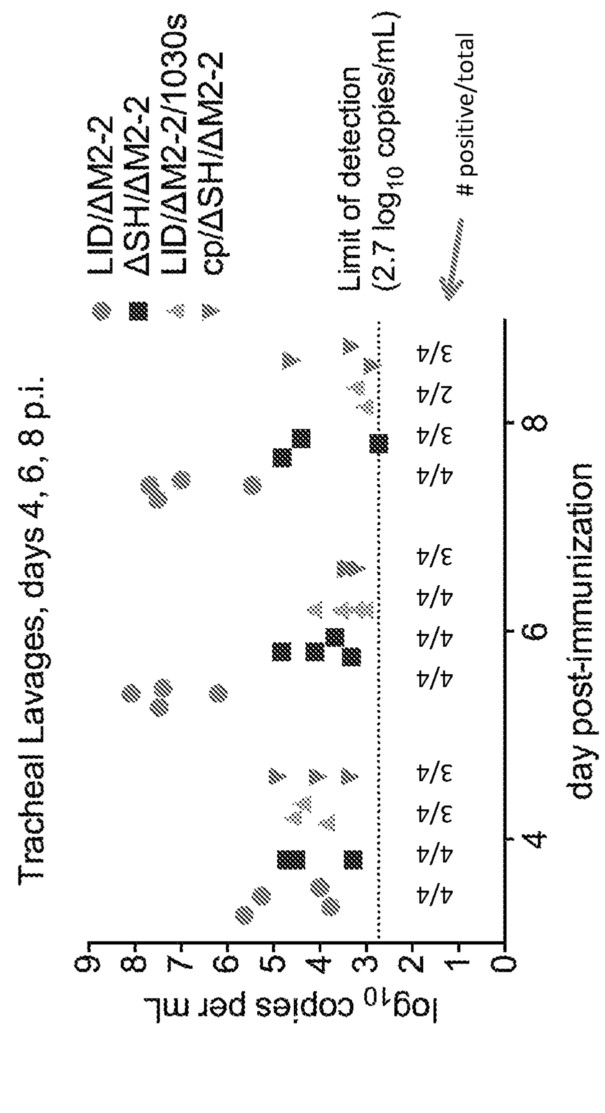
FIGS. 8A and 8B. Replication of exemplary RSV recombinant viruses in the respiratory tract of African green monkeys (AGMs). Replication data of RSV LID/ΔM2-2, RSV ΔSH/ΔM2-2, RSV LID/ΔM2-2/1030s, and RSV cp/4SH/ΔM2-2 in the respiratory tract of AGMs with shedding evaluated by RT-qPCR, is shown. AGMs in groups of 4 were inoculated by the combined IN and intratracheal (IT) routes with (per site) 6.0 $\log_{10}$ PHI of the indicated virus in 1.0 ml. Nasopharyngeal (NP) swabs and tracheal lavages from the indicated days were evaluated by RT-qPCR specific to the RSV M gene, with copy number determined based on a cloned M cDNA evaluated in parallel. Graphed results are from the assays described in Example 2, Tables 1 and 2.
Figure 8B:
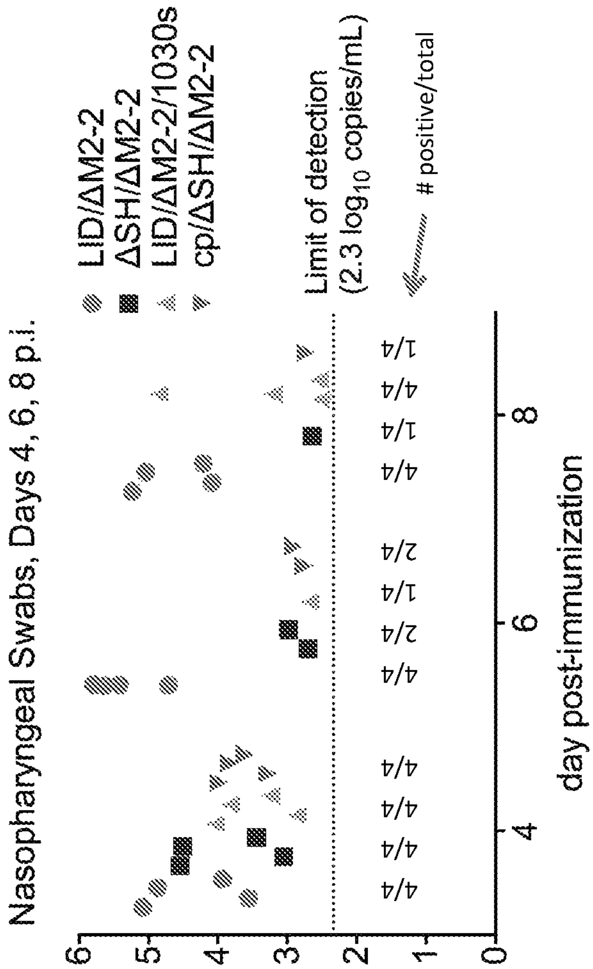

The same four ΔM2-2-containing viruses were investigated for replication in the respiratory tract of AGMs, namely: RSV LID/ΔM2-2, RSV 4SH/ΔM2-2, RSV LID/ΔM2-2/1030s, and RSV cp/4SH/ΔM2-2 (FIGS. 8A and 8B, Tables 1-3). The AGM is a more authentic model for RSV replication than are rodents because of its closer phylogenetic and anatomical relatedness to the natural human host for RSV. In addition, AGMs support somewhat-higher levels of RSV replication compared to rhesus macaques and cynomolgous monkeys, and therefore appear to be the most suitable available monkey model. However, AGMs are nonetheless only semi-permissive for RSV replication, and the level of RSV replication in AGMs is substantially less than in chimpanzees or humans. AGMs in groups of four were inoculated by the combined IN and IT routes with 6 $\log_{10}$ PFU per ml per each of the two sites (IN and IT). NP swabs were taken daily on days 1-10 and 12, and tracheal lavages were taken on days 2, 4, 6, 8, 10, and 12 (Tables 1 and 2). This showed that all three viruses that contained one or more additional attenuating mutations were more attenuated than RSV LID/ΔM2-2. In particular, the RSV ΔM2-2/1030s virus appeared to be the most attenuated. All three of these viruses induced titers of RSV-neutralizing serum antibodies that were approximately 2-fold (RSV 4SH/ΔM2-2 and RSV cp4SH/ΔM2-2) or 4-fold (RSV LID/ΔM2-2/41030s) less than that of RSV LID/ΔM2-2 (Table 3), consistent with the general expectation that a decreased level of replication and resulting decreased antigenic load can be associated with decreased immunogenicity, and thus care should be taken to identify an RSV vaccine candidate that is well-tolerated but is sufficiently immunogenic.

TABLE 1

Viral titers of nasopharyngeal swab samples from AGMs inoculated with RSV LID/ΔM2-2, RSV ΔSH/ΔM2-2, RSV LID/ΔM2-2/1030s, or RSV cp/ΔSH/ΔM2-2[a].

| RSV Vaccine candidate | AGM ID | NP virus titer ($\log_{10}$ PFU/mL) on indicated days[b] 1 | 2 | 3 | 4 | 5 | 6 | 7 | 8 | 9 | 10 | 12 | Duration of shedding[c] | Peak virus titer | Sum of daily titers[d] |
|---|---|---|---|---|---|---|---|---|---|---|---|---|---|---|---|
| RSV LID/ ΔM2-2 | 7806 | — | 1.4 | 1.7 | 2.7 | 2.6 | 4.0 | 3.9 | 1.4 | — | 2.7 | — | 9 | 4.0 | 21.4 |
| | 7705 | — | — | — | 2.7 | 2.3 | 3.6 | 2.4 | 1.2 | — | — | — | 5 | 3.6 | 14.3 |
| | 7747 | — | — | 1.3 | 0.7 | — | 1.5 | 1.3 | — | — | — | — | 5 | 1.5 | 7.2 |
| | 7674 | — | 0.7 | — | — | — | 2.3 | 1.8 | 1.5 | — | — | — | 7 | 2.3 | 8.8 |
| | | | | | | Mean: | | | | | | | 6.5 | 2.9 | 12.9 |
| RSV ΔSH/ ΔM2-2 | 7811 | — | — | — | — | — | — | — | — | — | — | — | 0 | 0.35 | 3.9 |
| | 7796 | — | — | — | — | 1.4 | — | — | — | — | — | — | 1 | 1.4 | 4.9 |

TABLE 1-continued

Viral titers of nasopharyngeal swab samples from AGMs inoculated with RSV LID/ΔM2-2, RSV ΔSH/ΔM2-2, RSV LID/ΔM2-2/1030s, or RSV cp/ΔSH/ΔM2-2[a].

| RSV Vaccine candidate | AGM ID | NP virus titer ($log_{10}$ PFU/mL) on indicated days[b] 1 | 2 | 3 | 4 | 5 | 6 | 7 | 8 | 9 | 10 | 12 | Duration of shedding[c] | Peak virus titer | Sum of daily titers[d] |
|---|---|---|---|---|---|---|---|---|---|---|---|---|---|---|---|
| | 7789 | — | — | — | — | — | — | — | — | — | — | — | 0 | 0.35 | 3.9 |
| | 7808 | — | — | — | — | — | — | — | — | — | — | — | 0 | 0.35 | 3.9 |
| | | | | | | Mean: | | | | | | | 0.3 | 0.6 | 4.1 |
| RSV LID/ΔM2-2/1030s | 8033 | — | — | — | — | — | — | — | — | — | — | — | 0 | 0.35 | 3.9 |
| | 7720 | — | — | — | — | — | — | — | — | — | — | — | 0 | 0.35 | 3.9 |
| | 7844 | — | — | — | — | — | — | — | — | — | — | — | 0 | 0.35 | 3.9 |
| | 7847 | — | — | — | — | — | — | — | — | — | — | — | 0 | 0.35 | 3.9 |
| | | | | | | Mean: | | | | | | | 0 | 0.35 | 3.9 |
| RSV cp/ΔSH/ΔM2-2 | 8008 | — | — | — | — | — | — | — | — | — | — | — | 0 | 0.35 | 3.9 |
| | 7741 | — | — | — | 1.2 | 1.0 | — | 0.7 | — | 1.2 | — | — | 6 | 1.2 | 6.6 |
| | 7765 | — | — | — | — | — | — | — | — | — | — | — | 0 | 0.35 | 3.9 |
| | 7637 | — | — | — | — | — | — | — | — | — | — | — | 0 | 0.35 | 3.9 |
| | | | | | | Mean: | | | | | | | 1.5 | 0.6 | 4.5 |

[a]AGMs were inoculated by the combined intranasal and intratracheal routes with 6.0 $log_{10}$ PFU of the indicated virus in a 1 mL inoculum per site (total dose: 6.3 $log_{10}$ PFU per animal).

[b]Combined NP swabs were placed in 2 mL of L-15 medium with sucrose phosphate buffer as stabilizer. Virus titrations were performed on Vero cells at 37° C. The lower limit of detection was 0.7 $log_{10}$ PFU/mL. Samples with no detectable virus are represented as "—". Peak titers for each animal are underlined.

[c]The period of days from the first to the last day on which virus was detected, including negative days (if any) in between.

[d]The sum of daily titers is used as an estimate for the magnitude of shedding (area under the curve). A value of 0.35 was used for samples with no detectable virus.

TABLE 2

Viral titers of tracheal lavage samples from AGMs inoculated with RSV LID/ΔM2-2, RSV ΔSH/ΔM2-2, RSV LID/ΔM2-2/1030s, or RSV cp/ΔSH/ΔM2-2[a].

| RSV vaccine candidate | AGM ID | Tracheal lavage virus titer ($log_{10}$ PFU/mL) on indicated days[b] 2 | 4 | 6 | 8 | 10 | 12 | Duration of shedding[c] | Peak virus titer | Sum of daily titers[d] |
|---|---|---|---|---|---|---|---|---|---|---|
| RSV LID/ΔM2-2 | 7806 | 2.5 | 3.4 | 4.6 | — | — | — | 7 | 4.6 | 12.6 |
| | 7705 | 1.6 | — | 3.3 | 1.5 | — | — | 9 | 3.3 | 8.5 |
| | 7747 | 1.8 | 1.0 | 6.0 | 2.3 | — | — | 9 | 6.0 | 12.5 |
| | 7674 | — | 1.3 | 2.7 | 2.3 | 1.0 | — | 9 | 2.7 | 8.7 |
| | | | Mean: | | | | | 9.0 | 4.2 | 10.6 |
| RSV ΔSH/ΔM2-2 | 7811 | — | — | — | — | 1.3 | — | 3 | 1.3 | 4.8 |
| | 7796 | — | — | — | — | — | — | 0 | 0.7 | 4.2 |
| | 7789 | — | — | — | — | — | — | 0 | 0.7 | 4.2 |
| | 7808 | — | 1.6 | — | — | — | — | 3 | 1.6 | 5.1 |
| | | | Mean: | | | | | 1.5 | 1.1 | 4.5 |
| RSV LID/ΔM2-2/1030s | 8033 | — | — | — | — | — | — | 0 | 0.7 | 4.2 |
| | 7720 | — | — | — | — | — | — | 0 | 0.7 | 4.2 |
| | 7844 | — | — | — | — | — | — | 0 | 0.7 | 4.2 |
| | 7847 | — | — | — | — | — | — | 0 | 0.7 | 4.2 |
| | | | Mean: | | | | | 0 | 0.7 | 4.2 |
| RSV cp/ΔSH/ΔM2-2 | 8008 | — | — | — | — | — | — | 0 | 0.7 | 4.2 |
| | 7741 | — | — | — | — | — | — | 0 | 0.7 | 4.2 |
| | 7765 | — | — | — | — | — | — | 0 | 0.7 | 4.2 |
| | 7637 | 1.0 | — | — | — | — | — | 3 | 1.0 | 4.5 |
| | | | Mean: | | | | | 0.8 | 0.8 | 4.3 |

[a]AGMs were inoculated by the combined intranasal and intratracheal routes with 6.0 $log_{10}$ PFU of the indicated virus in a 1 mL inoculum per site (total dose: 6.3 $log_{10}$ PFU per animal). The AGM study was approved by the Animal Care and Use Committee of NIAID, NIH.

[b]On days 2, 4, 6, 8, 10, and 12, tracheal lavage was performed with 3 mL of PBS. Virus titrations were performed on Vero cells at 37° C. The lower limit of detection was 1.0 $log_{10}$ PFU/mL of lavage solution. Samples with no detectable virus are represented as "—". Peak titers for each animal are underlined.

[c]The period of days from the first to the last day on which virus was detected, including negative days (if any) in between.

[d]The sum of daily titers is used as an estimate for the magnitude of shedding (area under the curve). A value of 0.7 was used for samples with no detectable virus.

TABLE 3

Neutralizing antibody titers of from AGMs inoculated with RSV LID/ΔM2-2, RSV ΔSH/ΔM2-2, RSV LID/ΔM2-2/1030s, or RSV cp/ΔSH/ΔM2-2[a]

| RSV Vaccine candidate | AGM ID | Neutralizing antibody titers ($PRNT_{60}$, reciprocal $log_2$) on indicated days[b] 0 | 21 | 28 |
|---|---|---|---|---|
| RSV LID/ΔM2-2 | 7806 | <3.3 | 7.2 | 7.2 |
| | 7705 | <3.3 | 8.8 | 8.2 |
| | 7747 | <3.3 | 8.3 | 8.4 |
| | 7674 | <3.3 | 6.7 | 6.2 |
| | Mean: | <3.3 | 7.8 | 7.5 |
| RSV ΔSH/ ΔM2-2 | 7811 | <3.3 | 6.9 | 5.9 |
| | 7796 | <3.3 | 7.2 | 7.1 |
| | 7789 | <3.3 | 6.5 | 5.8 |
| | 7808 | <3.3 | 7.1 | 7.2 |
| | Mean: | <3.3 | 6.9 | 6.5 |
| RSV LID/ ΔM2-2/1030s | 8033 | <3.3 | 5.4 | 6.6 |
| | 7720 | <3.3 | <3.3 | <3.3 |
| | 7844 | <3.3 | <3.3 | 4.3 |
| | 7847 | <3.3 | 6.8 | 6.8 |
| | Mean: | <3.3 | 4.7 | 5.2 |
| RSV cp/ΔSH/ ΔM2-2 | 8008 | <3.3 | 6.3 | 6.8 |
| | 7741 | <3.3 | 6.4 | 5.8 |
| | 7765 | <3.3 | 6.0 | 5.9 |
| | 7637 | <3.3 | 6.3 | 6.3 |
| | Mean: | <3.3 | 6.3 | 6.2 |

[a]AGMs were inoculated i.n. and i.t. with 6.0 $log_{10}$ of the indicated virus in a 1 mL inoculum per site (total dose = 6.3 $log_{10}$ PFU per animal).
[b]On days 0, 21, and 28 p.i., serum was obtained. Neutralizing antibody titers were determined in a 60% plaque reduction neutralization assay. The lower limit of detection was 3.3 (1:10).

Another experiment was performed in AGMs to compare RSV LID/ΔM2-2 with the following three viruses: D46/ΔM2-2, RSV D46/cp/ΔM2-2, D46/cp/ΔM2-2/HEK (Tables 4-6). This showed that the RSV LID/ΔM2-2 virus replicated substantially more efficiently in the upper (Table 4) and lower (Table 5) respiratory tracts than RSV D46/ΔM2-2. Importantly, since the only difference between these viruses was the 6120 mutation present in RSV LID/ΔM2-2, this showed that the 6120 mutation conferred increased replication in a primate host. It therefore provides a means to incrementally reduce the level of viral restriction and attenuation. Thus, the LID and D46 backbones provide a substantial difference in replication efficiency, such that the inclusion of additional mutations into either backbone can provide a range of attenuation phenotypes. RSV D46 viruses with additional mutations, namely RSV D46/cp/ΔM2-2/HEK and RSV D46/cp/ΔM2-2, had substantially reduced replication, indicative of increased attenuation. All of the viruses induced substantial titers of RSV-neutralizing serum antibodies (Table 6). RSV LID/ΔM2-2 induced the highest titers; the titers induced by RSV D46/ΔM2-2 and RSV D46/cp/ΔM2-2 were lower by less than 2-fold, and the titer induced by RSV D46/cp/ΔM2-2/HEK was almost 6-fold lower. This indicated that the inclusion of mutations specifying varying degrees of attenuation yielded a range of attenuation phenotypes. It also provided a further indication that reduced replication can result in reduced immunogenicity.

TABLE 4

Viral titers of nasopharyngeal swab samples from AGMs inoculated with D46/cp/ΔM2-2/HEK, D46/cp/ΔM2-2, D46/ΔM2-2, or RSV LID/ΔM2-2[a].

| RSV Vaccine candidate | AGM ID | NP virus titer ($log_{10}$ PFU/mL) on indicated days[b] 1 | 2 | 3 | 4 | 5 | 6 | 7 | 8 | 9 | 10 | 12 | Duration of shedding[c] | Peak virus titer | Sum of daily titers[d] |
|---|---|---|---|---|---|---|---|---|---|---|---|---|---|---|---|
| D46/cp/ ΔM2- 2/HEK | 8401 | — | — | — | — | 0.7 | — | — | — | — | — | — | 1 | 0.7 | 4.2 |
| | 8195 | — | — | — | — | — | — | — | 2.0 | — | 0.7 | — | 3 | 2.0 | 5.8 |
| | 7867 | — | — | — | — | — | — | — | — | — | — | — | 0 | 0.35 | 3.9 |
| | 8392 | — | — | — | 0.7 | 1.0 | 0.7 | — | — | — | — | — | 3 | 1.0 | 5.2 |
| | Mean: | | | | | | | | | | | | 1.8 | 1.0 | 4.8 |
| D46/cp/ ΔM2-2 | 57413 | — | — | — | — | — | — | — | 0.7 | — | — | — | 1 | 0.7 | 4.2 |
| | 8054 | — | — | — | — | 1.2 | — | — | — | — | — | — | 1 | 1.2 | 4.7 |
| | 8172 | — | — | — | — | — | — | — | — | — | — | — | 0 | 0.35 | 3.9 |
| | 8445 | — | — | — | — | — | — | — | 0.7 | — | — | — | 1 | 0.7 | 4.2 |
| | Mean: | | | | | | | | | | | | 0.8 | 0.7 | 4.2 |
| D46/ΔM2-2 | 8279 | — | — | — | — | — | — | 1.2 | 1.2 | — | — | — | 2 | 1.2 | 5.5 |
| | 32956 | — | — | — | — | — | — | — | — | — | — | — | 0 | 0.35 | 3.9 |
| | 8246 | — | — | — | — | — | — | — | — | — | — | — | 0 | 0.35 | 3.9 |
| | 7856 | — | — | — | — | — | — | 1.9 | — | — | — | — | 1 | 1.9 | 5.4 |
| | Mean: | | | | | | | | | | | | 0.8 | 1.0 | 4.7 |
| RSV LID/ ΔM2-2 | 62403 | — | 1.2 | 1.9 | 3.6 | 3.6 | 4.2 | 3.1 | 1.7 | — | — | — | 7 | 4.2 | 20.7 |
| | 8258 | — | 1.7 | 3.0 | 3.2 | 2.5 | 1.5 | 2.7 | 2.3 | 1.4 | — | — | 8 | 3.2 | 19.4 |
| | 8232 | — | 2.2 | 3.0 | 3.8 | 3.1 | 1.5 | 2.8 | 2.4 | 1.7 | — | — | 8 | 3.8 | 21.7 |
| | 582126 | 0.7 | 2.0 | 3.0 | 3.7 | 3.8 | 1.6 | 2.5 | 2.1 | 1.0 | — | — | 9 | 3.8 | 22.4 |
| | Mean: | | | | | | | | | | | | 8 | 3.7 | 21.0 |

[a]AGMs were inoculated by the combined intranasal and intratracheal routes with 6.7 $log_{10}$ PFU of the indicated virus in a 1 mL inoculum per site (total dose: 7.0 $log_{10}$ PFU per animal). The AGM study was approved by the Animal Care and Use Committee of NIAID, NIH.
[b]Combined NP swabs were placed in 2 mL of L-15 medium with sucrose phosphate buffer as stabilizer. Virus titrations were performed on Vero cells at 32° C. The lower limit of detection was 0.7 $log_{10}$ PFU/mL. Samples with no detectable virus are represented as "—". Peak titers for each animal are underlined.
[c]The period of days from the first to the last day on which virus was detected, including negative days (if any) in between.
[d]The sum of daily titers is used as an estimate for the magnitude of shedding (area under the curve). A value of 0.35 was used for samples with no detectable virus.

TABLE 5

Viral titers of tracheal lavage samples from AGMs inoculated with D46/cp/ΔM2-2/HEK, D46/cp/ΔM2-2, D46/ΔM2-2, or RSV LID/ΔM2-2[a].

| RSV vaccine candidate | AGM ID | Tracheal lavage virus titer ($log_{10}$ PFU/mL) on indicated days[b] 2 | 4 | 6 | 8 | 10 | 12 | Duration of shedding[c] | Peak virus titer | Sum of daily titers[d] |
|---|---|---|---|---|---|---|---|---|---|---|
| D46/cp/ | 8401 | 1.5 | — | — | — | — | — | 3 | 1.5 | 5.0 |
| ΔM2-2/HEK | 8195 | 1.3 | — | — | 1.7 | — | — | 9 | 1.7 | 5.8 |
| | 7867 | — | — | 1.0 | 1.0 | — | — | 5 | 1.0 | 4.8 |
| | 8392 | 1.5 | — | 1.0 | 1.3 | — | — | 9 | 1.5 | 5.6 |
| | | | Mean: | | | | | 6.5 | 1.4 | 5.3 |
| D46/cp/ | 57413 | 1.0 | — | — | — | — | — | 3 | 1.0 | 4.5 |
| ΔM2-2 | 8054 | — | — | 1.0 | — | — | — | 3 | 1.0 | 4.5 |
| | 8172 | 1.6 | — | — | — | — | — | 3 | 1.6 | 5.1 |
| | 8445 | — | 1.6 | 2.2 | — | — | — | 5 | 2.2 | 6.6 |
| | | | Mean: | | | | | 3.5 | 1.5 | 5.4 |
| D46/ΔM2-2 | 8279 | — | — | — | — | — | — | 0 | 0.7 | 4.2 |
| | 32956 | 1.7 | 1.8 | — | — | — | — | 5 | 1.8 | 6.3 |
| | 8246 | 1.0 | — | 1.6 | — | — | — | 7 | 1.6 | 5.4 |
| | 7856 | — | — | — | — | 1.0 | — | 3 | 1.0 | 4.5 |
| | | | Mean: | | | | | 3.8 | 1.3 | 5.1 |
| RSV LID/ | 62403 | 1.0 | 3.5 | 3.9 | 1.0 | — | — | 7 | 3.9 | 10.5 |
| ΔM2-2 | 8258 | 1.0 | 1.7 | 1.0 | 2.9 | 1.8 | — | 9 | 2.9 | 8.8 |
| | 8232 | 1.6 | 4.2 | 3.1 | 2.7 | — | — | 9 | 4.2 | 12.9 |
| | 582126 | 1.6 | 2.4 | 2.5 | 2.8 | — | — | 9 | 2.8 | 10.7 |
| | | | Mean: | | | | | 8.5 | 3.5 | 10.7 |

[a]AGMs were inoculated by the combined intranasal and intratracheal routes with 6.7 $log_{10}$ PFU of the indicated virus in a 1 mL inoculum per site (total dose: 7.0 $log_{10}$ PFU per animal).
[b]On days 2, 4, 6, 8, 10, and 12, tracheal lavage was performed with 3 mL of PBS. Virus titrations were performed on Vero cells at 32° C. The lower limit of detection was 1.0 $log_{10}$ PFU/mL of lavage solution. Samples with no detectable virus are represented as "—". Peak titers for each animal are underlined.
[c]The period of days from the first to the last day on which virus was detected, including negative days (if any) in between.
[d]The sum of daily titers is used as an estimate for the magnitude of shedding (area under the curve). A value of 0.7 was used for samples with no detectable virus.

TABLE 6

Neutralizing Antibody Titers of AGMs inoculated with D46/cp/ΔM2-2/HEK, D46/cp/ΔM2-2, D46/ΔM2-2, or RSV LID/ΔM2-2[a].

| RSV Vaccine candidate | AGM ID | Neutralizing antibody titers ($PRNT_{60}$, reciprocal $log_2$) on indicated days[b] 0 | 14 | 21 | 28 |
|---|---|---|---|---|---|
| D46/cp/ | 8401 | <3.3 | <5.3 | 5.3 | 6.3 |
| ΔM2-2/HEK | 8195 | <3.3 | <5.3 | 6.9 | 7.1 |
| | 7867 | <3.3 | <5.3 | 7.1 | 7.4 |
| | 8392 | <3.3 | <5.3 | 5.3 | 5.9 |
| | Mean: | <3.3 | <5.3 | 6.2 | 6.7 |
| D46/cp/ | 57413 | <3.3 | 5.8 | 6.8 | 7.9 |
| ΔM2-2 | 8054 | <3.3 | 7.3 | 9.9 | 10.6 |
| | 8172 | <3.3 | <5.3 | 8.0 | 8.6 |
| | 8445 | <3.3 | 6.0 | 7.7 | 8.0 |
| | Mean: | <3.3 | 6.1 | 8.1 | 8.8 |
| D46/ΔM2-2 | 8279 | <3.3 | <5.3 | 8.3 | 7.9 |
| | 32956 | <3.3 | 6.1 | 8.6 | 8.1 |
| | 8246 | <3.3 | 5.8 | 8.4 | 8.6 |
| | 7856 | <3.3 | 5.6 | 8.2 | 9.1 |
| | Mean: | <3.3 | 5.7 | 8.4 | 8.4 |
| RSV LID/ | 62403 | <3.3 | 5.9 | 7.8 | 8.7 |
| ΔM2-2 | 8258 | <3.3 | <5.3 | 7.6 | 8.8 |
| | 8232 | <3.3 | 7.8 | 8.7 | 9.0 |
| | 582126 | <3.3 | 8.2 | 9.4 | 10.2 |
| | Mean: | <3.3 | 6.8 | 8.4 | 9.2 |

[a]AGMs were inoculated i.n. and i.t. with 6.7 $log_{10}$ PFU of the indicated virus in a 1 mL inoculum per site (total dose = 7.0 $log_{10}$ PFU per animal).
[b]On days 0, 21, and 28 p.i., serum was obtained. Neutralizing antibody titers were determined in a 60% plaque reduction neutralization assay. The lower limit of detection was 3.3 (1:10).

Example 3

This example describes the clinical evaluation of RSV MEDI/ΔM2-2 virus.

Another RSV mutant with modified M2-2 designated as RSV MEDI/ΔM2-2 was previously described (Jin, et al. 2000. J Virol 74:74-82). The RSV MEDI/ΔM2-2 virus was made by introducing HindIII sites at nucleotide positions 8197-8201 and 8431-8436 in the antigenomic cDNA, followed by HindIII restriction digestion and ligation to delete the intervening 234 nucleotides from the M2-2 ORF (Jin, et al. 2000. J Virol 74:74-82). Thus, the RSV MEDI/ΔM2-2 virus does not contain the "ΔM2-2" mutation as described herein (see, for example, FIG. 1). This virus was not derived from D46 (which was developed from preparations of the RSV A2 strains by Collins and colleagues (Collins et al. Proc Natl Acad Sci USA 1995 92:11563-11567); instead it was derived from a different preparation of the RSV A2 strain (Example 5 below describes the differences between these backbones). Clinical trial material (CTM) of RSV MEDI/ΔM2-2 suitable for human evaluation as a live attenuated intranasal vaccine was manufactured. The nucleotide sequence of the RSV MEDI/ΔM2-2 CTM was determined and was found to be identical to that of its cDNA clone of origin except for dimorphisms (mixtures of two different nucleotide assignments) at three sequence positions: (i) nucleotide 285, in the NS1 gene, was a mixture of A/G in the CTM compared to A in the cDNA, resulting in a mixture of amino acid assignments S/G in the CTM compared to S in the cDNA; (ii) nucleotide 900, in the NS2 gene, was a mixture of C/T, compared to C in the cDNA, with no effect on amino acid coding; and (iii) nucleotide 4311, in the SH gene, was a mixture of T/G in the CTM compared to T in the cDNA, resulting in a mixture of amino acid assignments N/K in the CTM, compared to N in the cDNA. It is common to find polymorphisms in an RNA virus and, since the CTM had a high level of infectivity (determined by plaque assay), did not exhibit dimorphism in plaque phenotype, and replicated efficiently in vitro, these were deemed likely to be inconsequential. Sequence evaluation of virus shed from experimental animals and clinical subjects may be conducted to determine whether any of these sequence differences was favored in vivo, which will indicate whether any of them are significant. Sequence from one clinical vaccine isolate was obtained, and traces of dimorphisms were still present at all of indicated sites, showing that none of these changes was significant.

RSV MEDI/ΔM2-2 was evaluated as an intranasal vaccine candidate in phase 1 clinical studies successively in adults, RSV seropositive children, and RSV seronegative infants and children 6-24 months of age (ClinicalTrials.gov NCT01459198; Karron, et al. 2015. Science Transl Med 2015 7(312):312ra175). The adult study was open-label, and the studies in seropositive and seronegative infants and children were double-blind, randomized, and placebo-controlled. The study was performed at the Center for Immunization Research (CIR) at the Johns Hopkins University Bloomberg School of Public Health (JHU).

When evaluated in adults and RSV seropositive children, this experimental vaccine was very poorly infectious, very poorly immunogenic, and well-tolerated, as would be expected for an attenuated strain of RSV. In RSV-seronegative infants and young children, 20 vaccines received a single dose of 5.0 $\log_{10}$ PFU of the RSV MEDI/ΔM2-2 vaccine and 10 subjects received placebo. Rates of fever and cough were similar in vaccines versus placebo, whereas upper respiratory illness occurred twice as frequently in vaccines versus placebos (85% versus 44%), although this was not statistically different. There was frequent isolation of various adventitious respiratory viruses from both groups, which likely caused much of the illness and which confounded determination of vaccine tolerability in this particular study. The incidence of infection and disease by adventitious viruses can vary unpredictably between different studies, and in this case the incidence was unusually high and will necessitate further studies to assess the tolerability of RSV MEDI/ΔM2-2. The shedding of vaccine virus in nasal washes was detected by plaque assay in 12/20 recipients and by RT-qPCR in 17/20 recipients. The mean titer of shed virus in those children who shed infectious virus was 1.5 login PFU/ml (FIG. 9, left hand side). These findings raised the possibility that the vaccine might be overly restricted in replication, since studies generally aim at >90% shedding based on plaque assay, and a mean titer of infectious shed virus of approximately 2.5 $\log_{10}$ PFU/ml. With regard to antibody responses, 19/20 seronegative children had increases of ≥4-fold in RSV-neutralizing serum antibody titers, with a mean titer of 6.6 $\log_2$ (1:97). This suggested that the RSV MEDI/ΔM2-2 virus was substantially immunogenic. However, the observation that only 12/20 subjects shed infectious virus, combined with the low titers of shed vaccine virus, raised the possibility that the RSV MEDI/ΔM2-2 virus had suboptimal replication, and that a M2-2 mutant virus that replicated somewhat more efficiently might be more effective. This is a relevant issue because immune protection of the superficial epithelium of the respiratory tract, where RSV replicates and causes disease, is inefficient, and therefore it is desirable for an RSV vaccine to be as immunogenic as practicable.

Example 4

This example illustrates the clinical evaluation of RSV LID/ΔM2-2.

As noted above, comparison of RSV D46/ΔM2-2 and RSV LID/ΔM2-2 in AGMs indicated that the presence of the "6120" mutation in RSV LID/ΔM2-2 was associated with increased replication (Tables 4 and 5). Further comparison was made of the replication in AGMs of RSV LID/ΔM2-2 versus the CTM of RSV MEDI/ΔM2-2, in parallel with wt RSV (Tables 7-9). Analysis of the shedding of infectious virus in NP swabs (Table 7) or tracheal lavage specimens (Table 8) showed that both viruses were more attenuated than wt RSV evaluated in parallel. However, there was no evident difference in shedding, and hence replication, between RSV LID/ΔM2-2 and RSV MEDI/ΔM2-2. All three viruses (RSV LID/ΔM2-2, RSV MEDI/ΔM2-2, and wt RSV) induced similar titers of RSV-neutralizing serum antibodies (Table 9).

The RSV LID/ΔM2-2 virus was evaluated in a clinical study to determine whether it might replicate more efficiently in humans than RSV MEDI/ΔM2-2 and might be more immunogenic. A lot of CTM for RSV LID/ΔM2-2 suitable for human administration as an experimental intranasal RSV vaccine was manufactured. Nucleotide sequence analysis showed that the CTM had the same sequence as its cDNA clone, indicating an absence of detectable adventitious mutations during manufacture. Its replication efficiency in Vero cells (which are used for vaccine manufacture) was essentially the same as RSV MEDI/ΔM2-2. The RSV LID/ΔM2-2 CTM was evaluated in parallel with wt RSV for replication and immunogenicity in AGMs (Tables 10-12). Titration of infectious virus from NP swabs (Table 10) and tracheal lavage specimens (Table 11) confirmed the attenuated phenotype of the RSV LID/ΔM2-2 CTM. Nonetheless, the titer of RSV-neutralizing serum antibodies induced by the CTM was nearly the same as that induced by wt RSV (Table 12), indicating that this experimental vaccine retained much of the immunogenicity of its wt parent.

Figure 9A:
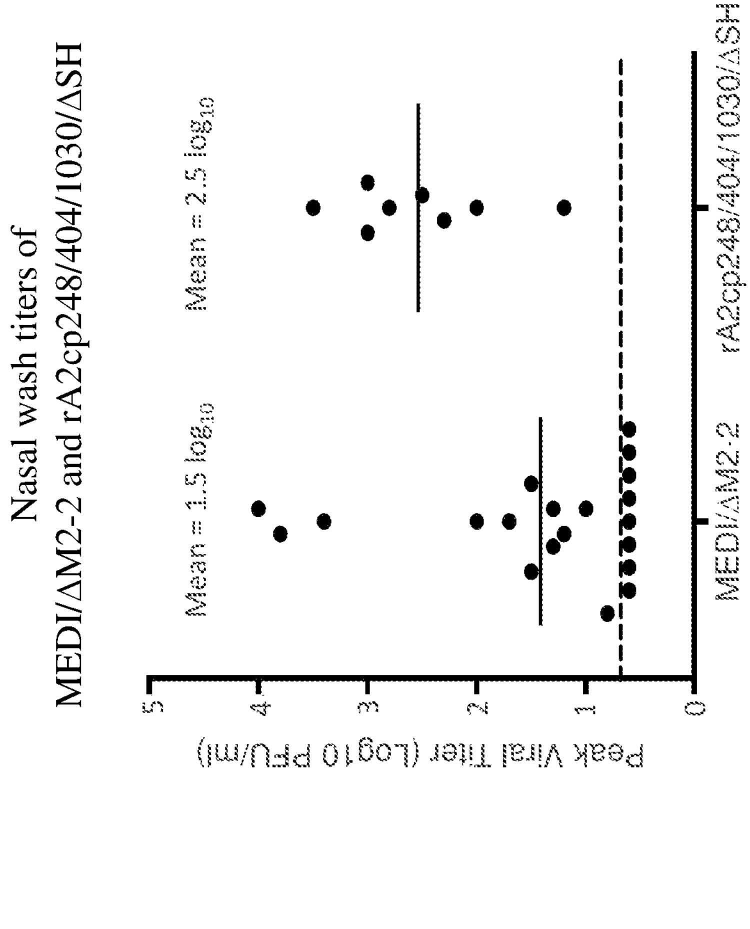
FIGS. 9A and 9B. Peak titers of exemplary recombinant RSV in seronegative infants and children. Peak titers of RSV MEDI/ΔM2-2 and RSV rA2cp248/404/1030ΔSH (FIG. 9A) or RSV LID/ΔM2-2 (FIG. 9B) in nasal washes of seronegative infants and children (6-24 months of age) following a single IN inoculation are shown. The results for RSV MEDI/ΔM2-2 and rA2cp248/404/1030ΔSH are from Karron, et al. 2015. Science Transl Med 2015 7(312):312ra175. Viral titers were determined by plaque titration of nasal wash specimens: specimens from the RSV MEDI/ΔM2-2 and RSV rA2cp248/404/1030ΔSH studies were assayed side-by-side, whereas specimens from the RSV LID/ΔM2-2 study were assayed separately. Symbols indicate peak values for individual subjects. The mean peak titers are shown. Vaccinees had each received a single IN dose of 5.0 $log_{10}$ PFU (RSV MEDI/ΔM2-2, RSV LID/ΔM2-2) or 5.3 $log_{10}$ PHI (RSV rA2cp248/404/1030ΔSH) vaccine virus. The original report of the rA2cp248/404/1030ΔSH vaccine candidate was Karron, et al. 2005. J Infect Dis 191:1093-1104.
Figure 9B:
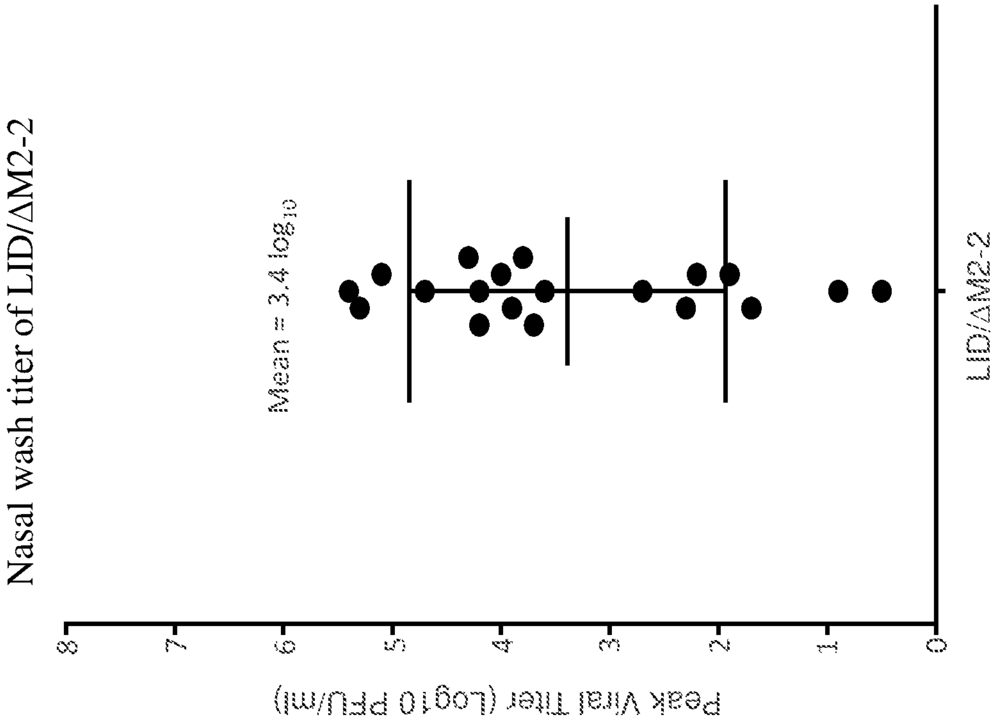

The RSV LID/ΔM2-2 CTM was evaluated in RSV-seronegative infants and children of 6-24 months of age in a double-blinded placebo-controlled study that was performed with CIR/JHU (ClinicalTrials.gov NCT02040831) and with seven clinical sites from the International Maternal Pediatric Adolescent AIDS Clinical Trials Network (IMPAACT, ClinicalTrials.gov NCT02237209). In total, 20 subjects received a single dose of 5.0 $\log_{10}$ PFU of vaccine, and nine received placebo. With respect to respiratory illness following vaccination, respiratory illnesses occurred frequently in both vaccines and placebo recipients. The rates of fever, otitis media, upper respiratory illness, lower respiratory illness, cough, or any respiratory or febrile illness were essentially the same between the two groups. Adventitious viruses, including rhinovirus, adenovirus, parainfluenza, and coronavirus, were detected frequently in both vaccines and placebo recipients. A single vaccinee experienced a brief episode of mild lower respiratory tract illness (rhonchi) on day 9 that resolved by day 11 and was coincident with shedding of vaccine virus as well as detection of rhinovirus and enterovirus as adventitious agents. Thus, causality of this clinical illness remains unclear. Infectious shed vaccine virus was recovered from 19/20 vaccines, with a mean peak titer of 3.4 $\log_{10}$ PFU/ml (FIG. 9B).

Thus, the RSV LID/ΔM2-2 virus was more infectious than RSV MEDI/ΔM2-2 in the human host based on the number of individuals shedding infectious virus (19/20 versus 12/20) and on the basis of the mean peak titer (3.4 $\log_{10}$ PFU/ml compared to 1.5 login PFU/ml, which was significantly different). The RSV LID/ΔM2-2 virus also replicated more efficiently than a previous lead candidate called rA2cp248/404/10304SH that had been evaluated in a previous clinical study (Karron, et al. 2005. J Infect Dis 191:1093-1104): a number of specimens from this previous study were analyzed side-by-side with specimens from the MEDI/ΔM2-2 study, showing that rA2cp248/404/10304SH had a mean peak titer of 2.5 $\log_{10}$ (FIG. 9A, right panel). The RSV LID/ΔM2-2 virus also induced a higher mean titer of RSV-neutralizing serum antibodies (1:137) compared to RSV MEDI/ΔM2-2 (1:97) and rA2cp248/404/10304SH (1:34) analyzed in parallel (Karron, et al. 2015. Science Transl Med 2015 7(312):312ra175).

The clinical study described above showed that the RSV LID/ΔM2-2 virus was more infectious and replicated more efficiently than RSV MEDI/ΔM2-2 in the human host. It also was more immunogenic. As noted, a difference in the efficiency of virus replication between these two viruses had not been demonstrated reproducibly in cell lines or in AGMs, and greater immunogenicity for LID/ΔM2-2 versus MEDI/ΔM2-2 in AGMs also had not been demonstrated. Thus, contrary to pre-clinical studies, RSV LID/ΔM2-2 provides a more replication-competent, more immunogenic alternative to RSV MEDI/ΔM2-2.

Additional derivatives of RSV LID/ΔM2-2 that possess one or more additional attenuating mutations were designed and constructed. Examples of these strains include: RSV LID/cp/ΔM2-2 (see Example 8), RSV LID/ΔSH/ΔM2-2, RSV LID/cp/4SH/ΔM2-2, and RSV LID/ΔM2-2/1030s. Based on the previous evaluation of the cp, ΔSH, 1030s, and ΔM2-2 mutations in seronegative chimpanzees, it is expected that the order of increasing attenuation of the present strains would be: RSV LID/cp/ΔM2-2≈RSV LID/ΔSH/ΔM2-2<RSV LID/cp/ΔSH/ΔM2-2<RSV LID/ΔM2-2/1030s. Additional strains are also provided, such as ones that include mutations described Examples 5-8.

TABLE 7

Titers of virus in Nasopharyngeal Swab Samples from AGMs Inoculated with RSV LID/ΔM2-2 or wt RSV rA2[a].

| RSV Vaccine candidate | AGM ID | NP virus titer ($\log_{10}$ PFU/mL) on indicated days[b]: 1 | 2 | 3 | 4 | 5 | 6 | 7 | 8 | 9 | 10 | 12 | Duration of shedding[c] | Peak virus titer | Sum of daily titers[d] |
|---|---|---|---|---|---|---|---|---|---|---|---|---|---|---|---|
| RSV LID/ | 7845 | — | — | — | — | 1.2 | 1.5 | 0.7 | — | — | — | — | 3 | 1.5 | 6.2 |
| ΔM2-2 | 7394 | — | — | 0.7 | — | 2.1 | 2.4 | 2.6 | 1.9 | — | — | — | 6 | 2.6 | 11.8 |
| | 7802 | — | — | — | — | — | — | — | — | — | — | — | 0 | 0.35 | 3.9 |
| | 7832 | — | — | — | — | — | 2.1 | — | — | — | 0.7 | — | 5 | 2.1 | 6.0 |
| | | | | | | Mean: | | | | | | | 3.5 | 1.6 | 7.0 |
| RSV MEDI | 7534 | — | — | — | — | — | — | 0.7 | — | — | — | — | 1 | 0.7 | 4.2 |
| ΔM2-2 | 7882 | — | — | 1.2 | 0.7 | 0.7 | 1.0 | 1.4 | 1.7 | 2.2 | 1.2 | — | 8 | 2.2 | 11.2 |
| | 7568 | — | — | — | — | 0.7 | — | — | — | — | — | — | 1 | 0.7 | 4.2 |
| | 7890 | — | — | 2.2 | 2.3 | 1.3 | — | 1.9 | 0.7 | — | — | — | 6 | 2.3 | 10.5 |
| | | | | | | Mean: | | | | | | | 4.0 | 1.5 | 7.5 |
| wt RSV | 7822 | — | — | 1.0 | 1.3 | 1.0 | 2.6 | 2.7 | 0.7 | — | 1.0 | — | 8 | 2.7 | 11.7 |
| rA2 | 7894 | — | 0.7 | 1.0 | 0.7 | 1.4 | 4.0 | 3.7 | 1.7 | 2.0 | 1.5 | 1.0 | 11 | 4.0 | 18.1 |
| | 7622 | — | — | 2.0 | 1.4 | 2.5 | 2.3 | — | 1.9 | 1.3 | — | — | 7 | 2.5 | 13.2 |
| | 7831 | — | — | — | 1.0 | — | — | — | — | 2.1 | — | — | 6 | 2.1 | 6.3 |
| | | | | | | Mean: | | | | | | | 8.0 | 2.9 | 12.3 |

[a]AGMs were inoculated by the combined intranasal and intratracheal routes with 6.0 $\log_{10}$ PFU of the indicated virus in a 1 mL inoculum per site (total dose: 6.3 $\log_{10}$ PFU per animal). The AGM study was approved by the Animal Care and Use Committee of NIAID, NIH.

[b]Combined NP swabs were placed in 2 mL of L-15 medium with sucrose phosphate buffer as stabilizer. Virus titrations were performed on Vero cells at 37° C. The lower limit of detection was 0.7 $\log_{10}$ PFU/mL. Samples with no detectable virus are represented as "—". Peak titers for each animal are underlined.

[c]The period of days from the first to the last day on which virus was detected, including negative days (if any) in between.

[d]The sum of daily titers is used as an estimate for the magnitude of shedding (area under the curve). A value of 0.35 was used for samples with no detectable virus

TABLE 8

Titers of Virus in Tracheal Lavage Samples from AGMs Inoculated with RSV LID/ΔM2-2 or wt RSV rA2[a].

| RSV vaccine candidate | AGM ID | Tracheal lavage virus titer ($\log_{10}$ PFU/mL) on indicated days[b] 2 | 4 | 6 | 8 | 10 | 12 | Duration of shedding[c] | Peak virus titer | Sum of daily titers[d] |
|---|---|---|---|---|---|---|---|---|---|---|
| RSV | 7845 | 1.0 | 1.9 | 2.2 | — | 1.3 | — | 11 | 2.2 | 7.7 |
| LID/ | 7394 | 1.6 | 2.5 | 2.6 | — | — | — | 7 | 2.6 | 9.0 |
| ΔM2-2 | 7802 | 2.0 | 1.5 | 2.3 | — | — | — | 7 | 2.3 | 7.9 |
| | 7832 | 1.0 | 2.8 | 4.1 | 3.3 | 2.6 | — | 11 | 4.1 | 14.6 |
| | | | | Mean: | | | | 9.0 | 2.8 | 9.8 |
| RSV | 7534 | 1.3 | 2.1 | 2.8 | 2.1 | — | — | 9 | 2.8 | 9.7 |
| MEDI | 7882 | 2.4 | 1.5 | 2.9 | 2.3 | — | — | 9 | 2.9 | 10.5 |
| ΔM2-2 | 7568 | — | 2.0 | 2.7 | 1.6 | — | — | 7 | 2.7 | 8.4 |
| | 7890 | 2.4 | 2.7 | 2.0 | 1.9 | 1.3 | — | 11 | 2.7 | 10.9 |
| | | | | Mean: | | | | 9.0 | 2.8 | 9.9 |
| wt RSV | 7822 | 2.5 | 2.5 | 4.7 | 2.6 | 1.3 | — | 11 | 4.7 | 14.2 |
| rA2 | 7894 | 3.3 | 2.9 | 4.0 | 3.5 | 2.0 | — | 11 | 4.0 | 16.4 |
| | 7622 | 2.3 | 2.8 | 4.3 | 2.0 | 1.0 | 1.0 | 13 | 4.3 | 13.5 |
| | 7831 | 2.0 | 3.8 | 4.3 | 4.2 | 2.5 | — | 11 | 4.3 | 17.4 |
| | | | | Mean: | | | | 11.5 | 4.3 | 15.4 |

[a]AGMs were inoculated by the combined intranasal and intratracheal routes with 6.0 $\log_{10}$ of the indicated virus in a 1 mL inoculum per site (total dose: 6.3 $\log_{10}$ PFU per animal).
[b]On Days 2, 4, 6, 8, 10, and 12, tracheal lavage was performed with 3 mL of PBS. Virus titrations were performed on Vero cells at 37° C. The lower limit of detection was 1.0 $\log_{10}$ PFU/mL of lavage solution. Samples with no detectable virus are represented as "—". Peak titers for each animal are underlined.
[c]The period of days from the first to the last day on which virus was detected, including negative days (if any) in between.
[d]The sum of daily titers is used as an estimate for the magnitude of shedding (area under the curve). A value of 0.7 was used for samples with no detectable virus.

TABLE 9

Neutralizing Antibody Titers of from AGMs inoculated with RSV LID/ΔM2-2 or WT RSV rA2[a].

| RSV Vaccine candidate | AGM ID | Neutralizing antibody titers ($PRNT_{60}$, reciprocal $\log_2$) on indicated days[b] 0 | 21 | 28 |
|---|---|---|---|---|
| RSV LID | 7845 | <3.3 | 3.3 | 6.7 |
| ΔM2-2 | 7394 | <3.3 | 5.8 | 6.1 |
| | 7802 | <3.3 | 8.9 | 9.7 |
| | 7832 | <3.3 | 6.1 | 6.2 |
| | Mean: | <3.3 | 6.0 | 7.2 |

TABLE 9-continued

Neutralizing Antibody Titers of from AGMs inoculated with RSV LID/ΔM2-2 or WT RSV rA2[a].

| RSV Vaccine candidate | AGM ID | Neutralizing antibody titers ($PRNT_{60}$, reciprocal $\log_2$) on indicated days[b] 0 | 21 | 28 |
|---|---|---|---|---|
| RSV MEDI | 7534 | <3.3 | 8.7 | 8.2 |
| ΔM2-2 | 7882 | <3.3 | 6.9 | 9.1 |
| | 7568 | <3.3 | 7 | 7.5 |
| | 7890 | <3.3 | 7.6 | 8.8 |
| | Mean: | <3.3 | 7.6 | 8.4 |
| wt RSV rA2 | 7822 | <3.3 | 8 | 8.4 |
| | 7894 | <3.3 | 7.8 | 7.7 |
| | 7622 | <3.3 | 6.9 | 8 |
| | 7831 | <3.3 | 5.7 | 6.1 |
| | Mean: | <3.3 | 7.1 | 7.6 |

[a]AGMs were inoculated i.n. and i.t. with 6.0 $\log_{10}$ PFU of the indicated virus in a 1 mL inoculum per site (total dose = 6.3 $\log_{10}$ PFU per animal).
[b]On Days 0, 21, and 28 p.i., serum was obtained. Neutralizing antibody titers were determined in a 60% plaque reduction neutralization assay. The lower limit of detection was 3.3 (1:10).

TABLE 10

Titers of virus in nasopharyngeal swab samples from AGMs inoculated with the CTM RSV LID/ΔM2-2, or with recombinant wt RSV rA2.

| Virus[a] | AGM ID | NP virus titer ($\log_{10}$ PFU/mL) on indicated days[b] 1 | 2 | 3 | 4 | 5 | 6 | 7 | 8 | 9 | 10 | 12 | Peak virus titer | Sum of daily titers[c] |
|---|---|---|---|---|---|---|---|---|---|---|---|---|---|---|
| RSV | 7728 | — | — | — | — | — | 0.7 | — | — | — | 1.2 | — | 1.2 | 5.0 |
| LID/ΔM2-2 | 7833 | — | — | 3.6 | 2.6 | 3.6 | 4.3 | 1.7 | — | 1.3 | — | — | 4.3 | 18.9 |
| | 7706 | — | — | — | 1.2 | 2.0 | 2.7 | 0.7 | — | 1.7 | — | — | 2.7 | 10.3 |
| | 7767 | — | — | — | — | 0.7 | — | — | — | — | 1.0 | — | 1.0 | 4.8 |
| | Mean: | | | | | | | | | | | | 2.3 | 9.8 |
| RSV rA2 | 7877 | — | — | 3.4 | 3.5 | 3.4 | 1.6 | 3.4 | 2.9 | 1.5 | — | — | 3.5 | 21.1 |
| wt RSV | 7885 | — | — | 2.3 | 3.8 | 3.3 | 3.1 | 2.9 | 2.3 | 1.7 | — | — | 3.8 | 20.9 |
| | 7758 | — | 0.7 | — | 0.7 | 0.7 | 2.1 | 2.2 | 2.7 | 1.5 | 1.0 | — | 2.7 | 12.6 |
| | 7724 | — | 1.4 | 2.2 | 2.8 | 2.1 | 3.4 | 3.0 | 2.4 | 3.1 | 2.0 | — | 3.4 | 23.2 |
| | Mean: | | | | | | | | | | | | 3.4 | 19.4 |

[a]Monkeys were inoculated i.n. and i.t. with 5.9 $\log_{10}$ PFU of the indicated virus in a 1 mL inoculum per site (total dose = 6.2 $\log_{10}$ PFU/AGM).
[b]Virus titrations were performed on Vero cells at 37° C. The lower limit of detection was 0.7 $\log_{10}$ PFU/mL. Samples with no detectable virus are represented as "—". Peak titers for each animal are underlined. The results show that RSV LID ΔM2-2 is strongly restricted in the URT of AGMs compared to RSV rA2.
[c]The sum of daily titers is used as an estimate for the magnitude of shedding (area under the curve). A value of 0.35 was used for samples with no detectable virus.

TABLE 11

Titers of virus in tracheal lavage samples from AGMs inoculated with the CTM RSV LID/ΔM2-2, or with recombinant wt RSV rA2.

| Virus Test Article[a] | AGM ID | TL virus titer ($\log_{10}$ PFU/mL) on indicated day[b] 2 | 4 | 6 | 8 | 10 | 12 | Peak virus titer | Sum of daily titers[c] |
|---|---|---|---|---|---|---|---|---|---|
| RSV LID ΔM2-2 | 7728 | 1.3 | — | 2.0 | — | — | — | 2.0 | 6.1 |
| | 7833 | 2.2 | 2.6 | 2.0 | 2.1 | — | — | 2.6 | 10.2 |

TABLE 11-continued

Titers of virus in tracheal lavage samples from AGMs inoculated with the CTM RSV LID/ΔM2-2, or with recombinant wt RSV rA2.

| Virus Test Article[a] | AGM ID | TL virus titer ($log_{10}$ PFU/mL) on indicated day[b] 2 | 4 | 6 | 8 | 10 | 12 | Peak virus titer | Sum of daily titers[c] |
|---|---|---|---|---|---|---|---|---|---|
| | 7706 | — | 2.5 | 2.7 | 1.7 | 1.3 | — | 2.7 | 9.6 |
| | 7767 | 1.0 | — | — | 2.6 | 2.0 | — | 2.6 | 7.7 |
| | Mean: | | | | | | | 2.5 | 8.4 |
| RSV rA2 | 7877 | 2.4 | 3.0 | 3.9 | 2.8 | 1.0 | — | 3.9 | 13.8 |
| wt RSV | 7885 | 1.8 | 2.9 | 3.5 | 3.0 | — | — | 3.5 | 12.6 |
| | 7758 | 1.9 | 2.9 | 3.7 | 3.9 | 1.3 | — | 3.9 | 14.5 |
| | 7724 | — | 2.3 | 2.7 | 3.5 | 4.1 | 2.1 | 4.1 | 15.4 |
| | Mean: | | | | | | | 3.8 | 14.1 |

[a]Monkeys were inoculated i.n. and i.t. with 5.9 $log_{10}$ PFU of the indicated virus in a 1 mL inoculum per site (total dose = 6.2 $log_{10}$ PFU/AGM).
[b]Virus titrations were performed on Vero cells at 32° C. The lower limit of detection was 1.0 $log_{10}$ PFU/mL. Samples with no detectable virus are represented as "—". Underlined value indicates maximum titer for each animal. As expected, the highly temperature sensitive virus RSV LID ΔM2-2 did not replicate in the LRT of AGMs (body temperature: 39° C.). TL, tracheal lavage.
[c]The sum of daily titers is used as an estimate for the magnitude of shedding (area under the curve). Values of 0.7 are used for samples with no detectable virus.

TABLE 12

Serum $PRNT_{60}$ antibody titers in AGMs inoculated with the CTM RSV LID/ΔM2-2 or with recombinant wt RSV rA2.

| Virus[a] | AGM ID | RSV Neutralization Titer ($Log_2$ of reciprocal) on days 0 | 21 | 28 |
|---|---|---|---|---|
| RSV LID/ | 7728 | — | 8.1 | 10.1 |
| ΔM2-2 | 7833 | — | 7.2 | 7.4 |
| | 7706 | — | 5.7 | 6.4 |
| | 7767 | — | 6.4 | 6.3 |
| | Mean: | — | 6.9 | 7.6 |
| RSV rA2 | 7877 | — | 8.6 | 8.5 |
| wt RSV | 7885 | — | 8.2 | 9.1 |
| | 7758 | — | 7.8 | 7.9 |
| | 7724 | — | 7.5 | 7.8 |
| | Mean: | | 8.0 | 8.3 |

[a] Monkeys were inoculated i.n. and i.t. with 5.9 $log_{10}$ PFU of the indicated virus in a 1 mL inoculum per site (total dose = 6.2 $log_{10}$ PFU/AGM).
[b]The lower limit of detection of the 60% Plaque Reduction assay is 3.3 ($Log_2$ of the dilution reciprocal). Samples below the lower limit of detection are recorded as "—".

Example 5

This example illustrates differences in RSV LID/ΔM2-2, RSV D46/ΔM2-2, and RSV MEDI/ΔM2-2 that may affect replication efficiency in vivo.

As noted above, the RSV D46/ΔM2-2 and RSV LID/ΔM2-2 viruses are identical by sequence except for the 6120 mutation in the SH gene of RSV LID/ΔM2-2, which removes 112 nucleotides from the downstream non-translated region and makes silent nucleotide changes in the last three codons and stop codon of the SH ORF (FIG. 3). RSV LID/ΔM2-2 replicated significantly more efficiently than RSV D46/ΔM2-2 in the upper (Table 4) and lower (Table 5) respiratory tract of AGMs. Since these viruses are otherwise identical, this showed that the 6120 mutation is associated with increased replication in primates, and the effect was sufficiently great to detect unequivocally in AGMs.

As noted above, the RSV LID/ΔM2-2 and RSV MEDI/ΔM2-2 viruses could not be distinguished with regard to replication efficiency in cell culture and in AGMs, yet the former was significantly more efficient in replication in seronegative infants and children and was more immunogenic. Thus, these viruses also differ in replicative efficiency, but this was only evident in the fully permissive human host. RSV LID/ΔM2-2 has the 6210 mutation while RSV MEDI/ΔM2-2 does not. Yet, in this case the 6120 mutation was not associated with increased replication in semi-permissive AGMs, but was associated with increased replication in seronegative infants and children, the permissive natural host. These observations suggest that, while RSV LID/ΔM2-2 clearly has greater replication efficiency than RSV MEDI/ΔM2-2, this may be somewhat reduced by some other difference between the LID and MEDI viruses. There are two such differences additional to the 6120 mutation:

One of the differences is that the details of the mutations that silence the M2-2 ORF are different between RSV LID/ΔM2-2 and RSV MEDI/ΔM2-2. In RSV LID/ΔM2-2 (and RSV D46/ΔM2-2), the deletion is 241-nt in length and begins after nucleotide 8187 and, in addition, all three ATG translational start codons are changed to ACG, such that there should be little or no translation of any M2-2-derived peptides (FIG. 1). In contrast, in RSV MEDI/ΔM2-2, the deletion mutation involved the insertion of a foreign HindIII restriction site beginning at nucleotide 8196, involved a deletion of 234 nt, and would encode a 12-amino acid peptide representing the N-terminus of the longest version of the M2-2 protein (Jin, et al. 2000. J Virol 74:74-82).

The second of the differences is that the RSV MEDI/ΔM2-2 and RSV LID/ΔM2-2 cDNAs differ at 21 additional nucleotide sequence positions scattered through the two backbones (Table 13). Of these, 6 nucleotide differences (including a 1-nucleotide insert at position 1099 of RSV LID/ΔM2-2) are due to restriction sites that were added during the construction of the D46 cDNA clone (Collins, et al. 1995. Proc Natl Acad Sci USA 92:11563-11567). These six changes are thought to be phenotypically silent because biological wt RSV and recombinant wt D46 RSV replicate with similar efficiencies in chimpanzees and cause a similar level of disease (e.g. Whitehead, et al. 1998. J Virol 72:4467-4471). These changes also are present in a number of vaccine candidates evaluated to date in humans. It therefore seems unlikely that these 6 nucleotides and their associated restriction sites influence replication, although this has not be unequivocally determined. The remaining 15 nucleotide differences between RSV MEDIAM2-2 and RSV LID/ΔM2-2 are point mutations that are thought to reflect adventitious differences present in the two different parent biologic virus stocks of strain A2 from which the two independent reverse genetics systems were derived. It is not uncommon to find numerous nucleotide differences between two preparations of the same RSV strain that have different passage histories. Two of these 15 nucleotide differences result in amino acid differences, one in the NS2 protein (K51R), and the other in the N protein (T24A) (amino acid assignments are given with LID first followed by MEDI). A recent study indicated that neither of these two amino acid differences had an affect on replication efficiency in vitro (Lawlor, Schickli, and Tang. 2013. J Gen Virol 94:2627-2635).

TABLE 13

Differences in genomic sequence (positive sense) between RSV MEDI/ΔM2-2 and RSV LID/ΔM2-2, in addition to the 6120 and ΔM2-2 mutations.

| | RSV Nucleotide | | | Amino Acid (Comment) | | |
|---|---|---|---|---|---|---|
| | | RSV | | | | |
| Gene Region | Genomic nucleotide position[1] | MEDI/ ΔM2-2 cDNA | RSV LID/ΔM2 cDNA | Amino Acid Position | RSV MEDI/ ΔM2-2 cDNA | RSV LID/ΔM2-2 cDNA |
| NS1 | 404 | C | T | 102 | N | N |
| NS2 | 779 | G | A | 51 | R | K |
| NS2/N ig | 1099 | T | C* | ncr[2] | n/a | (1-nt insert, creates AflII restriction site in RSV LID/ΔM2-2) |
| N | 1138 | A | C* | ncr[2] | n/a | (creates NcoI |
| N | 1139 | G | C* | ncr[2] | n/a | restriction site in RSV LID/ΔM2-2) |
| N | 1181 | G | A | 14 | K | K |
| N | 1209 | G | A | 24 | A | T |
| N | 1937 | A | G | 266 | S | S |
| G/F ig | 5611 | A | G* | ncr[2] | n/a | |
| G/F ig | 5615 | A | T* | ncr[2] | n/a | (creates StuI restriction site in RSV LID/ΔM2-2) |
| G/F ig | 5639 | G | A | ncr[2] | n/a | n/a |
| F | 6215 | C | T | 185 | V | V |
| F | 6221 | C | T | 187 | V | V |
| F | 6386 | T | C | 242 | G | G |
| F | 7214 | C | T | 518 | A | A |
| F | 7481 | T | C | ncr2 | n/a | n/a |
| F/M2 ig | 7559 | A | C* | ncr[2] | n/a | (creates SphI restriction site in RSV LID/ΔM2-2) |
| M2 | 7701 | G | C | 32 | P | P |
| L | 10514 | T | C | 673 | L | L |
| L | 13633 | A | C | 1712 | T | T |
| L | 13900 | T | C | 1801 | S | S |

[1]Genomic position numbered relative to WT RSV strain A2 (Genbank accession number M74568). All sequences are positive-sense.
[2]ncr, non-coding region
[4]ig, intergenic region
*Changes engineered as markers into the original LID antigenomic cDNA clone (Collins et al. PNAS 92: 11563-7 1995 PMID 8524804). These changes are present in most of the recombinant RSV vaccine candidates that have been evaluated in humans.

Thus, new reagents and information are provided that indicate that:

1. RSV LID/ΔM2-2 replicates substantially more efficiently in AGMs than RSV D46/ΔM2-2. Since these viruses differ only in the presence of the 6120 mutation in RSV LID/ΔM2-2, it is concluded that this mutation confers a phenotype of increased replication in primates, a difference that was detectable even in the semi-permissive AGM model. This substantial difference in replication efficiency between RSV LID/ΔM2-2 and RSV D46/ΔM2-2 provides two backbones that differ considerably in attenuation. Therefore, one can introduce a common set of attenuating mutations (e.g., cp, ΔSH, 1030s) into each backbone and obtain a broad spectrum of attenuation phenotypes that is directly linked to benchmark data in humans (i.e., the clinical study of RSV LID/ΔM2-2).

2. RSV LID/ΔM2-2 did not replicate more efficiently than RSV MEDI/ΔM2-2 in AGMs, but did so in the more permissive natural host, namely seronegative infants and children. This suggests that RSV LID/ΔM2-2 has a replication advantage versus RSV MEDI/ΔM2-2, but less than it has versus RSV D46/ΔM2-2. Thus, the order of replicative efficiency in humans for RSV LID/ΔM2-2 and RSV MEDI/ΔM2-2 is RSV LID/ΔM2-2>RSV MEDI/ΔM2-2, and the data from AGMs supports the further conclusion that RSV D46/ΔM2-2 is even more attenuated, giving the order of attenuation: RSV LID/ΔM2-2>RSV MEDI/ΔM2-2>D46/ΔM2-2. This suggests that one or more difference in RSV MEDI/ΔM2-2 versus the D46/LID backbones is responsible for its intermediate phenotype. The likeliest candidates are the K51R and T24A mutations in NS2 and N, respectively, despite the published data noted immediately above suggesting that they are phenotypically silent (Lawlor, Schickli, and Tang. 2013. J Gen Virol 94:2627-2635). These two amino acid substitutions are considered to be the most likely candidates because amino acid changes are more likely to affect phenotype through effects on protein structure and function—than are silent nucleotide signals not contained in a cis-acting signal. An alternative or additional possibility is that the difference in the details of the construction of the ΔM2-2 mutations plays a role. A further possibility is that one or more of the 19 other translationally silent nucleotide differences play a role. These possibilities can be distinguished using strains selected from panels described below.

Example 6

This example illustrates additional ΔM2-2 constructs with combinations of features from RSV LID/ΔM2-2, RSV D46/ΔM2-2, and RSV MEDI/ΔM2-2.

Additional ΔM2-2-based viruses were constructed using the above results as guidance to obtain different combinations containing one of several ΔM2-2 mutations, the 6120 mutation, the K51R/T24A mutations, and the other incidental differences between the MEDI and D46/LID backbones.

Figure 10A:
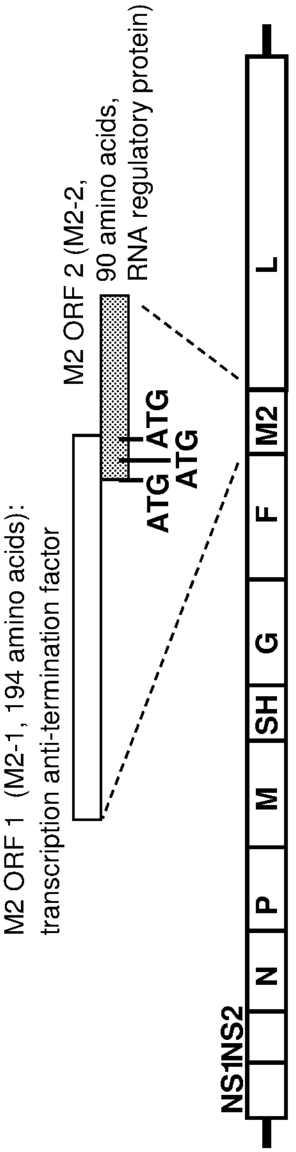
FIGS. 10A and 10B. The "ΔM2-2-AclI" and "ΔM2-2-HindIII" mutations to the RSV genome. The ΔM2-2-AclI mutation silences the M2-2 ORF by site directed mutagenesis to delete 234 nucleotides and introduce two point mutations creating an AclI restriction site and a translational termination site (TER). The ΔM2-2-HindIII mutation silences the M2-2 ORF by site directed mutagenesis to delete 234 nucleotides and introduce two point mutations creating a HindIII restriction site and a translational termination site (TER). Sequence numbering is according to the complete sequence of the wt human RSV strain A2 that is represented by GenBank accession number M74568.
Figure 10B:
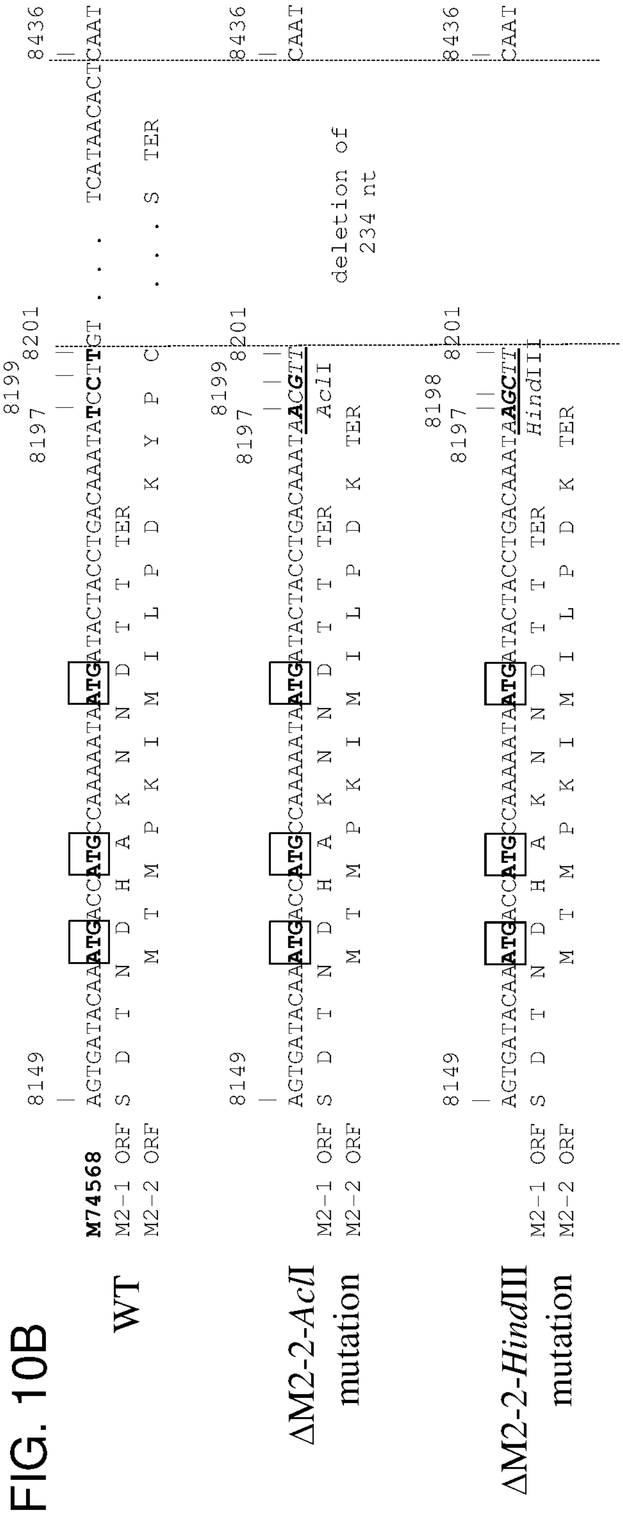
Figure 11:
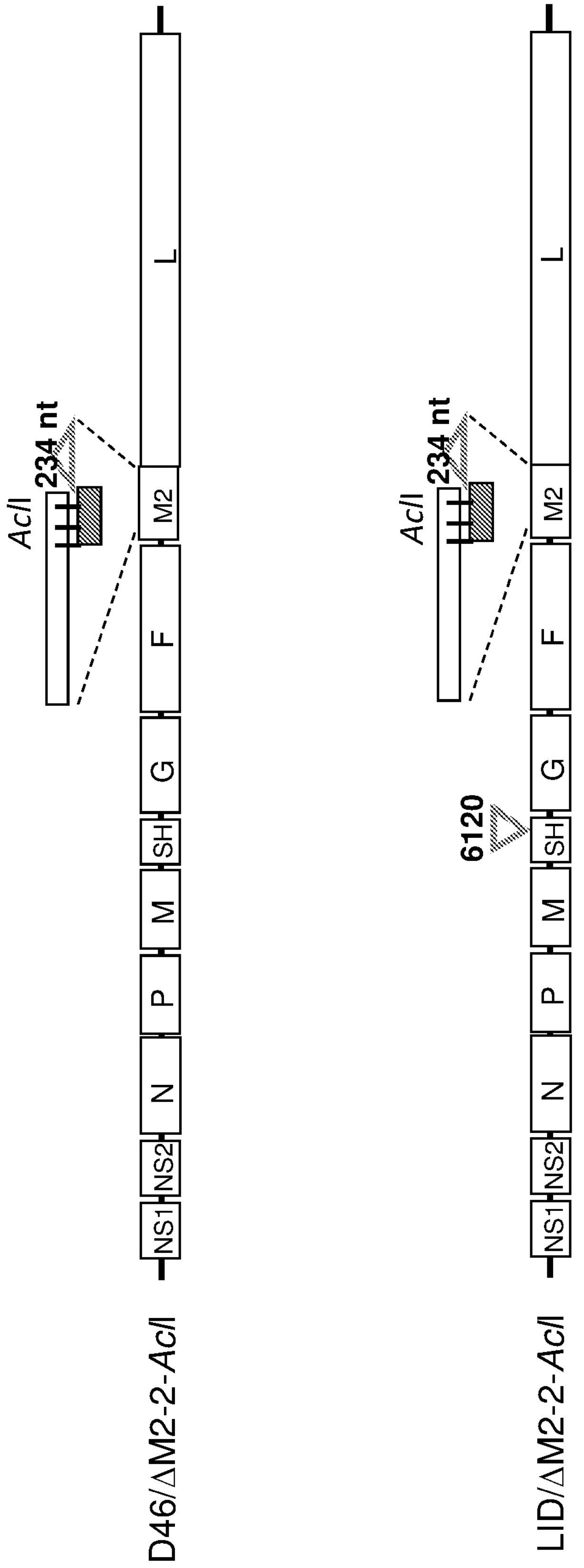
FIG. 11. Schematic diagrams of RSV D46 and LID genomes bearing the ΔM2-2-AclI mutation, termed D46/ΔM2-2-AclI and LID/ΔM2-2-AclI. Antigenomic cDNA sequences of these two constructs are denoted by SEQ ID NO: 3 and SEQ ID NO: 6 respectively.

An additional M2-2 deletion was created that is based on site-directed mutagenesis that deleted 234 nucleotides of the M2-2 ORF (nucleotides 8202-8435) and introduced T8197A and C8199G point mutations that created an AclI site and introduced a termination codon at codon 13 in the M2-2 ORF (FIG. 10). This modification was done to both the RSV D46 and RSV LID backbones, resulting in RSV D46/ΔM2-2-AclI and RSV LID/ΔM2-2-AclI (FIG. 11). These viruses combine the D46 or LID backbone (i.e., without and with the 6120 mutation, respectively, but otherwise identical) with a ΔM2-2 mutation (ΔM2-2-AclI) that resembles that of RSV MEDI/ΔM2-2, including the potential for expression of a peptide representing the 12 N-terminal amino acids of M2-2 (FIG. 11).

Figure 12A:
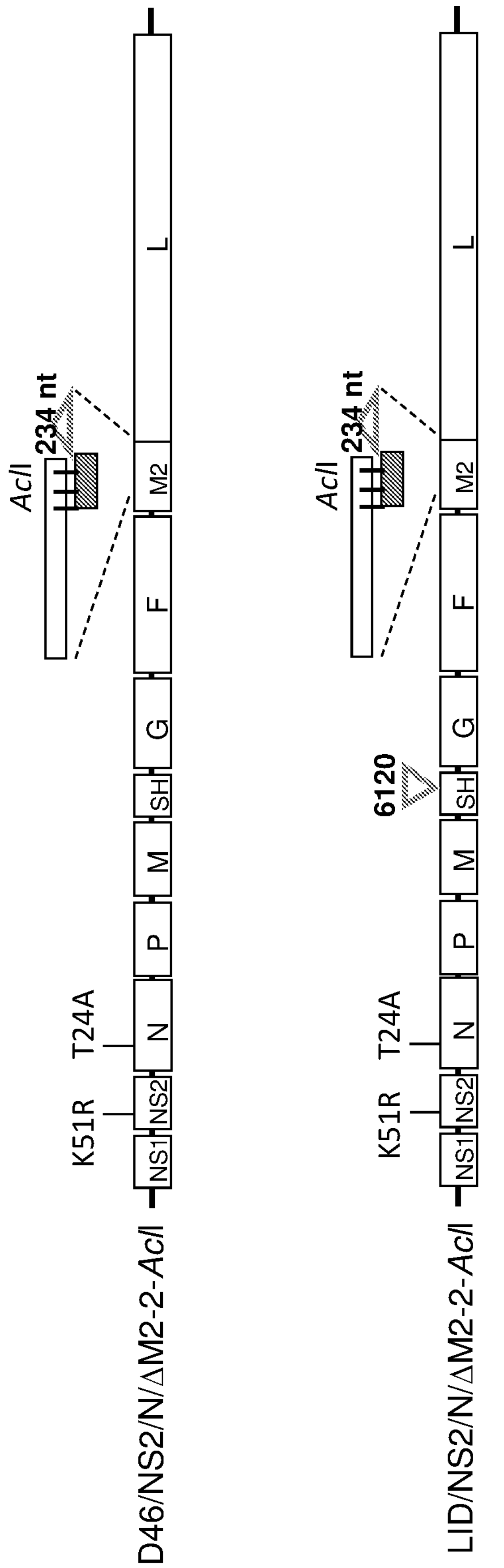
FIGS. 12A-12C. Schematic diagrams of genomes of examples of ΔM2-2 viruses into which the K51R (NS2 gene) and T24A (N gene) mutations have been introduced. In the viral names, K51R and T24A are abbreviated as "NS2" and "N", respectively.

The RSV D46/ΔM2-2-AclI and RSV LID/ΔM2-2-AclI cDNAs were further modified by inclusion of the K51R mutation in the NS2 protein and the T24A mutation in the N protein (FIG. 12A). Thus, this incorporated into the D46/ΔM2-2 and LID/ΔM2-2 backbones the two most prominent differences versus the MEDI backbone.

Figure 12B:
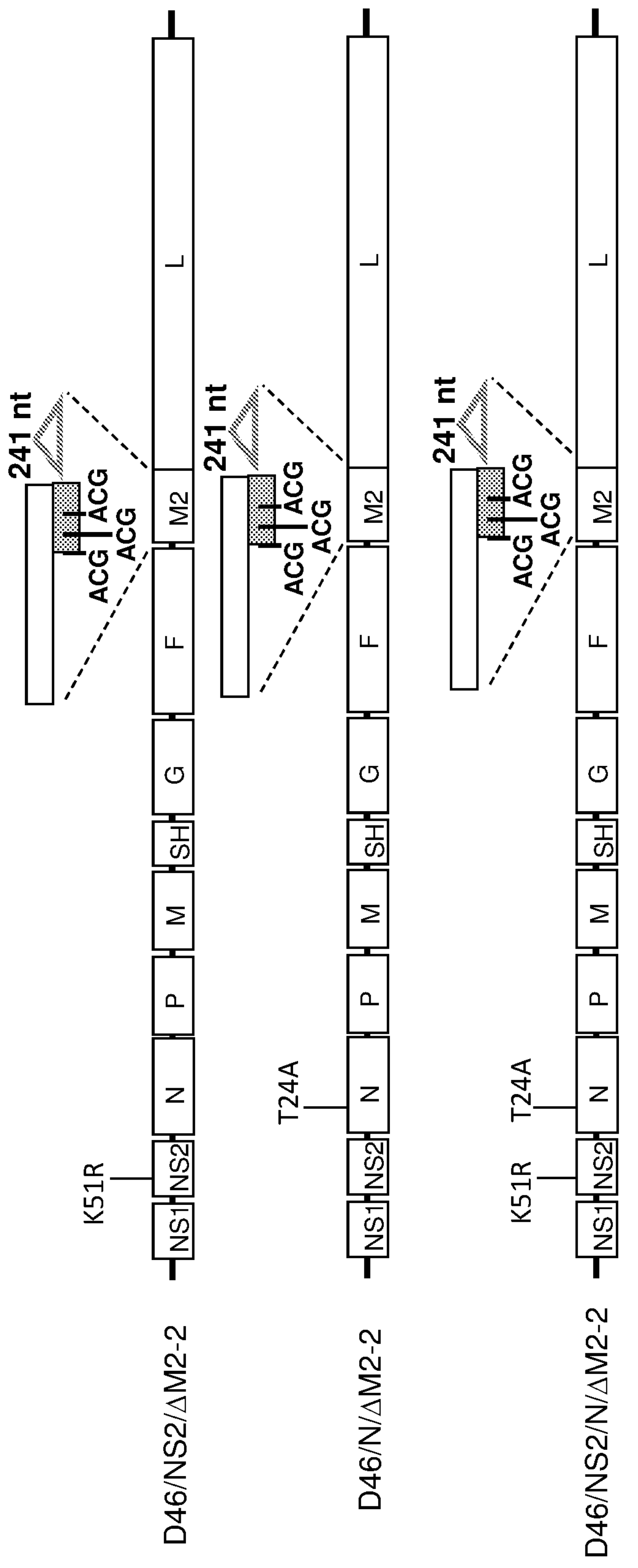
Figure 12C:
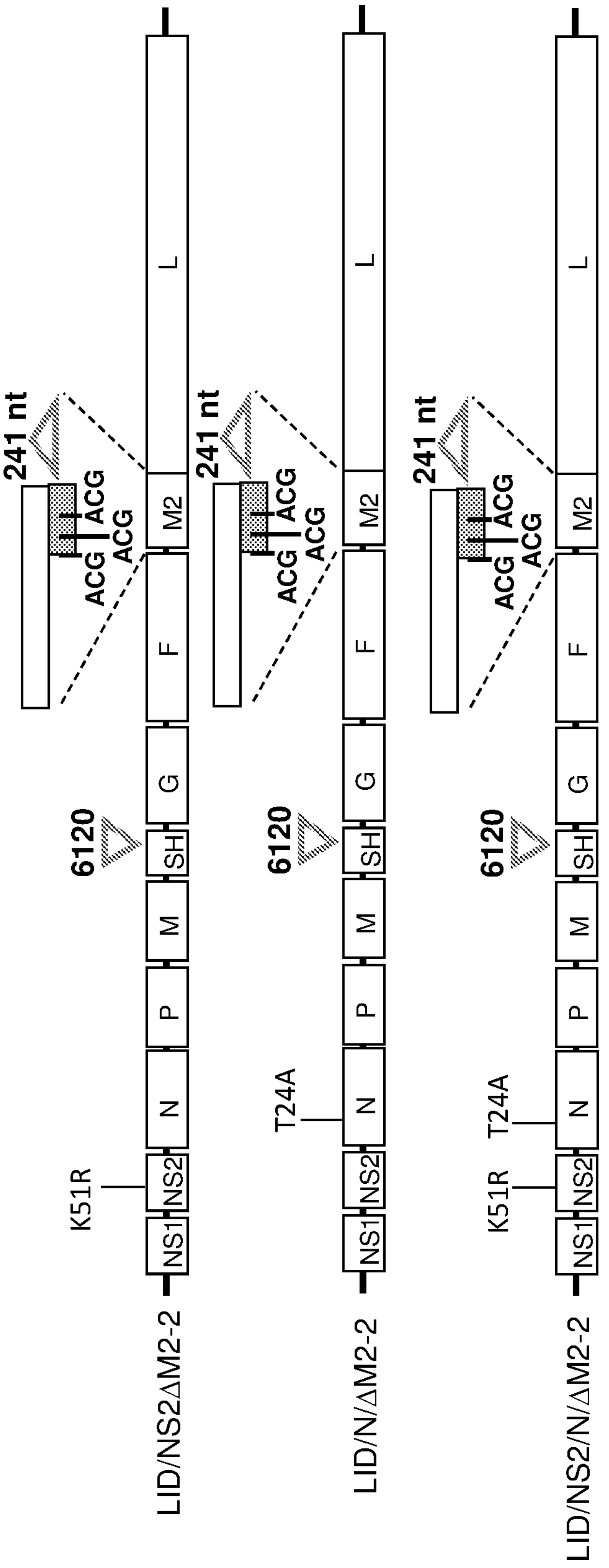

As further examples, the K51R mutation in the NS2 protein and the T24A mutation in the N protein also were introduced into the D46/ΔM2-2 backbone individually (FIG. 12B, first and second constructs from the top) and together (third construct). These mutations were also introduced into the LID/ΔM2-2 backbone (FIG. 12C) individually (fourth (under construction) and fifth constructs) and together (bottom construct).

Figure 13:
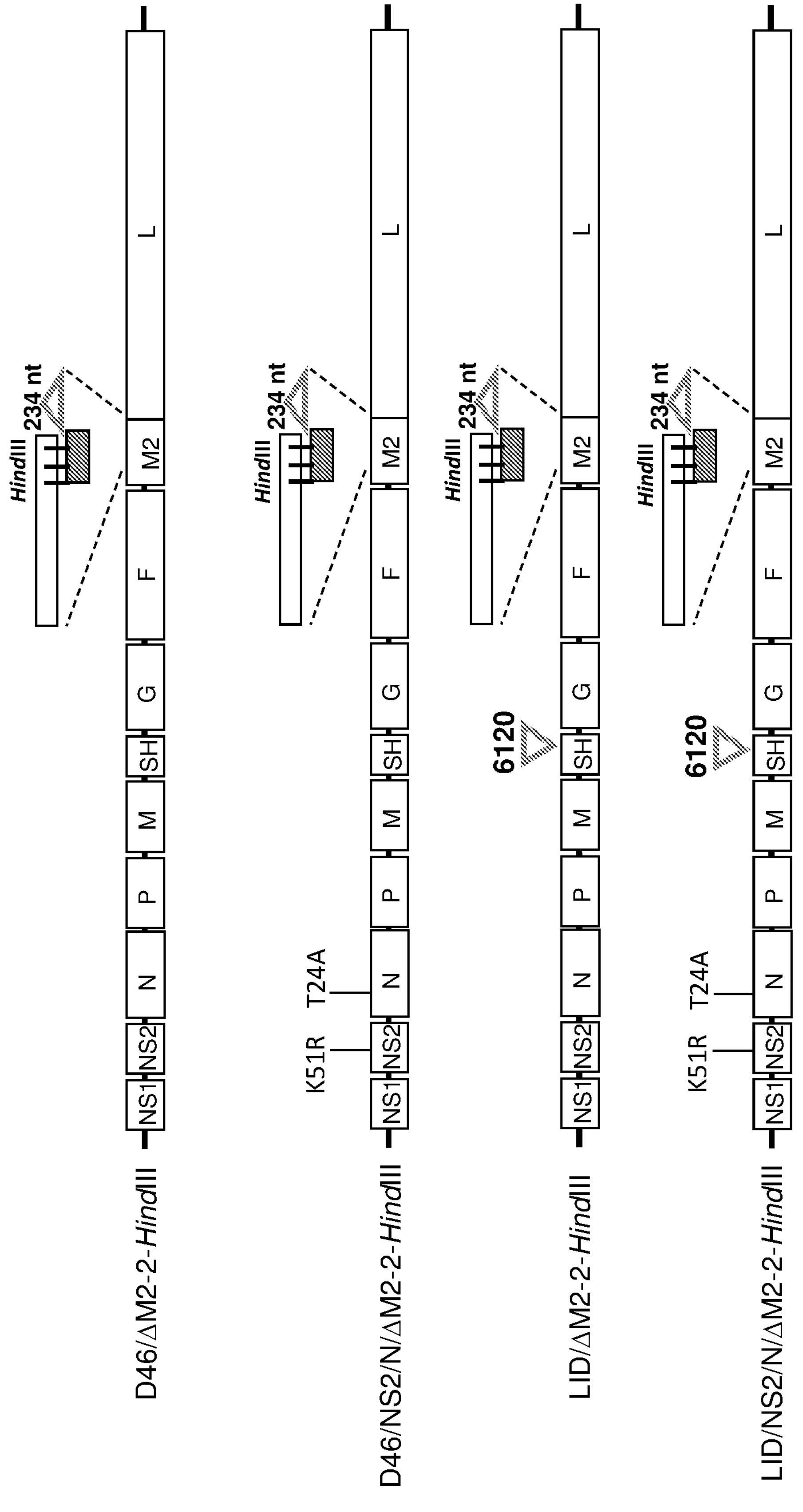
FIG. 13. Schematic diagrams of the genomes of examples of derivatives of RSV D46 and LID bearing the "ΔM2-2-HindIII" mutation, as well as derivatives bearing the ΔM2-2-HindIII genome in combination with the K51R and T24A mutations. The introduction of the ΔM2-2-HindIII mutation alone into the D46 or LID backbones resulted in the genomes D46/ΔM2-2-HindIII and LID/ΔM2-2-HindIII (the first and third genomes from the top). The introduction of the ΔM2-2-HindIII mutation into the D46 or LID backbones in combination with the K51R and T24A mutations resulted in the genomes D46/NS2/N/ΔM2-2-HindIII and LID/NS2/N/ΔM2-2-HindIII (the second and fourth genomes from the top). Sequences of D46/ΔM2-2-HindIII and RSV LID/ΔM2-2-HindIII constructs are denoted by SEQ ID NO: 4 and SEQ ID NO: 7 respectively.

In addition, the ΔM2-2-HindIII mutation (described in FIG. 10) was introduced into D46 to generate the D46/ΔM2-2-HindIII and LID/ΔM2-2-HindIII backbones (FIG. 13, the first and third constructs from the top). Further derivatives included the further additions of the K51R and T24A amino acid substitutions in the NS2 and N proteins (FIG. 13, the second and fourth constructs from the top).

Example 7

This example illustrates additional ΔM2-2 constructs with additional modifications to the F and/or G genes.

RSV LID/ΔM2-2 (FIG. 2) was modified with further alterations to the F and/or G genes. In general, these modifications were not designed primarily to affect attenuation, but rather to affect other parameters such as the efficiency of antigen expression or the inclusion of genes from another strain. Note that these strains use the terminology "6120" rather than "LID" to indicate the presence of the 6120 mutation. These constructs are as follows:

RSV 6120/G001BB/FBB/ΔM2-2 (FIG. 14A): contains the codon optimized G gene (G001BB) from a recent (year 2011), low-passage clinical isolate A/Maryland/001/11. This construct also contains a codon-optimized strain A2 F gene (FBB). Note that the native sequence of the G0001 sequence proved to be unstable during cloning in bacteria. The codon optimization, resulting in G001BB, had the effect of conferring stability.

RSV 6120/FBB/G001BB/ΔM2-2 (FIG. 14A); contains codon-optimized A2 F gene (FBB) and the codon optimized G gene from the recent clinical isolate (G001BB), but their order in the gene map has been reversed, from G-F to F-G, in order to obtain increased expression of the F protein, the major RSV neutralization and protective antigen.

RSV 6120/G001BB/F/ΔM2-2 (FIG. 14A): contains G001BB and native A2 F gene.

RSV 6120/G/FBB/ΔM2-2 (FIG. 14A, fourth construct from the top): contains the native A2 G gene and codon-optimized A2 F gene (FBB).

RSV 6120/G/FBBHEK/ΔM2-2 (FIG. 14B): contains the native A2 G gene and codon-optimized A2 F gene (FBB) that also has the two HEK mutations, K66E and Q101P.

RSV 6120/G/FBBcpHEK/ΔM2-2 (FIG. 14C): contains the native A2 G gene and codon-optimized A2F gene (FBB) that also has the two HEK mutations, K66E and Q101P and the two cp mutations contained in the F gene, namely E218A and T523I.

RSV 6120/FBB/G/ΔM2-2 (FIG. 14C): contains codon optimized A2 F (FBB) and the native A2 G gene, but their order in the gene map has been reversed, from G-F to F-G.

RSV 6120/G001BB/F001BB/ΔM2-2 (FIG. 14C): contains the G001BB gene and the F001 gene that have been codon optimized (G001BB, F001BB).

In brief, the use of G and/or F genes from the recent clinical isolate called A/Maryland/001/11 (which was isolated in 2011 from a health care provider with substantial respiratory illness) was to investigate whether these combinations might yield improved replication and/or immunogenicity. It also would show that a live RSV vaccine could be up-dated readily to contain surface proteins from more recent strains. The use of codon-optimization (BB) was to increase expression of one or both major protective antigens. The change in gene order of G and F from G-F to F-G was designed to increase antigen expression, and was done knowing that moving F and G all the way to the promoter-proximal positions in the gene map in the context of a ΔM2-2 mutation resulted in viruses that unexpectedly exhibited a reduced level of replication in vitro, as described in Example 1. The use of HEK mutations, with or without the two F cp mutations, was done to obtain a more stable F protein, which might have superior immunogenicity due to the preservation of neutralization epitopes. This is based on the idea that the meta-stable nature of the RSV F protein might contribute to immune evasion by presenting denatured antigen (Sakurai, et al. 1999. J Virol 73:2956-2962; Collins and Graham, 2008. J Virol 82:2040-2055), and thus providing a more stable form might induce a qualitatively superior immune response.

Figure 14A:
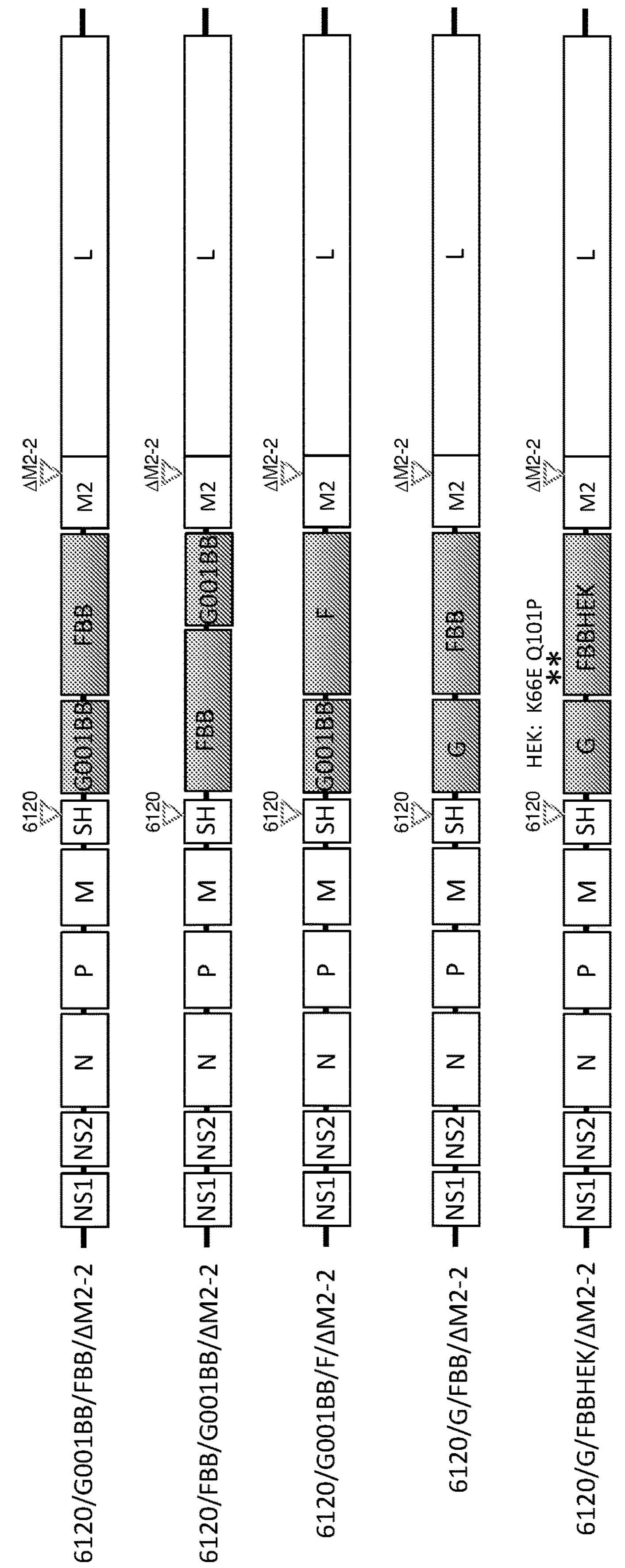
FIGS. 14A and 14B. Schematic diagrams of the genomes of examples of derivatives of RSV LID/ΔM2-2 (i.e., containing the ΔM2-2 mutation shown in FIG. 1 and the 6120 mutation shown in FIG. 3) containing additional modifications to the F and G genes. For these constructs, the identifier "6120" is used instead of "LID" to refer to the 6120 mutation. G001 and F001 refer to the G and F genes, respectively, of a clinical isolate of a subgroup A strain (not A2) called RSV A/Maryland/001/11. All other genes are from strain A2. "BB" refers to codon-optimized sequence. HEK refers to the two amino acid substitutions in the F protein, K66E and Q101P. In this case, "FBBcpHEK," refers to a codon optimized F sequence further including the HEK substitutions, and the "cp" substitutions that fall within the F protein, namely E218A and T523I.
Figure 14B:
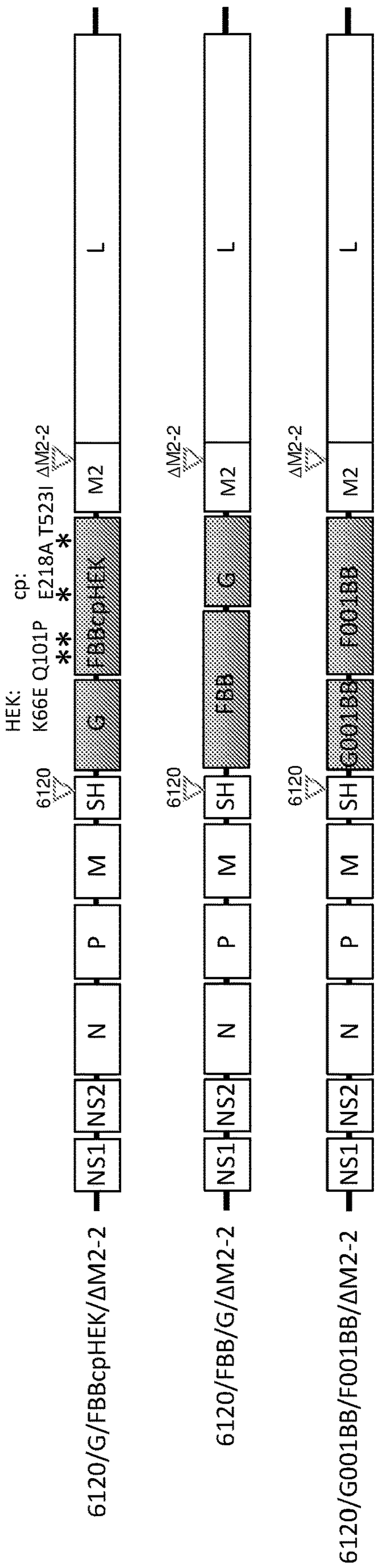

Each of the viruses shown in FIGS. 14A and 14B was readily recovered from cDNA. Passage P1 is the first passage following transfection, and is performed without titering the inoculum (blind passage). The resulting P1 yields of the constructs in FIGS. 14A and 14B were compared to wt RSV containing the 6120 mutation (wt LID), and to RSV LID/ΔM2-2, which was the parent of the constructs (FIG. 15). This showed that the P1 titers of all of the viruses compared favorably with the two controls, with the sole exception that the P1 titer of RSV 6120/G001BB/F001BB/ΔM2-2 was approximately 3.0 $\log_{10}$ reduced. However, this titer rebounded during the P2 passage to levels consistent with the other constructs (FIG. 15). In general, this showed that all of the modifications were well tolerated, including the novel genes, the change in gene order, the codon optimization, and the introduction of HEK and/or cp mutations.

Example 8

This example illustrates evaluation of additional RSV ΔM2-2 constructs.

As described above, RSV D46/cp/ΔM2-2 (FIG. 4, top genome), was found to replicate efficiently in Vero cells, necessary for vaccine manufacture, and to be highly attenuated yet highly immunogenic in AGMs (Tables 4-6). Therefore, vaccine seed virus was prepared and used to manufacture clinical trial material (CTM) of D46/cp/ΔM2-2. As noted, this construct had a single adventitious nucleotide change in the D46 backbone, at the DNA level: specifically, G3878A, which is present in the M ORF and is silent at the amino acid level. Automated sequence analysis showed that the sequence of the CTM was identical to that of the cDNA. Analysis of the replication and immunogenicity of this CTM in AGMs confirmed that it is highly attenuated (Tables 14 and 15) yet highly immunogenic (Table 16). This vaccine candidate was evaluated in a double-blind placebo-controlled study in 15 RSV seropositive children 12 to 59 months of age (10 vaccine recipients, 5 placebo recipients), performed at CIR/JHU (ClinicalTrials.gov identifier NCT02601612). Following intranasal administration at a dose of $10^6$ PFU, vaccine shedding was undetectable, and D46/cp/ΔM2-2 was poorly immunogenic in seropositive children. This indicates that the vaccine is highly restricted and attenuated, predicting that it will be safe and appropriate for evaluation in seronegative infants and children. Evaluation in RSV seronegative infants and children 6-24 months of age is currently ongoing. This will provide information on a promising vaccine candidate, indicating whether it is suitable for expanded studies. This information also will provide a further benchmark linking preclinical and clinical studies.

In addition, the LID counterpart of this virus, LID/cp/ΔM2-2 (FIG. 5, top genome) was constructed. It was found to replicate efficiently in Vero cells, and analysis of the replication and immunogenicity of this virus in AGMs showed that it is highly attenuated (Tables 17 and 18) yet highly immunogenic (Table 19). This showed that the addition of the cp mutations to LID/ΔM2-2, which was incompletely attenuated in seronegative infants and children (FIG. 9B), to create LID/cp/ΔM2-2, resulted in increased attenuation in AGMs (i.e., compare data for LID/ΔM2-2, Tables 1 and 2, 4 and 5, 7 and 8, and 10 and 11, to that for LID/cp/ΔM2-2, Tables 17 and 18). This suggests that LID/cp/ΔM2-2 should have increased attenuation in seronegative humans, although clinical evaluation is needed to confirm this, to determine the magnitude of the increased attenuation, and to confirm safety.

Clinical trial material was then manufactured for LID/cp/ΔM2-2 using the antigenomic cDNA whose sequence is shown in SEQ ID NO: 17. The sequence of the clinical trial material (LIDcpΔM2-2, Lot RSV #009B) was confirmed by consensus sequence analysis to match that of the cDNA from which the recombinant virus was derived except for a C-to-T point mutation at nucleotide position 9,972 (note that all sequences are reported in positive, or antigenomic sense). This mutation is silent at the amino acid level and was also present in the seed virus used to generate LIDcpΔM2-2, Lot RSV #009B. Adventitious mutations can appear during passage of RSV, as with most RNA viruses, due to the high error rate of the RNA-dependent RNA polymerase. When such changes do not involve a known cis-acting signal or change amino acid coding, and if they do not measurably affect in vitro replication and plaque size of the virus, they are considered likely to be biologically inconsequential. The silent C9972T point mutation in the LIDcpΔM2-2 clinical trial material likely is inconsequential, but will be monitored.

The LID/cp/ΔM2-2 vaccine virus is being evaluated in seronegative children 6-24 months of age in a double-blind placebo-controlled clinical trial. At least 5 subjects have received the vaccine, with no evidence of reactogenicity during the period when the vaccine virus would be anticipated to be shedding, suggesting that this vaccine is well-tolerated.

As already noted, a non-clinical experimental lot of the LID/ΔM2-2/1030s virus (FIG. 5, second genome from the top) was prepared, and was found to replicate efficiently in Vero cells. It was evaluated in AGMs and shown to be highly attenuated (Tables 1 and 2) and yet highly immunogenic (Table 3).

A preparation of CTM was manufactured was prepared for LID/ΔM2-2/1030s using the antigenomic cDNA shown in SEQ ID NO: 16, and automated sequence analysis showed that the sequence of the clinical trial material (CTM) was identical to that of the cDNA. This vaccine was evaluated in seronegative children 6-24 months of age in a double-blind placebo-controlled trial. A total of 33 subjects were enrolled, with an anticipated vaccinee:placebo ratio of 2:1. Nasal washes from 30 participants were evaluated by plaque assay (viral culture) as well as by quantitative RT-PCR (qPCR) for shedding of vaccine virus LID/ΔM2-2/1030s, as a measure of attenuation. This showed that 17 of the subjects had apparent vaccine virus shedding (it is anticipated that a total of 20 subjects received vaccine). 15/30 subjects in the LID/ΔM2-2/1030s trial were positive by plaque assay, and that all 15 of these plus two additional subjects were positive by qPCR, which is a more sensitive assay. It is anticipated that subjects that shed virus during the 14-18 days following administration of the vaccine will be found to be vaccinee recipients, and hence these data can be used as a presumptive assessment of vaccine virus shedding and hence attenuation. In comparison, a similar shedding analysis for RSV LID/ΔM2-2 in a comparable cohort of seronegative children 6-24 months of age, ClinicalTrials.gov NCT02040831, found viral shedding in 19 of 20 vaccine recipients by plaque assay and qRT-PCR. In the LID/ΔM2-2/1030s trial, the presumptive mean peak titers were: 5.1 $\log_{10}$ copies/ml by PCR, and 2.9 log 10 PFU/ml by culture, whereas for the LID/ΔM2-2 trial, the mean peak titers were 5.9 $\log_{10}$ copies/ml by PCR, and 3.4 $\log_{10}$ PFU/ml by culture. Thus, the LID/ΔM2-2/1030s virus appeared to be more attenuated than the LID/ΔM2-2 virus based on the rate of infection and the titers of shed virus. With the LID/ΔM2-2/1030s virus, the three highest individual peak titers were 4.7, 4.5, and 4.1 $\log_{10}$ PFU/ml, compared to 5.4, 5.3, and 5.1 $\log_{10}$ PFU/ml for LID/ΔM2-2. In addition, for the LID/ΔM2-2/1030s virus, six subjects shed infectious virus for only a single day, compared to two for the LID/ΔM2-2 virus. Thus, by each of these measures, the insertion of the 1030s mutation into LID/ΔM2-2 provided a measurable, consistent decrease in viral shedding in seronegative children, who are the vaccine target.

The RSV LID/ΔM2-2/1030s virus was evaluated for the temperature-sensitive phenotype, since the 1030s mutation is a temperature sensitivity mutation (Table 20). This analysis showed that RSV LID/ΔM2-2/1030s has a shut-off temperature ($T_{SH}$) of 40° C. and a small plaque temperature ($T_{SP}$) of 38° C., whereas wild type RSV, LID/ΔM2-2, MEDI/ΔM2-2, LID/cp/ΔM2-2, and D46/cp/ΔM2-2 have $T_{SH}$ and $T_{SP}$ of >40° C. Thus, RSV LID/ΔM2-2/1030s, but not these other wild type and ΔM2-2-based viruses, has a temperature sensitivity phenotype. Two other known temperature-sensitive viruses, RSV ΔNS2/Δ1313/I1314L and RSV cps2, were included as positive controls, and confirmed that the assay was accurate. Thus, introduction of the 1030s mutation into RSV LID/ΔM2-2 conferred the temperature-sensitive phenotype. This is significant because the temperature-sensitive phenotype is thought to preferentially restrict replication in the warmer lower respiratory tract compared to the cooler upper respiratory tract, and thus confers additional safety against reactogenicity. This is thought to be the case even if the $T_{SH}$ and/or $T_{SP}$ are higher than physiological temperature.

Thus, this provides a spectrum of attenuated viruses with increasingly reduced replication: LID/ΔM2-2>LID/cp/ΔM2-2>LID/ΔM2-2/1030s, having varying balances of attenuation and immunogenicity.

TABLE 14

Viral titers of nasopharyngeal swab samples from AGMs inoculated with D46/cp/ΔM2-2.

| RSV Vaccine candidate[a] | AGM ID | NP virus titer ($log_{10}$ PFU/mL) on indicated days[b] 1 | 2 | 3 | 4 | 5 | 6 | 7 | 8 | 9 | 10 | 14 | Peak virus titer |
|---|---|---|---|---|---|---|---|---|---|---|---|---|---|
| D46/cp/ ΔM2-2 | 8573 | — | — | 0.7 | — | — | — | — | — | 0.7 | — | — | 0.7 |
| | N1327 | — | — | 0.7 | — | — | — | 1.0 | — | — | — | — | 1.0 |
| | 8555 | — | — | — | — | — | — | — | — | — | — | — | 0.35 |
| | 8577 | — | — | — | — | — | — | 0.7 | — | — | — | — | 0.7 |
| | Mean: | — | — | 0.5 | — | — | — | 0.6 | — | 0.4 | — | — | 0.7 |
| L-15 | 8551 | — | — | — | — | — | — | — | — | — | — | — | — |
| | 8417 | — | — | — | — | — | — | — | — | — | — | — | — |
| | 8489 | — | — | — | — | — | — | — | — | — | — | — | — |
| | 8565 | — | — | — | — | — | — | — | — | — | — | — | — |
| | Mean | — | — | — | — | — | — | — | — | — | — | — | — |

[a]Monkeys were inoculated i.n. and i.t. with 6 $log_{10}$ PFU of the indicated virus in a 1 mL inoculum per site (total dose = 6.3 $log_{10}$ PFU/AGM).

[b]Combined NP swabs were placed in 2 mL of L-15 medium with sucrose phosphate buffer as stabilizer. Virus titrations were performed on Vero cells at 32° C. The lower limit of detection was 0.7 $log_{10}$ PFU/mL. Samples with no detectable virus are represented as "—". A value of 0.35 was used for samples with no detectable virus. The results show that D46/c/pΔM2-2 is strongly restricted in the URT of AGMs.

TABLE 15

Viral titers of tracheal lavage samples from AGMs inoculated with D46/cp/ΔM2-2.

| RSV Vaccine candidate[a] | AGM ID | TL virus titer ($log_{10}$ PFU/mL) on indicated day[b] 2 | 4 | 6 | 8 | 10 | 14 | Peak virus titer |
|---|---|---|---|---|---|---|---|---|
| D46/cp/ΔM2-2 | 8573 | 1.0 | — | 1.9 | 1.3 | — | — | 1.9 |
| | N1327 | — | 1.0 | 1.8 | 1.0 | — | — | 1.8 |
| | 8555 | — | — | — | — | — | — | 0.7 |
| | 8577 | — | — | — | — | — | — | 0.7 |
| | Mean: | 0.8 | 0.8 | 1.3 | 0.9 | — | — | 1.9 |
| L-15 | 8551 | — | — | — | — | — | — | — |
| | 8417 | — | — | — | — | — | — | — |
| | 8489 | — | — | — | — | — | — | — |
| | 8565 | — | — | — | — | — | — | — |
| | Mean: | — | — | — | — | — | — | — |

[a]Monkeys were inoculated i.n. and i.t. with 6 $log_{10}$ PFU of the indicated virus in a 1 mL inoculum per site (total dose = 6.3 $log_{10}$ PFU/AGM).

[b]On days 2, 4, 6, 8, 10, and 14, tracheal lavage (TL) was performed with 3 mL of PBS Virus. Titrations were performed on Vero cells at 32° C. The lower limit of detection was 1.0 $log_{10}$ PFU/mL. Samples with no detectable virus are represented as "—". A value of 0.7 was used for samples with no detectable virus. D46/cp/ΔM2-2 is strongly restricted in the LRT of AGMs.

TABLE 16

Serum $PRNT_{60}$ titers from AGMs inoculated with D46/cp/ΔM2-2.

| RSV Vaccine candidate | AGM ID | Neutralizing antibody titers ($PRNT_{60}$, reciprocal $log_2$) on indicated days[b] 0 | 21 | 29 |
|---|---|---|---|---|
| D46/cp/ ΔM2-2[a] | 8573 | — | 8.4 | 8.4 |
| | N1327 | — | 8.4 | 9.1 |
| | 8555 | — | 6.6 | 6.1 |
| | 8577 | — | 7.2 | 6.9 |
| | Mean: | — | 7.7 | 7.6 |
| L-15 | 8551 | — | — | — |
| | 8417 | — | — | — |
| | 8489 | — | — | — |
| | 8565 | — | — | — |
| | Mean: | — | — | — |

[a]AGMs were inoculated i.n. and i.t. with 6.0 $log_{10}$ PFU of the indicated virus in a 1 mL inoculum per site (total dose = 6.3 $log_{10}$ PFU per animal).

[b]On days 0, 21, and 29 p.i., serum was obtained. Neutralizing antibody titers were determined in a 60% plaque reduction neutralization assay. The lower limit of detection was 3.3 (1:10).

TABLE 17

Viral titers of nasopharyngeal swab samples from AGMs inoculated with LID/cp/ΔM2-2.

| RSV Vaccine candidate[a] | AGM ID | NP virus titer ($log_{10}$ PFU/mL) on indicated days[b] 1 | 2 | 3 | 4 | 5 | 6 | 7 | 8 | 9 | 10 | 12 | Peak virus titer |
|---|---|---|---|---|---|---|---|---|---|---|---|---|---|
| LID/cp/ ΔM2-2 | 8120 | — | — | — | — | — | — | — | — | — | — | — | 0.35 |
| | 8528 | — | — | — | — | — | — | — | — | — | — | — | 0.35 |
| | 8336 | — | — | — | 0.7 | — | — | — | — | — | — | — | 0.7 |
| | Mean: | — | — | — | 0.5 | — | — | — | — | — | — | — | 0.5 |

[a]Monkeys were inoculated i.n. and i.t. with 6 $log_{10}$ PFU of the indicated virus in a 1 mL inoculum per site (total dose = 6.3 $log_{10}$ PFU/AGM). A value of 0.35 was used for samples with no detectable virus.

[b]Combined NP swabs were placed in 2 mL of L-15 medium with sucrose phosphate buffer as stabilizer. Virus titrations were performed on Vero cells at 32° C. The lower limit of detection was 0.7 $log_{10}$ PFU/mL. Samples with no detectable virus are represented as "—". A value of 0.35 was used for samples with no detectable virus. The results show that LID/cp/ΔM2-2 is strongly restricted in the URT of AGMs.

TABLE 18

Viral titers of tracheal lavage samples from AGMs inoculated with LID/cp/ΔM2-2.

| RSV Vaccine candidate[a] | AGM ID | TL virus titer ($\log_{10}$ PFU/mL) on indicated day[b] | | | | | | Peak virus titer |
|---|---|---|---|---|---|---|---|---|
| | | 2 | 4 | 6 | 8 | 10 | 12 | |
| LID/cp/ΔM2-2 | 8120 | 2.1 | — | — | — | — | — | 2.1 |
| | 8528 | 1.0 | — | — | — | — | — | 1.0 |
| | 8336 | — | 1.0 | — | — | — | — | 1.0 |
| | Mean: | 1.3 | 0.8 | — | — | — | — | 1.4 |

[a]AGMs were inoculated by the combined intranasal and intratracheal routes with 6 $\log_{10}$ PFU of the indicated virus in a 1 mL inoculum per site (total dose: 6.3 $\log_{10}$ PFU per animal).
[b]On days 2, 4, 6, 8, 10, and 12, tracheal lavage was performed with 3 mL of PBS. Virus titrations were performed on Vero cells at 32° C. The lower limit of detection was 1.0 $\log_{10}$ PFU/mL of lavage solution. Samples with no detectable virus are represented as "—". A value of 0.7 was used for samples with no detectable virus. LID/cp/ΔM2-2 is strongly restricted in the LRT of AGMs.

TABLE 19

Serum PRNT$_{60}$ titers from AGMs inoculated with LID/cp/ΔM2-2.

| RSV Vaccine candidate | AGM ID | Neutralizing antibody titers (PRNT$_{60}$, reciprocal $\log_2$) on indicated days[b] | | |
|---|---|---|---|---|
| | | 0 | 21 | 29 |
| LID/cp/ΔM2-2[a] | 8120 | — | 10.0 | 10.5 |
| | 8528 | — | 10.1 | 9.8 |
| | 8336 | — | 8.1 | 7.7 |
| | Mean: | — | 9.4 | 9.3 |

[a]AGMs were inoculated i.n. and i.t. with 6.0 $\log_{10}$ PFU of the indicated virus in a 1 mL inoculum per site (total dose = 6.3 $\log_{10}$ PFU per animal).
[b]On days 0, 21, and 29 p.i., serum was obtained. Neutralizing antibody titers were determined in a 60% plaque reduction neutralization assay. The lower limit of detection was 3.3 (1:10).

TABLE 20

Temperature sensitivity of RSV LID/ΔM2-2/1030s and related viruses

| Virus | Virus titer ($\log_{10}$ PFU per mL) at indicated temperature (° C.)[a] | | | | | | | $T_{SH}$[b] | $T_{SP}$[c] |
|---|---|---|---|---|---|---|---|---|---|
| | 32 | 35 | 36 | 37 | 38 | 39 | 40 | | |
| RSV A2 | 7.3 | 7.2 | 7.2 | 7.2 | 7.3 | 7.2 | 7.0 | >40 | >40 |
| D46 6120 | 7.7 | 7.7 | 7.6 | 7.6 | 7.6 | 7.4 | 7.4 | >40 | >40 |
| LID ΔM2-2 | 5.9 | 5.9 | 5.8 | 5.7 | 5.7 | 5.6 | 5.4 | >40 | >40 |
| Medi ΔM2-2 | 7.0 | 7.0 | 6.9 | 7.0 | 7.0 | 6.9 | 6.8 | >40 | >40 |
| LID cp ΔM2-2 | 4.5 | 4.5 | 4.4 | 4.2 | 4.1 | 3.9 | 3.5 | >40 | >40 |
| LID ΔM2-2 1030s | 7.1 | 7.0 | 7.0 | 7.0 | 6.8* | 6.1 | **_1.7_** | 40 | 38 |
| D46 cp ΔM2-2 | 6.2 | 6.2 | 6.1 | 6.0 | 5.9 | 5.7 | 5.5 | >40 | >40 |
| RSV ΔNS2 Δ1313 I1314L[xx] | 7.1 | 6.9 | 6.8* | 6.4 | *6.4*[d] | **_<2_** | <2 | 39 | 36 |
| RSV cps2[xx] | 6.4 | 5.8* | *4.7*[d] | **_<2_** | <2 | <2 | <2 | 37 | 35 |

[a]The ts phenotype for each virus was evaluated by plaque assay on Vero cells at the indicated temperatures. For viruses with ts phenotype, titers at shut-off temperatures ($T_{SH}$) are marked (bold, underlined). See footnote [b] for the definition of $T_{SH}$.
[b]$T_{SH}$ (bold, underlined) is defined as the lowest restrictive temperature at which the reduction compared to 32° C. is 100-fold or greater than that observed for wt RSV at the two temperatures. The ts phenotype is defined as having a $T_{SH}$ of 40° C. or less.
[c]$T_{SP}$, Small plaque temperature is defined as the lowest restrictive temperature at which the small-plaque phenotype is observed. Titers at lowest restrictive temperature are marked with an asterisk.
[d]Italics: micro plaque temperature is defined as the lowest restrictive temperature at which the small-plaque phenotype is observed. Titers at lowest restrictive temperature for the microplaque phenotype are marked with an asterisk.
[xx]Control ts viruses

Example 9

This example describes the construction of RSV D46/276/ΔM2-2-AclI, and its comparison in African green monkeys with RSV D46/NS2/N/ΔM2-2-HindIII and selected control viruses.

An additional M2-2 mutant virus was constructed to represent a further combination of features from the D46/ΔM2-2 and MEDI/ΔM2-2 backbones, yielding a virus called RSV D46/276/ΔM2-2-AclI, which is also referred to herein as "RSV 276" or "276".

Figure 16:
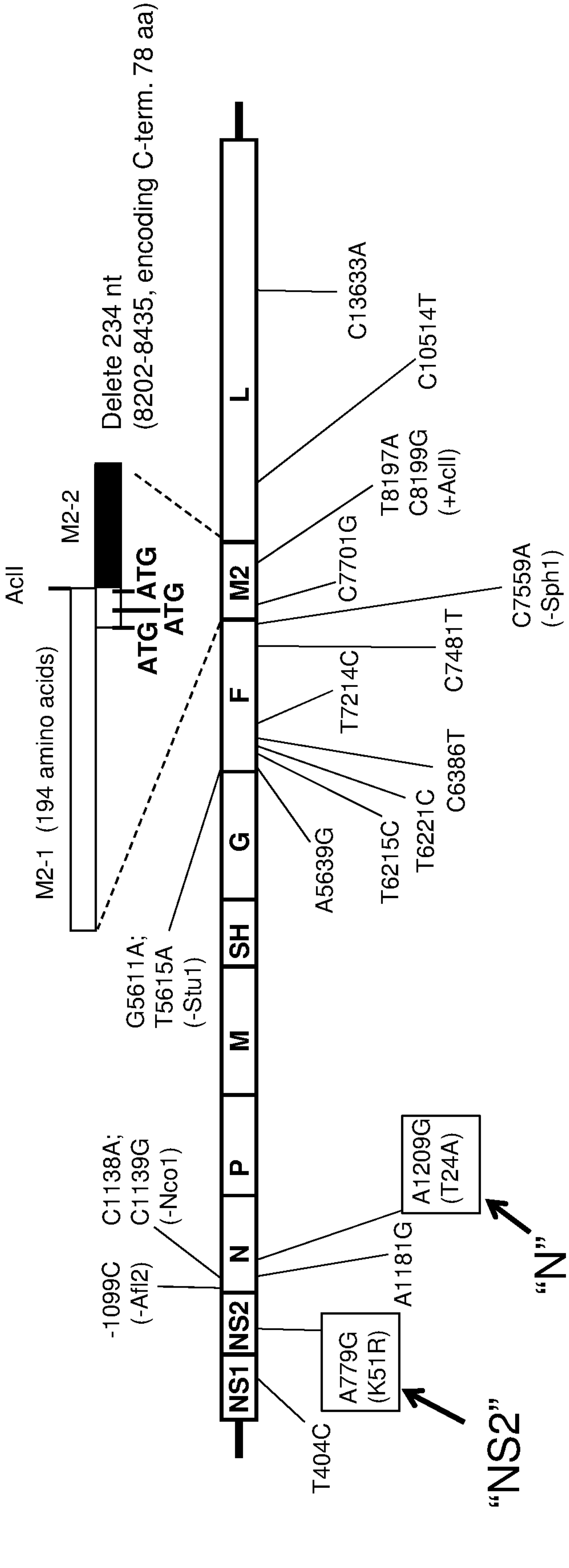
FIG. 16. Schematic diagram illustrating the genome of RSV D46/276/ΔM2-2-AclI.

The structure of RSV 276 is summarized in FIG. 16 and in Table 21 and is provided in SEQ ID NO: 19. Compared to D46 (i.e., the complete wild type antigenomic cDNA, SEQ ID NO: 1), RSV 276 differed by a total of 21 nucleotide differences (including the deletion of a single nt at position 1099) plus the deletion of nucleotides 8202-8435 inclusive, yielding a deletion of 234 nucleotides). The nucleotide changes removed four non-native restriction sites (AflII, NcoI, StuI, and SphI) that had been intentionally inserted into D46 during its original construction (Collins, et al. 1995 Proc Natl Acad Sci USA 92:11563-11567), and in addition inserted an AclI site spanning the M2-2 deletion (thus, the ΔM2-2-AclI deletion is that same as described in FIG. 10). These changes in restriction sites involved eight nucleotides. Most of the other 13 changes introduced selected assignments from RSV MEDI/ΔM2-2 into the D46-derived backbone of the new RSV 276 virus.

TABLE 21

Comparison of genomic sequences (positive sense) of wt RSV D46 (cDNA, SEQ ID NO: 1) and RSV 276 (cDNA and CTM Lot RSV#014A, SEQ ID NO: 19)

| Gene Region | RSV Nucleotide (cDNA) | | | | Encoded Amino Acid Residue | | |
|---|---|---|---|---|---|---|---|
| | Genomic nt position[1] | SEQ ID NO: 1 position | WT D46 RSV | RSV 276 | Amino Acid Position[1] | WT D46 RSV | RSV 276 |
| NS1 | 404 | 404 | T | C | 102 | N | N |
| NS2 | 779 | 779 | A | G | 51 | K | R[3] |
| NS2/N ig[4] | 1099 | 1099 | C* | — | ncr[2] | n/a | n/a |
| N | 1138 | 1139 | C* | A | ncr[2] | n/a | n/a |
| N | 1139 | 1140 | C* | G | ncr[2] | n/a | n/a |
| N | 1181 | 1182 | A | G | 14 | K | K |
| N | 1209 | 1210 | A | G | 24 | T | A[3] |
| G/F ig[4] | 5611 | 5612 | G* | A | ncr[2] | n/a | n/a |
| G/F ig[4] | 5615 | 5616 | T* | A | ncr[2] | n/a | n/a |
| G/F ig[4] | 5639 | 5640 | A | G | ncr[2] | n/a | n/a |
| F | 6215 | 6216 | T | C | 185 | V | V |
| F | 6221 | 6222 | T | C | 187 | V | V |
| F | 6386 | 6387 | C | T | 242 | G | G |
| F | 7214 | 7215 | T | C | 518 | A | A |
| F | 7481 | 7482 | C | T | ncr[2] | n/a | n/a |
| F/M2 ig[4] | 7559 | 7560 | C* | A | ncr[2] | n/a | n/a |
| M2-1 | 7701 | 7702 | C | G | 32 | P | P |
| M2-2 | 8197 | 8198 | T | A** | 13 | Y | stop codon |
| M2-2 | 8199 | 8200 | C | G** | 15 | C | nontranslated aa 13-90[3]: |
| M2-2 deletion | | | | 8202-8435 (234 nt) | | | M2-2 deletion |
| L | 10514 | 10515 | C | T | 673 | L | L |
| L | 13633 | 13634 | C | A | 1712 | T | T |

[1]In table 21, the numbering of the nucleotide and amino acid sequences is relative to biological wt RSV strain A2 (GenBank accession number M74568), which was the first complete sequence of RSV strain A2. That genome is 15,222 nt in length. Thus, deletions or insertions in viruses do not change the sequence numbering of the remaining nucleotides (or amino acids). Nucleotide and amino acid sequence assignments are relative to RSV D46 WT (SEQ ID NO: 1) unless otherwise indicated. D46 is a second, recombinantly-derived version of strain A2 that differs in nucleotide length due to a single nucleotide insert at position 1099 (as indicated), resulting in a genome nucleotide length of 15,223. This insertion was removed in RSV 276 and the assignment at that position became T.
[2]ncr, non-coding region.
[3]Amino acids in RSV 276 that differ from RSV D46 are shaded in grey.
[4]ig, intergenic region
*Changes engineered into D46 to create four restriction site markers (Collins et al PNAS 92: 11563-7 1995 PMID 8524804). These were removed in RSV 276.
**Nucleotide changes that create an AclI site in RSV 276.

The 276 virus was constructed using the D46 antigenomic cDNA (SEQ ID NO: 1) in combination with synthetic cDNA fragments. Specifically, a cDNA was synthesized that spanned from a unique NotI site in the plasmid vector upstream of the leader region to the unique AvrII site at positions 2129-2134 in the N gene in D46. A second cDNA was synthesized spanning from the unique XhoI site in D46 (positions 4481-4486) to the unique BamHI site (positions 8499-8505). This latter piece also contained the ΔM2-2-AclI mutation, except that the desired AclI site was HindIII (a restriction site that differs by inversion of the order of two nucleotides, not shown). These two pieces were substituted into D46 by conventional molecular cloning techniques, thereby achieving most of the desired nucleotide changes shown in FIG. 16 and Table 21. Then, three site-directed mutagenesis steps were performed: the HindIII site was changed to the desired AclI site (involving changing two adjacent nucleotides), and the C10514T and C13633A substitutions in L were made. This resulted in the antigenomic cDNA for RSV 276 (SEQ ID NO: 19).

RSV 276 virus was readily recovered as experimental lots, and was confirmed to replicate efficiently in Vero cells. In addition, a lot of RSV 276 virus clinical trial material was recovered and manufactured under conditions suitable for human use, in preparation for a clinical trial. Its sequence was confirmed to be free of adventitious mutations.

In addition, a lot of clinical trial material was made for the virus D46/NS2/N/ΔM2-2-HindIII (see FIG. 13, the second virus from the top). The sequence of the D46/NS2/N/ΔM2-2-HindIII antigenomic cDNA is shown in SEQ ID NO: 18. The sequence of the clinical trial material of D46/NS2/N/ΔM2-2-HindIII (Lot RSV #011B) matched that of the cDNA plasmid from which the recombinant virus was derived, except for three polymorphisms: (1) G2485A (~20-40% A); codon: GAT to AAT; amino acid: D47N in the P ORF; (2) a single-nucleotide thymidine insertion in a poly-thymidine stretch (nt 4537-39) in the 3' noncoding region of the SH gene (+1 nt; present in a subpopulation of about 30%); (3) a two-nucleotide adenosine insertion in a poly-adenosine stretch (nt 14,830-35) of the L gene end signal (+1A in about 30% of the population, +2A in about 70% of the population). These polymorphisms are considered biologically inconsequential.

In a series of studies, an experimental lot of RSV 276 and three different lots of RSV D46/NS2/N/ΔM2-2-HindIII were assayed for replication and immunogenicity in African green monkeys. Each preparation was evaluated separately due to constraints of timing and animal availability. The results are compared together in Tables 22, 23, and 24 in parallel with data for two comparators (LID/ΔM2-2 and LID/ΔM2-2/1030s) taken from Table 1. Virus replication was evaluated by quantitation of viral shedding sampled by NP swab (Table 22) and tracheal lavage (Table 23), quantified by plaque assay. This showed that, in the upper respiratory tract (by NP swab) two of the three lots of D46/NS2/N/ΔM2-2-HindIII (studies 2 and 3) shed detectably (mean peak titers of 1.1-1.6 log 10 PFU/ml) over a period of 5.5-7.3 days, whereas shedding for the third lot (study 1) was minimal. In the lower respiratory tract (tracheal lavage), the results for the three lots were very similar, with moderate levels of shedding (2.2-2.6 log 10 PFU/ml) over 7.8-9.2 days. In comparison, shedding for RSV 276 was very similar to that of D46/NS2/N/ΔM2-2-HindIII studies 2 and 3 in the upper respiratory tract, and was very similar to all three studies for shedding in the lower respiratory tract. In comparison, shedding by LID/ΔM2-2 in both anatomical compartments was substantially greater, while shedding by LID/ΔM2-2/1030s was substantially less. The 60% PRNT titer of these viruses at day 28 was 8.3 and 8.5 recip. log 2 for two of the lots of D46/NS2/N/ΔM2-2-HindIII, and 6.3 recip. log 2 for the third lot, and 8.5 recip. log 2 for RSV 276. These titers generally equaled or exceeded those shown for LID/ΔM2-2 and LID/ΔM2-2/1030s (Table 24). Thus, these viruses provide a further spectrum of attenuation phenotypes based on ΔM2-2 backbones.

TABLE 22

Viral titers of nasopharyngeal swab samples from AGMs inoculated with LID ΔM2-2, LID ΔM2-2 1030s, D46/NS2/N/ΔM2-2-HindIII, or RSV 276[a]

| RSV Vaccine candidate | AGM ID | NP virus titer ($log_{10}$ PFU/mL) on indicated days[b] 1 | 2 | 3 | 4 | 5 | 6 | 7 | 8 | 9 | 10 | 12 | Duration of shedding[c] | Peak virus titer | Sum of daily titers[d] |
|---|---|---|---|---|---|---|---|---|---|---|---|---|---|---|---|
| LID ΔM2-2 | 7806 | — | 1.4 | 1.7 | 2.7 | 2.6 | 4.0 | 3.9 | 1.4 | — | 2.7 | — | 9 | 4.0 | 21.4 |
| | 7705 | — | — | — | 2.7 | 2.3 | 3.6 | 2.4 | 1.2 | — | — | — | 5 | 3.6 | 14.3 |
| | 7747 | — | — | 1.3 | 0.7 | — | 1.5 | 1.3 | — | — | — | — | 5 | 1.5 | 7.2 |
| | 7674 | — | 0.7 | — | — | — | 2.3 | 1.8 | 1.5 | — | — | — | 7 | 2.3 | 8.8 |
| | | | | | Mean: | | | | | | | | 6.5 | 2.9 | 12.9 |
| LID ΔM2-2 1030s | 8033 | — | — | — | — | — | — | — | — | — | — | — | 0 | 0.35 | 3.9 |
| | 7720 | — | — | — | — | — | — | — | — | — | — | — | 0 | 0.35 | 3.9 |
| | 7844 | — | — | — | — | — | — | — | — | — | — | — | 0 | 0.35 | 3.9 |
| | 7847 | — | — | — | — | — | — | — | — | — | — | — | 0 | 0.35 | 3.9 |
| | | | | | Mean: | | | | | | | | 0 | 0.35 | 3.9 |
| D46/NS2/N/ ΔM2-2- HindIII (study 1) | 8417 | 0.7 | — | — | — | — | — | — | — | — | — | — | 1 | 0.7 | 4.2 |
| | 8489 | — | — | — | — | — | — | — | — | — | — | — | 0 | 0.35 | 3.9 |
| | 8515 | — | — | — | — | — | — | — | — | — | — | — | 0 | 0.35 | 3.9 |
| | 8574 | — | — | — | — | — | — | — | 1.2 | — | — | — | 8 | 1.2 | 4.7 |
| | | | | | Mean: | | | | | | | | 2.3 | 0.7 | 4.2 |
| D46/NS2/N/ ΔM2-2- HindIII (study 2) | N1330 | — | — | — | — | — | — | — | — | — | — | — | 0 | 0.35 | 3.9 |
| | N1326 | — | — | — | 1.0 | 0.7 | — | 1.8 | — | 1.0 | — | — | 6 | 1.8 | 6.9 |
| | 8566 | — | — | — | 1.0 | 0.7 | 0.7 | — | 0.7 | 0.7 | — | — | 6 | 1.0 | 5.9 |
| | 8551 | — | — | — | 1.0 | 0.7 | 1.0 | — | — | — | — | — | 3 | 1.0 | 5.5 |
| | | | | | Mean: | | | | | | | | 3.8 | 1.1 | 5.5 |
| D46/NS2/N/ ΔM2-2- HindIII (study 3) | 9041 | — | — | — | — | — | — | — | — | — | — | — | 0 | 0.35 | 3.9 |
| | 8938 | — | — | — | — | 1.3 | 1.3 | 1.3 | 1.9 | 1.0 | — | — | 5 | 1.9 | 8.9 |
| | 8926 | — | — | — | — | — | 0.7 | — | 1.4 | 1.4 | — | — | 4 | 1.4 | 6.3 |
| | 8911 | — | — | — | 0.7 | 1.0 | 1.0 | 2.2 | 2.3 | 1.0 | — | — | 6 | 2.3 | 10.0 |
| | | | | | Mean: | | | | | | | | 3.8 | 1.6 | 7.3 |
| RSV 276 | 8918 | — | — | — | — | — | — | — | — | — | — | — | 0 | 0.35 | 3.9 |
| | 8902 | — | 1.5 | 2.0 | 2.9 | 2.5 | 3.0 | 3.1 | 2.5 | 1.4 | 1.3 | — | 9 | 3.1 | 21.0 |
| | 8913 | — | — | — | — | — | 0.7 | 1.4 | 1.0 | — | — | — | 3 | 1.4 | 6.0 |
| | 8952 | — | — | — | — | 0.7 | 0.7 | 1.5 | — | — | 1.2 | — | 6 | 1.5 | 6.5 |
| | | | | | Mean: | | | | | | | | 4.5 | 1.6 | 9.3 |

[a]AGMs were inoculated by the combined nasopharyngeal and intratracheal routes with $10^6$ PFU of the indicated virus in a 1 mL inoculum per site (total dose: $2 \times 10^6$ PFU per animal). AGM studies were approved by the Animal Care and Use Committee of NIAID, NIH. Results from a previous study of LID ΔM2-2 and LID ΔM2-2 1030s are shown for comparison.

[b]Combined NP swabs were placed in 2 mL of L-15 medium with sucrose phosphate buffer as stabilizer. Virus titrations were performed on Vero cells at 37° C. The lower limit of detection was 0.7 $log_{10}$ PFU/mL. Samples with no detectable virus are represented as "—". Peak titers for each animal are underlined.

[c]The period of days from the first to the last day on which virus was detected, including negative days (if any) in between.

[d]The sum of daily titers is used as an estimate for the magnitude of shedding (area under the curve). A value of 0.35 was used for samples with no detectable virus.

TABLE 23

Viral titers of tracheal lavage samples from AGMs inoculated with LID ΔM2-2, LID ΔM2-2 1030s, D46/NS2/N/ΔM2-2-HindIII, or RSV 276[a]

| RSV vaccine candidate | AGM ID | Tracheal lavage virus titer ($log_{10}$ PFU/mL) on indicated days[b] 2 | 4 | 6 | 8 | 10 | 12 | Duration of shedding[c] | Peak virus titer | Sum of daily titers[d] |
|---|---|---|---|---|---|---|---|---|---|---|
| LID ΔM2-2 | 7806 | 2.5 | 3.4 | 4.6 | — | — | — | 7 | 4.6 | 12.6 |
| | 7705 | 1.6 | — | 3.3 | 1.5 | — | — | 9 | 3.3 | 8.5 |
| | 7747 | 1.8 | 1.0 | 6.0 | 2.3 | — | — | 9 | 6.0 | 12.5 |
| | 7674 | — | 1.3 | 2.7 | 2.3 | 1.0 | — | 9 | 2.7 | 8.7 |
| | | | | Mean: | | | | 9 | 4.2 | 10.6 |
| LID ΔM2-2 | 8033 | — | — | — | — | — | — | 0 | 0.7 | 4.2 |
| 1030s | 7720 | — | — | — | — | — | — | 0 | 0.7 | 4.2 |
| | 7844 | — | — | — | — | — | — | 0 | 0.7 | 4.2 |
| | 7847 | — | — | — | — | — | — | 0 | 0.7 | 4.2 |
| | | | | Mean: | | | | 0 | 0.7 | 4.2 |
| D46/NS2/N/ | 8417 | — | 2.3 | 2.5 | 1.6 | 1.3 | — | 7 | 2.5 | 9.1 |
| ΔM2-2- | 8489 | 1.0 | 2.7 | 3.2 | 3.2 | — | — | 9 | 3.2 | 11.5 |
| HindIII | 8515 | 1.3 | 2.0 | — | 1.7 | — | — | 9 | 2.0 | 7.1 |
| (study 1) | 8574 | 1.8 | 2.1 | 2.2 | 1.7 | — | — | 9 | 2.2 | 9.1 |
| | | | | Mean: | | | | 9 | 2.5 | 9.2 |
| D46/NS2/N/ | N1330 | 0.7 | 1.0 | 0.7 | 0.7 | — | — | 3 | 1.0 | 4.5 |
| ΔM2-2- | N1326 | 1.7 | 1.7 | 1.8 | 2.5 | — | — | 9 | 2.5 | 9.1 |
| HindIII | 8566 | 1.8 | 0.7 | 3.2 | 2.4 | — | — | 9 | 3.2 | 9.5 |
| (study 2) | 8551 | 1.9 | 2.3 | 1.7 | 0.7 | — | — | 7 | 2.3 | 8.0 |
| | | | | Mean: | | | | 7 | 2.2 | 7.8 |
| D46/NS2/N/ | 9041 | 2.0 | 1.9 | 2.3 | 0.7 | — | — | 9 | 2.3 | 8.3 |
| ΔM2-2- | 8938 | 1.0 | 1.6 | 2.5 | 2.5 | — | — | 9 | 2.5 | 9.0 |
| HindIII | 8926 | 0.7 | 0.7 | 2.6 | 1.7 | — | — | 9 | 2.6 | 7.1 |
| (study 3) | 8911 | 2.2 | 2.6 | 0.7 | 3.0 | — | — | 9 | 3.0 | 9.8 |
| | | | | Mean: | | | | 9 | 2.6 | 8.6 |
| RSV 276 | 8918 | 0.7 | 1.7 | 2.3 | 1.6 | 1.0 | — | 9 | 2.3 | 8.0 |
| | 8902 | 2.2 | 1.6 | 2.9 | 2.1 | 0.7 | — | 9 | 2.9 | 10.3 |
| | 8913 | 0.7 | 0.7 | 3.2 | 1.3 | 0.7 | — | 5 | 3.2 | 7.3 |
| | 8952 | 1.8 | 2.1 | 1.6 | 1.8 | 0.7 | — | 9 | 2.1 | 8.8 |
| | | | | Mean: | | | | 8.0 | 2.6 | 8.6 |

[a]AGMs were inoculated by the combined nasopharyngeal and IT routes with $10^6$ PFU of the indicated virus in a 1 mL inoculum per site (total dose: 2 × $10^6$ PFU per animal). Results from a previous study of LID ΔM2-2 and LID ΔM2-2 1030s are shown for comparison.
[b]On days 2, 4, 6, 8, 10, and 12, tracheal lavage was performed with 3 mL of PBS. Virus titrations were performed on Vero cells at 37° C. The lower limit of detection was 1.0 $log_{10}$ PFU/mL of lavage solution. Samples with no detectable virus are represented as "—". Peak titers for each animal are underlined.
[c]The period of days from the first to the last day on which virus was detected, including negative days (if any) in between.
[d]The sum of daily titers is used as an estimate for the magnitude of shedding (area under the curve). A value of 0.7 was used for samples with no detectable virus.

TABLE 24

Neutralizing antibody titers of AGMs inoculated with LID ΔM2-2, LID ΔM2-2 1030s, D46/NS2/N/ΔM2-2-HindIII, or RSV 276[a]

| RSV Vaccine candidate | AGM ID | Neutralizing antibody titers ($PRNT_{60}$, reciprocal $log_2$) on indicated days[b] 0 | 21 | 28 |
|---|---|---|---|---|
| LID ΔM2-2 | 7806 | <3.3 | 7.2 | 7.2 |
| | 7705 | <3.3 | 8.8 | 8.2 |
| | 7747 | <3.3 | 8.3 | 8.4 |
| | 7674 | <3.3 | 6.7 | 6.2 |
| | Mean: | <3.3 | 7.8 | 7.5 |
| LID ΔM2-2 1030s | 8033 | <3.3 | 5.4 | 6.6 |
| | 7720 | <3.3 | <3.3 | <3.3 |
| | 7844 | <3.3 | <3.3 | 4.3 |
| | 7847 | <3.3 | 6.8 | 6.8 |
| | Mean: | <3.3 | 4.7 | 5.2 |
| D46/NS2/N/ | 8417 | <3.3 | 8.8 | 10.4 |
| ΔM2-2-HindIII | 8489 | <3.3 | 6.6 | 8 |
| (study 1) | 8515 | <3.3 | 6.1 | 6.4 |
| | 8574 | <3.3 | 9.4 | 8.2 |
| | Mean: | <3.3 | 7.7 | 8.3 |
| D46/NS2/N/ | N1330 | <3.3 | 8.2 | 8.8 |
| ΔM2-2-HindIII | N1326 | <3.3 | 8.3 | 9.1 |
| (study 2) | 8566 | <3.3 | 7 | 7.3 |

TABLE 24-continued

Neutralizing antibody titers of AGMs inoculated with LID ΔM2-2, LID ΔM2-2 1030s, D46/NS2/N/ΔM2-2-HindIII, or RSV 276[a]

| RSV Vaccine candidate | AGM ID | Neutralizing antibody titers ($PRNT_{60}$, reciprocal $log_2$) on indicated days[b] 0 | 21 | 28 |
|---|---|---|---|---|
| | 8551 | <3.3 | 8.9 | 8.7 |
| | Mean: | <3.3 | 8.1 | 8.5 |
| D46/NS2/N/ | 9041 | <3.3 | 6.9 | 6.4 |
| ΔM2-2-HindIII | 8938 | <3.3 | 7.1 | 7.2 |
| (study 3) | 8926 | <3.3 | 6.7 | 5.5 |
| | 8911 | <3.3 | 7.2 | 5.9 |
| | Mean: | <3.3 | 7.0 | 6.3 |
| RSV 276 | 8918 | <3.3 | 6.1 | 6.2 |
| | 8902 | <3.3 | 8.4 | 8.8 |
| | 8913 | <3.3 | 8.8 | 8.9 |
| | 8952 | <3.3 | 9.7 | 9.9 |
| | Mean: | <3.3 | 8.3 | 8.5 |

[a]AGMs were inoculated i.n. and i.t. with $10^6$ PFU of the indicated virus in a 1 mL inoculum per site (total dose = $10^{6.3}$ PFU per animal). Results from a previous study of LID ΔM2-2 and LID ΔM2-2 1030s are shown for comparison.
[b]On days 0, 21, and 28 p.i., serum was obtained. Neutralizing antibody titers were determined in a 60% plaque reduction neutralization assay. The lower limit of detection was 3.3 (1:10).

It will be apparent that the precise details of the methods or compositions described may be varied or modified without departing from the spirit of the described embodiments. We claim all such modifications and variations that fall within the scope and spirit of the claims below.

The invention claimed is:

1. A recombinant respiratory syncytial virus (RSV) attenuated by one or more modifications to a recombinant RSV genome, wherein the one or more modifications comprise:

(a) a deletion in a M2-2 open reading frame (ORF) corresponding to a deletion of 241 nucleotides at positions 8189-8429 of SEQ ID NO: 1, combined with nucleotide mutations at positions corresponding to T8161, T8167 and T8179 of SEQ ID NO: 1 ("ΔM2-2");

(b) a deletion in a M2-2 ORF corresponding to a deletion of 234 nucleotides at positions 8203-8436 of SEQ ID NO: 1, combined with nucleotide mutations at positions corresponding to 8198A and 8200G of SEQ ID NO: 1 ("ΔM2-2-AclI"); or (c) a deletion in a M2-2 ORF corresponding to a deletion of 234 nucleotides at positions 8203-8436 of SEQ ID NO: 1, combined with nucleotide mutations at positions corresponding to 8198A and 8199G of SEQ ID NO: 1 ("ΔM2-2-HindIII"), wherein the recombinant RSV genome is a D46 genome attenuated by the one or more modifications.

2. The recombinant RSV of claim 1, wherein the one or more modifications further comprise a deletion of 112 nucleotides corresponding to positions 4499-4610 of SEQ ID NO: 1, combined with nucleotide mutations at positions corresponding to C4489T, C4492T, A4495T, A4497G, and G4498A of SEQ ID NO: 1 ("6120").

3. A recombinant respiratory syncytial virus (RSV) attenuated by one or more modifications to a recombinant RSV genome, wherein the one or more modifications comprise:

a deletion in a M2-2 ORF corresponding to a deletion of 234 nucleotides at positions 8203-8436 of SEQ ID NO: 1, combined with nucleotide mutations at positions corresponding to 8198A and 8199G of SEQ ID NO: 1 ("ΔM2-2-HindIII"), and a deletion of 112 nucleotides corresponding to positions 4499-4610 of SEQ ID NO: 1, combined with nucleotide mutations at positions corresponding to C4489T, C4492T, A4495T, A4497G, and G4498A of SEQ ID NO: 1 ("6120").

4. The recombinant RSV of claim 1, wherein:

the one or more modifications further comprise nucleotide mutations encoding amino acid substitutions of V267I in the N protein, E218A and T523I in the F protein, and C319Y and H1690Y in the L protein of the RSV ("cp");

the one or more modifications further comprise nucleotide mutations encoding amino acid substitution K51R in the NS2 protein of the RSV ("NS2");

the one or more modifications further comprise nucleotide mutations encoding amino acid substitution T24A in the N protein of the RSV ("N");

the one or more modifications further comprise nucleotide mutations encoding amino acid substitution K51R in the NS2 protein and T24A in the N protein of the RSV ("NS2/N");

the one or more modifications further comprise a deletion in a SH ORF corresponding to deletion of 419 nucleotides at positions 4198-4616 of SEQ ID NO: 1 ("ΔSH");

the one or more modifications further comprise replacing the nucleotide sequence encoding a G protein of the RSV with a corresponding codon optimized nucleotide sequence encoding a G protein from the clinical isolate A/Maryland/001/11 comprising a nucleotide sequence corresponding to SEQ ID NO: 8 (G001BB);

the one or more modifications further comprise replacing the nucleotide sequence encoding a F protein of the RSV with a corresponding codon-optimized nucleotide sequence set forth as SEQ ID NO: 9 (FBB);

the one or more modifications further comprise replacing the nucleotide sequence encoding a F protein of the RSV with a corresponding nucleotide sequence set forth as SEQ ID NO: 10 (F001), which encodes the F protein from the clinical isolate A/Maryland/001/11;

the one or more modifications further comprise replacing the nucleotide sequence encoding a F protein of the RSV with a corresponding codon optimized nucleotide sequence encoding the F protein from the clinical isolate A/Maryland/001/11 comprising a nucleotide sequence corresponding to SEQ ID NO: 11 (F001BB);

the one or more modifications further comprise replacing the nucleotide sequence encoding a F protein of the RSV with a corresponding nucleotide sequence set forth as SEQ ID NO: 10 (F001), which encodes the F protein from the clinical isolate A/Maryland/001/11;

the one or more modifications further comprise replacing the nucleotide sequence encoding a F protein of the RSV with a corresponding codon optimized nucleotide sequence encoding the F protein from the clinical isolate A/Maryland/001/11 comprising a nucleotide sequence corresponding to SEQ ID NO: 11 (F001BB);

the one or more modifications further comprise nucleotide mutations encoding amino acid substitutions K66E and Q101P in the F protein of the RSV ("HEK");

the one or more modifications further comprise nucleotide mutations encoding amino acid substitutions E218A and T523I in the F protein of the RSV (F cp substitutions); or the one or more modifications further comprises reversing the order of the genes encoding the G and the F proteins in the RSV genome.

5. The recombinant RSV of claim 1, wherein the one or more modifications further comprise nucleotide mutations to introduce a Y1321K substitution in the L protein of the RSV, and wherein the L protein comprises a S1313 residue, wherein the codons encoding Y1321K substitution and the S1313 residue are AAA and TCA codons respectively ("1030s").

6. The recombinant RSV of claim 1, wherein the one or more modifications comprise or consist of a combination of mutations selected from any one of:

ΔM2-2, cp/ΔM2-2, cp/ΔM2-2/HEK, ΔM2-2/1030s, NS2/N/ΔM2-2, NS2/ΔM2-2, N/ΔM2-2, ASH/ΔM2-2, cp/ΔSH/ΔM2-2, 6120/ΔM2-2, 6120/cp/ΔM2-2, 6120/ΔM2-2/1030s, 6120/NS2/N/ΔM2-2, 6120/G001BB/FBB/ΔM2-2, 6120/FBB/G001BB/ΔM2-2, 6120/G001BB/F/ΔM2-2, 6120/G/FBB/ΔM2-2, 6120/G/FBBHEK/ΔM2-2, 6120/G/FBBcpHEK/ΔM2-2, 6120/FBB/G/ΔM2-2, 6120/G001BB/F001BB/ΔM2-2, 6120/NS2/ΔM2-2, or 6120/N/ΔM2-2; or

ΔM2-2-AclI, cp/ΔM2-2-AclI, cp/ΔM2-2-Ac/l/HEK, ΔM2-2-AclI/1030s, NS2/N/ΔM2-2-AclI, NS2/ΔM2-2-AclI, N/ΔM2-2-AclI, ASH/ΔM2-2-AclI, cp/ΔSH/ΔM2-2-AclI, 6120/ΔM2-2-AclI, 6120/cp/ΔM2-2-AclI, 6120/ΔM2-2-AclI/1030s, 6120/NS2/N/ΔM2-2-AclI, 6120/G001BB/FBB/ΔM2-2-AclI, 6120/FBB/G001BB/ΔM2-2-AclI, 6120/G001BB/F/ΔM2-2-AclI, 6120/G/FBB/ΔM2-2-AclI, 6120/G/FBBHEK/ΔM2-2-AclI, 6120/G/FBBcpHEK/ΔM2-2-AclI, 6120/FBB/G/ΔM2-2-AclI, 6120/G001BB/F001BB/ΔM2-2-AclI, 6120/NS2/ΔM2-2-AclI, or 6120/N/ΔM2-2-AclI; or

ΔM2-2-HindIII, cp/ΔM2-2-HindIII, cp/ΔM2-2-HindIII/HEK, ΔM2-2-HindIII/1030s, NS2/N/ΔM2-2-HindIII, NS2/ΔM2-2-HindIII, N/ΔM2-2-HindIII, ASH/ΔM2-2-HindIII, cp/ΔSH/ΔM2-2-HindIII, 6120/ΔM2-2-HindIII, 6120/cp/ΔM2-2-HindIII, 6120/ΔM2-2-HindIII/1030s, 6120/NS2/N/ΔM2-2-HindIII, 6120/G001BB/FBB/ΔM2-2-HindIII, 6120/FBB/G001BB/ΔM2-2-HindIII, 6120/G001B B/F/ΔM2-2-HindIII, 6120/G/FBB/ΔM2-2-HindIII, 6120/G/FBBHEK/ΔM2-2-HindIII, 6120/G/FBBcpHEK/ΔM2-2-HindIII, 6120/FBB/G/ΔM2-2-HindIII, 6120/G001BB/F001BB/ΔM2-2-HindIII, 6120/NS2/ΔM2-2-HindIII, or 6120/N/ΔM2-2-HindIII.

7. The recombinant RSV of claim 1, wherein the recombinant RSV genome comprises the one or more modifications, and a nucleotide sequence corresponding to a positive-sense sequence at least 90% identical to SEQ ID NO: 1.

8. The recombinant RSV of claim 1, wherein the recombinant RSV genome comprises 6120, ΔM2-2, and 1030s mutations, and a nucleotide sequence corresponding to a positive-sense sequence at least 90% identical, at least 95% identical, and/or at least 99% identical to SEQ ID NO: 16 (LID/ΔM2-2/1030s sequence).

9. The recombinant RSV of claim 1, wherein the recombinant RSV genome is a D46 genome comprising the one or more modifications.

10. The recombinant RSV of claim 1, wherein the recombinant RSV genome comprises one of:

(a) 6120 and ΔM2-2 mutations, and a nucleotide sequence corresponding to a positive-sense sequence at least 90% identical, at least 95% identical, and/or at least 99% identical to SEQ ID NO: 5 (LID/ΔM2-2 sequence);

(b) cp and ΔM2-2 mutations, and a nucleotide sequence corresponding to a positive-sense sequence at least 90% identical, at least 95% identical, and/or at least 99% identical to SEQ ID NO: 1 (D46 sequence);

(c) cp and ΔM2-2 mutations, and a nucleotide sequence corresponding to a positive-sense sequence at least 90% identical, at least 95% identical, and/or at least 99% identical to SEQ ID NO: 15 (D46/cp/ΔM2-2 sequence);

(d) 6120, cp, and ΔM2-2 mutations, and a nucleotide sequence corresponding to a positive-sense sequence at least 90% identical, at least 95% identical, and/or at least 99% identical to SEQ ID NO: 17 (LID/cp/ΔM2-2 sequence);

(e) NS2, N, ΔM2-2-HindIII mutations, and a nucleotide sequence corresponding to a positive-sense sequence at least 90% identical, at least 95% identical, and/or at least 99% identical to SEQ ID NO: 4 (D46/ΔM2-2-HindIII sequence);

(f) NS2, N, ΔM2-2-HindIII mutations, and a nucleotide sequence corresponding to a positive-sense sequence at least 90% identical, at least 95% identical, and/or at least 99% identical to SEQ ID NO: 18 (D46/NS2/N/ΔM2-2-HindIII sequence);

(g) NS2, N, ΔM2-2-AclI mutations, and a nucleotide sequence corresponding to a positive-sense sequence at least 90% identical, at least 95% identical, and/or at least 99% identical to SEQ ID NO: 3 (D46/ΔM2-2-AclII sequence); or (h) NS2, N, and ΔM2-2-AclI mutations, the following nucleotide mutations with positions relative to SEQ ID NO: 1: 404C, 779G, deletion of C1099, 1139A, 1140G, 1182G, 1210G, 5612A, 5616A, 5640G, 6216C, 6222C, 6387T, 7215C, 7482T, 7560A, 7702G, 10515T, and 13634A; and a nucleotide sequence corresponding to a positive-sense sequence at least 90% identical, at least 95% identical, and/or at least 99% identical to SEQ ID NO: 19 (276 sequence).

11. The recombinant RSV of claim 1, wherein the recombinant RSV genome is one of:

a D46/cp/ΔM2-2 genome;

a LID/ΔM2-2/1030s genome;

a LID/cp/ΔM2-2 genome;

a D46/NS2/N/ΔM2-2-HindIII genome;

a LID/ΔM2-2 genome; or a 276 genome.

12. The recombinant RSV of claim 1, wherein the nucleotide sequence of the recombinant RSV genome comprises or consists of a nucleotide sequence corresponding to a positive-sense sequence set forth as any one of SEQ ID NO: 2, SEQ ID NO: 3, SEQ ID NO: 4, SEQ ID NO: 5, SEQ ID NO: 6, SEQ ID NO: 7, SEQ ID NO: 15, SEQ ID NO: 16, SEQ ID NO: 17, SEQ ID NO: 18, or SEQ ID NO: 19.

13. The recombinant RSV of claim 1, wherein:

the recombinant RSV genome comprises a nucleotide sequence corresponding to a positive-sense sequence set forth as SEQ ID NO: 3 further modified by introduction of the following nucleotide mutations relative to SEQ ID NO: 1: 404C, 779G, 1099T, 1139A, 1140G, 1182G, 1210G, 5612A, 5616A, 5640G, 6216C, 6222C, 6387T, 7215C, 7482T, 7560A, 7702G, 10515T, and 13634A;

the recombinant RSV genome comprises a nucleotide sequence corresponding to a positive-sense sequence set forth as SEQ ID NO: 3 further modified by introduction of the following nucleotide mutations relative to SEQ ID NO: 1: 404C, 779G, deletion of C1099, 1139A, 1140G, 1182G, 1210G, 5612A, 5616A, 5640G, 6216C, 6222C, 6387T, 7215C, 7482T, 7560A, 7702G, 10515T, and 13634A; or the recombinant RSV genome or antigenome comprises a sequence selected from the group consisting of SEQ ID NO: 2, SEQ ID NO: 3 and SEQ ID NO: 4, further modified by introduction of one or more of the following nucleotide substitutions with positions relative to SEQ ID NO: 1: 404C, 779G, 1099T, 1139A, 1140G, 1182G, 1210G, 1938A, 5612A, 5616A, 5640G, 6216C, 6222C, 6387T, 7215C, 7482T, 7560A, 7702G, 10515T, 13634A, 13901T.

14. The recombinant RSV of claim 1, wherein the RSV is a subtype A RSV or a subtype B RSV.

15. The recombinant RSV of claim 1, wherein the RSV is infectious, attenuated, and self-replicating.

16. An isolated polynucleotide molecule comprising the nucleotide sequence of the recombinant RSV genome of claim 1, or an antigenomic cDNA or RNA sequence of the RSV genome.

17. A vector comprising the polynucleotide molecule of claim 16.

18. A cell comprising the polynucleotide molecule of claim 16.

19. A method of producing a recombinant RSV, comprising:

transfecting a permissive cell culture with the vector of claim 17;

incubating the cell culture for a sufficient period of time to allow for viral replication; and purifying the replicated recombinant RSV.

20. A recombinant RSV produced by the method of claim 19.

21. A pharmaceutical composition comprising the recombinant RSV of claim 1.

22. A method of eliciting an immune response to RSV in a subject comprising administering an immunogenically effective amount of the pharmaceutical composition of claim 21 to the subject.

23. The method of claim 22, wherein:

the immune response is a protective immune response;

the pharmaceutical composition is administered intranasally;

the RSV is administered via injection, aerosol delivery, nasal spray or nasal droplets;

the subject is between 1 and 6 months of age the subject is a human; and/or the subject is seronegative for RSV.

24. A recombinant RSV comprising a recombinant RSV genome comprising or consisting of a nucleic acid sequence corresponding to the positive sense sequence set forth as SEQ ID NO: 19.

* * * * *

UNITED STATES PATENT AND TRADEMARK OFFICE

CERTIFICATE OF CORRECTION

PATENT NO. : 10,655,109 B2
APPLICATION NO. : 16/061314
DATED : May 19, 2020
INVENTOR(S) : Collins et al.

It is certified that error appears in the above-identified patent and that said Letters Patent is hereby corrected as shown below:

In the Claims

Column 362, Lines 36-37, in Claim 23:
“the subject is between 1 and 6 months of age the subject is a human; and/or”
Should be:
--the subject is between 1 and 6 months of age;
the subject is a human; and/or--

Signed and Sealed this
Second Day of August, 2022

Katherine Kelly Vidal

Katherine Kelly Vidal
*Director of the United States Patent and Trademark Office*